US011572407B2

(12) United States Patent
Jahchan et al.

(10) Patent No.: US 11,572,407 B2
(45) Date of Patent: Feb. 7, 2023

(54) ANTI-MARCO ANTIBODIES AND USES THEREOF

(71) Applicant: Pionyr Immunotherapeutics, Inc., South San Francisco, CA (US)

(72) Inventors: Nadine Jahchan, San Carlos, CA (US); Michel Streuli, Atherton, CA (US); Xi Yang, Hillsborough, CA (US); Linda Liang, Mountain View, CA (US); Venkataraman Sriram, Berkeley, CA (US); Joshua Pollack, Richmond, CA (US); Kara Mojica, Dublin, CA (US); Vladislava Juric, San Mateo, CA (US); Linnea Haeggblom, San Francisco, CA (US); Leonard G. Presta, San Francisco, CA (US); Sayantan Mitra, Mountain View, CA (US)

(73) Assignee: PIONYR IMMUNOTHERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 17/529,927

(22) Filed: Nov. 18, 2021

(65) Prior Publication Data

US 2022/0153832 A1 May 19, 2022

Related U.S. Application Data

(60) Provisional application No. 63/244,662, filed on Sep. 15, 2021, provisional application No. 63/115,272, filed on Nov. 18, 2020.

(51) Int. Cl.
*C07K 16/28* (2006.01)
*A61P 35/00* (2006.01)
*A61K 39/00* (2006.01)

(52) U.S. Cl.
CPC .............. *C07K 16/28* (2013.01); *A61P 35/00* (2018.01); *A61K 2039/505* (2013.01); *A61K 2039/507* (2013.01); *C07K 2317/21* (2013.01); *C07K 2317/24* (2013.01); *C07K 2317/92* (2013.01)

(58) Field of Classification Search
CPC ................ C07K 16/28; C07K 2317/21; C07K 2317/24; C07K 2317/92; A61K 2039/505; A61K 2039/507
See application file for complete search history.

(56) References Cited

U.S. PATENT DOCUMENTS

| | | | |
|---|---|---|---|
| 5,916,766 A | 6/1999 | Elshourbagy et al. | |
| 6,197,931 B1 | 3/2001 | Elshourbagy et al. | |
| 8,597,946 B2 | 12/2013 | Mule et al. | |
| 10,882,917 B2 | 1/2021 | Karlsson et al. | |
| 2010/0227415 A1 | 9/2010 | Winqvist et al. | |
| 2012/0231023 A1 | 9/2012 | Murawski et al. | |
| 2018/0000899 A1 | 1/2018 | Francois et al. | |
| 2018/0171021 A1 | 6/2018 | Karlsson et al. | |
| 2019/0263877 A1 | 8/2019 | Yeung et al. | |
| 2019/0336615 A1 | 11/2019 | Thompson et al. | |
| 2020/0071417 A1 | 3/2020 | Loew et al. | |
| 2020/0369773 A1 | 11/2020 | Whitfield et al. | |
| 2021/0000920 A1 | 1/2021 | Quay | |

FOREIGN PATENT DOCUMENTS

| | | |
|---|---|---|
| EP | 3302558 A4 | 1/2019 |
| EP | 3759129 A1 | 1/2021 |
| WO | 2016/196612 A1 | 12/2016 |
| WO | 2017/062363 A1 | 4/2017 |
| WO | 2018/140831 A2 | 8/2018 |
| WO | 2018/195283 A1 | 10/2018 |
| WO | 2019/005641 A1 | 1/2019 |
| WO | 2019/036724 A2 | 2/2019 |
| WO | 2019/068007 A1 | 4/2019 |
| WO | 2019/126538 A1 | 6/2019 |
| WO | 2020/065406 A2 | 4/2020 |
| WO | 2020/142659 A2 | 7/2020 |
| WO | 2020/162696 A1 | 8/2020 |
| WO | 2020/191069 A1 | 9/2020 |
| WO | 2020/226633 A1 | 11/2020 |
| WO | 2020/252208 A2 | 12/2020 |
| WO | 2021/022218 A1 | 2/2021 |

OTHER PUBLICATIONS

Arredouani et al., "Scavenger Receptors SR-AI/II and MARCO limit pulmonary dendritic cell migration and allergic airway inflammation." The Journal of Immunology 178, No. 9 (2007): 5912-5920.
Arredouani et al., "The scavenger receptor MARCO is required for lung defense against pneumococcal pneumonia and inhaled particles." The Journal of experimental medicine 200, No. 2 (2004): 267-272.
Arredouani, "Is the scavenger receptor MARCO a new immune checkpoint? " Oncoimmunology 3, No. 10 (2014): e955709.
Bin et al., "Identification of uteroglobin-related protein 1 and macrophage scavenger receptor with collagenous structure as a lung-specific ligand-receptor pair." The Journal of Immunology 171, No. 2 (2003): 924-930.
Bowdish et al., "MARCO, TLR2, and CD14 are required for macrophage cytokine responses to mycobacterial trehalose dimycolate and Mycobacterium tuberculosis." PLoS pathogens 5, No. 6 (2009): e1000474.
Brown et al, "Silica-directed mast cell activation is enhanced by scavenger receptors." American journal of respiratory sell and molecular biology 36, No. 1 (2007): 43-52.
Chen et al., "Defective microarchitecture of the spleen marginal zone and impaired response to a thymus-independent type 2 antigen in mice lacking scavenger receptors MARCO and SR-A." The Journal of Immunology 175, No. 12 (2005): 8173-8180.
Czerkies et al., "An interplay between scavenger receptor A and CD14 during activation of J774 cells by high concentrations of LPS." Immunobiology 218, No. 10 (2013): 1217-1226.

(Continued)

*Primary Examiner* — Ruixiang Li
(74) *Attorney, Agent, or Firm* — Goodwin Procter LLP

(57) ABSTRACT

Provided herein are anti-MARCO antibodies. Provided are also methods of generating and using anti-MARCO antibodies.

58 Claims, 80 Drawing Sheets

Specification includes a Sequence Listing.

(56) References Cited

OTHER PUBLICATIONS

Dahl et al., "Protection against inhaled oxidants through scavenging of oxidized lipids by macrophage receptors MARCO and SR-AI/II." The Journal of clinical investigation 117, No. 3 (2007): 757-764.

Dorrington et al., "MARCO is required for TLR2-and Nod2-mediated responses to *Streptococcus pneumoniae* and clearance of pneumococcal colonization in the murine nasopharynx." The Journal of Immunology 190, No. 1 (2013): 250-258.

Eisinger et al., "Targeting a scavenger receptor on tumor-associated macrophages activates tumor cell killing by natural killer cells" Proceedings of the National Academy of Sciences 117, No. 50 (2020): 32005-32016.

Elomaa et al., "Cloning of a novel bacteria-binding receptor structurally related to scavenger receptors and expressed n a subset of macrophages." Cell 80, No. 4 (1995): 603-609.

Elomaa et al., "Structure of the human macrophage MARCO receptor and characterization of its bacteria-binding region." Journal of Biological Chemistry 273, No. 8 (1998): 4530-4538.

Elshourbagy et al.,"Molecular characterization of a human scavenger receptor, human MARCO." European journal of biochemistry 267, No. 3 (2000): 919-926.

Georgoudaki et al., "Reprogramming tumor-associated macrophages by antibody targeting inhibits cancer progression and metastasis." Cell reports 15, No. 9 (2016): 2000-2011.

Ghosh et al., "MARCO regulates early inflammatory responses against influenza: a useful macrophage function with adverse outcome." American journal of respiratory cell and molecular biology 45, No. 5 (2011): 1036-1044.

Granucci et al., "The scavenger receptor MARCO mediates cytoskeleton rearrangements in dendritic cells and microglia." Blood 102, No. 8 (2003): 2940-2947.

Grolleau et al., "Inducible expression of macrophage receptor Marco by dendritic cells following phagocytic uptake of dead cells uncovered by oligonucleotide arrays." The Journal of Immunology 171, No. 6 (2003): 2879-2888.

Hamilton et al., "MARCO mediates silica uptake and toxicity in alveolar macrophages from C57BL/6 mice." Journal of Biological Chemistry 281, No. 45 (2006): 34218-34226.

Hirano et al., "Macrophage receptor with collagenous structure (MARCO) is a dynamic adhesive molecule that enhances uptake of carbon nanotubes by CHO-K1 cells." Toxicology and applied pharmacology 259, No. 1 (2012): 96-103.

Hirano et al., "Macrophage receptor with collagenous structure (MARCO) is processed by either macropinocytosis or endocytosis-autophagy pathway." PloS one 10, No. 11 (2015): e0142062.

Hornburg et al., "Single-cell dissection of cellular components and interactions shaping the tumor immune phenotypes in ovarian cancer." Cancer Cell (2021).

Jahchan et al., "Tuning the tumor myeloid microenvironment to fight cancer." Frontiers in immunology 10 (2019): 1611.

Jing et al., "Role of macrophage receptor with collagenous structure in innate immune tolerance." The Journal of mmunology 190, No. 12 (2013): 6360-6367.

Józefowsk et al., "Role of scavenger receptor MARCO in macrophage responses to CpG oligodeoxynucleotides." Journal of leukocyte biology 80, No. 4 (2006): 870-879.

Józefowski et al., Disparate regulation and function of the class A scavenger receptors SR-AI/II and MARCO. The Journal of Immunology 175, No. 12 (2005): 8032-8041.

Kissick et al., "The scavenger receptor MARCO modulates TLR-induced responses in dendritic cells." PLoS One 9, No. 8 (2014): e104148.

Komine et al., "Examination of MARCO activity on dendritic cell phenotype and function using a gene knockout mouse." PloS one 8, No. 7 (2013): e67795.

Kraal et al., "The macrophage receptor MARCO." Microbes and infection 2, No. 3 (2000): 313-316.

La Fleur et al., "Expression of scavenger receptor MARCO defines a targetable tumor-associated macrophage subset n non-small cell lung cancer." International journal of cancer 143, No. 7 (2018): 1741-1752.

La Fleur et al., "Targeting MARCO and IL37R on Immunosuppressive Macrophages in Lung Cancer Blocks Regulatory T Cells and Supports Cytotoxic Lymphocyte Function." Cancer Research 81, No. 4 (2021): 956-967.

Lavin et al., "Innate immune landscape in early lung adenocarcinoma by paired single-cell analyses." Cell 169, No. 4 (2017): 750-765.

Matsushita et al., "Targeting MARCO can lead to enhanced dendritic cell motility and anti-melanoma activity." Cancer immunology, immunotherapy 59, No. 6 (2010): 875-884.

Mukhopadhyay et al., "SR-A/MARCO-mediated ligand delivery enhances intracellular TLR and NLR function, but ligand scavenging from cell surface limits TLR4 response to pathogens." Blood, The Journal of the American Society of Hematology 117, No. 4 (2011): 1319-1328.

Novakowski et al., "A naturally occurring transcript variant of MARCO reveals the SRCR domain is critical for function." mmunology and cell biology 94, No. 7 (2016): 646-655.

Ojala et al., "Crystal structure of the cysteine-rich domain of scavenger receptor MARCO reveals the presence of a basic and an acidic cluster that both contribute to ligand recognition." Journal of Biological Chemistry 282, No. 22 (2007): 16654-16666.

Palecanda et al., "Role of the scavenger receptor MARCO in alveolar macrophage binding of unopsonized environmental particles." The Journal of experimental medicine 189, No. 9 (1999): 1497-1506.

Pikkarainen et al., "Expression of macrophage MARCO receptor induces formation of dendritic plasma membrane processes " Journal of Biological Chemistry 274, No. 16 (1999): 10975-10982.

Prokopec et al., "Cutting edge: Marginal zone macrophages regulate antigen transport by B cells to the follicle in the spleen via CD21." The Journal of Immunology 197, No. 6 (2016): 2063-2068.

van der Laan et al., "Macrophage scavenger receptor MARCO: in vitro and in vivo regulation and involvement in the anti-bacterial host defense." Immunology letters 57, No. 1-3 (1997): 203-208.

van der Laan et al., "Regulation and functional involvement of macrophage scavenger receptor MARCO in clearance of bacteria in vivo." The Journal of Immunology 162, No. 2 (1999): 939-947.

Kangas et al., "Structure and chromosomal localization of the human and murine genes for the macrophage MARCO receptor." Genomics 58, No. 1 (1999): 82-89.

Shi et al., "The Scavenger Receptor MARCO Expressed by Tumor-Associated Macrophages Are Highly Associated With Poor Pancreatic Cancer Prognosis." Frontiers in Oncology (2021): 4518.

Xing et al., "Scavenger receptor MARCO contributes to macrophage phagocytosis and clearance of tumor cells." Experimental Cell Research 408, No. 2 (2021): 112862.

Eisinger, "Revealing the secrets of MARCO: a target for cancer immunotherapy." PhD diss., Karolinska Institutet (Sweden), 2019, 84 pages.

PCT/US2021/059955—Invitation to Pay Additional Fees, Feb. 10, 2022, 3 pages.

PCT/US2021/059955—International Search Report and Written Opinion, dated Apr. 12, 2022, 21 pages.

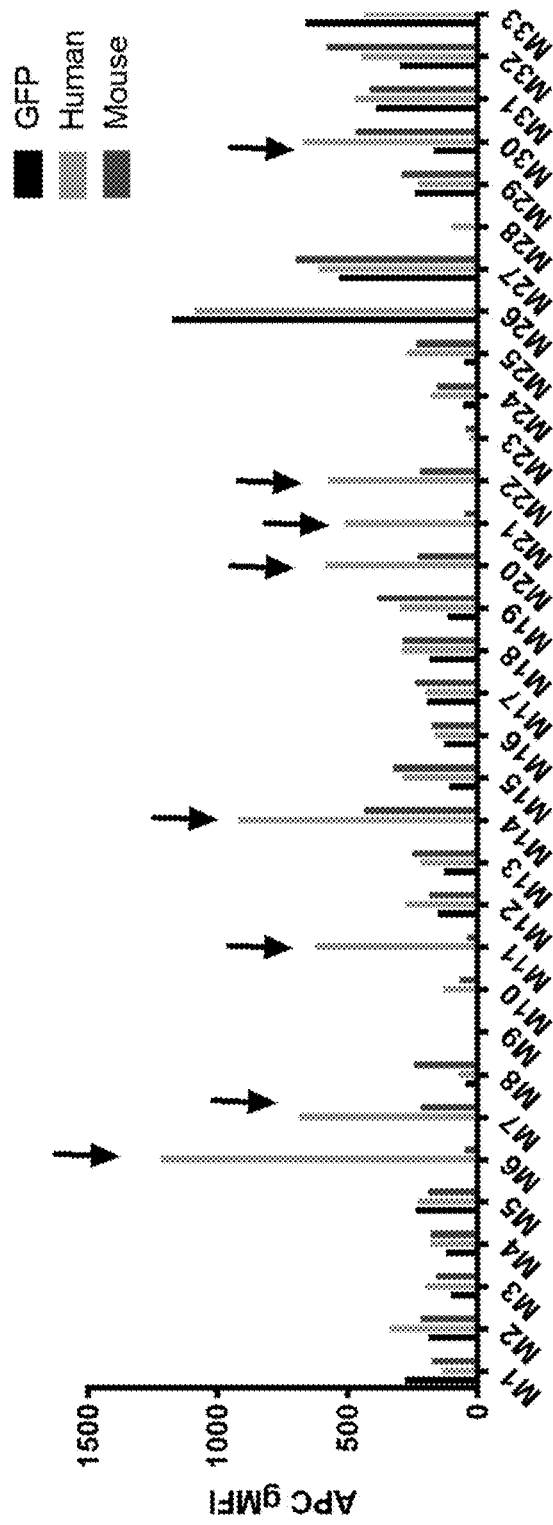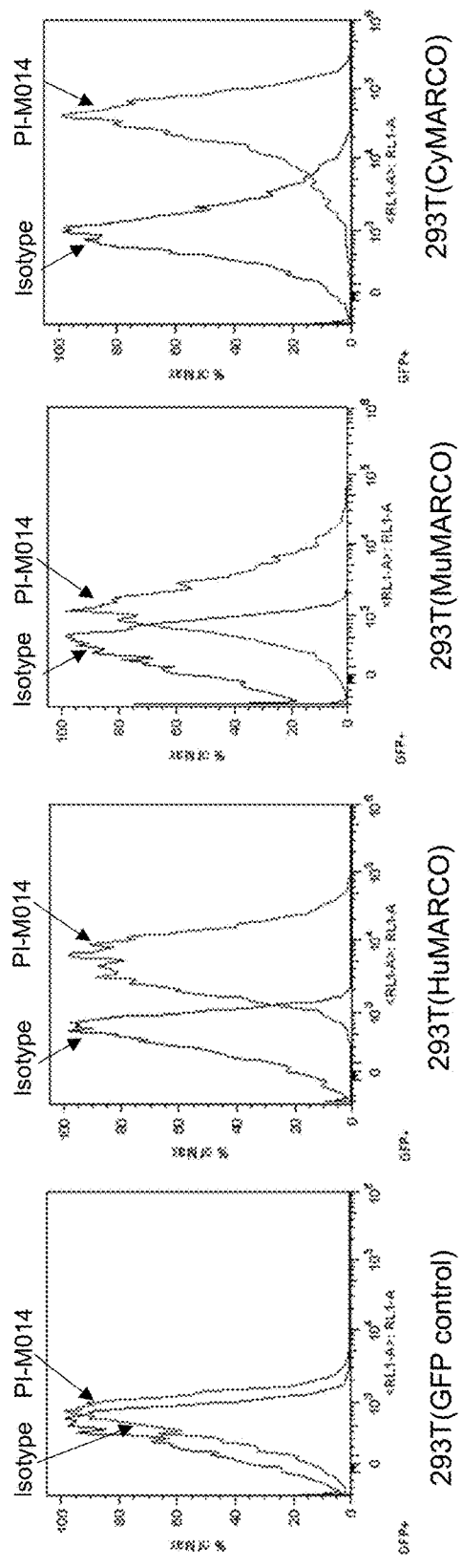

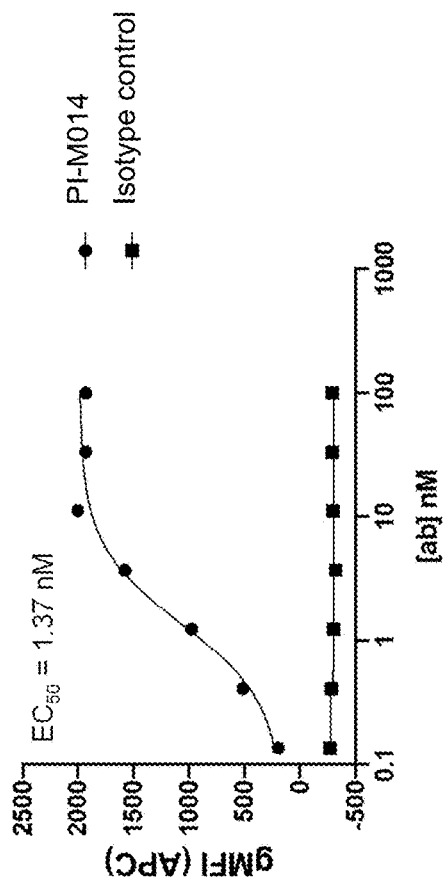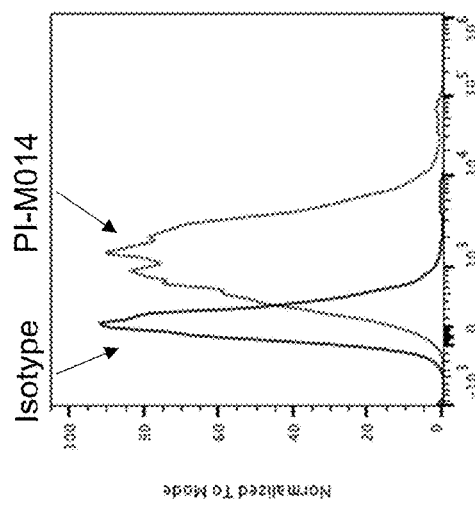

Anti-PD-1

PI-3009 + anti-PD-1

Controls

PI-3008 + anti-PD-1

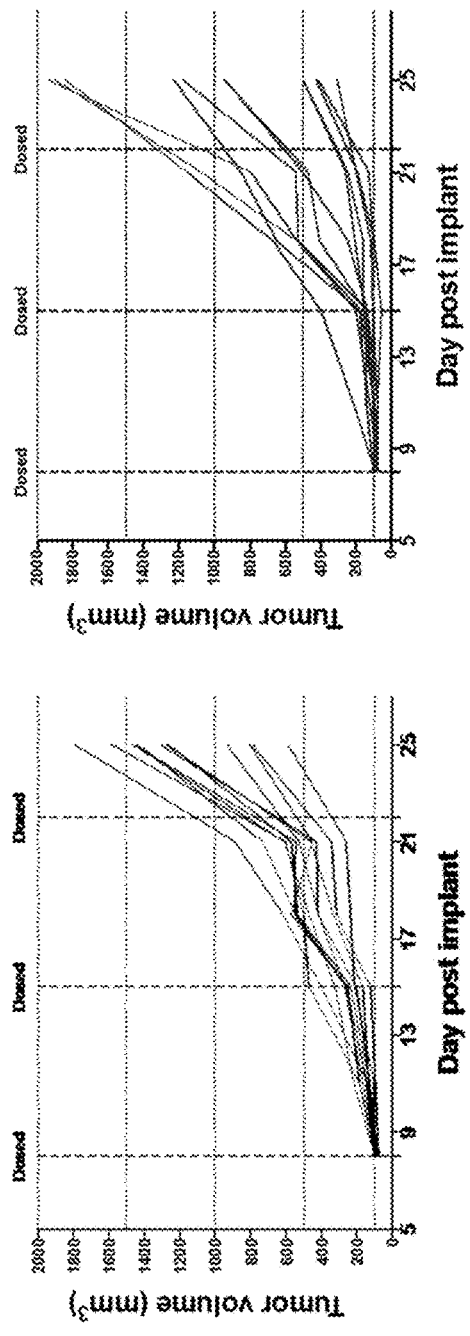
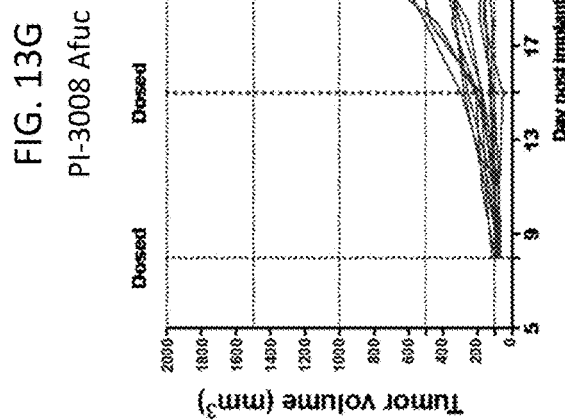
FIG. 13E Isotype
FIG. 13F PI-3008
FIG. 13G PI-3008 Afuc

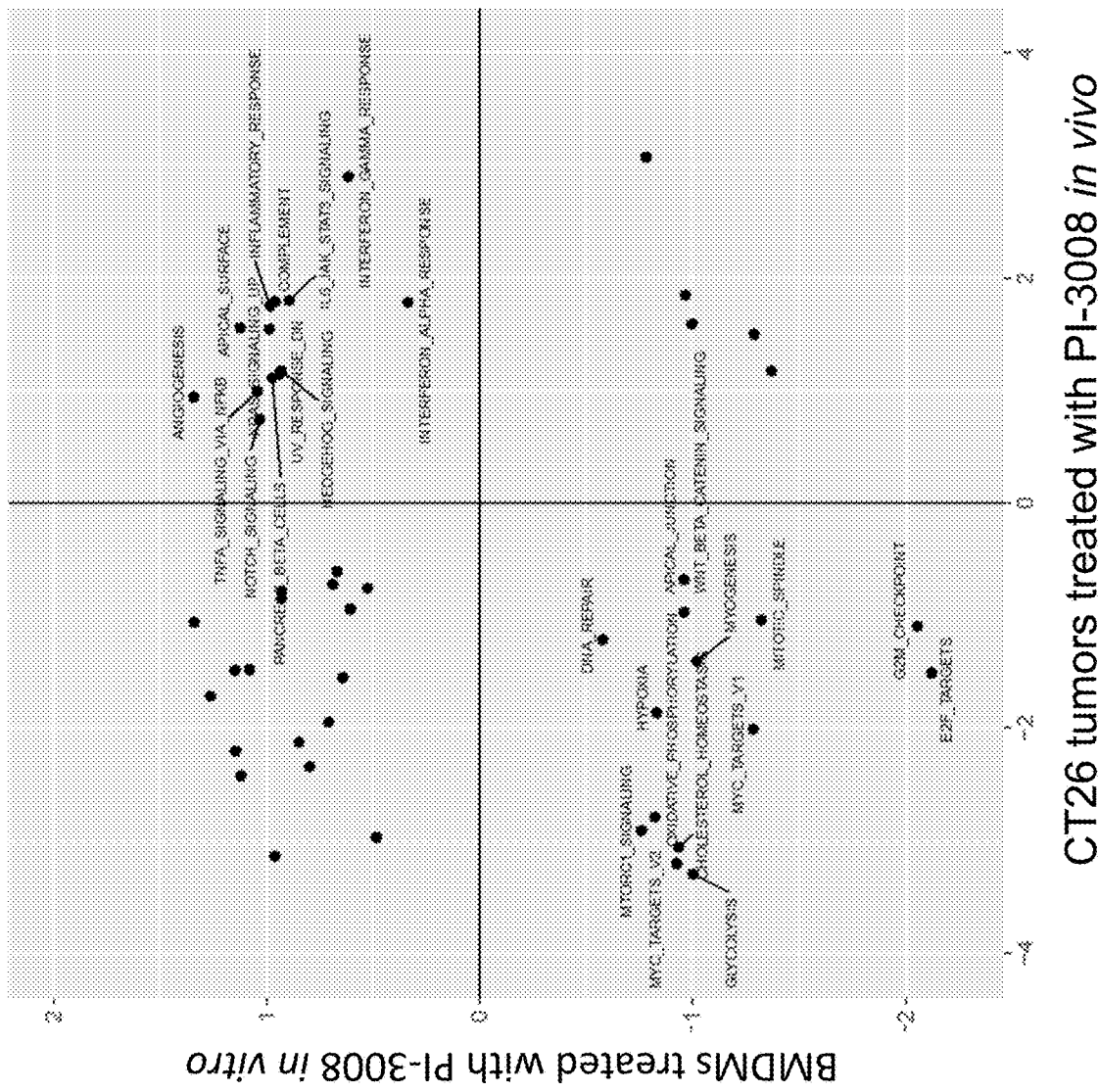

FIG. 17A

```
seq             10         20         30         40         50
AbM             10         20         30         40         50  a
3061      EVQLVESGGGLVQPGSSLKLSCVAS KFTFSNYGMN WIRQAPKKGLEWIA LIYYNSNNKY
                                    *  *  *                 *  *  * *
3-23*04   EVQLVESGGGLVQPGGSLRLSCAAS GFTFSSYAMS WVRQAPGKGLEWVS AISGSGGSTY
h3061-H1  EVQLVESGGGLVQPGGSLRLSCAAS KFTFSNYGMN WVRQAPGKGLEWVS LIYYNSNNKY
h3061-H2  EVQLVESGGGLVQPGGSLRLSCAAS KFTFSNYGMN WIRQAPGKGLEWIA LIYYNSNNKY
h3061-H3  EVQLVESGGGLVQPGGSLRLSCAAS GFTFSNYGMN WIRQAPGKGLEWIA LIYYNSNNKY
                                        #                     @ ## seq             60         70         80         90        100        110        120
AbM             60         70         80  abc    90                   110
3061      YADSVKGRFTISRDNSKNTLYLEMNSLRSEDTAMYYCAK SLTGGSDYFDS WGQGVMVTVSS
                                    *       *  *  *                   * *
3-23*04   YADSVKGRFTISRDNSKNTLYLQMNSLRAEDTAVYYCAK             WGQGTLVTVSS
h3061-H1  YADSVKGRFTISRDNSKNTLYLQMNSLRAEDTAVYYCAK SLTGGSDYFDS WGQGTLVTVSS
h3061-H2  YADSVKGRFTISRDNSKNTLYLQMNSLRAEDTAVYYCAK SLTGGSDYFDS WGQGTLVTVSS
h3061-H3  YADSVKGRFTISRDNSKNTLYLQMNSLRAEDTAVYYCAK SLTGGSDYFDS WGQGTLVTVSS
                                                      M              V
```

@ isoaspartate formation substitutions: S/Q/A
asparagine deamidation substitutions: Q/S/A

FIG. 17B

```
seq             10         20         30         40         50
AbM             10         20         30         40         50
3061      DVQMTQSPSYLAASPGESVSISC KASKSIGTFLA WYQEKPEKTNKLLIY SGSTLQS
              *     *  * **  *                 *    *  **
1-39*01   DIQMTQSPSSLSASVGDRVTITC RASQSISSYLN WYQQKPGKAPKLLIY AASSLQS
h3061-L1  DIQMTQSPSSLSASVGDRVTITC RASKSIGTFLA WYQQKPGKAPKLLIY SGSTLQS
              V                      K             E    TN seq             60         70         80         90        100
AbM             60         70         80         90        100
3061      GTPSRFSGSGSGTDFTLTIRNLEPEDFAVYYC QQHDEYPFT FGSGTKLEIK
              *                ** *      *                  *
1-39*01   GVPSRFSGSGSGTDFTLTISSLQPEDFATYYC QQSYSTPP  FGQGTKLEIK
h3061-L1  GVPSRFSGSGSGTDFTLTISSLQPEDFATYYC QQHDEYPFT FGQGTKLEIK
              T
```

FIG. 18

```
seq              10         20         30         40         50
AbM    bbb      pp    bbb   b    bi bi b    bi bi i    ii ibbi
3031   DIQMTQSPASLSTSLGETVSIEC LASEGISNDLA WYQQKSGKSPQLLIY AA
        *  *  *  ***  *          *          *    *

1-39*01  DIQMTQSPSSLSASVGDRVTITC RASQSISSYLN WYQQKPGKAPKLLIY AA
h3031-L1 DIQMTQSPSSLSASVGDRVTITC RASEGISNDLA WYQQKPGKAPKLLIY AA
h3031-L2 DIQMTQSPSSLSASVGDRVTITC RASEGISNDLA WYQQKPGKAPKLLIY AA
h3031-L3 DIQMTQSPSSLSASVGDRVTITC RASEGISNDLA WYQQKPGKAPKLLIY AA
h3031-L2b DIQMTQSPSSLSASVGDRVTITC RASEGISNDLA WYQQKPGKAPKLLIY AA
h3031-L2c DIQMTQSPSSLSTSVGDRVTITC RASEGISNDLA WYQQKPGKSPKLLIY AA
h3031-L2d DIQMTQSPSSLSTSVGDRVTITC RASEGISNDLA WYQQKPGKSPKLLIY AA
                            T           #
                            L           S seq              60         70         80         90        100
AbM    b       bbb   b     ib bib  ibii-ib    i    b  b
3031   GVPSRFSGSGSGTDFTLTISGMQPEDEADYFC QQSVSTPP   FGQGTKLEIK
       ***  *  *               *  *              *

1-39*01  GVPSRFSGSGSGTDFTLTISSLQPEDFATYYC QQSYSTPP FGQGTKLEIK
h3031-L1 GVPSRFSGSGSGTDFTLTISSLQPEDFATYYC QQSYKYPLT FGQGTKLEIK
h3031-L2 GVPSRFSGSGSGTDYTLTISSLQPEDFATYYC QQSYKYPLT FGQGTKLEIK
h3031-L3 GVPSRFSGSGSGTDYTLTISSMQPEDFATYYC QQSYKYPLT FGQGTKLEIK
h3031-L2b GVPSRFSGSGSGTDYTLTISSLQPEDFATYYC QQSYKYPLT FGQGTKLEIK
h3031-L2c GVPSRFSGSGSGTDYTLTISSLQPEDFATYYC QQSYKYPLT FGQGTKLEIK
h3031-L2d GVPSRFSGSGSGTDYTLTISSLQPEDEATYFC QQSYKYPLT FGQGTKLEIK
                                   E F
```

\# deamidation substitutions: Q/S/A/D

FIG. 21

```
humMARCO_SRCR   NSVSVRIVGSSNRGRAEVYYYSGTWGTICDDEWQNSDAIVFCRMLGYSKGRALYKVGAGTGQIWLDNVQCRGTESTLWSCTKNSWGHHDCSHEEDAGVECSV
murMARCO_SRCR   SFQRVRIMGGTNRGRAEVYYNNEWGTICDDDWDNDATVFCRMLGYSKGRALSSYGGGSGNIWLDNVNCRGTENSLWDCSKNSWGNHNCVHNEDAGVECS-
                **                     ***           * * *                 *                   *   *        * mur_variant1    SFQRVRIMGGTNRGRAEVYYSGTWGTICDDDWDNDATVFCRMLGYSKGRALSSYGGGSGNIWLDNVNCRGTENSLWDCSKNSWGNHNCVHNEDAGVECS-
mur_variant2    SFQRVRIMGGTNRGRAEVYYNNEWGTICDDDEWQNSDATVFCRMLGYSKGRALSSYGGGSGNIWLDNVNCRGTENSLWDCSKNSWGNHNCVHNEDAGVECS-
mur_variant3    SFQRVRIMGGTNRGRAEVYYNNEWGTICDDDWQNNDATVFCRMLGYSKGRALKSYGGGSGNIWLDNVNCRGTENSLWDCSKNSWGNHNCVHNEDAGVECS-
mur_variant4    SFQRVRIMGGTNRGRAEVYYNNEWGTICDDDWDNDATVFCRMLGYSRGRALYKYGGGSGNIWLDNVNCRGTENSLWDCSKNSWGNHNCVHNEDAGVECS-
mur_variant5    SFQRVRIMGGTNRGRAEVYYNNEWGTICDDDWDNDATVFCRMLGYSKGRALSSYGGGSGNIWLDNVNCRGTESTLWSCTKNSWGNHNCVHNEDAGVECS-
mur_variant6    SFQRVRIMGGTNRGRAEVYYNNEWGTICDDEWQNNDATVFCRMLGYSKGRALSSYGGGSGNIWLDNVNCRGTENSLWDCSKNSWGNHHDCSHEEDAGVECS-
mur_variant7    NSVSVRIMGSSNRGRAEVYYNNEWGTICDDDWDNDATVFCRMLGYSKGRALSSYGGGSGNIWLDNVNCRGTENSLWDCSKNSWGNHNCVHNEDAGVECShumMARCO_SRCR   NSVSVRIVGSSNRGRAEVYYYSGTWGTICDDEWQNSDAIVFCRMLGYSKGRALYKVGAGTGQIWLDNVQCRGTESTLWSCTKNSWGHHDCSHEEDAGVECSV
murMARCO_SRCR   SFQRVRIMGGTNRGRAEVYYNNEWGTICDDDWDNDATVFCRMLGYSKGRALSSYGGGSGNIWLDNVNCRGTENSLWDCSKNSWGNHNCVHNEDAGVECS-
                **                     ***           * * *                 *                   *   *        * hum-variant 1   NSVSVRIVGSSNRGRAEVYYYSGTWGTICDDEWQNSDAIVFCRMLGYSKGRALYKVGAGTGQIWLDNVQCRGTESTLWSCTKNSWGHHDCSHEEDAGVECSV
hum-variant 2   NSVSVRIVGSSNRGRAEVYYYSGTWGTICDDDWDNDAIVFCRMLGYSKGRALYKVGAGTGQIWLDNVQCRGTESTLWSCTKNSWGHHDCSHEEDAGVECSV
hum-variant 3   NSVSVRIVGSSNRGRAEVYYYSGTWGTICDDEWQNSDAIVFCRMLGYSKGRALSSVGAGTGQIWLDNVQCRGTESTLWSCTKNSWGHHDCSHEEDAGVECSV
hum-variant 4   NSVSVRIVGSSNRGRAEVYYYSGTWGTICDDEWQNSDAIVFCRMLGYSKGRALYKVGAGTGQIWLDNVQCRGTENSLWDCSKNSWGHHDCSHEEDAGVECSV
hum-variant 5   NSVSVRIVGSSNRGRAEVYYYSGTWGTICDDEWQNSDAIVFCRMLGYSKGRALYKVGAGTGQIWLDNVQCRGTESTLWSCTKNSCSKNSWGHHDCSHEEDAGVECSV
hum-variant 6   NSVSVRIVGSSNRGRAEVYYYSGTWGTICDDEWQNSDAIVFCRMLGYSKGRALYKVGAGTGQIWLDNVNCRGTESTLWSCTKNSWGNHNCVHNEDAGVECSV
hum-variant 7   SFQRVRIVGGTNRGRAEVYYYSGTWGTICDDEWQNSDAIVFCRMLGYSKGRALYKVGAGTGQIWLDNVQCRGTESTLWSCTKNSWGHHDCSHEEDAGVECSV
```

FIG. 22

| | |
|---|---|
| humMARCO_SRCR | NSVSVRIVGSSNRGRAEVYYSGTWGTICDDEWQNSDAIVFCRMLGYSRGRALYKVGAGTGQIWLDNVQCRGTESTLWSCTKNSWGHHDCSHEEDAGVECSV |
| murMARCO_SRCR | SFQRVRIMGGTNRGRAEVYINNEWGTICDDWDNNDATVFCRMLGYSRGRALSSYGGGSGNIWLDNVNCRGTENSLWDCSKNSWNHNCVHNEDAGVECS- |
| | **** ** ** *** * * ** * * ** * |
| hVar3 | NSVSVRIVGSSNRGRAEVYYSGTWGTICDDEWQNSDAIVFCRMLGYSRGRALSSVGAGTGQIWLDNVQCRGTESTLWSCTKNSWGHHDCSHEEDAGVECSV |
| hVar5 | NSVSVRIVGSSNRGRAEVYYSGTWGTICDDEWQNSDAIVFCRMLGYSKGRALYKVGAGTGQIWLDNVQCRGTESTLNSCTKNSWGHHDCSHEEDAGVECSV |
| hVar6 | NSVSVRIVGSSNRGRAEVYYSGTWGTICDDEWDNSDAIVFCRMLGYSRGRALYKVGAGTGQIWLDNVNCRGTESTLWSCKNSWGHHDCSHEEDAGVECSV |
| humMARCO wt | NSVSVRIVGSSNRGRAEVYYSGTWGTICDDEWQNSDAIVFCRMLGYSRGRALYKVGAGTGQIWLDNVQCRGTESTLWSCTKNSWGHHDCSHEEDAGVECSV |
| mVar6 | SFQRVRIMGGTNRGRAEVYINNEWGTICDDEWQNNDATVFCEMRLGYSRGRALSSYGGGSGNIWLDNVQCRGTENSLWDCTKNSWGNHNCVHNEDAGVECS- |
| mMARCO wt | SFQRVRIMGGTNRGRAEVYINNEWGTICDDWDNNDATVFCRMLGYSRGRALSSYGGGSGNIWLDNVNCRGTENSLWDCSKNSWNHNCVHNEDAGVECS |

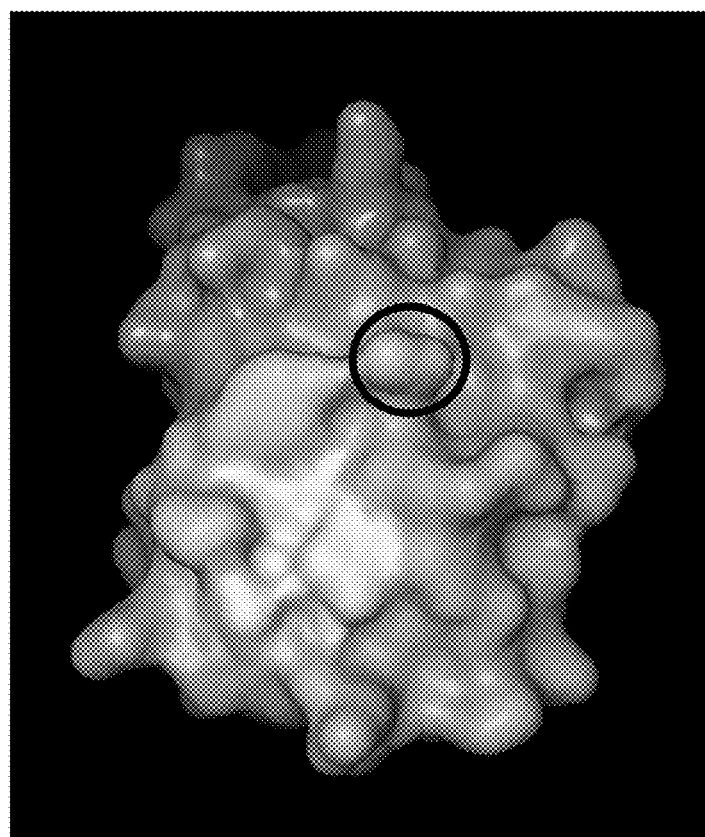
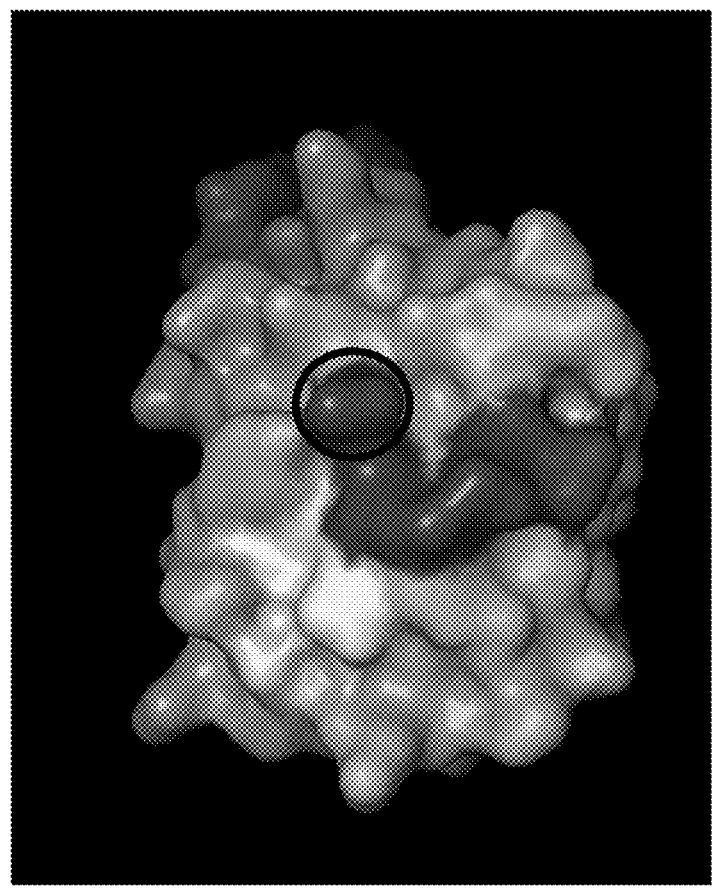
FIG. 24

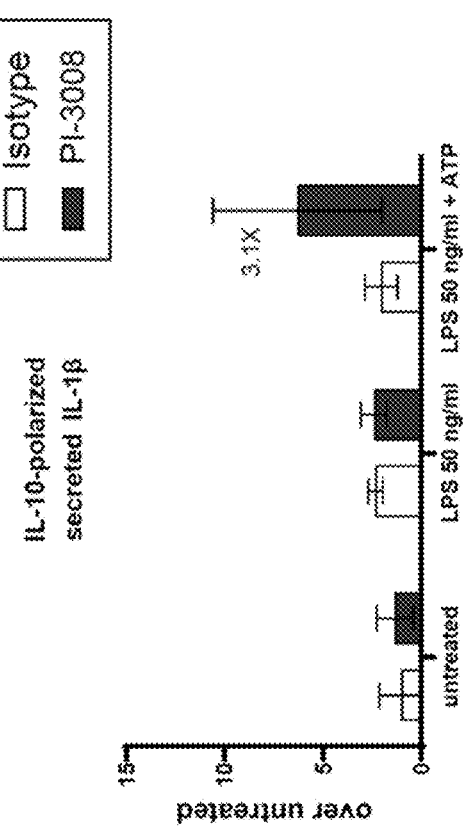
FIG. 33A C57BL/6 non-polarized secreted IL-1β
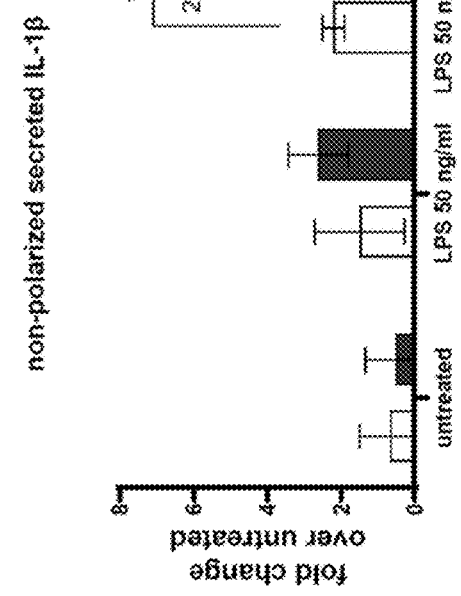
FIG. 33B IL-10-polarized secreted IL-1β
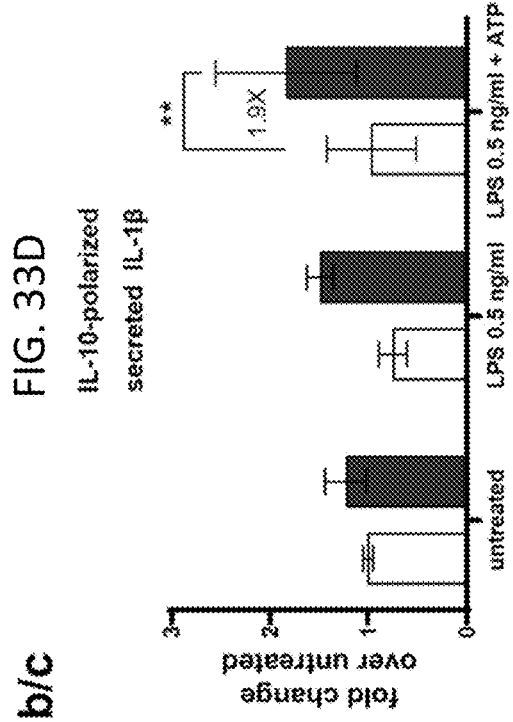
FIG. 33C Balb/c non-polarized secreted IL-1β
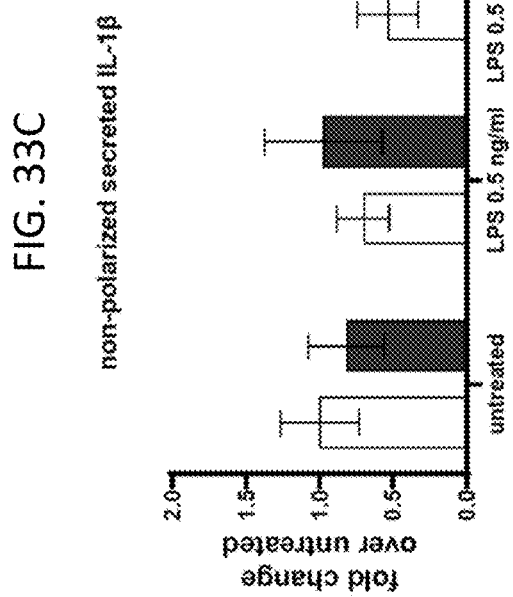
FIG. 33D IL-10-polarized secreted IL-1β

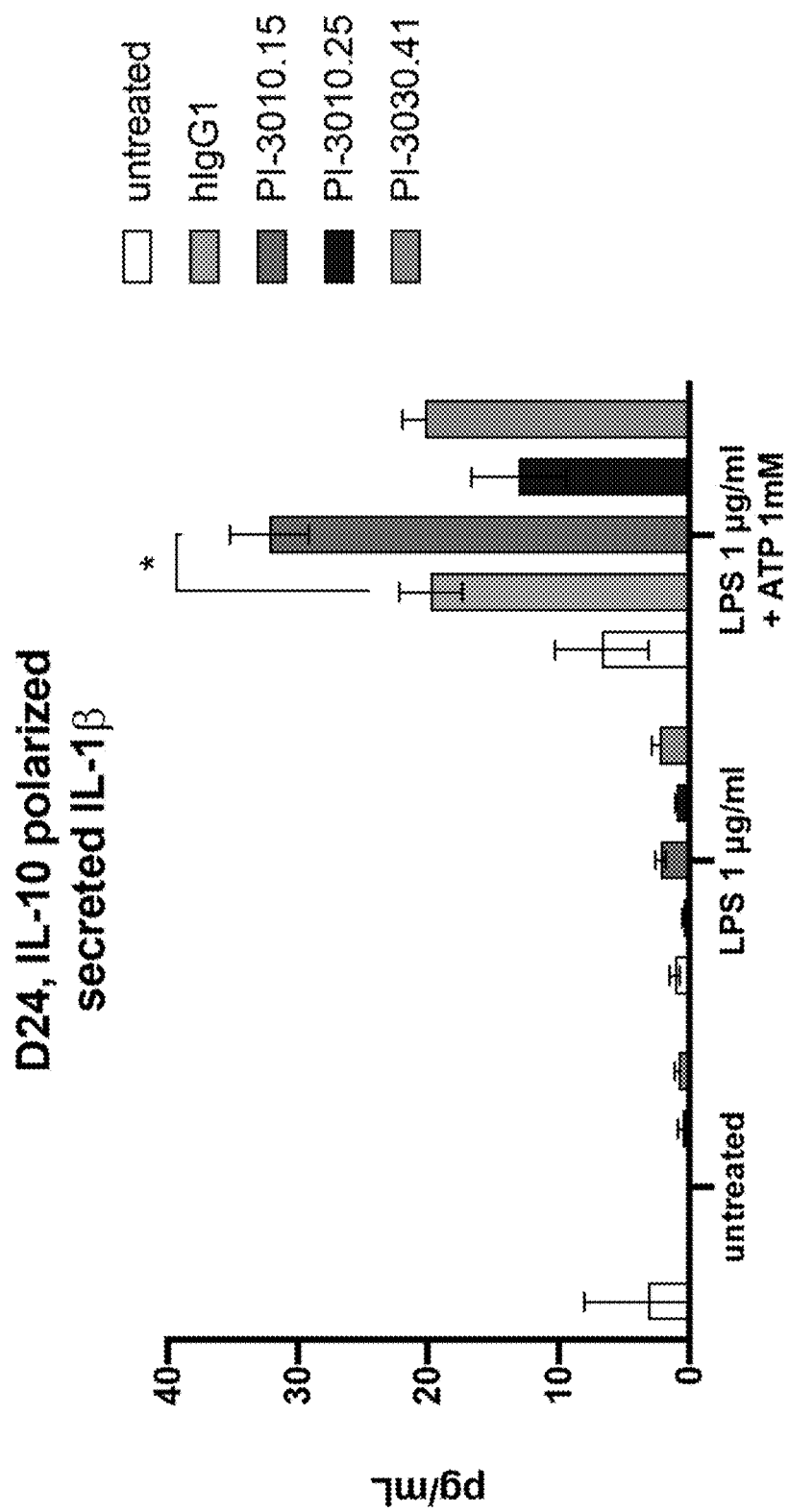

Myeloid, Spleen

Myeloid, Spleen

Lymphoid, Spleen

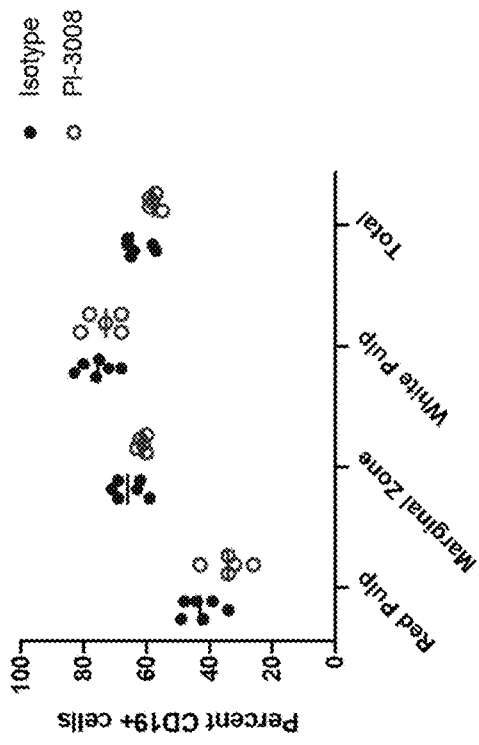
FIG. 48A MARCO
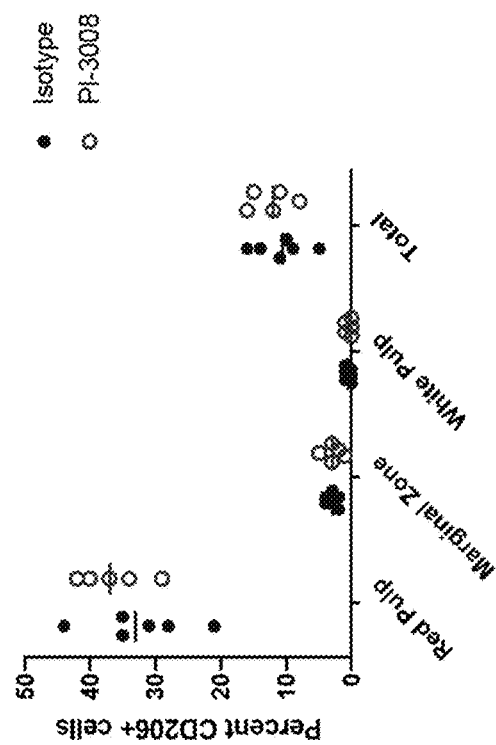
FIG. 48B CD19
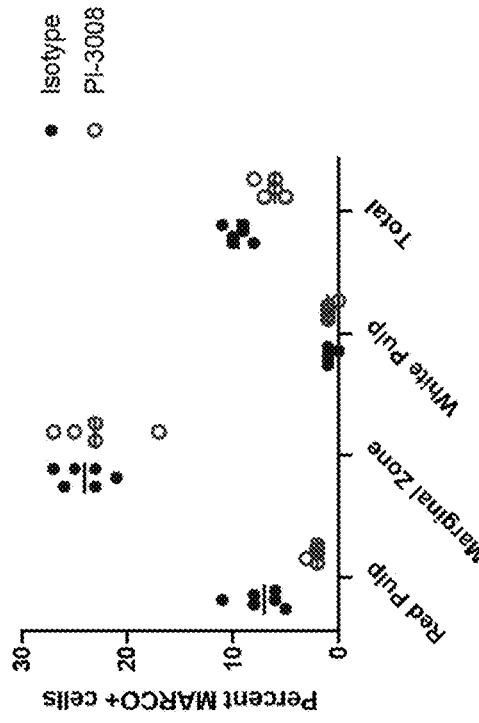
FIG. 48C CD8
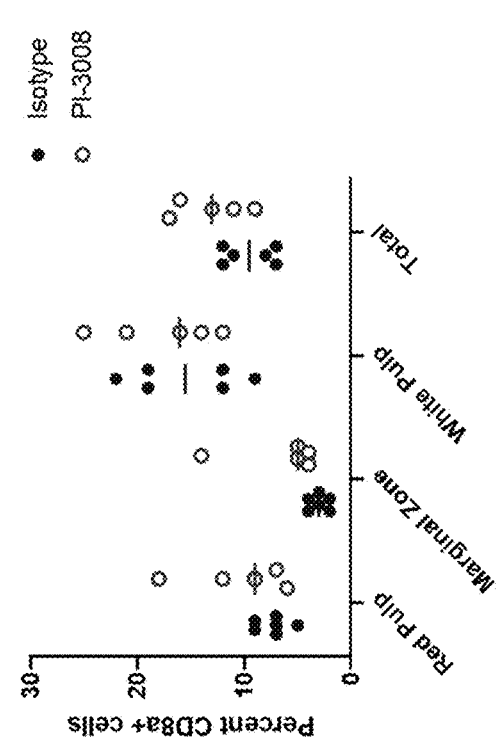
FIG. 48D CD206

FIG. 58
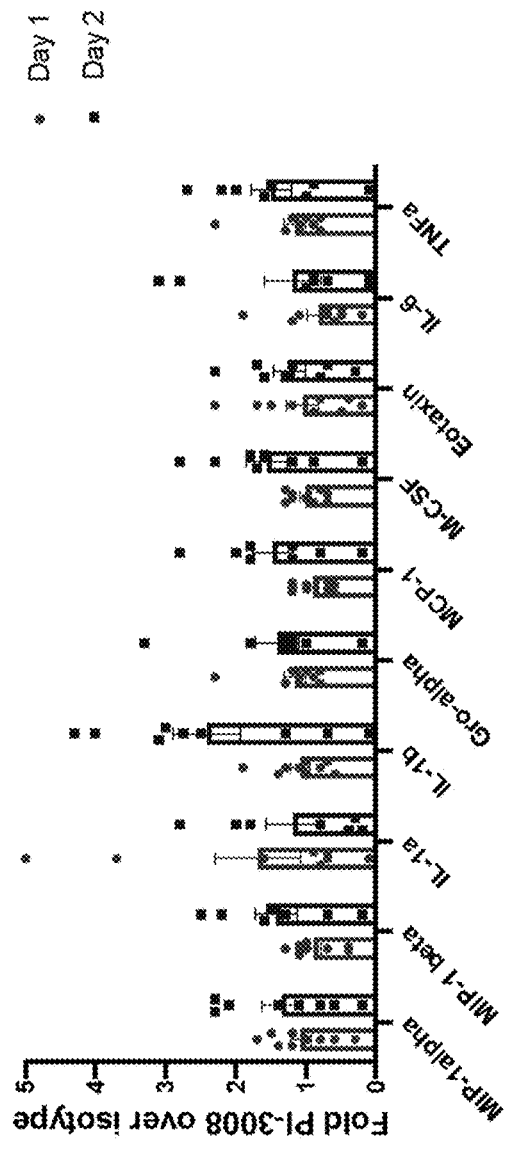
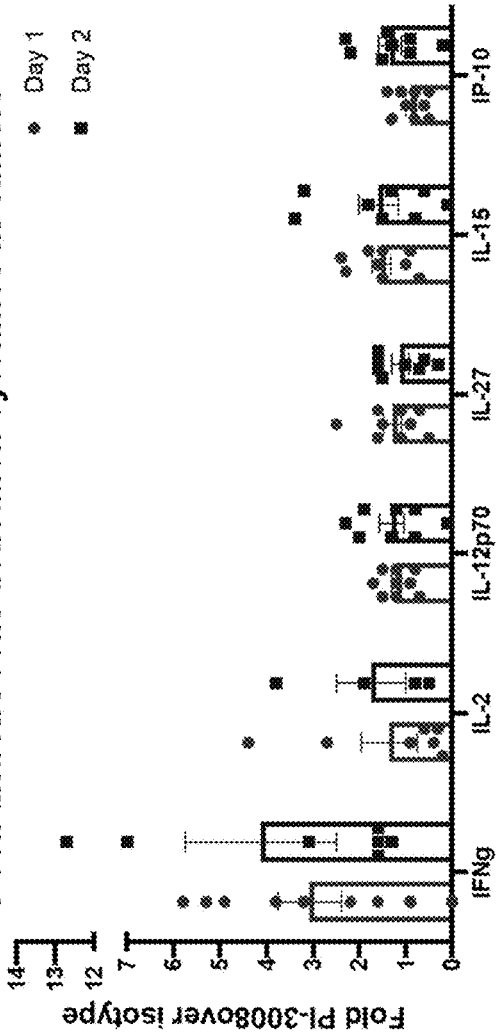

SEQUENCE LISTING

<160> NUMBER OF SEQ ID NOS: 527

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
            35                  40                  45

Gly Ala Ile Trp Thr Gly Gly Ser Ile Ala Tyr Asn Ser Leu Leu Lys
        50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Thr Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Val Met Val Thr Val Ser Thr
            115                 120

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Ser Leu Thr Ser Tyr His Val Ser
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ile Trp Thr Gly Gly Ser Ile Ala
1               5

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Leu Ser Asp Tyr Tyr Ser Ser Tyr Thr Ser Phe Asp Tyr
1               5                   10

<210> SEQ ID NO 5
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met 35                  40                  45
Gly Ala Ile Trp Thr Gly Gly Ser Ile Ala Tyr Asn Ser Leu Leu Lys
 50                  55                  60

Ser Arg Leu Ser Ile Ser Arg Asp Thr Ser Lys Ser Gln Val Phe Leu
 65                  70                  75                  80

Lys Met Asn Ser Leu Gln Thr Glu Asp Thr Ala Thr Tyr Tyr Cys Ala
                 85                  90                  95

Arg Asp Leu Ser Asp Tyr Tyr Ser Ser Tyr Thr Ser Phe Asp Tyr Trp
                100                 105                 110

Gly Gln Gly Val Met Val Thr Val Ser Thr Ala Glu Thr Thr Ala Pro
                115                 120                 125

Ser Val Tyr Pro Leu Ala Pro Gly Thr Ala Leu Lys Ser Asn Ser Met
                130                 135                 140

Val Thr Leu Gly Cys Leu Val Lys Gly Tyr Phe Pro Glu Pro Val Thr
145                 150                 155                 160

Val Thr Trp Asn Ser Gly Ala Leu Ser Ser Gly Val His Thr Phe Pro
                165                 170                 175

Ala Val Leu Gln Ser Gly Leu Tyr Thr Leu Thr Ser Ser Val Thr Val
                180                 185                 190

Pro Ser Ser Thr Trp Ser Ser Gln Ala Val Thr Cys Asn Val Ala His
                195                 200                 205

Pro Ala Ser Ser Thr Lys Val Asp Lys Lys Ile Val Pro Arg Glu Cys
210                 215                 220

Asn Pro Cys Gly Cys Thr Gly Ser Glu Val Ser Ser Val Phe Ile Phe
225                 230                 235                 240

Pro Pro Lys Thr Lys Asp Val Leu Thr Ile Thr Leu Thr Pro Lys Val
                245                 250                 255

Thr Cys Val Val Val Asp Ile Ser Gln Asn Asp Pro Glu Val Arg Phe
                260                 265                 270

Ser Trp Phe Ile Asp Asp Val Glu Val His Thr Ala Gln Thr His Ala
                275                 280                 285

Pro Glu Lys Gln Ser Asn Ser Thr Leu Arg Ser Val Ser Glu Leu Pro
                290                 295                 300

Ile Val His Arg Asp Trp Leu Asn Gly Lys Thr Phe Lys Cys Lys Val
305                 310                 315                 320

Asn Ser Gly Ala Phe Pro Ala Pro Ile Glu Lys Ser Ile Ser Lys Pro
                325                 330                 335

Glu Gly Thr Pro Arg Gly Pro Gln Val Tyr Thr Met Ala Pro Pro Lys
                340                 345                 350

Glu Glu Met Thr Gln Ser Gln Val Ser Ile Thr Cys Met Val Lys Gly
                355                 360                 365

Phe Tyr Pro Pro Asp Ile Tyr Thr Glu Trp Lys Met Asn Gly Gln Pro
                370                 375                 380

Gln Glu Asn Tyr Lys Asn Thr Pro Pro Thr Met Asp Thr Asp Gly Ser
385                 390                 395                 400

Tyr Phe Leu Tyr Ser Lys Leu Asn Val Lys Lys Glu Thr Trp Gln Gln
                405                 410                 415

Gly Asn Thr Phe Thr Cys Ser Val Leu His Glu Gly Leu His Asn His
                420                 425                 430

His Thr Glu Lys Ser Leu Ser His Ser Pro
                435                 440

<210> SEQ ID NO 6

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ala Ser Leu Ser Thr Ser Leu Gly
1               5                   10                  15

Glu Thr Val Ser Ile Glu Cys Leu Ala Ser Glu Gly Ile Ser Asn Asp
            20                  25                  30

Leu Ala Trp Tyr Gln Gln Lys Ser Gly Lys Ser Pro Gln Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Arg Tyr Ser Leu Lys Ile Ser Gly Met Gln Pro
65                  70                  75                  80

Glu Asp Glu Ala Asp Tyr Phe Cys Gln Gln Ser Tyr Lys Tyr Pro Leu
                85                  90                  95

Thr Phe Gly Ser Gly Thr Lys Leu Glu Ile Lys
            100                 105

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Ala Ser Glu Gly Ile Ser Asn Asp Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Ser Arg Leu Gln Asp
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Ser Tyr Lys Tyr Pro Leu Thr
1               5

<210> SEQ ID NO 10
<211> LENGTH: 214
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 10

Asp Ile Gln Met Thr Gln Ser Pro Ala Ser Leu Ser Thr Ser Leu Gly
1               5                   10                  15

Glu Thr Val Ser Ile Glu Cys Leu Ala Ser Glu Gly Ile Ser Asn Asp
            20                  25                  30

Leu Ala Trp Tyr Gln Gln Lys Ser Gly Lys Ser Pro Gln Leu Leu Ile
        35                  40                  45

Tyr Ala Ala Ser Arg Leu Gln Asp Gly Val Pro Ser Arg Phe Ser Gly
50                  55                  60

Ser Gly Ser Gly Thr Arg Tyr Ser Leu Lys Ile Ser Gly Met Gln Pro
65                  70                  75                  80

Glu Asp Glu Ala Asp Tyr Phe Cys Gln Gln Ser Tyr Lys Tyr Pro Leu
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val Val His Lys Thr Ser Ser Ser Pro Val Val Lys Ser
        195                 200                 205

Phe Asn Arg Asn Glu Cys
    210

<210> SEQ ID NO 11
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
        35                  40                  45

Gly Ala Ile Trp Thr Gly Gly Ser Ile Ala Tyr Asn Ser Leu Leu Lys
50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Thr Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Val Met Val Thr Val Ser Thr

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Ser Leu Thr Ser Tyr His Val Ser
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ile Trp Thr Gly Gly Ser Ile Ala
1               5

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Leu Ser Asp Tyr Tyr Ser Ser Tyr Thr Ser Phe Asp Tyr
1               5                   10

<210> SEQ ID NO 15
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
        35                  40                  45

Gly Ala Ile Trp Thr Gly Gly Ser Ile Ala Tyr Asn Ser Leu Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Thr Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Val Met Val Thr Val Ser Thr Ala Ser Thr Lys Gly Pro
        115                 120                 125

```
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ala Ser Leu Ser Thr Ser Leu Gly
1               5                   10                  15
Glu Thr Val Ser Ile Glu Cys Leu Ala Ser Glu Gly Ile Ser Asn Asp
            20                  25                  30
```

```
Leu Ala Trp Tyr Gln Gln Lys Ser Gly Lys Ser Pro Gln Leu Leu Ile
            35                  40                  45

Tyr Ala Ala Ser Arg Leu Gln Asp Gly Val Pro Ser Arg Phe Ser Gly
     50                  55                  60

Ser Gly Ser Gly Thr Arg Tyr Ser Leu Lys Ile Ser Gly Met Gln Pro
 65                  70                  75                  80

Glu Asp Glu Ala Asp Tyr Phe Cys Gln Gln Ser Tyr Lys Tyr Pro Leu
                 85                  90                  95

Thr Phe Gly Ser Gly Thr Lys Leu Glu Ile Lys
            100                 105
```

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Leu Ala Ser Glu Gly Ile Ser Asn Asp Leu Ala
 1               5                   10
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Ala Ala Ser Arg Leu Gln Asp
 1               5
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Gln Gln Ser Tyr Lys Tyr Pro Leu Thr
 1               5
```

<210> SEQ ID NO 20
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Asp Ile Gln Met Thr Gln Ser Pro Ala Ser Leu Ser Thr Ser Leu Gly
 1               5                   10                  15

Glu Thr Val Ser Ile Glu Cys Leu Ala Ser Glu Gly Ile Ser Asn Asp
             20                  25                  30

Leu Ala Trp Tyr Gln Gln Lys Ser Gly Lys Ser Pro Gln Leu Leu Ile
            35                  40                  45

Tyr Ala Ala Ser Arg Leu Gln Asp Gly Val Pro Ser Arg Phe Ser Gly
     50                  55                  60
```

Ser Gly Ser Gly Thr Arg Tyr Ser Leu Lys Ile Ser Gly Met Gln Pro
65                  70                  75                  80

Glu Asp Glu Ala Asp Tyr Phe Cys Gln Gln Ser Tyr Lys Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Ile Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Phe Ser Leu Thr Ser Tyr His Val Ser

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ile Trp Thr Gly Gly Ser Ile Ala
1               5

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Leu Ser Asp Tyr Tyr Ser Ser Tyr Thr Ser Phe Asp Tyr
1               5                   10

<210> SEQ ID NO 25
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Ile Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ala Ser Glu Gly Ile Ser Asn Asp Leu Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ala Ser Arg Leu Gln Asp
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Ser Tyr Lys Tyr Pro Leu Thr
1               5

<210> SEQ ID NO 30
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
                20                  25                  30

Leu Ala Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120
```

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Gly Phe Ser Leu Thr Ser Tyr His Val Ser
1               5                   10
```

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Ala Ile Trp Thr Gly Gly Ser Ile Ala
```

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Leu Ser Asp Tyr Tyr Ser Ser Tyr Thr Ser Phe Asp Tyr
1               5                   10

<210> SEQ ID NO 35
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
                20                  25                  30

His Val Ser Trp Val Arg Gln Pro Pro Gly Lys Gly Leu Glu Trp Ile
            35                  40                  45

Gly Ala Ile Trp Thr Gly Gly Ser Ile Ala Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu

```
                275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Gly Ile Ser Asn Asp
            20                  25                  30
Leu Ala Trp Tyr Gln Gln Lys Pro Gly Lys Ala Pro Lys Leu Leu Ile
        35                  40                  45
Tyr Ala Ala Ser Arg Leu Gln Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Ser Tyr Lys Tyr Pro Leu
                85                  90                  95
Thr Phe Gly Gln Gly Thr Lys Leu Glu Ile Lys
            100                 105

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ala Ser Glu Gly Ile Ser Asn Asp Leu Ala
```

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ala Ser Arg Leu Gln Asp
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gln Ser Tyr Lys Tyr Pro Leu Thr
1               5

<210> SEQ ID NO 40
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

```
Phe Asn Arg Gly Glu Cys
    210

<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Phe Ser Leu Thr Ser Tyr His Val Ser
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Ile Trp Thr Gly Gly Ser Ile Ala
1               5

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Leu Ser Asp Tyr Tyr Ser Ser Tyr Thr Ser Phe Asp Tyr
```

<210> SEQ ID NO 45
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350
```

```
Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Tyr Thr Leu Thr Ile Ser Ser Met Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ala Ser Glu Gly Ile Ser Asn Asp Leu Ala
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Ala Ser Arg Leu Gln Asp
```

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Gln Ser Tyr Lys Tyr Pro Leu Thr
1               5

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Tyr Thr Leu Thr Ile Ser Ser Met Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
            35                  40                  45

Gly Ala Ile Trp Thr Gly Gly Ser Ile Ala Tyr Asn Pro Ser Leu Lys
        50                  55                  60

Ser Arg Leu Thr Ile Ser Arg Asp Thr Ser Lys Asn Gln Val Ser Leu
65                  70                  75                  80

Lys Met Ser Ser Leu Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Phe Ser Leu Thr Ser Tyr His Val Ser
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ile Trp Thr Gly Gly Ser Ile Ala
1               5

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Leu Ser Asp Tyr Tyr Ser Ser Tyr Thr Ser Phe Asp Tyr
1               5                   10

<210> SEQ ID NO 55
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Gln Glu Ser Gly Pro Gly Leu Val Lys Pro Ser Glu
```

```
1               5                   10                  15
Thr Leu Ser Leu Thr Cys Thr Val Ser Gly Phe Ser Leu Thr Ser Tyr
                20                  25                  30
His Val Ser Trp Val Arg Gln Pro Gly Lys Gly Leu Glu Trp Met
                35                  40                  45
Gly Ala Ile Trp Thr Gly Gly Ser Ile Ala Tyr Asn Pro Ser Leu Lys
    50                  55                  60
Ser Arg Leu Thr Ile Ser Arg Asp Thr Ser Lys Asn Gln Val Ser Leu
65                  70                  75                  80
Lys Met Ser Ser Leu Thr Ala Ala Asp Thr Ala Val Tyr Tyr Cys Ala
                85                  90                  95
Arg Asp Leu Ser Asp Tyr Tyr Ser Ser Tyr Thr Ser Phe Asp Tyr Trp
                100                 105                 110
Gly Gln Gly Thr Leu Val Thr Val Ser Ala Ser Thr Lys Gly Pro
                115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
                275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Arg Asp Glu Leu Thr Lys Asn Gln Val
                355                 360                 365
Ser Leu Thr Cys Leu Val Lys Gly Phe Tyr Pro Ser Asp Ile Ala Val
                370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
```

```
Met His Glu Ala Leu His Asn His Tyr Thr Gln Lys Ser Leu Ser Leu
            435                 440                 445

Ser Pro Gly Lys
    450

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ala Ser Glu Gly Ile Ser Asn Asp Leu Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ala Ser Arg Leu Gln Asp
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Ser Tyr Lys Tyr Pro Leu Thr
```

<210> SEQ ID NO 60
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Gly Ile Ser Asn Asp
            20                  25                  30
Leu Ala Trp Tyr Gln Gln Lys Pro Gly Lys Ala Pro Lys Leu Leu Ile
        35                  40                  45
Tyr Ala Ala Ser Arg Leu Gln Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Ser Tyr Lys Tyr Pro Leu
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Ser Tyr
            20                  25                  30
His Val Ser Trp Val Arg Gln Pro Pro Gly Lys Gly Leu Glu Trp Met
        35                  40                  45
Gly Ala Ile Trp Thr Gly Gly Ser Ile Ala Tyr Asn Pro Ser Leu Lys
    50                  55                  60
Ser Arg Leu Thr Ile Ser Arg Asp Thr Ser Lys Asn Gln Val Ser Leu

```
                65                  70                  75                  80
Lys Met Ser Ser Leu Thr Ala Ala Asp Thr Ala Val Tyr Tyr Cys Ala
                    85                  90                  95

Arg Asp Leu Ser Asp Tyr Tyr Ser Ser Tyr Thr Ser Phe Asp Tyr Trp
                100                 105                 110

Gly Gln Gly Thr Leu Val Thr Val Ser Ser
        115                 120

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Phe Ser Leu Thr Ser Tyr His Val Ser
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Ile Trp Thr Gly Gly Ser Ile Ala
1               5

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Ser Asp Tyr Tyr Ser Ser Tyr Thr Ser Phe Asp Tyr
1               5                   10

<210> SEQ ID NO 65
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
                20                  25                  30

His Val Ser Trp Val Arg Gln Pro Pro Gly Lys Gly Leu Glu Trp Met
            35                  40                  45

Gly Ala Ile Trp Thr Gly Gly Ser Ile Ala Tyr Asn Pro Ser Leu Lys
        50                  55                  60

Ser Arg Leu Thr Ile Ser Arg Asp Thr Ser Lys Asn Gln Val Ser Leu
65                  70                  75                  80
```

```
Lys Met Ser Ser Leu Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 66

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Gly Ile Ser Asn Asp
            20                  25                  30
Leu Ala Trp Tyr Gln Gln Lys Pro Gly Lys Ala Pro Lys Leu Leu Ile
        35                  40                  45
Tyr Ala Ala Ser Arg Leu Gln Ser Gly Val Pro Ser Arg Phe Ser Gly
    50                  55                  60
Ser Gly Ser Gly Thr Asp Tyr Thr Leu Thr Ile Ser Ser Met Gln Pro
65                  70                  75                  80
Glu Asp Phe Ala Thr Tyr Tyr Cys Gln Gln Ser Tyr Lys Tyr Pro Leu
                85                  90                  95
Thr Phe Gly Gln Gly Thr Lys Leu Glu Ile Lys
            100                 105
```

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Arg Ala Ser Glu Gly Ile Ser Asn Asp Leu Ala
1               5                   10
```

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Ala Ala Ser Arg Leu Gln Asp
1               5
```

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Gln Gln Ser Tyr Lys Tyr Pro Leu Thr
1               5
```

<210> SEQ ID NO 70
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Asp Ile Gln Met Thr Gln Ser Pro Ser Ser Leu Ser Ala Ser Val Gly
```

```
            1               5                  10                 15
          Asp Arg Val Thr Ile Thr Cys Arg Ala Ser Glu Gly Ile Ser Asn Asp
                          20                 25                 30

Leu Ala Trp Tyr Gln Gln Lys Pro Gly Lys Ala Pro Lys Leu Leu Ile
                          35                 40                 45

Tyr Ala Ala Ser Arg Leu Gln Ser Gly Val Pro Ser Arg Phe Ser Gly
                          50                 55                 60

Ser Gly Ser Gly Thr Asp Tyr Thr Leu Thr Ile Ser Ser Met Gln Pro
          65                  70                 75                 80

Glu Asp Phe Ala Thr Tyr Tyr Cys Gln Gln Ser Tyr Lys Tyr Pro Leu
                          85                 90                 95

Thr Phe Gly Gln Gly Thr Lys Leu Glu Ile Lys Arg Thr Val Ala Ala
                          100                105                110

Pro Ser Val Phe Ile Phe Pro Pro Ser Asp Glu Gln Leu Lys Ser Gly
                          115                120                125

Thr Ala Ser Val Val Cys Leu Leu Asn Asn Phe Tyr Pro Arg Glu Ala
                          130                135                140

Lys Val Gln Trp Lys Val Asp Asn Ala Leu Gln Ser Gly Asn Ser Gln
          145                 150                155                160

Glu Ser Val Thr Glu Gln Asp Ser Lys Asp Ser Thr Tyr Ser Leu Ser
                          165                170                175

Ser Thr Leu Thr Leu Ser Lys Ala Asp Tyr Glu Lys His Lys Val Tyr
                          180                185                190

Ala Cys Glu Val Thr His Gln Gly Leu Ser Ser Pro Val Thr Lys Ser
                          195                200                205

Phe Asn Arg Gly Glu Cys
                          210

<210> SEQ ID NO 71
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Lys Glu Ser Gly Pro Gly Leu Val Gln Pro Ser Gln
          1               5                  10                 15

Thr Leu Ser Leu Thr Cys Thr Val Ser Gly Phe Ser Leu Thr Ser Tyr
                          20                 25                 30

His Val Ser Trp Val Arg Gln Pro Pro Gly Lys Gly Leu Glu Trp Met
                          35                 40                 45

Gly Ala Ile Trp Thr Gly Gly Ser Ile Ala Tyr Asn Ser Leu Leu Lys
                          50                 55                 60

Ser Arg Leu Ser Ile Ser Arg Asp Thr Ser Lys Ser Gln Val Phe Leu
          65                  70                 75                 80

Lys Met Asn Ser Leu Gln Thr Glu Asp Thr Ala Thr Tyr Tyr Cys Ala
                          85                 90                 95

Arg Asp Leu Ser Asp Tyr Tyr Ser Ser Tyr Thr Ser Phe Asp Tyr Trp
                          100                105                110

Gly Gln Gly Val Met Val Thr Val Ser Thr
                          115                120

<210> SEQ ID NO 72
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Phe Ser Leu Thr Ser Tyr His Val Ser
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Ile Trp Thr Gly Gly Ser Ile Ala
1               5

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Leu Ser Asp Tyr Tyr Ser Ser Tyr Thr Ser Phe Asp Tyr
1               5                   10

<210> SEQ ID NO 75
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
        35                  40                  45

Gly Ala Ile Trp Thr Gly Gly Ser Ile Ala Tyr Asn Ser Leu Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Thr Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Val Met Val Thr Val Ser Thr Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160
```

```
Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
    195                 200                 205

His Lys Pro Ser Asn Thr Lys Val Asp Lys Arg Val Glu Ser Lys Tyr
210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
        420                 425                 430

Ala Leu His Asn His Tyr Thr Gln Lys Ser Leu Ser Leu Ser Leu Gly
    435                 440                 445

Lys

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ala Ser Leu Ser Thr Ser Leu Gly
1               5                   10                  15

Glu Thr Val Ser Ile Glu Cys Leu Ala Ser Glu Gly Ile Ser Asn Asp
            20                  25                  30

Leu Ala Trp Tyr Gln Gln Lys Ser Gly Lys Ser Pro Gln Leu Leu Ile
        35                  40                  45

Tyr Ala Ala Ser Arg Leu Gln Asp Gly Val Pro Ser Arg Phe Ser Gly
    50                  55                  60
```

```
Ser Gly Ser Gly Thr Arg Tyr Ser Leu Lys Ile Ser Gly Met Gln Pro
 65                  70                  75                  80

Glu Asp Glu Ala Asp Tyr Phe Cys Gln Gln Ser Tyr Lys Tyr Pro Leu
                 85                  90                  95

Thr Phe Gly Ser Gly Thr Lys Leu Glu Ile Lys
            100                 105
```

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

```
Leu Ala Ser Glu Gly Ile Ser Asn Asp Leu Ala
 1               5                  10
```

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

```
Ala Ala Ser Arg Leu Gln Asp
 1               5
```

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

```
Gln Gln Ser Tyr Lys Tyr Pro Leu Thr
 1               5
```

<210> SEQ ID NO 80
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Asp Ile Gln Met Thr Gln Ser Pro Ala Ser Leu Ser Thr Ser Leu Gly
 1               5                  10                  15

Glu Thr Val Ser Ile Glu Cys Leu Ala Ser Glu Gly Ile Ser Asn Asp
                 20                  25                  30

Leu Ala Trp Tyr Gln Gln Lys Ser Gly Lys Ser Pro Gln Leu Leu Ile
             35                  40                  45

Tyr Ala Ala Ser Arg Leu Gln Asp Gly Val Pro Ser Arg Phe Ser Gly
     50                  55                  60

Ser Gly Ser Gly Thr Arg Tyr Ser Leu Lys Ile Ser Gly Met Gln Pro
 65                  70                  75                  80

Glu Asp Glu Ala Asp Tyr Phe Cys Gln Gln Ser Tyr Lys Tyr Pro Leu
                 85                  90                  95
```

```
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 81
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Phe Ser Leu Thr Ser Tyr His Val Ser
1               5                   10

<210> SEQ ID NO 83
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 83

Ala Ile Trp Thr Gly Gly Ser Ile Ala
1               5

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Leu Ser Asp Tyr Tyr Ser Ser Tyr Thr Ser Phe Asp Tyr
1               5                   10

<210> SEQ ID NO 85
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Gly Ile Ser Asn Asp
            20                  25                  30
Leu Ala Trp Tyr Gln Gln Lys Pro Gly Lys Ala Pro Lys Leu Leu Ile
        35                  40                  45
Tyr Ala Ala Ser Arg Leu Gln Asp Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Ser Tyr Lys Tyr Pro Leu
                85                  90                  95
Thr Phe Gly Gln Gly Thr Lys Leu Glu Ile Lys
            100                 105

<210> SEQ ID NO 87
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 87

Arg Ala Ser Glu Gly Ile Ser Asn Asp Leu Ala
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ala Ser Arg Leu Gln Asp
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Ser Tyr Lys Tyr Pro Leu Thr
1               5

<210> SEQ ID NO 90
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Tyr Thr Ser Phe Asp Tyr Trp
            100                 105                 110

Gly Gln Gly Thr Leu Val Thr Val Ser Ser
        115                 120

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Phe Ser Leu Thr Ser Tyr His Val Ser
1               5                   10

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Ile Trp Thr Gly Gly Ser Ile Ala
1               5

<210> SEQ ID NO 94
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 94

Asp Leu Ser Asp Tyr Tyr Ser Ser Tyr Thr Ser Phe Asp Tyr
1               5                   10

<210> SEQ ID NO 95
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
                20                  25                  30

His Val Ser Trp Val Arg Gln Pro Pro Gly Lys Gly Leu Glu Trp Ile
            35                  40                  45

Gly Ala Ile Trp Thr Gly Gly Ser Ile Ala Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
```

```
                305                 310                 315                 320
        Gly Lys Glu Tyr Lys Cys Lys Val Ser Asn Lys Ala Leu Pro Ala Pro
                        325                 330                 335

Ile Glu Lys Thr Ile Ser Lys Ala Lys Gly Gln Pro Arg Glu Pro Gln
                        340                 345                 350

Val Tyr Thr Leu Pro Pro Ser Arg Asp Glu Leu Thr Lys Asn Gln Val
                        355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Lys Leu Thr
                        405                 410                 415

Val Asp Lys Ser Arg Trp Gln Gln Gly Asn Val Phe Ser Cys Ser Val
                        420                 425                 430

Met His Glu Ala Leu His Asn His Tyr Thr Gln Lys Ser Leu Ser Leu
                        435                 440                 445

Ser Pro Gly Lys
                450

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
                20                  25                  30

Leu Ala Trp Tyr Gln Gln Lys Pro Gly Lys Ser Pro Lys Leu Leu Ile
            35                  40                  45

Tyr Ala Ala Ser Arg Leu Gln Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ala Ser Glu Gly Ile Ser Asn Asp Leu Ala
1               5                   10

<210> SEQ ID NO 98
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 98

Ala Ala Ser Arg Leu Gln Asp
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Gln Ser Tyr Lys Tyr Pro Leu Thr
1               5

<210> SEQ ID NO 100
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Leu Ser Thr Ser Val Gly
1               5                   10                  15

Asp Arg Val Thr Ile Thr Cys Arg Ala Ser Glu Gly Ile Ser Asn Asp
                20                  25                  30

Leu Ala Trp Tyr Gln Gln Lys Pro Gly Lys Ser Pro Lys Leu Leu Ile
            35                  40                  45

Tyr Ala Ala Ser Arg Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 101
```

<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Phe Ser Leu Thr Ser Tyr His Val Ser
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Ile Trp Thr Gly Gly Ser Ile Ala
1               5

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Leu Ser Asp Tyr Tyr Ser Ser Tyr Thr Ser Phe Asp Tyr
1               5                   10

<210> SEQ ID NO 105
<211> LENGTH: 452
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 105

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Glu Ala Thr Tyr Phe Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ala Ser Glu Gly Ile Ser Asn Asp Leu Ala
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Ala Ser Arg Leu Gln Asp
1               5

<210> SEQ ID NO 109
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 109

Gln Gln Ser Tyr Lys Tyr Pro Leu Thr
1               5

<210> SEQ ID NO 110
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Glu Ala Thr Tyr Phe Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 111
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30
```

```
His Val Ser Trp Val Arg Gln Pro Gly Lys Gly Leu Glu Trp Ile
        35                  40                  45

Gly Ala Ile Trp Thr Gly Gly Ser Ile Ala Tyr Asn Pro Ser Leu Lys
 50                  55                  60

Ser Arg Val Thr Ile Ser Arg Asp Thr Ser Lys Asn Gln Val Ser Leu
 65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Phe Ser Leu Thr Ser Tyr His Val Ser
1               5                   10

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Ile Trp Thr Gly Gly Ser Ile Ala
1               5

<210> SEQ ID NO 114
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Leu Ser Asp Tyr Tyr Ser Ser Tyr Thr Ser Phe Asp Tyr
1               5                   10

<210> SEQ ID NO 115
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
```

```
            35                  40                  45
Gly Ala Ile Trp Thr Gly Gly Ser Ile Ala Tyr Asn Pro Ser Leu Lys
 50                  55                  60

Ser Arg Val Thr Ile Ser Arg Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Asp Leu Ser Asp Tyr Tyr Ser Ser Tyr Thr Ser Phe Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
            450
```

<210> SEQ ID NO 116
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Glu Ala Thr Tyr Phe Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ala Ser Glu Gly Ile Ser Asn Asp Leu Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Ala Ser Arg Leu Gln Asp
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Gln Ser Tyr Lys Tyr Pro Leu Thr
1               5

<210> SEQ ID NO 120
<211> LENGTH: 214
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 120

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Glu Ala Thr Tyr Phe Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Val Gln Leu Gln Glu Ser Gly Pro Gly Leu Val Lys Pro Ser Glu Thr
1               5                   10                  15

Leu Ser Leu Thr Cys Thr Val Ser Gly Phe Ser Leu Thr Ser Tyr His
            20                  25                  30

Val Ser Trp Val Arg Gln Pro Pro Gly Lys Gly Leu Glu Trp Ile Gly
        35                  40                  45

Ala Ile Trp Thr Gly Gly Ser Ile Ala Tyr Asn Pro Ser Leu Lys Ser
    50                  55                  60

Arg Val Thr Ile Ser Arg Asp Thr Ser Lys Asn Gln Val Ser Leu Lys
65                  70                  75                  80

Leu Ser Ser Val Thr Ala Ala Asp Thr Ala Val Tyr Tyr Cys Ala Arg
                85                  90                  95

Asp Leu Ser Asp Tyr Tyr Ser Ser Tyr Thr Ser Phe Asp Tyr Trp Gly

```
                    100                 105                 110
Gln Gly Thr Leu Val Thr Val Ser Ser
            115                 120

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Phe Ser Leu Thr Ser Tyr His Val Ser
1               5                   10

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Ile Trp Thr Gly Gly Ser Ile Ala
1               5

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asp Leu Ser Asp Tyr Tyr Ser Ser Tyr Thr Ser Phe Asp Tyr
1               5                   10

<210> SEQ ID NO 125
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110
```

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ala Ser Glu Gly Ile Ser Asn Asp Leu Ala
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Ala Ser Arg Leu Gln Asp
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln Ser Tyr Lys Tyr Pro Leu Thr
1               5

<210> SEQ ID NO 130
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ser Pro Lys Leu Leu Ile

```
                35                  40                  45
Tyr Ala Ala Ser Arg Leu Gln Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Phe Cys Gln Gln Ser Tyr Lys Tyr Pro Leu
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 131
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                20                  25                  30

His Val Ser Trp Val Arg Gln Pro Pro Gly Lys Gly Leu Glu Trp Ile
            35                  40                  45

Gly Ala Ile Trp Thr Gly Gly Ser Ile Ala Tyr Asn Pro Ser Leu Lys
 50                  55                  60

Ser Arg Val Thr Ile Ser Arg Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Asp Leu Ser Asp Tyr Tyr Ser Ser Tyr Thr Ser Phe Asp Tyr Trp
                100                 105                 110

Gly Gln Gly Thr Leu Val Thr Val Ser Ser
            115                 120

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 132

Gly Phe Ser Leu Thr Ser Tyr His Val Ser
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ile Trp Thr Gly Gly Ser Ile Ala
1               5

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Leu Ser Asp Tyr Tyr Ser Ser Tyr Thr Ser Phe Asp Tyr
1               5                   10

<210> SEQ ID NO 135
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

Val Pro Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Glu Ala Thr Tyr Phe Cys Gln Gln Ser Tyr Lys Tyr Pro Leu

```
                85                  90                  95
Thr Phe Gly Gln Gly Thr Lys Leu Glu Ile Lys
            100                 105

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Ala Ser Glu Gly Ile Ser Asn Asp Leu Ala
1               5                   10

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ala Ser Arg Leu Gln Asp
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Gln Ser Tyr Lys Tyr Pro Leu Thr
1               5

<210> SEQ ID NO 140
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Glu Ala Thr Tyr Phe Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 141
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Glu Ser Gly Gly Gly Leu Val Gln Pro Gly Ser
1               5                   10                  15

Ser Leu Lys Leu Ser Cys Val Ala Ser Lys Phe Thr Phe Ser Asn Tyr
            20                  25                  30

Gly Met Asn Trp Ile Arg Gln Ala Pro Lys Lys Gly Leu Glu Trp Ile
        35                  40                  45

Ala Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Lys Ser Leu Thr Gly Gly Ser Asp Tyr Phe Asp Ser Trp Gly Gln
            100                 105                 110

Gly Val Met Val Thr Val Ser Ser
        115                 120

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Lys Phe Thr Phe Ser Asn Tyr Gly Met Asn
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 143

Leu Ile Tyr Tyr Asn Ser Asn Asn Lys Tyr
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Leu Thr Gly Gly Ser Asp Tyr Phe Asp Ser
1               5                   10

<210> SEQ ID NO 145
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Gln Pro Gly Ser
1               5                   10                  15

Ser Leu Lys Leu Ser Cys Val Ala Ser Lys Phe Thr Phe Ser Asn Tyr
            20                  25                  30

Gly Met Asn Trp Ile Arg Gln Ala Pro Lys Lys Gly Leu Glu Trp Ile
        35                  40                  45

Ala Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Lys Ser Leu Thr Gly Gly Ser Asp Tyr Phe Asp Ser Trp Gly Gln
            100                 105                 110

Gly Val Met Val Thr Val Ser Ser Ala Glu Thr Thr Ala Pro Ser Val
        115                 120                 125

Tyr Pro Leu Ala Pro Gly Thr Ala Leu Lys Ser Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ala Leu Ser Ser Gly Val His Thr Phe Pro Ala Val
                165                 170                 175

Leu Gln Ser Gly Leu Tyr Thr Leu Thr Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asn Cys Gly Gly
    210                 215                 220

Asp Cys Lys Pro Cys Ile Cys Thr Gly Ser Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Gln Asp Asp Pro Glu Val
```

```
                260                 265                 270

His Phe Ser Trp Phe Val Asp Asp Val Glu Val His Thr Ala Gln Thr
            275                 280                 285

Arg Pro Pro Glu Glu Gln Phe Asn Ser Thr Phe Arg Ser Val Ser Glu
            290                 295                 300

Leu Pro Ile Leu His Gln Asp Trp Leu Asn Gly Arg Thr Phe Arg Cys
305                 310                 315                 320

Lys Val Thr Ser Ala Ala Phe Pro Ser Pro Ile Glu Lys Thr Ile Ser
                325                 330                 335

Lys Pro Glu Gly Arg Thr Gln Val Pro His Val Tyr Thr Met Ser Pro
            340                 345                 350

Thr Lys Glu Glu Met Thr Gln Asn Glu Val Ser Ile Thr Cys Met Val
            355                 360                 365

Lys Gly Phe Tyr Pro Pro Asp Ile Tyr Val Glu Trp Gln Met Asn Gly
        370                 375                 380

Gln Pro Gln Glu Asn Tyr Lys Asn Thr Pro Pro Thr Met Asp Thr Asp
385                 390                 395                 400

Gly Ser Tyr Phe Leu Tyr Ser Lys Leu Asn Val Lys Lys Glu Lys Trp
                405                 410                 415

Gln Gln Gly Asn Thr Phe Thr Cys Ser Val Leu His Glu Gly Leu His
            420                 425                 430

Asn His His Thr Glu Lys Ser Leu Ser His Ser Pro
            435                 440

<210> SEQ ID NO 146
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Gly Thr Phe
            20                  25                  30

Leu Ala Trp Tyr Gln Glu Lys Pro Glu Lys Thr Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Asn Leu Glu Pro
65                  70                  75                  80

Glu Asp Phe Ala Val Tyr Tyr Cys Gln Gln His Asp Glu Tyr Pro Phe
                85                  90                  95

Thr Phe Gly Ser Gly Thr Lys Leu Glu Ile Lys
            100                 105

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Lys Ala Ser Lys Ser Ile Gly Thr Phe Leu Ala
```

```
1               5                    10
```

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Gly Ser Thr Leu Gln Ser
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Gln His Asp Glu Tyr Pro Phe Thr
1               5

<210> SEQ ID NO 150
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Gly Thr Phe
            20                  25                  30

Leu Ala Trp Tyr Gln Glu Lys Pro Glu Lys Thr Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Asn Leu Glu Pro
65                  70                  75                  80

Glu Asp Phe Ala Val Tyr Tyr Cys Gln Gln His Asp Glu Tyr Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
    130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val Val His Lys Thr Ser Ser Ser Pro Val Val Lys Ser
        195                 200                 205

```
Phe Asn Arg Asn Glu Cys
    210

<210> SEQ ID NO 151
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Lys Phe Thr Phe Ser Asn Tyr
            20                  25                  30

Gly Met Asn Trp Val Arg Gln Ala Pro Gly Lys Gly Leu Glu Trp Val
        35                  40                  45

Ser Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Thr Gly Gly Ser Asp Tyr Phe Asp Ser Trp Gly Gln
            100                 105                 110

Gly Thr Leu Val Thr Val Ser Ser
        115                 120

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Lys Phe Thr Phe Ser Asn Tyr Gly Met Asn
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Leu Ile Tyr Tyr Asn Ser Asn Asn Lys Tyr
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Leu Thr Gly Gly Ser Asp Tyr Phe Asp Ser
```

-continued

```
1               5                   10
```

<210> SEQ ID NO 155
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

```
Glu Val Gln Leu Val Glu Ser Gly Gly Gly Leu Val Gln Pro Gly Gly
1               5                   10                  15

Ser Leu Arg Leu Ser Cys Ala Ala Ser Lys Phe Thr Phe Ser Asn Tyr
            20                  25                  30

Gly Met Asn Trp Val Arg Gln Ala Pro Gly Lys Gly Leu Glu Trp Val
        35                  40                  45

Ser Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Thr Gly Gly Ser Asp Tyr Phe Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 156
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys
            100                 105

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Ala Ser Lys Ser Ile Gly Thr Phe Leu Ala
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Gly Ser Thr Leu Gln Ser
```

-continued

```
<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gln Gln His Asp Glu Tyr Pro Phe Thr
1               5

<210> SEQ ID NO 160
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 161
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161
```

```
Glu Val Gln Leu Val Glu Ser Gly Gly Gly Leu Val Gln Pro Gly Gly
1               5                   10                  15

Ser Leu Arg Leu Ser Cys Ala Ala Ser Lys Phe Thr Phe Ser Asn Tyr
            20                  25                  30

Gly Met Asn Trp Ile Arg Gln Ala Pro Gly Lys Gly Leu Glu Trp Ile
        35                  40                  45

Ala Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Thr Gly Gly Ser Asp Tyr Phe Asp Ser Trp Gly Gln
            100                 105                 110

Gly Thr Leu Val Thr Val Ser Ser
        115                 120
```

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

```
Lys Phe Thr Phe Ser Asn Tyr Gly Met Asn
1               5                   10
```

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

```
Leu Ile Tyr Tyr Asn Ser Asn Asn Lys Tyr
1               5                   10
```

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

```
Ser Leu Thr Gly Gly Ser Asp Tyr Phe Asp Ser
1               5                   10
```

<210> SEQ ID NO 165
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Lys Phe Thr Phe Ser Asn Tyr
            20                  25                  30

Gly Met Asn Trp Ile Arg Gln Ala Pro Gly Lys Gly Leu Glu Trp Ile
            35                  40                  45

Ala Leu Ile Tyr Tyr Asn Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Leu Thr Gly Gly Ser Asp Tyr Phe Asp Ser Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445
Gly Lys
    450

<210> SEQ ID NO 166
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys
            100                 105

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Ala Ser Lys Ser Ile Gly Thr Phe Leu Ala
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Gly Ser Thr Leu Gln Ser
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Gln His Asp Glu Tyr Pro Phe Thr
```

<210> SEQ ID NO 170
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 171
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Ile Arg Gln Ala Pro Gly Lys Gly Leu Glu Trp Ile
        35                  40                  45

Ala Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Lys Ser Leu Thr Gly Gly Ser Asp Tyr Phe Asp Ser Trp Gly Gln
                100                 105                 110

Gly Thr Leu Val Thr Val Ser Ser
        115                 120

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Lys Phe Thr Phe Ser Asn Tyr Gly Met Asn
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Ile Tyr Tyr Asn Ser Asn Asn Lys Tyr
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Leu Thr Gly Gly Ser Asp Tyr Phe Asp Ser
1               5                   10

<210> SEQ ID NO 175
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met Asn Trp Ile Arg Gln Ala Pro Gly Lys Gly Leu Glu Trp Ile
            35                  40                  45

Ala Leu Ile Tyr Tyr Asn Ser Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
            85                  90                  95

Ala Lys Ser Leu Thr Gly Gly Ser Asp Tyr Phe Asp Ser Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys
            100                 105

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Arg Ala Ser Lys Ser Ile Gly Thr Phe Leu Ala
1               5                   10

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Gly Ser Thr Leu Gln Ser
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gln Gln His Asp Glu Tyr Pro Phe Thr
1               5

<210> SEQ ID NO 180
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Asp Ile Gln Met Thr Gln Ser Pro Ser Ser Leu Ser Ala Ser Val Gly

-continued

```
                1               5                  10                  15
Asp Arg Val Thr Ile Thr Cys Arg Ala Ser Lys Ser Ile Gly Thr Phe
                   20                  25                  30

Leu Ala Trp Tyr Gln Gln Lys Pro Gly Lys Ala Pro Lys Leu Leu Ile
                   35                  40                  45

Tyr Ser Gly Ser Thr Leu Gln Ser Gly Val Pro Ser Arg Phe Ser Gly
                   50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln His Asp Glu Tyr Pro Phe
                   85                  90                  95

Thr Phe Gly Gln Gly Thr Lys Leu Glu Ile Lys Arg Thr Val Ala Ala
                  100                 105                 110

Pro Ser Val Phe Ile Phe Pro Pro Ser Asp Glu Gln Leu Lys Ser Gly
                  115                 120                 125

Thr Ala Ser Val Val Cys Leu Leu Asn Asn Phe Tyr Pro Arg Glu Ala
                  130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                  165                 170                 175

Ser Thr Leu Thr Leu Ser Lys Ala Asp Tyr Glu Lys His Lys Val Tyr
                  180                 185                 190

Ala Cys Glu Val Thr His Gln Gly Leu Ser Ser Pro Val Thr Lys Ser
                  195                 200                 205

Phe Asn Arg Gly Glu Cys
    210

<210> SEQ ID NO 181
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Val Glu Ser Gly Gly Gly Leu Val Gln Pro Gly Ser
 1               5                  10                  15

Ser Leu Lys Leu Ser Cys Val Ala Ser Lys Phe Thr Phe Ser Asn Tyr
                   20                  25                  30

Gly Met Asn Trp Ile Arg Gln Ala Pro Lys Lys Gly Leu Glu Trp Ile
                   35                  40                  45

Ala Leu Ile Tyr Tyr Asn Ser Asn Asn Lys Tyr Tyr Ala Asp Ser Val
                   50                  55                  60

Lys Gly Arg Phe Thr Ile Ser Arg Asp Asn Ser Lys Asn Thr Leu Tyr
 65                 70                  75                  80

Leu Glu Met Asn Ser Leu Arg Ser Glu Asp Thr Ala Met Tyr Tyr Cys
                   85                  90                  95

Ala Lys Ser Leu Thr Gly Gly Ser Asp Tyr Phe Asp Ser Trp Gly Gln
                  100                 105                 110

Gly Val Met Val Thr Val Ser Ser
                  115                 120

<210> SEQ ID NO 182
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Lys Phe Thr Phe Ser Asn Tyr Gly Met Asn
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Leu Ile Tyr Tyr Asn Ser Asn Lys Tyr
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Leu Thr Gly Gly Ser Asp Tyr Phe Asp Ser
1               5                   10

<210> SEQ ID NO 185
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Val Glu Ser Gly Gly Gly Leu Val Gln Pro Gly Ser
1               5                   10                  15

Ser Leu Lys Leu Ser Cys Val Ala Ser Lys Phe Thr Phe Ser Asn Tyr
            20                  25                  30

Gly Met Asn Trp Ile Arg Gln Ala Pro Lys Lys Gly Leu Glu Trp Ile
        35                  40                  45

Ala Leu Ile Tyr Tyr Asn Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Lys Ser Leu Thr Gly Gly Ser Asp Tyr Phe Asp Ser Trp Gly Gln
            100                 105                 110

Gly Val Met Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160
```

Trp Asn Ser Gly Ser Leu Ser Ser Gly Val His Thr Phe Pro Ala Val
            165                 170                 175

Leu Gln Ser Asp Leu Tyr Thr Leu Ser Ser Val Thr Val Thr Ser
        180                 185                 190

Ser Thr Trp Pro Ser Gln Ser Ile Thr Cys Asn Val Ala His Pro Ala
            195                 200                 205

Ser Ser Thr Lys Val Asp Lys Lys Ile Glu Pro Arg Gly Pro Thr Ile
        210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
            245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
        290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
            325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
        370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
            405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 186
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Gly Thr Phe
            20                  25                  30

Leu Ala Trp Tyr Gln Glu Lys Pro Glu Lys Thr Asn Lys Leu Leu Ile
        35                  40                  45

Tyr Ser Gly Ser Thr Leu Gln Ser Gly Thr Pro Ser Arg Phe Ser Gly

```
                    50                  55                  60
Ser Gly Ser Gly Thr Asp Phe Thr Leu Thr Ile Arg Asn Leu Glu Pro
 65                  70                  75                  80

Glu Asp Phe Ala Val Tyr Tyr Cys Gln Gln His Asp Glu Tyr Pro Phe
                     85                  90                  95

Thr Phe Gly Ser Gly Thr Lys Leu Glu Ile Lys
                100                 105

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Lys Ala Ser Lys Ser Ile Gly Thr Phe Leu Ala
 1               5                  10

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Gly Ser Thr Leu Gln Ser
 1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Gln His Asp Glu Tyr Pro Phe Thr
 1               5

<210> SEQ ID NO 190
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Val Gln Met Thr Gln Ser Pro Ser Tyr Leu Ala Ala Ser Pro Gly
 1               5                  10                  15

Glu Ser Val Ser Ile Ser Cys Lys Ala Ser Lys Ser Ile Gly Thr Phe
                20                  25                  30

Leu Ala Trp Tyr Gln Glu Lys Pro Glu Lys Thr Asn Lys Leu Leu Ile
            35                  40                  45

Tyr Ser Gly Ser Thr Leu Gln Ser Gly Thr Pro Ser Arg Phe Ser Gly
        50                  55                  60

Ser Gly Ser Gly Thr Asp Phe Thr Leu Thr Ile Arg Asn Leu Glu Pro
 65                  70                  75                  80
```

```
Glu Asp Phe Ala Val Tyr Tyr Cys Gln Gln His Asp Glu Tyr Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 191
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Val Glu Ser Gly Gly Gly Leu Val Gln Pro Gly Ser
1               5                   10                  15

Ser Leu Lys Leu Ser Cys Val Ala Ser Lys Phe Thr Phe Ser Asn Tyr
            20                  25                  30

Gly Met Asn Trp Ile Arg Gln Ala Pro Lys Lys Gly Leu Glu Trp Ile
        35                  40                  45

Ala Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Lys Ser Leu Thr Gly Gly Ser Asp Tyr Phe Asp Ser Trp Gly Gln
            100                 105                 110

Gly Val Met Val Thr Val Ser Ser
        115                 120

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Lys Phe Thr Phe Ser Asn Tyr Gly Met Asn
1               5                   10

<210> SEQ ID NO 193
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Leu Ile Tyr Tyr Asn Ser Asn Asn Lys Tyr
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Leu Thr Gly Gly Ser Asp Tyr Phe Asp Ser
1               5                   10

<210> SEQ ID NO 195
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Leu Val Gln Pro Gly Ser
1               5                   10                  15

Ser Leu Lys Leu Ser Cys Val Ala Ser Lys Phe Thr Phe Ser Asn Tyr
            20                  25                  30

Gly Met Asn Trp Ile Arg Gln Ala Pro Lys Gly Leu Glu Trp Ile
        35                  40                  45

Ala Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Lys Ser Leu Thr Gly Gly Ser Asp Tyr Phe Asp Ser Trp Gly Gln
            100                 105                 110

Gly Val Met Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
```

```
                    225                 230                 235                 240

Pro Ser Val Phe Ile Phe Pro Pro Lys Ile Lys Asp Val Leu Met Ile
                        245                 250                 255

Ser Leu Ser Pro Ile Val Thr Cys Val Val Val Asp Val Ser Glu Asp
                        260                 265                 270

Asp Pro Asp Val Gln Ile Ser Trp Phe Val Asn Asn Val Glu Val His
                        275                 280                 285

Thr Ala Gln Thr Gln Thr His Arg Glu Asp Tyr Asn Ser Thr Leu Arg
                        290                 295                 300

Val Val Ser Ala Leu Pro Ile Gln His Gln Asp Trp Met Ser Gly Lys
        305                 310                 315                 320

Glu Phe Lys Cys Lys Val Asn Asn Lys Asp Leu Pro Ala Pro Ile Glu
                        325                 330                 335

Arg Thr Ile Ser Lys Pro Lys Gly Ser Val Arg Ala Pro Gln Val Tyr
                        340                 345                 350

Val Leu Pro Pro Pro Glu Glu Glu Met Thr Lys Lys Gln Val Thr Leu
                        355                 360                 365

Thr Cys Met Val Thr Asp Phe Met Pro Glu Asp Ile Tyr Val Glu Trp
                        370                 375                 380

Thr Asn Asn Gly Lys Thr Glu Leu Asn Tyr Lys Asn Thr Glu Pro Val
        385                 390                 395                 400

Leu Asp Ser Asp Gly Ser Tyr Phe Met Tyr Ser Lys Leu Arg Val Glu
                        405                 410                 415

Lys Lys Asn Trp Val Glu Arg Asn Ser Tyr Ser Cys Ser Val Val His
                        420                 425                 430

Glu Gly Leu His Asn His His Thr Thr Lys Ser Phe Ser Arg Thr Pro
                        435                 440                 445

Gly Lys
            450

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Val Gln Met Thr Gln Ser Pro Ser Tyr Leu Ala Ala Ser Pro Gly
        1               5                   10                  15

Glu Ser Val Ser Ile Ser Cys Lys Ala Ser Lys Ser Ile Gly Thr Phe
                        20                  25                  30

Leu Ala Trp Tyr Gln Glu Lys Pro Glu Lys Thr Asn Lys Leu Leu Ile
                        35                  40                  45

Tyr Ser Gly Ser Thr Leu Gln Ser Gly Thr Pro Ser Arg Phe Ser Gly
            50                  55                  60

Ser Gly Ser Gly Thr Asp Phe Thr Leu Thr Ile Arg Asn Leu Glu Pro
        65                  70                  75                  80

Glu Asp Phe Ala Val Tyr Tyr Cys Gln Gln His Asp Glu Tyr Pro Phe
                        85                  90                  95

Thr Phe Gly Ser Gly Thr Lys Leu Glu Ile Lys
                        100                 105

<210> SEQ ID NO 197
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Lys Ala Ser Lys Ser Ile Gly Thr Phe Leu Ala
1               5                   10

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Gly Ser Thr Leu Gln Ser
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Gln His Asp Glu Tyr Pro Phe Thr
1               5

<210> SEQ ID NO 200
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Gly Thr Phe
            20                  25                  30

Leu Ala Trp Tyr Gln Glu Lys Pro Glu Lys Thr Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Asn Leu Glu Pro
65                  70                  75                  80

Glu Asp Phe Ala Val Tyr Tyr Cys Gln Gln His Asp Glu Tyr Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160
```

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 201
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Glu Ser Gly Gly Gly Leu Val Gln Pro Gly Ser
1               5                   10                  15

Ser Leu Lys Leu Ser Cys Val Ala Ser Lys Phe Thr Phe Ser Asn Tyr
            20                  25                  30

Gly Met Asn Trp Ile Arg Gln Ala Pro Lys Lys Gly Leu Glu Trp Ile
        35                  40                  45

Ala Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Lys Ser Leu Thr Gly Gly Ser Asp Tyr Phe Asp Ser Trp Gly Gln
            100                 105                 110

Gly Val Met Val Thr Val Ser Ser
        115                 120

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Lys Phe Thr Phe Ser Asn Tyr Gly Met Asn
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Leu Ile Tyr Tyr Asn Ser Asn Asn Lys Tyr
1               5                   10

<210> SEQ ID NO 204
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Leu Thr Gly Gly Ser Asp Tyr Phe Asp Ser
1               5                   10

<210> SEQ ID NO 205
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Val Gln Leu Val Glu Ser Gly Gly Gly Leu Val Gln Pro Gly Ser
1               5                   10                  15

Ser Leu Lys Leu Ser Cys Val Ala Ser Lys Phe Thr Phe Ser Asn Tyr
            20                  25                  30

Gly Met Asn Trp Ile Arg Gln Ala Pro Lys Lys Gly Leu Glu Trp Ile
        35                  40                  45

Ala Leu Ile Tyr Tyr Asn Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Lys Ser Leu Thr Gly Gly Ser Asp Tyr Phe Asp Ser Trp Gly Gln
            100                 105                 110

Gly Val Met Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
            325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
                420                 425                 430

Glu Gly Leu His Asn His His Thr Thr Lys Ser Phe Ser Arg Thr Pro
            435                 440                 445

Gly Lys
    450

<210> SEQ ID NO 206
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Gly Thr Phe
            20                  25                  30

Leu Ala Trp Tyr Gln Glu Lys Pro Glu Lys Thr Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Asn Leu Glu Pro
65                  70                  75                  80

Glu Asp Phe Ala Val Tyr Tyr Cys Gln Gln His Asp Glu Tyr Pro Phe
                85                  90                  95

Thr Phe Gly Ser Gly Thr Lys Leu Glu Ile Lys
            100                 105

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Lys Ala Ser Lys Ser Ile Gly Thr Phe Leu Ala
1               5                   10

<210> SEQ ID NO 208
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Gly Ser Thr Leu Gln Ser
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Gln His Asp Glu Tyr Pro Phe Thr
1               5

<210> SEQ ID NO 210
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Gly Thr Phe
                20                  25                  30

Leu Ala Trp Tyr Gln Glu Lys Pro Glu Lys Thr Asn Lys Leu Leu Ile
            35                  40                  45

Tyr Ser Gly Ser Thr Leu Gln Ser Gly Thr Pro Ser Arg Phe Ser Gly
50                  55                  60

Ser Gly Ser Gly Thr Asp Phe Thr Leu Thr Ile Arg Asn Leu Glu Pro
65                  70                  75                  80

Glu Asp Phe Ala Val Tyr Tyr Cys Gln Gln His Asp Glu Tyr Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

```
<210> SEQ ID NO 211
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Lys Phe Thr Phe Ser Asn Tyr
            20                  25                  30

Gly Met Asn Trp Ile Arg Gln Ala Pro Gly Lys Gly Leu Glu Trp Ile
        35                  40                  45

Ala Leu Ile Tyr Tyr Asn Ser Asn Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Thr Gly Gly Ser Asp Tyr Phe Asp Ser Trp Gly Gln
            100                 105                 110

Gly Thr Leu Val Thr Val Ser Ser
        115                 120

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Lys Phe Thr Phe Ser Asn Tyr Gly Met Asn
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Leu Ile Tyr Tyr Asn Ser Asn Asn Lys Tyr
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Leu Thr Gly Gly Ser Asp Tyr Phe Asp Ser
1               5                   10

<210> SEQ ID NO 215
<211> LENGTH: 450
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

```
Glu Val Gln Leu Val Glu Ser Gly Gly Gly Leu Val Gln Pro Gly Gly
1               5                   10                  15

Ser Leu Arg Leu Ser Cys Ala Ala Ser Lys Phe Thr Phe Ser Asn Tyr
            20                  25                  30

Gly Met Asn Trp Ile Arg Gln Ala Pro Gly Lys Gly Leu Glu Trp Ile
        35                  40                  45

Ala Leu Ile Tyr Tyr Asn Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Thr Gly Gly Ser Asp Tyr Phe Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

Gly Lys
    450

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Ser Gly Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys
            100                 105

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Lys Ala Ser Lys Ser Ile Gly Thr Phe Leu Ala
1               5                   10

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Gly Ser Thr Leu Gln Ser
1               5

<210> SEQ ID NO 219
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Gln His Asp Glu Tyr Pro Phe Thr
1               5

<210> SEQ ID NO 220
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Ser Gly Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 221
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Val Gln Leu Val Glu Ser Gly Gly Gly Leu Val Gln Pro Gly Gly
1               5                   10                  15

Ser Leu Arg Leu Ser Cys Ala Ala Ser Lys Phe Thr Phe Ser Asn Tyr
```

-continued

```
                    20                  25                  30
Gly Met Asn Trp Ile Arg Gln Ala Pro Gly Lys Gly Leu Glu Trp Ile
            35                  40                  45

Ala Leu Ile Tyr Tyr Asn Ser Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Thr Gly Gly Ser Asp Tyr Phe Asp Ser Trp Gly Gln
            100                 105                 110

Gly Thr Leu Val Thr Val Ser Ser
        115                 120

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Lys Phe Thr Phe Ser Asn Tyr Gly Met Asn
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Leu Ile Tyr Tyr Asn Ser Asn Asn Lys Tyr
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ser Leu Thr Gly Gly Ser Asp Tyr Phe Asp Ser
1               5                   10

<210> SEQ ID NO 225
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Glu Val Gln Leu Val Glu Ser Gly Gly Gly Leu Val Gln Pro Gly Gly
1               5                   10                  15

Ser Leu Arg Leu Ser Cys Ala Ala Ser Lys Phe Thr Phe Ser Asn Tyr
            20                  25                  30
```

-continued

```
Gly Met Asn Trp Ile Arg Gln Ala Pro Gly Lys Gly Leu Glu Trp Ile
         35                  40                  45
Ala Leu Ile Tyr Tyr Asn Ser Asn Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Ser Leu Thr Gly Gly Ser Asp Tyr Phe Asp Ser Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
```

<210> SEQ ID NO 226
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys
            100                 105

<210> SEQ ID NO 227
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Lys Ala Ser Lys Ser Ile Gly Thr Phe Leu Ala
1               5                   10

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ser Gly Ser Thr Leu Gln Ser
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gln Gln His Asp Glu Tyr Pro Phe Thr
1               5

<210> SEQ ID NO 230
<211> LENGTH: 214

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Gly Thr Phe
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 231
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ala Val Asn Trp Val Lys Gln Ala Pro Gly Asn Gly Leu Lys Trp Met
        35                  40                  45

Gly Trp Ile Asn Thr Gln Thr Gly Lys Pro Thr Tyr Ala Asp Asp Phe
    50                  55                  60

Lys Gln Arg Phe Val Phe Ser Leu Glu Thr Ser Ala Ser Thr Ser Phe
65                  70                  75                  80

Leu Gln Ile Asn Asn Leu Asn Ile Glu Asp Thr Ala Thr Tyr Phe Cys
                85                  90                  95

Thr Arg Asp Ser Tyr Tyr Tyr Ser Ser Ser Leu Asp Tyr Trp Gly Gln
            100                 105                 110

Gly Val Met Val Thr Val Ser Ser
        115                 120

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Tyr Thr Phe Thr Asp Tyr Ala Val Asn
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Trp Ile Asn Thr Gln Thr Gly Lys Pro Thr
1               5                   10

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Ser Tyr Tyr Tyr Ser Ser Ser Leu Asp Tyr
1               5                   10

<210> SEQ ID NO 235
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ala Val Asn Trp Val Lys Gln Ala Pro Gly Asn Gly Leu Lys Trp Met
        35                  40                  45

Gly Trp Ile Asn Thr Gln Thr Gly Lys Pro Thr Tyr Ala Asp Asp Phe
    50                  55                  60

Lys Gln Arg Phe Val Phe Ser Leu Glu Thr Ser Ala Ser Thr Ser Phe
65                  70                  75                  80

Leu Gln Ile Asn Asn Leu Asn Ile Glu Asp Thr Ala Thr Tyr Phe Cys
                85                  90                  95

Thr Arg Asp Ser Tyr Tyr Tyr Ser Ser Ser Leu Asp Tyr Trp Gly Gln
            100                 105                 110

Gly Val Met Val Thr Val Ser Ser Ala Glu Thr Thr Ala Pro Ser Val
            115                 120                 125

Tyr Pro Leu Ala Pro Gly Thr Ala Leu Lys Ser Asn Ser Met Val Thr
            130                 135                 140

Leu Gly Cys Leu Val Lys Gly Tyr Phe Pro Glu Pro Val Thr Val Thr
145                 150                 155                 160

Trp Asn Ser Gly Ala Leu Ser Ser Gly Val His Thr Phe Pro Ala Val
                165                 170                 175

Leu Gln Ser Gly Leu Tyr Thr Leu Ser Ser Val Thr Val Pro Ser
            180                 185                 190

Ser Thr Trp Ser Ser Gln Ala Val Thr Cys Asn Val Ala His Pro Ala
            195                 200                 205

Ser Ser Thr Lys Val Asp Lys Lys Ile Val Pro Arg Glu Cys Asn Pro
            210                 215                 220

Cys Gly Cys Thr Gly Ser Glu Val Ser Ser Val Phe Ile Phe Pro Pro
225                 230                 235                 240

Lys Thr Lys Asp Val Leu Thr Ile Thr Leu Thr Pro Lys Val Thr Cys
                245                 250                 255

Val Val Val Asp Ile Ser Gln Asn Asp Pro Glu Val Arg Phe Ser Trp
            260                 265                 270

Phe Ile Asp Asp Val Glu Val His Thr Ala Gln Thr His Ala Pro Glu
            275                 280                 285

Lys Gln Ser Asn Ser Thr Leu Arg Ser Val Ser Glu Leu Pro Ile Val
            290                 295                 300

His Arg Asp Trp Leu Asn Gly Lys Thr Phe Lys Cys Lys Val Asn Ser
305                 310                 315                 320

Gly Ala Phe Pro Ala Pro Ile Glu Lys Ser Ile Ser Lys Pro Glu Gly
                325                 330                 335

Thr Pro Arg Gly Pro Gln Val Tyr Thr Met Ala Pro Pro Lys Glu Glu
            340                 345                 350

Met Thr Gln Ser Gln Val Ser Ile Thr Cys Met Val Lys Gly Phe Tyr
            355                 360                 365

Pro Pro Asp Ile Tyr Thr Glu Trp Lys Met Asn Gly Gln Pro Gln Glu
            370                 375                 380

Asn Tyr Lys Asn Thr Pro Pro Thr Met Asp Thr Asp Gly Ser Tyr Phe
385                 390                 395                 400

Leu Tyr Ser Lys Leu Asn Val Lys Lys Glu Thr Trp Gln Gln Gly Asn
                405                 410                 415

Thr Phe Thr Cys Ser Val Leu His Glu Gly Leu His Asn His His Thr
            420                 425                 430

Glu Lys Ser Leu Ser His Ser Pro
            435                 440

<210> SEQ ID NO 236
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Asp Ile Gln Met Thr Gln Ser Pro Ala Ser Leu Ser Ala Ser Leu Gly
1               5                   10                  15

Glu Thr Val Ser Ile Glu Cys Leu Ala Ser Ala Gly Ile Ser Asn Asp

```
                    20                  25                  30

Leu Ala Trp Tyr Gln Gln Lys Ser Gly Lys Ser Pro Gln Leu Leu Ile
            35                  40                  45

Tyr Ala Ala Ser Arg Leu Gln Asp Gly Val Pro Ser Arg Phe Ser Gly
        50                  55                  60

Ser Gly Ser Gly Thr Arg Phe Ser Leu Lys Ile Ser Asp Met Gln Pro
65                  70                  75                  80

Glu Asp Glu Ala Asp Tyr Phe Cys Gln Gln Ser Tyr Lys Tyr Pro Trp
                85                  90                  95

Thr Phe Gly Gly Gly Thr Lys Leu Glu Leu Lys
            100                 105

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Leu Ala Ser Ala Gly Ile Ser Asn Asp Leu Ala
1               5                   10

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ala Ala Ser Arg Leu Gln Asp
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gln Gln Ser Tyr Lys Tyr Pro Trp Thr
1               5

<210> SEQ ID NO 240
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Asp Ile Gln Met Thr Gln Ser Pro Ala Ser Leu Ser Ala Ser Leu Gly
1               5                   10                  15

Glu Thr Val Ser Ile Glu Cys Leu Ala Ser Ala Gly Ile Ser Asn Asp
            20                  25                  30

Leu Ala Trp Tyr Gln Gln Lys Ser Gly Lys Ser Pro Gln Leu Leu Ile
        35                  40                  45
```

Tyr Ala Ala Ser Arg Leu Gln Asp Gly Val Pro Ser Arg Phe Ser Gly
            50                  55                  60

Ser Gly Ser Gly Thr Arg Phe Ser Leu Lys Ile Ser Asp Met Gln Pro
65                  70                  75                  80

Glu Asp Glu Ala Asp Tyr Phe Cys Gln Gln Ser Tyr Lys Tyr Pro Trp
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Thr Glu Gln Leu Ala Thr Gly
            115                 120                 125

Gly Ala Ser Val Val Cys Leu Met Asn Asn Phe Tyr Pro Arg Asp Ile
130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val Val His Lys Thr Ser Ser Pro Val Val Lys Ser
            195                 200                 205

Phe Asn Arg Asn Glu Cys
            210

<210> SEQ ID NO 241
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ala Val Asn Trp Val Lys Gln Ala Pro Gly Asn Gly Leu Lys Trp Met
        35                  40                  45

Gly Trp Ile Asn Thr Gln Thr Gly Lys Pro Thr Tyr Ala Asp Asp Phe
    50                  55                  60

Lys Gln Arg Phe Val Phe Ser Leu Glu Thr Ser Ala Ser Thr Ser Phe
65                  70                  75                  80

Leu Gln Ile Asn Asn Leu Asn Ile Glu Asp Thr Ala Thr Tyr Phe Cys
                85                  90                  95

Thr Arg Asp Ser Tyr Tyr Tyr Ser Ser Ser Leu Asp Tyr Trp Gly Gln
            100                 105                 110

Gly Val Met Val Thr Val Ser Ser
        115                 120

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Tyr Thr Phe Thr Asp Tyr Ala Val Asn
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Trp Ile Asn Thr Gln Thr Gly Lys Pro Thr
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Ser Tyr Tyr Tyr Ser Ser Ser Leu Asp Tyr
1               5                   10

<210> SEQ ID NO 245
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
                20                  25                  30

Ala Val Asn Trp Val Lys Gln Ala Pro Gly Asn Gly Leu Lys Trp Met
            35                  40                  45

Gly Trp Ile Asn Thr Gln Thr Gly Lys Pro Thr Tyr Ala Asp Asp Phe
    50                  55                  60

Lys Gln Arg Phe Val Phe Ser Leu Glu Thr Ser Ala Ser Thr Ser Phe
65                  70                  75                  80

Leu Gln Ile Asn Asn Leu Asn Ile Glu Asp Thr Ala Thr Tyr Phe Cys
                85                  90                  95

Thr Arg Asp Ser Tyr Tyr Tyr Ser Ser Ser Leu Asp Tyr Trp Gly Gln
            100                 105                 110

Gly Val Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys

```
            195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 246
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Asp Ile Gln Met Thr Gln Ser Pro Ala Ser Leu Ser Ala Ser Leu Gly
1               5                   10                  15
Glu Thr Val Ser Ile Glu Cys Leu Ala Ser Ala Gly Ile Ser Asn Asp
            20                  25                  30
Leu Ala Trp Tyr Gln Gln Lys Ser Gly Lys Ser Pro Gln Leu Leu Ile
        35                  40                  45
Tyr Ala Ala Ser Arg Leu Gln Asp Gly Val Pro Ser Arg Phe Ser Gly
    50                  55                  60
Ser Gly Ser Gly Thr Arg Phe Ser Leu Lys Ile Ser Asp Met Gln Pro
65                  70                  75                  80
Glu Asp Glu Ala Asp Tyr Phe Cys Gln Gln Ser Tyr Lys Tyr Pro Trp
                85                  90                  95
```

```
Thr Phe Gly Gly Gly Thr Lys Leu Glu Leu Lys
            100                 105
```

```
<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Leu Ala Ser Ala Gly Ile Ser Asn Asp Leu Ala
1               5                   10
```

```
<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Ala Ser Arg Leu Gln Asp
1               5
```

```
<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Gln Ser Tyr Lys Tyr Pro Trp Thr
1               5
```

```
<210> SEQ ID NO 250
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Asp Ile Gln Met Thr Gln Ser Pro Ala Ser Leu Ser Ala Ser Leu Gly
1               5                   10                  15

Glu Thr Val Ser Ile Glu Cys Leu Ala Ser Ala Gly Ile Ser Asn Asp
            20                  25                  30

Leu Ala Trp Tyr Gln Gln Lys Ser Gly Lys Ser Pro Gln Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Arg Phe Ser Leu Lys Ile Ser Asp Met Gln Pro
65                  70                  75                  80

Glu Asp Glu Ala Asp Tyr Phe Cys Gln Gln Ser Tyr Lys Tyr Pro Trp
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 251
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gln Val Asn Leu Leu Gln Ser Arg Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Leu His Trp Val Lys Gln Ser His Ala Lys Ser Leu Glu Trp Ile
        35                  40                  45

Gly Tyr Ile Asn Pro Asn Asn Ala Tyr Thr Ser Tyr Asn Glu Lys Phe
    50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Ala Asp Ser Ala Thr Tyr Tyr Cys
                85                  90                  95

Ala Arg Asp Thr Thr Asp Tyr Tyr Asn Leu His Phe Ala Tyr Trp Gly
            100                 105                 110

Gln Gly Thr Leu Val Thr Val Ser Ser
        115                 120

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Tyr Thr Phe Thr Asp Tyr Tyr Leu His
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253
```

Tyr Ile Asn Pro Asn Asn Ala Tyr Thr Ser
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asp Thr Thr Asp Tyr Tyr Asn Leu His Phe Ala Tyr
1               5                   10

<210> SEQ ID NO 255
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gln Val Asn Leu Leu Gln Ser Arg Ala Ala Leu Val Lys Pro Gly Ala
1               5                   10                  15

Ser Val Lys Leu Ser Cys Lys Ala Ser Gly Tyr Thr Phe Thr Asp Tyr
                20                  25                  30

Tyr Leu His Trp Val Lys Gln Ser His Ala Lys Ser Leu Glu Trp Ile
            35                  40                  45

Gly Tyr Ile Asn Pro Asn Asn Ala Tyr Thr Ser Tyr Asn Glu Lys Phe
        50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Ala Asp Ser Ala Thr Tyr Tyr Cys
                85                  90                  95

Ala Arg Asp Thr Thr Asp Tyr Tyr Asn Leu His Phe Ala Tyr Trp Gly
                100                 105                 110

Gln Gly Thr Leu Val Thr Val Ser Ser Ala Glu Thr Thr Ala Pro Ser
            115                 120                 125

Val Tyr Pro Leu Ala Pro Gly Thr Ala Leu Lys Ser Asn Ser Met Val
        130                 135                 140

Thr Leu Gly Cys Leu Val Lys Gly Tyr Phe Pro Glu Pro Val Thr Val
145                 150                 155                 160

Thr Trp Asn Ser Gly Ala Leu Ser Ser Gly Val His Thr Phe Pro Ala
                165                 170                 175

Val Leu Gln Ser Gly Leu Tyr Thr Leu Thr Ser Ser Val Thr Val Pro
            180                 185                 190

Ser Ser Thr Trp Ser Ser Gln Ala Val Thr Cys Asn Val Ala His Pro
        195                 200                 205

Ala Ser Ser Thr Lys Val Asp Lys Lys Ile Val Pro Arg Glu Cys Asn
    210                 215                 220

Pro Cys Gly Cys Thr Gly Ser Glu Val Ser Ser Val Phe Ile Phe Pro
225                 230                 235                 240

Pro Lys Thr Lys Asp Val Leu Thr Ile Thr Leu Thr Pro Lys Val Thr
                245                 250                 255

Cys Val Val Val Asp Ile Ser Gln Asn Asp Pro Glu Val Arg Phe Ser
                260                 265                 270

```
Trp Phe Ile Asp Asp Val Glu Val His Thr Ala Gln Thr His Ala Pro
            275                 280                 285
Glu Lys Gln Ser Asn Ser Thr Leu Arg Ser Val Ser Glu Leu Pro Ile
        290                 295                 300
Val His Arg Asp Trp Leu Asn Gly Lys Thr Phe Lys Cys Lys Val Asn
305                 310                 315                 320
Ser Gly Ala Phe Pro Ala Pro Ile Glu Lys Ser Ile Ser Lys Pro Glu
                325                 330                 335
Gly Thr Pro Arg Gly Pro Gln Val Tyr Thr Met Ala Pro Pro Lys Glu
            340                 345                 350
Glu Met Thr Gln Ser Gln Val Ser Ile Thr Cys Met Val Lys Gly Phe
        355                 360                 365
Tyr Pro Pro Asp Ile Tyr Thr Glu Trp Lys Met Asn Gly Gln Pro Gln
370                 375                 380
Glu Asn Tyr Lys Asn Thr Pro Pro Thr Met Asp Thr Asp Gly Ser Tyr
385                 390                 395                 400
Phe Leu Tyr Ser Lys Leu Asn Val Lys Lys Glu Thr Trp Gln Gln Gly
                405                 410                 415
Asn Thr Phe Thr Cys Ser Val Leu His Glu Gly Leu His Asn His His
            420                 425                 430
Thr Glu Lys Ser Leu Ser His Ser Pro
            435                 440
```

<210> SEQ ID NO 256
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 256

```
Asp Ile Gln Met Thr Gln Ser Pro Ala Ser Leu Ser Ala Ser Leu Gly
1               5                   10                  15
Glu Thr Val Ser Ile Glu Cys Leu Thr Ser Glu Gly Ile Ser Asn Asp
            20                  25                  30
Leu Ala Trp Tyr Gln Gln Lys Ser Gly Lys Ser Pro Gln Leu Leu Ile
        35                  40                  45
Tyr Asp Ala Ser Arg Leu Glu Asp Gly Val Pro Ser Arg Phe Ser Gly
    50                  55                  60
Ser Gly Ser Gly Thr Arg Tyr Ser Leu Lys Ile Ser Gly Met Gln Thr
65                  70                  75                  80
Glu Asp Glu Ala Asp Tyr Phe Cys Gln Gln Ser Tyr Lys Tyr Pro Leu
                85                  90                  95
Thr Phe Gly Ser Gly Thr Lys Leu Glu Ile Lys
            100                 105
```

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

```
Leu Thr Ser Glu Gly Ile Ser Asn Asp Leu Ala
1               5                   10
```

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 258

Asp Ala Ser Arg Leu Glu Asp
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Gln Gln Ser Tyr Lys Tyr Pro Leu Thr
1               5

<210> SEQ ID NO 260
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 260

Asp Ile Gln Met Thr Gln Ser Pro Ala Ser Leu Ser Ala Ser Leu Gly
1               5                   10                  15

Glu Thr Val Ser Ile Glu Cys Leu Thr Ser Glu Gly Ile Ser Asn Asp
            20                  25                  30

Leu Ala Trp Tyr Gln Gln Lys Ser Gly Lys Ser Pro Gln Leu Leu Ile
        35                  40                  45

Tyr Asp Ala Ser Arg Leu Glu Asp Gly Val Pro Ser Arg Phe Ser Gly
    50                  55                  60

Ser Gly Ser Gly Thr Arg Tyr Ser Leu Lys Ile Ser Gly Met Gln Thr
65                  70                  75                  80

Glu Asp Glu Ala Asp Tyr Phe Cys Gln Gln Ser Tyr Lys Tyr Pro Leu
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
    130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val Val His Lys Thr Ser Ser Ser Pro Val Val Lys Ser
        195                 200                 205

Phe Asn Arg Asn Glu Cys

-continued

```
<210> SEQ ID NO 261
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gln Val Asn Leu Leu Gln Ser Arg Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Leu His Trp Val Lys Gln Ser His Ala Lys Ser Leu Glu Trp Ile
        35                  40                  45

Gly Tyr Ile Asn Pro Asn Asn Ala Tyr Thr Ser Tyr Asn Glu Lys Phe
    50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Ala Asp Ser Ala Thr Tyr Tyr Cys
                85                  90                  95

Ala Arg Asp Thr Thr Asp Tyr Tyr Asn Leu His Phe Ala Tyr Trp Gly
            100                 105                 110

Gln Gly Thr Leu Val Thr Val Ser Ser
        115                 120

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Tyr Thr Phe Thr Asp Tyr Tyr Leu His
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Tyr Ile Asn Pro Asn Asn Ala Tyr Thr Ser
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asp Thr Thr Asp Tyr Tyr Asn Leu His Phe Ala Tyr
1               5                   10
```

<210> SEQ ID NO 265
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 265

Gln Val Asn Leu Leu Gln Ser Arg Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Leu His Trp Val Lys Gln Ser His Ala Lys Ser Leu Glu Trp Ile
        35                  40                  45

Gly Tyr Ile Asn Pro Asn Asn Ala Tyr Thr Ser Tyr Asn Glu Lys Phe
    50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Ala Asp Ser Ala Thr Tyr Tyr Cys
                85                  90                  95

Ala Arg Asp Thr Thr Asp Tyr Tyr Asn Leu His Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

```
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 266
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asp Ile Gln Met Thr Gln Ser Pro Ala Ser Leu Ser Ala Ser Leu Gly
1               5                   10                  15

Glu Thr Val Ser Ile Glu Cys Leu Thr Ser Glu Gly Ile Ser Asn Asp
            20                  25                  30

Leu Ala Trp Tyr Gln Lys Ser Gly Lys Ser Pro Gln Leu Leu Ile
        35                  40                  45

Tyr Asp Ala Ser Arg Leu Glu Asp Gly Val Pro Ser Arg Phe Ser Gly
    50                  55                  60

Ser Gly Ser Gly Thr Arg Tyr Ser Leu Lys Ile Ser Gly Met Gln Thr
65                  70                  75                  80

Glu Asp Glu Ala Asp Tyr Phe Cys Gln Gln Ser Tyr Lys Tyr Pro Leu
                85                  90                  95

Thr Phe Gly Ser Gly Thr Lys Leu Glu Ile Lys
            100                 105

<210> SEQ ID NO 267
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Leu Thr Ser Glu Gly Ile Ser Asn Asp Leu Ala
1               5                   10

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asp Ala Ser Arg Leu Glu Asp
1               5
```

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gln Gln Ser Tyr Lys Tyr Pro Leu Thr
1               5

<210> SEQ ID NO 270
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Asp Ile Gln Met Thr Gln Ser Pro Ala Ser Leu Ser Ala Ser Leu Gly
1               5                   10                  15

Glu Thr Val Ser Ile Glu Cys Leu Thr Ser Glu Gly Ile Ser Asn Asp
            20                  25                  30

Leu Ala Trp Tyr Gln Gln Lys Ser Gly Lys Ser Pro Gln Leu Leu Ile
        35                  40                  45

Tyr Asp Ala Ser Arg Leu Glu Asp Gly Val Pro Ser Arg Phe Ser Gly
    50                  55                  60

Ser Gly Ser Gly Thr Arg Tyr Ser Leu Lys Ile Ser Gly Met Gln Thr
65                  70                  75                  80

Glu Asp Glu Ala Asp Tyr Phe Cys Gln Gln Ser Tyr Lys Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 271
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Glu Val Gln Leu Val Glu Ser Gly Gly Gly Leu Val Lys Pro Gly Ala

```
1               5                   10                  15
Ser Leu Lys Leu Ser Cys Val Ala Ser Gly Phe Thr Phe Ser Asp Tyr
            20                  25                  30

Trp Met Asn Trp Val Arg Gln Thr Pro Gly Lys Thr Met Glu Trp Ile
            35                  40                  45

Gly Asp Ile Lys Asp Asp Gly Ser Tyr Thr Asn Tyr Thr Pro Ser Leu
        50                  55                  60

Lys Asn Arg Phe Thr Ile Ser Arg Asp Asn Ala Lys Ser Thr Leu Tyr
65                  70                  75                  80

Leu Gln Met Asn Asn Val Arg Ser Glu Asp Thr Gly Thr Tyr Tyr Cys
                85                  90                  95

Thr Ser Gly Gly Val Phe Asp Tyr Trp Gly Gln Gly Val Met Val Thr
            100                 105                 110

Val Ser Ser
        115
```

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

```
Gly Phe Thr Phe Ser Asp Tyr Trp
1               5
```

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 273

```
Ile Lys Asp Asp Gly Ser Tyr Thr
1               5
```

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

```
Thr Ser Gly Gly Val Phe Asp Tyr
1               5
```

<210> SEQ ID NO 275
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 275

```
Glu Val Gln Leu Val Glu Ser Gly Gly Gly Leu Val Lys Pro Gly Ala
1               5                   10                  15
```

-continued

```
Ser Leu Lys Leu Ser Cys Val Ala Ser Gly Phe Thr Phe Ser Asp Tyr
             20                  25                  30
Trp Met Asn Trp Val Arg Gln Thr Pro Gly Lys Thr Met Glu Trp Ile
         35                  40                  45
Gly Asp Ile Lys Asp Asp Gly Ser Tyr Thr Asn Tyr Thr Pro Ser Leu
     50                  55                  60
Lys Asn Arg Phe Thr Ile Ser Arg Asp Asn Ala Lys Ser Thr Leu Tyr
 65                  70                  75                  80
Leu Gln Met Asn Asn Val Arg Ser Glu Asp Thr Gly Thr Tyr Tyr Cys
                 85                  90                  95
Thr Ser Gly Gly Val Phe Asp Tyr Trp Gly Gln Gly Val Met Val Thr
             100                 105                 110
Val Ser Ser Ala Lys Thr Thr Ala Pro Ser Val Tyr Pro Leu Ala Pro
         115                 120                 125
Val Cys Gly Asp Thr Thr Gly Ser Ser Val Thr Leu Gly Cys Leu Val
     130                 135                 140
Lys Gly Tyr Phe Pro Glu Pro Val Thr Leu Thr Trp Asn Ser Gly Ser
145                 150                 155                 160
Leu Ser Ser Gly Val His Thr Phe Pro Ala Val Leu Gln Ser Asp Leu
                165                 170                 175
Tyr Thr Leu Ser Ser Ser Val Thr Val Thr Ser Ser Thr Trp Pro Ser
            180                 185                 190
Gln Ser Ile Thr Cys Asn Val Ala His Pro Ala Ser Ser Thr Lys Val
        195                 200                 205
Asp Lys Lys Ile Glu Pro Arg Gly Pro Thr Ile Lys Pro Cys Pro Pro
    210                 215                 220
Cys Lys Cys Pro Ala Pro Asn Leu Leu Gly Gly Pro Ser Val Phe Ile
225                 230                 235                 240
Phe Pro Pro Lys Ile Lys Asp Val Leu Met Ile Ser Leu Ser Pro Ile
                245                 250                 255
Val Thr Cys Val Val Val Asp Val Ser Glu Asp Pro Asp Val Gln
            260                 265                 270
Ile Ser Trp Phe Val Asn Asn Val Glu Val His Thr Ala Gln Thr Gln
        275                 280                 285
Thr His Arg Glu Asp Tyr Asn Ser Thr Leu Arg Val Val Ser Ala Leu
    290                 295                 300
Pro Ile Gln His Gln Asp Trp Met Ser Gly Lys Glu Phe Lys Cys Lys
305                 310                 315                 320
Val Asn Asn Lys Asp Leu Pro Ala Pro Ile Glu Arg Thr Ile Ser Lys
                325                 330                 335
Pro Lys Gly Ser Val Arg Ala Pro Gln Val Tyr Val Leu Pro Pro Pro
            340                 345                 350
Glu Glu Glu Met Thr Lys Lys Gln Val Thr Leu Thr Cys Met Val Thr
        355                 360                 365
Asp Phe Met Pro Glu Asp Ile Tyr Val Glu Trp Thr Asn Asn Gly Lys
    370                 375                 380
Thr Glu Leu Asn Tyr Lys Asn Thr Glu Pro Val Leu Asp Ser Asp Gly
385                 390                 395                 400
Ser Tyr Phe Met Tyr Ser Lys Leu Arg Val Glu Lys Lys Asn Trp Val
                405                 410                 415
Glu Arg Asn Ser Tyr Ser Cys Ser Val Val His Glu Gly Leu His Asn
            420                 425                 430
His His Thr Thr Lys Ser Phe Ser Arg Thr Pro Gly Lys
```

<210> SEQ ID NO 276
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Glu Ile Val Leu Thr Gln Ser Pro Thr Thr Met Ala Ala Ser Pro Gly
1               5                   10                  15

Glu Met Val Thr Ile Thr Cys Arg Ala Ser Ser Ser Val Asn Tyr Met
            20                  25                  30

His Trp Phe Gln Gln Lys Ser Gly Thr Ser Pro Lys Pro Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ser Tyr Tyr Cys Leu Gln Arg Ser Thr Phe Pro Pro Thr
                85                  90                  95

Phe Gly Ala Gly Thr Lys Leu Glu Leu Lys
            100                 105

<210> SEQ ID NO 277
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ser Ser Val Asn Tyr
1               5

<210> SEQ ID NO 278
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Asp Thr Ser
1

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Leu Gln Arg Ser Thr Phe Pro Pro Thr
1               5

<210> SEQ ID NO 280
<211> LENGTH: 213

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Glu Ile Val Leu Thr Gln Ser Pro Thr Thr Met Ala Ala Ser Pro Gly
1               5                   10                  15

Glu Met Val Thr Ile Thr Cys Arg Ala Ser Ser Val Asn Tyr Met
            20                  25                  30

His Trp Phe Gln Gln Lys Ser Gly Thr Ser Pro Lys Pro Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ser Tyr Tyr Cys Leu Gln Arg Ser Thr Phe Pro Pro Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 281
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Gln Val Arg Leu Val Gln Ser Gly Thr Ala Leu Val Arg Pro Gly Ala
1               5                   10                  15

Ser Val Arg Met Ser Cys Thr Ala Ser Gly Tyr Ser Phe Thr Asp Tyr
            20                  25                  30

Trp Val Ser Trp Val Lys Gln Ser His Gly Gln Ser Leu Glu Trp Ile
        35                  40                  45

Gly Glu Ile Tyr Pro Asn Ser Gly Thr Thr Asn Phe Asn Glu Lys Phe
    50                  55                  60

Glu Gly Lys Ala Thr Leu Thr Val Asp Lys Ser Thr Ser Thr Ala Tyr
65                  70                  75                  80

Met Glu Leu Ser Arg Leu Thr Ser Glu Asp Ser Ala Ile Tyr Tyr Cys
                85                  90                  95

```
Thr Gly Glu Gly Thr Phe Asp Tyr Trp Gly Gln Gly Val Met Val Thr
                100                 105                 110

Val Ser Ser
        115

<210> SEQ ID NO 282
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gly Tyr Ser Phe Thr Asp Tyr Trp
1               5

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ile Tyr Pro Asn Ser Gly Thr Thr
1               5

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Thr Gly Glu Gly Thr Phe Asp Tyr
1               5

<210> SEQ ID NO 285
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Gln Val Arg Leu Val Gln Ser Gly Thr Ala Leu Val Arg Pro Gly Ala
1               5                   10                  15

Ser Val Arg Met Ser Cys Thr Ala Ser Gly Tyr Ser Phe Thr Asp Tyr
                20                  25                  30

Trp Val Ser Trp Val Lys Gln Ser His Gly Gln Ser Leu Glu Trp Ile
            35                  40                  45

Gly Glu Ile Tyr Pro Asn Ser Gly Thr Thr Asn Phe Asn Glu Lys Phe
        50                  55                  60

Glu Gly Lys Ala Thr Leu Thr Val Asp Lys Ser Thr Ser Thr Ala Tyr
65                  70                  75                  80

Met Glu Leu Ser Arg Leu Thr Ser Glu Asp Ser Ala Ile Tyr Tyr Cys
                85                  90                  95

Thr Gly Glu Gly Thr Phe Asp Tyr Trp Gly Gln Gly Val Met Val Thr
                100                 105                 110
```

Val Ser Ser Ala Lys Thr Thr Ala Pro Ser Val Tyr Pro Leu Ala Pro
    115                 120                 125

Val Cys Gly Asp Thr Thr Gly Ser Ser Val Thr Leu Gly Cys Leu Val
130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
        195                 200                 205

Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270

Ile Ser Trp Phe Val Asn Asn Val Glu Val His Thr Ala Gln Thr Gln
        275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
        355                 360                 365

Asp Phe Met Pro Glu Asp Ile Tyr Val Glu Trp Thr Asn Asn Gly Lys
    370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
        435                 440                 445

<210> SEQ ID NO 286
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Glu Ile Val Leu Thr Gln Ser Pro Thr Thr Met Ala Ala Ser Pro Gly
1               5                   10                  15

Glu Lys Val Thr Ile Thr Cys Arg Pro Ser Ser Ser Leu Ser Asn Met

```
                    20                  25                  30

His Trp Phe Gln Gln Lys Ser Gly Thr Ser Pro Lys Pro Trp Ile Tyr
            35                  40                  45

Asp Thr Ser Lys Leu Ala Ser Gly Val Pro Asp Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Leu Gln Arg Ser Ser Tyr Pro Pro Thr
                85                  90                  95

Phe Gly Ala Gly Thr Lys Leu Glu Leu Lys
                100                 105

<210> SEQ ID NO 287
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ser Ser Leu Ser Asn
1               5

<210> SEQ ID NO 288
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Asp Thr Ser
1

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Leu Gln Arg Ser Ser Tyr Pro Pro Thr
1               5

<210> SEQ ID NO 290
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Glu Ile Val Leu Thr Gln Ser Pro Thr Thr Met Ala Ala Ser Pro Gly
1               5                   10                  15

Glu Lys Val Thr Ile Thr Cys Arg Pro Ser Ser Ser Leu Ser Asn Met
            20                  25                  30

His Trp Phe Gln Gln Lys Ser Gly Thr Ser Pro Lys Pro Trp Ile Tyr
        35                  40                  45
```

Asp Thr Ser Lys Leu Ala Ser Gly Val Pro Asp Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Leu Gln Arg Ser Ser Tyr Pro Pro Thr
                 85                  90                  95

Phe Gly Ala Gly Thr Lys Leu Glu Leu Lys Arg Ala Asp Ala Ala Pro
             100                 105                 110

Thr Val Ser Ile Phe Pro Pro Ser Glu Gln Leu Thr Ser Gly Gly
         115                 120                 125

Ala Ser Val Val Cys Phe Leu Asn Asn Phe Tyr Pro Lys Asp Ile Asn
 130                 135                 140

Val Lys Trp Lys Ile Asp Gly Ser Glu Arg Gln Asn Gly Val Leu Asn
 145                 150                 155                 160

Ser Trp Thr Asp Gln Asp Ser Lys Asp Ser Thr Tyr Ser Met Ser Ser
                 165                 170                 175

Thr Leu Thr Leu Thr Lys Asp Glu Tyr Glu Arg His Asn Ser Tyr Thr
             180                 185                 190

Cys Glu Ala Thr His Lys Thr Ser Thr Ser Pro Ile Val Lys Ser Phe
         195                 200                 205

Asn Arg Asn Glu Cys
     210

<210> SEQ ID NO 291
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Glu Val Gln Leu Val Glu Ser Gly Gly Gly Leu Val Lys Pro Gly Ala
 1               5                  10                  15

Ser Leu Lys Leu Ser Cys Val Ala Ser Gly Phe Thr Phe Ser Asp Asp
                 20                  25                  30

Trp Met Asn Trp Val Arg Gln Thr Pro Gly Lys Ala Met Glu Trp Ile
             35                  40                  45

Gly Asp Ile Lys Tyr Asp Gly Ser Tyr Thr Asn Tyr Val Pro Ser Leu
         50                  55                  60

Lys Asn Arg Leu Thr Ile Ser Arg Asp Asn Ala Lys Asn Thr Leu Tyr
 65                  70                  75                  80

Leu Gln Met Thr Asn Val Arg Ser Glu Asp Thr Ala Thr Tyr Tyr Cys
                 85                  90                  95

Thr Ser Gly Gly Val Phe Asp Tyr Trp Gly Gln Gly Val Met Val Thr
             100                 105                 110

Val Ser Ser
        115

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

```
Gly Phe Thr Phe Ser Asp Asp Trp
1               5

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ile Lys Tyr Asp Gly Ser Tyr Thr
1               5

<210> SEQ ID NO 294
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Thr Ser Gly Gly Val Phe Asp Tyr
1               5

<210> SEQ ID NO 295
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Glu Val Gln Leu Val Glu Ser Gly Gly Gly Leu Val Lys Pro Gly Ala
1               5                   10                  15

Ser Leu Lys Leu Ser Cys Val Ala Ser Gly Phe Thr Phe Ser Asp Asp
            20                  25                  30

Trp Met Asn Trp Val Arg Gln Thr Pro Gly Lys Ala Met Glu Trp Ile
        35                  40                  45

Gly Asp Ile Lys Tyr Asp Gly Ser Tyr Thr Asn Tyr Val Pro Ser Leu
    50                  55                  60

Lys Asn Arg Leu Thr Ile Ser Arg Asp Asn Ala Lys Asn Thr Leu Tyr
65                  70                  75                  80

Leu Gln Met Thr Asn Val Arg Ser Glu Asp Thr Ala Thr Tyr Tyr Cys
                85                  90                  95

Thr Ser Gly Gly Val Phe Asp Tyr Trp Gly Gln Gly Val Met Val Thr
            100                 105                 110

Val Ser Ser Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
```

```
            195                 200                 205

Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
                260                 265                 270

Ile Ser Trp Phe Val Asn Asn Val Glu Val His Thr Ala Gln Thr Gln
                275                 280                 285

Thr His Arg Glu Asp Tyr Asn Ser Thr Leu Arg Val Val Ser Ala Leu
                290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
                340                 345                 350

Glu Glu Glu Met Thr Lys Lys Gln Val Thr Leu Thr Cys Met Val Thr
                355                 360                 365

Asp Phe Met Pro Glu Asp Ile Tyr Val Glu Trp Thr Asn Asn Gly Lys
370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
                420                 425                 430

His His Thr Thr Lys Ser Phe Ser Arg Thr Pro Gly Lys
                435                 440                 445

<210> SEQ ID NO 296
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Glu Ile Val Leu Ser Gln Ser Pro Thr Thr Met Ala Ala Ser Pro Gly
1               5                   10                  15

Glu Lys Val Thr Ile Thr Cys Arg Ala Ser Ser Ser Val Ser Tyr Met
                20                  25                  30

His Trp Phe Gln Gln Lys Ser Gly Thr Ser Pro Lys Pro Trp Ile Tyr
            35                  40                  45

Asp Thr Ser Lys Leu Ala Ser Gly Val Pro Asp Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Leu Gln Arg Ser Gly Tyr Pro Pro Thr
                85                  90                  95

Phe Gly Ala Gly Thr Lys Leu Glu Val Lys
            100                 105
```

<210> SEQ ID NO 297
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Ser Ser Val Ser Tyr
1               5

<210> SEQ ID NO 298
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Asp Thr Ser
1

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 299

Leu Gln Arg Ser Gly Tyr Pro Pro Thr
1               5

<210> SEQ ID NO 300
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 300

Glu Ile Val Leu Ser Gln Ser Pro Thr Thr Met Ala Ala Ser Pro Gly
1               5                   10                  15

Glu Lys Val Thr Ile Thr Cys Arg Ala Ser Ser Ser Val Ser Tyr Met
                20                  25                  30

His Trp Phe Gln Gln Lys Ser Gly Thr Ser Pro Lys Pro Trp Ile Tyr
            35                  40                  45

Asp Thr Ser Lys Leu Ala Ser Gly Val Pro Asp Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Leu Gln Arg Ser Gly Tyr Pro Pro Thr
                85                  90                  95

Phe Gly Ala Gly Thr Lys Leu Glu Val Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 301
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Glu Val Gln Leu Val Glu Ser Gly Gly Gly Leu Val Gln Pro Gly Arg
1               5                   10                  15

Ser Leu Lys Phe Ser Cys Ser Ala Ser Gly Phe Thr Phe Ser Ala Tyr
            20                  25                  30

Ser Met Ala Trp Val Arg Gln Ala Pro Lys Thr Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg Leu Gly Tyr Ser Gly His Tyr Phe Asp Tyr Trp Gly Gln Gly
            100                 105                 110

Val Met Val Thr Val Ser Ser
        115

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gly Phe Thr Phe Ser Ala Tyr Ser
1               5

<210> SEQ ID NO 303
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ile Ile Tyr Asp Gly Ser Ser Thr
1               5

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ala Arg Leu Gly Tyr Ser Gly His Tyr Phe Asp Tyr
1               5                   10

<210> SEQ ID NO 305
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Glu Val Gln Leu Val Glu Ser Gly Gly Gly Leu Val Gln Pro Gly Arg
1               5                   10                  15

Ser Leu Lys Phe Ser Cys Ser Ala Ser Gly Phe Thr Phe Ser Ala Tyr
            20                  25                  30

Ser Met Ala Trp Val Arg Gln Ala Pro Lys Thr Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg Leu Gly Tyr Ser Gly His Tyr Phe Asp Tyr Trp Gly Gln Gly
            100                 105                 110

Val Met Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

```
Ala Gln Thr Gln Thr His Arg Glu Asp Tyr Asn Ser Thr Leu Arg Val
    290                 295                 300
Val Ser Ala Leu Pro Ile Gln His Gln Asp Trp Met Ser Gly Lys Glu
305                 310                 315                 320
Phe Lys Cys Lys Val Asn Asn Lys Asp Leu Pro Ala Pro Ile Glu Arg
                325                 330                 335
Thr Ile Ser Lys Pro Lys Gly Ser Val Arg Ala Pro Gln Val Tyr Val
            340                 345                 350
Leu Pro Pro Pro Glu Glu Glu Met Thr Lys Lys Gln Val Thr Leu Thr
        355                 360                 365
Cys Met Val Thr Asp Phe Met Pro Glu Asp Ile Tyr Val Glu Trp Thr
    370                 375                 380
Asn Asn Gly Lys Thr Glu Leu Asn Tyr Lys Asn Thr Glu Pro Val Leu
385                 390                 395                 400
Asp Ser Asp Gly Ser Tyr Phe Met Tyr Ser Lys Leu Arg Val Glu Lys
                405                 410                 415
Lys Asn Trp Val Glu Arg Asn Ser Tyr Ser Cys Ser Val Val His Glu
            420                 425                 430
Gly Leu His Asn His His Thr Thr Lys Ser Phe Ser Arg Thr Pro Gly
        435                 440                 445
Lys

<210> SEQ ID NO 306
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Asp Thr Val Leu Thr Gln Ser Pro Ala Leu Ala Val Ser Leu Gly Gln
1               5                   10                  15
Arg Val Thr Ile Ser Cys Gln Ala Ser Glu Ser Val Ser Ser Ser Leu
            20                  25                  30
His Ser Tyr Leu His Trp Tyr Gln Gln Lys Pro Gly Gln Gln Pro Lys
        35                  40                  45
Leu Leu Ile Tyr Arg Ala Ser Asn Leu Glu Ser Gly Val Pro Ala Arg
    50                  55                  60
Phe Ser Gly Ser Gly Ser Gly Thr Asp Phe Thr Leu Asn Ile Asp Pro
65                  70                  75                  80
Val Glu Ala Asp Asp Ile Ala Thr Tyr Phe Cys Gln Gln Ser Trp Asn
                85                  90                  95
Asp Pro Arg Thr Phe Gly Gly Gly Thr Lys Leu Glu Leu Lys
            100                 105                 110

<210> SEQ ID NO 307
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Glu Ser Val Ser Ser Ser Leu His Ser Tyr
1               5                   10
```

```
<210> SEQ ID NO 308
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Arg Ala Ser
1

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gln Gln Ser Trp Asn Asp Pro Arg Thr
1               5

<210> SEQ ID NO 310
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Asp Thr Val Leu Thr Gln Ser Pro Ala Leu Ala Val Ser Leu Gly Gln
1               5                   10                  15

Arg Val Thr Ile Ser Cys Gln Ala Ser Glu Ser Val Ser Ser Ser Leu
            20                  25                  30

His Ser Tyr Leu His Trp Tyr Gln Gln Lys Pro Gly Gln Gln Pro Lys
        35                  40                  45

Leu Leu Ile Tyr Arg Ala Ser Asn Leu Glu Ser Gly Val Pro Ala Arg
    50                  55                  60

Phe Ser Gly Ser Gly Ser Gly Thr Asp Phe Thr Leu Asn Ile Asp Pro
65                  70                  75                  80

Val Glu Ala Asp Asp Ile Ala Thr Tyr Phe Cys Gln Gln Ser Trp Asn
                85                  90                  95

Asp Pro Arg Thr Phe Gly Gly Gly Thr Lys Leu Glu Leu Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215
```

<210> SEQ ID NO 311
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Val Gln Leu Val Gln Ser Gly Ala Glu Val Lys Lys Pro Gly Ala Ser
1               5                   10                  15

Val Lys Val Ser Cys Lys Ala Ser Gly Tyr Thr Phe Thr Asp Tyr Ala
            20                  25                  30

Val Asn Trp Val Arg Gln Ala Pro Gly Gln Gly Leu Glu Trp Met Gly
        35                  40                  45

Trp Ile Asn Thr Gln Thr Gly Lys Pro Thr Tyr Ala Gln Lys Phe Gln
    50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Asp Ser Tyr Tyr Tyr Ser Ser Leu Asp Tyr Trp Gly Gln Gly
            100                 105                 110

Thr Leu Val Thr Val Ser Ser
        115

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Tyr Thr Phe Thr Asp Tyr Ala Val Asn
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Trp Ile Asn Thr Gln Thr Gly Lys Pro Thr
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Asp Ser Tyr Tyr Tyr Ser Ser Ser Leu Asp Tyr
1               5                   10

```
<210> SEQ ID NO 315
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Val Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Tyr Tyr Tyr Ser Ser Leu Asp Tyr Trp Gly Gln Gly
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 316
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys
            100                 105

<210> SEQ ID NO 317
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Arg Ala Ser Ala Gly Ile Ser Asn Asp Leu Ala
1               5                   10

<210> SEQ ID NO 318
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ala Ala Ser Arg Leu Gln Asp
1               5
```

```
<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gln Gln Ser Tyr Lys Tyr Pro Trp Thr
1               5

<210> SEQ ID NO 320
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 321
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Gln Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Asp Tyr
            20                  25                  30

Ala Val Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Gln Lys Phe
50                  55                  60

Gln Gly Arg Val Thr Met Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Ser Tyr Tyr Tyr Ser Ser Leu Asp Tyr Trp Gly Gln
            100                 105                 110

Gly Thr Leu Val Thr Val Ser Ser
        115                 120

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gly Tyr Thr Phe Thr Asp Tyr Ala Val Asn
1               5                   10

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Trp Ile Asn Thr Gln Thr Gly Lys Pro Thr
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Asp Ser Tyr Tyr Tyr Ser Ser Leu Asp Tyr
1               5                   10

<210> SEQ ID NO 325
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
```

```
            20                  25                  30
Ala Val Asn Trp Val Arg Gln Ala Pro Gly Gln Gly Leu Glu Trp Met
        35                  40                  45
Gly Trp Ile Asn Thr Gln Thr Gly Lys Pro Thr Tyr Ala Gln Lys Phe
    50                  55                  60
Gln Gly Arg Val Thr Met Thr Leu Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Asp Ser Tyr Tyr Ser Ser Ser Leu Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

```
Gly Lys
    450

<210> SEQ ID NO 326
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys
            100                 105

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Arg Ala Ser Ala Gly Ile Ser Asn Asp Leu Ala
1               5                   10

<210> SEQ ID NO 328
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ala Ala Ser Arg Leu Gln Asp
1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gln Gln Ser Tyr Lys Tyr Pro Trp Thr
1               5
```

```
<210> SEQ ID NO 330
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 331
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ala Val Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Gln Lys Phe
50                  55                  60

Gln Gly Arg Phe Thr Phe Thr Leu Asp Thr Ser Thr Ser Thr Ala Tyr
65                  70                  75                  80

Leu Glu Ile Ser Ser Leu Arg Ser Glu Asp Thr Ala Val Tyr Tyr Cys
```

```
                    85                  90                  95

Thr Arg Asp Ser Tyr Tyr Tyr Ser Ser Ser Leu Asp Tyr Trp Gly Gln
                100                 105                 110

Gly Thr Leu Val Thr Val Ser Ser
        115                 120

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gly Tyr Thr Phe Thr Asp Tyr Ala Val Asn
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Trp Ile Asn Thr Gln Thr Gly Lys Pro Thr
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Asp Ser Tyr Tyr Tyr Ser Ser Ser Leu Asp Tyr
1               5                   10

<210> SEQ ID NO 335
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ala Val Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Gln Lys Phe
    50                  55                  60

Gln Gly Arg Phe Thr Phe Thr Leu Asp Thr Ser Thr Ser Thr Ala Tyr
65                  70                  75                  80

Leu Glu Ile Ser Ser Leu Arg Ser Glu Asp Thr Ala Val Tyr Tyr Cys
                85                  90                  95
```

```
Thr Arg Asp Ser Tyr Tyr Ser Ser Ser Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 336
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys
            100                 105
```

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

```
Arg Ala Ser Ala Gly Ile Ser Asn Asp Leu Ala
1               5                   10
```

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

```
Ala Ala Ser Arg Leu Gln Asp
1               5
```

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

```
Gln Gln Ser Tyr Lys Tyr Pro Trp Thr
1               5
```

<210> SEQ ID NO 340
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
```

```
                    20                  25                  30
Leu Ala Trp Tyr Gln Gln Lys Pro Gly Lys Ala Pro Lys Leu Leu Ile
            35                  40                  45

Tyr Ala Ala Ser Arg Leu Gln Asp Gly Val Pro Ser Arg Phe Ser Gly
 50                  55                  60

Ser Gly Ser Gly Thr Asp Phe Thr Leu Thr Ile Ser Ser Met Gln Pro
 65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 341
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                20                  25                  30

Ala Val Asn Trp Val Arg Gln Ala Pro Gly Gln Gly Leu Glu Trp Met
            35                  40                  45

Gly Trp Ile Asn Thr Gln Thr Gly Lys Pro Thr Tyr Ala Gln Lys Phe
 50                  55                  60

Gln Gly Arg Val Thr Met Thr Leu Asp Thr Ser Thr Ser Thr Ser Tyr
 65                  70                  75                  80

Met Glu Leu Ser Ser Leu Arg Ser Glu Asp Thr Ala Val Tyr Tyr Cys
                85                  90                  95

Thr Arg Asp Ser Tyr Tyr Ser Ser Leu Asp Tyr Trp Gly Gln
                100                 105                 110

Gly Thr Leu Val Thr Val Ser Ser
            115                 120

<210> SEQ ID NO 342
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 342

Gly Tyr Thr Phe Thr Asp Tyr Ala Val Asn
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Trp Ile Asn Thr Gln Thr Gly Lys Pro Thr
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Asp Ser Tyr Tyr Tyr Ser Ser Ser Leu Asp Tyr
1               5                   10

<210> SEQ ID NO 345
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ala Val Asn Trp Val Arg Gln Ala Pro Gly Gln Gly Leu Glu Trp Met
            35                  40                  45

Gly Trp Ile Asn Thr Gln Thr Gly Lys Pro Thr Tyr Ala Gln Lys Phe
    50                  55                  60

Gln Gly Arg Val Thr Met Thr Leu Asp Thr Ser Thr Ser Thr Ser Tyr
65                  70                  75                  80

Met Glu Leu Ser Ser Leu Arg Ser Glu Asp Thr Ala Val Tyr Tyr Cys
                85                  90                  95

Thr Arg Asp Ser Tyr Tyr Tyr Ser Ser Ser Leu Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 346
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro

```
              65                  70                  75                  80
Glu Asp Phe Ala Thr Tyr Tyr Cys Gln Gln Ser Tyr Lys Tyr Pro Trp
                    85                  90                  95
Thr Phe Gly Gln Gly Thr Lys Leu Glu Ile Lys
            100                 105
```

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

```
Arg Ala Ser Ala Gly Ile Ser Asn Asp Leu Ala
1               5                   10
```

<210> SEQ ID NO 348
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

```
Ala Ala Ser Arg Leu Gln Asp
1               5
```

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

```
Gln Gln Ser Tyr Lys Tyr Pro Trp Thr
1               5
```

<210> SEQ ID NO 350
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp
                85                  90                  95
```

```
Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 351
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 351

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ala Val Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Gln Lys Phe
    50                  55                  60

Gln Gly Arg Phe Thr Phe Thr Leu Asp Thr Ser Thr Ser Thr Ser Tyr
65                  70                  75                  80

Leu Glu Ile Ser Ser Leu Arg Ser Glu Asp Thr Ala Val Tyr Tyr Cys
                85                  90                  95

Thr Arg Asp Ser Tyr Tyr Tyr Ser Ser Ser Leu Asp Tyr Trp Gly Gln
            100                 105                 110

Gly Thr Leu Val Thr Val Ser Ser
        115                 120
```

<210> SEQ ID NO 352
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

```
Gly Tyr Thr Phe Thr Asp Tyr Ala Val Asn
1               5                   10
```

<210> SEQ ID NO 353
<211> LENGTH: 10
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 353

Trp Ile Asn Thr Gln Thr Gly Lys Pro Thr
1               5                   10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asp Ser Tyr Tyr Tyr Ser Ser Ser Leu Asp Tyr
1               5                   10

<210> SEQ ID NO 355
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ala Val Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Gln Lys Phe
    50                  55                  60

Gln Gly Arg Phe Thr Phe Thr Leu Asp Thr Ser Thr Ser Thr Ser Tyr
65                  70                  75                  80

Leu Glu Ile Ser Ser Leu Arg Ser Glu Asp Thr Ala Val Tyr Tyr Cys
                85                  90                  95

Thr Arg Asp Ser Tyr Tyr Tyr Ser Ser Ser Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile

```
                        245                 250                 255
Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 356
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys
            100                 105

<210> SEQ ID NO 357
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 357

Arg Ala Ser Ala Gly Ile Ser Asn Asp Leu Ala
1               5                   10

<210> SEQ ID NO 358
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ala Ala Ser Arg Leu Gln Asp
1               5

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Gln Gln Ser Tyr Lys Tyr Pro Trp Thr
1               5

<210> SEQ ID NO 360
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 361
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Thr Leu Ser Trp Val Arg Gln Pro Pro Gly Lys Gly Leu Glu Trp Ile
        35                  40                  45

Gly Ala Ile Trp Gly Gly Asp Asn Thr Asp Tyr Asn Ser Ala Leu Lys
    50                  55                  60

Ser Arg Leu Ser Ile Thr Trp Asp Thr Ser Lys Ser Gln Val Leu Leu
65                  70                  75                  80

Lys Met Asn Ser Leu Gln Thr Glu Asp Thr Ala Ile Tyr Phe Cys Thr
                85                  90                  95

Arg Glu Leu Gly Gly Ser Phe Asp Tyr Trp Gly Gln Gly Val Met Val
            100                 105                 110

Thr Val Ser Ser
        115

<210> SEQ ID NO 362
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Gly Phe Ser Leu Thr Ser Tyr Thr Leu Ser
1               5                   10

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ala Ile Trp Gly Gly Asp Asn Thr Asp
1               5

<210> SEQ ID NO 364
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 364

Glu Leu Gly Gly Ser Phe Asp Tyr
1               5

<210> SEQ ID NO 365
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
                20                  25                  30

Thr Leu Ser Trp Val Arg Gln Pro Pro Gly Lys Gly Leu Glu Trp Ile
            35                  40                  45

Gly Ala Ile Trp Gly Gly Asp Asn Thr Asp Tyr Asn Ser Ala Leu Lys
    50                  55                  60

Ser Arg Leu Ser Ile Thr Trp Asp Thr Ser Lys Ser Gln Val Leu Leu
65                  70                  75                  80

Lys Met Asn Ser Leu Gln Thr Glu Asp Thr Ala Ile Tyr Phe Cys Thr
                85                  90                  95

Arg Glu Leu Gly Gly Ser Phe Asp Tyr Trp Gly Gln Gly Val Met Val
            100                 105                 110

Thr Val Ser Ser Ala Glu Thr Thr Ala Pro Ser Val Tyr Pro Leu Ala
        115                 120                 125

Pro Gly Thr Ala Leu Lys Ser Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ala Leu Ser Ser Gly Val His Thr Phe Pro Ala Val Leu Gln Ser Gly
                165                 170                 175

Leu Tyr Thr Leu Thr Ser Ser Val Thr Val Pro Ser Ser Thr Trp Ser
            180                 185                 190

Ser Gln Ala Val Thr Cys Asn Val Ala His Pro Ala Ser Ser Thr Lys
        195                 200                 205

Val Asp Lys Lys Ile Val Pro Arg Glu Cys Asn Pro Cys Gly Cys Thr
    210                 215                 220

Gly Ser Glu Val Ser Ser Val Phe Ile Phe Pro Pro Lys Thr Lys Asp
225                 230                 235                 240

Val Leu Thr Ile Thr Leu Thr Pro Lys Val Thr Cys Val Val Val Asp
                245                 250                 255

Ile Ser Gln Asn Asp Pro Glu Val Arg Phe Ser Trp Phe Ile Asp Asp
            260                 265                 270

Val Glu Val His Thr Ala Gln Thr His Ala Pro Glu Lys Gln Ser Asn
        275                 280                 285

Ser Thr Leu Arg Ser Val Ser Glu Leu Pro Ile Val His Arg Asp Trp
    290                 295                 300

Leu Asn Gly Lys Thr Phe Lys Cys Lys Val Asn Ser Gly Ala Phe Pro
305                 310                 315                 320

```
Ala Pro Ile Glu Lys Ser Ile Ser Lys Pro Glu Gly Thr Pro Arg Gly
            325                 330                 335

Pro Gln Val Tyr Thr Met Ala Pro Pro Lys Glu Glu Met Thr Gln Ser
        340                 345                 350

Gln Val Ser Ile Thr Cys Met Val Lys Gly Phe Tyr Pro Pro Asp Ile
        355                 360                 365

Tyr Thr Glu Trp Lys Met Asn Gly Gln Pro Gln Glu Asn Tyr Lys Asn
        370                 375                 380

Thr Pro Pro Thr Met Asp Thr Asp Gly Ser Tyr Phe Leu Tyr Ser Lys
385                 390                 395                 400

Leu Asn Val Lys Lys Glu Thr Trp Gln Gln Gly Asn Thr Phe Thr Cys
            405                 410                 415

Ser Val Leu His Glu Gly Leu His Asn His His Thr Glu Lys Ser Leu
            420                 425                 430

Ser His Ser Pro
        435

<210> SEQ ID NO 366
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Asp Ile Gln Met Thr Gln Ser Pro Pro Val Leu Ser Ala Ser Val Gly
1               5                   10                  15

Asp Arg Val Thr Leu Ser Cys Lys Thr Ser Gln Asn Ile Asn Lys Lys
            20                  25                  30

Leu Asp Trp Tyr Gln Gln Lys His Gly Glu Ala Pro Lys Leu Leu Ile
        35                  40                  45

Tyr Tyr Thr Asn Asn Leu Gln Thr Gly Ile Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Val Ala Thr Tyr Tyr Cys Tyr Gln Tyr Asp Ser Gly Phe Thr
                85                  90                  95

Phe Gly Ala Gly Thr Lys Leu Glu Leu Lys
            100                 105

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Lys Thr Ser Gln Asn Ile Asn Lys Lys Leu Asp
1               5                   10

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 368

Tyr Thr Asn Asn Leu Gln Thr
1               5

<210> SEQ ID NO 369
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Tyr Gln Tyr Asp Ser Gly Phe Thr
1               5

<210> SEQ ID NO 370
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Asp Ile Gln Met Thr Gln Ser Pro Val Leu Ser Ala Ser Val Gly
1               5                   10                  15

Asp Arg Val Thr Leu Ser Cys Lys Thr Ser Gln Asn Ile Asn Lys Lys
                20                  25                  30

Leu Asp Trp Tyr Gln Gln Lys His Gly Glu Ala Pro Lys Leu Leu Ile
        35                  40                  45

Tyr Tyr Thr Asn Asn Leu Gln Thr Gly Ile Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Val Ala Thr Tyr Tyr Cys Tyr Gln Tyr Asp Ser Gly Phe Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Thr Glu Gln Leu Ala Thr Gly Gly
        115                 120                 125

Ala Ser Val Val Cys Leu Met Asn Asn Phe Tyr Pro Arg Asp Ile Ser
    130                 135                 140

Val Lys Trp Lys Ile Asp Gly Thr Glu Arg Arg Asp Gly Val Leu Asp
145                 150                 155                 160

Ser Val Thr Asp Gln Asp Ser Lys Asp Ser Thr Tyr Ser Met Ser Ser
                165                 170                 175

Thr Leu Ser Leu Thr Lys Ala Asp Tyr Glu Ser His Asn Leu Tyr Thr
            180                 185                 190

Cys Glu Val Val His Lys Thr Ser Ser Pro Val Val Lys Ser Phe
        195                 200                 205

Asn Arg Asn Glu Cys
    210

<210> SEQ ID NO 371
<211> LENGTH: 116
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 371

Gln Val Gln Leu Lys Glu Ser Gly Pro Gly Leu Val Gln Pro Ser Gln
1               5                   10                  15
Thr Leu Ser Leu Thr Cys Thr Val Ser Gly Phe Ser Leu Thr Ser Tyr
            20                  25                  30
Thr Leu Ser Trp Val Arg Gln Pro Pro Gly Lys Gly Leu Glu Trp Ile
        35                  40                  45
Gly Ala Ile Trp Gly Gly Asp Asn Thr Asp Tyr Asn Ser Ala Leu Lys
    50                  55                  60
Ser Arg Leu Ser Ile Ser Arg Asp Thr Ser Lys Ser Gln Val Leu Leu
65                  70                  75                  80
Lys Met Asn Ser Leu Gln Thr Glu Asp Thr Ala Ile Tyr Phe Cys Thr
                85                  90                  95
Arg Glu Leu Gly Gly Ser Phe Asp Tyr Trp Gly Gln Gly Val Met Val
            100                 105                 110
Thr Val Ser Ser
        115

<210> SEQ ID NO 372
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Gly Phe Ser Leu Thr Ser Tyr Thr Leu Ser
1               5                   10

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ala Ile Trp Gly Gly Asp Asn Thr Asp
1               5

<210> SEQ ID NO 374
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Glu Leu Gly Gly Ser Phe Asp Tyr
1               5

<210> SEQ ID NO 375
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 375

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Thr Leu Ser Trp Val Arg Gln Pro Pro Gly Lys Gly Leu Glu Trp Ile
        35                  40                  45

Gly Ala Ile Trp Gly Gly Asp Asn Thr Asp Tyr Asn Ser Ala Leu Lys
    50                  55                  60

Ser Arg Leu Ser Ile Ser Arg Asp Thr Ser Lys Ser Gln Val Leu Leu
65                  70                  75                  80

Lys Met Asn Ser Leu Gln Thr Glu Asp Thr Ala Ile Tyr Phe Cys Thr
                85                  90                  95

Arg Glu Leu Gly Gly Ser Phe Asp Tyr Trp Gly Gln Gly Val Met Val
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
    370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415
```

```
Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
            435                 440                 445
```

<210> SEQ ID NO 376
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

```
Asp Ile Gln Met Thr Gln Ser Pro Pro Val Leu Ser Ala Ser Val Gly
1               5                   10                  15

Asp Arg Val Thr Leu Ser Cys Lys Thr Ser Gln Asn Ile Asn Lys Lys
            20                  25                  30

Leu Asp Trp Tyr Gln Gln Lys His Gly Glu Ala Pro Lys Leu Leu Ile
        35                  40                  45

Tyr Tyr Thr Asn Asn Leu Gln Thr Gly Ile Pro Ser Arg Phe Ser Gly
50                  55                  60

Ser Gly Ser Gly Thr Asp Phe Thr Leu Thr Ile Ser Thr Leu Gln Pro
65                  70                  75                  80

Glu Asp Val Ala Thr Tyr Tyr Cys Tyr Gln Tyr Asp Ser Gly Phe Thr
                85                  90                  95

Phe Gly Ala Gly Thr Lys Leu Glu Leu Lys
            100                 105
```

<210> SEQ ID NO 377
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

```
Lys Thr Ser Gln Asn Ile Asn Lys Lys Leu Asp
1               5                   10
```

<210> SEQ ID NO 378
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

```
Tyr Thr Asn Asn Leu Gln Thr
1               5
```

<210> SEQ ID NO 379
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

```
Tyr Gln Tyr Asp Ser Gly Phe Thr
```

<210> SEQ ID NO 380
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 380

Asp Ile Gln Met Thr Gln Ser Pro Val Leu Ser Ala Ser Val Gly
1               5                   10                  15

Asp Arg Val Thr Leu Ser Cys Lys Thr Ser Gln Asn Ile Asn Lys Lys
            20                  25                  30

Leu Asp Trp Tyr Gln Gln Lys His Gly Glu Ala Pro Lys Leu Leu Ile
        35                  40                  45

Tyr Tyr Thr Asn Asn Leu Gln Thr Gly Ile Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Val Ala Thr Tyr Tyr Cys Tyr Gln Tyr Asp Ser Gly Phe Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 381
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: R or L

<400> SEQUENCE: 381

Xaa Ala Ser Ala Gly Ile Ser Asn Asp Leu Ala
1               5                   10

<210> SEQ ID NO 382
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R or K

<400> SEQUENCE: 382

Xaa Ala Ser Lys Ser Ile Gly Thr Phe Leu Ala
1               5                   10

<210> SEQ ID NO 383
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R or L

<400> SEQUENCE: 383

Xaa Ala Ser Glu Gly Ile Ser Asn Asp Leu Ala
1               5                   10

<210> SEQ ID NO 384
<211> LENGTH: 520
<212> TYPE: PRT
<213> ORGANISM: Homo sapiens

<400> SEQUENCE: 384

Met Arg Asn Lys Lys Ile Leu Lys Glu Asp Glu Leu Leu Ser Glu Thr
1               5                   10                  15

Gln Gln Ala Ala Phe His Gln Ile Ala Met Glu Pro Phe Glu Ile Asn
            20                  25                  30

Val Pro Lys Pro Lys Arg Arg Asn Gly Val Asn Phe Ser Leu Ala Val
        35                  40                  45

Val Val Ile Tyr Leu Ile Leu Leu Thr Ala Gly Ala Gly Leu Leu Val
    50                  55                  60

Val Gln Val Leu Asn Leu Gln Ala Arg Leu Arg Val Leu Glu Met Tyr
65                  70                  75                  80

Phe Leu Asn Asp Thr Leu Ala Ala Glu Asp Ser Pro Ser Phe Ser Leu
                85                  90                  95

Leu Gln Ser Ala His Pro Gly Glu His Leu Ala Gln Gly Ala Ser Arg
            100                 105                 110

Leu Gln Val Leu Gln Ala Gln Leu Thr Trp Val Arg Val Ser His Glu
        115                 120                 125

His Leu Leu Gln Arg Val Asp Asn Phe Thr Gln Asn Pro Gly Met Phe
    130                 135                 140

Arg Ile Lys Gly Glu Gln Gly Ala Pro Gly Leu Gln Gly His Lys Gly
145                 150                 155                 160

Ala Met Gly Met Pro Gly Ala Pro Gly Pro Gly Pro Pro Ala Glu
                165                 170                 175

Lys Gly Ala Lys Gly Ala Met Gly Arg Asp Gly Ala Thr Gly Pro Ser
            180                 185                 190

Gly Pro Gln Gly Pro Pro Gly Val Lys Gly Glu Ala Gly Leu Gln Gly
        195                 200                 205

Pro Gln Gly Ala Pro Gly Lys Gln Gly Ala Thr Gly Pro Gly Pro
    210                 215                 220
```

Gln Gly Glu Lys Gly Ser Lys Gly Asp Gly Gly Leu Ile Gly Pro Lys
225                 230                 235                 240

Gly Glu Thr Gly Thr Lys Gly Glu Lys Gly Asp Leu Gly Leu Pro Gly
            245                 250                 255

Ser Lys Gly Asp Arg Gly Met Lys Gly Asp Ala Gly Val Met Gly Pro
        260                 265                 270

Pro Gly Ala Gln Gly Ser Lys Gly Asp Phe Gly Arg Pro Gly Pro Pro
    275                 280                 285

Gly Leu Ala Gly Phe Pro Gly Ala Lys Gly Asp Gln Gly Gln Pro Gly
290                 295                 300

Leu Gln Gly Val Pro Gly Pro Pro Gly Ala Val Gly His Pro Gly Ala
305                 310                 315                 320

Lys Gly Glu Pro Gly Ser Ala Gly Ser Pro Gly Arg Ala Gly Leu Pro
            325                 330                 335

Gly Ser Pro Gly Ser Pro Gly Ala Thr Gly Leu Lys Gly Ser Lys Gly
        340                 345                 350

Asp Thr Gly Leu Gln Gly Gln Gln Gly Arg Lys Gly Glu Ser Gly Val
    355                 360                 365

Pro Gly Pro Ala Gly Val Lys Gly Glu Gln Gly Ser Pro Gly Leu Ala
370                 375                 380

Gly Pro Lys Gly Ala Pro Gly Gln Ala Gly Gln Lys Gly Asp Gln Gly
385                 390                 395                 400

Val Lys Gly Ser Ser Gly Glu Gln Gly Val Lys Gly Glu Lys Gly Glu
            405                 410                 415

Arg Gly Glu Asn Ser Val Ser Val Arg Ile Val Gly Ser Ser Asn Arg
        420                 425                 430

Gly Arg Ala Glu Val Tyr Tyr Ser Gly Thr Trp Gly Thr Ile Cys Asp
    435                 440                 445

Asp Glu Trp Gln Asn Ser Asp Ala Ile Val Phe Cys Arg Met Leu Gly
450                 455                 460

Tyr Ser Lys Gly Arg Ala Leu Tyr Lys Val Gly Ala Gly Thr Gly Gln
465                 470                 475                 480

Ile Trp Leu Asp Asn Val Gln Cys Arg Gly Thr Glu Ser Thr Leu Trp
            485                 490                 495

Ser Cys Thr Lys Asn Ser Trp Gly His His Asp Cys Ser His Glu Glu
        500                 505                 510

Asp Ala Gly Val Glu Cys Ser Val
        515                 520

<210> SEQ ID NO 385
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 385
atggattgga cttggcgctt cttgtttgtg gtggcggcgg ctactggagt gcagtcacaa       60
gtgcaactta aggaatccgg accgggactc gtgcagccgt cacaaactct ttcgcttacc      120
tgtaccgtgt ccggattttc cctgacttcc taccatgtgt cctgggtcag acagcctcct      180
ggaaagggac tggaatggat gggtgccatt tggactgggg gatccattgc gtataactcg      240
ctgctgaagt cgcgcttgtc catttcgaga gatacctcca gtcccaagt gtttctgaag       300

```
atgaactccc tgcaaactga agatactgcc acttactact gtgcccgcga tctgtccgac    360
tattactcga gttacacctc gttcgattac tggggacagg gtgtaatggt cactgtgtcg    420
actgccagca ccaagggccc atcggtcttc cccctggcac cctcctccaa gagcacctct    480
gggggcacag cggccctggg ctgcctggtc aaggactact ccccgaacc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt ccccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgggtggt cagcgtcctc accgtcctgc accaggactg gctgaatggc   1020
aaggagtaca agtgcaaggt cagcaacaaa gccctcccag cccccatcga gaaaaccatc   1080
tccaaagcca aagggcagcc ccgagaacca caggtgtaca ccctgccccc atcccgggat   1140
gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaagt ccctctccct gtctccgggt aaatag                             1416
```

<210> SEQ ID NO 386
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 386

```
atggatatgc gggtgccggc ccagcttctg ggcctgttgc tgctctggct ctccggagcg     60
cgctgtgaca tccaaatgac tcagtccccc gcctcgcttt caacctccct gggagaaacc    120
gtgtccatcg aatgcctggc ttccgaaggg atttccaacg atctggcctg gtaccagcag    180
aagtccggaa agtcacctca gctcctgatc tacgcggcca gccggctgca ggacggcgtg    240
ccttcccgct tttccggttc gggatcaggg actcggtact cgctgaagat ttccgggatg    300
cagcctgagg acgaagcgga ctacttctgc caacaatcct acaagtaccc gctgaccttc    360
ggctccggca ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgcccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
```

<210> SEQ ID NO 387
<211> LENGTH: 1416
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 387

```
atggattgga cttggcgctt cttgtttgtg gtggcggcgg ctactggagt gcagtcacaa      60
gtgcaacttc aagaatccgg accgggactc gtgaagccgt cagaaactct ttcgcttacc     120
tgtaccgtgt ccggattttc cctgacttcc taccatgtgt cctggatcag acagcctcct    180
ggaaagggac tggaatggat cggtgccatt tggactgggg gatccattgc gtataacccg    240
tccctgaagt cgcgcgtgac tatttcggtg gataccacca gaaccaatt cagcctgaag     300
ttgtcctccg tgactgccgc cgatactgcc gtatactact gtgcccgcga tctgtccgac    360
tattactcga gttacacctc gttcgattac tggggacagg gtactctggt cactgtgtcg    420
tcggccagca ccaagggccc atcggtcttc cccctggcac cctcctccaa gagcacctct    480
gggggcacag cggccctggg ctgcctggtc aaggactact ccccgaaccc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt ccccccaaaa cccaaggaca cctcatgat ctcccggacc     840
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgggtggt cagcgtcctc accgtcctgc accaggactg gctgaatggc   1020
aaggagtaca agtgcaaggt cagcaacaaa gccctcccag cccccatcga gaaaaccatc   1080
tccaaagcca agggcagcc ccgagaacca caggtgtaca ccctgccccc atcccgggat    1140
gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaagt ccctctcccct gtctccgggt aaatag                            1416
```

<210> SEQ ID NO 388
<211> LENGTH: 711
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 388

```
atggatatgc gggtgccggc ccagcttctg ggcctgttgc tgctctggct ctccggagcg      60
cgctgtgaca tccaaatgac tcagtccccc tcatcgcttt cagcctccgt gggagacaga    120
gtgaccatca cttgccgggc ttccgaaggg atttccaacg atctggcctg gtaccagcag    180
aagcccggaa aggcccctaa gctcctgatc tacgcggcca gcggctgca gtccggcgtg    240
ccttcccgct tttccggttc gggatcaggg actgacttca ccctgaccat ttccagcctg    300
cagcctgagg acttcgcgac ctactactgc caacaatcct acaagtaccc gctgaccttc    360
ggccaaggca ccaagctcga aatcaagcga actgtggctg caccatctgt cttcatcttc    420
ccgccatctg atgagcagtt gaaatctgga actgcctctg ttgtgtgcct gctgaataac    480
```
ttctatccca gagaggccaa agtacagtgg aagtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgtta a              711

<210> SEQ ID NO 389
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 389
atggattgga cttggcgctt cttgtttgtg gtggcggcgg ctactggagt gcagtcacaa       60
gtgcaacttc aagaatccgg accgggactc gtgaagccgt cagaaactct ttcgcttacc      120
tgtaccgtgt ccggattttc cctgacttcc taccatgtgt cctgggtcag acagcctcct      180
ggaaagggac tggaatggat cggtgccatt tggactgggg gatccattgc gtataacccg      240
tccctgaagt cgcgcgtaac tatttcgaga gatacctcca agaaccaagt gtccctgaag      300
ctgtcgtccg tgactgccgc cgatactgcc gtgtactact gtgcccgcga tctgtccgac      360
tattactcga gttacaccct cgttcgattac tggggacagg gtactctggt cactgtgtcg      420
tcggccagca ccaagggccc atcggtcttc cccctggcac cctcctccaa gagcacctct      480
gggggcacag cggccctggg ctgcctggtc aaggactact cccccgaacc ggtgacggtg      540
tcgtggaact caggcgccct gaccagcggc gtgcacacct tcccggctgt cctacagtcc      600
tcaggactct actccctcag cagcgtggtg accgtgccct ccagcagctt gggcacccag      660
acctacatct gcaacgtgaa tcacaagccc agcaacacca aggtggacaa gaaagttgag      720
cccaaatctt gtgacaaaac tcacacatgc ccaccgtgcc cagcacctga actcctgggg      780
ggaccgtcag tcttcctctt cccccccaaaa cccaaggaca ccctcatgat ctcccggacc      840
cctgaggtca catgcgtggt ggtggacgtg agccacgaag accctgaggt caagttcaac      900
tggtacgtgg acggcgtgga ggtgcataat gccaagacaa agccgcggga ggagcagtac      960
aacagcacgt accgggtggt cagcgtcctc accgtcctgc accaggactg gctgaatggc     1020
aaggagtaca agtgcaaggt cagcaacaaa gccctcccag cccccatcga gaaaaccatc     1080
tccaaagcca aagggcagcc ccgagaacca caggtgtaca ccctgccccc atcccgggat     1140
gagctgacca agaaccaggt cagcctgacc tgcctggtca aaggcttcta tcccagcgac     1200
atcgccgtgg agtgggagag caatgggcag ccggagaaca actacaagac cacgcctccc     1260
gtgctggact ccgacggctc cttcttcctc tacagcaagc tcaccgtgga caagagcagg     1320
tggcagcagg ggaacgtctt ctcatgctcc gtgatgcatg aggctctgca caaccactac     1380
acgcagaagt ccctctccct gtctccgggt aaatag                              1416

<210> SEQ ID NO 390
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 390

```
atggatatgc gggtgccggc ccagcttctg ggcctgttgc tgctctggct ctccggagcg    60
cgctgtgaca tccaaatgac tcagtccccc tcatcgcttt cagcctccgt gggagacaga   120
gtgaccatca cttgccgggc ttccgaaggg atttccaacg atctggcctg gtaccagcag   180
aagcccggaa aggcccctaa gctcctgatc tacgcggcca gccggctgca gtccggcgtg   240
ccttcccgct tttccggttc gggatcaggg actgactaca ccctgaccat ttccagcctg   300
cagcctgagg acttcgcgac ctactactgc aacaatcct acaagtaccc gctgaccttc   360
ggccaaggca ccaagctcga aatcaagcga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta a            711
```

<210> SEQ ID NO 391
<211> LENGTH: 1416
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 391

```
atggattgga cttggcgctt cttgtttgtg gtggcggcgg ctactggagt gcagtcacaa    60
gtgcaacttc aagaatccgg accgggactc gtgaagccgt cagaaactct ttcgcttacc   120
tgtaccgtgt ccggattttc cctgacttcc taccatgtgt cctgggtcag acagcctcct   180
ggaaagggac tggaatggat cggtgccatt tggactgggg gatccattgc gtataaccg   240
tccctgaagt cgcgcgtaac tatttcgaga gatacctcca agaaccaagt gtccctgaag   300
ctgtcgtccg tgactgccgc cgatactgcc gtgtactact gtgcccgcga tctgtccgac   360
tattactcga gttacaccta gttcgattac tggggacagg gtactctggt cactgtgtcg   420
tcggccagca ccaagggccc atcggtcttc cccctggcac cctcctccaa gagcacctct   480
gggggcacag cggccctggg ctgcctggtc aaggactact ccccgaaccc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacccag   660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt ccccccaaaa cccaaggaca cctcatgat ctcccggacc   840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgggtggt cagcgtcctc accgtcctgc accaggactg gctgaatggc  1020
aaggagtaca agtgcaaggt cagcaacaaa gccctcccag cccccatcga gaaaaccatc  1080
tccaaagcca aagggcagcc ccgagaacca caggtgtaca ccctgccccc atcccgggat  1140
gagctgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
```

| | |
|---|---|
| tggcagcagg ggaacgtctt ctcatgctcc gtgatgcatg aggctctgca caaccactac | 1380 |
| acgcagaagt ccctctccct gtctccgggt aaatag | 1416 |

<210> SEQ ID NO 392
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 392

| | |
|---|---|
| atggatatgc gggtgccggc ccagcttctg ggcctgttgc tgctctggct ctccggagcg | 60 |
| cgctgtgaca tccaaatgac tcagtccccc tcatcgcttt cagcctccgt gggagacaga | 120 |
| gtgaccatca cttgccgggc ttccgaaggg atttccaacg atctggcctg gtaccagcag | 180 |
| aagcccggaa aggcccctaa gctcctgatc tacgcggcca gccggctgca gtccggcgtg | 240 |
| ccttcccgct tttccggttc gggatcaggg actgactaca ccctgaccat ttccagcatg | 300 |
| cagcctgagg acttcgcgac ctactactgc caacaatcct acaagtaccc gctgaccttc | 360 |
| ggccaaggca ccaagctcga aatcaagcga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata cgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta a | 711 |

<210> SEQ ID NO 393
<211> LENGTH: 1416
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 393

| | |
|---|---|
| atggattgga cttggcgctt cttgtttgtg gtggcggcgg ctactggagt gcagtcacaa | 60 |
| gtgcaacttc aagaatccgg accgggactc gtgaagccgt cagaaactct ttcgcttacc | 120 |
| tgtaccgtgt ccggattttc cctgacttcc taccatgtgt cctgggtcag acagcctcct | 180 |
| ggaaagggac tggaatggat gggtgccatt tggactgggg gatccattgc gtataacccg | 240 |
| tccctgaagt cgcgcttgac tatttcgaga gatacctcca agaaccaagt gtcgctgaag | 300 |
| atgtcctccc tgactgccgc cgatactgcc gtatactact gtgcccgcga tctgtccgac | 360 |
| tattactcga gttacacctc gttcgattac tggggacagg gtactctggt cactgtgtcg | 420 |
| tcggccagca ccaagggccc atcggtcttc cccctggcac cctcctccaa gagcacctct | 480 |
| gggggcacag cggccctggg ctgcctggtc aaggactact tccccgaacc ggtgacggtg | 540 |
| tcgtggaact caggcgccct gaccagcggc gtgcacacct tcccggctgt cctacagtcc | 600 |
| tcaggactct actccctcag cagcgtggtg accgtgccct ccagcagctt gggcacccag | 660 |
| acctacatct gcaacgtgaa tcacaagccc agcaacacca aggtggacaa gaaagttgag | 720 |
| cccaaatctt gtgacaaaac tcacacatgc ccaccgtgcc cagcacctga actcctgggg | 780 |
| ggaccgtcag tcttcctctt ccccccaaaa cccaaggaca cctcatgat ctcccggacc | 840 |
| cctgaggtca catgcgtggt ggtggacgtg agccacgaag accctgaggt caagttcaac | 900 |

```
tggtacgtgg acggcgtgga ggtgcataat gccaagacaa agccgcggga ggagcagtac    960
aacagcacgt accgggtggt cagcgtcctc accgtcctgc accaggactg gctgaatggc   1020
aaggagtaca agtgcaaggt cagcaacaaa gccctcccag cccccatcga gaaaaccatc   1080
tccaaagcca aagggcagcc ccgagaacca caggtgtaca ccctgccccc atcccgggat   1140
gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaagt ccctctccct gtctccgggt aaatag                             1416
```

<210> SEQ ID NO 394
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 394

```
atggatatgc gggtgccggc ccagcttctg ggcctgttgc tgctctggct ctccggagcg     60
cgctgtgaca tccaaatgac tcagtccccc tcatcgcttt cagcctccgt gggagacaga    120
gtgaccatca cttgccgggc ttccgaaggg atttccaacg atctggcctg gtaccagcag    180
aagcccggaa aggcccctaa gctcctgatc tacgcggcca gccggctgca gtccggcgtg    240
ccttcccgct tttccggttc gggatcaggg actgactaca ccctgaccat ttccagcctg    300
cagcctgagg acttcgcgac ctactactgc caacaatcct acaagtaccc gctgaccttc    360
ggccaaggca ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgcctccaa atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
```

<210> SEQ ID NO 395
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 395

```
atggattgga cttggcgctt cttgtttgtg gtggcggcgg ctactggagt gcagtcacaa     60
gtgcaacttc aagaatccgg accgggactc gtgaagccgt cagaaactct ttcgcttacc    120
tgtaccgtgt ccggattttc cctgacttcc taccatgtgt cctgggtcag acagcctcct    180
ggaaagggac tggaatggat gggtgccatt tggactgggg atccattgc gtataacccg    240 tccctgaagt cgcgcttgac tatttcgaga gatacctcca gaaccaagt gtcgctgaag    300 atgtcctccc tgactgccgc cgatactgcc gtatactact gtgcccgcga tctgtccgac    360
tattactcga gttacaccct cgttcgattac tggggacagg gtactctggt cactgtgtcg    420
```

| | |
|---|---|
| tcggccagca ccaagggccc atcggtcttc ccctggcac cctcctccaa gagcacctct | 480 |
| ggggcacag cggccctggg ctgcctggtc aaggactact tccccgaacc ggtgacggtg | 540 |
| tcgtggaact caggcgccct gaccagcggc gtgcacacct tcccggctgt cctacagtcc | 600 |
| tcaggactct actccctcag cagcgtggtg accgtgccct ccagcagctt gggcacccag | 660 |
| acctacatct gcaacgtgaa tcacaagccc agcaacacca aggtggacaa gaaagttgag | 720 |
| cccaaatctt gtgacaaaac tcacacatgc ccaccgtgcc cagcacctga actcctgggg | 780 |
| ggaccgtcag tcttcctctt ccccccaaaa cccaaggaca ccctcatgat ctcccggacc | 840 |
| cctgaggtca catgcgtggt ggtggacgtg agccacgaag accctgaggt caagttcaac | 900 |
| tggtacgtgg acggcgtgga ggtgcataat gccaagacaa agccgcggga ggagcagtac | 960 |
| aacagcacgt accgggtggt cagcgtcctc accgtcctgc accaggactg gctgaatggc | 1020 |
| aaggagtaca agtgcaaggt cagcaacaaa gccctcccag cccccatcga gaaaaccatc | 1080 |
| tccaaagcca aagggcagcc ccgagaacca caggtgtaca ccctgccccc atcccgggat | 1140 |
| gagctgacca agaaccaggt cagcctgacc tgcctggtca aaggcttcta tcccagcgac | 1200 |
| atcgccgtgg agtgggagag caatgggcag ccggagaaca actacaagac cacgcctccc | 1260 |
| gtgctggact ccgacggctc cttcttcctc tacagcaagc tcaccgtgga caagagcagg | 1320 |
| tggcagcagg ggaacgtctt ctcatgctcc gtgatgcatg aggctctgca caaccactac | 1380 |
| acgcagaagt ccctctcct gtctccgggt aaatag | 1416 |

<210> SEQ ID NO 396
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 396

| | |
|---|---|
| atggatatgc gggtgccggc ccagcttctg ggcctgttgc tgctctggct ctccggagcg | 60 |
| cgctgtgaca tccaaatgac tcagtccccc tcatcgcttt cagcctccgt gggagacaga | 120 |
| gtgaccatca cttgccgggc ttccgaaggg atttccaacg atctggcctg gtaccagcag | 180 |
| aagcccggaa aggcccctaa gctcctgatc tacgcggcca gccggctgca gtccggcgtg | 240 |
| ccttcccgct tttccggttc gggatcaggg actgactaca ccctgaccat ttccagcatg | 300 |
| cagcctgagg acttcgcgac ctactactgc caacaatcct acaagtaccc gctgaccttc | 360 |
| ggccaaggca ccaagctcga aatcaagcga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata acgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcaccat | 660 |
| cagggcctga gctcgcccgt cacaaagagc ttcaacaggg gagagtgtta a | 711 |

<210> SEQ ID NO 397
<211> LENGTH: 1416
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 397

```
atggattgga cttggcgctt cttgtttgtg gtggcggcgg ctactggagt gcagtcacaa    60
gtgcaacttc aagaatccgg accgggactc gtgaagccgt cagaaactct ttcgcttacc   120
tgtaccgtgt ccggattttc cctgacttcc taccatgtgt cctgggtcag acagcctcct   180
ggaaagggac tggaatggat cggtgccatt tggactgggg gatccattgc gtataacccg   240
tccctgaagt cgcgcgtaac tatttcgaga gatacctcca agaaccaagt gtccctgaag   300
ctgtcgtccg tgactgccgc cgatactgcc gtgtactact gtgcccgcga tctgtccgac   360
tattactcga gttacacctc gttcgattac tggggacagg gtactctggt cactgtgtcg   420
tcggccagca ccaagggccc atcggtcttc cccctggcac cctcctccaa gagcacctct   480
gggggcacag cggccctggg ctgcctggtc aaggactact tccccgaacc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacccag   660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt ccccccaaaa cccaaggaca cctcatgat ctcccggacc   840 cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgggtggt cagcgtcctc accgtcctgc accaggactg gctgaatggc  1020
aaggagtaca agtgcaaggt cagcaacaaa gccctcccag cccccatcga gaaaaccatc  1080
tccaaagcca agggcagccc cgagaaccca caggtgtaca ccctgccccc atcccgggat  1140
gagctgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaagt ccctctcccct gtctccgggt aaatag                           1416
```

<210> SEQ ID NO 398
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 398

```
atggatatgc gggtgccggc ccagcttctg ggcctgttgc tgctctggct ctccggagcg    60
cgctgtgaca tccaaatgac tcagtccccc tcatcgcttt cagcctccgt gggagacaga   120
gtgaccatca cttgccgggc ttccgaaggg atttccaacg atctggcctg gtaccagcag   180
aagcccggaa aggcccctaa gctcctgatc tacgcggcca gccggctgca ggacggcgtg   240
ccttcccgct tttccggttc gggatcaggg actgactaca ccctgaccat ttccagcctg   300
cagcctgagg acttcgcgac ctactactgc caacaatcct acaagtaccc gctgaccttc   360
ggccaaggca ccaagctcga aatcaagcga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
```
ctgacgctga gcaaagcaga ctacgagaaa cacaaagtct acgcctgcga agtcacccat      660
cagggcctga gctcgcccgt cacaaagagc ttcaacaggg gagagtgtta a               711

<210> SEQ ID NO 399
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 399
atggattgga cttggcgctt cttgtttgtg gtggcggcgg ctactggagt gcagtcacaa       60
gtgcaacttc aagaatccgg accgggactc gtgaagccgt cagaaactct ttcgcttacc      120
tgtaccgtgt ccggattttc cctgacttcc taccatgtgt cctgggtcag acagcctcct      180
ggaaagggac tggaatggat cggtgccatt tggactgggg gatccattgc gtataacccg      240
tccctgaagt cgcgcgtaac tatttcgaga gatacctcca agaaccaagt gtccctgaag      300
ctgtcgtccg tgactgccgc cgatactgcc gtgtactact gtgcccgcga tctgtccgac      360
tattactcga gttacacctc gttcgattac tggggacagg gtactctggt cactgtgtcg      420
tcggccagca ccaagggccc atcggtcttc cccctggcac cctcctccaa gagcacctct      480
gggggcacag cggccctggg ctgcctggtc aaggactact ccccgaacc ggtgacggtg      540 tcgtggaact caggcgccct gaccagcggc gtgcacacct tcccggctgt cctacagtcc      600
tcaggactct actccctcag cagcgtggtg accgtgccct ccagcagctt gggcacccag      660
acctacatct gcaacgtgaa tcacaagccc agcaacacca aggtggacaa gaaagttgag      720
cccaaatctt gtgacaaaac tcacacatgc ccaccgtgcc cagcacctga actcctgggg      780
ggaccgtcag tcttcctctt ccccccaaaa cccaaggaca ccctcatgat ctcccggacc      840
cctgaggtca catgcgtggt ggtggacgtg agccacgaag accctgaggt caagttcaac      900
tggtacgtgg acggcgtgga ggtgcataat gccaagacaa agccgcggga ggagcagtac      960
aacagcacgt accgggtggt cagcgtcctc accgtcctgc accaggactg gctgaatggc     1020
aaggagtaca agtgcaaggt cagcaacaaa gccctcccag cccccatcga gaaaaccatc     1080
tccaaagcca aagggcagcc ccgagaacca caggtgtaca ccctgccccc atcccgggat     1140
gagctgacca agaaccaggt cagcctgacc tgcctggtca aaggcttcta tcccagcgac     1200
atcgccgtgg agtgggagag caatgggcag ccggagaaca actacaagac cacgcctccc     1260
gtgctggact ccgacggctc cttcttcctc tacagcaagc tcaccgtgga caagagcagg     1320
tggcagcagg ggaacgtctt ctcatgctcc gtgatgcatg aggctctgca caaccactac     1380
acgcagaagt ccctctccct gtctccgggt aaatag                               1416

<210> SEQ ID NO 400
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 400
atggatatgc gggtgccggc ccagcttctg ggcctgttgc tgctctggct ctccggagcg       60
cgctgtgaca tccaaatgac tcagtccccc tcatcgcttt caacctccgt gggagacaga      120

```
gtgaccatca cttgccgggc ttccgaaggg atttccaacg atctggcctg gtaccagcag    180
aagcccggaa agtcgcctaa gctcctgatc tacgcggcca gccggctgca gtccggcgtg    240
ccttcccgct tttccggttc gggatcaggg actgactaca ccctgaccat ttccagcctg    300
cagcctgagg acttcgcgac ctacttctgc aacaatcct acaagtaccc gctgaccttc     360
ggccaaggca ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a            711

<210> SEQ ID NO 401
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 401
atggattgga cttggcgctt cttgtttgtg gtggcggcgg ctactggagt gcagtcacaa     60
gtgcaacttc aagaatccgg accgggactc gtgaagccgt cagaaactct ttcgcttacc    120
tgtaccgtgt ccggattttc cctgacttcc taccatgtgt cctgggtcag acagcctcct    180
ggaaagggac tggaatggat cggtgccatt tggactgggg gatccattgc gtataacccg    240
tccctgaagt cgcgcgtaac tatttcgaga gatacctcca agaaccaagt gtccctgaag    300
ctgtcgtccg tgactgccgc cgatactgcc gtgtactact gtgcccgcga tctgtccgac    360
tattactcga gttacaccctc gttcgattac tggggacagg gtactctggt cactgtgtcg    420
tcggccagca ccaagggccc atcggtcttc ccctggcac cctcctccaa gagcacctct    480
gggggcacag cggccctggg ctgcctggtc aaggactact ccccgaacc ggtgacggtg    540 tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt ccccccaaaa cccaaggaca cctcatgat ctcccggacc     840 cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgggtggt cagcgtcctc accgtcctgc accaggactg gctgaatggc    1020
aaggagtaca agtgcaaggt cagcaacaaa gccctcccag cccccatcga gaaaaccatc    1080
tccaaagcca aagggcagcc ccgagaacca caggtgtaca ccctgccccc atcccgggat    1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
acgcagaagt ccctctccct gtctccgggt aaatag                              1416
```

<210> SEQ ID NO 402
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 402

| atggatatgc gggtgccggc ccagcttctg ggcctgttgc tgctctggct ctccggagcg | 60 |
| cgctgtgaca tccaaatgac tcagtccccc tcatcgcttt caacctccgt gggagacaga | 120 |
| gtgaccatca cttgccgggc ttccgaaggg atttccaacg atctggcctg gtaccagcag | 180 |
| aagcccggaa agtcccctaa gctcctgatc tacgcggcca gccggctgca ggacggcgtg | 240 |
| ccttcccgct tttccggttc gggatcaggg actgactaca ccctgaccat ttccagcctg | 300 |
| cagcctgagg acgaagcgac ctacttctgc aacaatcct acaagtaccc gctgaccttc | 360 |
| ggccaaggca ccaagctcga aatcaagcga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata cgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta a | 711 |

<210> SEQ ID NO 403
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 403

| atggattgga cttggcgctt cttgtttgtg gtggcggcgg ctactggagt gcagtcagaa | 60 |
| gtgcaacttc aagaatccgg accgggactc gtgaagccgt cagaaactct ttcgcttacc | 120 |
| tgtaccgtgt ccggatttc cctgacttcc taccatgtgt cctgggtcag acagcctcct | 180 |
| ggaaagggac tggaatggat cggtgccatt tggactgggg gatccattgc gtataacccg | 240 |
| tccctgaagt cgcgcgtaac tatttcgaga gatacctcca agaaccaagt gtccctgaag | 300 |
| ctgtcgtccg tgactgccgc cgatactgcc gtgtactact gtgcccgcga tctgtccgac | 360 |
| tattactcga gttacaccct cgttcgattac tggggacagg gtactctggt cactgtgtcg | 420 |
| tcggccagca ccaagggccc atcggtcttc cccctggcac cctcctccaa gagcacctct | 480 |
| gggggcacag cggccctggg ctgcctggtc aaggactact tccccgaacc ggtgacggtg | 540 |
| tcgtggaact caggcgccct gaccagcggc gtgcacacct tcccggctgt cctacagtcc | 600 |
| tcaggactct actccctcag cagcgtggtg accgtgccct ccagcagctt gggcacccag | 660 |
| acctacatct gcaacgtgaa tcacaagccc agcaacacca aggtggacaa gaaagttgag | 720 |
| cccaaatctt gtgacaaaac tcacacatgc ccaccgtgcc cagcacctga actcctgggg | 780 |
| ggaccgtcag tcttcctctt ccccccaaaa cccaaggaca ccctcatgat ctcccggacc | 840 |
| cctgaggtca catgcgtggt ggtggacgtg agccacgaag accctgaggt caagttcaac | 900 |
| tggtacgtgg acggcgtgga ggtgcataat gccaagacaa agccgcggga ggagcagtac | 960 |
| aacagcacgt accgggtggt cagcgtcctc accgtcctgc accaggactg gctgaatggc | 1020 |

| | |
|---|---|
| aaggagtaca agtgcaaggt cagcaacaaa gccctcccag cccccatcga gaaaaccatc | 1080 |
| tccaaagcca aagggcagcc ccgagaacca caggtgtaca ccctgccccc atcccgggat | 1140 |
| gagctgacca agaaccaggt cagcctgacc tgcctggtca aaggcttcta tcccagcgac | 1200 |
| atcgccgtgg agtgggagag caatgggcag ccggagaaca actacaagac cacgcctccc | 1260 |
| gtgctggact ccgacggctc cttcttcctc tacagcaagc tcaccgtgga caagagcagg | 1320 |
| tggcagcagg ggaacgtctt ctcatgctcc gtgatgcatg aggctctgca caaccactac | 1380 |
| acgcagaagt ccctctccct gtctccgggt aaatag | 1416 |

<210> SEQ ID NO 404
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404

| | |
|---|---|
| atggatatgc gggtgccggc ccagcttctg ggcctgttgc tgctctggct ctccggagcg | 60 |
| cgctgtgaca tccaaatgac tcagtccccc tcatcgcttt cagcctccgt gggagacaga | 120 |
| gtgaccatca cttgccgggc ttccgaaggg atttccaacg atctggcctg gtaccagcag | 180 |
| aagcccggaa aggcccctaa gctcctgatc tacgcggcca gccggctgca ggacggcgtg | 240 |
| ccttcccgct tttccggttc gggatcaggg actgactaca ccctgaccat ttccagcctg | 300 |
| cagcctgagg acttcgcgac ctactactgc caacaatcct acaagtaccc gctgaccttc | 360 |
| ggccaaggca ccaagctcga aatcaagcga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata acgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta a | 711 |

<210> SEQ ID NO 405
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 405

| | |
|---|---|
| atggattgga cttggcgctt cttgtttgtg gtggcggcgg ctactggagt gcagtcagaa | 60 |
| gtgcaacttc aagaatccgg accgggactc gtgaagccgt cagaaactct ttcgcttacc | 120 |
| tgtaccgtgt ccggattttc cctgacttcc taccatgtgt cctgggtcag acagcctcct | 180 |
| ggaaagggac tggaatggat cggtgccatt tggactgggg gatccattgc gtataacccg | 240 |
| tccctgaagt cgcgcgtaac tatttcgaga gatacctcca agaaccaagt gtccctgaag | 300 |
| ctgtcgtccg tgactgccgc cgatactgcc gtgtactact gtgcccgcga tctgtccgac | 360 |
| tattactcga gttacaccct cgttcgattac tggggacagg gtactctggt cactgtgtcg | 420 |
| tcggccagca ccaagggccc atcggtcttc cccctggcac cctcctccaa gagcacctct | 480 |
| gggggcacag cggccctggg ctgcctggtc aaggactact tccccgaacc ggtgacggtg | 540 |

```
tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt ccccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgggtggt cagcgtcctc accgtcctgc accaggactg gctgaatggc   1020
aaggagtaca agtgcaaggt cagcaacaaa gccctcccag cccccatcga gaaaaccatc   1080
tccaaagcca agggcagccc cgagaaccac aggtgtacac cctgccccc atcccgggat    1140 gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaagt ccctctccct gtctccgggt aaatag                             1416
```

<210> SEQ ID NO 406
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406

```
atggatatgc gggtgccggc ccagcttctg ggcctgttgc tgctctggct ctccggagcg     60
cgctgtgaca tccaaatgac tcagtccccc tcatcgcttt caacctccgt gggagacaga    120
gtgaccatca cttgccgggc ttccgaaggg atttccaacg atctggcctg gtaccagcag    180
aagcccggaa agtcgcctaa gctcctgatc tacgcggcca gccggctgca gtccggcgtg    240
ccttcccgct tttccggttc gggatcaggg actgactaca ccctgaccat ttccagcctg    300
cagcctgagg acttcgcgac ctacttctgc aacaatcct acaagtaccc gctgaccttc    360
ggccaaggca ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
```

<210> SEQ ID NO 407
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 407

```
atggattgga cttggcgctt cttgtttgtg gtggcggcgg ctactggagt gcagtcagaa     60
gtgcaacttc aagaatccgg accgggactc gtgaagccgt cagaaactct ttcgcttacc    120
```

```
tgtaccgtgt ccggattttc cctgacttcc taccatgtgt cctgggtcag acagcctcct      180
ggaaagggac tggaatggat cggtgccatt tggactgggg gatccattgc gtataacccg      240
tccctgaagt cgcgcgtaac tatttcgaga gatacctcca agaaccaagt gtccctgaag      300
ctgtcgtccg tgactgccgc cgatactgcc gtgtactact gtgcccgcga tctgtccgac      360
tattactcga gttacacctc gttcgattac tggggacagg gtactctggt cactgtgtcg      420
tcggccagca ccaagggccc atcggtcttc cccctggcac cctcctccaa gagcacctct      480
gggggcacag cggccctggg ctgcctggtc aaggactact ccccgaaccg gtgacggtg      540 tcgtggaact caggcgccct gaccagcggc gtgcacacct tcccggctgt cctacagtcc      600
tcaggactct actccctcag cagcgtggtg accgtgccct ccagcagctt gggcacccag      660
acctacatct gcaacgtgaa tcacaagccc agcaacacca aggtggacaa gaaagttgag      720
cccaaatctt gtgacaaaac tcacacatgc ccaccgtgcc cagcacctga actcctgggg      780
ggaccgtcag tcttcctctt ccccccaaaa cccaaggaca ccctcatgat ctcccggacc      840
cctgaggtca catgcgtggt ggtggacgtg agccacgaag accctgaggt caagttcaac      900
tggtacgtgg acggcgtgga ggtgcataat gccaagacaa agccgcggga ggagcagtac      960
aacagcacgt accgggtggt cagcgtcctc accgtcctgc accaggactg gctgaatggc      1020
aaggagtaca agtgcaaggt cagcaacaaa gccctcccag cccccatcga gaaaaccatc      1080
tccaaagcca aagggcagcc ccgagaacca caggtgtaca ccctgccccc atcccgggat      1140
gagctgacca agaaccaggt cagcctgacc tgcctggtca aaggcttcta tcccagcgac      1200
atcgccgtgg agtgggagag caatgggcag ccggagaaca actacaagac cacgcctccc      1260
gtgctggact ccgacggctc cttcttcctc tacagcaagc tcaccgtgga caagagcagg      1320
tggcagcagg ggaacgtctt ctcatgctcc gtgatgcatg aggctctgca caaccactac      1380
acgcagaagt ccctctccct gtctccgggt aaatag                               1416
```

<210> SEQ ID NO 408
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 408

```
atggatatgc gggtgccggc ccagcttctg ggcctgttgc tgctctggct ctccggagcg       60
cgctgtgaca tccaaatgac tcagtccccc tcatcgcttt caacctccgt gggagacaga      120
gtgaccatca cttgccgggc ttccgaaggg atttccaacg atctggcctg gtaccagcag      180
aagcccggaa agtcccctaa gctcctgatc tacgcggcca gccggctgca ggacggcgtg      240
ccttcccgct tttccggttc gggatcaggg actgactaca ccctgaccat ttccagcctg      300
cagcctgagg acgaagcgac ctacttctgc caacaatcct acaagtaccc gctgaccttc      360
ggccaaggca ccaagctcga aatcaagcga actgtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcaccat      660 cagggcctga gctcgcccgt cacaaagagc ttcaacaggg gagagtgtta a              711
```

<210> SEQ ID NO 409
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 409

```
atggattgga cttggcgctt cttgtttgtg gtggcggcgg ctactggagt gcagtcacaa      60
atccagctcg tgcagtccgg gccagagctg aaaaagcccg agaatccgtc aagattagc     120
tgcaaggcct ccggctacac cttcaccgac tacgcagtga actgggtcaa gcaggccccg     180
ggaaatggtc tgaagtggat gggctggatt aacacgcaga ccgggaagcc tacctacgcc     240
gacgacttca agcaacggtt cgtgttctcg cttgaaacta gcgcctcgac ctcgttcctg     300
caaatcaaca acctgaacat cgaggacacc gccacctact tctgcacaag agactcctac     360
tattactcat cctccctcga ttactgggga cagggcgtga tggtcactgt gtccagcgcc     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttccccccc aaaacccaag gacacccctca tgatctcccg gacccctgag    840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccggg tggtcagcgt cctcaccgtc ctgcaccagg actggctgaa tggcaaggag    1020
tacaagtgca aggtcagcaa caaagccctc ccagccccca tcgagaaaac catctccaaa    1080
gccaaagggc agccccgaga accacaggtg tacaccctgc ccccatcccg ggatgagctg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagtccctct ccctgtctcc gggtaaatag                                    1410
```

<210> SEQ ID NO 410
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 410

```
atggatatgc gggtgccggc ccagcttctg ggcctgttgc tgctctggct ctccggagcg      60
cgctgtgaca tccaaatgac tcagtcccct gcatccctga gcgcgagcct gggggagact     120
gtgtccattg aatgcctcgc ctccgccgga atttctaacg acctggcctg gtaccagcag     180
aagtccggaa agtcgcccca gctgctgatc tacgccgctt cgaggcttca ggatggtgtc     240
```

```
ccgtcacggt ttagcggatc aggatccggc accagattct ccctgaaaat cagcgacatg      300
cagccagagg acgaagccga ctacttctgc aacaatcgt acaagtatcc ctggaccttc       360
ggcgggggca ccaagctcga actgaagcga actgtggctg caccatctgt cttcatcttc     420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc   600
ctgacgctga gcaaagcaga ctacgagaaa cacaaagtct acgcctgcga agtcacccat     660
cagggcctga gctcgcccgt cacaaagagc ttcaacaggg gagagtgtta a              711
```

<210> SEQ ID NO 411
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 411

```
atggactgga cctggagatt tttattcgtc gtcgctgccg ccaccggagt gcaatcacaa      60
gtacaactgg tgcagagcgg ggccgaagtc aagaagcccg gcgcctccgt gaaagtgtcg     120
tgcaaagcct cgggttacac attcactgac tacgcagtga actgggtcag acaggcaccg     180
ggccagggac tcgagtggat gggctggatc aacactcaga ctgggaagcc cacctatgct     240
cagaagttcc agggaagggt caccatgacc cgcgacacca gcacctccac cgtgtacatg    300
gaattgagca gcctgcggtc cgaagataca gccgtgtact attgtgcgag ggactcctac   360
tactactcat cctcgctcga ctactggggc cagggtaccc tcgtgaccgt tagctcggcc    420
tctactaagg gtccgtccgt gttcccgttg gccccgagct cgaagtccac ctccggggga   480
accgctgcgc ttggatgcct ggtcaaggac tacttcccg agcccgtgac ggtgtcctgg    540
aactccgggg ccctgacctc gggagtgcac actttccctg cggtgctgca gagctcagga   600
ctgtacagcc tcagctccgt cgtgaccgtg ccttcgtcct cgctgggcac ccagacctac    660
atctgcaacg tgaaccacaa gccgagcaac accaaggtcg acaagaaagt cgagccgaag   720
tcatgcgaca agactcacac ttgcccgccg tgccccgcgc ctgagcttct ggcgggccc   780 tccgtgttcc tgtttccgcc aaagcccaag gatactctga tgatttcgcg gactcctgaa   840
gtgacctgtg tggtcgtcga tgtgtcccat gaggacccg aggtcaagtt caattggtac    900
gtggacggcg tggaggtcca caatgccaag acgaagccgc gggaagaaca gtacaactcc    960
acttatcgcg tggtgtccgt gctcaccgtg ctgcatcagg actggctgaa cggaaaggag  1020
tacaagtgca aagtgtccaa caaggccctg cctgccccaa ttgaaaagac catctccaaa  1080
gcgaagggcc agccgcgcga accacaagtg tacaccctgc ctccttcccg ggatgaactg  1140
accaagaacc aagtgtccct gacttgcctc gtgaagggtt tctacccgtc cgacatcgcc  1200
gtggaatggg agagcaacgg acagccggag aacaattaca agactacccc acccgtgctc  1260
gattcggacg gcagcttctt cctgtactcc aagctgaccg tggataagtc ccgctggcaa  1320
cagggaaacg tgttcagttg ttccgtgatg cacgaagccc tgcacaacca ctacacccag  1380
aagtcactgt ccctgtctcc gggaaaataa                                    1410
```

<210> SEQ ID NO 412
<211> LENGTH: 711
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 412

| | | | | | |
|---|---|---|---|---|---|
| atggatatga | gagtgcctgc | acaacttctt | ggattactgc | tgctttggtt | gtcgggagcc | 60 |
| agatgcgata | tccagatgac | ccagtccccg | tcgagcctgt | cagcttccgt | gggcgaccgg | 120 |
| gtcaccatta | cttgtcgcgc | tcggccggt | attagcaatg | acttggcctg | gtaccagcag | 180 |
| aagcctggga | aggcccccaa | gctcctcatc | tacgcggctt | cccgctgca | agacggcgtg | 240 |
| ccgtcaaggt | tcagcggttc | gggctccgga | actgacttca | ccctcactat | ctcgtccctg | 300 |
| caacccgaag | atttcgcaac | ctactactgc | cagcagtcct | ataagtaccc | tggactttc | 360 |
| ggacaaggca | ccaagctcga | gatcaagcgg | accgtggccg | ccccgagcgt | gtttatcttc | 420 |
| ccgccatctg | acgaacagct | gaagtccggg | acagcgtccg | tggtctgcct | gctcaacaac | 480 |
| ttctaccccc | gcgaggccaa | agtgcagtgg | aaagtcgata | acgcgctgca | gtccggaaac | 540 |
| agccaggaaa | gcgtgactga | gcaagactcc | aaggactcca | cctactccct | gtcatccacc | 600 |
| ctgacgctgt | ccaaggccga | ctacgaaaag | cacaaggtct | acgcctgcga | agtgacccat | 660 |
| cagggcctgt | caagccctgt | gaccaagtcg | ttcaaccggg | gagagtgtta | a | 711 |

<210> SEQ ID NO 413
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 413

| | | | | | |
|---|---|---|---|---|---|
| atggactgga | cctggagatt | tttattcgtc | gtcgctgccg | ccaccggagt | gcaatcacaa | 60 |
| gtacaactgg | tgcagagcgg | ggccgaagtc | aagaagcccg | gcgcctccgt | gaaagtgtcg | 120 |
| tgcaaagcct | cgggttacac | attcactgac | tacgcagtga | actgggtcag | acaggcaccg | 180 |
| ggccagggac | tcgagtggat | gggctggatc | aacactcaga | ctgggaagcc | cacctatgct | 240 |
| cagaagttcc | agggaagggt | caccatgacc | ctggacacca | gcacctccac | cgcatacatg | 300 |
| gaattgagca | gcctgcggtc | cgaagataca | gccgtgtact | attgtactag | ggactcctac | 360 |
| tactactcat | cctcgctcga | ctactgggc | cagggtaccc | tcgtgaccgt | tagctcggcc | 420 |
| tctactaagg | gtccgtccgt | gttcccgttg | gccccgagct | cgaagtccac | ctccggggga | 480 |
| accgctgcgc | ttggatgcct | ggtcaaggac | tacttccccg | agcccgtgac | ggtgtcctgg | 540 |
| aactccgggg | ccctgacctc | gggagtgcac | actttccctg | cggtgctgca | gagctcagga | 600 |
| ctgtacagcc | tcagctccgt | cgtgaccgtg | ccttcgtcct | cgctgggcac | ccagacctac | 660 |
| atctgcaacg | tgaaccacaa | gccgagcaac | accaaggtcg | acaagaaagt | cgagccgaag | 720 |
| tcatgcgaca | agactcacac | ttgcccgccg | tgccccgcgc | ctgagcttct | ggcgggccc | 780 |
| tccgtgttcc | tgtttccgcc | aaagcccaag | gatactctga | tgatttcgcg | gactcctgaa | 840 |
| gtgacctgtg | tggtcgtcga | tgtgtcccat | gaggaccccg | aggtcaagtt | caattggtac | 900 |
| gtggacggcg | tggaggtcca | caatgccaag | acgaagccgc | gggaagaaca | gtacaactcc | 960 |
| acttatcgcg | tggtgtccgt | gctcaccgtg | ctgcatcagg | actggctgaa | cggaaaggag | 1020 |
| tacaagtgca | aagtgtccaa | caaggccctg | cctgccccaa | ttgaaaagac | catctcaaaa | 1080 |
| gcgaagggcc | agccgcgcga | accacaagtg | tacaccctgc | ctccttcccg | ggatgaactg | 1140 |

```
accaagaacc aagtgtccct gacttgcctc gtgaagggtt tctacccgtc cgacatcgcc    1200
gtggaatggg agagcaacgg acagcccgag aacaattaca agactacccc acccgtgctc    1260
gattcggacg gcagcttctt cctgtactcc aagctgaccg tggataagtc ccgctggcaa    1320
cagggaaacg tgttcagttg ttccgtgatg cacgaagccc tgcacaacca ctacacccag    1380
aagtcactgt ccctgtctcc gggaaaataa                                     1410

<210> SEQ ID NO 414
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414
atggatatga gagtgcctgc acaacttctt ggattactgc tgctttggtt gtcgggagcc     60
agatgcgata tccagatgac ccagtccccg tcgagcctgt cagcttccgt gggcgaccgg    120
gtcaccatta cttgtcgcgc ctcggccggt attagcaatg acttggcctg gtaccagcag    180
aagcctggga aggcccccaa gctcctcatc tacgcggctt cccgcctgca agacggcgtg    240
ccgtcaaggt tcagcggttc gggctccgga actgacttca ccctcactat ctcgtccctg    300
caacccgaag atttcgcaac ctactactgc cagcagtcct ataagtaccc ctggactttc    360
ggacaaggca ccaagctcga gatcaagcgg accgtggccg ccccgagcgt gtttatcttc    420
ccgccatctg acgaacagct gaagtccggg acagcgtccg tggtctgcct gctcaacaac    480
ttctaccccc gcgaggccaa agtgcagtgg aaagtcgata cgcgctgca gtccggaaac    540 agccaggaaa gcgtgactga gcaagactcc aaggactcca cctactccct gtcatccacc    600
ctgacgctgt ccaaggccga ctacgaaaag cacaaggtct acgcctgcga agtgacccat    660
cagggcctgt caagccctgt gaccaagtcg ttcaaccggg gagagtgtta a             711

<210> SEQ ID NO 415
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415
atggactgga cctggagatt tttattcgtc gtcgctgccg ccaccggagt gcaatcacaa     60
gtacaactgg tgcagagcgg ggccgaagtc aagaagcccg gcgcctccgt gaaaatctcg    120
tgcaaagcct cgggttacac attcactgac tacgcagtga actgggtcag acaggcaccg    180
ggccagggac tcgagtggat gggctggatc aacactcaga ctgggaagcc cacctatgct    240
cagaagttcc agggaaggtt cacctttacc ttggacacca gcacctccac cgcgtacttg    300
gaaattagca gcctgcggtc cgaagataca gccgtgtact attgtactag ggactcctac    360
tactactcat cctcgctcga ctactggggc cagggtaccc tcgtgaccgt tagctcggcc    420
tctactaagg gtccgtccgt gttcccgttg gccccgagct cgaagtccac ctccggggga    480
accgctgcgc ttggatgcct ggtcaaggac tacttccccg agcccgtgac ggtgtcctgg    540
aactccgggg ccctgaccct gggagtgcac actttccctg cggtgctgca gagctcagga    600
ctgtacagcc tcagctccgt cgtgaccgtg ccttcgtcct cgctgggcac ccagacctac    660
```

```
atctgcaacg tgaaccacaa gccgagcaac accaaggtcg acaagaaagt cgagccgaag      720
tcatgcgaca agactcacac ttgcccgccg tgcccgcgc ctgagcttct tggcgggccc      780
tccgtgttcc tgtttccgcc aaagcccaag gatactctga tgatttcgcg gactcctgaa      840
gtgacctgtg tggtcgtcga tgtgtcccat gaggacccg aggtcaagtt caattggtac      900
gtggacggcg tggaggtcca caatgccaag acgaagccgc gggaagaaca gtacaactcc      960
acttatcgcg tggtgtccgt gctcaccgtg ctgcatcagg actggctgaa cggaaaggag     1020
tacaagtgca aagtgtccaa caaggccctg cctgccccaa ttgaaaagac catctcaaaa     1080
gcgaagggcc agccgcgcga accacaagtg tacaccctgc ctccttcccg ggatgaactg     1140
accaagaacc aagtgtccct gacttgcctc gtgaagggtt tctacccgtc cgacatcgcc     1200
gtggaatggg agagcaacgg acagcccgag aacaattaca agactacccc acccgtgctc     1260
gattcggacg gcagcttctt cctgtactcc aagctgaccg tggataagtc ccgctggcaa     1320
cagggaaacg tgttcagttg ttccgtgatg cacgaagccc tgcacaacca ctacacccag     1380
aagtcactgt ccctgtctcc gggaaaataa                                      1410

<210> SEQ ID NO 416
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416
atggatatga gagtgcctgc acaacttctt ggattactgc tgctttggtt gtcgggagcc       60
agatgcgata tccagatgac ccagtccccg tcgagcctgt cagcttccgt gggcgaccgg      120
gtcaccatta cttgtcgcgc ctcggccggt attagcaatg acttggcctg gtaccagcag      180
aagcctggga aggcccccaa gctcctcatc tacgcggctt cccgcctgca agacggcgtg      240
ccgtcaaggt tcagcggttc gggctccgga actgacttca ccctcactat ctcgtccctg      300
caacccgaag atttcgcaac ctactactgc cagcagtcct ataagtaccc ctggactttc      360
ggacaaggca ccaagctcga gatcaagcgg accgtggccg ccccgagcgt gtttatcttc      420
ccgccatctg acgaacagct gaagtccggg acagcgtccg tggtctgcct gctcaacaac      480
ttctaccccc gcgaggccaa agtgcagtgg aaagtcgata cgcgctgca gtccggaaac      540 agccaggaaa gcgtgactga gcaagactcc aaggactcca cctactccct gtcatccacc      600
ctgacgctgt ccaaggccga ctacgaaaag cacaaggtct acgcctgcga agtgaccccat      660 cagggcctgt caagccctgt gaccaagtcg ttcaaccggg gagagtgtta a               711

<210> SEQ ID NO 417
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 417
atggactgga cctggagatt tttattcgtc gtcgctgccg ccaccggagt gcaatcacaa       60
gtacaactgg tgcagagcgg ggccgaagtc aagaagcccg gcgcctccgt gaaagtgtcg      120
tgcaaagcct cgggttacac attcactgac tacgcagtga actgggtcag acaggcaccg      180
ggccagggac tcgagtggat gggctggatc aacactcaga ctgggaagcc cacctatgct      240
```

-continued

```
cagaagttcc agggaagggt caccatgacc ttggacacca gcacctccac ctcctacatg    300
gaattgagca gcctgcggtc cgaagataca gccgtgtact attgtactag ggactcctac    360
tactactcat cctcgctcga ctactggggc cagggtaccc tcgtgaccgt tagctcggcc    420
tctactaagg gtccgtccgt gttcccgttg gccccgagct cgaagtccac ctccggggga    480
accgctgcgc ttggatgcct ggtcaaggac tacttccccg agcccgtgac ggtgtcctgg    540
aactccgggg ccctgacctc gggagtgcac actttccctg cggtgctgca gagctcagga    600
ctgtacagcc tcagctccgt cgtgaccgtg ccttcgtcct cgctgggcac ccagacctac    660
atctgcaacg tgaaccacaa gccgagcaac accaaggtcg acaagaaagt cgagccgaag    720
tcatgcgaca agactcacac ttgcccgccg tgccccgcgc ctgagcttct tggcgggccc    780
tccgtgttcc tgtttccgcc aaagcccaag gatactctga tgatttcgcg gactcctgaa    840
gtgacctgtg tggtcgtcga tgtgtcccat gaggaccccg aggtcaagtt caattggtac    900
gtggacggcg tggaggtcca caatgccaag acgaagccgc gggaagaaca gtacaactcc    960
acttatcgcg tggtgtccgt gctcaccgtg ctgcatcagg actggctgaa cggaaaggag   1020
tacaagtgca agtgtccaa caaggccctg cctgccccaa ttgaaaagac catctcaaaa   1080
gcgaagggcc agccgcgcga accacaagtg tacaccctgc ctccttcccg ggatgaactg   1140
accaagaacc aagtgtccct gacttgcctc gtgaagggtt tctacccgtc cgacatcgcc   1200
gtggaatggg agagcaacgg acagcccgag aacaattaca agactacccc accgtgctc   1260 gattcggacg gcagcttctt cctgtactcc aagctgaccg tggataagtc ccgctggcaa   1320
cagggaaacg tgttcagttg ttccgtgatg cacgaagccc tgcacaacca ctacacccag   1380
aagtcactgt ccctgtctcc gggaaaataa                                    1410
```

<210> SEQ ID NO 418
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 418

```
atggatatga gagtgcctgc acaacttctt ggattactgc tgctttggtt gtcgggagcc     60
agatgcgata tccagatgac ccagtccccg tcgagcctgt cagcttccgt gggcgaccgg    120
gtcaccatta cttgtcgcgc ctcggccggt attagcaatg acttggcctg gtaccagcag    180
aagcctggga aggcccccaa gctcctcatc tacgcggctt cccgcctgca agacggcgtg    240
ccgtcaaggt tcagcggttc gggctccgga actgacttca ccctcactat ctcgtccctg    300
caacccgaag atttcgcaac ctactactgc cagcagtcct ataagtaccc ctggactttc    360
ggacaaggca ccaagctcga gatcaagcgg accgtggccg ccccgagcgt gtttatcttc    420
ccgccatctg acgaacagct gaagtccggg acagcgtccg tggtctgcct gctcaacaac    480
ttctaccccc gcgaggccaa agtgcagtgg aaagtcgata cgcgctgca gtccggaaac    540 agccaggaaa gcgtgactga gcaagactcc aaggactcca cctactccct gtcatccacc    600
ctgacgctgt ccaaggccga ctacgaaaag cacaaggtct acgcctgcga agtgacccat    660
cagggcctgt caagccctgt gaccaagtcg ttcaaccggg gagagtgtta a              711
```

<210> SEQ ID NO 419
<211> LENGTH: 1410

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 419

```
atggactgga cctggagatt tttattcgtc gtcgctgccg ccaccggagt gcaatcacaa     60
gtacaactgg tgcagagcgg ggccgaagtc aagaagcccg gcgcctccgt gaaaatctcg    120
tgcaaagcct cgggttacac attcactgac tacgcagtga actgggtcag acaggcaccg    180
ggccagggac tcgagtggat gggctggatc aacactcaga ctgggaagcc cacctatgct    240
cagaagttcc agggaaggtt taccttcacc ctcgacacca gcacctccac ctcctacttg    300
gaaattagca gcctgcggtc cgaagataca gccgtgtact attgtactag ggactcctac    360
tactactcat cctcgctcga ctactggggc cagggtaccc tcgtgaccgt tagctcggcc    420
tctactaagg gtccgtccgt gttcccgttg gccccgagct cgaagtccac ctccggggga    480
accgctgcgc ttggatgcct ggtcaaggac tacttccccg agcccgtgac ggtgtcctgg    540
aactccgggg ccctgacctc gggagtgcac actttccctg cggtgctgca gagctcagga    600
ctgtacagcc tcagctccgt cgtgaccgtg ccttcgtcct cgctgggcac ccagacctac    660
atctgcaacg tgaaccacaa gccgagcaac accaaggtcg acaagaaagt cgagccgaag    720
tcatgcgaca gactcacaca ttgcccgccg tgccccgcgc tgagcttct tggcgggccc     780
tccgtgttcc tgtttccgcc aaagcccaag gatactctga tgatttcgcg gactcctgaa    840
gtgacctgtg tggtcgtcga tgtgtcccat gaggaccccg aggtcaagtt caattggtac    900
gtggacggcg tggaggtcca caatgccaag acgaagccgc gggaagaaca gtacaactcc    960
acttatcgcg tggtgtccgt gctcaccgtg ctgcatcagg actggctgaa cggaaaggag   1020
tacaagtgca agtgtccaa caaggccctg cctgccccaa ttgaaaagac catctcaaaa   1080
gcgaagggcc agccgcgcga accacaagtg tacaccctgc ctccttcccg ggatgaactg   1140
accaagaacc aagtgtccct gacttgcctc gtgaagggtt tctacccgtc cgacatcgcc   1200
gtggaatggg agagcaacgg acagcccgag aacaattaca agactacccc acccgtgctc   1260
gattcggacg gcagcttctt cctgtactcc aagctgaccg tggataagtc ccgctggcaa   1320
cagggaaacg tgttcagttg ttccgtgatg cacgaagccc tgcacaacca ctacacccag   1380
aagtcactgt ccctgtctcc gggaaaataa                                    1410
```

<210> SEQ ID NO 420
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 420

```
atggatatga gagtgcctgc acaacttctt ggattactgc tgctttggtt gtcgggagcc     60
agatgcgata tccagatgac ccagtccccg tcgagcctgt cagcttccgt gggcgaccgg    120
gtcaccatta cttgtcgcgc ctcggccggt attagcaatg acttggcctg gtaccagcag    180
aagcctggga aggcccccaa gctcctcatc tacgcggctt ccgcctgcaa agacggcgtg    240
ccgtcaaggt tcagcggttc gggctccgga actgacttca ccctcactat ctcgtccctg    300
caacccgaag atttcgcaac ctactactgc cagcagtcct ataagtaccc ctggactttc    360
```

| | |
|---|---|
| ggacaaggca ccaagctcga gatcaagcgg accgtggccg ccccgagcgt gtttatcttc | 420 |
| ccgccatctg acgaacagct gaagtccggg acagcgtccg tggtctgcct gctcaacaac | 480 |
| ttctaccccc gcgaggccaa agtgcagtgg aaagtcgata acgcgctgca gtccggaaac | 540 |
| agccaggaaa gcgtgactga gcaagactcc aaggactcca cctactccct gtcatccacc | 600 |
| ctgacgctgt ccaaggccga ctacgaaaag cacaaggtct acgcctgcga agtgacccat | 660 |
| cagggcctgt caagccctgt gaccaagtcg ttcaaccggg gagagtgtta a | 711 |

<210> SEQ ID NO 421
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 421

| | |
|---|---|
| atggattgga cttggagatt tttgtttgtg gtggcggcgg ccactggagt gcaatccgaa | 60 |
| gtgcaattgg tggaatcggg tggtggactt gtgcagcctg gatcgtcact taagctgtcc | 120 |
| tgtgtggcct cgaagtttac cttctccaac tatgggatga actggattag acaagccccg | 180 |
| aagaagggac tggaatggat tgcgctgatc tattacaact cgaacaacaa gtactacgct | 240 |
| gattccgtga agggtcgctt cactatttcc cgcgacaact cgaagaacac tctgtacctt | 300 |
| gagatgaact ccctgcgctc ggaagatact gccatgtact actgtgccaa gtcgctgact | 360 |
| ggcggatccg attacttcga ttcctgggga caaggagtga tggtcactgt atccagtgcc | 420 |
| agcaccaagg gcccatcggt cttcccctg gcaccctcct ccaagagcac ctctggggc | 480 |
| acagcggccc tgggctgcct ggtcaaggac tacttccccg aaccggtgac ggtgtcgtgg | 540 |
| aactcaggcg ccctgaccag cggcgtgcac accttcccgg ctgtcctaca gtcctcagga | 600 |
| ctctactccc tcagcagcgt ggtgaccgtg ccctccagca gcttgggcac ccagacctac | 660 |
| atctgcaacg tgaatcacaa gcccagcaac accaaggtgg acaagaaagt tgagcccaaa | 720 |
| tcttgtgaca aaactcacac atgcccaccg tgcccagcac ctgaactcct ggggggaccg | 780 |
| tcagtcttcc tcttcccccc aaaacccaag gacaccctca tgatctcccg gacccctgag | 840 |
| gtcacatgcg tggtggtgga cgtgagccac gaagaccctg aggtcaagtt caactggtac | 900 |
| gtggacggcg tggaggtgca taatgccaag acaaagccgc gggaggagca gtacaacagc | 960 |
| acgtaccggg tggtcagcgt cctcaccgtc ctgcaccagg actggctgaa tggcaaggag | 1020 |
| tacaagtgca aggtcagcaa caaagccctc ccagccccca tcgagaaaac catctccaaa | 1080 |
| gccaaagggc agccccgaga accacaggtg tacaccctgc ccccatcccg ggatgagctg | 1140 |
| accaagaacc aggtcagcct gacctgcctg gtcaaaggct tctatcccag cgacatcgcc | 1200 |
| gtggagtggg agagcaatgg gcagccggag aacaactaca agaccacgcc tcccgtgctg | 1260 |
| gactccgacg gctccttctt cctctacagc aagctcaccg tggacaagag caggtggcag | 1320 |
| caggggaacg tcttctcatg ctccgtgatg catgaggctc tgcacaacca ctacacgcag | 1380 |
| aagtccctct ccctgtctcc gggtaaatag | 1410 |

<210> SEQ ID NO 422
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 422

```
atggacatgc gcgtgcctgc gcaattgctg gggctgcttc tcctgtggct ttcgggagcc    60
cgctgcgacg tgcagatgac ccagtcccct tcctacctgg ctgcgtcacc gggagaatca   120
gtgtccatca gctgcaaggc ctccaagtcc attggtacct tcctggcctg gtaccaagag   180
aagcctgaaa agaccaacaa gctcctgatc tactcgggat caaccctgca atccggcact   240
ccgtcgcggt tctccggatc cgggtccggc accgacttta ctctgaccat tcggaacctg   300
gaacccgaag atttcgccgt gtactactgt cagcagcacg acgaataccc gtttactttc   360
ggctccggca ccaagctcga aatcaagcga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta a            711
```

<210> SEQ ID NO 423
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 423

```
atggattgga cttggagatt tttgtttgtg gtggcggcgg ccactggagt gcaatccgaa    60
gtgcaattgg tggaatcggg tggtggactt gtgcagcctg gatcgtcact taagctgtcc   120
tgtgtggcct cgaagtttac cttctccaac tatgggatga actggattag acaagccccg   180
aagaagggac tggaatggat tgcgctgatc tattacaact cgaacaacaa gtactacgct   240
gattccgtga agggtcgctt cactatttcc cgcgacaact cgaagaacac tctgtacctt   300
gagatgaact ccctgcgctc ggaagatact gccatgtact actgtgccaa gtcgctgact   360
ggcggatccg attacttcga ttcctgggga caaggagtga tggtcactgt atccagtgcc   420
agcacaaagg gcccatccgt cttcccctg cgccctgct ccaggagcac ctccgagagc    480
acagccgccc tgggctgcct ggtcaaggac tacttcccg aaccggtgac ggtgtcgtgg    540
aactcaggcg ccctgaccag cggcgtgcac accttcccgg ctgtcctaca gtcctcagga   600
ctctactccc tcagcagcgt ggtgaccgtg ccctccagca gcttgggcac gaagacctac   660
acctgcaacg tagatcacaa gcccagcaac accaaggtgg acaagagagt tgagtccaaa   720
tatggtcccc catgcccatc ctgcccagca cctgagttcc tggggggacc atcagtcttc   780
ctgttcccc aaaacccaa ggacactctc atgatctccc ggaccctga ggtcacgtgc      840
gtggtggtgg acgtgagcca ggaagacccc gaggtccagt tcaactggta cgtggatggc   900
gtggaggtgc ataatgccaa gacaaagccg cgggaggagc agttcaacag cacgtaccgt   960
gtggtcagcg tcctcaccgt cctgcaccag gactggctga acggcaagga gtacaagtgc  1020
aaggtcagca acaaaggcct cccgtcctcc atcgagaaaa ccatctccaa agccaagggg  1080
cagccccgag agccacaggt gtacaccctg cccccatccc aggaggagat gaccaagaac  1140
caggtcagcc tgacctgcct ggtcaaaggc ttctacccca gcgacatcgc cgtggagtgg  1200
gagagcaatg ggcagccgga gaacaactac aagaccacgc ctcccgtgct ggactccgac  1260
```

-continued

```
ggctccttct tcctctacag caggctaacc gtggacaaga gcaggtggca ggagggaat     1320 gtcttctcat gctccgtgat gcatgaggct ctgcacaacc actacacaca gaagtccctc   1380
tccctgtctc tgggtaaata g                                             1401
```

<210> SEQ ID NO 424
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 424

```
atggacatgc gcgtgcctgc gcaattgctg gggctgcttc tcctgtggct ttcgggagcc     60
cgctgcgacg tgcagatgac ccagtcccct tcctacctgg ctgcgtcacc gggagaatca    120
gtgtccatca gctgcaaggc ctccaagtcc attggtacct tcctggcctg gtaccaagag    180
aagcctgaaa agaccaacaa gctcctgatc tactcgggat caaccctgca atccggcact    240
ccgtcgcggt tctccggatc cgggtccggc accgacttta ctctgaccat tcggaacctg    300
gaacccgaag atttcgccgt gtactactgt cagcagcacg acgaataccc gtttactttc    360
ggctccggca ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
```

<210> SEQ ID NO 425
<211> LENGTH: 1413
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 425

```
atggattgga cttggcgctt cttgtttgtg gtggcggcgg ctactggagt gcagtcacaa     60
gtcaaccttc tgcaatcccg ggcagcactc gtgaagcccg gtgcttcagt gaagctgagc    120
tgcaaggcct ccgggtacac cttcaccgac tactatctgc attgggtcaa gcagtcccac    180
gccaagagcc tggagtggat tggctacatc aacccgaaca acgcctacac ctcgtacaat    240
gagaagttca gtccaaagc gaccctgacc gtggataagt ccactaacac cgcctacatg    300
gaactgtcca gactcacgtc cgccgactcg gccacctatt actgtgcccg ggacaccaca    360
gactactaca acctccactt cgcctactgg ggccagggaa ctctggtcac cgtgtcgagc    420
gccagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
```

```
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gggtggtcag cgtcctcacc gtcctgcacc aggactggct gaatggcaag    1020
gagtacaagt gcaaggtcag caacaaagcc ctcccagccc ccatcgagaa aaccatctcc    1080
aaagccaaag gcagccccg agaaccacag gtgtacaccc tgcccccatc ccgggatgag    1140
ctgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagtccc tctccctgtc tccgggtaaa tag    1413
```

<210> SEQ ID NO 426
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 426

```
atggatatgc gggtgccggc ccagcttctg ggcctgttgc tgctctggct ctccggagcg    60
cgctgtgaca ttcaaatgac ccagtcccct gcatcactga gcgcctcact ggggaaact    120 gtcagcattg agtgcctgac ctccgaggga atctcgaacg acctggcctg gtatcagcag    180
aagtccggaa agtcgccgca gctgcttatc tacgacgcca gcagactcga ggacggcgtg    240
ccctcccgct tttccggctc tggttccggc actcggtaca gcctgaagat ctccggaatg    300
cagaccgaag atgaagctga ctacttctgc caacaatcgt acaaataccc actgaccttc    360
ggttccggga ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcaccca    660 cagggcctga gctcgcccgt cacaaagagc ttcaacaggg gagagtgtta a    711
```

<210> SEQ ID NO 427
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 427

```
atggattgga cttggcgctt cttgtttgtg gtggcggcgg ctactggagt gcagtca    57
```

<210> SEQ ID NO 428
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 428

Met Asp Trp Thr Trp Arg Phe Leu Phe Val Val Ala Ala Ala Thr Gly
1               5                   10                  15

Val Gln Ser

<210> SEQ ID NO 429
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 430
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
atggatatgc gggtgccggc ccagcttctg ggcctgttgc tgctctggct ctccggagcg    60
cgctgt                                                              66

<210> SEQ ID NO 431
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Ala Ser Glu Gly Ile Ser Asn Asp Leu Ala
1               5                   10

<210> SEQ ID NO 432
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ala Ser Ala Gly Ile Ser Asn Asp Leu Ala
1               5                   10

<210> SEQ ID NO 433
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Ala Ser Lys Ser Ile Gly Thr Phe Leu Ala

-continued

```
1               5                   10
```

<210> SEQ ID NO 434
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120
```

<210> SEQ ID NO 435
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

```
Gly Phe Ser Leu Thr Ser Tyr His Val Ser
1               5                   10
```

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

```
Ala Ile Trp Thr Gly Gly Ser Ile Ala
1               5
```

<210> SEQ ID NO 437
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

```
Asp Leu Ser Asp Tyr Tyr Ser Ser Tyr Thr Ser Phe Asp Tyr
1               5                   10
```

<210> SEQ ID NO 438
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 438

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Ile
        35                  40                  45

Gly Ala Ile Trp Thr Gly Gly Ser Ile Ala Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 439
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 440
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Arg Ala Ser Glu Gly Ile Ser Asn Asp Leu Ala
1               5                   10

<210> SEQ ID NO 441
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Ala Ala Ser Arg Leu Gln Asp
1               5
```

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Gln Gln Ser Tyr Lys Tyr Pro Leu Thr
1               5

<210> SEQ ID NO 443
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 444
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Glu Val Gln Leu Gln Glu Ser Gly Pro Gly Leu Val Lys Pro Ser Glu

-continued

```
                1               5                  10                  15

Thr Leu Ser Leu Thr Cys Thr Val Ser Gly Phe Ser Leu Thr Ser Tyr
                        20                  25                  30

His Val Ser Trp Val Arg Gln Pro Pro Gly Lys Gly Leu Glu Trp Ile
                        35                  40                  45

Gly Ala Ile Trp Thr Gly Gly Ser Ile Ala Tyr Asn Pro Ser Leu Lys
                    50                  55                  60

Ser Arg Val Thr Ile Ser Arg Asp Thr Ser Lys Asn Gln Val Ser Leu
        65                  70                  75                  80

Lys Leu Ser Ser Val Thr Ala Ala Asp Thr Ala Val Tyr Tyr Cys Ala
                            85                  90                  95

Arg Asp Leu Ser Asp Tyr Tyr Ser Ser Tyr Thr Ser Phe Asp Tyr Trp
                        100                 105                 110

Gly Gln Gly Thr Leu Val Thr Val Ser Ser
                    115                 120

<210> SEQ ID NO 445
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Gly Phe Ser Leu Thr Ser Tyr His Val Ser
1               5                   10

<210> SEQ ID NO 446
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Ala Ile Trp Thr Gly Gly Ser Ile Ala
1               5

<210> SEQ ID NO 447
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Asp Leu Ser Asp Tyr Tyr Ser Ser Tyr Thr Ser Phe Asp Tyr
1               5                   10

<210> SEQ ID NO 448
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Glu Val Gln Leu Gln Glu Ser Gly Pro Gly Leu Val Lys Pro Ser Glu
1               5                   10                  15
```

Thr Leu Ser Leu Thr Cys Thr Val Ser Gly Phe Ser Leu Thr Ser Tyr
            20                  25                  30

His Val Ser Trp Val Arg Gln Pro Gly Lys Gly Leu Glu Trp Ile
        35                  40                  45

Gly Ala Ile Trp Thr Gly Gly Ser Ile Ala Tyr Asn Pro Ser Leu Lys
50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly

Lys

<210> SEQ ID NO 449
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 450
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Arg Ala Ser Glu Gly Ile Ser Asn Asp Leu Ala
1               5                   10

<210> SEQ ID NO 451
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Ala Ala Ser Arg Leu Gln Asp
1               5

<210> SEQ ID NO 452
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Gln Gln Ser Tyr Lys Tyr Pro Leu Thr
1               5

```
<210> SEQ ID NO 453
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 454
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ala Val Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Gln Lys Phe
    50                  55                  60

Gln Gly Arg Phe Thr Phe Thr Leu Asp Thr Ser Thr Ser Thr Ser Tyr
65                  70                  75                  80

Leu Glu Ile Ser Ser Leu Arg Ser Glu Asp Thr Ala Val Tyr Tyr Cys
```

85                  90                  95

Thr Arg Asp Ser Tyr Tyr Tyr Ser Ser Ser Leu Asp Tyr Trp Gly Gln
                 100                 105                 110

Gly Thr Leu Val Thr Val Ser Ser
         115                 120

<210> SEQ ID NO 455
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Gly Tyr Thr Phe Thr Asp Tyr Ala Val Asn
1               5                   10

<210> SEQ ID NO 456
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Trp Ile Asn Thr Gln Thr Gly Lys Pro Thr
1               5                   10

<210> SEQ ID NO 457
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Asp Ser Tyr Tyr Tyr Ser Ser Ser Leu Asp Tyr
1               5                   10

<210> SEQ ID NO 458
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Ala Val Asn Trp Val Arg Gln Ala Pro Gly Gln Gly Leu Glu Trp Met
            35                  40                  45

Gly Trp Ile Asn Thr Gln Thr Gly Lys Pro Thr Tyr Ala Gln Lys Phe
        50                  55                  60

Gln Gly Arg Phe Thr Phe Thr Leu Asp Thr Ser Thr Ser Thr Ser Tyr
65                  70                  75                  80

Leu Glu Ile Ser Ser Leu Arg Ser Glu Asp Thr Ala Val Tyr Tyr Cys
                85                  90                  95

Thr Arg Asp Ser Tyr Tyr Ser Ser Ser Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 459
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys
            100                 105
```

<210> SEQ ID NO 460
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

```
Arg Ala Ser Ala Gly Ile Ser Asn Asp Leu Ala
1               5                   10
```

<210> SEQ ID NO 461
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

```
Ala Ala Ser Arg Leu Gln Asp
1               5
```

<210> SEQ ID NO 462
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

```
Gln Gln Ser Tyr Lys Tyr Pro Trp Thr
1               5
```

<210> SEQ ID NO 463
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
```

```
                    20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
 50                  55                  60

Ser Gly Ser Gly Thr Asp Phe Thr Leu Thr Ile Ser Ser Met Gln Pro
 65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 464
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ala Val Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Gln Lys Phe
    50                  55                  60

Gln Gly Arg Phe Thr Phe Thr Leu Asp Thr Ser Thr Ser Thr Ser Tyr
65                  70                  75                  80

Leu Glu Ile Ser Ser Leu Arg Ser Glu Asp Thr Ala Val Tyr Tyr Cys
                85                  90                  95

Thr Arg Asp Ser Tyr Tyr Ser Ser Ser Leu Asp Tyr Trp Gly Gln
            100                 105                 110

Gly Thr Leu Val Thr Val Ser Ser
        115                 120

<210> SEQ ID NO 465
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 465

Gly Tyr Thr Phe Thr Asp Tyr Ala Val Asn
1               5                   10

<210> SEQ ID NO 466
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Trp Ile Asn Thr Gln Thr Gly Lys Pro Thr
1               5                   10

<210> SEQ ID NO 467
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Asp Ser Tyr Tyr Tyr Ser Ser Ser Leu Asp Tyr
1               5                   10

<210> SEQ ID NO 468
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Ala Val Asn Trp Val Arg Gln Ala Pro Gly Gln Gly Leu Glu Trp Met
            35                  40                  45

Gly Trp Ile Asn Thr Gln Thr Gly Lys Pro Thr Tyr Ala Gln Lys Phe
        50                  55                  60

Gln Gly Arg Phe Thr Phe Thr Leu Asp Thr Ser Thr Ser Thr Ser Tyr
65                  70                  75                  80

Leu Glu Ile Ser Ser Leu Arg Ser Glu Asp Thr Ala Val Tyr Tyr Cys
                85                  90                  95

Thr Arg Asp Ser Tyr Tyr Tyr Ser Ser Ser Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 469
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp

```
                    85                  90                  95

Thr Phe Gly Gln Gly Thr Lys Leu Glu Ile Lys
            100                 105

<210> SEQ ID NO 470
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Arg Ala Ser Ala Gly Ile Ser Asn Asp Leu Ala
1               5                   10

<210> SEQ ID NO 471
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Ala Ala Ser Arg Leu Gln Asp
1               5

<210> SEQ ID NO 472
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Gln Gln Ser Tyr Lys Tyr Pro Trp Thr
1               5

<210> SEQ ID NO 473
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Thr Tyr Tyr Cys Gln Gln Ser Tyr Lys Tyr Pro Trp
                85                  90                  95

Thr Phe Gly Gln Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 474
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
        35                  40                  45

Gly Ala Ile Trp Thr Gly Gly Ser Ile Ala Tyr Asn Pro Ser Leu Lys
    50                  55                  60

Ser Arg Leu Thr Ile Ser Arg Asp Thr Ser Lys Asn Gln Val Ser Leu
65                  70                  75                  80

Lys Met Ser Ser Leu Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser
        115                 120

<210> SEQ ID NO 475
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Gly Phe Ser Leu Thr Ser Tyr His Val Ser
1               5                   10

<210> SEQ ID NO 476
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 476

Ala Ile Trp Thr Gly Gly Ser Ile Ala
1               5

<210> SEQ ID NO 477
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Asp Leu Ser Asp Tyr Tyr Ser Ser Tyr Thr Ser Phe Asp Tyr
1               5                   10

<210> SEQ ID NO 478
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
        35                  40                  45

Gly Ala Ile Trp Thr Gly Gly Ser Ile Ala Tyr Asn Pro Ser Leu Lys
    50                  55                  60

Ser Arg Leu Thr Ile Ser Arg Asp Thr Ser Lys Asn Gln Val Ser Leu
65                  70                  75                  80

Lys Met Ser Ser Leu Thr Ala Ala Asp Thr Ala Val Tyr Tyr Cys Ala
                85                  90                  95

Arg Asp Leu Ser Asp Tyr Tyr Ser Ser Tyr Thr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
```

```
                    260                 265                 270
Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 479
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Gly Ile Ser Asn Asp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Tyr Thr Leu Thr Ile Ser Ser Met Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys
            100                 105

<210> SEQ ID NO 480
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480
```

Arg Ala Ser Glu Gly Ile Ser Asn Asp Leu Ala
1               5                   10

<210> SEQ ID NO 481
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Ala Ala Ser Arg Leu Gln Asp
1               5

<210> SEQ ID NO 482
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gln Gln Ser Tyr Lys Tyr Pro Leu Thr
1               5

<210> SEQ ID NO 483
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Asp Ile Gln Met Thr Gln Ser Pro Ser Leu Ser Ala Ser Val Gly
1               5                   10                  15

Asp Arg Val Thr Ile Thr Cys Arg Ala Ser Glu Gly Ile Ser Asn Asp
                20                  25                  30

Leu Ala Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
    50                  55                  60

Ser Gly Ser Gly Thr Asp Tyr Thr Leu Thr Ile Ser Ser Met Gln Pro
65                  70                  75                  80

Glu Asp Phe Ala Thr Tyr Tyr Cys Gln Gln Ser Tyr Lys Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 484
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

His His His His His His His Gly Glu Arg Gly Ser Pro Gly Pro
1               5                   10                  15

Lys Gly Ala Pro Gly Ala Pro Gly Ile Pro Gly Leu Pro Gly Pro Ala
            20                  25                  30

Ala Glu Lys Gly Glu Lys Gly Ala Ala Gly Arg Asp Gly Thr Pro Gly
        35                  40                  45

Val Gln Gly Pro Gln Gly Pro Pro Gly Ser Lys Gly Glu Ala Gly Leu
    50                  55                  60

Gln Gly Leu Thr Gly Ala Pro Gly Lys Gln Gly Ala Thr Gly Ala Pro
65                  70                  75                  80

Gly Pro Arg Gly Glu Lys Gly Ser Lys Gly Asp Ile Gly Leu Thr Gly
                85                  90                  95

Pro Lys Gly Glu His Gly Thr Lys Gly Asp Lys Gly Asp Leu Gly Leu
            100                 105                 110

Pro Gly Asn Lys Gly Asp Met Gly Met Lys Gly Asp Thr Gly Pro Met
        115                 120                 125

Gly Ser Pro Gly Ala Gln Gly Lys Gly Asp Ala Gly Lys Pro Gly
    130                 135                 140

Leu Pro Gly Leu Ala Gly Ser Pro Gly Val Lys Gly Asp Gln Gly Lys
145                 150                 155                 160

Pro Gly Val Gln Gly Val Pro Gly Pro Gln Gly Ala Pro Gly Leu Ser
                165                 170                 175

Gly Ala Lys Gly Glu Pro Gly Arg Thr Gly Leu Pro Gly Pro Ala Gly
            180                 185                 190

Pro Pro Gly Ile Ala Gly Asn Pro Gly Ile Ala Gly Val Lys Gly Ser
        195                 200                 205

Lys Gly Asp Thr Gly Ile Gln Gly Gln Lys Gly Thr Lys Gly Glu Ser
    210                 215                 220

Gly Val Pro Gly Leu Val Gly Arg Lys Gly Asp Thr Gly Ser Pro Gly
225                 230                 235                 240

Leu Ala Gly Pro Lys Gly Glu Pro Gly Arg Val Gly Gln Lys Gly Asp
                245                 250                 255

Pro Gly Met Lys Gly Ser Ser Gly Gln Gln Gly Gln Lys Gly Glu Lys
            260                 265                 270

Gly Gln Lys Gly Glu Ser Phe Gln Arg Val Arg Ile Met Gly Gly Thr
        275                 280                 285

Asn Arg Gly Arg Ala Glu Val Tyr Tyr Asn Asn Glu Trp Gly Thr Ile
    290                 295                 300

Cys Asp Asp Asp Trp Asp Asn Asn Asp Ala Thr Val Phe Cys Arg Met
305                 310                 315                 320

Leu Gly Tyr Ser Arg Gly Arg Ala Leu Ser Ser Tyr Gly Gly Gly Ser
                325                 330                 335

```
Gly Asn Ile Trp Leu Asp Asn Val Asn Cys Arg Gly Thr Glu Asn Ser
            340                 345                 350

Leu Trp Asp Cys Ser Lys Asn Ser Trp Gly Asn His Asn Cys Val His
        355                 360                 365

Asn Glu Asp Ala Gly Val Glu Cys Ser
    370                 375

<210> SEQ ID NO 485
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

His His His His His His His Lys Gly Glu Arg Gly Ser Pro Gly
1               5                   10                  15

Pro Lys Gly Ala Pro Gly Ala Pro Gly Ile Pro Gly Leu Pro Gly Pro
            20                  25                  30

Ala Ala Glu Lys Gly Glu Lys Gly Ala Ala Gly Arg Asp Gly Thr Pro
        35                  40                  45

Gly Val Gln Gly Pro Gln Gly Pro Gly Ser Lys Gly Glu Ala Gly
    50                  55                  60

Leu Gln Gly Leu Thr Gly Ala Pro Gly Lys Gln Gly Ala Thr Gly Ala
65                  70                  75                  80

Pro Gly Pro Arg Gly Glu Lys Gly Ser Lys Gly Asp Ile Gly Leu Thr
                85                  90                  95

Gly Pro Lys Gly Glu His Gly Thr Lys Gly Asp Lys Gly Asp Leu Gly
            100                 105                 110

Leu Pro Gly Asn Lys Gly Asp Met Gly Met Lys Gly Asp Thr Gly Pro
        115                 120                 125

Met Gly Ser Pro Gly Ala Gln Gly Gly Lys Gly Asp Ala Gly Lys Pro
    130                 135                 140

Gly Leu Pro Gly Leu Ala Gly Ser Pro Gly Val Lys Gly Asp Gln Gly
145                 150                 155                 160

Lys Pro Gly Val Gln Gly Val Pro Gly Pro Gln Gly Ala Pro Gly Leu
                165                 170                 175

Ser Gly Ala Lys Gly Glu Pro Gly Arg Thr Gly Leu Pro Gly Pro Ala
            180                 185                 190

Gly Pro Pro Gly Ile Ala Gly Asn Pro Gly Ile Ala Gly Val Lys Gly
        195                 200                 205

Ser Lys Gly Asp Thr Gly Ile Gln Gly Gln Lys Gly Thr Lys Gly Glu
    210                 215                 220

Ser Gly Val Pro Gly Leu Val Gly Arg Lys Gly Asp Thr Gly Ser Pro
225                 230                 235                 240

Gly Leu Ala Gly Pro Lys Gly Glu Pro Gly Arg Val Gly Gln Lys Gly
                245                 250                 255

Asp Pro Gly Met Lys Gly Ser Ser Gly Gln Gln Gly Gln Lys Gly Glu
            260                 265                 270

Lys Gly Gln Lys Gly Glu Asn Ser Val Ser Val Arg Ile Val Gly Ser
        275                 280                 285

Ser Asn Arg Gly Arg Ala Glu Val Tyr Tyr Ser Gly Thr Trp Gly Thr
    290                 295                 300

Ile Cys Asp Asp Glu Trp Gln Asn Ser Asp Ala Ile Val Phe Cys Arg
```

```
                 305                 310                 315                 320
Met Leu Gly Tyr Ser Lys Gly Arg Ala Leu Tyr Lys Val Gly Ala Gly
                325                 330                 335

Thr Gly Gln Ile Trp Leu Asp Asn Val Gln Cys Arg Gly Thr Glu Ser
                340                 345                 350

Thr Leu Trp Ser Cys Thr Lys Asn Ser Trp Gly His His Asp Cys Ser
                355                 360                 365

His Glu Glu Asp Ala Gly Val Glu Cys Ser Val
                370                 375

<210> SEQ ID NO 486
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

His His His His His Lys Gly Glu Gln Gly Ala Pro Gly Leu Gln
1               5                   10                  15

Gly His Lys Gly Ala Met Gly Met Pro Gly Ala Pro Gly Pro Pro Gly
                20                  25                  30

Pro Pro Ala Glu Lys Gly Ala Lys Gly Ala Met Gly Arg Asp Gly Ala
            35                  40                  45

Thr Gly Pro Ser Gly Pro Gln Gly Pro Pro Gly Val Lys Gly Glu Ala
    50                  55                  60

Gly Leu Gln Gly Pro Gln Gly Ala Pro Gly Lys Gln Gly Ala Thr Gly
65                  70                  75                  80

Thr Pro Gly Pro Gln Gly Glu Lys Gly Ser Lys Gly Asp Gly Gly Leu
                85                  90                  95

Ile Gly Pro Lys Gly Glu Thr Gly Thr Lys Gly Glu Lys Gly Asp Leu
                100                 105                 110

Gly Leu Pro Gly Ser Lys Gly Asp Arg Gly Met Lys Gly Asp Ala Gly
            115                 120                 125

Val Met Gly Pro Pro Gly Ala Gln Gly Ser Lys Gly Asp Phe Gly Arg
    130                 135                 140

Pro Gly Pro Pro Gly Leu Ala Gly Phe Pro Gly Ala Lys Gly Asp Gln
145                 150                 155                 160

Gly Gln Pro Gly Leu Gln Gly Val Pro Gly Pro Gly Ala Val Gly
                165                 170                 175

His Pro Gly Ala Lys Gly Glu Pro Gly Ser Ala Gly Ser Pro Gly Arg
                180                 185                 190

Ala Gly Leu Pro Gly Ser Pro Gly Ser Pro Gly Ala Thr Gly Leu Lys
            195                 200                 205

Gly Ser Lys Gly Asp Thr Gly Leu Gln Gly Gln Gln Gly Arg Lys Gly
    210                 215                 220

Glu Ser Gly Val Pro Gly Pro Ala Gly Val Lys Gly Glu Gln Gly Ser
225                 230                 235                 240

Pro Gly Leu Ala Gly Pro Lys Gly Ala Pro Gly Gln Ala Gly Gln Lys
                245                 250                 255

Gly Asp Gln Gly Val Lys Gly Ser Ser Gly Glu Gln Gly Val Lys Gly
            260                 265                 270

Glu Lys Gly Glu Arg Gly Glu Ser Phe Gln Arg Val Arg Ile Met Gly
    275                 280                 285
```

```
Gly Thr Asn Arg Gly Arg Ala Glu Val Tyr Tyr Asn Asn Glu Trp Gly
    290                 295                 300

Thr Ile Cys Asp Asp Asp Trp Asp Asn Asp Ala Thr Val Phe Cys
305                 310                 315                 320

Arg Met Leu Gly Tyr Ser Arg Gly Arg Ala Leu Ser Ser Tyr Gly Gly
                325                 330                 335

Gly Ser Gly Asn Ile Trp Leu Asp Asn Val Asn Cys Arg Gly Thr Glu
                340                 345                 350

Asn Ser Leu Trp Asp Cys Ser Lys Asn Ser Trp Gly Asn His Asn Cys
                355                 360                 365

Val His Asn Glu Asp Ala Gly Val Glu Cys Ser
    370                 375

<210> SEQ ID NO 487
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
ttgtcgttca ctgccatcaa tc                                                22

<210> SEQ ID NO 488
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
acattgatgt ctttggggta gaag                                              24

<210> SEQ ID NO 489
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
agctgggaag gtgtgcacac                                                   20

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
gggatccaga gttccaggtc                                                   20

<210> SEQ ID NO 491
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 491
gtgaggatga tgtcttatga aca                                         23

<210> SEQ ID NO 492
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 492
gccatcaatc ttccacttga cac                                         23

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493 gagatgstttt tctcgatggg                                             20

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
gsgggaagat gaagacagat g                                           21

<210> SEQ ID NO 495
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495
```

His His His His His His Lys Gly Glu Gln Gly Ala Pro Gly Leu Gln
1               5                   10                  15

Gly His Lys Gly Ala Met Gly Met Pro Gly Ala Pro Gly Pro Pro Gly
            20                  25                  30

Pro Pro Ala Glu Lys Gly Ala Lys Gly Ala Met Gly Arg Asp Gly Ala
        35                  40                  45

Thr Gly Pro Ser Gly Pro Gln Gly Pro Pro Gly Val Lys Gly Glu Ala
    50                  55                  60

Gly Leu Gln Gly Pro Gln Gly Ala Pro Gly Lys Gln Gly Ala Thr Gly
65                  70                  75                  80

Thr Pro Gly Pro Gln Gly Glu Lys Gly Ser Lys Gly Asp Gly Gly Leu
                85                  90                  95

Ile Gly Pro Lys Gly Glu Thr Gly Thr Lys Gly Glu Lys Gly Asp Leu
            100                 105                 110

Gly Leu Pro Gly Ser Lys Gly Asp Arg Gly Met Lys Gly Asp Ala Gly
        115                 120                 125

Val Met Gly Pro Pro Gly Ala Gln Gly Ser Lys Gly Asp Phe Gly Arg

```
                    130                 135                 140
Pro Gly Pro Pro Gly Leu Ala Gly Phe Pro Gly Ala Lys Gly Asp Gln
145                 150                 155                 160

Gly Gln Pro Gly Leu Gln Gly Val Pro Gly Pro Gly Ala Val Gly
                    165                 170                 175

His Pro Gly Ala Lys Gly Glu Pro Gly Ser Ala Gly Ser Pro Gly Arg
                    180                 185                 190

Ala Gly Leu Pro Gly Ser Pro Gly Ser Pro Gly Ala Thr Gly Leu Lys
                    195                 200                 205

Gly Ser Lys Gly Asp Thr Gly Leu Gln Gly Gln Gln Gly Arg Lys Gly
                    210                 215                 220

Glu Ser Gly Val Pro Gly Pro Ala Gly Val Lys Gly Glu Gln Gly Ser
225                 230                 235                 240

Pro Gly Leu Ala Gly Pro Lys Gly Ala Pro Gly Gln Ala Gly Gln Lys
                    245                 250                 255

Gly Asp Gln Gly Val Lys Gly Ser Ser Gly Glu Gln Gly Val Lys Gly
                    260                 265                 270

Glu Lys Gly Glu Arg Gly Glu Asn Ser Val Ser Val Arg Ile Val Gly
                    275                 280                 285

Ser Ser Asn Arg Gly Arg Ala Glu Val Tyr Tyr Ser Gly Thr Trp Gly
                    290                 295                 300

Thr Ile Cys Asp Asp Glu Trp Gln Asn Ser Asp Ala Ile Val Phe Cys
305                 310                 315                 320

Arg Met Leu Gly Tyr Ser Lys Gly Arg Ala Leu Tyr Lys Val Gly Ala
                    325                 330                 335

Gly Thr Gly Gln Ile Trp Leu Asp Asn Val Gln Cys Arg Gly Thr Glu
                    340                 345                 350

Ser Thr Leu Trp Ser Cys Thr Lys Asn Ser Trp Gly His His Asp Cys
                    355                 360                 365

Ser His Glu Glu Asp Ala Gly Val Glu Cys Ser Val
                    370                 375                 380

<210> SEQ ID NO 496
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

His His His His His Lys Gly Glu Gln Gly Ala Pro Gly Leu Gln
1               5                   10                  15

Gly His Lys Gly Ala Met Gly Met Pro Gly Ala Pro Gly Pro Pro Gly
                20                  25                  30

Pro Pro Ala Glu Lys Gly Ala Lys Gly Ala Met Gly Arg Asp Gly Ala
                35                  40                  45

Thr Gly Pro Ser Gly Pro Gln Gly Pro Pro Gly Val Lys Gly Glu Ala
                50                  55                  60

Gly Leu Gln Gly Pro Gln Gly Ala Pro Gly Lys Gln Gly Ala Thr Gly
65                  70                  75                  80

Thr Pro Gly Pro Gln Gly Glu Lys Gly Ser Lys Gly Asp Gly Leu
                85                  90                  95

Ile Gly Pro Lys Gly Glu Thr Gly Thr Lys Gly Glu Lys Gly Asp Leu
                100                 105                 110
```

Gly Leu Pro Gly Ser Lys Gly Asp Arg Gly Met Lys Gly Asp Ala Gly
            115                 120                 125

Val Met Gly Pro Pro Gly Ala Gln Gly Ser Lys Gly Asp Phe Gly Arg
        130                 135                 140

Pro Gly Pro Pro Gly Leu Ala Gly Phe Pro Gly Ala Lys Gly Asp Gln
145                 150                 155                 160

Gly Gln Pro Gly Leu Gln Gly Val Pro Gly Pro Gly Ala Val Gly
                165                 170                 175

His Pro Gly Ala Lys Gly Glu Pro Gly Ser Ala Gly Ser Pro Gly Arg
            180                 185                 190

Ala Gly Leu Pro Gly Ser Pro Gly Ser Pro Gly Ala Thr Gly Leu Lys
        195                 200                 205

Gly Ser Lys Gly Asp Thr Gly Leu Gln Gly Gln Gln Gly Arg Lys Gly
    210                 215                 220

Glu Ser Gly Val Pro Gly Pro Ala Gly Val Lys Gly Glu Gln Gly Ser
225                 230                 235                 240

Pro Gly Leu Ala Gly Pro Lys Gly Ala Pro Gly Gln Ala Gly Gln Lys
                245                 250                 255

Gly Asp Gln Gly Val Lys Gly Ser Ser Gly Glu Gln Gly Val Lys Gly
            260                 265                 270

Glu Lys Gly Glu Arg Gly Glu Asn Ser Val Ser Val Arg Ile Val Gly
        275                 280                 285

Ser Ser Asn Arg Gly Arg Ala Glu Val Tyr Tyr Asn Asn Glu Trp Gly
    290                 295                 300

Thr Ile Cys Asp Asp Glu Trp Gln Asn Ser Asp Ala Ile Val Phe Cys
305                 310                 315                 320

Arg Met Leu Gly Tyr Ser Lys Gly Arg Ala Leu Tyr Lys Val Gly Ala
                325                 330                 335

Gly Thr Gly Gln Ile Trp Leu Asp Asn Val Gln Cys Arg Gly Thr Glu
            340                 345                 350

Ser Thr Leu Trp Ser Cys Thr Lys Asn Ser Trp Gly His His Asp Cys
        355                 360                 365

Ser His Glu Glu Asp Ala Gly Val Glu Cys Ser Val
    370                 375                 380

<210> SEQ ID NO 497
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497

His His His His His His Lys Gly Glu Gln Gly Ala Pro Gly Leu Gln
1               5                   10                  15

Gly His Lys Gly Ala Met Gly Met Pro Gly Ala Pro Gly Pro Pro Gly
            20                  25                  30

Pro Pro Ala Glu Lys Gly Ala Lys Gly Ala Met Gly Arg Asp Gly Ala
        35                  40                  45

Thr Gly Pro Ser Gly Pro Gln Gly Pro Gly Val Lys Gly Glu Ala
    50                  55                  60

Gly Leu Gln Gly Pro Gln Gly Ala Pro Gly Lys Gln Gly Ala Thr Gly
65                  70                  75                  80

Thr Pro Gly Pro Gln Gly Glu Lys Gly Ser Lys Gly Asp Gly Gly Leu
                85                  90                  95

```
Ile Gly Pro Lys Gly Glu Thr Gly Thr Lys Gly Glu Lys Gly Asp Leu
            100                 105                 110

Gly Leu Pro Gly Ser Lys Gly Asp Arg Gly Met Lys Gly Asp Ala Gly
            115                 120                 125

Val Met Gly Pro Pro Gly Ala Gln Gly Ser Lys Gly Asp Phe Gly Arg
130                 135                 140

Pro Gly Pro Pro Gly Leu Ala Gly Phe Pro Gly Ala Lys Gly Asp Gln
145                 150                 155                 160

Gly Gln Pro Gly Leu Gln Gly Val Pro Gly Pro Gly Ala Val Gly
            165                 170                 175

His Pro Gly Ala Lys Gly Glu Pro Gly Ser Ala Gly Ser Pro Gly Arg
            180                 185                 190

Ala Gly Leu Pro Gly Ser Pro Gly Ser Pro Gly Ala Thr Gly Leu Lys
            195                 200                 205

Gly Ser Lys Gly Asp Thr Gly Leu Gln Gly Gln Gln Gly Arg Lys Gly
            210                 215                 220

Glu Ser Gly Val Pro Gly Pro Ala Gly Val Lys Gly Glu Gln Gly Ser
225                 230                 235                 240

Pro Gly Leu Ala Gly Pro Lys Gly Ala Pro Gly Gln Ala Gly Gln Lys
            245                 250                 255

Gly Asp Gln Gly Val Lys Gly Ser Ser Gly Glu Gln Gly Val Lys Gly
            260                 265                 270

Glu Lys Gly Glu Arg Gly Glu Asn Ser Val Ser Val Arg Ile Val Gly
            275                 280                 285

Ser Ser Asn Arg Gly Arg Ala Glu Val Tyr Tyr Ser Gly Thr Trp Gly
            290                 295                 300

Thr Ile Cys Asp Asp Asp Trp Asp Asn Asp Ala Ile Val Phe Cys
305                 310                 315                 320

Arg Met Leu Gly Tyr Ser Arg Gly Arg Ala Leu Tyr Lys Val Gly Ala
            325                 330                 335

Gly Thr Gly Gln Ile Trp Leu Asp Asn Val Gln Cys Arg Gly Thr Glu
            340                 345                 350

Ser Thr Leu Trp Ser Cys Thr Lys Asn Ser Trp Gly His His Asp Cys
            355                 360                 365

Ser His Glu Glu Asp Ala Gly Val Glu Cys Ser Val
            370                 375                 380

<210> SEQ ID NO 498
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 498

His His His His His Lys Gly Glu Gln Gly Ala Pro Gly Leu Gln
1               5                   10                  15

Gly His Lys Gly Ala Met Gly Met Pro Gly Ala Pro Gly Pro Pro Gly
            20                  25                  30

Pro Pro Ala Glu Lys Gly Ala Lys Gly Ala Met Gly Arg Asp Gly Ala
            35                  40                  45

Thr Gly Pro Ser Gly Pro Gln Gly Pro Pro Gly Val Lys Gly Glu Ala
50                  55                  60

Gly Leu Gln Gly Pro Gln Gly Ala Pro Gly Lys Gln Gly Ala Thr Gly
```

```
                65                  70                  75                  80
Thr Pro Gly Pro Gln Gly Glu Lys Gly Ser Lys Gly Asp Gly Gly Leu
                    85                  90                  95
Ile Gly Pro Lys Gly Glu Thr Gly Thr Lys Gly Glu Lys Gly Asp Leu
                    100                 105                 110
Gly Leu Pro Gly Ser Lys Gly Asp Arg Gly Met Lys Gly Asp Ala Gly
                    115                 120                 125
Val Met Gly Pro Pro Gly Ala Gln Gly Ser Lys Gly Asp Phe Gly Arg
            130                 135                 140
Pro Gly Pro Pro Gly Leu Ala Gly Phe Pro Gly Ala Lys Gly Asp Gln
145                 150                 155                 160
Gly Gln Pro Gly Leu Gln Gly Val Pro Gly Pro Gly Ala Val Gly
                    165                 170                 175
His Pro Gly Ala Lys Gly Glu Pro Gly Ser Ala Gly Ser Pro Gly Arg
                    180                 185                 190
Ala Gly Leu Pro Gly Ser Pro Gly Ser Pro Gly Ala Thr Gly Leu Lys
                    195                 200                 205
Gly Ser Lys Gly Asp Thr Gly Leu Gln Gly Gln Gln Gly Arg Lys Gly
        210                 215                 220
Glu Ser Gly Val Pro Gly Pro Ala Gly Val Lys Gly Glu Gln Gly Ser
225                 230                 235                 240
Pro Gly Leu Ala Gly Pro Lys Gly Ala Pro Gly Gln Ala Gly Gln Lys
                    245                 250                 255
Gly Asp Gln Gly Val Lys Gly Ser Ser Gly Glu Gln Gly Val Lys Gly
                    260                 265                 270
Glu Lys Gly Glu Arg Gly Glu Asn Ser Val Ser Val Arg Ile Val Gly
                    275                 280                 285
Ser Ser Asn Arg Gly Arg Ala Glu Val Tyr Tyr Ser Gly Thr Trp Gly
        290                 295                 300
Thr Ile Cys Asp Asp Glu Trp Asp Asn Ser Asp Ala Ile Val Phe Cys
305                 310                 315                 320
Arg Met Leu Gly Tyr Ser Lys Gly Arg Ala Leu Ser Ser Val Gly Ala
                    325                 330                 335
Gly Thr Gly Gln Ile Trp Leu Asp Asn Val Gln Cys Arg Gly Thr Glu
                    340                 345                 350
Ser Thr Leu Trp Ser Cys Thr Lys Asn Ser Trp Gly His His Asp Cys
                    355                 360                 365
Ser His Glu Glu Asp Ala Gly Val Glu Cys Ser Val
        370                 375                 380

<210> SEQ ID NO 499
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

His His His His His His Lys Gly Glu Gln Gly Ala Pro Gly Leu Gln
1               5                   10                  15
Gly His Lys Gly Ala Met Gly Met Pro Gly Ala Pro Gly Pro Pro Gly
                    20                  25                  30
Pro Pro Ala Glu Lys Gly Ala Lys Gly Ala Met Gly Arg Asp Gly Ala
                    35                  40                  45
```

```
Thr Gly Pro Ser Gly Pro Gln Gly Pro Pro Gly Val Lys Gly Glu Ala
    50                  55                  60
Gly Leu Gln Gly Pro Gln Gly Ala Pro Gly Lys Gln Gly Ala Thr Gly
65                  70                  75                  80
Thr Pro Gly Pro Gln Gly Glu Lys Gly Ser Lys Gly Asp Gly Gly Leu
                85                  90                  95
Ile Gly Pro Lys Gly Glu Thr Gly Thr Lys Gly Glu Lys Gly Asp Leu
            100                 105                 110
Gly Leu Pro Gly Ser Lys Gly Asp Arg Gly Met Lys Gly Asp Ala Gly
        115                 120                 125
Val Met Gly Pro Pro Gly Ala Gln Gly Ser Lys Gly Asp Phe Gly Arg
130                 135                 140
Pro Gly Pro Pro Gly Leu Ala Gly Phe Pro Gly Ala Lys Gly Asp Gln
145                 150                 155                 160
Gly Gln Pro Gly Leu Gln Gly Val Pro Gly Pro Gly Ala Val Gly
                165                 170                 175
His Pro Gly Ala Lys Gly Glu Pro Gly Ser Ala Gly Ser Pro Gly Arg
            180                 185                 190
Ala Gly Leu Pro Gly Ser Pro Gly Ser Pro Gly Ala Thr Gly Leu Lys
        195                 200                 205
Gly Ser Lys Gly Asp Thr Gly Leu Gln Gly Gln Gln Gly Arg Lys Gly
    210                 215                 220
Glu Ser Gly Val Pro Gly Pro Ala Gly Val Lys Gly Glu Gln Gly Ser
225                 230                 235                 240
Pro Gly Leu Ala Gly Pro Lys Gly Ala Pro Gly Gln Ala Gly Gln Lys
                245                 250                 255
Gly Asp Gln Gly Val Lys Gly Ser Ser Gly Glu Gln Gly Val Lys Gly
            260                 265                 270
Glu Lys Gly Glu Arg Gly Glu Asn Ser Val Ser Val Arg Ile Val Gly
        275                 280                 285
Ser Ser Asn Arg Gly Arg Ala Glu Val Tyr Tyr Ser Gly Thr Trp Gly
    290                 295                 300
Thr Ile Cys Asp Asp Glu Trp Gln Asn Ser Asp Ala Ile Val Phe Cys
305                 310                 315                 320
Arg Met Leu Gly Tyr Ser Lys Gly Arg Ala Leu Tyr Lys Val Gly Ala
                325                 330                 335
Gly Thr Gly Gln Ile Trp Leu Asp Asn Val Gln Cys Arg Gly Thr Glu
            340                 345                 350
Asn Ser Leu Trp Asp Cys Ser Lys Asn Ser Trp Gly His His Asp Cys
        355                 360                 365
Ser His Glu Glu Asp Ala Gly Val Glu Cys Ser Val
    370                 375                 380

<210> SEQ ID NO 500
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

His His His His His Lys Gly Glu Gln Gly Ala Pro Gly Leu Gln
1               5                   10                  15

Gly His Lys Gly Ala Met Gly Met Pro Gly Ala Pro Gly Pro Pro Gly
            20                  25                  30
```

```
Pro Pro Ala Glu Lys Gly Ala Lys Gly Ala Met Gly Arg Asp Gly Ala
        35                  40                  45

Thr Gly Pro Ser Gly Pro Gln Gly Pro Pro Gly Val Lys Gly Glu Ala
 50                  55                  60

Gly Leu Gln Gly Pro Gln Gly Ala Pro Gly Lys Gln Gly Ala Thr Gly
 65                  70                  75                  80

Thr Pro Gly Pro Gln Gly Glu Lys Gly Ser Lys Gly Asp Gly Gly Leu
                 85                  90                  95

Ile Gly Pro Lys Gly Glu Thr Gly Thr Lys Gly Glu Lys Gly Asp Leu
             100                 105                 110

Gly Leu Pro Gly Ser Lys Gly Asp Arg Gly Met Lys Gly Asp Ala Gly
             115                 120                 125

Val Met Gly Pro Pro Gly Ala Gln Gly Ser Lys Gly Asp Phe Gly Arg
 130                 135                 140

Pro Gly Pro Pro Gly Leu Ala Gly Phe Pro Gly Ala Lys Gly Asp Gln
145                 150                 155                 160

Gly Gln Pro Gly Leu Gln Gly Val Pro Gly Pro Gly Ala Val Gly
                 165                 170                 175

His Pro Gly Ala Lys Gly Glu Pro Gly Ser Ala Gly Ser Pro Gly Arg
             180                 185                 190

Ala Gly Leu Pro Gly Ser Pro Gly Ser Pro Gly Ala Thr Gly Leu Lys
             195                 200                 205

Gly Ser Lys Gly Asp Thr Gly Leu Gln Gly Gln Gln Gly Arg Lys Gly
 210                 215                 220

Glu Ser Gly Val Pro Gly Pro Ala Gly Val Lys Gly Glu Gln Gly Ser
225                 230                 235                 240

Pro Gly Leu Ala Gly Pro Lys Gly Ala Pro Gly Gln Ala Gly Gln Lys
                 245                 250                 255

Gly Asp Gln Gly Val Lys Gly Ser Ser Gly Glu Gln Gly Val Lys Gly
             260                 265                 270

Glu Lys Gly Glu Arg Gly Glu Asn Ser Val Ser Val Arg Ile Val Gly
             275                 280                 285

Ser Ser Asn Arg Gly Arg Ala Glu Val Tyr Tyr Ser Gly Thr Trp Gly
 290                 295                 300

Thr Ile Cys Asp Asp Glu Trp Gln Asn Ser Asp Ala Ile Val Phe Cys
305                 310                 315                 320

Arg Met Leu Gly Tyr Ser Lys Gly Arg Ala Leu Tyr Lys Val Gly Ala
                 325                 330                 335

Gly Thr Gly Gln Ile Trp Leu Asp Asn Val Gln Cys Arg Gly Thr Glu
             340                 345                 350

Ser Thr Leu Trp Ser Cys Thr Lys Asn Ser Trp Gly Asn His Asn Cys
             355                 360                 365

Val His Asn Glu Asp Ala Gly Val Glu Cys Ser Val
 370                 375                 380

<210> SEQ ID NO 501
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

His His His His His His Lys Gly Glu Gln Gly Ala Pro Gly Leu Gln
```

```
1               5               10              15
Gly His Lys Gly Ala Met Gly Met Pro Gly Ala Pro Gly Pro Pro Gly
                20              25              30
Pro Pro Ala Glu Lys Gly Ala Lys Gly Ala Met Gly Arg Asp Gly Ala
                35              40              45
Thr Gly Pro Ser Gly Pro Gln Gly Pro Pro Gly Val Lys Gly Glu Ala
            50              55              60
Gly Leu Gln Gly Pro Gln Gly Ala Pro Gly Lys Gln Gly Ala Thr Gly
65              70              75              80
Thr Pro Gly Pro Gln Gly Glu Lys Gly Ser Lys Gly Asp Gly Gly Leu
                85              90              95
Ile Gly Pro Lys Gly Glu Thr Gly Thr Lys Gly Glu Lys Gly Asp Leu
                100             105             110
Gly Leu Pro Gly Ser Lys Gly Asp Arg Gly Met Lys Gly Asp Ala Gly
                115             120             125
Val Met Gly Pro Pro Gly Ala Gln Gly Ser Lys Gly Asp Phe Gly Arg
            130             135             140
Pro Gly Pro Pro Gly Leu Ala Gly Phe Pro Gly Ala Lys Gly Asp Gln
145             150             155             160
Gly Gln Pro Gly Leu Gln Gly Val Pro Gly Pro Gly Ala Val Gly
                165             170             175
His Pro Gly Ala Lys Gly Glu Pro Gly Ser Ala Gly Ser Pro Gly Arg
                180             185             190
Ala Gly Leu Pro Gly Ser Pro Gly Ser Pro Gly Ala Thr Gly Leu Lys
                195             200             205
Gly Ser Lys Gly Asp Thr Gly Leu Gln Gly Gln Gln Gly Arg Lys Gly
                210             215             220
Glu Ser Gly Val Pro Gly Pro Ala Gly Val Lys Gly Glu Gln Gly Ser
225             230             235             240
Pro Gly Leu Ala Gly Pro Lys Gly Ala Pro Gly Gln Ala Gly Gln Lys
                245             250             255
Gly Asp Gln Gly Val Lys Gly Ser Ser Gly Glu Gln Gly Val Lys Gly
                260             265             270
Glu Lys Gly Glu Arg Gly Glu Asn Ser Val Ser Val Arg Ile Val Gly
                275             280             285
Ser Ser Asn Arg Gly Arg Ala Glu Val Tyr Tyr Ser Gly Thr Trp Gly
                290             295             300
Thr Ile Cys Asp Asp Trp Asp Asn Ser Asp Ala Ile Val Phe Cys
305             310             315             320
Arg Met Leu Gly Tyr Ser Lys Gly Arg Ala Leu Tyr Lys Val Gly Ala
                325             330             335
Gly Thr Gly Gln Ile Trp Leu Asp Asn Val Asn Cys Arg Gly Thr Glu
                340             345             350
Ser Thr Leu Trp Ser Cys Ser Lys Asn Ser Trp Gly His His Asp Cys
                355             360             365
Ser His Glu Glu Asp Ala Gly Val Glu Cys Ser Val
                370             375             380

<210> SEQ ID NO 502
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 502

His His His His His His Lys Gly Glu Gln Gly Ala Pro Gly Leu Gln
1               5                   10                  15

Gly His Lys Gly Ala Met Gly Met Pro Gly Ala Pro Gly Pro Pro Gly
            20                  25                  30

Pro Pro Ala Glu Lys Gly Ala Lys Gly Ala Met Gly Arg Asp Gly Ala
        35                  40                  45

Thr Gly Pro Ser Gly Pro Gln Gly Pro Pro Gly Val Lys Gly Glu Ala
    50                  55                  60

Gly Leu Gln Gly Pro Gln Gly Ala Pro Gly Lys Gln Gly Ala Thr Gly
65                  70                  75                  80

Thr Pro Gly Pro Gln Gly Glu Lys Gly Ser Lys Gly Asp Gly Gly Leu
                85                  90                  95

Ile Gly Pro Lys Gly Glu Thr Gly Thr Lys Gly Glu Lys Gly Asp Leu
            100                 105                 110

Gly Leu Pro Gly Ser Lys Gly Asp Arg Gly Met Lys Gly Asp Ala Gly
        115                 120                 125

Val Met Gly Pro Pro Gly Ala Gln Gly Ser Lys Gly Asp Phe Gly Arg
130                 135                 140

Pro Gly Pro Pro Gly Leu Ala Gly Phe Pro Gly Ala Lys Gly Asp Gln
145                 150                 155                 160

Gly Gln Pro Gly Leu Gln Gly Val Pro Gly Pro Pro Gly Ala Val Gly
                165                 170                 175

His Pro Gly Ala Lys Gly Glu Pro Gly Ser Ala Gly Ser Pro Gly Arg
            180                 185                 190

Ala Gly Leu Pro Gly Ser Pro Gly Ser Pro Gly Ala Thr Gly Leu Lys
        195                 200                 205

Gly Ser Lys Gly Asp Thr Gly Leu Gln Gly Gln Gly Arg Lys Gly
210                 215                 220

Glu Ser Gly Val Pro Gly Pro Ala Gly Val Lys Gly Glu Gln Gly Ser
225                 230                 235                 240

Pro Gly Leu Ala Gly Pro Lys Gly Ala Pro Gly Gln Ala Gly Gln Lys
                245                 250                 255

Gly Asp Gln Gly Val Lys Gly Ser Ser Gly Glu Gln Gly Val Lys Gly
            260                 265                 270

Glu Lys Gly Glu Arg Gly Glu Ser Phe Gln Arg Val Arg Ile Val Gly
        275                 280                 285

Gly Thr Asn Arg Gly Arg Ala Glu Val Tyr Tyr Ser Gly Thr Trp Gly
290                 295                 300

Thr Ile Cys Asp Asp Glu Trp Gln Asn Ser Asp Ala Ile Val Phe Cys
305                 310                 315                 320

Arg Met Leu Gly Tyr Ser Lys Gly Arg Ala Leu Tyr Lys Val Gly Ala
                325                 330                 335

Gly Thr Gly Gln Ile Trp Leu Asp Asn Val Gln Cys Arg Gly Thr Glu
            340                 345                 350

Ser Thr Leu Trp Ser Cys Thr Lys Asn Ser Trp Gly His His Asp Cys
        355                 360                 365

Ser His Glu Glu Asp Ala Gly Val Glu Cys Ser Val
370                 375                 380

<210> SEQ ID NO 503
<211> LENGTH: 101
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 503

Ser Phe Gln Arg Val Arg Ile Val Gly Gly Thr Asn Arg Gly Arg Ala
1               5                   10                  15

Glu Val Tyr Tyr Ser Gly Thr Trp Gly Thr Ile Cys Asp Asp Glu Trp
            20                  25                  30

Gln Asn Ser Asp Ala Ile Val Phe Cys Arg Met Leu Gly Tyr Ser Lys
        35                  40                  45

Gly Arg Ala Leu Tyr Lys Val Gly Ala Gly Thr Gly Gln Ile Trp Leu
    50                  55                  60

Asp Asn Val Gln Cys Arg Gly Thr Glu Ser Thr Leu Trp Ser Cys Thr
65                  70                  75                  80

Lys Asn Ser Trp Gly His His Asp Cys Ser His Glu Glu Asp Ala Gly
                85                  90                  95

Val Glu Cys Ser Val
            100

<210> SEQ ID NO 504
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

His His His His His His His Gly Glu Arg Gly Ser Pro Gly Pro
1               5                   10                  15

Lys Gly Ala Pro Gly Ala Pro Gly Ile Pro Gly Leu Pro Gly Pro Ala
            20                  25                  30

Ala Glu Lys Gly Glu Lys Gly Ala Ala Gly Arg Asp Gly Thr Pro Gly
        35                  40                  45

Val Gln Gly Pro Gln Gly Pro Pro Gly Ser Lys Gly Glu Ala Gly Leu
    50                  55                  60

Gln Gly Leu Thr Gly Ala Pro Gly Lys Gln Gly Ala Thr Gly Ala Pro
65                  70                  75                  80

Gly Pro Arg Gly Glu Lys Gly Ser Lys Gly Asp Ile Gly Leu Thr Gly
                85                  90                  95

Pro Lys Gly Glu His Gly Thr Lys Gly Asp Lys Gly Asp Leu Gly Leu
                100                 105                 110

Pro Gly Asn Lys Gly Asp Met Gly Met Lys Gly Asp Thr Gly Pro Met
            115                 120                 125

Gly Ser Pro Gly Ala Gln Gly Gly Lys Gly Asp Ala Gly Lys Pro Gly
        130                 135                 140

Leu Pro Gly Leu Ala Gly Ser Pro Gly Val Lys Gly Asp Gln Gly Lys
145                 150                 155                 160

Pro Gly Val Gln Gly Val Pro Gly Pro Gln Gly Ala Pro Gly Leu Ser
                165                 170                 175

Gly Ala Lys Gly Glu Pro Gly Arg Thr Gly Leu Pro Gly Pro Ala Gly
                180                 185                 190

Pro Pro Gly Ile Ala Gly Asn Pro Gly Ile Ala Gly Val Lys Gly Ser
            195                 200                 205

Lys Gly Asp Thr Gly Ile Gln Gly Gln Lys Gly Thr Lys Gly Glu Ser

```
                 210                 215                 220

Gly Val Pro Gly Leu Val Gly Arg Lys Gly Asp Thr Gly Ser Pro Gly
225                 230                 235                 240

Leu Ala Gly Pro Lys Gly Glu Pro Gly Arg Val Gly Gln Lys Gly Asp
                245                 250                 255

Pro Gly Met Lys Gly Ser Ser Gly Gln Gln Gly Gln Lys Gly Glu Lys
            260                 265                 270

Gly Gln Lys Gly Glu Ser Phe Gln Arg Val Arg Ile Met Gly Gly Thr
        275                 280                 285

Asn Arg Gly Arg Ala Glu Val Tyr Tyr Ser Gly Thr Trp Gly Thr Ile
    290                 295                 300

Cys Asp Asp Trp Asp Asn Asn Asp Ala Thr Val Phe Cys Arg Met
305                 310                 315                 320

Leu Gly Tyr Ser Arg Gly Arg Ala Leu Ser Ser Tyr Gly Gly Ser
                325                 330                 335

Gly Asn Ile Trp Leu Asp Asn Val Asn Cys Arg Gly Thr Glu Asn Ser
            340                 345                 350

Leu Trp Asp Cys Ser Lys Asn Ser Trp Gly Asn His Asn Cys Val His
        355                 360                 365

Asn Glu Asp Ala Gly Val Glu Cys Ser
    370                 375

<210> SEQ ID NO 505
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

His His His His His His His Gly Glu Arg Gly Ser Pro Gly Pro
1               5                   10                  15

Lys Gly Ala Pro Gly Ala Pro Gly Ile Pro Gly Leu Pro Gly Pro Ala
                20                  25                  30

Ala Glu Lys Gly Glu Lys Gly Ala Ala Gly Arg Asp Gly Thr Pro Gly
            35                  40                  45

Val Gln Gly Pro Gln Pro Pro Gly Ser Lys Gly Glu Ala Gly Leu
        50                  55                  60

Gln Gly Leu Thr Gly Ala Pro Gly Lys Gln Gly Ala Thr Gly Ala Pro
65                  70                  75                  80

Gly Pro Arg Gly Glu Lys Gly Ser Lys Gly Asp Ile Gly Leu Thr Gly
                85                  90                  95

Pro Lys Gly Glu His Gly Thr Lys Gly Asp Lys Gly Asp Leu Gly Leu
            100                 105                 110

Pro Gly Asn Lys Gly Asp Met Gly Met Lys Gly Asp Thr Gly Pro Met
        115                 120                 125

Gly Ser Pro Gly Ala Gln Gly Gly Lys Gly Asp Ala Gly Lys Pro Gly
    130                 135                 140

Leu Pro Gly Leu Ala Gly Ser Pro Gly Val Lys Gly Asp Gln Gly Lys
145                 150                 155                 160

Pro Gly Val Gln Gly Val Pro Gly Pro Gln Gly Ala Pro Gly Leu Ser
                165                 170                 175

Gly Ala Lys Gly Glu Pro Gly Arg Thr Gly Leu Pro Gly Pro Ala Gly
            180                 185                 190
```

-continued

```
Pro Pro Gly Ile Ala Gly Asn Pro Gly Ile Ala Gly Val Lys Gly Ser
        195                 200                 205

Lys Gly Asp Thr Gly Ile Gln Gly Gln Lys Gly Thr Lys Gly Glu Ser
    210                 215                 220

Gly Val Pro Gly Leu Val Gly Arg Lys Gly Asp Thr Gly Ser Pro Gly
225                 230                 235                 240

Leu Ala Gly Pro Lys Gly Glu Pro Gly Arg Val Gly Gln Lys Gly Asp
                245                 250                 255

Pro Gly Met Lys Gly Ser Ser Gly Gln Gly Gln Lys Gly Glu Lys
        260                 265                 270

Gly Gln Lys Gly Glu Ser Phe Gln Arg Val Arg Ile Met Gly Gly Thr
    275                 280                 285

Asn Arg Gly Arg Ala Glu Val Tyr Tyr Asn Asn Glu Trp Gly Thr Ile
290                 295                 300

Cys Asp Asp Glu Trp Gln Asn Ser Asp Ala Thr Val Phe Cys Arg Met
305                 310                 315                 320

Leu Gly Tyr Ser Lys Gly Arg Ala Leu Ser Ser Tyr Gly Gly Ser
                325                 330                 335

Gly Asn Ile Trp Leu Asp Asn Val Asn Cys Arg Gly Thr Glu Asn Ser
                340                 345                 350

Leu Trp Asp Cys Ser Lys Asn Ser Trp Gly Asn His Asn Cys Val His
        355                 360                 365

Asn Glu Asp Ala Gly Val Glu Cys Ser
        370                 375

<210> SEQ ID NO 506
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

His His His His His His His Gly Glu Arg Gly Ser Pro Gly Pro
1               5                   10                  15

Lys Gly Ala Pro Gly Ala Pro Gly Ile Pro Gly Leu Pro Gly Pro Ala
            20                  25                  30

Ala Glu Lys Gly Glu Lys Gly Ala Ala Gly Arg Asp Gly Thr Pro Gly
        35                  40                  45

Val Gln Gly Pro Gln Gly Pro Pro Gly Ser Lys Gly Glu Ala Gly Leu
    50                  55                  60

Gln Gly Leu Thr Gly Ala Pro Gly Lys Gln Gly Ala Thr Gly Ala Pro
65                  70                  75                  80

Gly Pro Arg Gly Glu Lys Gly Ser Lys Gly Asp Ile Gly Leu Thr Gly
                85                  90                  95

Pro Lys Gly Glu His Gly Thr Lys Gly Asp Lys Gly Asp Leu Gly Leu
            100                 105                 110

Pro Gly Asn Lys Gly Asp Met Gly Met Lys Gly Asp Thr Gly Pro Met
        115                 120                 125

Gly Ser Pro Gly Ala Gln Gly Gly Lys Gly Asp Ala Gly Lys Pro Gly
    130                 135                 140

Leu Pro Gly Leu Ala Gly Ser Pro Gly Val Lys Gly Asp Gln Gly Lys
145                 150                 155                 160

Pro Gly Val Gln Gly Val Pro Gly Pro Gln Gly Ala Pro Gly Leu Ser
                165                 170                 175
```

```
Gly Ala Lys Gly Glu Pro Gly Arg Thr Gly Leu Pro Gly Pro Ala Gly
            180                 185                 190

Pro Pro Gly Ile Ala Gly Asn Pro Gly Ile Ala Gly Val Lys Gly Ser
        195                 200                 205

Lys Gly Asp Thr Gly Ile Gln Gly Gln Lys Gly Thr Lys Gly Glu Ser
    210                 215                 220

Gly Val Pro Gly Leu Val Gly Arg Lys Gly Asp Thr Gly Ser Pro Gly
225                 230                 235                 240

Leu Ala Gly Pro Lys Gly Glu Pro Gly Arg Val Gly Gln Lys Gly Asp
                245                 250                 255

Pro Gly Met Lys Gly Ser Ser Gly Gln Gln Gly Leu Lys Gly Glu Lys
            260                 265                 270

Gly Gln Lys Gly Glu Ser Phe Gln Arg Val Arg Ile Met Gly Gly Thr
        275                 280                 285

Asn Arg Gly Arg Ala Glu Val Tyr Tyr Asn Asn Glu Trp Gly Thr Ile
    290                 295                 300

Cys Asp Asp Asp Trp Gln Asn Asn Asp Ala Thr Val Phe Cys Arg Met
305                 310                 315                 320

Leu Gly Tyr Ser Arg Gly Arg Ala Leu Tyr Lys Tyr Gly Gly Gly Ser
                325                 330                 335

Gly Asn Ile Trp Leu Asp Asn Val Asn Cys Arg Gly Thr Glu Asn Ser
            340                 345                 350

Leu Trp Asp Cys Ser Lys Asn Ser Trp Gly Asn His Asn Cys Val His
        355                 360                 365

Asn Glu Asp Ala Gly Val Glu Cys Ser
    370                 375

<210> SEQ ID NO 507
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

His His His His His His His Gly Glu Arg Gly Ser Pro Gly Pro
1               5                   10                  15

Lys Gly Ala Pro Gly Ala Pro Gly Ile Pro Gly Leu Pro Gly Pro Ala
            20                  25                  30

Ala Glu Lys Gly Glu Lys Gly Ala Ala Gly Arg Asp Gly Thr Pro Gly
        35                  40                  45

Val Gln Gly Pro Gln Gly Pro Pro Gly Ser Lys Gly Glu Ala Gly Leu
    50                  55                  60

Gln Gly Leu Thr Gly Ala Pro Gly Lys Gln Gly Ala Thr Gly Ala Pro
65                  70                  75                  80

Gly Pro Arg Gly Glu Lys Gly Ser Lys Gly Asp Ile Gly Leu Thr Gly
                85                  90                  95

Pro Lys Gly Glu His Gly Thr Lys Gly Asp Lys Gly Asp Leu Gly Leu
            100                 105                 110

Pro Gly Asn Lys Gly Asp Met Gly Met Lys Gly Asp Thr Gly Pro Met
        115                 120                 125

Gly Ser Pro Gly Ala Gln Gly Gly Lys Gly Asp Ala Gly Lys Pro Gly
    130                 135                 140

Leu Pro Gly Leu Ala Gly Ser Pro Gly Val Lys Gly Asp Gln Gly Lys
```

```
            145                 150                 155                 160
Pro Gly Val Gln Gly Val Pro Gly Pro Gln Gly Ala Pro Gly Leu Ser
                165                 170                 175
Gly Ala Lys Gly Glu Pro Gly Arg Thr Gly Leu Pro Gly Pro Ala Gly
                180                 185                 190
Pro Pro Gly Ile Ala Gly Asn Pro Gly Ile Ala Gly Val Lys Gly Ser
                195                 200                 205
Lys Gly Asp Thr Gly Ile Gln Gly Gln Lys Gly Thr Lys Gly Glu Ser
            210                 215                 220
Gly Val Pro Gly Leu Val Gly Arg Lys Gly Asp Thr Gly Ser Pro Gly
225                 230                 235                 240
Leu Ala Gly Pro Lys Gly Glu Pro Gly Arg Val Gly Gln Lys Gly Asp
                245                 250                 255
Pro Gly Met Lys Gly Ser Ser Gly Gln Gln Gly Lys Gly Glu Lys
                260                 265                 270
Gly Gln Lys Gly Glu Ser Phe Gln Arg Val Arg Ile Met Gly Gly Thr
            275                 280                 285
Asn Arg Gly Arg Ala Glu Val Tyr Tyr Asn Asn Glu Trp Gly Thr Ile
        290                 295                 300
Cys Asp Asp Asp Trp Asp Asn Asn Asp Ala Thr Val Phe Cys Arg Met
305                 310                 315                 320
Leu Gly Tyr Ser Arg Gly Arg Ala Leu Ser Ser Tyr Gly Gly Ser
                325                 330                 335
Gly Asn Ile Trp Leu Asp Asn Val Asn Cys Arg Gly Thr Glu Ser Thr
                340                 345                 350
Leu Trp Ser Cys Thr Lys Asn Ser Trp Gly Asn His Asn Cys Val His
            355                 360                 365
Asn Glu Asp Ala Gly Val Glu Cys Ser
            370                 375

<210> SEQ ID NO 508
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

His His His His His His His Gly Glu Arg Gly Ser Pro Gly Pro
1               5                   10                  15
Lys Gly Ala Pro Gly Ala Pro Gly Ile Pro Gly Leu Pro Gly Pro Ala
                20                  25                  30
Ala Glu Lys Gly Glu Lys Gly Ala Ala Gly Arg Asp Gly Thr Pro Gly
            35                  40                  45
Val Gln Gly Pro Gln Gly Pro Pro Gly Ser Lys Gly Glu Ala Gly Leu
        50                  55                  60
Gln Gly Leu Thr Gly Ala Pro Gly Lys Gln Gly Ala Thr Gly Ala Pro
65                  70                  75                  80
Gly Pro Arg Gly Glu Lys Gly Ser Lys Gly Asp Ile Gly Leu Thr Gly
                85                  90                  95
Pro Lys Gly Glu His Gly Thr Lys Gly Asp Lys Gly Asp Leu Gly Leu
                100                 105                 110
Pro Gly Asn Lys Gly Asp Met Gly Met Lys Gly Asp Thr Gly Pro Met
            115                 120                 125
```

```
Gly Ser Pro Gly Ala Gln Gly Gly Lys Gly Asp Ala Gly Lys Pro Gly
        130                 135                 140

Leu Pro Gly Leu Ala Gly Ser Pro Gly Val Lys Gly Asp Gln Gly Lys
145                 150                 155                 160

Pro Gly Val Gln Gly Val Pro Gly Pro Gln Gly Ala Pro Gly Leu Ser
            165                 170                 175

Gly Ala Lys Gly Glu Pro Gly Arg Thr Gly Leu Pro Gly Pro Ala Gly
        180                 185                 190

Pro Pro Gly Ile Ala Gly Asn Pro Gly Ile Ala Gly Val Lys Gly Ser
        195                 200                 205

Lys Gly Asp Thr Gly Ile Gln Gly Gln Lys Gly Thr Lys Gly Glu Ser
210                 215                 220

Gly Val Pro Gly Leu Val Gly Arg Lys Gly Asp Thr Gly Ser Pro Gly
225                 230                 235                 240

Leu Ala Gly Pro Lys Gly Glu Pro Gly Arg Val Gly Gln Lys Gly Asp
            245                 250                 255

Pro Gly Met Lys Gly Ser Ser Gly Gln Gln Gly Lys Gly Glu Lys
        260                 265                 270

Gly Gln Lys Gly Glu Ser Phe Gln Arg Val Arg Ile Met Gly Gly Thr
        275                 280                 285

Asn Arg Gly Arg Ala Glu Val Tyr Tyr Asn Asn Glu Trp Gly Thr Ile
290                 295                 300

Cys Asp Asp Asp Trp Asp Asn Asn Asp Ala Thr Val Phe Cys Arg Met
305                 310                 315                 320

Leu Gly Tyr Ser Arg Gly Arg Ala Leu Ser Ser Tyr Gly Gly Gly Ser
            325                 330                 335

Gly Asn Ile Trp Leu Asp Asn Val Asn Cys Arg Gly Thr Glu Asn Ser
        340                 345                 350

Leu Trp Asp Cys Ser Lys Asn Ser Trp Gly His His Asp Cys Ser His
        355                 360                 365

Glu Glu Asp Ala Gly Val Glu Cys Ser
        370                 375

<210> SEQ ID NO 509
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

His His His His His His His Gly Glu Arg Gly Ser Pro Gly Pro
1               5                   10                  15

Lys Gly Ala Pro Gly Ala Pro Gly Ile Pro Gly Leu Pro Gly Pro Ala
            20                  25                  30

Ala Glu Lys Gly Glu Lys Gly Ala Ala Gly Arg Asp Gly Thr Pro Gly
        35                  40                  45

Val Gln Gly Pro Gln Gly Pro Pro Gly Ser Lys Gly Glu Ala Gly Leu
    50                  55                  60

Gln Gly Leu Thr Gly Ala Pro Gly Lys Gln Gly Ala Thr Gly Ala Pro
65                  70                  75                  80

Gly Pro Arg Gly Glu Lys Gly Ser Lys Gly Asp Ile Gly Leu Thr Gly
            85                  90                  95

Pro Lys Gly Glu His Gly Thr Lys Gly Asp Lys Gly Asp Leu Gly Leu
        100                 105                 110
```

Pro Gly Asn Lys Gly Asp Met Gly Met Lys Gly Asp Thr Gly Pro Met
            115                 120                 125

Gly Ser Pro Gly Ala Gln Gly Lys Gly Asp Ala Gly Lys Pro Gly
        130                 135                 140

Leu Pro Gly Leu Ala Gly Ser Pro Gly Val Lys Gly Asp Gln Gly Lys
145                 150                 155                 160

Pro Gly Val Gln Gly Val Pro Gly Pro Gln Gly Ala Pro Gly Leu Ser
                165                 170                 175

Gly Ala Lys Gly Glu Pro Gly Arg Thr Gly Leu Pro Gly Pro Ala Gly
            180                 185                 190

Pro Pro Gly Ile Ala Gly Asn Pro Gly Ile Ala Gly Val Lys Gly Ser
            195                 200                 205

Lys Gly Asp Thr Gly Ile Gln Gly Gln Lys Gly Thr Lys Gly Glu Ser
            210                 215                 220

Gly Val Pro Gly Leu Val Gly Arg Lys Gly Asp Thr Gly Ser Pro Gly
225                 230                 235                 240

Leu Ala Gly Pro Lys Gly Glu Pro Gly Arg Val Gly Gln Lys Gly Asp
                245                 250                 255

Pro Gly Met Lys Gly Ser Ser Gly Gln Gln Gly Lys Gly Glu Lys
            260                 265                 270

Gly Gln Lys Gly Glu Ser Phe Gln Arg Val Arg Ile Met Gly Thr
            275                 280                 285

Asn Arg Gly Arg Ala Glu Val Tyr Tyr Asn Asn Glu Trp Gly Thr Ile
            290                 295                 300

Cys Asp Asp Glu Trp Gln Asn Asn Asp Ala Thr Val Phe Cys Arg Met
305                 310                 315                 320

Leu Gly Tyr Ser Arg Gly Arg Ala Leu Ser Ser Tyr Gly Gly Ser
                325                 330                 335

Gly Asn Ile Trp Leu Asp Asn Val Gln Cys Arg Gly Thr Glu Asn Ser
            340                 345                 350

Leu Trp Asp Cys Thr Lys Asn Ser Trp Gly Asn His Asn Cys Val His
            355                 360                 365

Asn Glu Asp Ala Gly Val Glu Cys Ser
            370                 375

<210> SEQ ID NO 510
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

His His His His His His His Gly Glu Arg Gly Ser Pro Gly Pro
1               5                   10                  15

Lys Gly Ala Pro Gly Ala Pro Gly Ile Pro Gly Leu Pro Gly Pro Ala
            20                  25                  30

Ala Glu Lys Gly Glu Lys Gly Ala Ala Gly Arg Asp Gly Thr Pro Gly
            35                  40                  45

Val Gln Gly Pro Gln Gly Pro Pro Gly Ser Lys Gly Glu Ala Gly Leu
    50                  55                  60

Gln Gly Leu Thr Gly Ala Pro Gly Lys Gln Gly Ala Thr Gly Ala Pro
65                  70                  75                  80

Gly Pro Arg Gly Glu Lys Gly Ser Lys Gly Asp Ile Gly Leu Thr Gly

```
                85                  90                  95

Pro Lys Gly Glu His Gly Thr Lys Gly Asp Lys Gly Asp Leu Gly Leu
            100                 105                 110

Pro Gly Asn Lys Gly Asp Met Gly Met Lys Gly Asp Thr Gly Pro Met
            115                 120                 125

Gly Ser Pro Gly Ala Gln Gly Lys Gly Asp Ala Gly Lys Pro Gly
        130                 135                 140

Leu Pro Gly Leu Ala Gly Ser Pro Gly Val Lys Gly Asp Gln Gly Lys
145                 150                 155                 160

Pro Gly Val Gln Gly Val Pro Gly Pro Gln Gly Ala Pro Gly Leu Ser
                165                 170                 175

Gly Ala Lys Gly Glu Pro Gly Arg Thr Gly Leu Pro Gly Pro Ala Gly
            180                 185                 190

Pro Pro Gly Ile Ala Gly Asn Pro Gly Ile Ala Gly Val Lys Gly Ser
            195                 200                 205

Lys Gly Asp Thr Gly Ile Gln Gly Gln Lys Gly Thr Lys Gly Glu Ser
        210                 215                 220

Gly Val Pro Gly Leu Val Gly Arg Lys Gly Asp Thr Gly Ser Pro Gly
225                 230                 235                 240

Leu Ala Gly Pro Lys Gly Glu Pro Gly Arg Val Gly Gln Lys Gly Asp
                245                 250                 255

Pro Gly Met Lys Gly Ser Ser Gly Gln Gln Gln Lys Gly Glu Lys
            260                 265                 270

Gly Gln Lys Gly Glu Asn Ser Val Ser Val Arg Ile Met Gly Ser Ser
        275                 280                 285

Asn Arg Gly Arg Ala Glu Val Tyr Tyr Asn Asn Glu Trp Gly Thr Ile
290                 295                 300

Cys Asp Asp Asp Trp Asp Asn Asn Asp Ala Thr Val Phe Cys Arg Met
305                 310                 315                 320

Leu Gly Tyr Ser Arg Gly Arg Ala Leu Ser Ser Tyr Gly Gly Ser
                325                 330                 335

Gly Asn Ile Trp Leu Asp Asn Val Asn Cys Arg Gly Thr Glu Asn Ser
        340                 345                 350

Leu Trp Asp Cys Ser Lys Asn Ser Trp Gly Asn His Asn Cys Val His
            355                 360                 365

Asn Glu Asp Ala Gly Val Glu Cys Ser
            370                 375

<210> SEQ ID NO 511
<211> LENGTH: 109
<212> TYPE: PRT
<213> ORGANISM: Homo sapiens

<400> SEQUENCE: 511

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Lys Trp Gly Gln Gly Thr Leu Val Thr Val Ser Ser
            100                 105

<210> SEQ ID NO 512
<211> LENGTH: 106
<212> TYPE: PRT
<213> ORGANISM: Homo sapiens

<400> SEQUENCE: 512

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Phe Gly Gln Gly Thr Lys Leu Glu Ile Lys
            100                 105

<210> SEQ ID NO 513
<211> LENGTH: 101
<212> TYPE: PRT
<213> ORGANISM: Homo sapiens

<400> SEQUENCE: 513

Asn Ser Val Ser Val Arg Ile Val Gly Ser Asn Arg Gly Arg Ala
1               5                   10                  15

Glu Val Tyr Tyr Ser Gly Thr Trp Gly Thr Ile Cys Asp Asp Glu Trp
            20                  25                  30

Gln Asn Ser Asp Ala Ile Val Phe Cys Arg Met Leu Gly Tyr Ser Lys
        35                  40                  45

Gly Arg Ala Leu Tyr Lys Val Gly Ala Gly Thr Gly Gln Ile Trp Leu
    50                  55                  60

Asp Asn Val Gln Cys Arg Gly Thr Glu Ser Thr Leu Trp Ser Cys Thr
65                  70                  75                  80

Lys Asn Ser Trp Gly His His Asp Cys Ser His Glu Glu Asp Ala Gly
                85                  90                  95

Val Glu Cys Ser Val
            100

<210> SEQ ID NO 514
<211> LENGTH: 100
<212> TYPE: PRT
<213> ORGANISM: Mus musculus

<400> SEQUENCE: 514

Ser Phe Gln Arg Val Arg Ile Met Gly Gly Thr Asn Arg Gly Arg Ala
1               5                   10                  15

Glu Val Tyr Tyr Asn Asn Glu Trp Gly Thr Ile Cys Asp Asp Trp
            20                  25                  30

Asp Asn Asn Asp Ala Thr Val Phe Cys Arg Met Leu Gly Tyr Ser Arg
```

```
                35                  40                  45
Gly Arg Ala Leu Ser Ser Tyr Gly Gly Gly Ser Gly Asn Ile Trp Leu
        50                  55                  60
Asp Asn Val Asn Cys Arg Gly Thr Glu Asn Ser Leu Trp Asp Cys Ser
 65                  70                  75                  80
Lys Asn Ser Trp Gly Asn His Asn Cys Val His Asn Glu Asp Ala Gly
                85                  90                  95
Val Glu Cys Ser
            100

<210> SEQ ID NO 515
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Ser Phe Gln Arg Val Arg Ile Met Gly Gly Thr Asn Arg Gly Arg Ala
 1               5                  10                  15
Glu Val Tyr Tyr Ser Gly Thr Trp Gly Thr Ile Cys Asp Asp Asp Trp
                20                  25                  30
Asp Asn Asn Asp Ala Thr Val Phe Cys Arg Met Leu Gly Tyr Ser Arg
                35                  40                  45
Gly Arg Ala Leu Ser Ser Tyr Gly Gly Gly Ser Gly Asn Ile Trp Leu
        50                  55                  60
Asp Asn Val Asn Cys Arg Gly Thr Glu Asn Ser Leu Trp Asp Cys Ser
 65                  70                  75                  80
Lys Asn Ser Trp Gly Asn His Asn Cys Val His Asn Glu Asp Ala Gly
                85                  90                  95
Val Glu Cys Ser
            100

<210> SEQ ID NO 516
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

Ser Phe Gln Arg Val Arg Ile Met Gly Gly Thr Asn Arg Gly Arg Ala
 1               5                  10                  15
Glu Val Tyr Tyr Asn Asn Glu Trp Gly Thr Ile Cys Asp Asp Glu Trp
                20                  25                  30
Gln Asn Ser Asp Ala Thr Val Phe Cys Arg Met Leu Gly Tyr Ser Lys
                35                  40                  45
Gly Arg Ala Leu Ser Ser Tyr Gly Gly Gly Ser Gly Asn Ile Trp Leu
        50                  55                  60
Asp Asn Val Asn Cys Arg Gly Thr Glu Asn Ser Leu Trp Asp Cys Ser
 65                  70                  75                  80
Lys Asn Ser Trp Gly Asn His Asn Cys Val His Asn Glu Asp Ala Gly
                85                  90                  95
Val Glu Cys Ser
            100
```

```
<210> SEQ ID NO 517
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 517

Ser Phe Gln Arg Val Arg Ile Met Gly Gly Thr Asn Arg Gly Arg Ala
1               5                   10                  15

Glu Val Tyr Tyr Asn Asn Glu Trp Gly Thr Ile Cys Asp Asp Asp Trp
            20                  25                  30

Gln Asn Asn Asp Ala Thr Val Phe Cys Arg Met Leu Gly Tyr Ser Arg
        35                  40                  45

Gly Arg Ala Leu Tyr Lys Tyr Gly Gly Ser Gly Asn Ile Trp Leu
    50                  55                  60

Asp Asn Val Asn Cys Arg Gly Thr Glu Asn Ser Leu Trp Asp Cys Ser
65                  70                  75                  80

Lys Asn Ser Trp Gly Asn His Asn Cys Val His Asn Glu Asp Ala Gly
                85                  90                  95

Val Glu Cys Ser
            100

<210> SEQ ID NO 518
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 518

Ser Phe Gln Arg Val Arg Ile Met Gly Gly Thr Asn Arg Gly Arg Ala
1               5                   10                  15

Glu Val Tyr Tyr Asn Asn Glu Trp Gly Thr Ile Cys Asp Asp Asp Trp
            20                  25                  30

Asp Asn Asn Asp Ala Thr Val Phe Cys Arg Met Leu Gly Tyr Ser Arg
        35                  40                  45

Gly Arg Ala Leu Ser Ser Tyr Gly Gly Gly Ser Gly Asn Ile Trp Leu
    50                  55                  60

Asp Asn Val Asn Cys Arg Gly Thr Glu Ser Thr Leu Trp Ser Cys Thr
65                  70                  75                  80

Lys Asn Ser Trp Gly Asn His Asn Cys Val His Asn Glu Asp Ala Gly
                85                  90                  95

Val Glu Cys Ser
            100

<210> SEQ ID NO 519
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

Ser Phe Gln Arg Val Arg Ile Met Gly Gly Thr Asn Arg Gly Arg Ala
1               5                   10                  15

Glu Val Tyr Tyr Asn Asn Glu Trp Gly Thr Ile Cys Asp Asp Asp Trp
            20                  25                  30
```

```
Asp Asn Asn Asp Ala Thr Val Phe Cys Arg Met Leu Gly Tyr Ser Arg
            35                  40                  45

Gly Arg Ala Leu Ser Ser Tyr Gly Gly Gly Ser Gly Asn Ile Trp Leu
 50                  55                  60

Asp Asn Val Asn Cys Arg Gly Thr Glu Asn Ser Leu Trp Asp Cys Ser
 65                  70                  75                  80

Lys Asn Ser Trp Gly His His Asp Cys Ser His Glu Glu Asp Ala Gly
                85                  90                  95

Val Glu Cys Ser
            100

<210> SEQ ID NO 520
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 520

Ser Phe Gln Arg Val Arg Ile Met Gly Gly Thr Asn Arg Gly Arg Ala
 1                5                  10                  15

Glu Val Tyr Tyr Asn Asn Glu Trp Gly Thr Ile Cys Asp Asp Glu Trp
                20                  25                  30

Gln Asn Asp Ala Thr Val Phe Cys Arg Met Leu Gly Tyr Ser Arg
            35                  40                  45

Gly Arg Ala Leu Ser Ser Tyr Gly Gly Gly Ser Gly Asn Ile Trp Leu
 50                  55                  60

Asp Asn Val Gln Cys Arg Gly Thr Glu Asn Ser Leu Trp Asp Cys Thr
 65                  70                  75                  80

Lys Asn Ser Trp Gly Asn His Asn Cys Val His Asn Glu Asp Ala Gly
                85                  90                  95

Val Glu Cys Ser
            100

<210> SEQ ID NO 521
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

Asn Ser Val Ser Val Arg Ile Met Gly Ser Ser Asn Arg Gly Arg Ala
 1                5                  10                  15

Glu Val Tyr Tyr Asn Asn Glu Trp Gly Thr Ile Cys Asp Asp Asp Trp
                20                  25                  30

Asp Asn Asn Asp Ala Thr Val Phe Cys Arg Met Leu Gly Tyr Ser Arg
            35                  40                  45

Gly Arg Ala Leu Ser Ser Tyr Gly Gly Gly Ser Gly Asn Ile Trp Leu
 50                  55                  60

Asp Asn Val Asn Cys Arg Gly Thr Glu Asn Ser Leu Trp Asp Cys Ser
 65                  70                  75                  80

Lys Asn Ser Trp Gly Asn His Asn Cys Val His Asn Glu Asp Ala Gly
                85                  90                  95

Val Glu Cys Ser
            100
```

<210> SEQ ID NO 522
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 522

```
Asn Ser Val Ser Val Arg Ile Val Gly Ser Ser Asn Arg Gly Arg Ala
1               5                   10                  15

Glu Val Tyr Tyr Asn Asn Glu Trp Gly Thr Ile Cys Asp Asp Glu Trp
            20                  25                  30

Gln Asn Ser Asp Ala Ile Val Phe Cys Arg Met Leu Gly Tyr Ser Lys
        35                  40                  45

Gly Arg Ala Leu Tyr Lys Val Gly Ala Gly Thr Gly Gln Ile Trp Leu
    50                  55                  60

Asp Asn Val Gln Cys Arg Gly Thr Glu Ser Thr Leu Trp Ser Cys Thr
65                  70                  75                  80

Lys Asn Ser Trp Gly His His Asp Cys Ser His Glu Glu Asp Ala Gly
                85                  90                  95

Val Glu Cys Ser Val
            100
```

<210> SEQ ID NO 523
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

```
Asn Ser Val Ser Val Arg Ile Val Gly Ser Ser Asn Arg Gly Arg Ala
1               5                   10                  15

Glu Val Tyr Tyr Ser Gly Thr Trp Gly Thr Ile Cys Asp Asp Asp Trp
            20                  25                  30

Asp Asn Asn Asp Ala Ile Val Phe Cys Arg Met Leu Gly Tyr Ser Arg
        35                  40                  45

Gly Arg Ala Leu Tyr Lys Val Gly Ala Gly Thr Gly Gln Ile Trp Leu
    50                  55                  60

Asp Asn Val Gln Cys Arg Gly Thr Glu Ser Thr Leu Trp Ser Cys Thr
65                  70                  75                  80

Lys Asn Ser Trp Gly His His Asp Cys Ser His Glu Glu Asp Ala Gly
                85                  90                  95

Val Glu Cys Ser Val
            100
```

<210> SEQ ID NO 524
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 524

```
Asn Ser Val Ser Val Arg Ile Val Gly Ser Ser Asn Arg Gly Arg Ala
1               5                   10                  15
```

```
Glu Val Tyr Tyr Ser Gly Thr Trp Gly Thr Ile Cys Asp Asp Glu Trp
            20                  25                  30

Asp Asn Ser Asp Ala Ile Val Phe Cys Arg Met Leu Gly Tyr Ser Lys
        35                  40                  45

Gly Arg Ala Leu Ser Ser Val Gly Ala Gly Thr Gly Gln Ile Trp Leu
    50                  55                  60

Asp Asn Val Gln Cys Arg Gly Thr Glu Ser Thr Leu Trp Ser Cys Thr
65                  70                  75                  80

Lys Asn Ser Trp Gly His His Asp Cys Ser His Glu Glu Asp Ala Gly
                85                  90                  95

Val Glu Cys Ser Val
            100

<210> SEQ ID NO 525
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 525

Asn Ser Val Ser Val Arg Ile Val Gly Ser Ser Asn Arg Gly Arg Ala
1               5                   10                  15

Glu Val Tyr Tyr Ser Gly Thr Trp Gly Thr Ile Cys Asp Asp Glu Trp
            20                  25                  30

Gln Asn Ser Asp Ala Ile Val Phe Cys Arg Met Leu Gly Tyr Ser Lys
        35                  40                  45

Gly Arg Ala Leu Tyr Lys Val Gly Ala Gly Thr Gly Gln Ile Trp Leu
    50                  55                  60

Asp Asn Val Gln Cys Arg Gly Thr Glu Asn Ser Leu Trp Asp Cys Ser
65                  70                  75                  80

Lys Asn Ser Trp Gly His His Asp Cys Ser His Glu Glu Asp Ala Gly
                85                  90                  95

Val Glu Cys Ser Val
            100

<210> SEQ ID NO 526
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 526

Asn Ser Val Ser Val Arg Ile Val Gly Ser Ser Asn Arg Gly Arg Ala
1               5                   10                  15

Glu Val Tyr Tyr Ser Gly Thr Trp Gly Thr Ile Cys Asp Asp Glu Trp
            20                  25                  30

Gln Asn Ser Asp Ala Ile Val Phe Cys Arg Met Leu Gly Tyr Ser Lys
        35                  40                  45

Gly Arg Ala Leu Tyr Lys Val Gly Ala Gly Thr Gly Gln Ile Trp Leu
    50                  55                  60

Asp Asn Val Gln Cys Arg Gly Thr Glu Ser Thr Leu Trp Ser Cys Thr
65                  70                  75                  80

Lys Asn Ser Trp Gly Asn His Asn Cys Val His Asn Glu Asp Ala Gly
                85                  90                  95
```

```
Val Glu Cys Ser Val
            100

<210> SEQ ID NO 527
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 527

Asn Ser Val Ser Val Arg Ile Val Gly Ser Ser Asn Arg Gly Arg Ala
1               5                   10                  15

Glu Val Tyr Tyr Ser Gly Thr Trp Gly Thr Ile Cys Asp Asp Asp Trp
            20                  25                  30

Asp Asn Ser Asp Ala Ile Val Phe Cys Arg Met Leu Gly Tyr Ser Lys
        35                  40                  45

Gly Arg Ala Leu Tyr Lys Val Gly Ala Gly Thr Gly Gln Ile Trp Leu
    50                  55                  60

Asp Asn Val Asn Cys Arg Gly Thr Glu Ser Thr Leu Trp Ser Cys Ser
65                  70                  75                  80

Lys Asn Ser Trp Gly His His Asp Cys Ser His Glu Glu Asp Ala Gly
                85                  90                  95

Val Glu Cys Ser Val
            100
```

ANTI-MARCO ANTIBODIES AND USES THEREOF

CROSS REFERENCE TO RELATED APPLICATIONS

This application claims priority to, and the benefit of, U.S. Application No. 63/115,272, filed Nov. 18, 2020, and U.S. Application No. 63/244,662, filed Sep. 15, 2021, each of which are hereby incorporated by reference in their entirety.

SEQUENCE LISTING

The instant application contains a Sequence Listing which has been submitted via EFS-Web and is hereby incorporated by reference in its entirety. Said ASCII copy, created on Feb. 3, 2022, is named PII-013US SL.txt, and is 566,278 bytes in size.

BACKGROUND

Myeloid populations of the tumor microenvironment prominently include monocytes and neutrophils (sometimes loosely grouped as myeloid-derived suppressor cells), macrophages, and dendritic cells. Although intra-tumoral myeloid populations, as a whole, have long been considered non-stimulatory or suppressive, it has more recently been appreciated that not all tumor-infiltrating myeloid cells are made equal.

Macrophage Receptor with Collagenous Structure (MARCO, also known as SCARA2; See HGNC: 6895 and NCBI: NM 006770.3 as available on May 8, 2020 via the NCBI website; herein incorporated by reference for all purposes) belongs to the class A scavenger receptor family and is expressed on peritoneal macrophages, as well as a subpopulation of macrophages in the spleen and lymph nodes (see Hirano S, PLoS ONE 2015: 10(11): e0142062). Recent studies have highlighted MARCO as a specific marker of TAMs in human cancer (Lavin et al., Cell; 2017: 169(4) 750-765). MARCO mediates macrophage internalization of unopsonized particles and microorganisms, such as bacteria (see Jing J, J Immunol 2013; 190:(12) 6360-6367). Recently, MARCO has been shown to be involved in the TLR-induced gene expression response in dendritic cells and may play a role in the inflammatory immune response (Kissick H T, PLoS oNE 2014; 9(8):2104148).

An unmet need exists for novel cancer therapeutic approaches that involve selectively removing, or re-programming or activating myeloid cells that are ineffective at stimulating immune cell responses (e.g., T-cells or NK cells), thereby enhancing the immune response within the tumor microenvironment.

SUMMARY

In some aspects, provided herein are isolated antibodies or antigen binding fragments thereof that binds to human Macrophage Receptor with Collagenous Structure (MARCO) (SEQ ID NO: 384).

In some embodiments, the antibody or antigen binding fragment thereof binds to a Scavenger Receptor Cysteine-Rich (SRCR) domain (residues 424-519 of SEQ ID NO: 384) of human MARCO.

In some aspects, provided herein are isolated antibodies or antigen binding fragments thereof that binds to a Scavenger Receptor Cysteine-Rich (SRCR) domain (residues 424-519 of SEQ ID NO: 384) of human Macrophage Receptor with Collagenous Structure (MARCO) (SEQ ID NO: 384).

In some embodiments, the antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GFSLTSYHVS (SEQ ID NO: 2), CDR-H2 comprises the sequence AIWTGGSIA (SEQ ID NO: 3), CDR-H3 comprises the sequence DLSDYYSSYTSFDY (SEQ ID NO: 4), CDR-L1 comprises the sequence ASEGISNDLA (SEQ ID NO: 431) or XASEGISNDLA (SEQ ID NO: 383), wherein X is arginine (R) or leucine (L), CDR-L2 comprises the sequence AASRLQD (SEQ ID NO: 8), and CDR-L3 comprises the sequence QQSYKYPLT (SEQ ID NO: 9).

In some embodiments, the antibody or antigen binding fragment thereof binds to at least one of the following residues: Q452, Y472, K473, E450, Q487, T499, H505, D507, S509, or E511 of MARCO (SEQ ID NO: 384).

In some embodiments, the antibody or antigen binding fragment comprises a chimeric, human, humanized, or rat antibody or antigen binding fragment.

In some embodiments, CDR-L1 comprises the sequence ASEGISNDLA (SEQ ID NO: 431).

In some embodiments, CDR-L1 comprises the sequence RASEGISNDLA (SEQ ID NO: 27).

In some embodiments, CDR-L1 comprises the sequence LASEGISNDLA (SEQ ID NO: 7).

In some embodiments, the VH sequence comprises the VH sequence set forth in SEQ ID NO: 61.

In some embodiments, the VH sequence comprises the VH sequence set forth in SEQ ID NO: 111.

In some embodiments, the VH sequence comprises a sequence selected from the sequences set forth in SEQ ID NO: 1, 11, 21, 31, 41, 51, 61, 71, 81, 91, 101, 111, 121, 131, 434, 444, and 474.

In some embodiments, the VL sequence comprises the VL sequence set forth in SEQ ID NO: 66.

In some embodiments, the VL sequence comprises the VL sequence set forth in SEQ ID NO: 116.

In some embodiments, the VL sequence comprises a sequence selected from the sequences set forth in SEQ ID NO: 6, 16, 26, 36, 46, 57, 66, 76, 86, 96, 106, 116, 126, 136, 439, 449, and 479.

In some embodiments, the VH sequence comprises the VH sequence set forth in SEQ ID NO: 61; and the VL sequence comprises the VL sequence set forth in SEQ ID NO: 66.

In some embodiments, the VH sequence comprises the VH sequence set forth in SEQ ID NO: 111; and the VL sequence comprises the VL sequence set forth in SEQ ID NO: 116.

In some embodiments, the VH sequence comprises a sequence selected from the sequences set forth in SEQ ID NO: 1, 11, 21, 31, 41, 51, 61, 71, 81, 91, 101, 111, 121, 131, 434, 444, and 474 and the VL sequence comprises a sequence selected from the sequences set forth in SEQ ID NO: 6, 16, 26, 36, 46, 57, 66, 76, 86, 96, 106, 116, 126, 136, 439, 449, and 479.

In some embodiments, the VH sequence comprises a sequence with at least 90%, 92%, 95%, 97%, 98%, or 99% identity to a sequence selected from the sequences set forth in SEQ ID NO: 1, 11, 21, 31, 41, 51, 61, 71, 81, 91, 101, 111, 121, 131, 434, 444, and 474 and/or the VL sequence comprises a sequence with at least 90%, 92%, 95%, 97%, 98%, or 99% identity to a sequence selected from the sequences set forth in SEQ ID NO: 6, 16, 26, 36, 46, 57, 66, 76, 86, 96, 106, 116, 126, 136, 439, 449, and 479.

In some embodiments, the antibody comprises a heavy chain sequence as set forth in SEQ ID NO: 65.

In some embodiments, the antibody comprises a heavy chain sequence as set forth in SEQ ID NO: 115.

In some embodiments, the antibody comprises a heavy chain sequence selected from the sequences set forth in SEQ ID NO: 5, 15, 125, 35, 45, 55, 65, 75, 85, 95, 105, 115, 125, 145, 438, 448, and 478.

In some embodiments, the antibody comprises a light chain sequence as set forth in SEQ ID NO: 70.

In some embodiments, the antibody comprises a light chain sequence as set forth in SEQ ID NO: 120.

In some embodiments, the antibody comprises a light chain sequence selected from the sequences set forth in SEQ ID NO: 10, 20, 30, 40, 50, 6, 70, 80, 90, 100, 110, 120, 130, 140, 443, 453, and 483.

In some embodiments, the antibody comprises a heavy chain sequence as set forth in SEQ ID NO: 65; and a light chain sequence as set forth in SEQ ID NO: 70.

In some embodiments, the antibody comprises a heavy chain sequence as set forth in SEQ ID NO: 115; and a light chain sequence as set forth in SEQ ID NO: 120.

In some embodiments, the antibody comprises a heavy chain sequence selected from the sequences set forth in SEQ ID NO: 5, 15, 125, 35, 45, 55, 65, 75, 85, 95, 105, 115, 125, 145, 438, 448, and 478; and a light chain sequence selected from the sequences set forth in SEQ ID NO: 10, 20, 30, 40, 50, 6, 70, 80, 90, 100, 110, 120, 130, 140, 443, 453, and 483.

In some embodiments, the antibody comprises a heavy chain sequence with at least 90%, 92%, 95%, 97%, 98%, or 99% identity to a sequence selected from the sequences set forth in SEQ ID NO: 5, 15, 125, 35, 45, 55, 65, 75, 85, 95, 105, 115, 125, 145, 438, 448, and 478; and/or a light chain sequence with at least 90%, 92%, 95%, 97%, 98%, or 99% identity to a sequence selected from the sequences set forth in SEQ ID NO: 10, 20, 30, 40, 50, 6, 70, 80, 90, 100, 110, 120, 130, 140, 443, 453, and 483.

In some aspects, provided herein are isolated antibodies or antigen binding fragments thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GYTFTDYAVN (SEQ ID NO: 232), CDR-H2 comprises the sequence WINTQTGKPT (SEQ ID NO: 233), CDR-H3 comprises the sequence DSYYYSSSLDY (SEQ ID NO: 234), CDR-L1 comprises the sequence ASAGISNDLA (SEQ ID NO: 432) or XASAGISNDLA (SEQ ID NO: 381), wherein X is arginine (R) or leucine (L), CDR-L2 comprises the sequence AASRLQD (SEQ ID NO: 238), and CDR-L3 comprises the sequence QQSYKYPWT (SEQ ID NO: 239).

In some embodiments, CDR-L1 comprises the sequence ASAGISNDLA (SEQ ID NO: 432).

In some embodiments, CDR-L1 comprises the sequence RASAGISNDLA (SEQ ID NO: 317).

In some embodiments, CDR-L1 comprises the sequence LASAGISNDLA (SEQ ID NO: 237).

In some embodiments, the VH sequence comprises the VH sequence as set forth in SEQ ID NO: 454.

In some embodiments, the VH sequence comprises a sequence selected from the sequences set forth in SEQ ID NO: 241, 311, 321, 331, 341, 351, 454, and 464.

In some embodiments, the VL sequence comprises the VL sequence as set forth in SEQ ID NO: 459.

In some embodiments, the VL sequence comprises a sequence selected from the sequences set forth in SEQ ID NO: 246, 316, 326, 336, 346, 356, 459, and 469.

In some embodiments, the VH sequence comprises the VH sequence as set forth in SEQ ID NO: 454; and the VL sequence comprises the VL sequence as set forth in SEQ ID NO: 459.

In some embodiments, the VH sequence comprises a sequence selected from the sequences set forth in SEQ ID NO: 241, 311, 321, 331, 341, 351, 454, and 464, and the VL sequence comprises a sequence selected from the sequences set forth in SEQ ID NO: 246, 316, 326, 336, 346, 356, 459, and 469.

In some embodiments, the VH sequence comprises a sequence with at least 90%, 92%, 95%, 97%, 98%, or 99% identity to a sequence selected from the sequences set forth in SEQ ID NO: 241, 311, 321, 331, 341, 351, 454, and 464; and/or the VL sequence comprises a sequence with at least 90%, 92%, 95%, 97%, 98%, or 99% identity to a sequence selected from the sequences set forth in SEQ ID NO: 246, 316, 326, 336, 346, 356, 459, and 469.

In some embodiments, the antibody comprises a heavy chain sequence as set forth in SEQ ID NO: 458.

In some embodiments, the antibody comprises a heavy chain sequence selected from the sequences set forth in SEQ ID NO: 245, 315, 325, 335, 345 355, 458, and 468.

In some embodiments, the antibody comprises a light chain sequence as set forth in SEQ ID NO: 463.

In some embodiments, the antibody comprises a light chain sequence selected from the sequences set forth in SEQ ID NO: 250, 320, 330, 340, 350, 360, 463, and 473.

In some embodiments, the antibody comprises a heavy chain sequence as set forth in SEQ ID NO: 458; and a light chain sequence as set forth in SEQ ID NO: 463.

In some embodiments, the antibody comprises a heavy chain sequence selected from the sequences set forth in SEQ ID NO: 245, 315, 325, 335, 345 355, 458, and 468; and a light chain sequence selected from the sequences set forth in SEQ ID NO: 250, 320, 330, 340, 350, 360, 463, and 473.

In some embodiments, the antibody comprises a heavy chain sequence with at least 90%, 92%, 95%, 97%, 98%, or 99% identity to a sequence selected from the sequences set forth in SEQ ID NO: 245, 315, 325, 335, 345 355, 458, and 468; and/or a light chain sequence with at least 90%, 92%, 95%, 97%, 98%, or 99% identity to a sequence selected from the sequences set forth in SEQ ID NO: 250, 320, 330, 340, 350, 360, 463, and 473.

In some aspects, provided herein are isolated antibodies or antigen binding fragments thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence KFTFSNYGMN (SEQ ID NO: 142), CDR-H2 comprises the sequence LIYYNSNNKY (SEQ ID NO: 143), CDR-H3 comprises the sequence SLTGGSDYFDS (SEQ ID NO: 144), CDR-L1 comprises the sequence ASKSIGTFLA (SEQ ID NO: 433) or XASKSIGTFLA (SEQ ID NO: 382), wherein X is arginine (R) or lysine (K), CDR-L2 comprises the sequence SGSTLQS (SEQ ID NO: 148), and CDR-L3 comprises the sequence QQHDEYPFT (SEQ ID NO: 149).

In some embodiments, CDR-L1 comprises the sequence ASKSIGTFLA (SEQ ID NO: 433).

In some embodiments, CDR-L1 comprises the sequence KASKSIGTFLA (SEQ ID NO: 147).

In some embodiments, CDR-L1 comprises the sequence RASKSIGTFLA (SEQ ID NO: 157).

In some embodiments, the VH sequence comprises a sequence selected from the sequences set forth in SEQ ID NO: 141, 151, 161, 171, 181, 191, 201, 211, and 221.

In some embodiments, the VL sequence comprises a sequence selected from the sequences set forth in SEQ ID NO: 146, 156, 166, 176, 186, 196, 206, 216, and 226.

In some embodiments, the VH sequence comprises a sequence selected from the sequences set forth in SEQ ID NO: 141, 151, 161, 171, 181, 191, 201, 211, and 221 and the VL sequence comprises a sequence selected from the sequences set forth in SEQ ID NO: 146, 156, 166, 176, 186, 196, 206, 216, and 226.

In some embodiments, the VH sequence comprises a sequence with at least 90%, 92%, 95%, 97%, 98%, or 99% identity to a sequence selected from the sequences set forth in SEQ ID NO: 141, 151, 161, 171, 181, 191, 201, 211, and 221 and/or the VL sequence comprises a sequence with at least 90%, 92%, 95%, 97%, 98%, or 99% identity to a sequence selected from the sequences set forth in SEQ ID NO: 146, 156, 166, 176, 186, 196, 206, 216, and 226.

In some embodiments, the antibody comprises a heavy chain sequence selected from the sequences set forth in SEQ ID NO: 145, 155, 165, 175, 185, 195, 205, 215, and 225.

In some embodiments, the antibody comprises a light chain sequence selected from the sequences set forth in SEQ ID NO: 150, 160, 170, 180, 190, 200, 210, 220, and 230.

In some embodiments, the antibody comprises a heavy chain sequence selected from the sequences set forth in SEQ ID NO: 145, 155, 165, 175, 185, 195, 205, 215, and 225 and a light chain sequence selected from the sequences set forth in SEQ ID NO: 150, 160, 170, 180, 190, 200, 210, 220, and 230.

In some embodiments, the antibody comprises a heavy chain sequence comprises a sequence with at least 90%, 92%, 95%, 97%, 98%, or 99% identity to a sequence selected from the sequences set forth in SEQ ID NO: 145, 155, 165, 175, 185, 195, 205, 215, and 225 and/or a light chain sequence comprises a sequence with at least 90%, 92%, 95%, 97%, 98%, or 99% identity to a sequence selected from the sequences set forth in SEQ ID NO: 150, 160, 170, 180, 190, 200, 210, 220, and 230.

In another aspect, provided herein are isolated antibodies or antigen binding fragments that bind to human MARCO (SEQ ID NO: 384), comprising a a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GYTFTDYYLH (SEQ ID NO: 252), CDR-H2 comprises the sequence YINPNNAYTS (SEQ ID NO: 253), CDR-H3 comprises the sequence DTTDYYNLHFAY (SEQ ID NO: 254), CDR-L1 comprises the sequence LTSEGISNDLA (SEQ ID NO: 257), CDR-L2 comprises the sequence DASRLED (SEQ ID NO: 258), and CDR-L3 comprises the sequence QQSYKYPLT (SEQ ID NO: 259).

In some embodiments, the VH sequence comprises a sequence as set forth in SEQ ID NO: 251 or 261.

In some embodiments, the VL sequence comprises a sequence as set forth in SEQ ID NO: 256 or 266.

In some embodiments, the VH sequence comprises a sequence as set forth in SEQ ID NO: 251 or 261, and the VL sequence comprises a sequence s set forth in SEQ ID NO: 256 or 266.

In some embodiments, the VH sequence comprises a sequence with at least 90%, 92%, 95%, 97%, 98, or 99% identity to a sequence as set forth in SEQ ID NO: 251 or 261, and/or the VL sequence comprises a sequence with at least 90%, 92%, 95%, 97%, 98, or 99% identity to a sequence set forth in SEQ ID NO: 256 or 266.

In some embodiments, the antibody comprises a heavy chain sequence as set forth in SEQ ID NO: 255 or 265.

In some embodiments, the antibody comprises a light chain sequence as set forth in SEQ ID NO: 260 or 270.

In some embodiments, the antibody comprises a heavy chain sequence as set forth in SEQ ID NO: 255 or 265; and a light chain sequence as set forth in SEQ ID NO: 260 or 270.

In some embodiments, the antibody comprises a heavy chain sequence comprises a sequence with at least 90%, 92%, 95%, 97%, 98%, or 99% identity to a sequence as set forth in SEQ ID NO: 255 or 265; and a light chain sequence comprises a sequence with at least 90%, 92%, 95%, 97%, 98%, or 99% identity to a sequence as set forth in SEQ ID NO: 260 or 270.

In another aspect, provided herein are isolated antibodies or antigen binding fragments that bind to human MARCO (SEQ ID NO: 384), comprising a a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GFSLTSYTLS (SEQ ID NO: 362), CDR-H2 comprises the sequence AIWGGDNTD (SEQ ID NO: 363), CDR-H3 comprises the sequence ELGGSFDY (SEQ ID NO: 364), CDR-L1 comprises the sequence KTSQNINKKLD (SEQ ID NO: 367), CDR-L2 comprises the sequence YTNNLQT (SEQ ID NO: 368), and CDR-L3 comprises the sequence YQYDSGFT (SEQ ID NO: 369).

In some embodiments, the VH sequence comprises a sequence as set forth in SEQ ID NO: 361 or 371.

In some embodiments, the VL sequence comprises a sequence as set forth in SEQ ID NO: 366 or 376.

In some embodiments, the VH sequence comprises a sequence as set forth in SEQ ID NO: 361 or 371, and the VL sequence comprises a sequence s set forth in SEQ ID NO: 366 or 376.

In some embodiments, the VH sequence comprises a sequence with at least 90%, 92%, 95%, 97%, 98, or 99% identity to a sequence as set forth in SEQ ID NO: 361 or 371, and/or the VL sequence comprises a sequence with at least 90%, 92%, 95%, 97%, 98, or 99% identity to a sequence set forth in SEQ ID NO: 366 or 376.

In some embodiments, the antibody comprises a heavy chain sequence as set forth in SEQ ID NO: 365 or 375; and a light chain sequence as set forth in SEQ ID NO: 370 or 380.

In some embodiments, the antibody comprises a heavy chain sequence comprises a sequence with at least 90%, 92%, 95%, 97%, 98%, or 99% identity to a sequence as set forth in SEQ ID NO: 365 or 375; and a light chain sequence comprises a sequence with at least 90%, 92%, 95%, 97%, 98%, or 99% identity to a sequence as set forth in SEQ ID NO: 370 or 380.

In some embodiments, the antibody is a monoclonal antibody, a neutral antibody, an antagonistic antibody, an agonist antibody, a polyclonal antibody, an afucosylated antibody, a human antibody, a humanized antibody, a chimeric antibody, a full-length antibody, and an scFv.

In some embodiments, the antibody is an scFv.

In some embodiments, the antibody is a monoclonal antibody.

In some embodiments, the antibody is a humanized antibody.

In some embodiments, the antibody is a human antibody.

In some embodiments, the antibody comprises an Fc region.

In some embodiments, the Fc region comprises a human Fc region.

In some embodiments, the antibody comprises an active human Fc region.

In some embodiments, the antibody comprises a heavy chain human constant region of a class selected from IgG, IgA, IgD, IgE, and IgM.

In some embodiments, the antibody comprises a human heavy chain constant region of the class IgG and a subclass selected from IgG1, IgG2, IgG3, and IgG4.

In some embodiments, the human Fc region comprises a wild-type, human IgG1 Fc region.

In some embodiments, the human Fc region comprises a wild-type, human IgG4 Fc region.

In some embodiments, the Fc region comprises one or more amino acid substitutions, wherein the one or more substitutions result in increased antibody half-life, increased ADCC activity, increased ADCP activity, increased CDC activity, decreased ADCC activity, decreased ADCP activity, or decreased CDC activity compared with an Fc region without the one or more substitutions.

In some embodiments, the Fc region binds an Fcγ Receptor selected from the group consisting of: FcγRI, FcγRIIa, FcγRIIb, FcγRIIc, FcγRIIIa, and FcγRIIIb.

In some embodiments, the antibody binds to human MARCO with a KD of less than or equal to about 0.5, 1, 2, 3, 4, 5, 6, or 7×10-9 M, as measured by surface plasmon resonance (SPR) assay.

In some embodiments, binding of the antibody to human MARCO is divalent cation dependent.

In some embodiments, binding of the antibody to human MARCO is divalent cation independent.

In some embodiments, the divalent cation comprises Ca2+ or Mg2+.

In some embodiments, the antibody binds an extracellular domain of human MARCO.

In some embodiments, the antibody binds to soluble MARCO.

In some embodiments, the antibody binds the SRCR domain of human MARCO, cynomolgus MARCO, or human and cynomolgus MARCO.

In some embodiments, the antibody binds the SRCR domain (residues 424-519 of SEQ ID NO: 384) of human MARCO.

In some embodiments, the antibody or antigen binding fragment thereof binds to at least one of: Q452, Y472, K473, E450, Q487, T499, H505, D507, S509, or E511 of MARCO (SEQ ID NO: 384).

In some embodiments, the antibody has receptor-ligand blocking activity.

In some embodiments, the antibody induces increased expression of at least one cytokine or chemokine upon contact with a cell as compared to an isotype control antibody, optionally as measured by a nucleic acid or protein assay.

In some embodiments, the at least one cytokine or chemokine comprises at least one of IL-1α, IL-1β, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin.

In some embodiments, upon cell contact the antibody induces increased NK cell activation, B cell regulation T cell proliferation, T cell activation, or T cell differentiation as compared to an isotype control antibody, optionally as measured by a nucleic acid or protein assay.

In some embodiments, upon cell contact the antibody induces IL-2-STATS signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response as compared to an isotype control antibody.

In some embodiments, upon cell contact the antibody decreases cell cycle pathway, cell survival, cell adhesion, Myc target pathway, E2F targets pathway, hypoxia, mTOR signaling pathway, PI3K-AKT signaling pathway, Src signaling pathway, PKC signaling pathway, epithelial to mesenchymal transition signaling pathway, oxidative phosphorylation, or MAPK signaling pathway as compared to an isotype control antibody.

In some embodiments, upon cell contact the antibody induces inflammasome activation as determined by IL-1β and/or IL-18 secretion and/or phagocytosis as compared to an isotype control antibody.

In some embodiments, upon cell contact the antibody induces repolarization of myeloid M2-like TAMS to M1-like tumor associated macrophages (TAMs), and/or repolarization of mMDSCs to pro-inflammatory monocytes as compared to an isotype control antibody.

In some embodiments, upon cell contact the antibody increases CD8+ T cells, CD4+ T cells, NK cells, dendritic cells, MHCII+ macrophages, MHCIIhigh monocytes, or MHCIImid monocytes as compared to an isotype control antibody.

In some embodiments, upon cell contact the antibody increases macrophages, marginal zone macrophages, follicular B cells, and/or red pulp macrophages in the spleen as compared to an isotype control antibody.

In some embodiments, upon cell contact the antibody decreases TAMs, tumor associated neutrophils, plasma B cells, marginal zone B cells, CD19+ B cells, MHCII- monocytes, and/or MHCII– macrophages as compared to an isotype control antibody.

In some embodiments, upon administration to a subject the antibody induces an increased anti-tumor memory response as compared to an isotype control antibody.

In some embodiments, a cell is a MARCO+ cell.

In some embodiments, the cell is a human MARCO+ cell.

In some embodiments, the MARCO+ cell is a monocyte, a monocytic Myeloid Derived Suppressor Cell (mMDSC), or a macrophage.

In some embodiments, the macrophage is a tumor associated macrophage (TAM) or a monocyte-derived macrophage (MDM).

In some embodiments, the antibody binds to MARCO on the cell surface of a MARCO+ cell.

In some embodiments, the antibody: competes for binding to human MARCO with humanized PI-HX-3011, PI-HX-3031, PI-HX-3043, PI-HX-3061, PI-HX-3092 antibody; binds to human MARCO; binds to cynomolgus MARCO;

binds to human and cynomolgus MARCO; binds to the SRCR domain of human MARCO; binds to the SRCR domain of cynomolgus MARCO; binds to the SRCR domain of human and cynomolgus MARCO; binds to human or cynomolgus MARCO in a divalent cation dependent manner; binds to human or cynomolgus MARCO in a divalent cation independent manner; stimulates MARCO signaling upon binding to a MARCO+ cell; induces one or more immune signaling pathways upon binding to a MARCO+ cell; induces cytokine or chemokine secretion upon binding to a MARCO+ cell, optionally wherein the cytokine or chemokine is IL-1α, IL-1α, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin; induces increased NK cell activation, B cell regulation, T cell proliferation, T cell activation, or T cell differentiation upon binding to a MARCO+ cell; induces IL-2-STATS signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response; decreases a cell cycle pathway, cell survival, cell adhesion, Myc target pathway, E2F targets pathway, hypoxia, mTOR signaling pathway, PI3K-AKT signaling pathway, Src signaling pathway, PKC signaling pathway, epithelial to mesenchymal transition signaling pathway, oxidative phosphorylation, or MAPK signaling pathway; induces inflammasome activation as determined by IL-1β and/or IL-18 secretion and/or phagocytosis; induces repolarization of myeloid M2-like TAMs to M1-like TAMS, and/or repolarization of mMDSCs to pro-inflammatory monocytes; modulates B cells in the spleen upon binding to a MARCO+ cell; increases CD8+ T cells, CD4+ T cells, NK cells, dendritic cells, MHCII+ macrophages, MHCIIhigh monocytes, and/or MHCIImid monocytes in the spleen and/or tumor; increases macrophages, marginal zone macrophages, follicular B cells, and/or red pulp macrophages in the spleen and/or tumor; decreases TAMs, tumor associated neutrophils, plasma B cells, marginal zone B cells, CD19+ B cells, MHCII– monocytes, and/or MHCII– macrophages in the spleen and/or tumor; induces changes in cell adhesion, cytoskeletal, chemotaxis and cell migration upon binding to a MARCO+ cell; induces cell signaling pathways comprising adhesion, migration, chemotaxis cell cycle, T cell receptor, phagocytosis, autophagy, and wnt pathways upon binding to a MARCO+ cell; disables MARCO+ myeloid cells; or is capable of any combination above.

In some embodiments, the antibody is for use as a medicament.

In some embodiments, the antibody is for use in the treatment of a cancer or infection.

In some embodiments, the antibody is for use in the treatment of a cancer, wherein the cancer is selected from a solid tumor and a liquid tumor.

In another aspect, provided herein are isolated polynucleotides or sets of polynucleotides encoding the antibody described herein, a VH thereof, a VL thereof, a light chain thereof, a heavy chain thereof, or an antigen-binding portion thereof; optionally the isolated polynucleotide or set of polynucleotides is cDNA.

In another aspect, provided herein are vectors or set of vectors comprising the polynucleotide or set of polynucleotides.

In another aspect, provided herein are host cells comprising the polynucleotide or set of polynucleotides or the vector or set of vectors.

In another aspect, provided herein are methods of producing an antibody comprising expressing the antibody or antigen binding fragment thereof with the host cell and isolating the expressed antibody.

In another aspect, provided herein are pharmaceutical compositions comprising the isolated antibody or antigen binding fragment thereof and a pharmaceutically acceptable excipient.

In another aspect, provided herein are kits comprising the isolated antibody or antigen binding fragment thereof or a pharmaceutical composition and instructions for use.

In another aspect, provided herein are methods of increasing an immune response in a subject comprising administering to the subject a composition comprising an anti-human MARCO antibody or antigen binding fragment thereof.

In some embodiments, the composition comprises an antibody that binds to the SRCR domain (residues 424-519 of SEQ ID NO: 384) of human MARCO.

In some embodiments, the composition comprises the isolated antibody or the pharmaceutical composition.

In some embodiments, the antibody has receptor-ligand blocking activity.

In some embodiments, the increased immune response is an adaptive immune response.

In some embodiments, the increased immune response is an innate immune response.

In some embodiments, the increased immune response comprises increased expression of at least one cytokine or chemokine by a cell as compared to an isotype control antibody, optionally as measured by a nucleic acid or protein assay.

In some embodiments, the at least one cytokine or chemokine comprises at least one of IL-1α, IL-1α, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin.

In some embodiments, the increased immune response comprises increased NK cell activation, B cell regulation T cell proliferation, T cell activation, or T cell differentiation as compared to an isotype control antibody, optionally as measured by a nucleic acid or protein assay.

In some embodiments, upon cell contact the antibody induces In some embodiments, upon cell contact the antibody induces IL-2-STATS signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response as compared to an isotype control antibody.

In some embodiments, upon cell contact the antibody decreases cell cycle pathway, cell survival, cell adhesion, Myc target pathway, E2F targets pathway, hypoxia, mTOR signaling pathway, PI3K-AKT signaling pathway, Src signaling pathway, PKC signaling pathway, epithelial to mesenchymal transition signaling pathway, oxidative phosphorylation, or MAPK signaling pathway as compared to an isotype control antibody.

In some embodiments, upon cell contact the antibody induces inflammasome activation as determined by IL-1(3 and/or IL-18 secretion and/or phagocytosis as compared to an isotype control antibody.

In some embodiments, upon cell contact the antibody induces repolarization of myeloid M2-like TAMs to M1-like TAMS, and/or repolarization of mMDSCs to pro-inflammatory monocytes as compared to an isotype control antibody.

In some embodiments, upon cell contact the antibody increases increases CD8+ T cells, CD4+ T cells, NK cells, dendritic cells, MHCII+ macrophages, MHCIIhigh monocytes, or MHCIImid monocytes as compared to an isotype control antibody.

In some embodiments, upon cell contact the antibody increases macrophages, marginal zone macrophages, follicular B cells, and/or red pulp macrophages in the spleen as compared to an isotype control antibody.

In some embodiments, upon cell contact the antibody decreases TAMs, tumor associated neutrophils, plasma B cells, marginal zone B cells, CD19+ B cells, MHCII- monocytes, and/or MHCII- macrophages as compared to an isotype control antibody.

In some embodiments, the antibody induces an increased memory immune response.

In some embodiments, the cell is a MARCO+ cell.

In some embodiments, the cell is a human MARCO+ cell.

In some embodiments, the MARCO+ cells is a monocyte, a monocytic Myeloid Derived Suppressor Cell (mMDSC), or a macrophage.

In some embodiments, the macrophage is a tumor associated macrophage (TAM) or a monocyte-derived macrophage (MDM).

In some embodiments, the antibody binds to MARCO on the cell surface of a MARCO+ cell.

In some embodiments, the subject is human.

In some embodiments, the subject has cancer.

In some embodiments, the cancer is a solid cancer.

In some embodiments, the cancer is a liquid cancer.

In some embodiments, the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

In some embodiments, the cancer is colon cancer, breast cancer, basal-like breast cancer, ovarian cancer, or gastric cancer.

In some embodiments, MARCO is expressed at a higher level on a tumor immune cell as compared to a non-tumor immune cell.

In some embodiments, IL-10 is expressed at a higher level on a tumor immune cell as compared to a non-tumor immune cell.

In another aspect, provided herein are methods of treating cancer in a subject, comprising administering to the subject a composition comprising an anti-human MARCO antibody or antigen binding fragment thereof.

In some embodiments, the composition comprises an antibody that binds to the SRCR domain (residues 424-519 of SEQ ID NO: 384) of human MARCO.

In some embodiments, the composition comprises the antibody disclosed herein or the pharmaceutical composition thereof.

In another aspect, provided herein are methods of treating cancer in a subject, comprising administering to the subject a composition comprising the anti-human MARCO antibody or antigen binding fragment thereof or a pharmaceutical composition thereof.

In some embodiments, the subject has previously received, is concurrently receiving, or will subsequently receive an immunotherapy.

In some embodiments, the immunotherapy is at least one of: a checkpoint inhibitor; a checkpoint inhibitor of T cells; and an anti-PD1 antibody.

In some embodiments, the immunotherapy comprises an anti-PD1 antibody.

In another aspect, provided herein are methods of treating cancer in a subject, comprising administering to the subject a composition comprising an anti-human MARCO antibody or antigen binding fragment thereof and an immunotherapy.

In some embodiments, the composition comprises an antibody that binds to the SRCR domain (residues 424-519 of SEQ ID NO: 384) of human MARCO.

In some embodiments, the composition comprises the antibody disclosed herein or the pharmaceutical composition thereof.

In some embodiments, the immunotherapy is at least one of: a checkpoint inhibitor; a checkpoint inhibitor of T cells; and an anti-PD1 antibody.

In some embodiments, the immunotherapy comprises an anti-PD1 antibody.

In some embodiments, the subject is human.

In some embodiments, the cancer is a solid cancer.

In some embodiments, the cancer is a liquid cancer.

In some embodiments, the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

In some embodiments, the cancer is colon cancer, breast cancer, basal-like breast cancer, ovarian cancer, or gastric cancer.

In some embodiments, MARCO is expressed at a higher level on a tumor immune cell as compared to a non-tumor immune cell.

In some embodiments, IL-10 is expressed at a higher level on a tumor immune cell as compared to a non-tumor immune cell.

In some embodiments, the antibody induces an increased anti-tumor memory response as compared to an isotype control antibody.

In some embodiments, the administration increases an immune response in the subject as compared to an isotype control antibody.

In some embodiments, the increased immune response is an adaptive immune response.

In some embodiments, the increased immune response is an innate immune response.

In some embodiments, the increased immune response comprises expression of at least one cytokine or chemokine by a cell as compared to an isotype control antibody, optionally as measured by a nucleic acid or protein assay.

In some embodiments, the at least one cytokine or chemokine comprises at least one of IL-1α, IL-1α, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin.

In some embodiments, the increased immune response comprises increased NK cell activation, B cell regulation T cell proliferation, T cell activation, or T cell differentiation as compared to an isotype control antibody, optionally as measured by a nucleic acid or protein assay.

In some embodiments, upon cell contact the antibody induces In some embodiments, upon cell contact the antibody induces IL-2-STATS signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response as compared to an isotype control antibody.

In some embodiments, upon cell contact the antibody decreases cell cycle pathway, cell survival, cell adhesion, Myc target pathway, E2F targets pathway, hypoxia, mTOR signaling pathway, PI3K-AKT signaling pathway, Src signaling pathway, PKC signaling pathway, epithelial to mesenchymal transition signaling pathway, oxidative phosphorylation, or MAPK signaling pathway as compared to an isotype control antibody.

In some embodiments, upon cell contact the antibody induces inflammasome activation as determined by IL-1β and/or IL-18 secretion and/or phagocytosis as compared to an isotype control antibody.

In some embodiments, upon cell contact the antibody induces repolarization of myeloid M2-like TAMs to M1-like TAMS, and/or repolarization of mMDSCs to pro-inflammatory monocytes as compared to an isotype control antibody.

In some embodiments, upon cell contact the antibody increases CD8+ T cells, CD4+ T cells, NK cells, dendritic cells, MHCII+ macrophages, MHCIIhigh monocytes, or MHCIImid monocytes as compared to an isotype control antibody.

In some embodiments, upon cell contact the antibody increases macrophages, marginal zone macrophages, follicular B cells, and/or red pulp macrophages in the spleen as compared to an isotype control antibody.

In some embodiments, upon cell contact the antibody decreases TAMs, tumor associated neutrophils (TANs), plasma B cells, marginal zone B cells, CD19+ B cells, MHCII− monocytes, and/or MHCII− macrophages as compared to an isotype control antibody.

In some embodiments, the cell is a MARCO+ cell.

In some embodiments, the cell is a human MARCO+ cell.

In some embodiments, the MARCO+ cell is a monocyte, a monocytic Myeloid Derived Suppressor Cell (mMDSC), or a macrophage.

In some embodiments, the macrophage is a tumor associated macrophage (TAM) or a monocyte-derived macrophage (MDM).

In some embodiments, the antibody binds to MARCO on the cell surface of a MARCO+ cell.

In another aspect, provided herein are methods of disabling myeloid cells that express MARCO on the cell surface, comprising contacting the myeloid cells with an anti-human MARCO antibody or antigen binding fragment thereof.

In another aspect, provided herein are methods of disabling myeloid cells that express MARCO on the cell surface, comprising contacting the myeloid cells with the antibody described herein or the pharmaceutical composition thereof.

In some embodiments, the antibody disables the myeloid cells by at least one of ADCC activity, CDC activity, or ADCP activity, optionally wherein the antibody disables the myeloid cells by ADCC activity, optionally wherein the antibody disables the myeloid cells by CDC activity, and optionally wherein the antibody disables the myeloid cells by ADCP activity.

In some embodiments, the myeloid cell is a MARCO+ cell.

In some embodiments, the myeloid cell is a human MARCO+ cell.

In some embodiments, the myeloid cell is a monocyte, a monocytic Myeloid Derived Suppressor Cell (mMDSC), or a macrophage.

In some embodiments, the macrophage is a tumor associated macrophage (TAM) or a monocyte-derived macrophage (MDM).

In some embodiments, the myeloid cells are intratumoral or splenic myeloid cells.

In some embodiments, the contacting is in vitro or in vivo.

In some embodiments, the contacting occurs in vivo in a subject, optionally wherein the subject has cancer.

In some embodiments, the subject is a human.

In some embodiments, the cancer is a solid cancer.

In some embodiments, the cancer is a liquid cancer.

In some embodiments, the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

In some embodiments, the cancer is colon cancer, breast cancer, basal-like breast cancer, ovarian cancer, or gastric cancer.

In some embodiments, the contacting increases an immune response in the subject as compared to an isotype control antibody.

In some embodiments, the increased immune response is an adaptive immune response.

In some embodiments, the increased immune response is an innate immune response.

In some embodiments, the increased immune response comprises expression of at least one cytokine or chemokine by a cell as compared to an isotype control antibody, optionally as measured by a nucleic acid or protein assay.

In some embodiments, the at least one cytokine or chemokine comprises at least one of IL-1α, IL-1α, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin.

In some embodiments, the increased immune response comprises increased NK cell activation, B cell regulation T cell proliferation, T cell activation, or T cell differentiation as compared to an isotype control antibody, optionally as measured by a nucleic acid or protein assay.

In some embodiments, upon cell contact the antibody IL-2-STATS signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response as compared to an isotype control antibody.

In some embodiments, upon cell contact the antibody decreases cell cycle pathway, cell survival, cell adhesion, Myc target pathway, E2F targets pathway, hypoxia pathway, mTOR signaling pathway, PI3K-AKT signaling pathway, Src signaling pathway, PKC signaling pathway, epithelial to mesenchymal transition signaling pathway, oxidative phosphorylation, or MAPK signaling pathway as compared to an isotype control antibody.

In some embodiments, upon cell contact the antibody induces inflammasome activation as determined by IL-1β and/or and IL-18 secretion and/or phagocytosis.

In some embodiments, upon cell contact the antibody induces repolarization of myeloid M2-like TAMs to M1-like TAMS, and/or repolarization of mMDSCs to pro-inflammatory monocytes.

In some embodiments, upon cell contact the antibody increases CD8+ T cells, CD4+ T cells, NK cells, dendritic cells, MHCII+ macrophages, MHCIIhigh monocytes, or MHCIImid monocytes as compared to an isotype control antibody.

In some embodiments, upon cell contact the antibody increases macrophages, marginal zone macrophages, follicular B cells, and/or red pulp macrophages in the spleen as compared to an isotype control antibody.

In some embodiments, upon cell contact the antibody decreases TAMs, tumor associated neutrophils, plasma B cells, marginal zone B cells, CD19+ B cells, MHCII- monocytes, and/or MHCII- macrophages as compared to an isotype control antibody.

In some embodiments, the subject has previously received, is concurrently receiving, or will subsequently receive an immunotherapy.

In some embodiments, the immunotherapy is at least one of: a checkpoint inhibitor; a checkpoint inhibitor of T cells; and an anti-PD1 antibody.

In some embodiments, the immunotherapy comprises an anti-PD1 antibody.

In some embodiments, of determining an expression level of MARCO protein in a sample from a subject comprising contacting the sample with an anti-MARCO antibody and performing an immunohistochemistry assay or a soluble MARCO assay.

In some embodiments, the assay is an immunohistochemistry assay and the antibody comprises RDM5, RDM9, PI-3010.15, PI-3010.25, or PI-3030.41.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 6A shows the binding of 33 anti-human MARCO antibodies to GFP-239T control cells (left bar), cells expressing human MARCO (middle bar), or cells expressing mouse MARCO (right bar). FIG. 6B shows flow cytometry histograms of one MARCO antibody, PI-M014, binding to cells expressing huMARCO, muMARCO, and CynoMARCO, as compared to control cells (GFP control). FIG. 6C shows a titration of PI-M014 and isotype control antibody binding to cells expressing huMARCO. FIG. 6D shows a flow cytometry histogram of PI-M014 binding to human monocyte-derived macrophages.

13K shows the shows the percentage of tumor growth inhibition (% TGI) in mice treated with isotype control antibody (effector dead Fc) as compared to dead Fc PI-3021 and PD-1 antibody.

Figure 14:
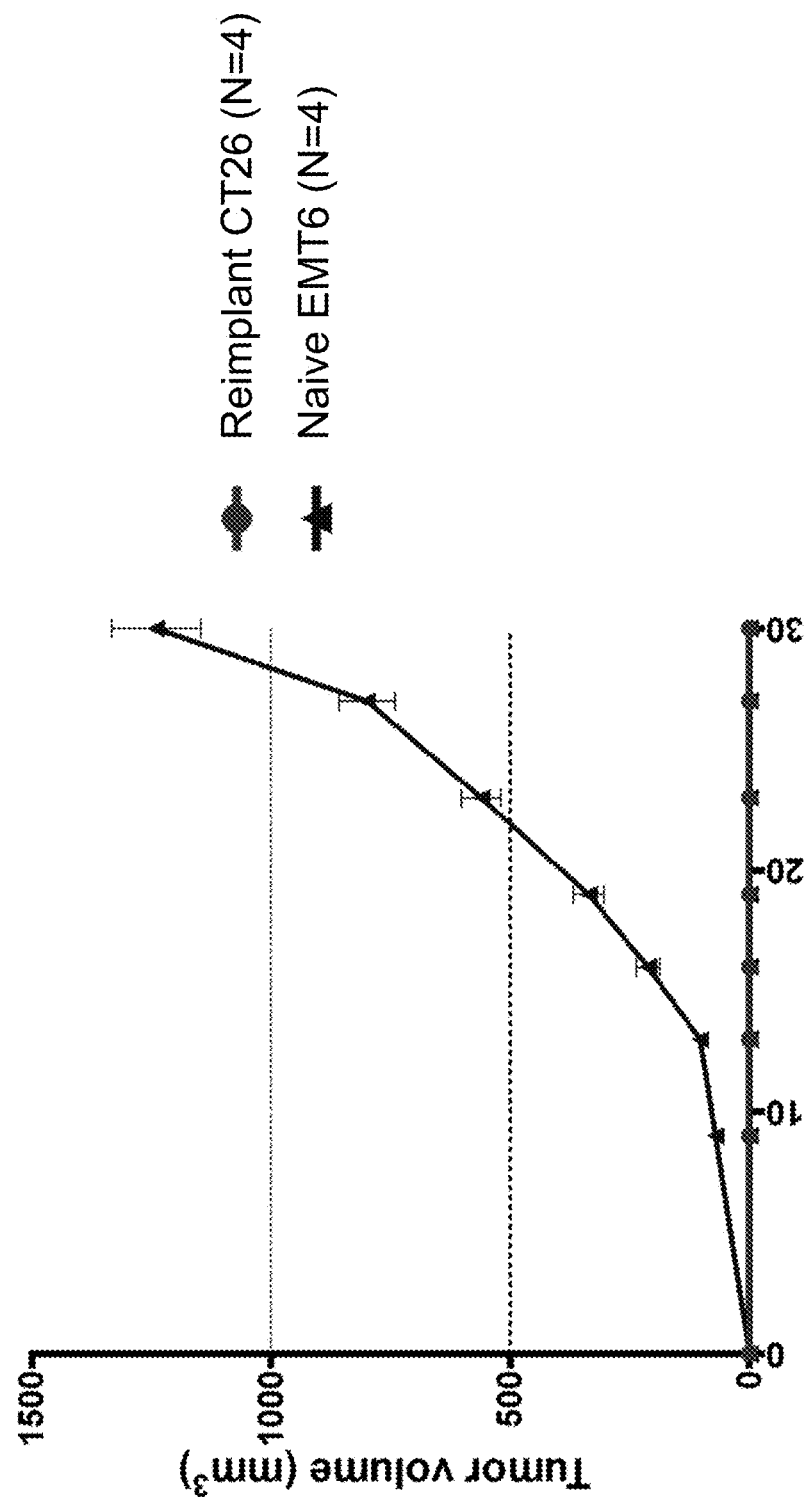

FIG. 14 shows the tumor volume of re-implanted CT26 tumor cells and EMT6 cells in mice that had been previously treated with anti-MARCO and anti-PD-1 antibodies.

Figure 15A:
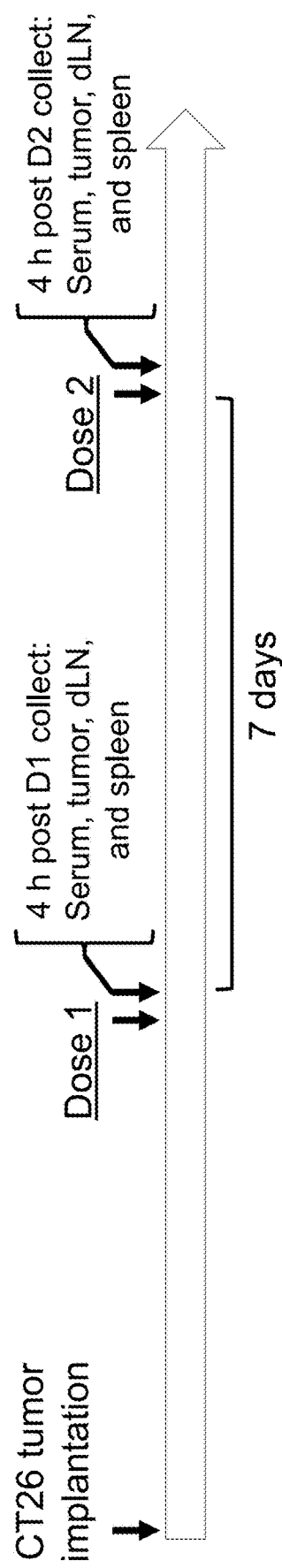
Figure 15C:
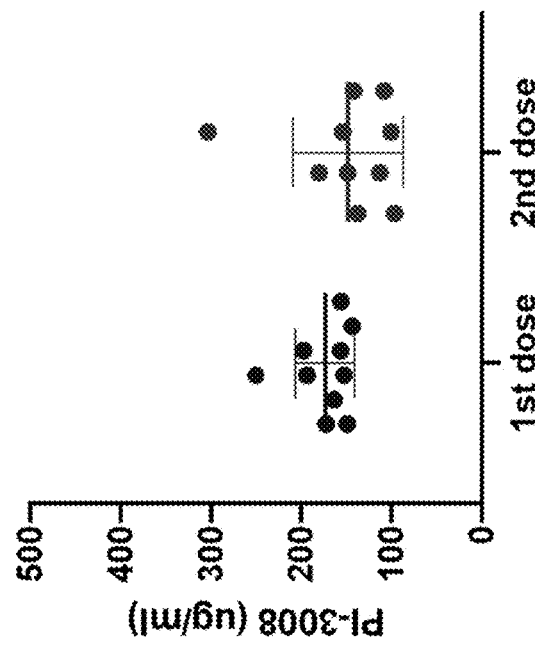
Figure 15B:
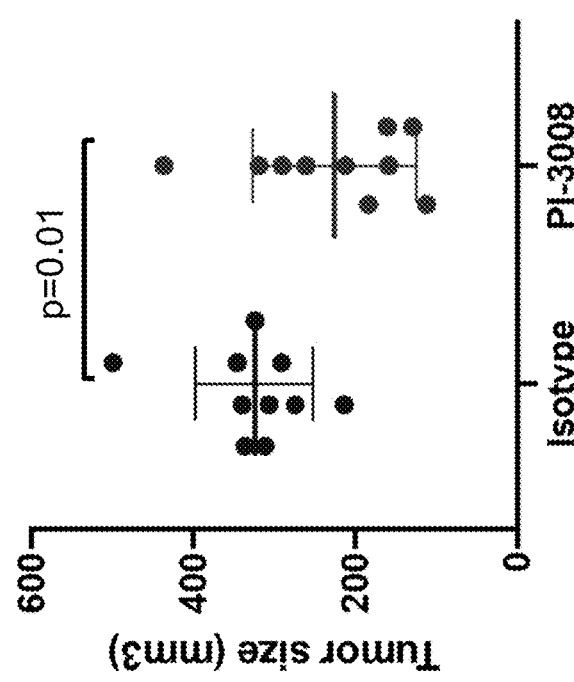

FIG. 15A shows a timeline of the PD study. FIG. 15B shows CT26 tumor volume in mice treated with isotype antibody or PI-3008. FIG. 15C shows quantification of the PI-3008 antibody in the mice after the first and second dose.

Figure 16A:
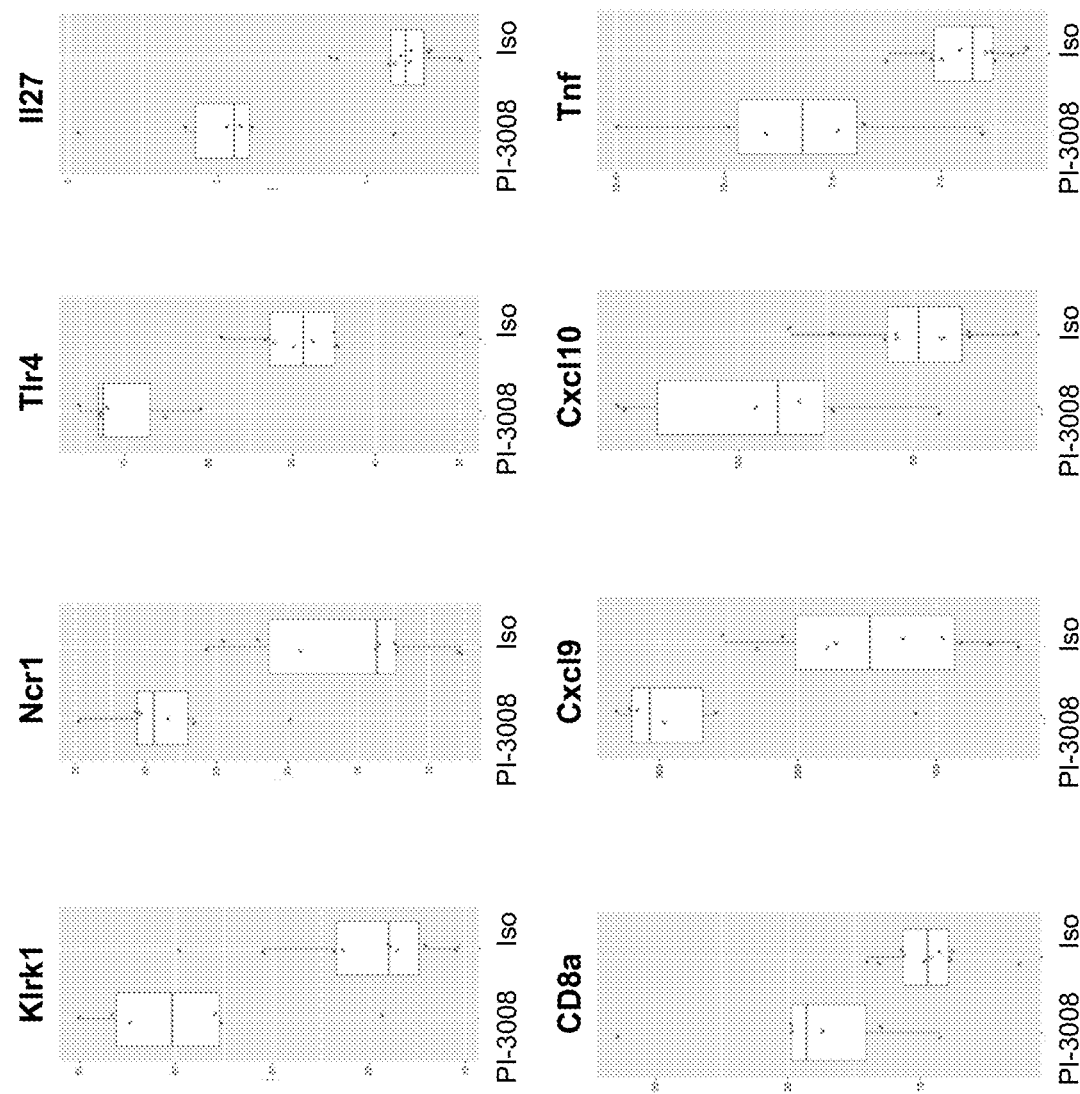

FIG. 16A show pro-inflammatory molecule expression within the TME of CT26 mice treated with PI-3008. FIG. 16B shows a comparison of the genes upregulated in BMDMs and CT26 tumors after in vitro or in vivo treatment with PI-3008.

FIG. 17A shows a sequence comparison of PI-HX-3061 VH with a human VH framework sequence and three humanized VH sequences based on PI-HX-3061 (SEQ ID NOS 141, 511, 151, 161, and 171, respectively, in order of appearance). FIG. 17B shows a sequence comparison of PI-HX-3061 VL with a human VL framework sequence and one humanized VL sequences based on PI-HX-3061 (SEQ ID NOS 146, 512, and 156, respectively, in order of appearance).

FIG. 18 shows a sequence comparison of PI-HX-3031 VL with a human VL framework sequence and 6 humanized VL sequences based on PI-HX-3031 (SEQ ID NOS 6, 512, 26, 36, 46, 86, 96, and 106, respectively, in order of appearance).

Figure 19:
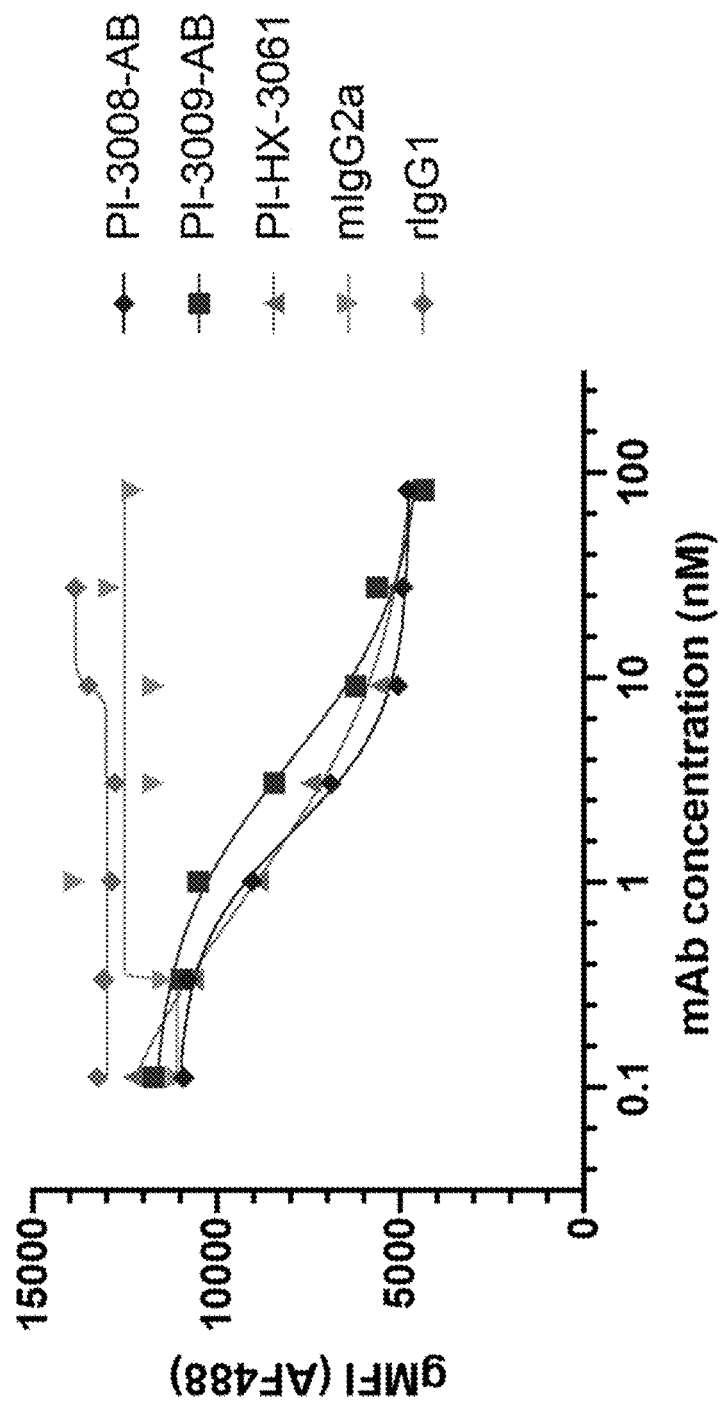

FIG. 19 shows the geometric mean fluorescent intensity (gMFI) of cells incubated with anti-MARCO antibodies and AF488 fluorescent bacteria in a competition assay. Pre-incubation of the cells with anti-MARCO antibodies reduced the bacteria binding and fluorescent signal in a dose dependent manner.

Figure 20A:
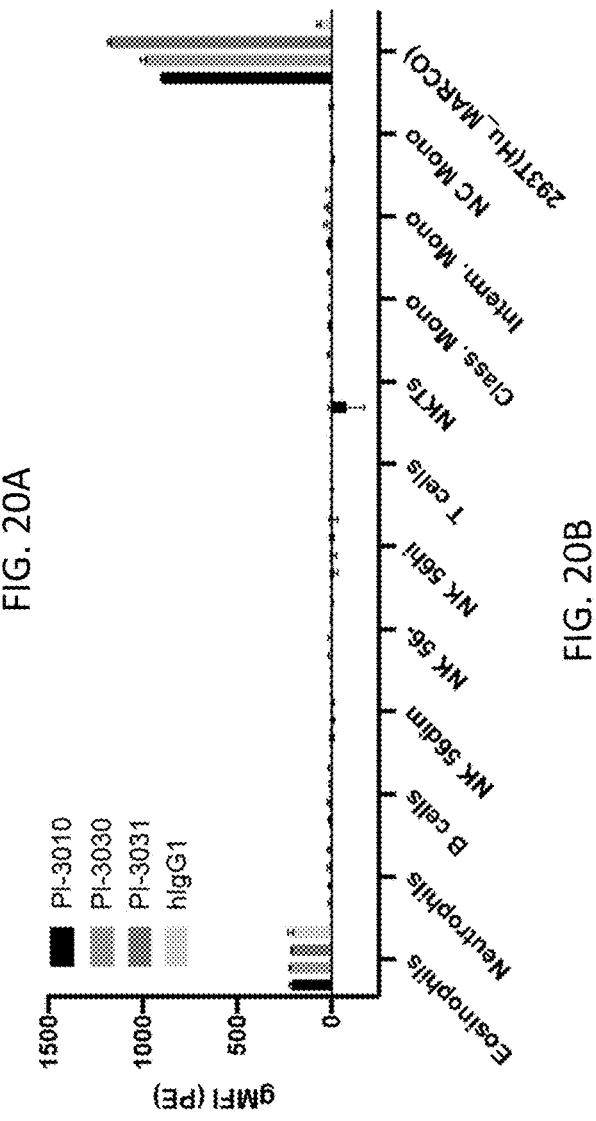
Figure 20B:
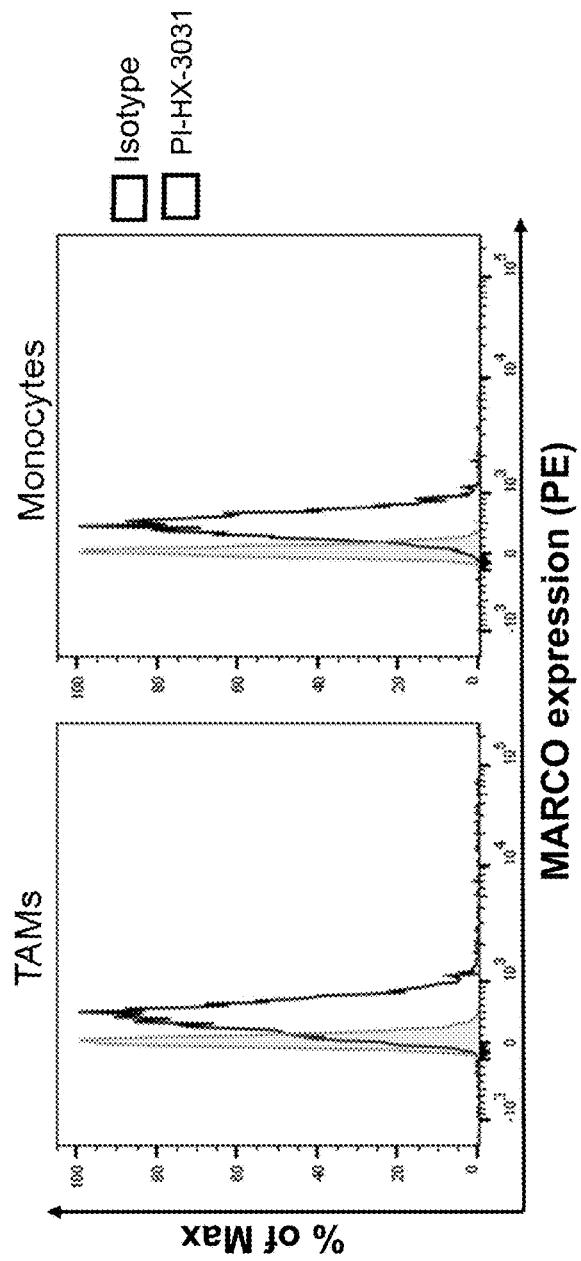

FIG. 20A shows binding of the chimera antibodies bound to 293T cells overexpressing MARCO but not to the immune cells present in PBLs (peripheral blood leukocytes). The eosinophil binding was non-specific across all tested antibodies including the hIgG1 isotype control. PI-3010 is shown on the left, PI-3030 is shown on the left middle, PI-3031 is shown on the right middle, and isotype control hIgG1 is shown on the right. FIG. 20B shows binding of PI-HX-3031 on TAMs and monocytes from an endometrial cancer (primary human tumor). Antibody binding is the right peak, isotype control binding is the left peak.

FIG. 21 shows a sequence comparison of the wild type SRCR domain in human and mouse MARCO and the mutations made in the indicated murine and human recombinant variant proteins. FIG. 21 discloses SEQ ID NOS 513-521, 513-514, 522-527, and 503, respectively, in order of appearance.

FIG. 22 shows the amino acids residues of the wild type SRCR domain in human and mouse MARCO and the mutations made in the indicated recombinant variant proteins. FIG. 22 discloses SEQ ID NOS 513-514, 524, 526-527, 513, 520, and 514, respectively, in order of appearance.

Figure 23:
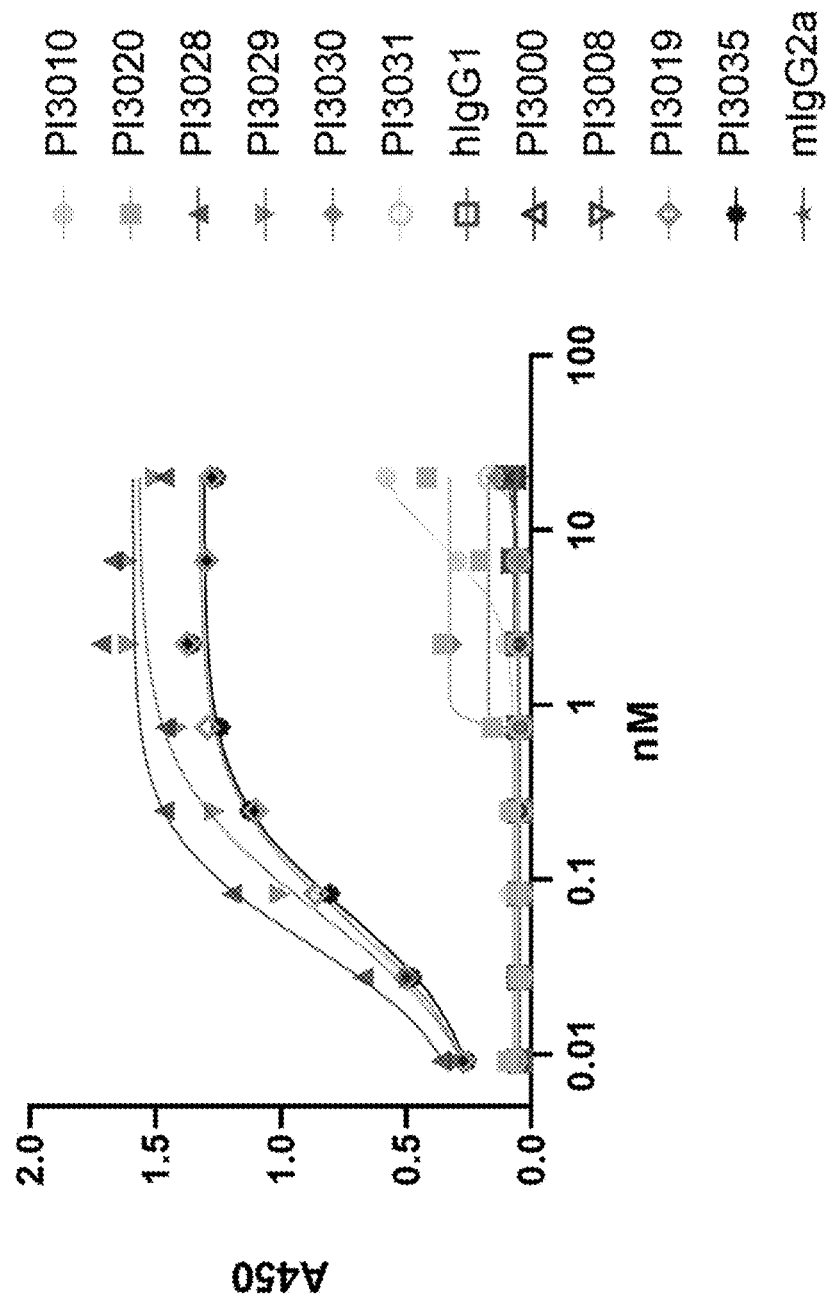

FIG. 23 shows binding of the indicated antibody to recombinant human SRCR MARCO hVar3 protein.

FIG. 24 shows the overlapping SRCR epitope residue (circled) in murine SRCR (left, Q452) and human SRCR (right, D452).

Figure 25A:
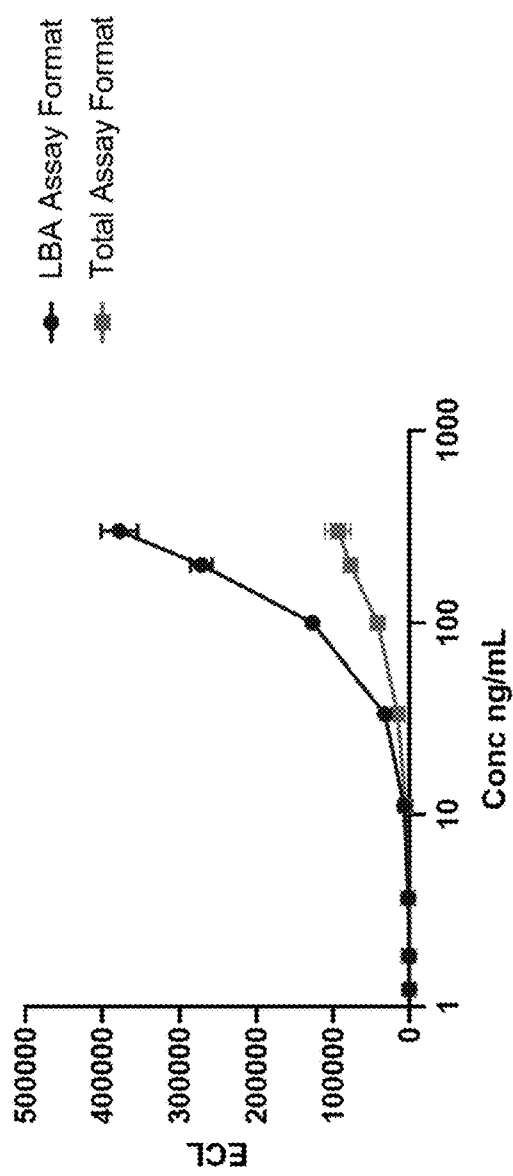
Figure 25B:
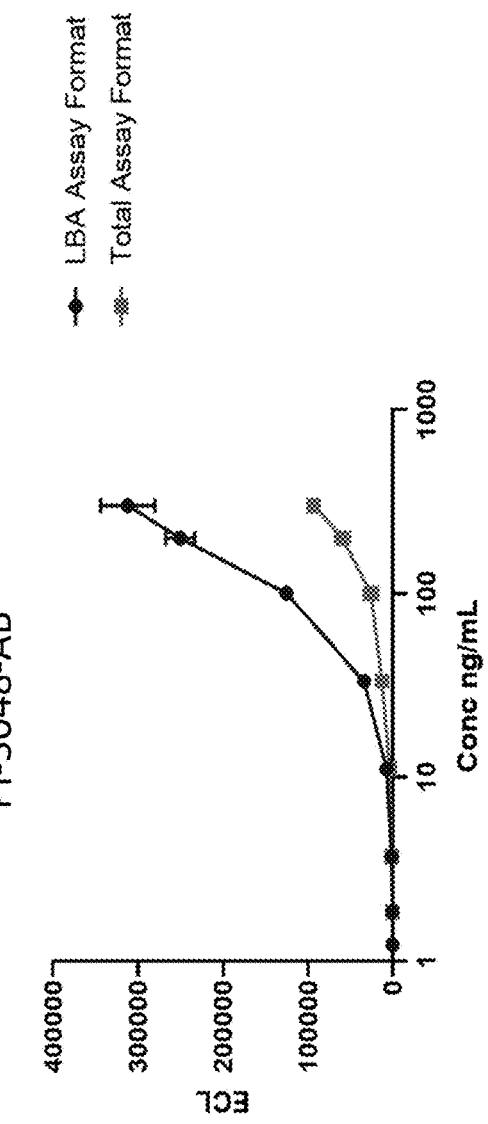

FIG. 25A shows the PK standard calibration curve for PI-3025. FIG. 25B shows the PK standard calibration curve for PI-3048.

Figure 26A:
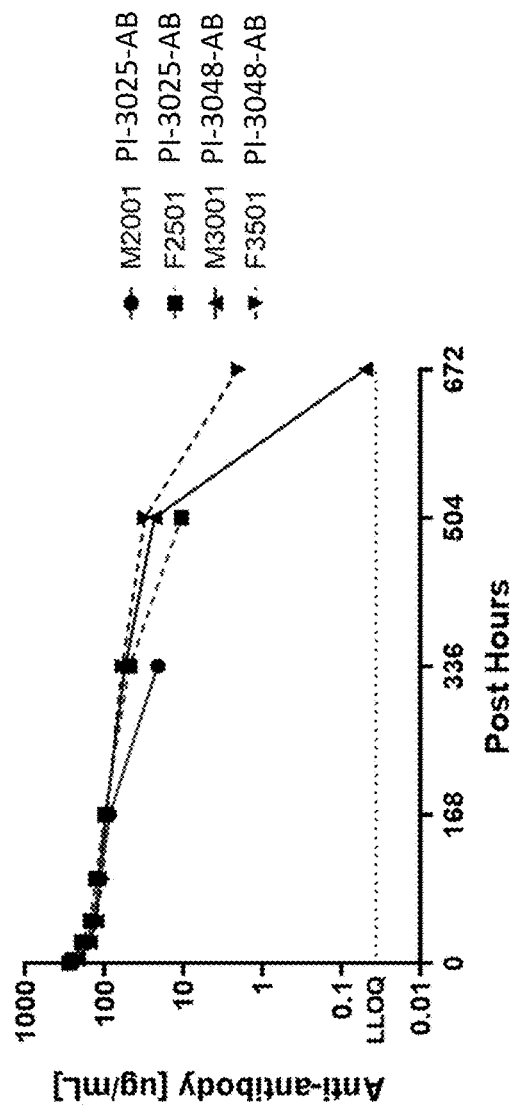
Figure 26B:
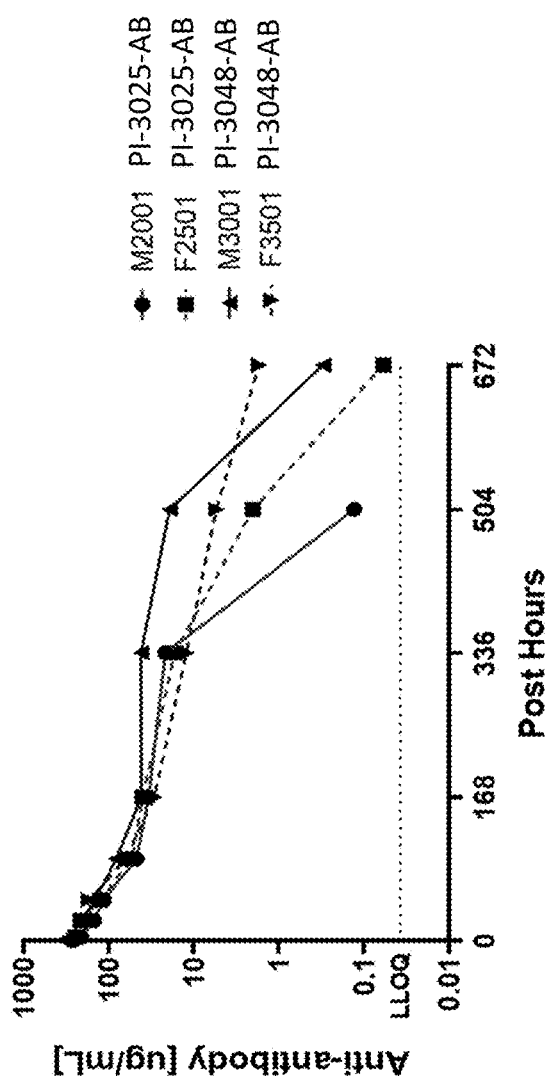

FIG. 26A shows the concentration-time profile of PI-3025 and PI-3048 in the ligand binding PK assay. FIG. 26B shows the concentration-time profile of PI-3025 and PI-3048 in the total PK assay.

Figure 27:
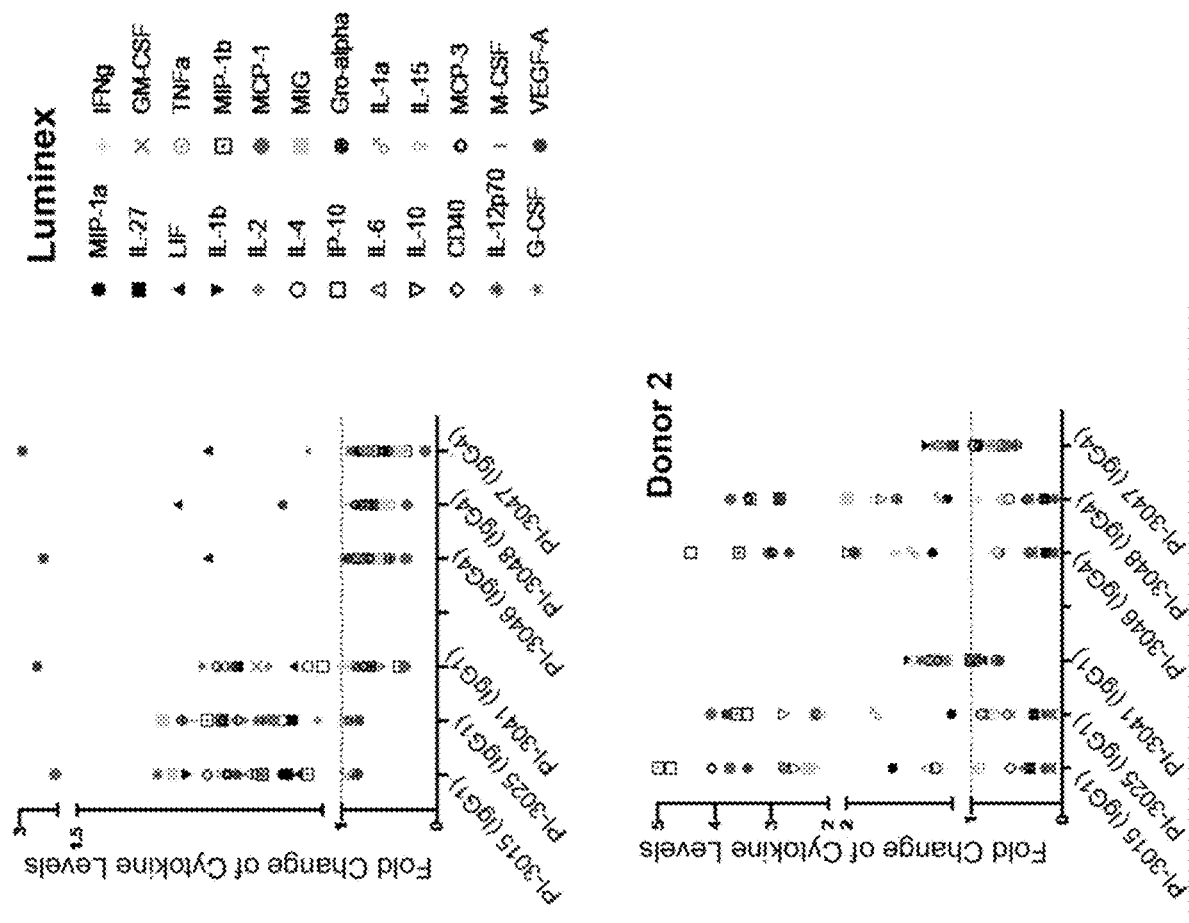

FIG. 27 provides cytokine and other relevant gene expression (MIP-1α, IL-27, LIF, IL-1α, IL-2, IL-4, IP-10, IL-6, IL-10, CD40, IL-12p70, G-CSF, IFNγ, GM-CSF, TNFα, MIP-1β, MCP-1, MIG, gro-alpha, IL-1α, IL-15, MCP-3, M-CSF, and VEGF-A) in hMDMs from two different donors after treatment with anti-MARCO antibody.

Figure 28:
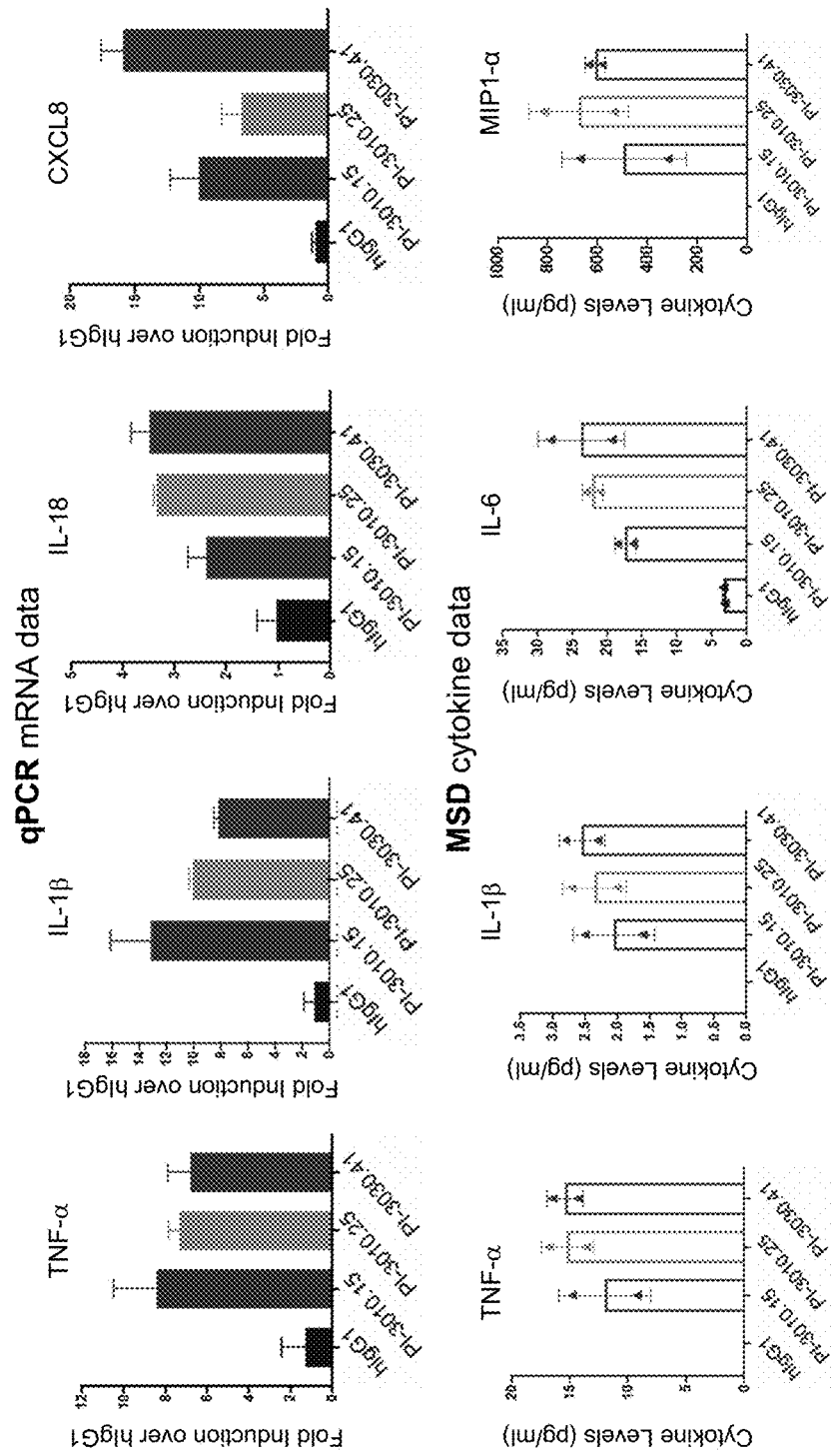

FIG. 28 provides the qPCR mRNA expression data for the indicated genes after treatment with PI-3010.15, PI-3010.25, PI-3030.41, or the hIgG1 control.

Figure 29:
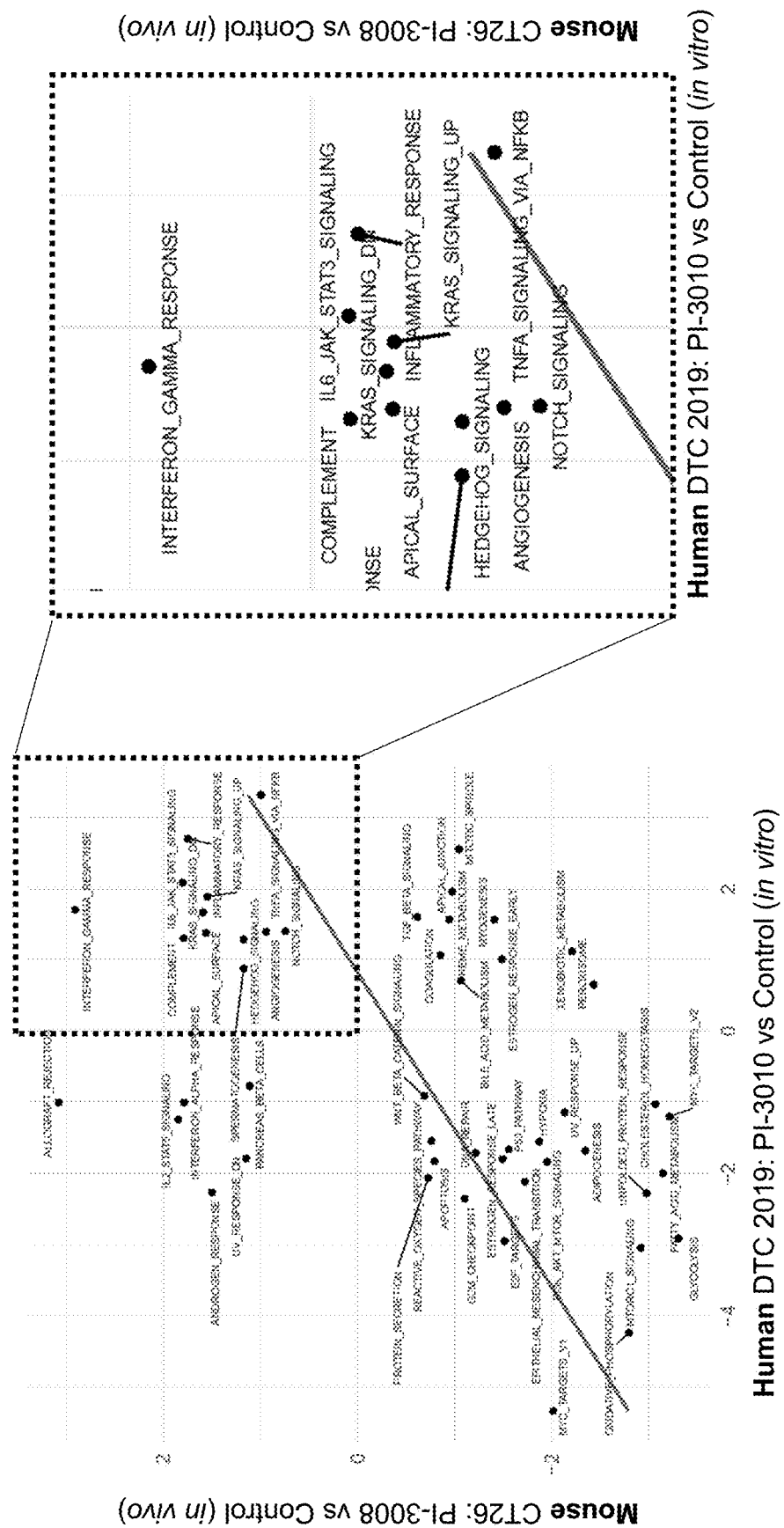

FIG. 29 shows that human and mouse MARCO mAbs drive similar pathway regulation.

Figure 30:
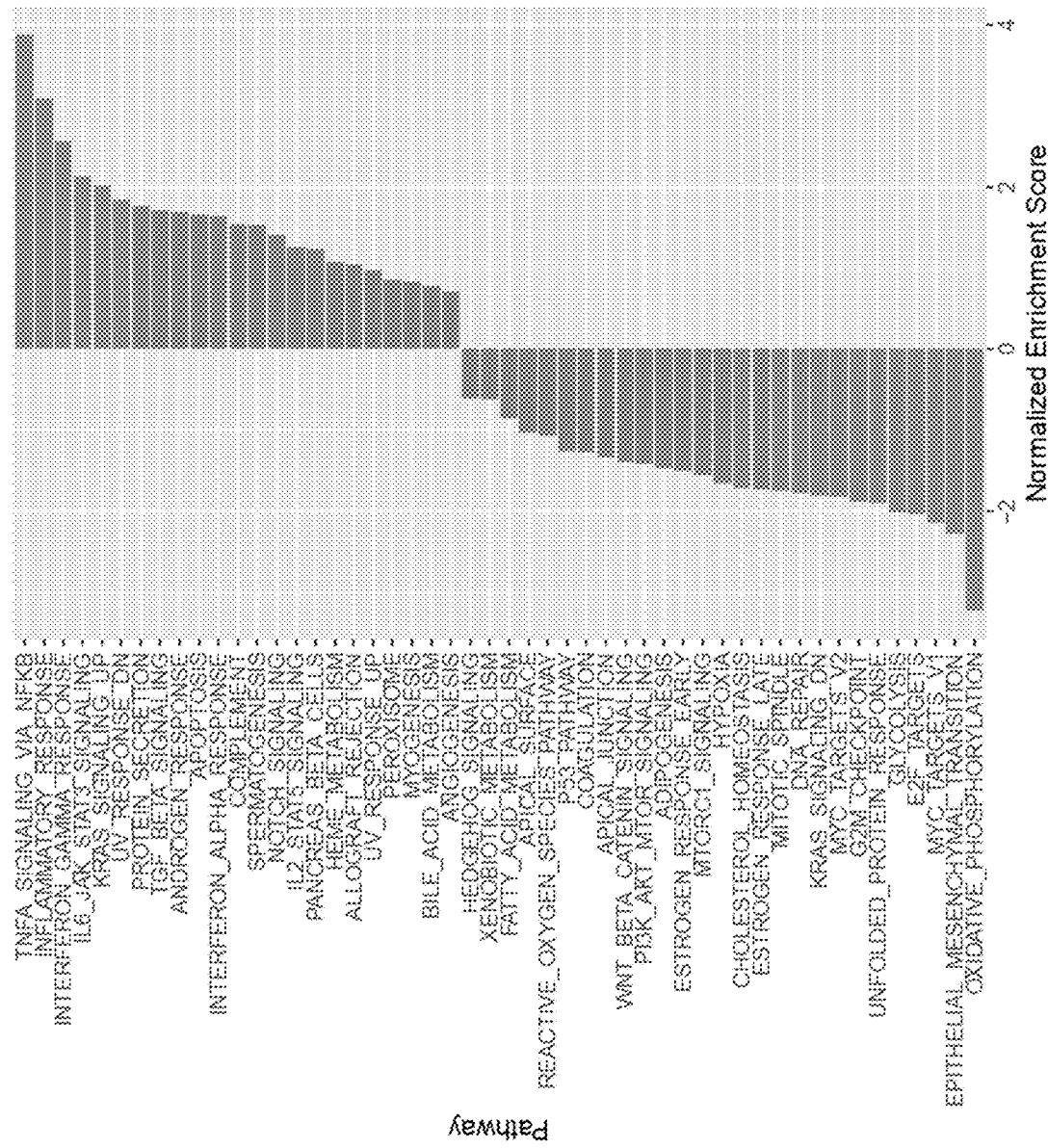

FIG. 30 shows the top immune activation genes and pathways increased by anti-MARCO antibody in hDTCs include IL-2-STATS signaling, TNFα signaling via NF-kB, IL-6-JAK-STAT3 signaling, the inflammatory response, IFNγ response, and IFNα response.

Figure 31:
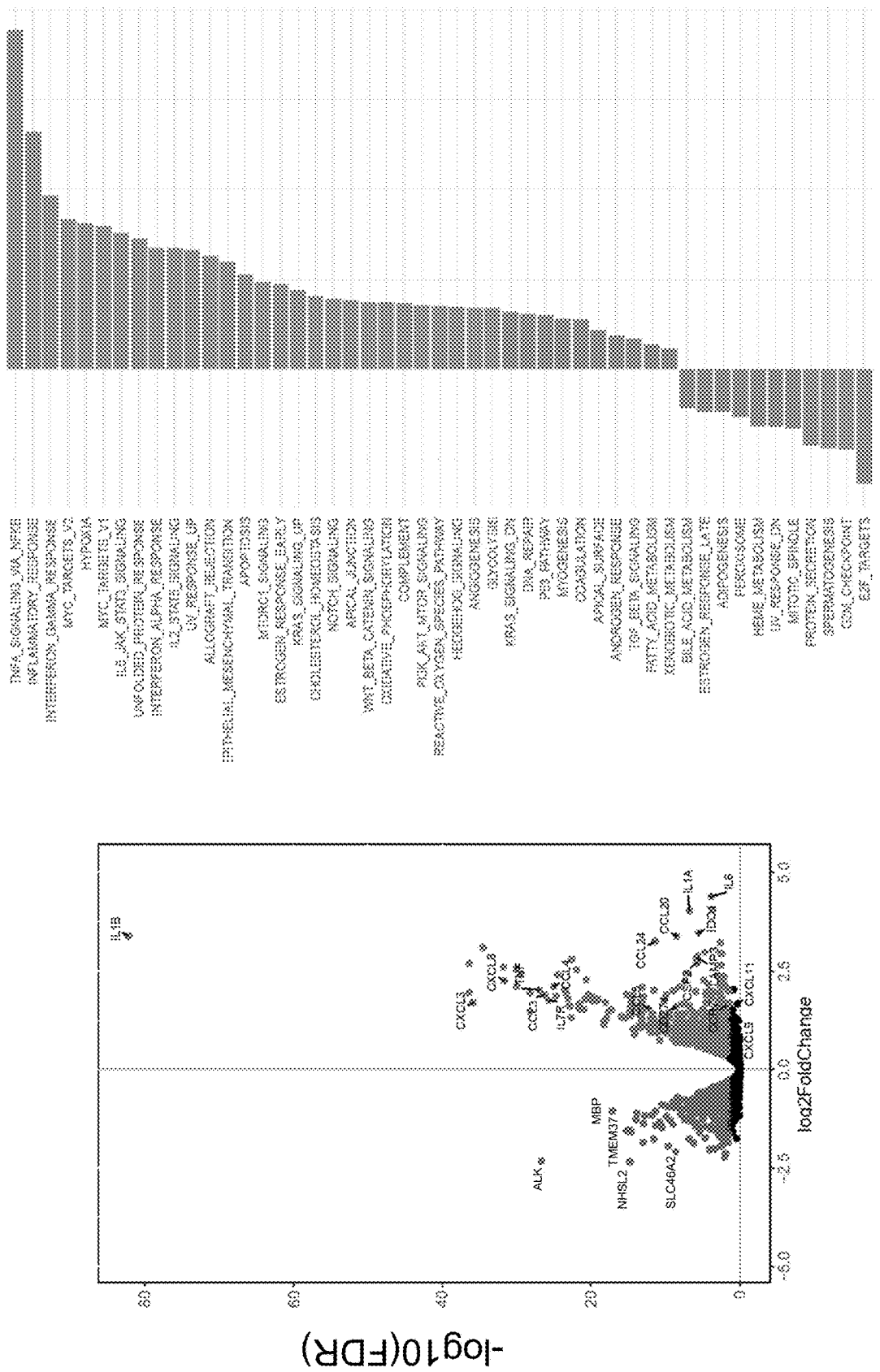

FIG. 31 shows that PI-3010.15 induced a pro-inflammatory signature in human suppressive macrophages (M2c).

Figure 32:
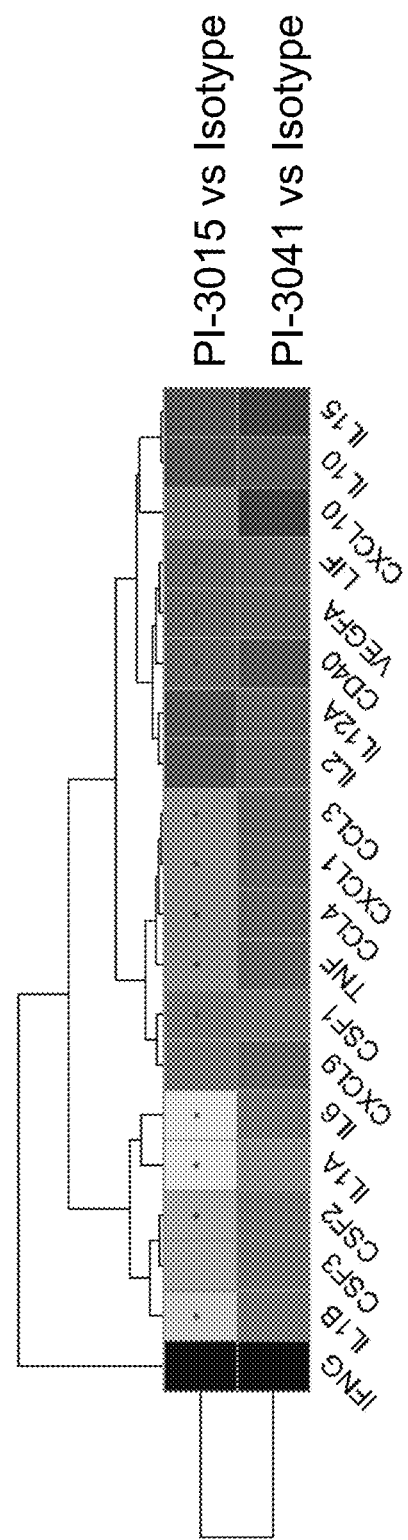

FIG. 32 provides a comparison of the indicated cytokine expression fold change induced by PI-3010.15 and PI-3030.41.

FIG. 33A shows that PI-3008 induced statistically significant IL-1(3 secretion by the inflammasome in non-polarized macrophages from C57BL/6 mice. FIG. 33B shows that PI-3008 induced statistically significant IL-1(3 secretion by the inflammasome in IL-10 polarized macrophages from C57BL/6 mice FIG. 33C shows that PI-3008 induced statistically significant IL-1(3 secretion by the inflammasome in non-polarized macrophages from Balb/c mice. FIG. 33D shows that PI-3008 induced statistically significant IL-1(3 secretion by the inflammasome in IL-10 polarized macrophages from Balb/c mice.

Figure 34A:
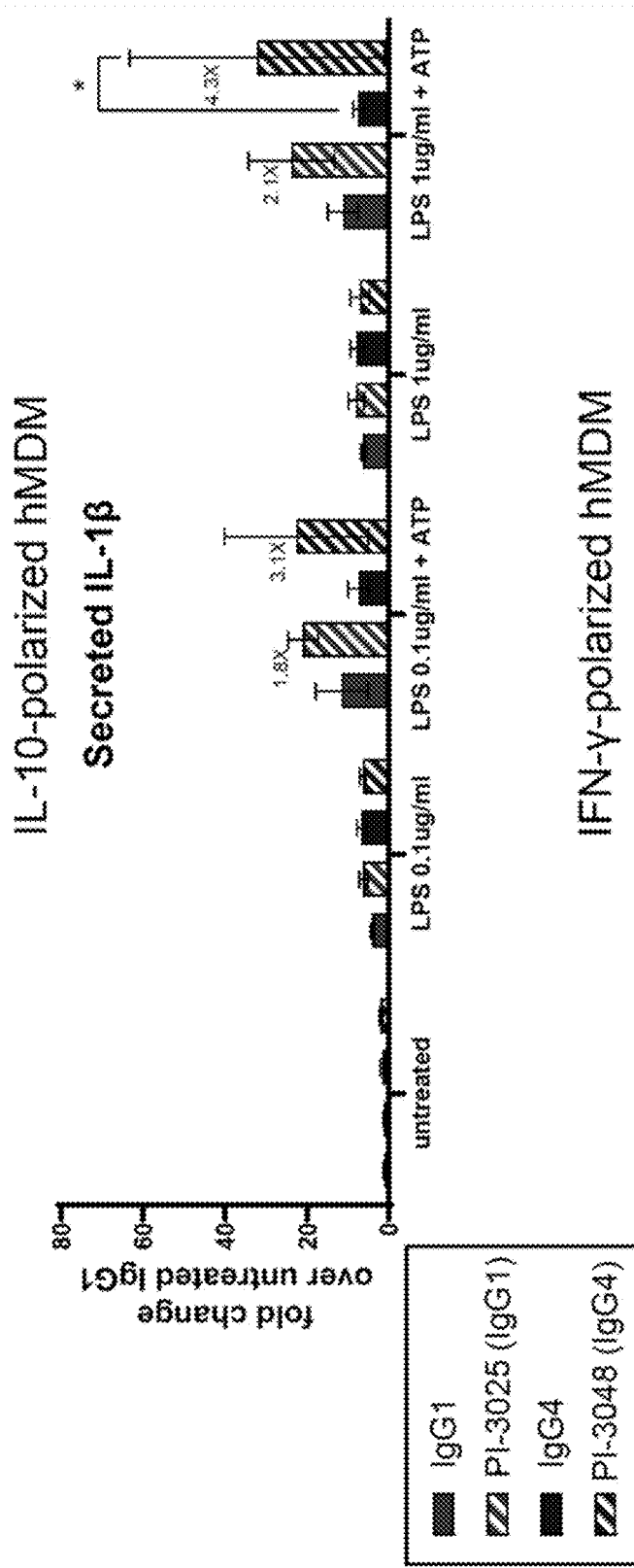
Figure 34B:
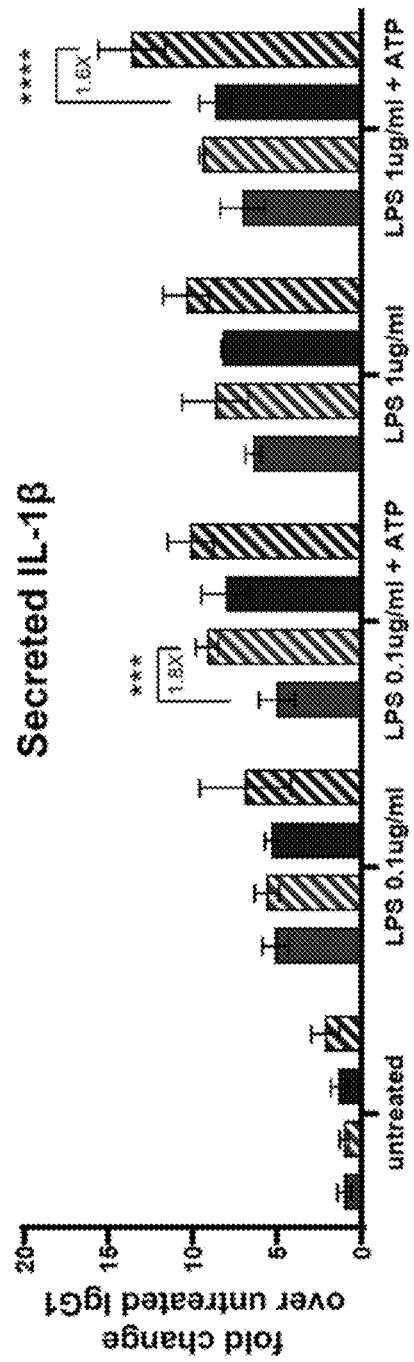

FIG. 34A shows that PI-3025 (IgG1 format) and PI-3048 (IgG4 format) induced statistically significant IL-1(3 secretion in IL-10 polarized macrophages after incubation with 0.1 μg/ml LPS+ATP and 1 μg/ml LSP+ATP. FIG. 34B shows that PI-3048 induced IL-113 secretion after treatment with 1 μg/ml LPS+ATP. Bars for PI-3025 are shown second from the left in each grouping, bars for PI-3048 are shown on the right in each grouping.

Figure 36:
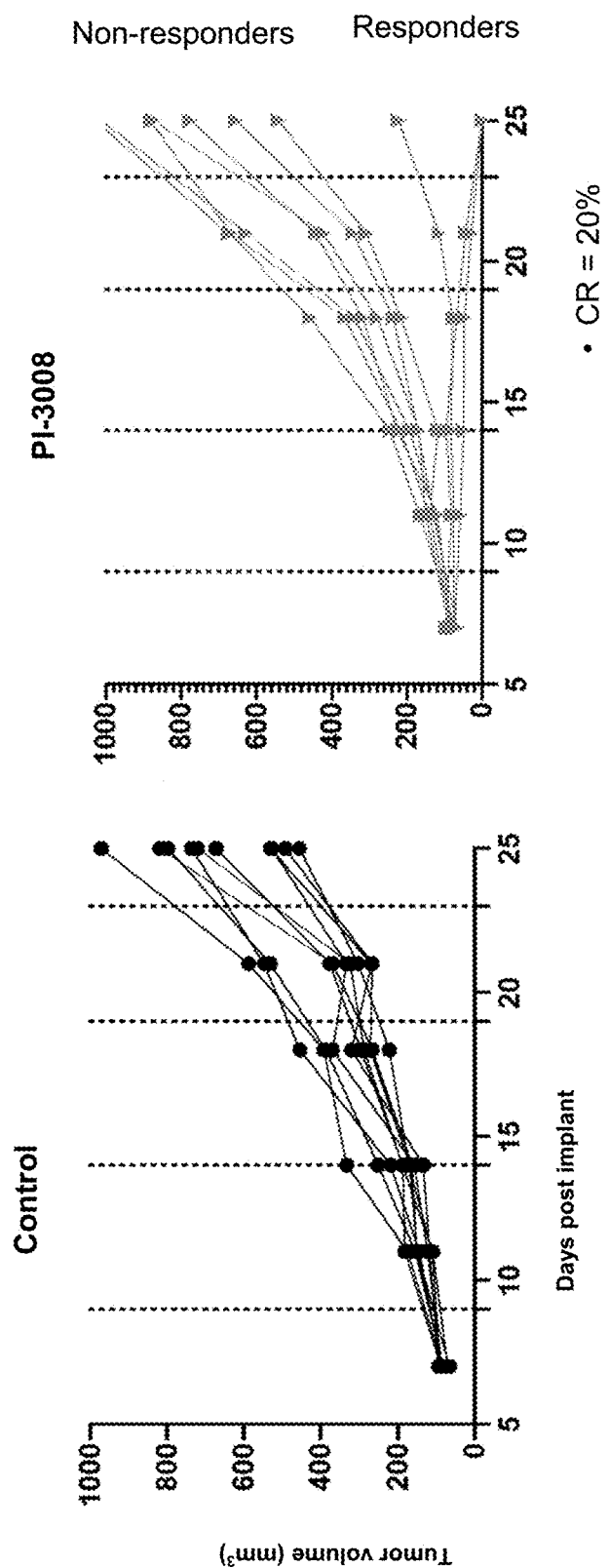

FIG. 35 shows that of PI-3010.15, PI-3010.25, and PI-3030.41 induced IL-1(3 production when treated with LPS and ATP compared to the untreated condition FIG. 36 shows that PI-3008 demonstrated anti-tumor activity as a single agent in the EMT6 model. Tumor volumes in isotype control antibody treated mice are shown in the right panel, tumor volumes in PI-3008 antibody treated mice are shown in the left panel. The PI-3008 treated mice grouped into responders and non-responders.

Figure 37:
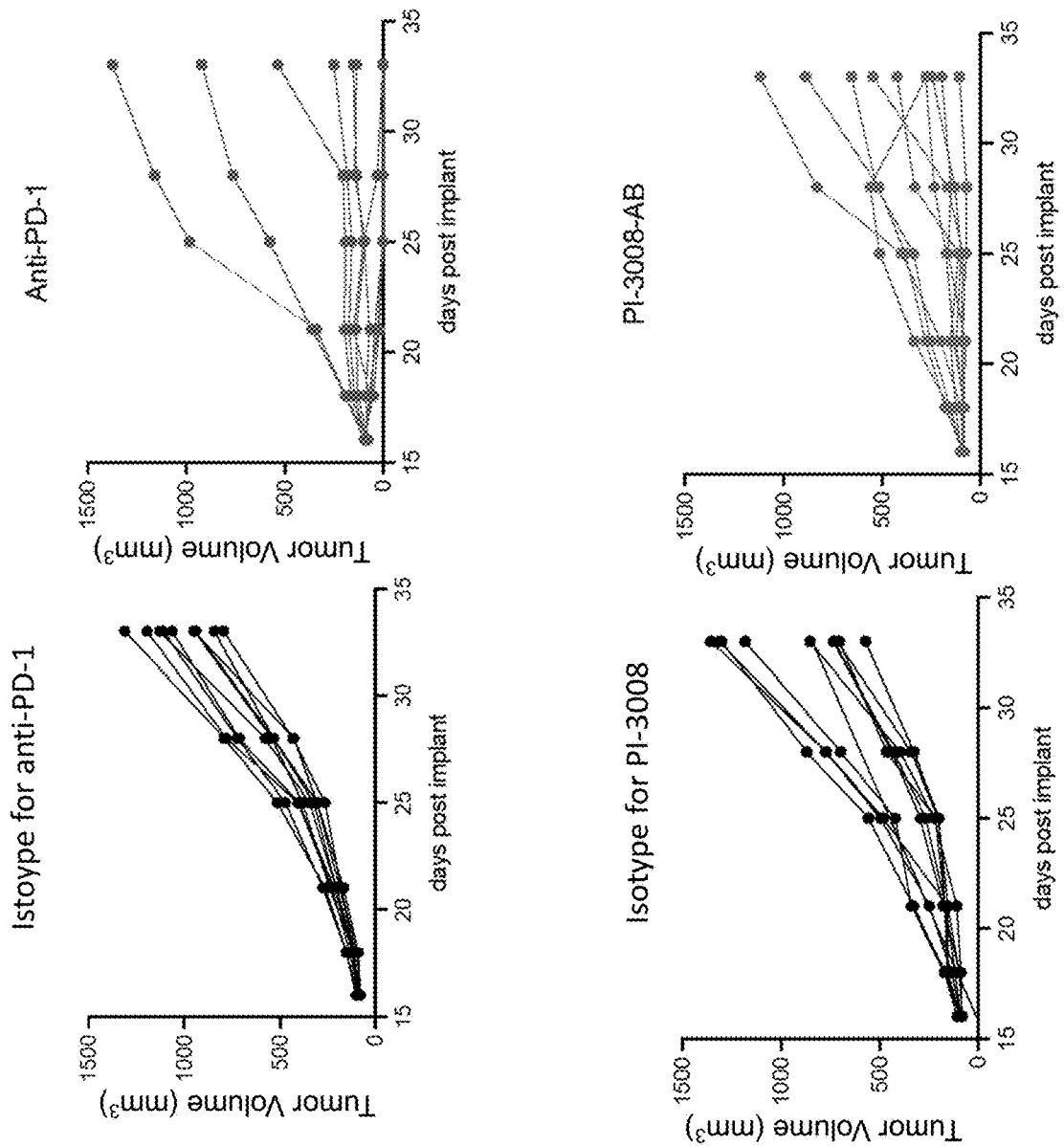

FIG. 37 shows that PI-3008 demonstrated anti-tumor activity as a single agent in the E0771 model. Tumor volumes in isotype control antibody treated mice are shown in the top right and bottom right panels, tumor volumes in PD-1 antibody treated mice are shown in the top left panel, and tumor volumes in PI-3008 antibody treated mice are shown in the bottom left panel.

Figure 38B:
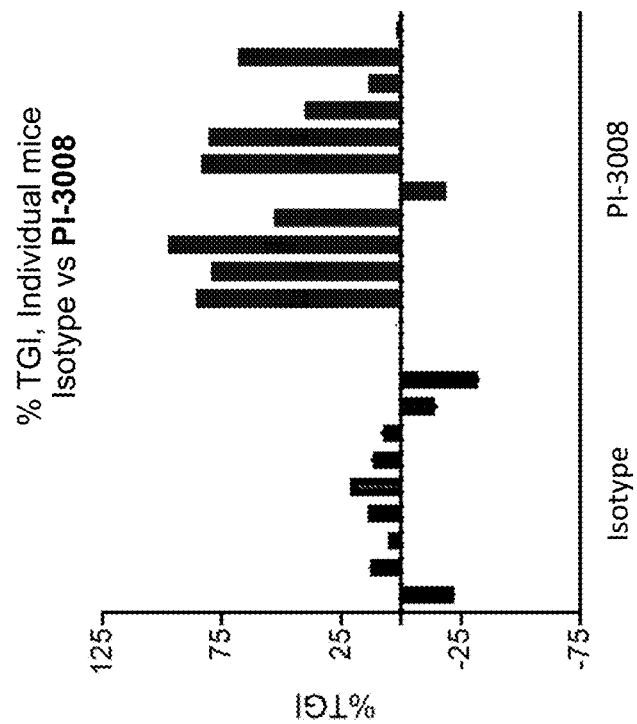
Figure 38A:
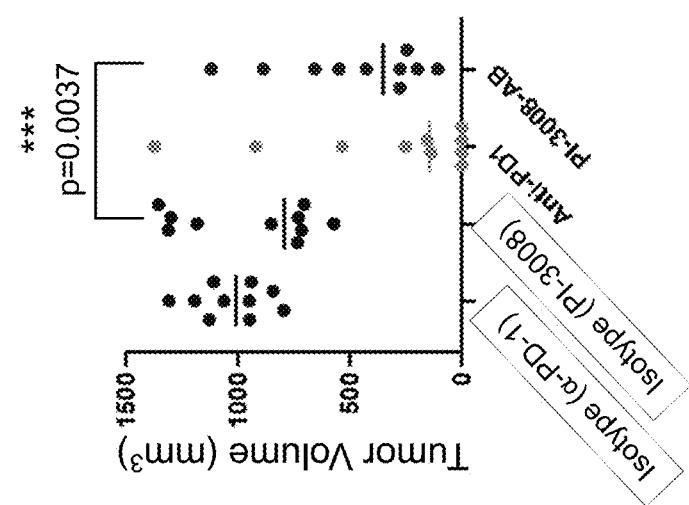
Figure 38C:
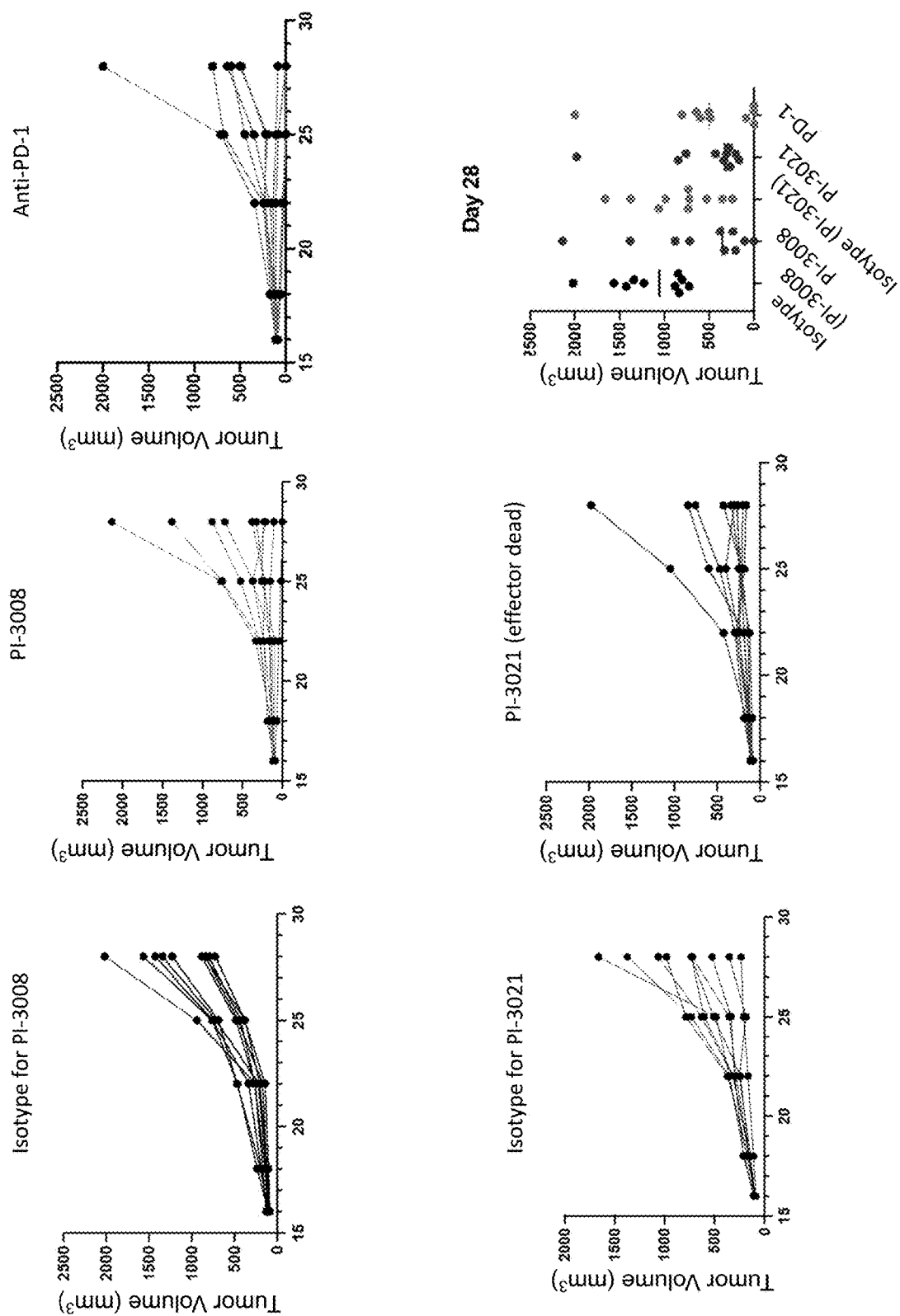

FIG. 38A shows that the mice dosed with PI-3008 showed a statistically significant reduction in tumor volume as compared to isotype controls (p=0.0037). FIG. 38B shows the percentage of tumor growth inhibition (TGI) for isotype antibody and PI-3008. FIG. 38C shows that PI-3008 and effector dead PI-3021 both have anti-tumor activity in the E0771 model.

Figure 39A:
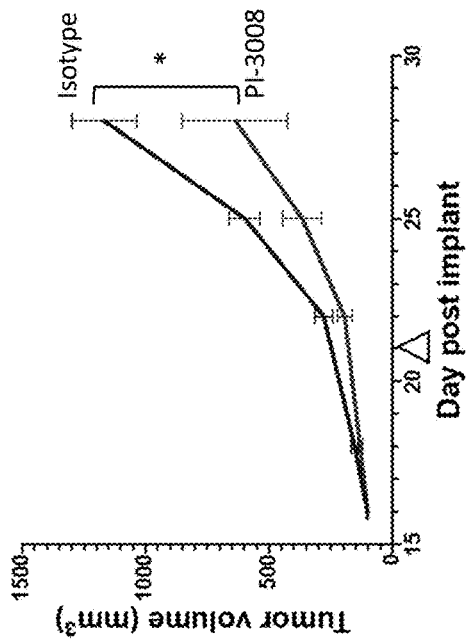
Figure 39B:
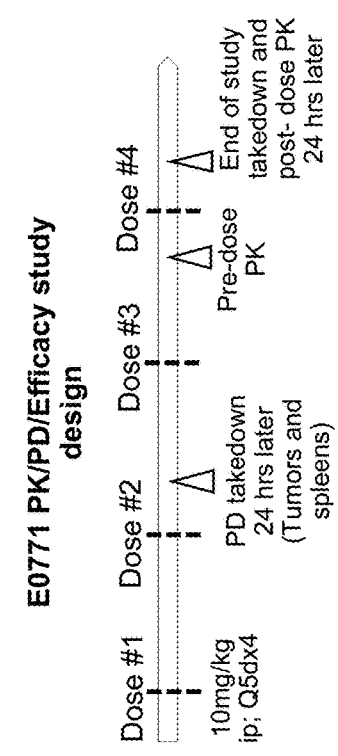
Figure 39C:
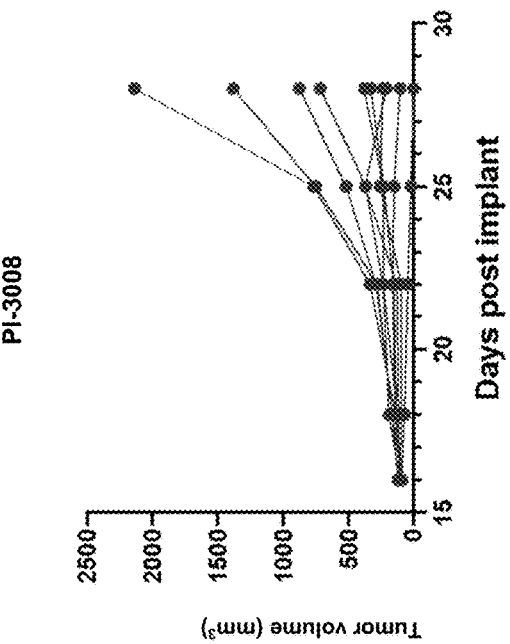
Figure 39D:
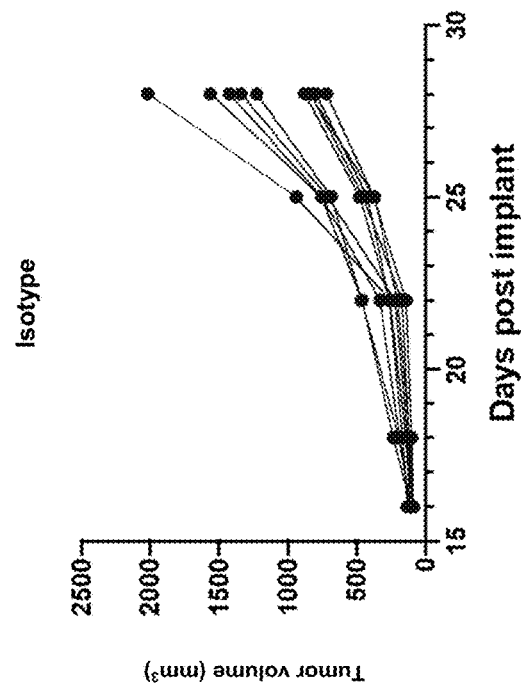
Figure 39F:
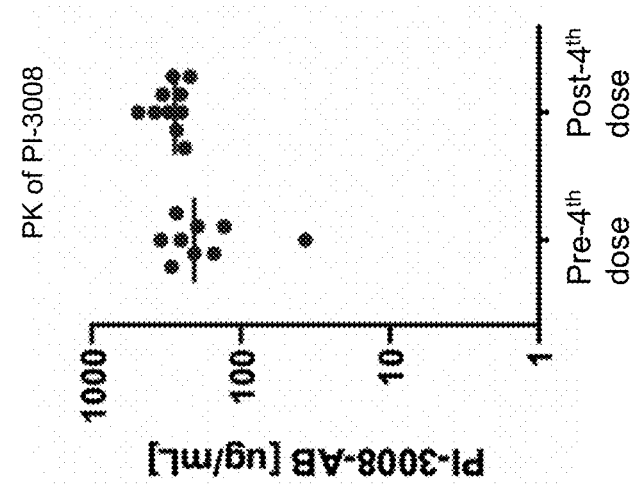
Figure 39E:
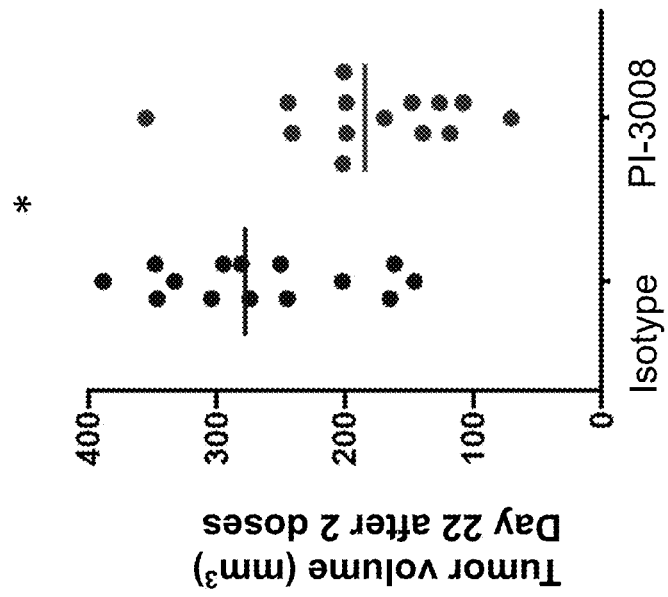

FIG. 39A provides a schematic of the E0771 PD/PK/efficacy study timeline. FIG. 39B shows the tumor volume in isotype control treated mice and PI-3008 treated mice over the course of the study. FIG. 39C provides individual tumor volumes in the isotype control mice. FIG. 39D provides individual tumor volumes in the PI-3008 mice. FIG. 39E provides the final tumor volumes at Day 28. FIG. 39F provides the serum levels of PI-3008.

Figure 40B:
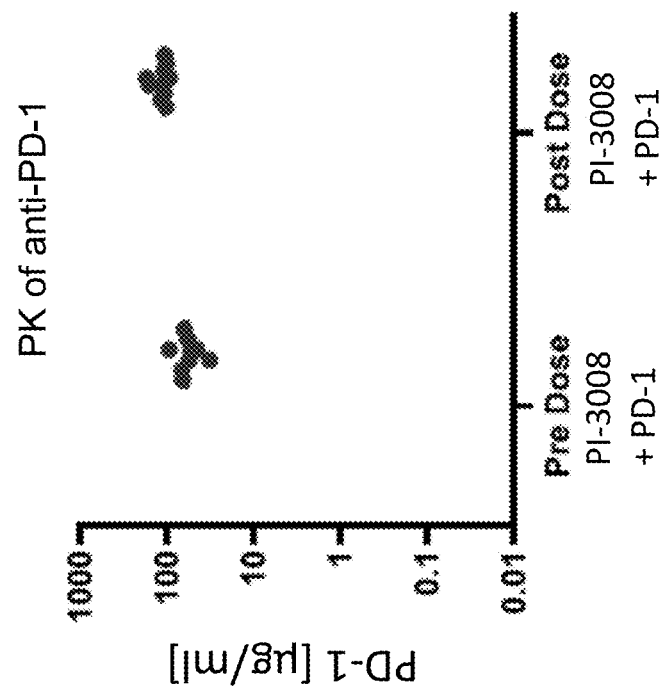
Figure 40A:
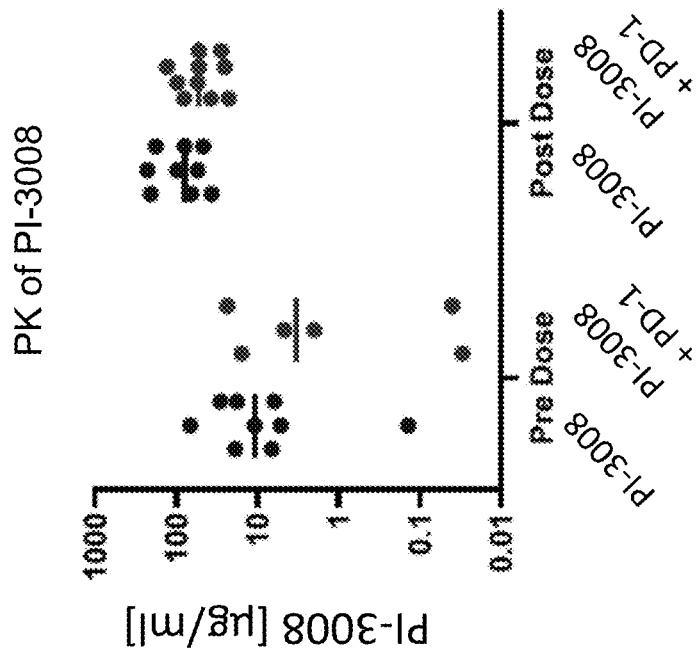

FIG. 40A provides the PI-3008 serum concentrations in mono and combination experiments with PD-1 antibody. FIG. 40B provides the PD-1 antibody serum concentrations in combination experiments.

Figure 41B:
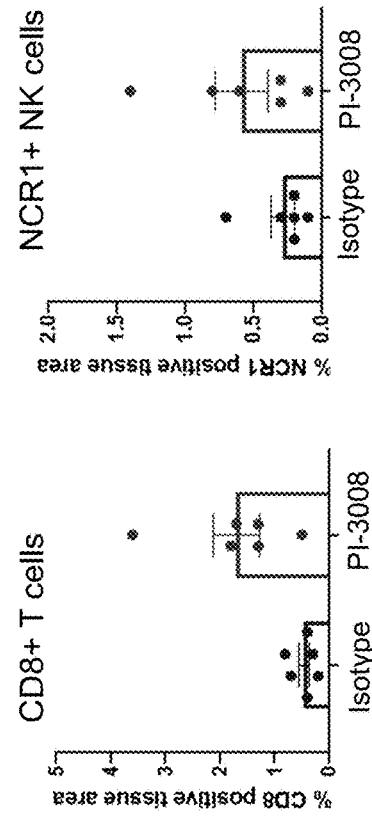
Figure 41C:
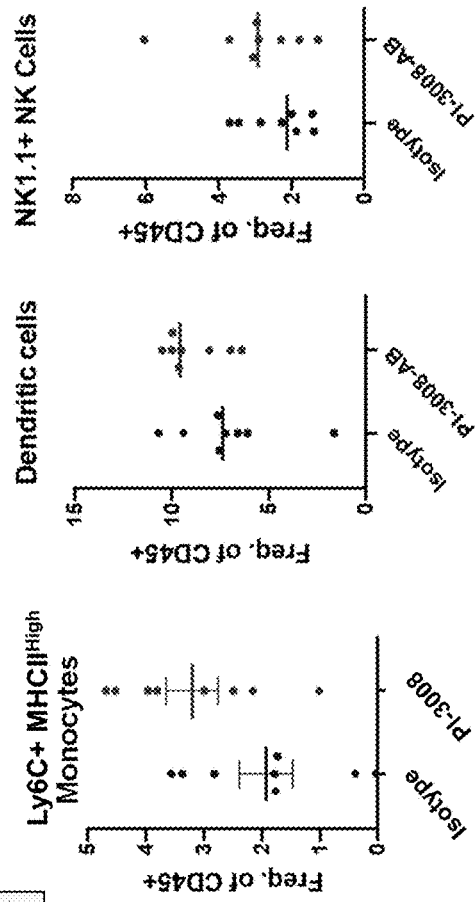
Figure 41A:
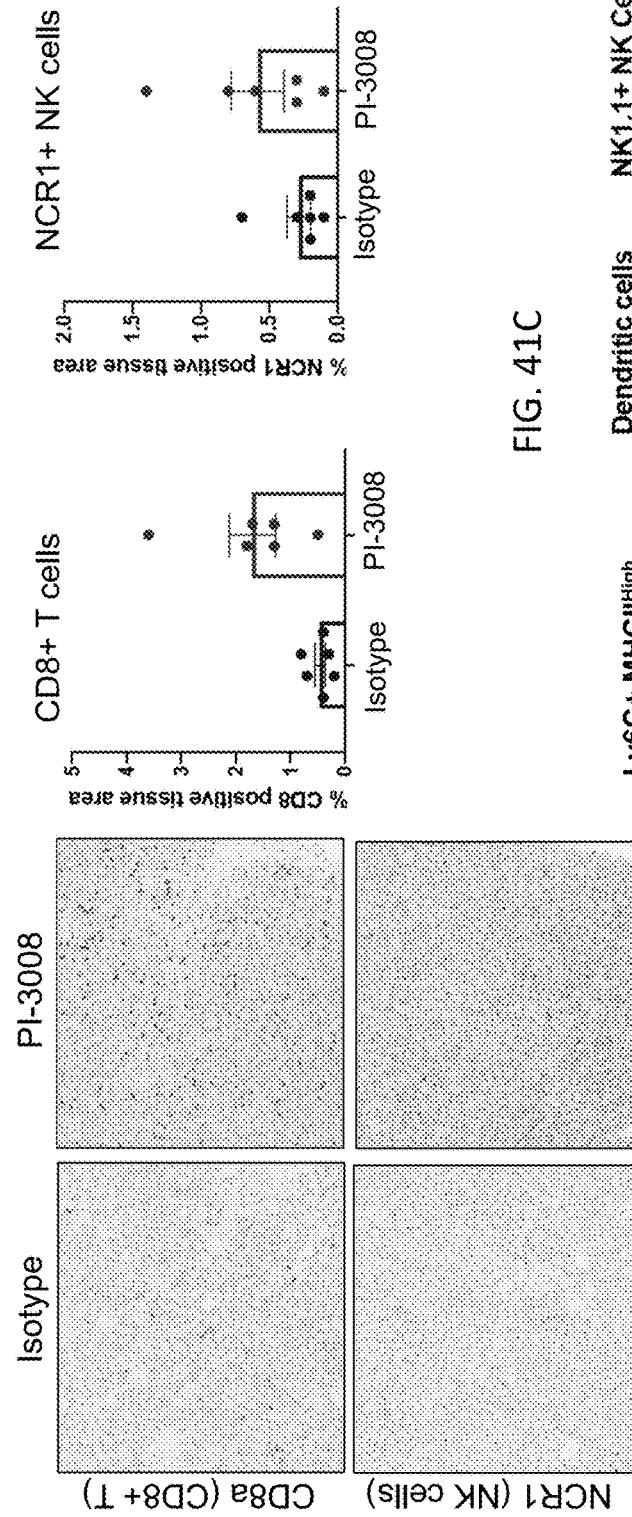

FIG. 41A provides IHC images of CD8 T cells and NCR1 (NK cells) stained with DAB after administration of isotype control or PI-3008. FIG. 41B provides quantification of inflammatory monocyte infiltration (CD8+ T cells, NCR1+ NK cells) by flow cytometry.

Figure 41D:
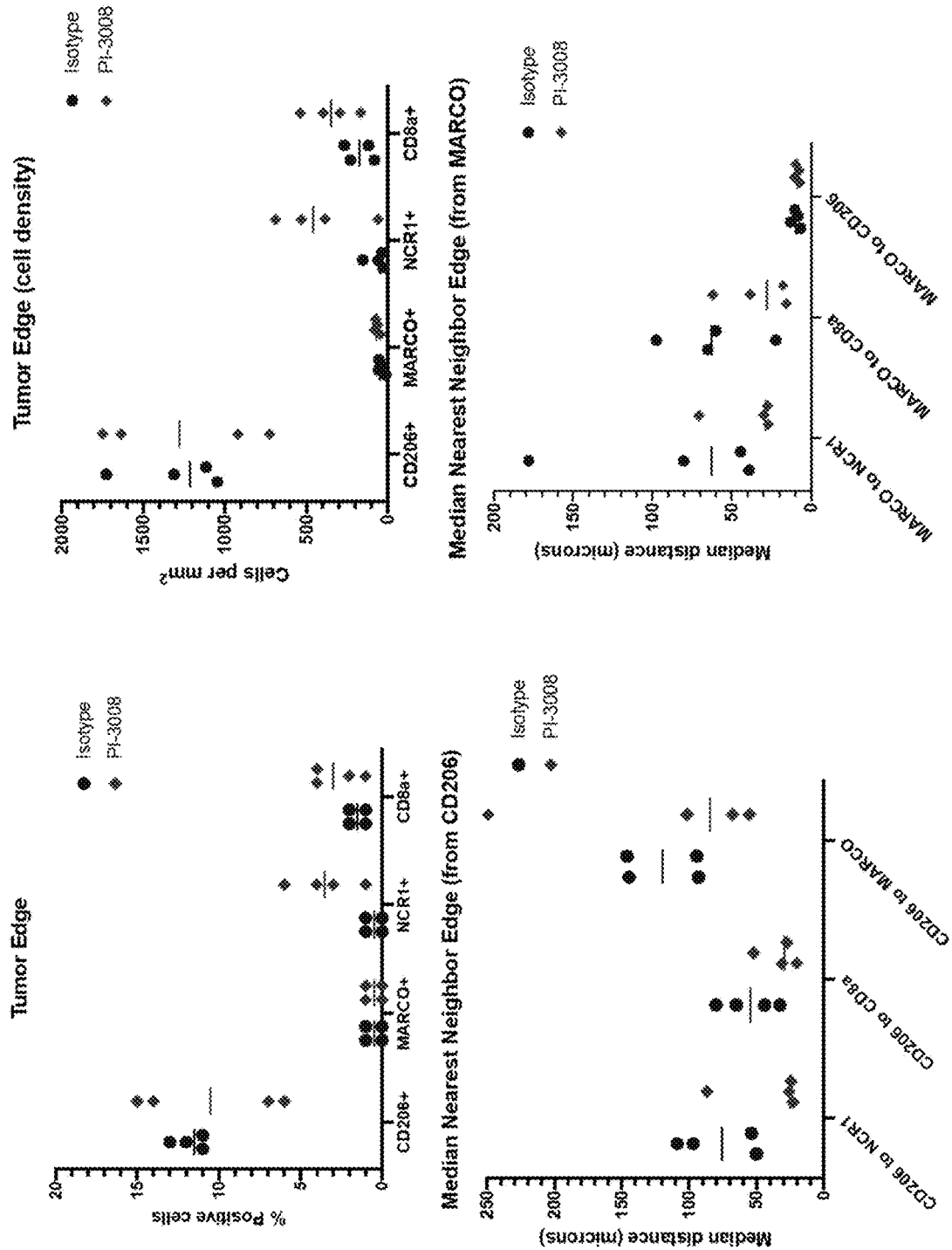

FIG. 41C provides quantification of MHCII$^{High}$ Ly6C+ monocytes, DC infiltration, and NK1.1 NK cells by flow cytometry. FIG. 41D provides quantification of CD206+, cells, MARCO+ cells, NCR1+ cells, and CD8a+ cells at the indicated region.

Figure 42A:
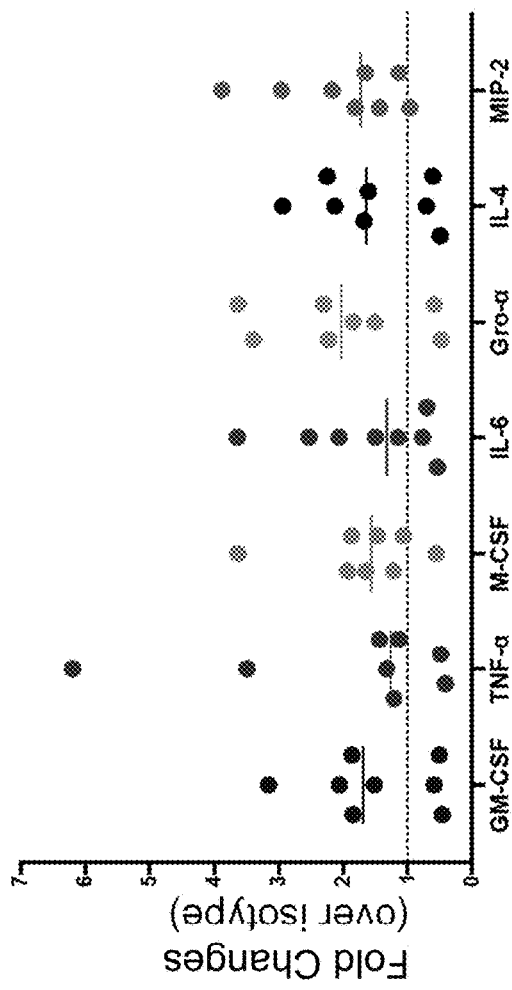
Figure 42B:
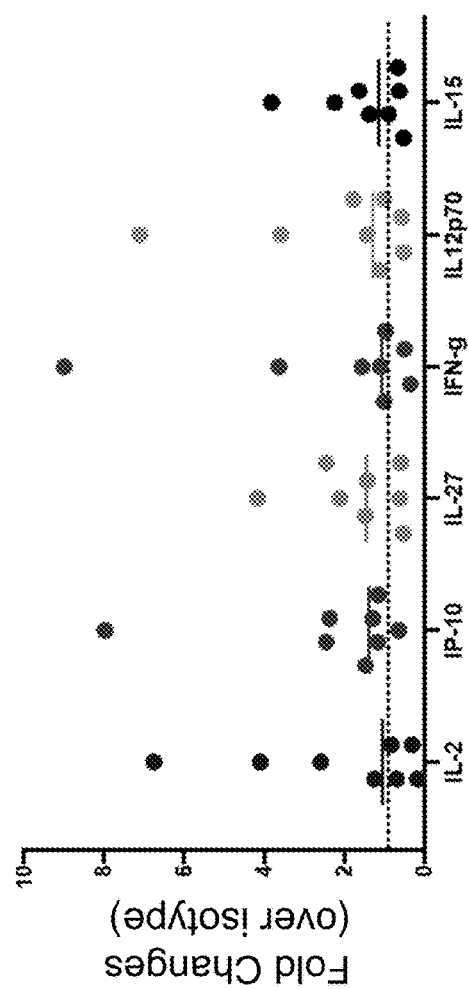

FIG. 42A provides expression levels of the indicated proinflammatory cytokines and chemokines induced by PI-3008 in the E0771 model tumor supernatants. FIG. 42B provides expression levels of the indicated cytokines associated with T-cell activation and NK cells activation observed at Day 1 post-dose 2 in the tumor supernatants.

Figure 43:
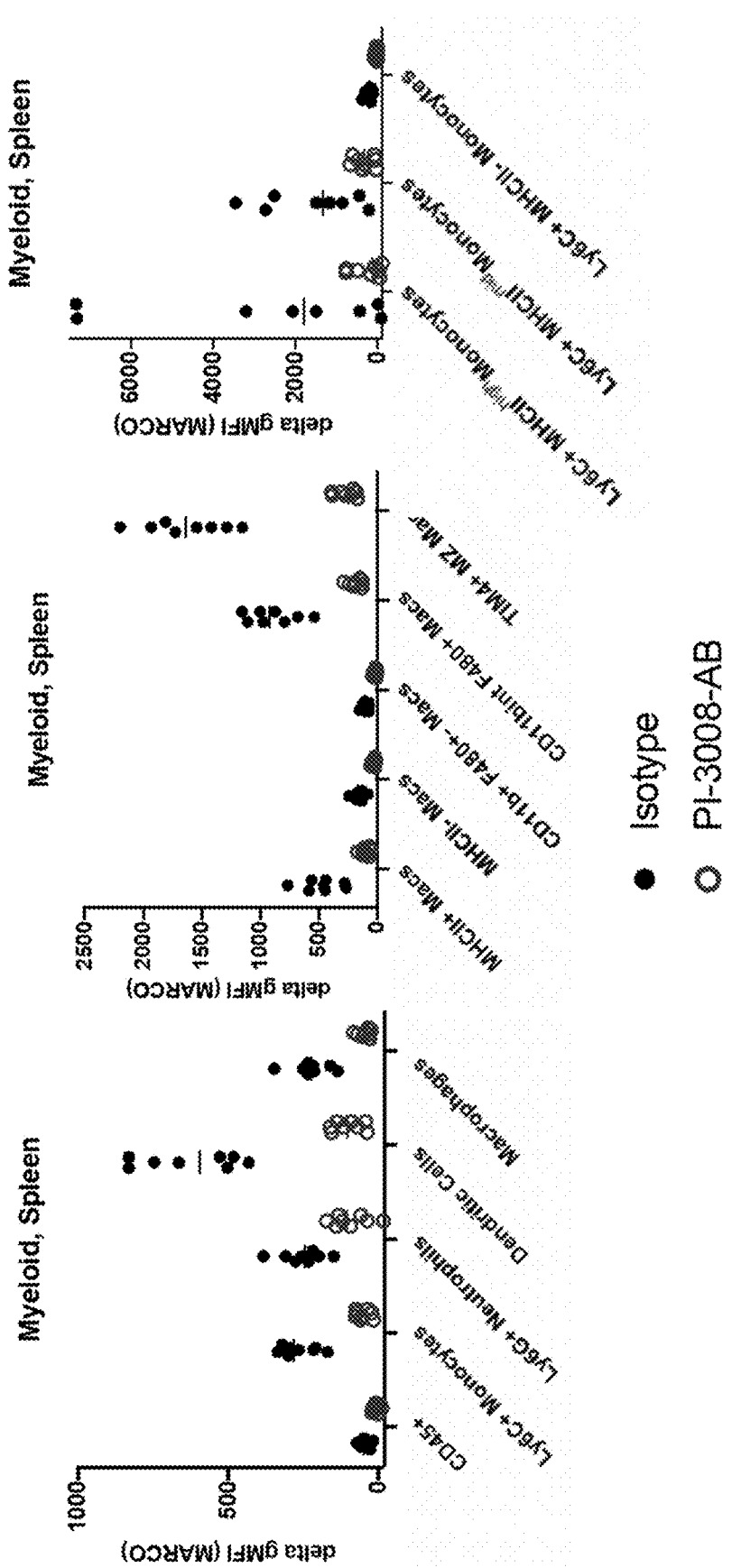

FIG. 43 provides the results of the receptor occupancy assay.

Figure 44A:
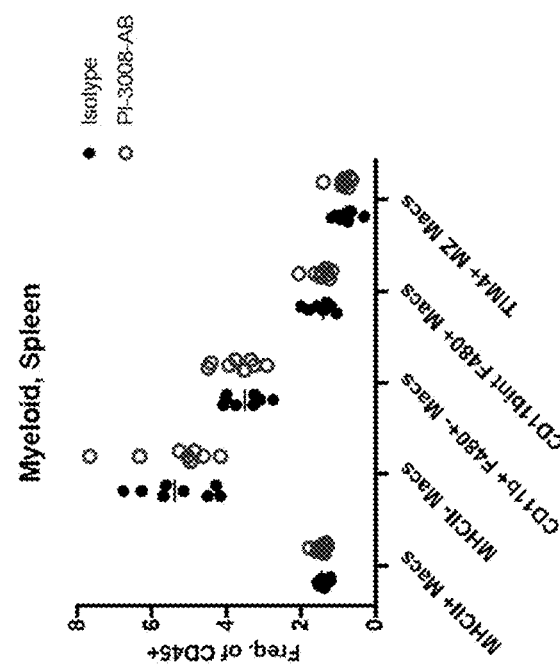
Figure 44B:
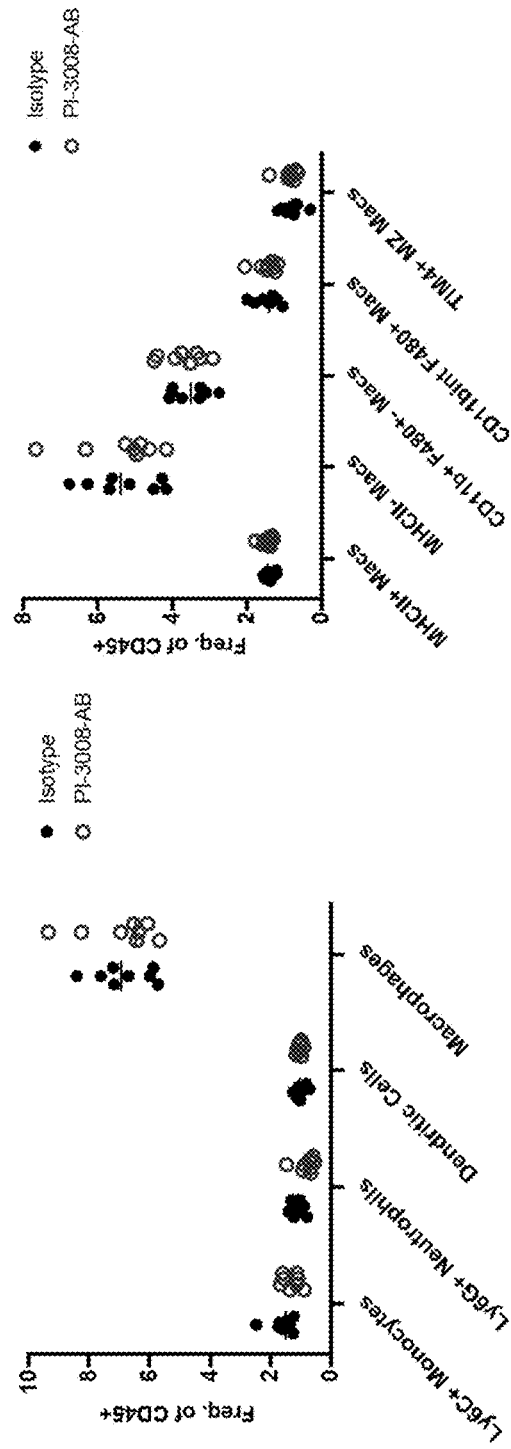

FIG. 44A provides quantification of the indicated cell types in the spleen after treatment with isotype control antibody or PI-3008. FIG. 44B provides quantification of the indicated cell types in the spleen after treatment with isotype control antibody or PI-3008.

Figure 44D:
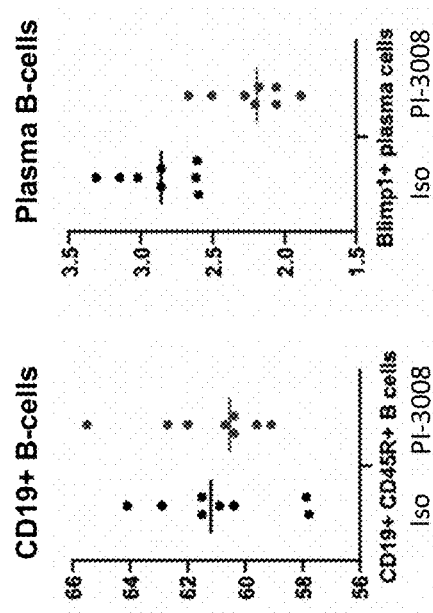
Figure 44C:
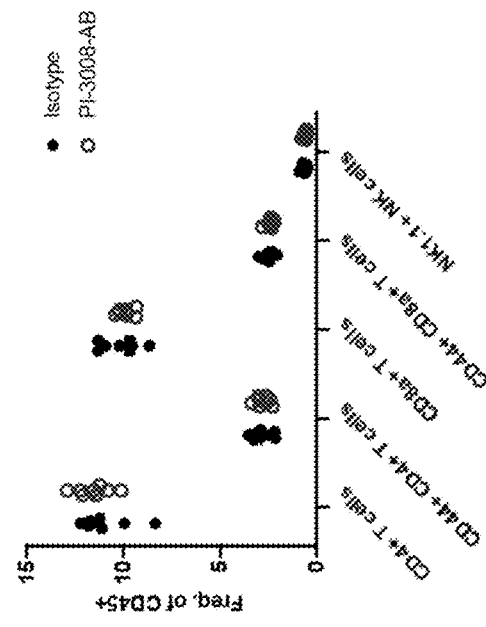

FIG. 44C provides quantification of the indicated cell types in the spleen after treatment with isotype control antibody or PI-3008. FIG. 44D provides quantification of the indicated cell types in the spleen after treatment with isotype control antibody or PI-3008. In each figure, isotype samples are shown on the left of the pairs, PI-3008 samples are shown on the right of the pairs.

Figure 45:
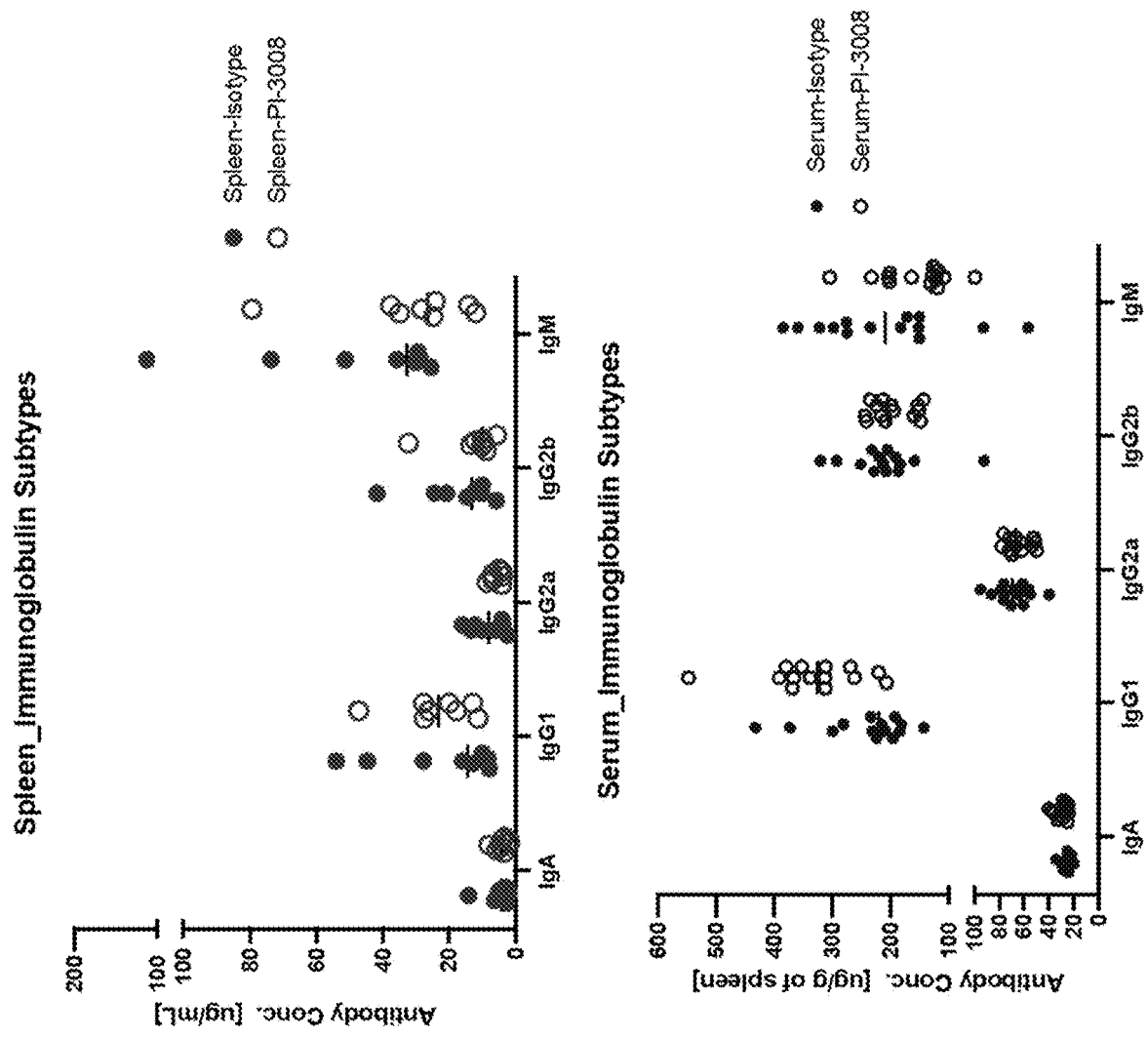

FIG. 45 provides quantification of the indicated immunoglobulin types in the spleen and serum after treatment with isotype control antibody or PI-3008.

Figure 46:
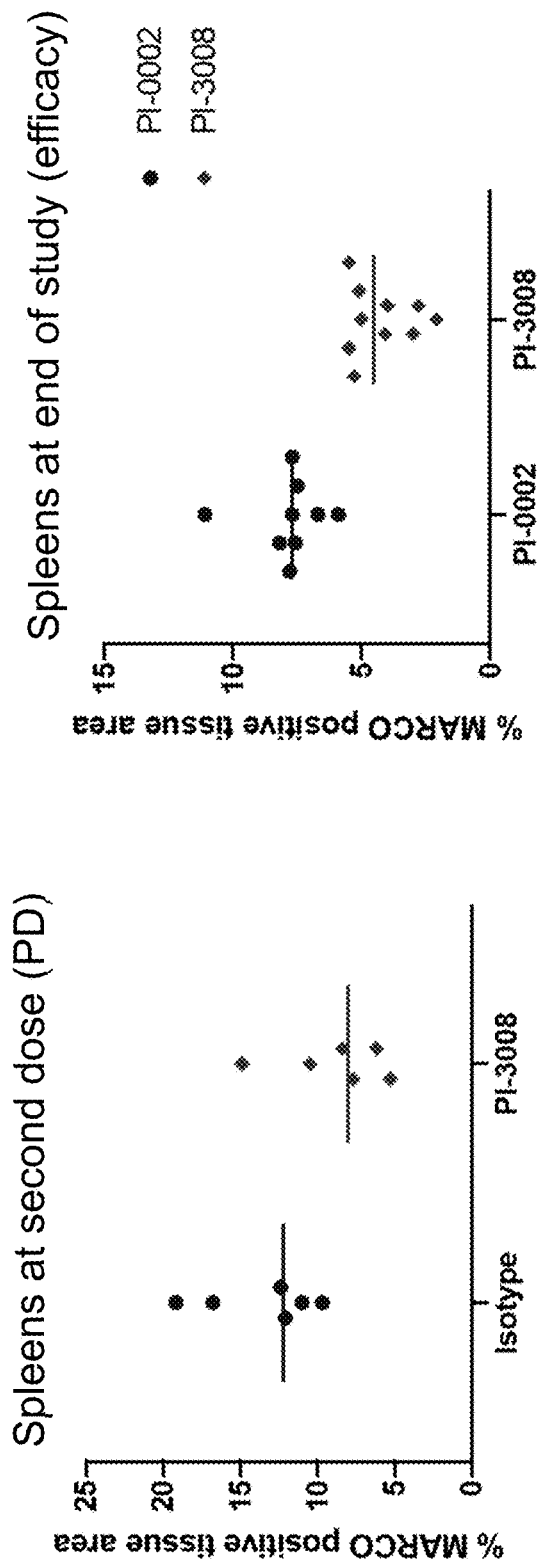

FIG. 46 provides quantification of MARCO positive cells in the spleens after the second dose and at the end of the study after treatment with isotype control antibody or PI-3008.

Figure 47B:
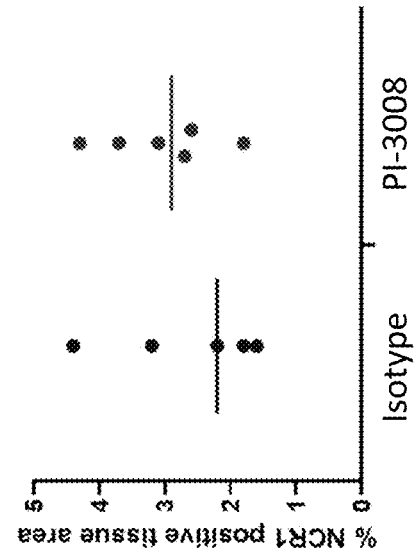
Figure 47D:
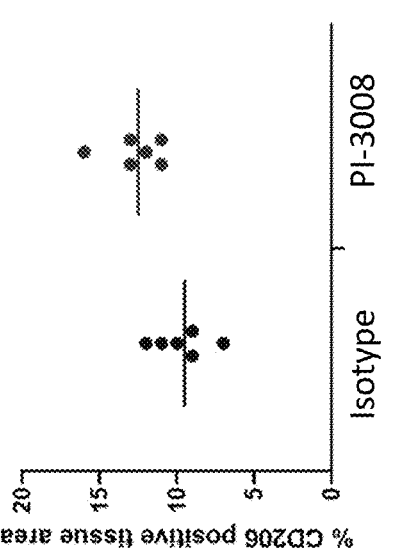
Figure 47A:
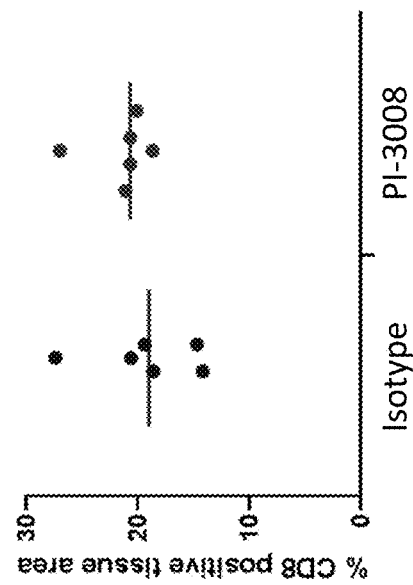

FIG. 47A provides quantification of the indicated cell type in the spleen after treatment with isotype control antibody or PI-3008. FIG. 47B provides quantification of the indicated cell type in the spleen after treatment with isotype control antibody or PI-3008.

Figure 47C:
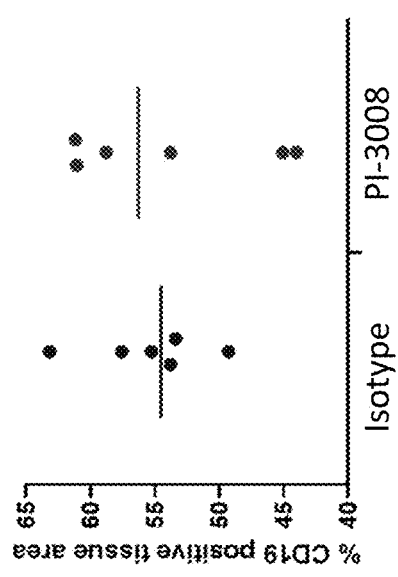

FIG. 47C provides quantification of the indicated cell type in the spleen after treatment with isotype control antibody or PI-3008. FIG. 47D provides quantification of the indicated cell type in the spleen after treatment with isotype control antibody or PI-3008.

FIG. 48A provides quantification of the percentage positive cells per tissue compartment in the spleen after treatment with isotype control antibody or PI-3008. FIG. 48B provides quantification of the percentage positive cells per tissue compartment in the spleen after treatment with isotype control antibody or PI-3008. FIG. 48C provides quantification of the percentage positive cells per tissue compartment in the spleen after treatment with isotype control antibody or PI-3008. FIG. 48D provides quantification of the percentage positive cells per tissue compartment in the spleen after treatment with isotype control antibody or PI-3008. In each figure, isotype samples are shown on the left of the pairs, PI-3008 samples are shown on the right of the pairs.

Figure 49:
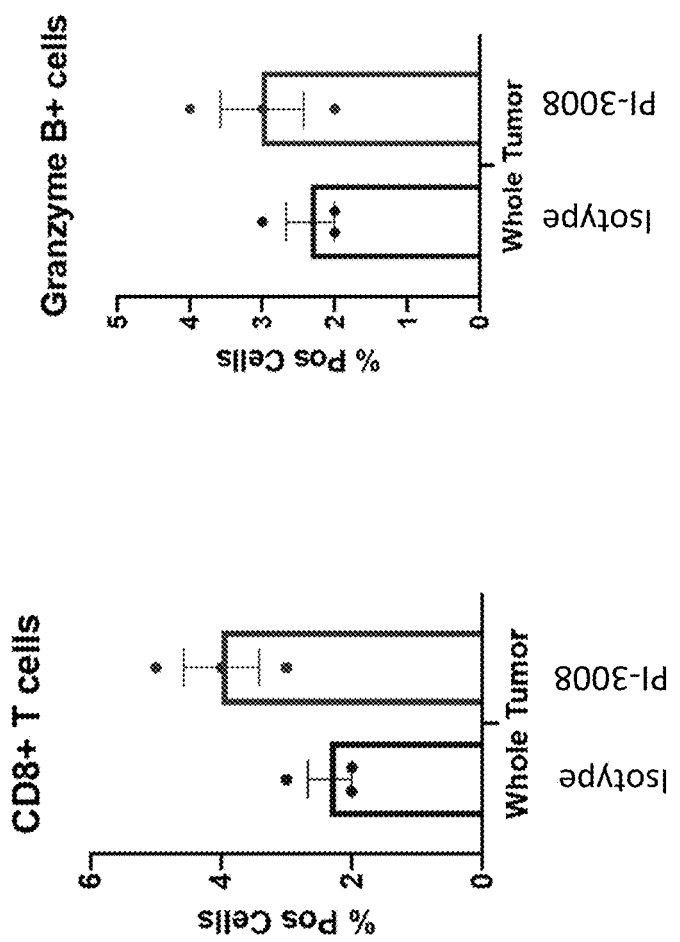

FIG. 49 shows that PI-3008 induced an increase in CD8+ T-cells and the cytotoxic marker granzyme B as measured by IHC compared to isotype control treated tumors.

Figure 50:
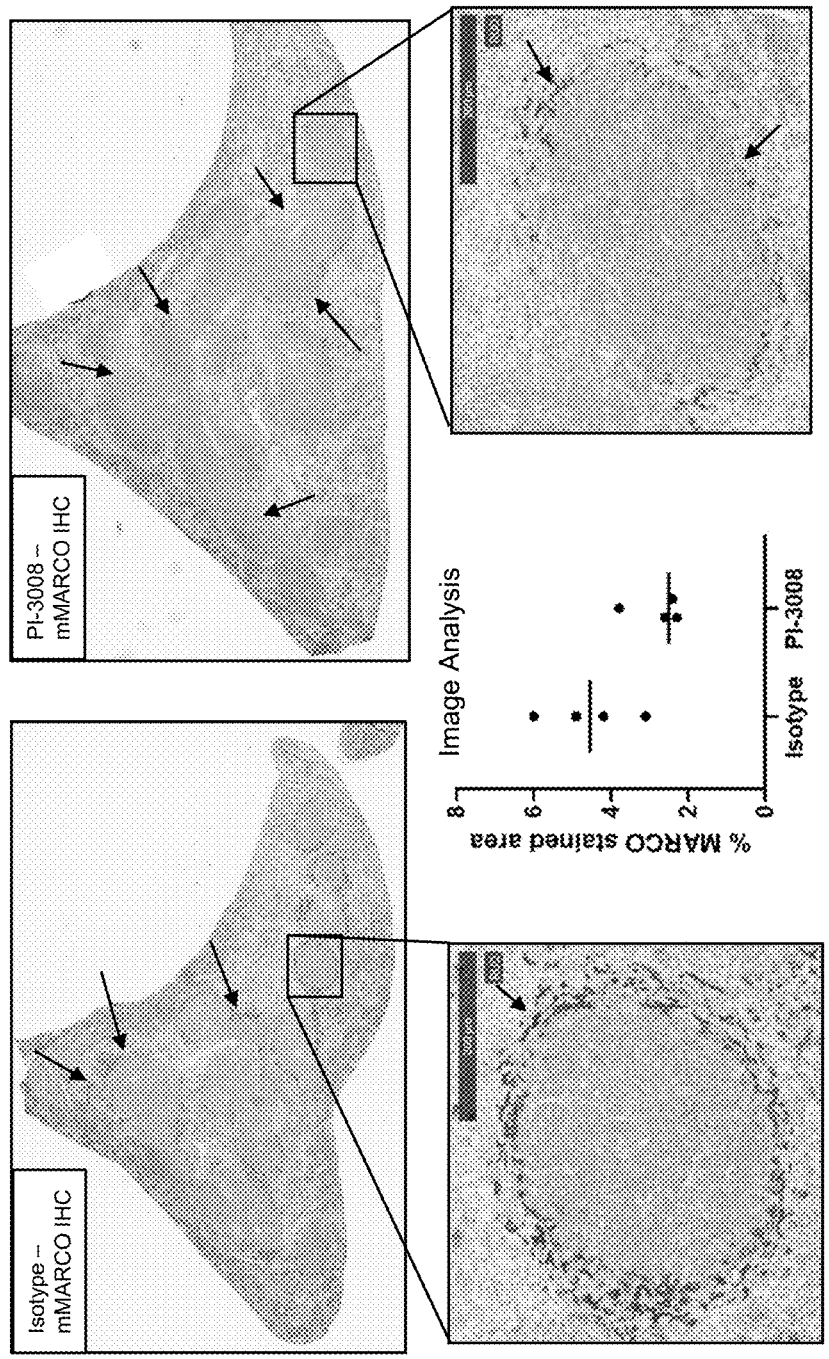

FIG. 50 shows changes in MARCO levels on the marginal zone macrophages in the spleen, with noticeable gaps in the marginal zone area when stained with a non-PI-3008 competing anti-mouse MARCO IHC compatible antibody.

Figure 51A:
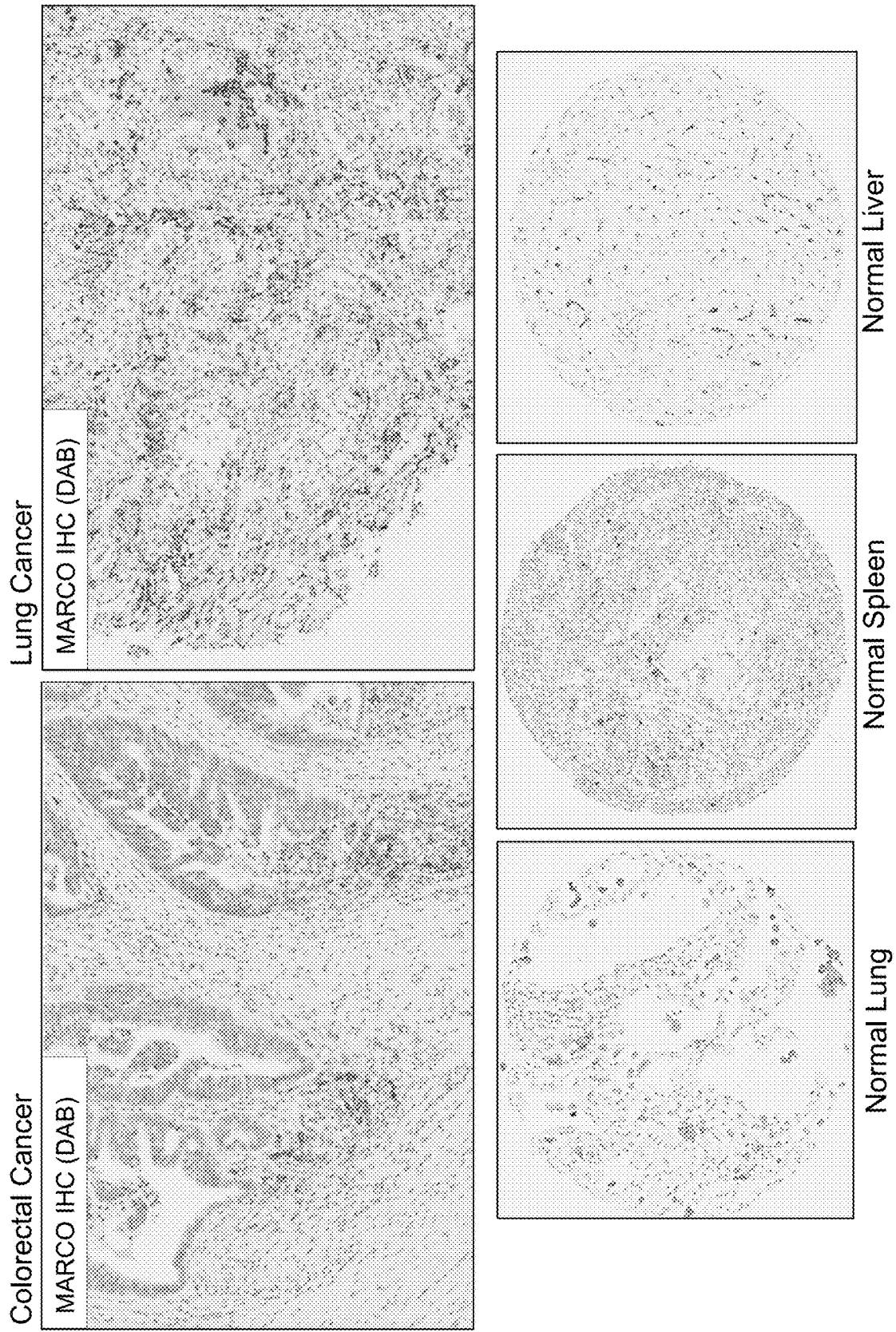
Figures 51B, 51C:
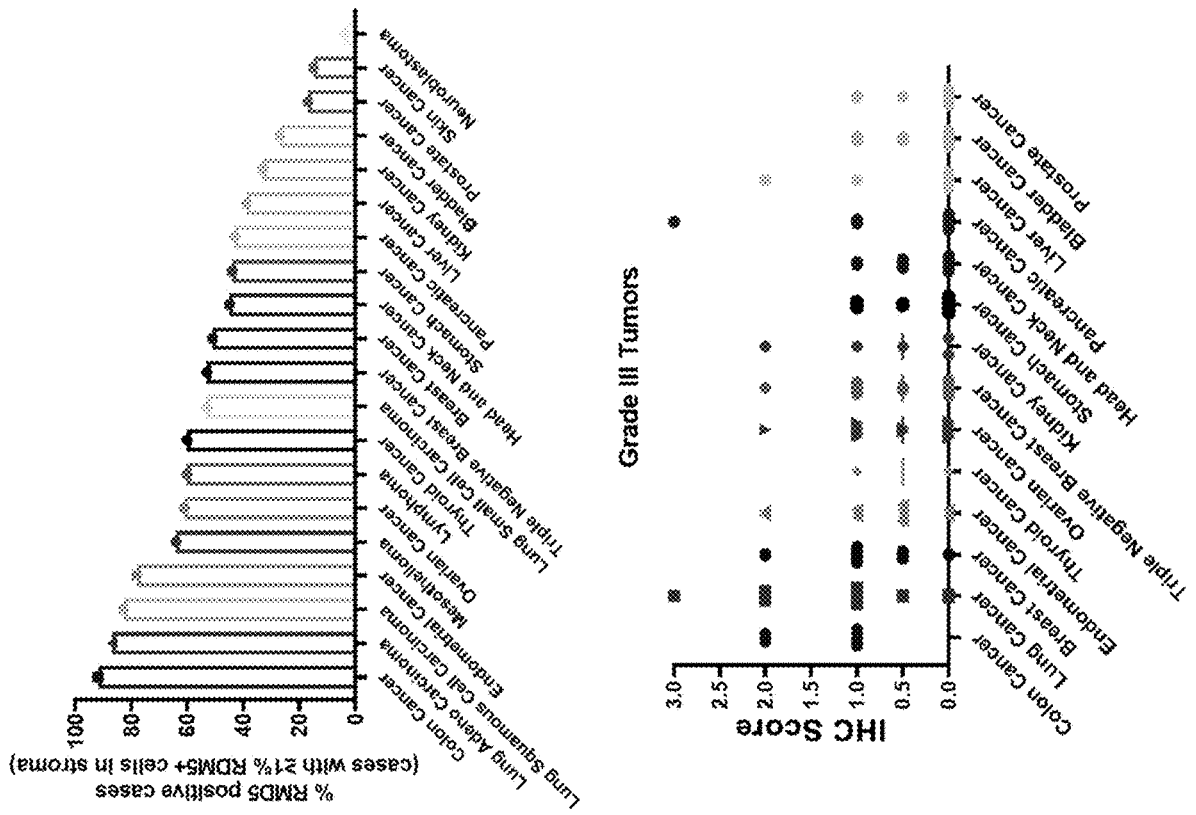

FIG. 51A shows representative images of colorectal tumor tissue (left) and lung tumor tissue (right) stained with 2.5 µg/mL RDM5 using high pH (ER2) epitope retrieval conditions on the top panels. The bottom panels provide representative images of normal tissue cores from lung, spleen, and liver, stained with 2.5 µg/ml RDM5 using high pH (ER2) epitope retrieval conditions. The dark gay color indicates positive staining of myeloid cells expressing MARCO. FIG. 51B shows the percentage of positive MARCO cancer cases in the indicated cancer type after IHC staining with the RDM5 antibody. FIG. 51C shows the IHC score in the indicated cancer type after IHC staining with the RDM5 antibody.

Figure 52:
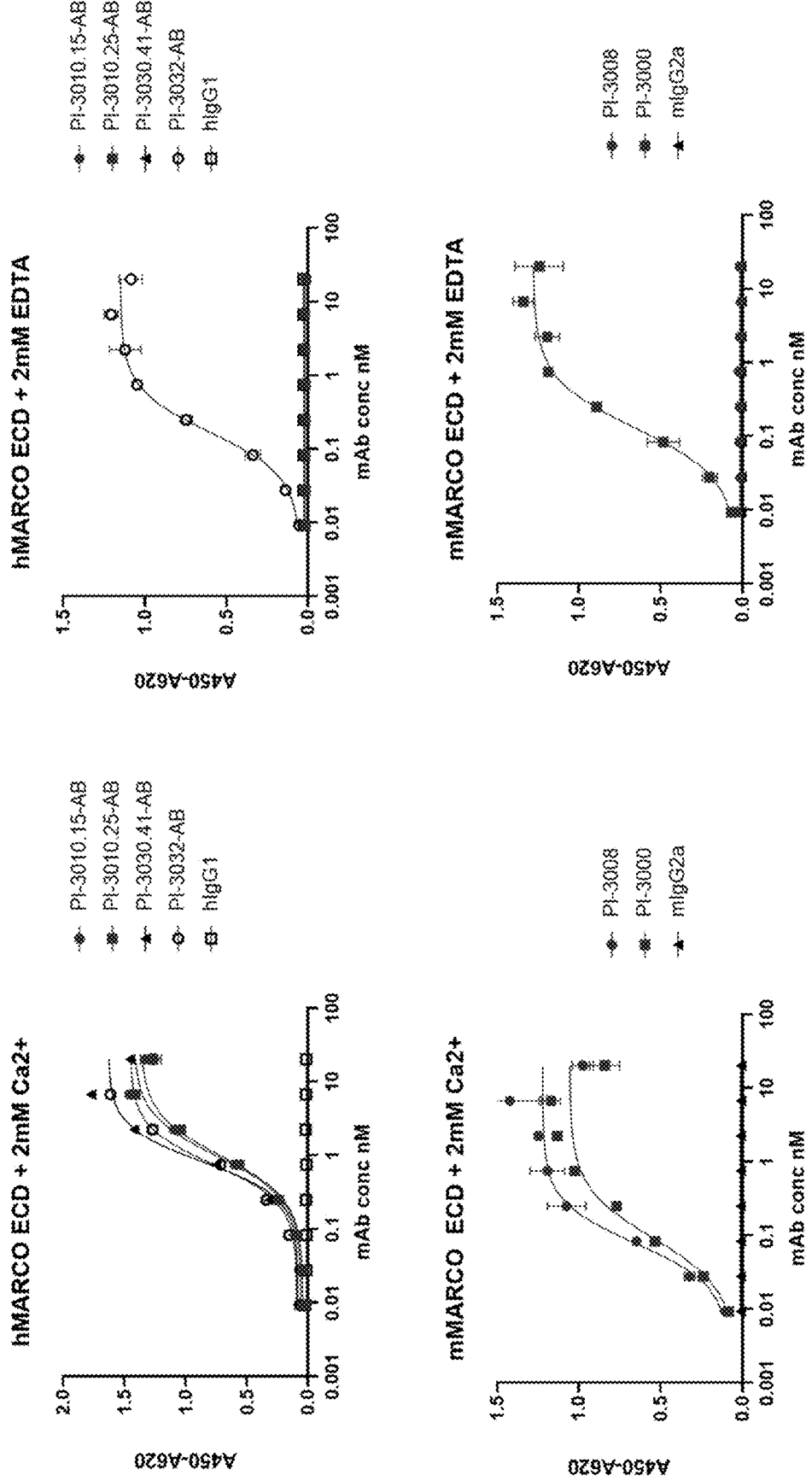

FIG. 52 shows that binding of some anti-MARCO antibodies to MARCO was calcium dependent.

Figure 53:
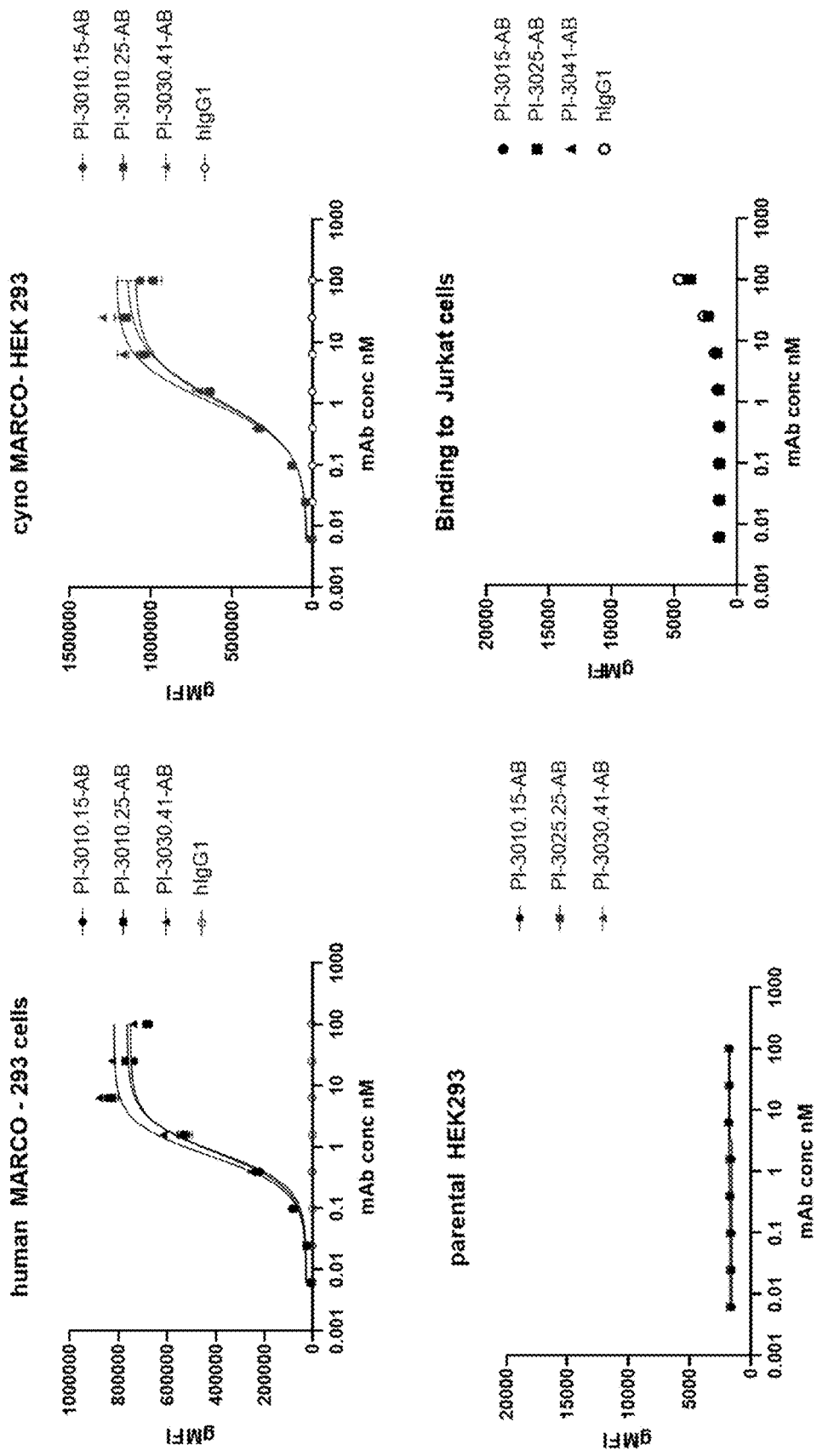

FIG. 53 shows binding of the indicated MARCO antibody to human and cynomolgus MARCO expressing cell lines.

Figure 54:
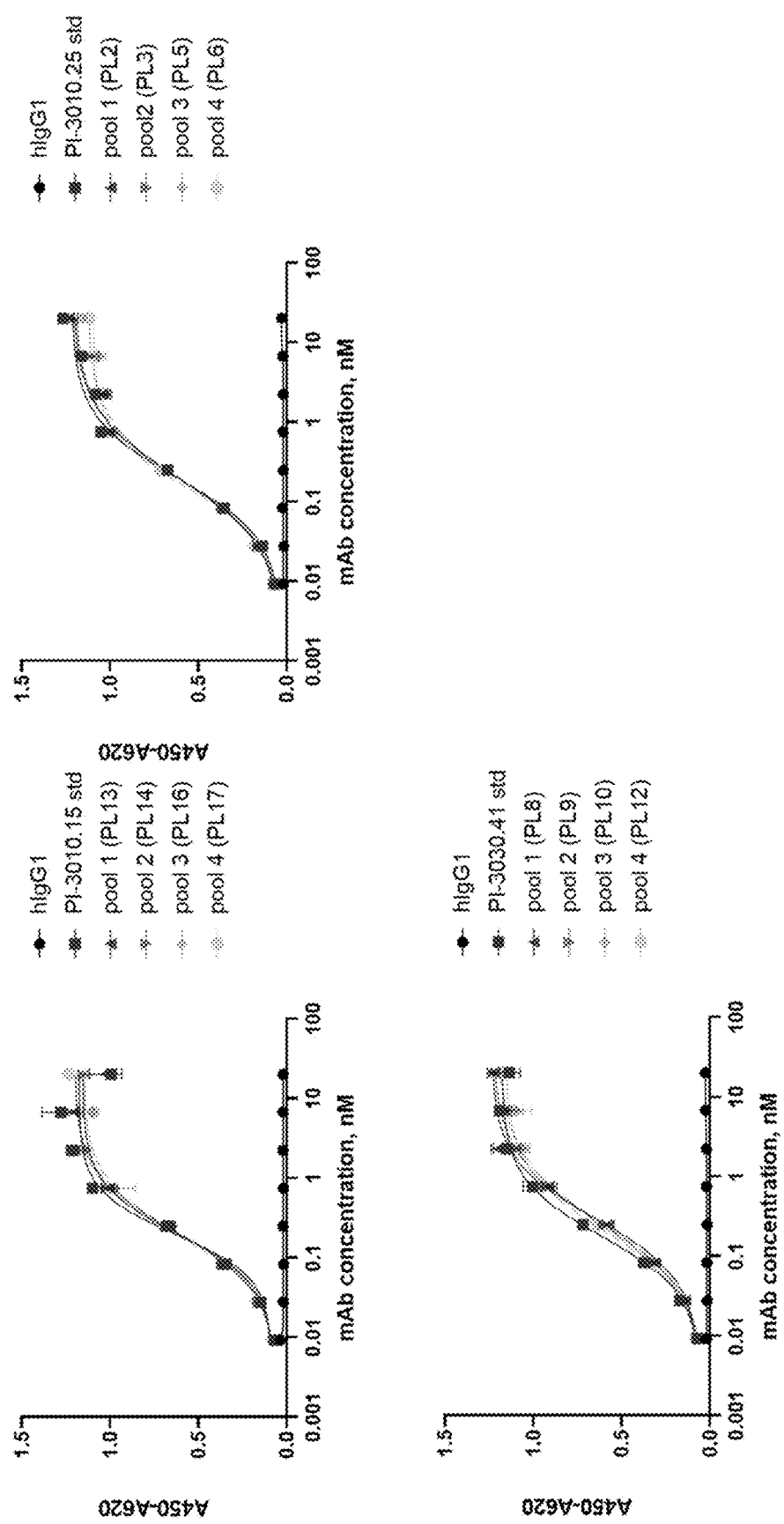

FIG. 54 shows binding of antibodies produced by the stable transfection method to MARCO expressing cells as compared to reference antibodies made via transient transfection.

Figure 55B:
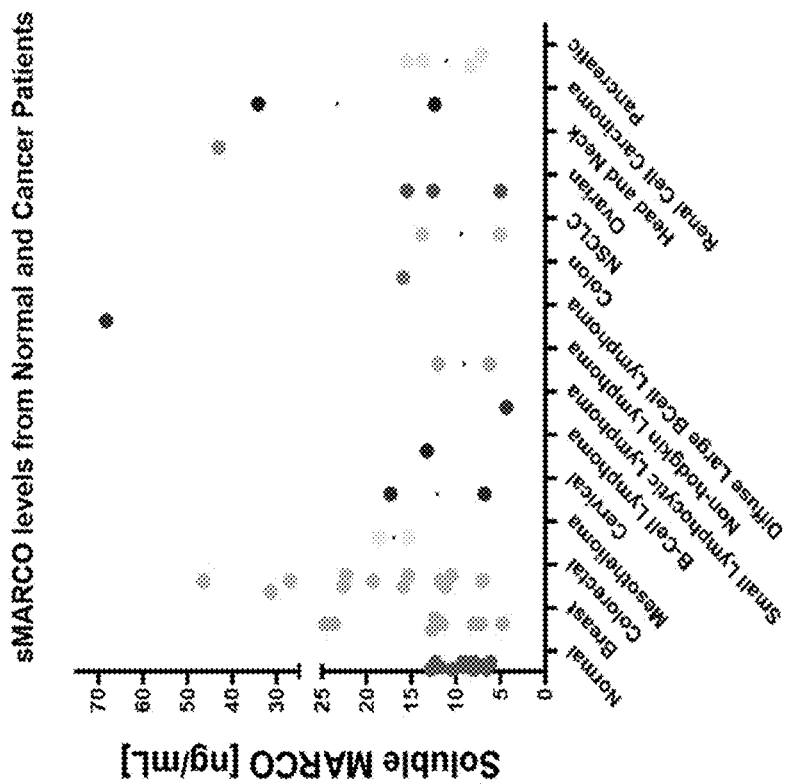
Figure 55A:
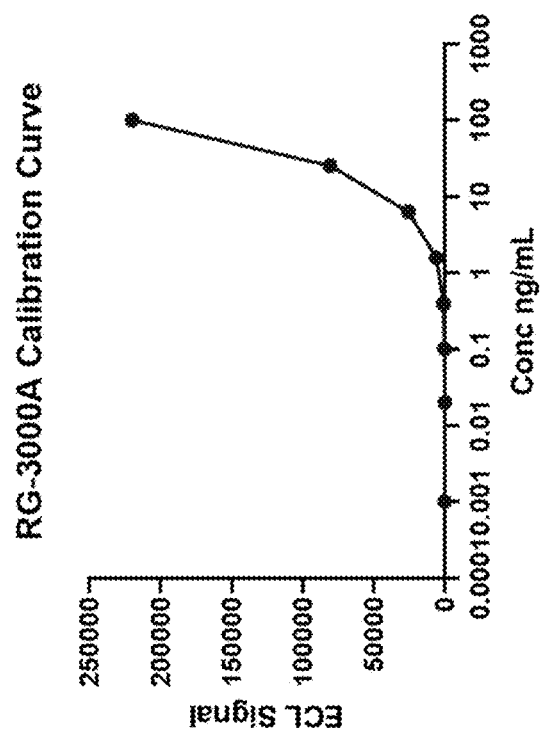

FIG. 55A shows the sMARCO calibration curve for RG-3000A. FIG. 55B shows the sMARCO levels in normal and cancer serum samples.

Figure 56:
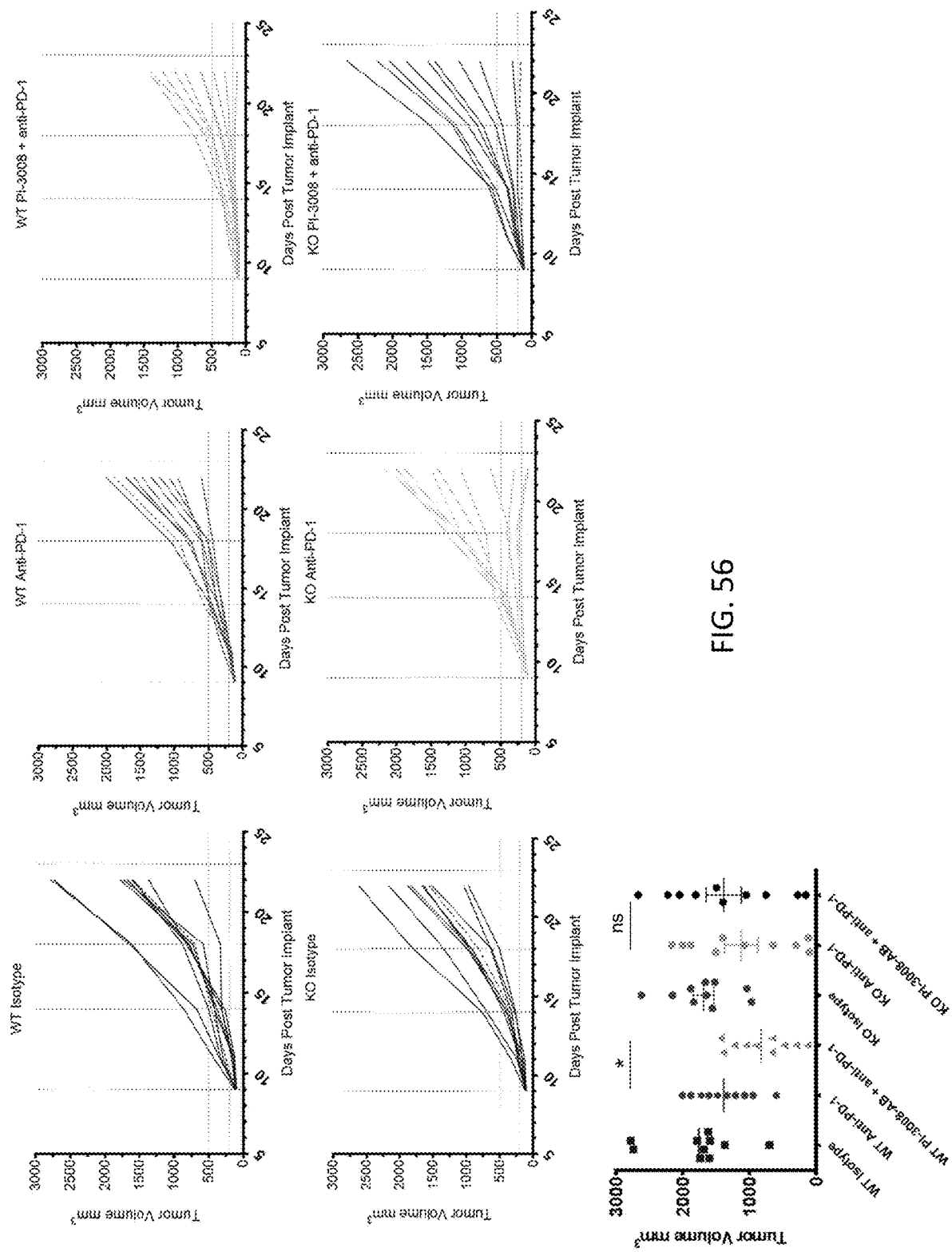

FIG. 56 shows the tumor volumes in B-cell deficient mice after MARCO antibody, PD-1 antibody, combination, or isotype antibody treatment.

Figure 57:
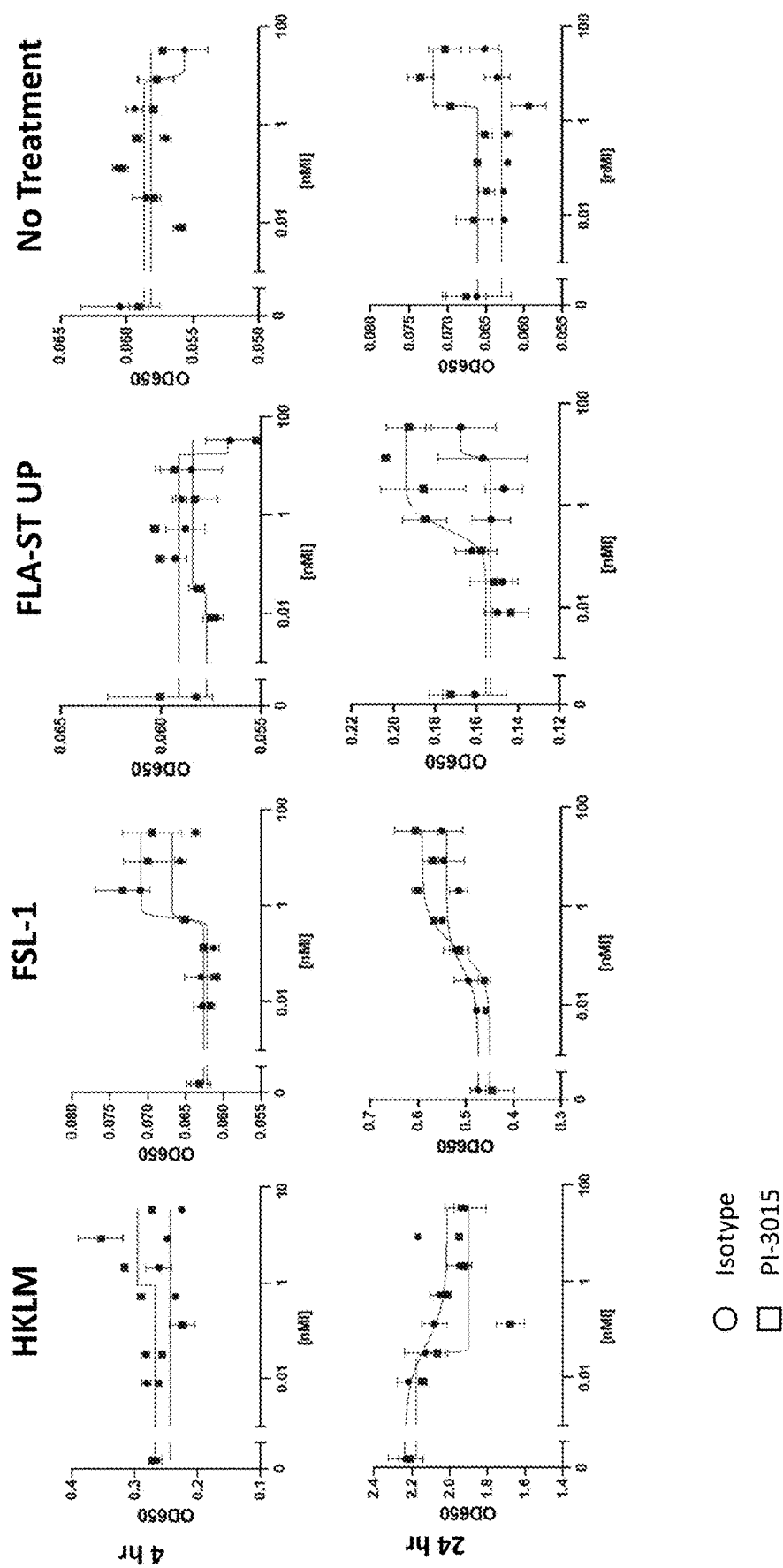

FIG. 57 shows the NF-kB reporter activity induced by PI-3010.15 or isotype antibody in combination with the indicated agonist at 4 hrs or 24 hrs.

FIG. 58 shows that PI-3008 treatment induced the indicated cytokines and chemokines in tumors in the E0771 model at early timepoints.

Figure 59:
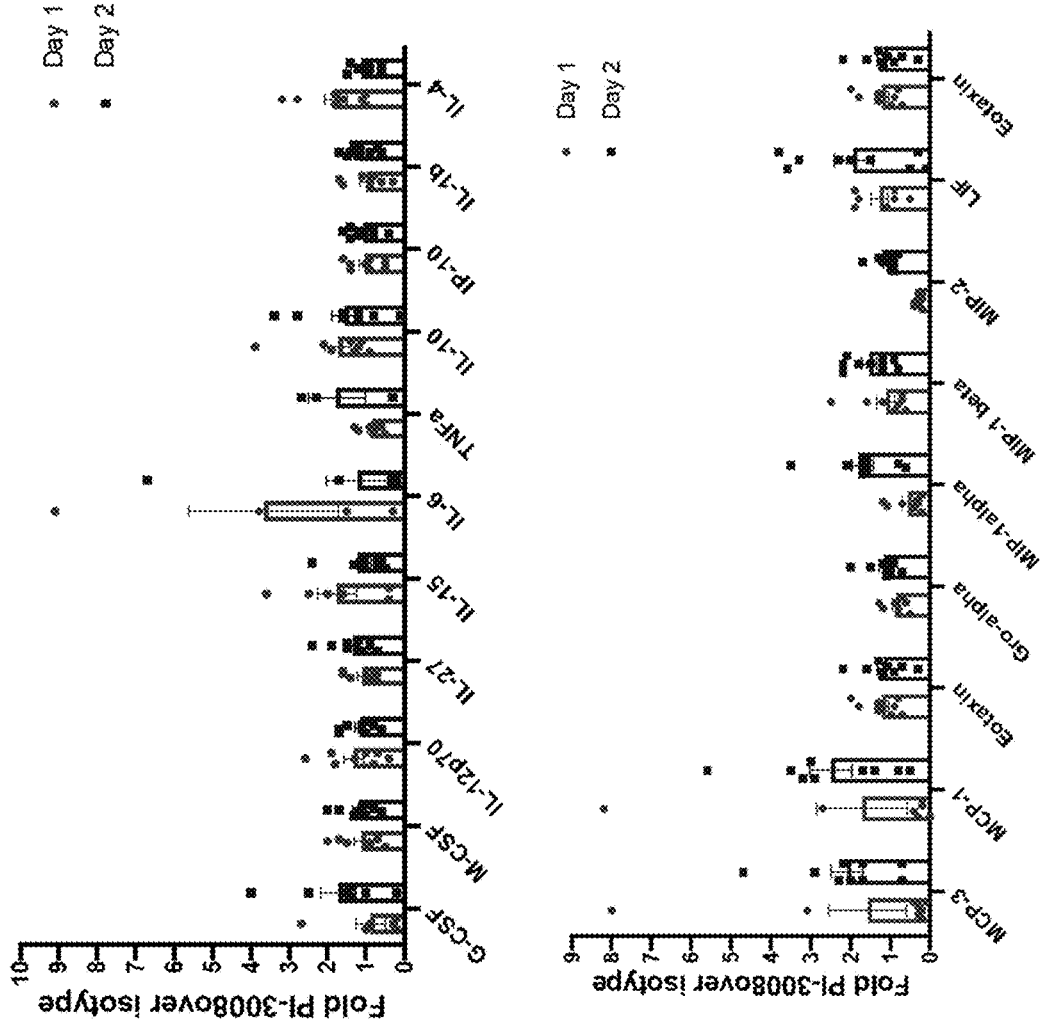

FIG. 59 shows that PI-3008 treatment induced the indicated cytokines and chemokines in the spleen in the E0771 model at early timepoints.

Figure 60:
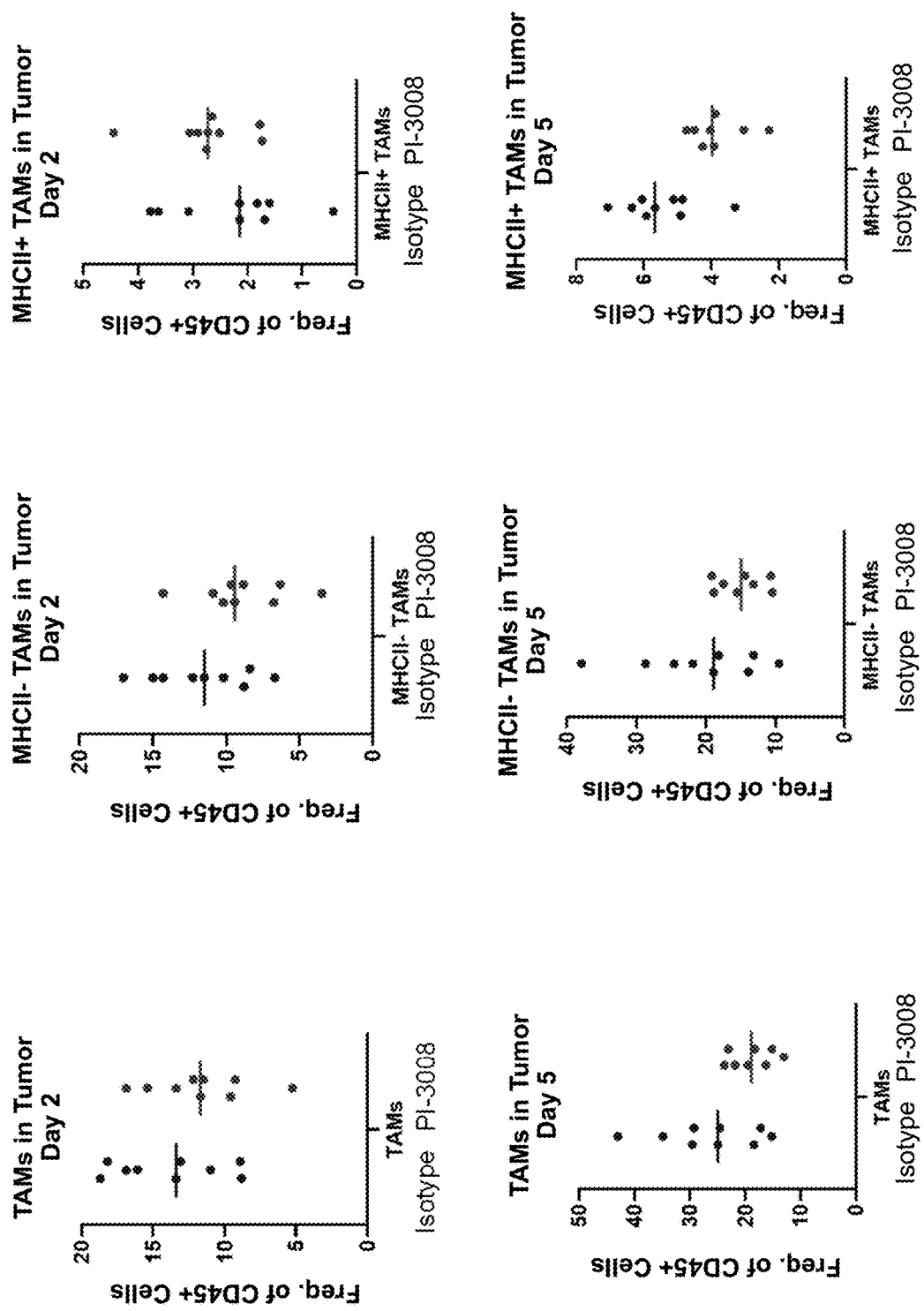

FIG. 60 provides quantification of the indicated tumor myeloid cell types at Day 2 and Day 5 post-administration of a isotype control antibody or PI-3008.

Figure 61:
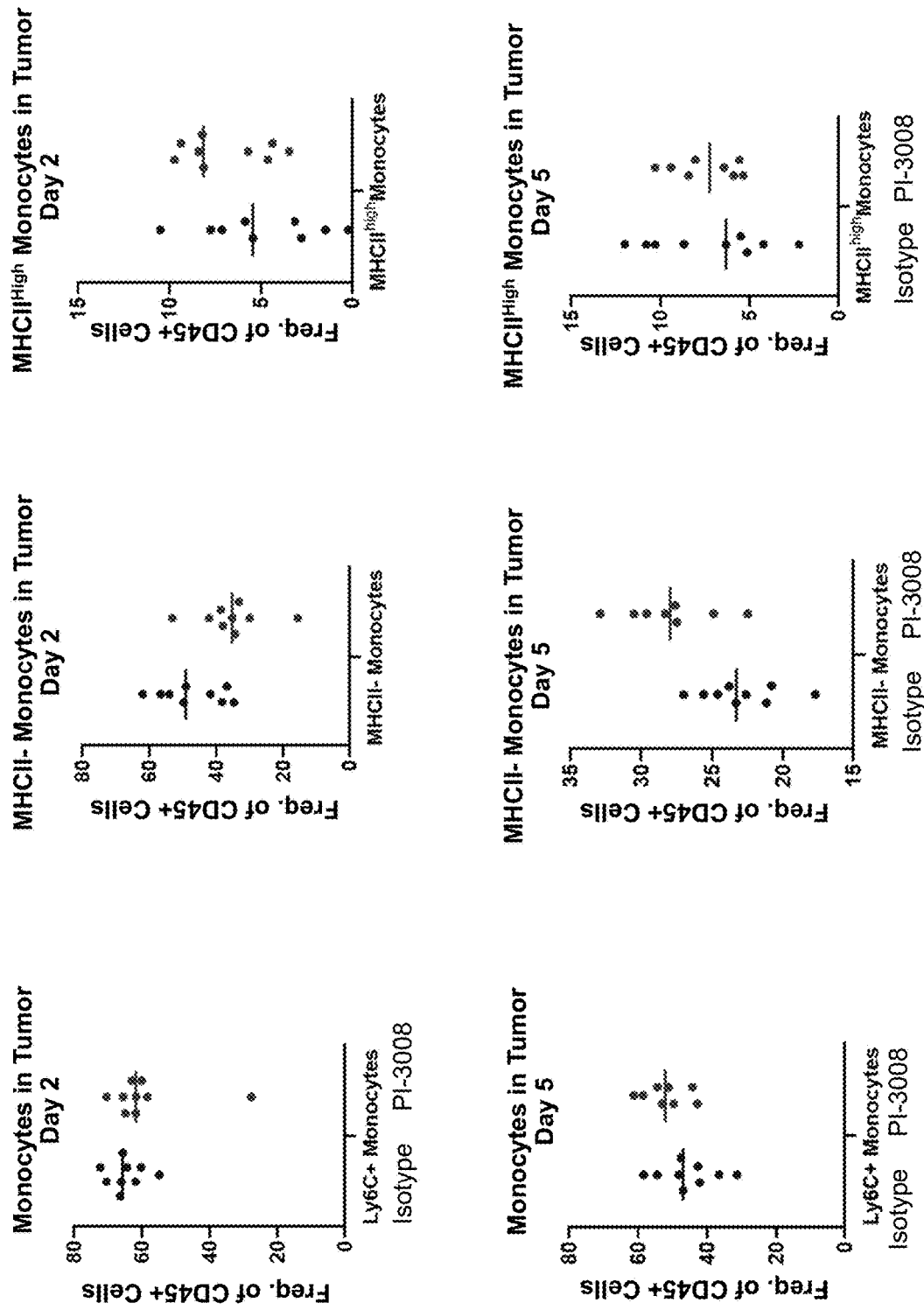

FIG. 61 provides quantification of the indicated tumor myeloid cell types at Day 2 and Day 5 post-administration of a isotype control antibody or PI-3008.

Figure 62:
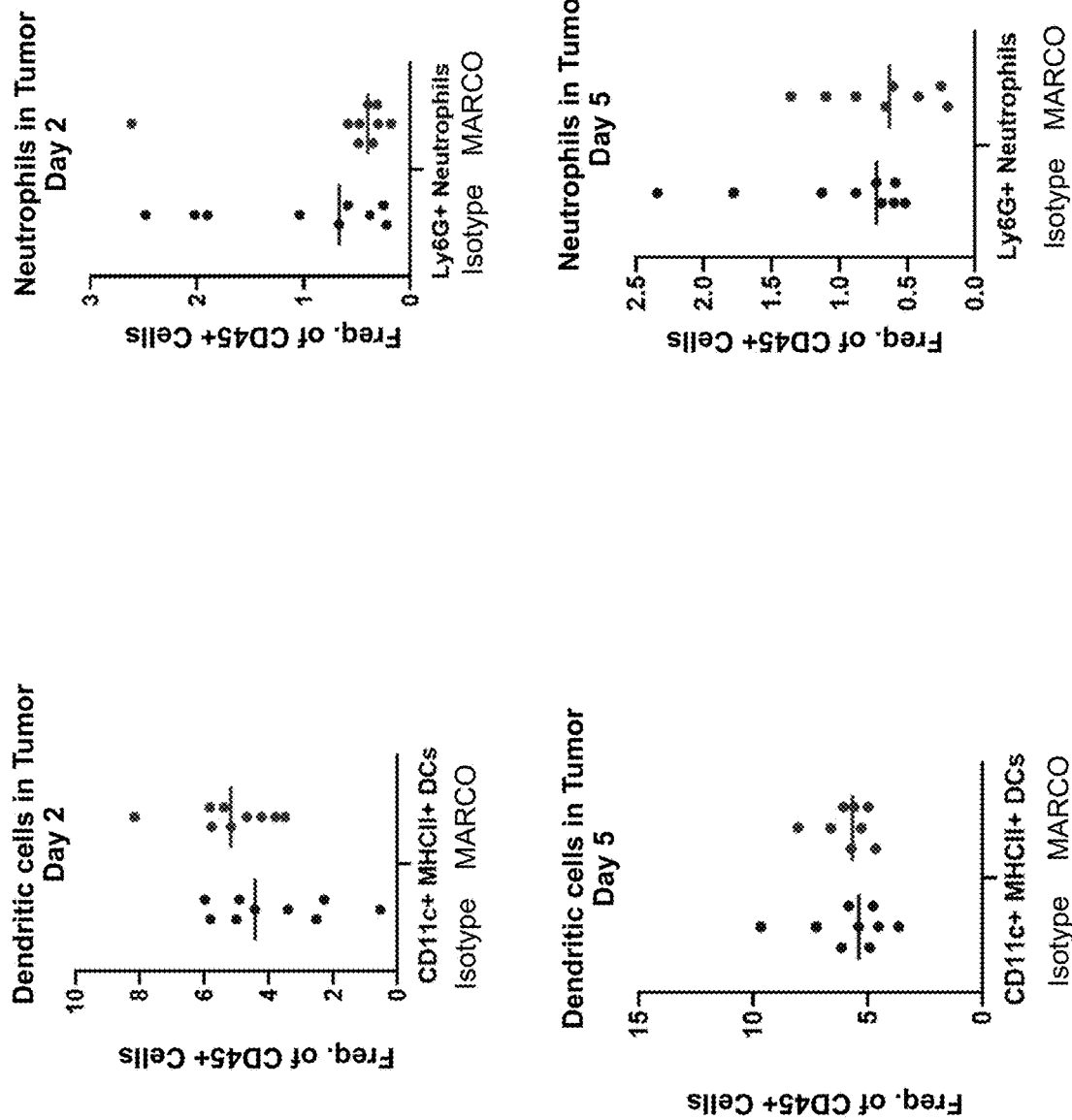

FIG. 62 provides quantification of the indicated tumor myeloid cell types at Day 2 and Day 5 post-administration of a isotype control antibody or PI-3008.

Figure 63:
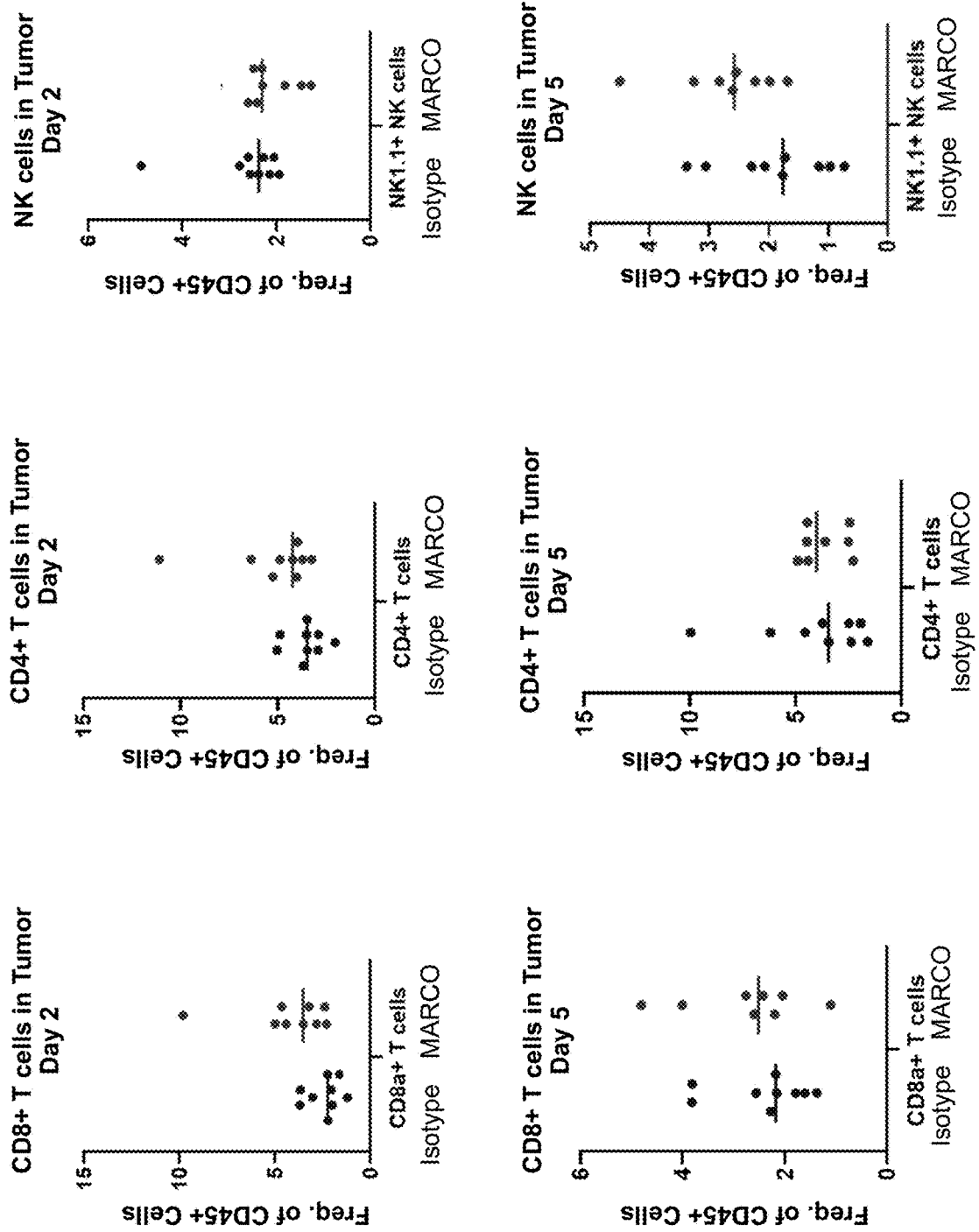

FIG. 63 provides quantification of the indicated tumor lymphoid cell types at Day 2 and Day 5 post-administration of a isotype control antibody or PI-3008.

Figure 64:
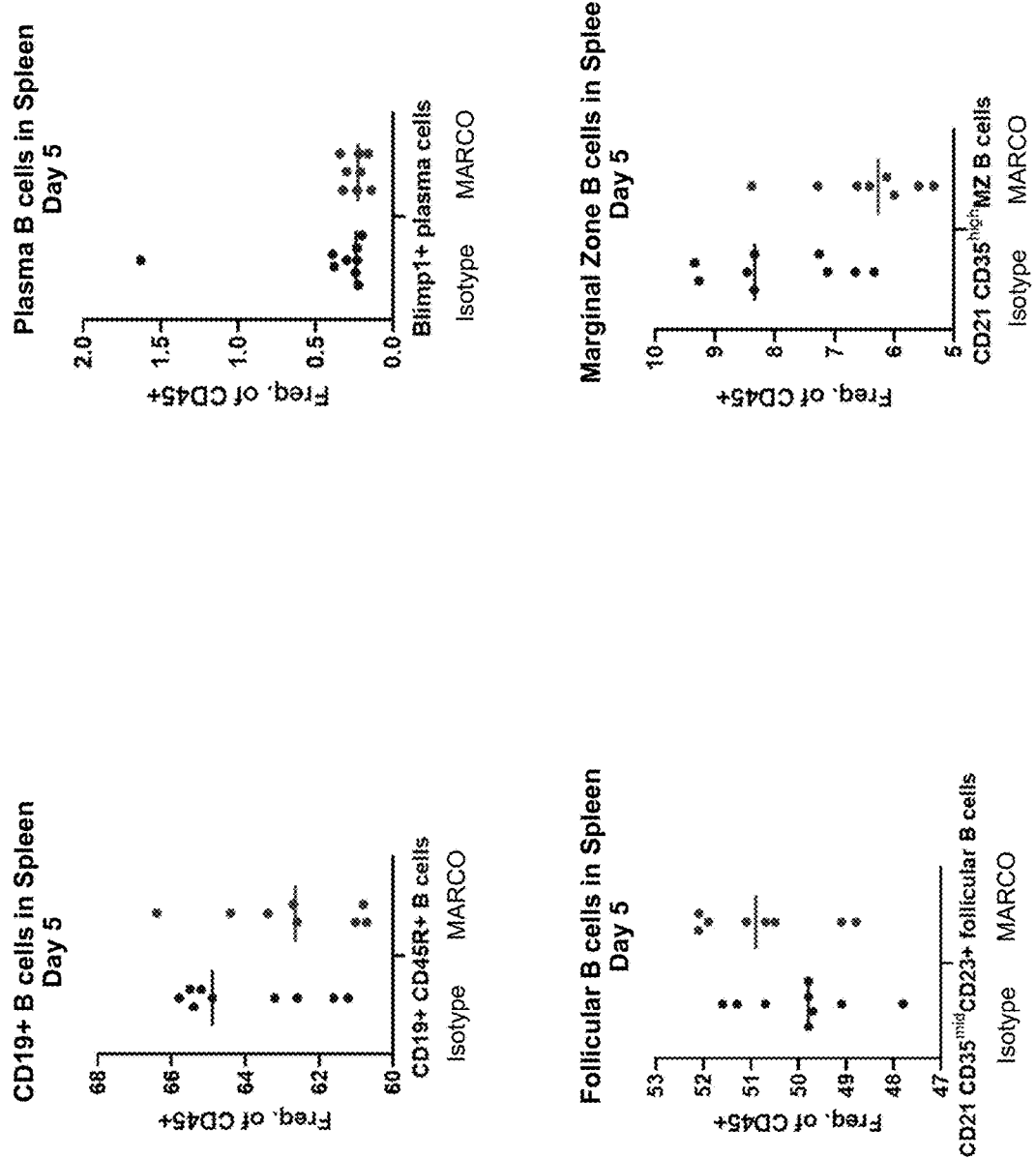

FIG. 64 provides quantification of the indicated spleen lymphoid cell types at Day 5 post-administration of a isotype control antibody or PI-3008.

Figure 65:
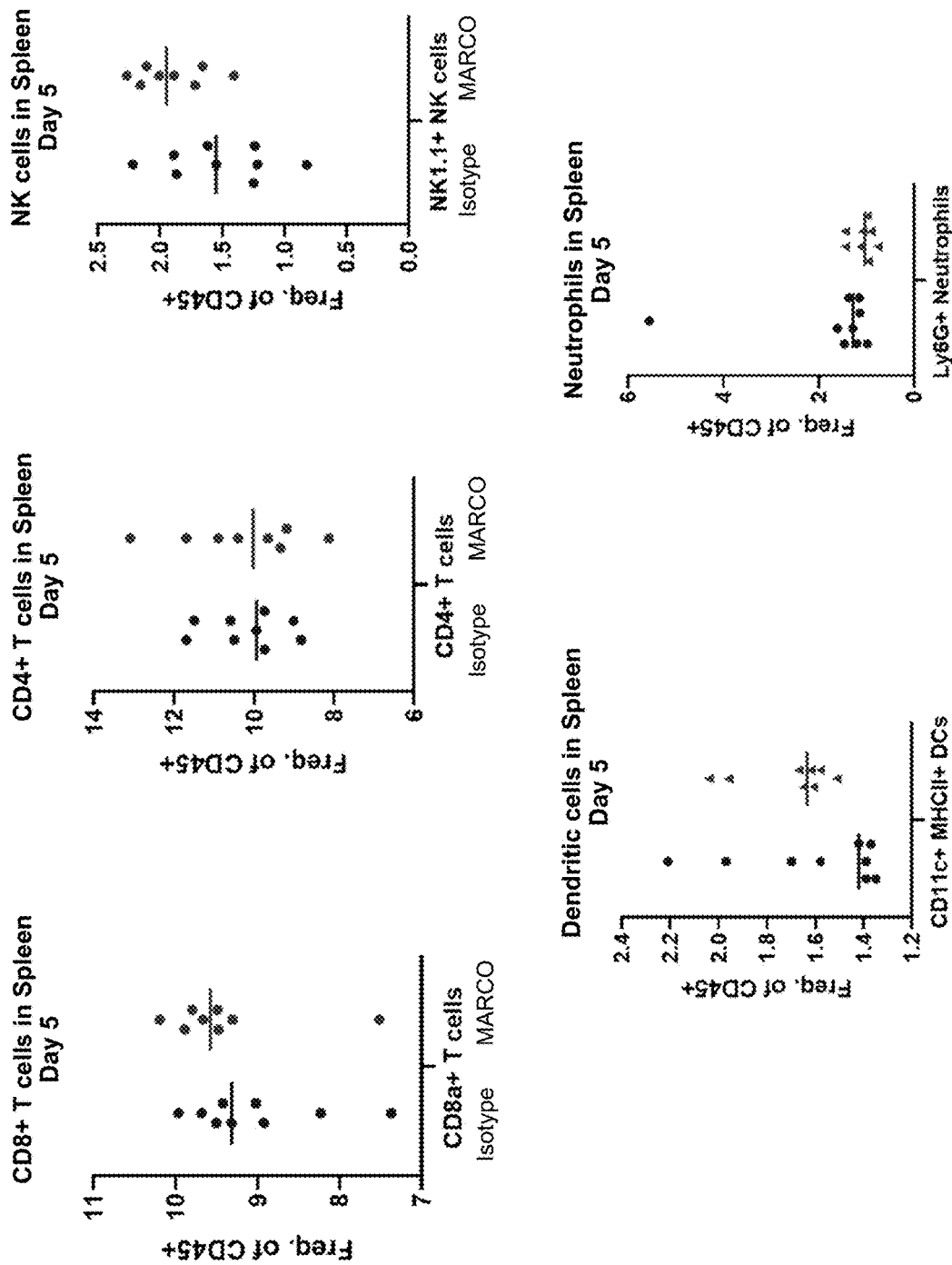

FIG. 65 provides quantification of the indicated spleen lymphoid or myeloid cell types at Day 5 post-administration of a isotype control antibody or PI-3008.

Figure 66:
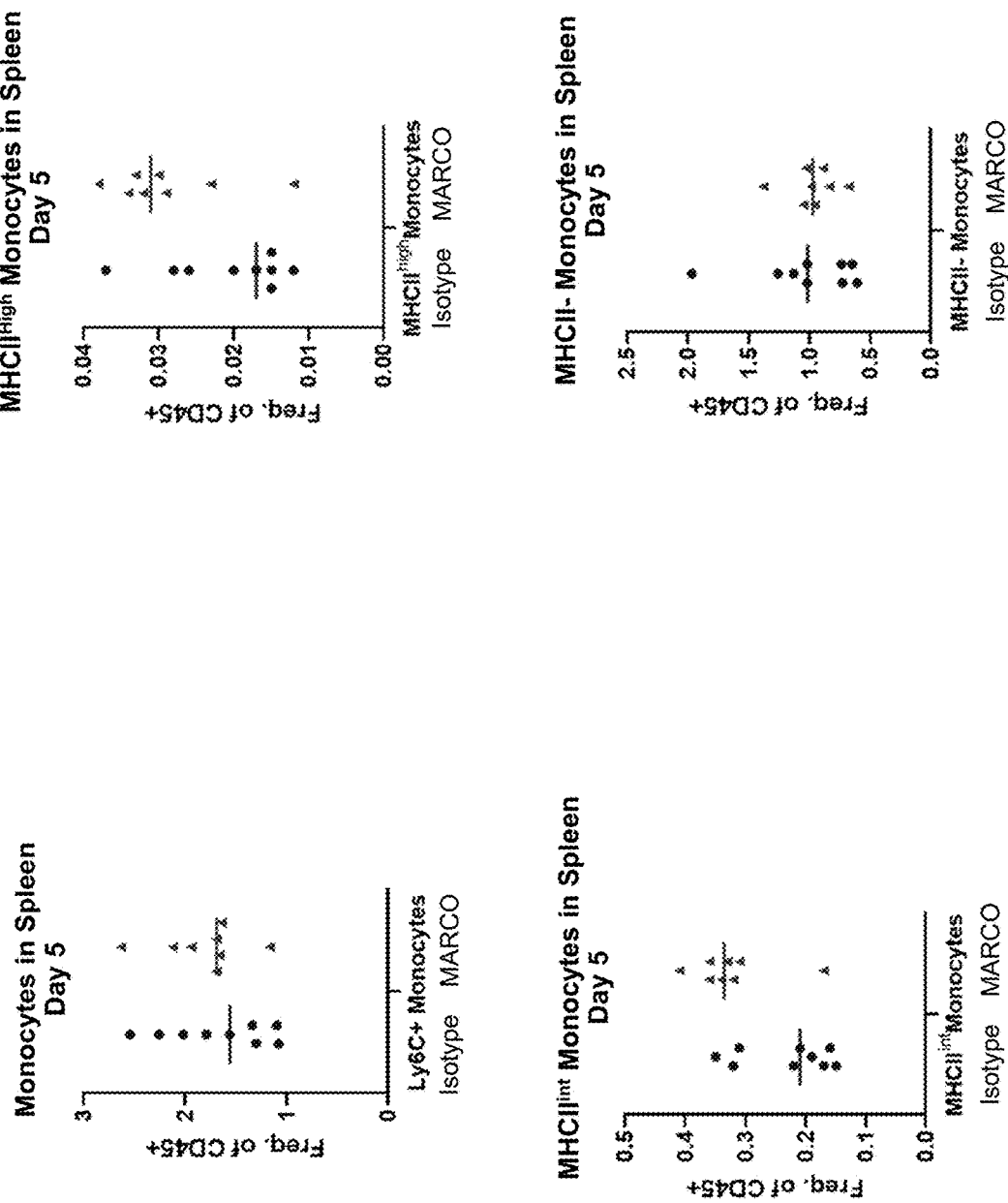

FIG. 66 provides quantification of the indicated spleen myeloid cell types at Day 5 post-administration of a isotype control antibody or PI-3008.

Figure 67:
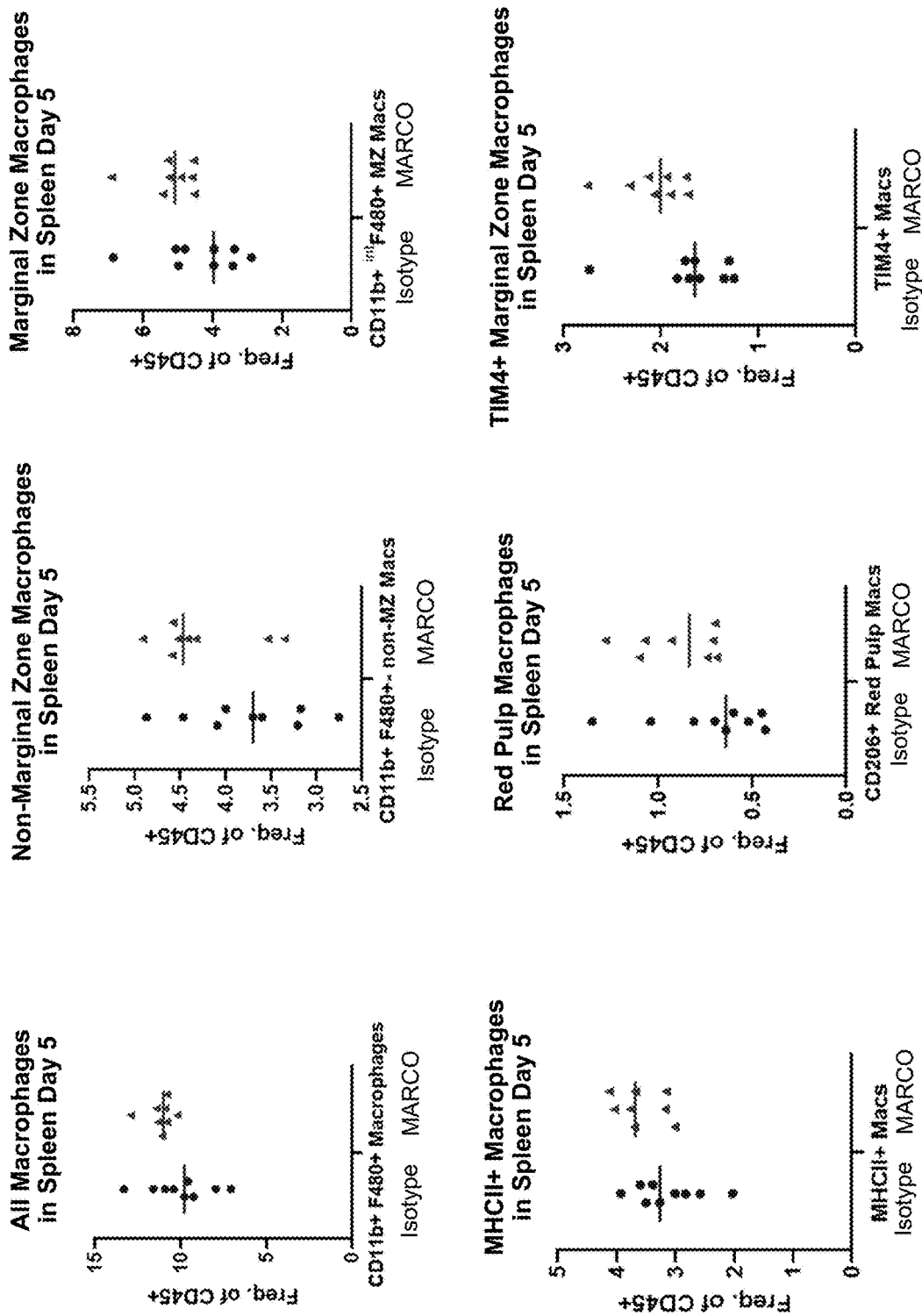

FIG. 67 provides quantification of the indicated spleen myeloid cell types at Day 5 post-administration of a isotype control antibody or PI-3008.

Figure 68:
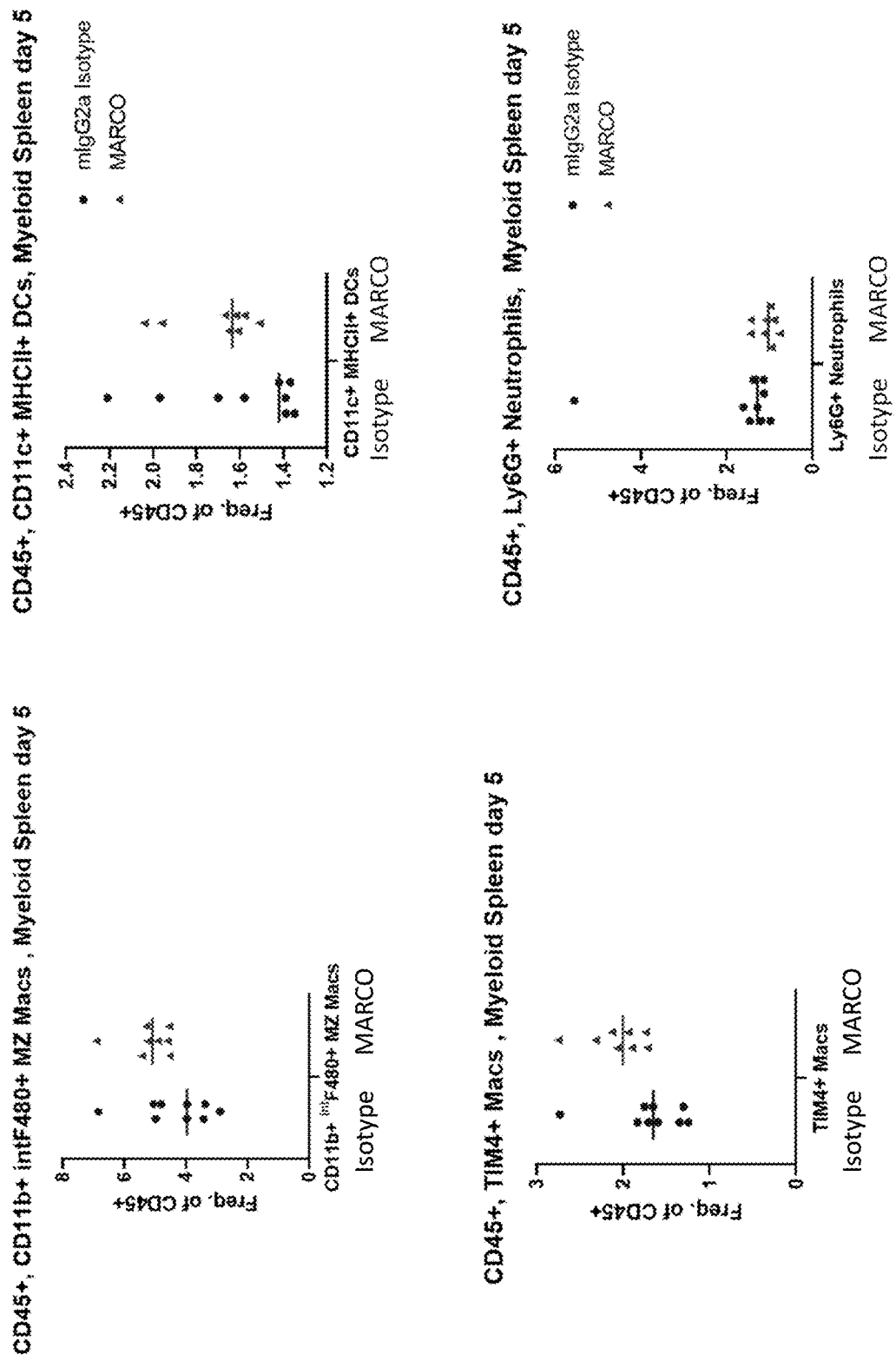

FIG. 68 provides quantification of the indicated spleen myeloid cell types at Day 5 post-administration of a isotype control antibody or PI-3008.

Figure 69:
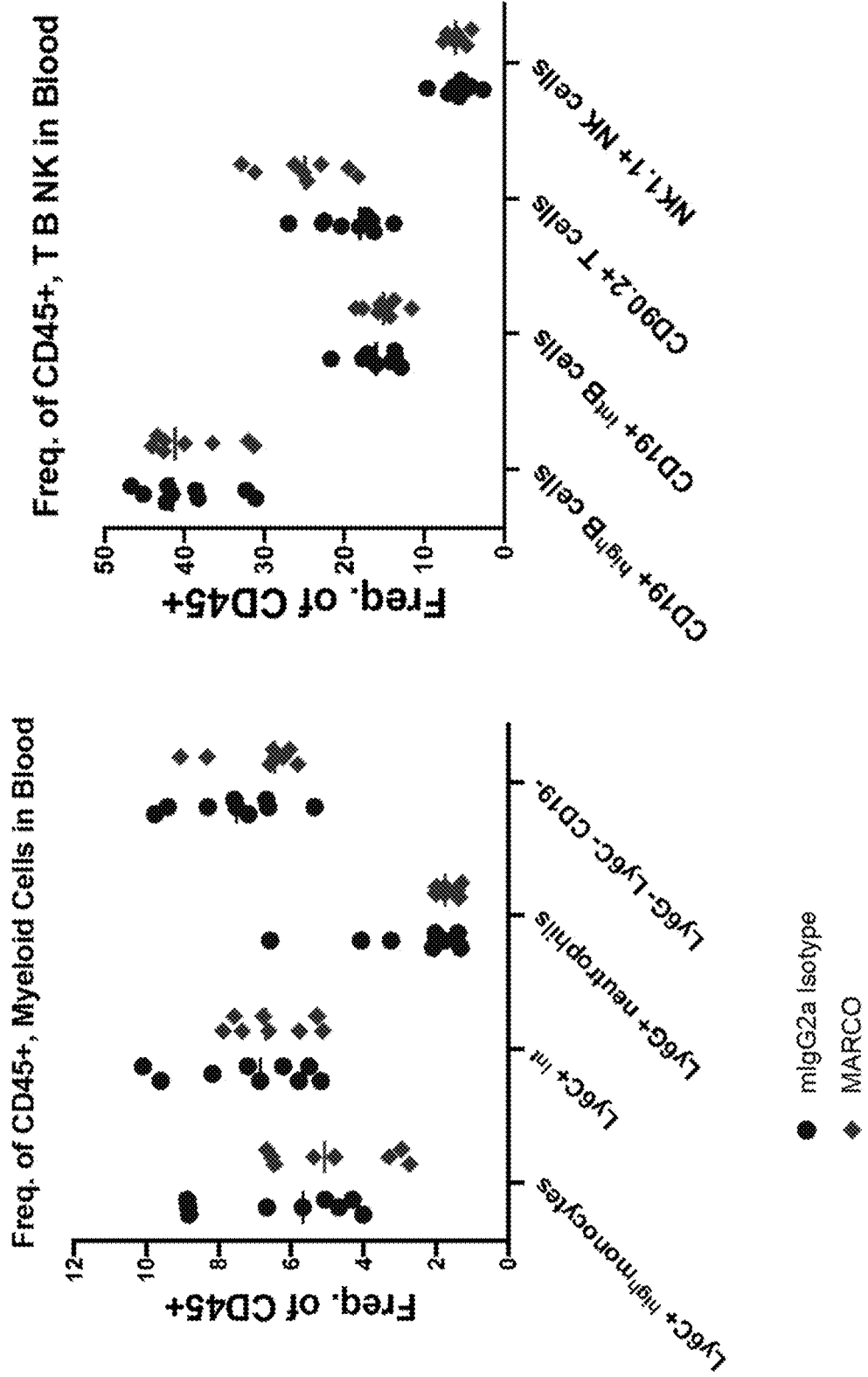

FIG. 69 provides quantification of the indicated cell types in the blood at Day 5 post-administration of a isotype control antibody or PI-3008.

Figure 70:
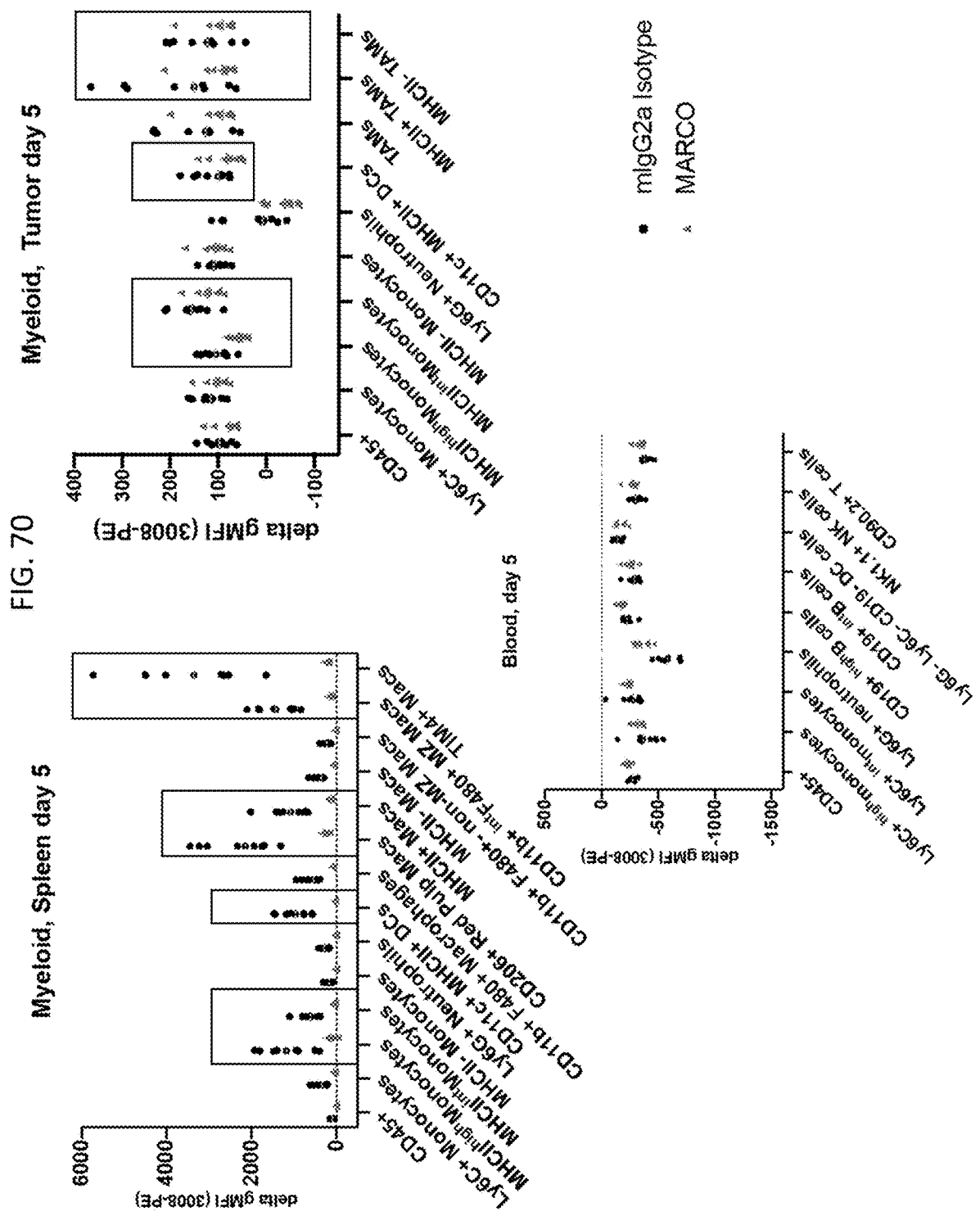

FIG. 70 shows that Receptor Occupancy of the therapeutic MARCO antibody was achieved in the MARCO expressing cells in the spleen and tumors.

Figure 71:
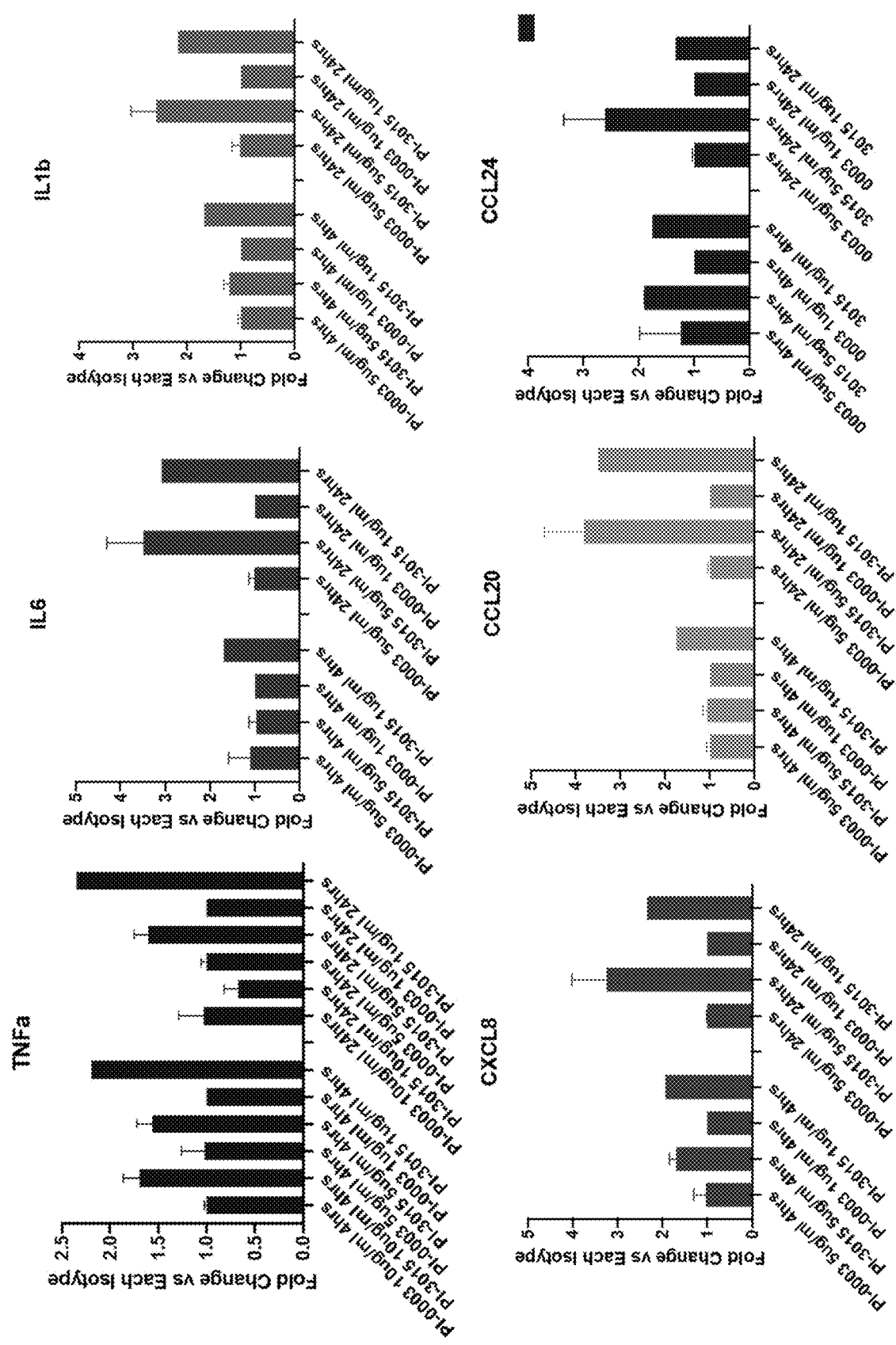

FIG. 71 shows that PI-3010.15 induced expression of the indicated pro-inflammatory cytokines.

DETAILED DESCRIPTION

Definitions

Terms used in the claims and specification are defined as set forth below unless otherwise specified.

The term "ameliorating" refers to any therapeutically beneficial result in the treatment of a disease state, e.g., a cancer disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

Abbreviations used in this application include the following:

It must be noted that, as used in the specification and the appended claims, the singular forms "a," "an" and "the" include plural referents unless the context clearly dictates otherwise.

Antibodies
Structure

The present application provides antibodies and compositions comprising an antibody which binds a MARCO protein. Such antibodies including antibodies that increase, enhance, or induce immune responses or kill, disable, or deplete myeloid cells.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\epsilon$, $\gamma$, and $\mu$, respectively.

An exemplary immunoglobulin (antibody) structural unit is composed of two pairs of polypeptide chains, each pair having one "light" (about 25 kD) and one "heavy" chain (about 50-70 kD), e.g., a homodimer of a paired light chain and heavy chain. The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at bioinf org.uk/abs/abnum/, and described in Abhinandan and Martin, *Immunology*, 2008, 45:3832-3839, incorporated by reference in its entirety.

TABLE A

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1 when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

As used herein, the term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarily determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')2" fragments contain two Fab' fragments joined, near the hinge region, by disulfide bonds. F(ab')2 fragments may be generated, for example, by recombinant methods or by pepsin digestion of an intact antibody. The F(ab') fragments can be dissociated, for example, by treatment with B-mercaptoethanol.

"Fv" fragments comprise a non-covalently-linked dimer of one heavy chain variable domain and one light chain variable domain.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$. Any suitable Fc domain known in the art or described herein may be used. In some cases, the Fc domain comprises an IgG4 Fc domain. In some cases, the Fc domain comprises an IgG1 Fc domain.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "epitope" means a portion of an antigen that specifically binds to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to MARCO variants with different point-mutations, or to chimeric MARCO variants. In some embodiments, the MARCO epitope is in the SRCR domain. In come embodiments, the MARCO epitope is in the collagen-like domain. In some embodiments, the anti-MARCO antibody or antigen binding fragment thereof binds the SRCR domain. In some embodiments, the anti-MARCO antibody or antigen binding fragment thereof binds the collagen-like domain.

A "multispecific antibody" is an antibody that comprises two or more different antigen-binding domains that collectively specifically bind two or more different epitopes. The two or more different epitopes may be epitopes on the same antigen (e.g., a single MARCO molecule expressed by a cell) or on different antigens (e.g., different MARCO molecules expressed by the same cell, or a MARCO molecule and a non-MARCO molecule). In some aspects, a multispecific antibody binds two different epitopes (i.e., a "bispecific antibody"). In some aspects, a multi-specific antibody binds three different epitopes (i.e., a "trispecific antibody").

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

"Effector functions" refer to those biological activities mediated by the Fc region of an antibody, which activities may vary depending on the antibody isotype. Examples of antibody effector functions include Clq binding to activate complement dependent cytotoxicity (CDC), Fc receptor binding to activate antibody-dependent cellular cytotoxicity (ADCC), and antibody dependent cellular phagocytosis (ADCP), receptor ligand blocking, agonism, or antagonism. An active Fc region is one that is capable of Fc-based effector functions such as ADCC, CDC, and/or ADCP.

Anti-MARCO antibodies can include those described herein such as the clones set forth in the tables. In some embodiments, the antibody comprises an alternative scaffold. In some embodiments, the antibody consists of an alternative scaffold. In some embodiments, the antibody consists essentially of an alternative scaffold. In some embodiments, the antibody comprises an antibody fragment. In some embodiments, the antibody consists of an antibody fragment. In some embodiments, the antibody consists essentially of an antibody fragment. A "MARCO antibody," "anti-MARCO antibody," or "MARCO-specific antibody" is an antibody, as provided herein, which specifically binds to the antigen MARCO. In some embodiments, the antibody binds the extracellular domain of MARCO. In certain embodiments, a MARCO antibody provided herein binds to an epitope of MARCO that is conserved between or among MARCO proteins from different species.

The term "chimeric antibody" or "chimera antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. The humanized antibody is less likely to induce an immune response, and/or induces a less severe immune response, as compared to the non-human species antibody, when it is administered to a human subject. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. Examples of how to make humanized antibodies can be found in U.S. Pat. Nos. 6,054,297, 5,886,152 and 5,877,293, each of which is incorporated by reference in its entirety. For further details, see Jones et al., *Nature*, 1986, 321:522-525; Riechmann et al., Nature, 1988, 332:323-329; and Presta, *Curr. Op. Struct. Biol.*, 1992, 2:593-596, each of which is incorporated by reference in its entirety.

In some embodiments, the antibody comprises a rat MARCO antibody. In some embodiments, the antibody comprises a chimeric MARCO antibody. In some embodiments, the antibody comprises a humanized MARCO antibody. In some embodiments, the antibody comprises a human MARCO antibody.

In some embodiments, the humanized MARCO antibody VH sequence comprises at least one of 16G, 19R, 23A, 37V, 42G, 48V, 49S, 82Q, 88A, 93V, 114T, 115L, S16G, K19R, V23A, I37V, K42G, I48V, A49S, E82Q, S88A, M93V, V114T, or M115L as compared to a rat VH sequence as shown in SEQ ID NO: 141. In some embodiments, the humanized MARCO antibody VH sequence comprises at least one of G16, R19, A23, V37, G42, V48, S49, Q82, A88, V93, T114, L115, numbering according to EU Index. In some embodiments, the humanized MARCO antibody VH sequence comprises at least one of I38, I48, A49, S54, Q54, A54, G56, S56, Q56, A56, S57, Q57, or A57, numbering according to EU Index.

In some embodiments, the humanized MARCO antibody VL sequence comprises at least one of 2I, 10S, 13S, 16V, 18D, 19R, 21T, 23T, 25R, 38Q, 41G, 43A, 44P, 50D, 51A, 53S, 55E, 58V, 76S, 77S, 79Q, 85T, 99Q, V2I, Y10S, A13S, P16V, E18D, S19R, S21T, S23T, K25R, E38Q, E41G, T43A, N44P, S50D, G51A, T53S, Q55E, T58V, R76S, N77S, E79Q, V85T, and S99Q, as compared to a rat VL sequence as shown in SEQ ID NO: 146. In some embodiments, the humanized MARCO antibody VL sequence comprises at least one of I2, S10, S13, V16, D18, R19, T21, T23, R25, Q38, G41, A43, P44, D50, A51, S53, E55, V58, S76, S77, Q79, T85, or Q99, numbering according to EU Index. In some embodiments, the humanized MARCO antibody VL sequence comprises at least one of V2, R24, K24, Q38, E38, A43, T43, N44, or P44, numbering according to EU Index.

In some embodiments, the humanized MARCO antibody VH sequence comprises at least one of 2V, 9A, 11V, 16A, 20V, 38R, 43Q, 46E, 62Q, 63K, 65Q, 66G, 68V, 69T, 70M, 71T, 72R, 73D, 76T, 78A, 79Y, 80M, 81E, 82L, 83S, 84S, 86R, 87S, 92V, 94Y, 96A, 114T, 115L, I2V, P9A, L11V, E16A, I20V, K38R, N43Q, K46E, D62Q, D63K, K65Q, Q66G, F68V, V69T, F70M, S71T, L72R, E73D, A76T, S78A, F79Y, L80M, Q81E, I82L, N83S, N84S, N86R, I87S, T92V, F94Y, T96A, V114T, M115L as compared to a rat VH sequence as shown in SEQ ID NO: 231. In some embodiments, the humanized MARCO antibody VH sequence comprises at least one of V2, A9, V11, A16, V20, R38, Q43, E46, Q62, K63, Q65, G66G, V68, T69, M70, T71, R72, D73, T76, A78, Y79, M80, E81, L82, S83, S84, R86, S87, V92, Y94, A96, T114, L115, numbering according to EU index.

In some embodiments, the humanized MARCO antibody VL sequence at least one of 9S, 15V, 17D, 18R, 20T, 22T, 24R, 40P, 43A, 45K, 70D, 72T, 73T, 76S, 77L, 82F, 84T, 86Y, 100Q, 106I, A9S, L15V, E17D, T18R, S20T, E22T, L24R, S40P, S43A, Q45K, R70D, S72T, K73T, D76S, M77L, E82F, D84T, F86Y, G100Q, L106I, as compared to a rat VL sequence as shown in SEQ ID NO: 236. In some embodiments, the humanized MARCO antibody VL sequence at least one of S9, V15, D17, R18, T20, T22, R24, P40, A43, K45, D70, T72, T73, S76, L77, F82, T84, Y86, Q100, or 106I, numbering according to EU index.

In some embodiments, the humanized MARCO antibody VH sequence comprises at least one of 1E, 5Q, 13K, 16E, 48I, 61P, 62S, 67V, 68T, 76N, 79S, 82L, 83S, 85V, 86T, 87A, 88A, 92V, 116T, 117L, Q1E, K5Q, Q13K, Q16E, M48I, S61P, L62S, L67V, S68T, S76N, F79S, M82L, N83S, L85V, Q86T, T87A, E88A, T92V, V116T, or M117L, as compared to a rat VH sequence as shown in SEQ ID NO: 1. In some embodiments, the humanized MARCO antibody VH sequence comprises at least one of E1, Q5, K13, E16, I48, P61, S62, V67, T68, N76, S79, L82, S83, V85, T86, A87, A88, V92, T116, or L117, numbering according to EU index.

In some embodiments, the humanized MARCO antibody VL sequence comprises at least one of 9S, 13A, 15V, 17D, 18R, 20T, 22T, 24R, 40P, 43A, 45K, 56S, 70D, 71F, 72T, 74T, 77S, 78L, 92F, 94T, 96Y, 100Q, 9S, T13A, L15V, E17D, T18R, S20T, E22T, L24R, S40P, S43A, Q45K, D56S, R70D, Y71F, S72T, K74T, G77S, M78L, E92F, D94T, F96Y, or S100Q, as compared to a rat VL sequence as shown in SEQ ID NO: 6. In some embodiments, the humanized MARCO antibody VL sequence comprises at least one of S9, T13, A13, D17, R18, T20, T22, L24, R24, N31, S31, Q31, A31, D31, P40, A43, S43, I43, K45, D56, S56, D70, Y71, F71, T72, T74, S77, L78, M78, F83, E83, T85, Y87, F87, F92, T94, S100, or Q100, numbering according to EU index.

In one embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies. In one embodiment, all of the variable and constant domains are derived from human immunoglobulin sequences (a fully human antibody). These antibodies may be prepared in a variety of ways including through the immunization with an antigen of interest of a mouse that is genetically modified to express antibodies derived from human heavy and/or light chain-encoding genes.

In some embodiments, the antibodies provided herein comprise an antibody fragment. In some embodiments, the antibodies provided herein consist of an antibody fragment. In some embodiments, the antibodies provided herein consist essentially of an antibody fragment. In some embodiments, the antibody fragment is an Fv fragment. In some embodiments, the antibody fragment is a Fab fragment. In some embodiments, the antibody fragment is a F(ab')$_2$ fragment. In some embodiments, the antibody fragment is a Fab' fragment. In some embodiments, the antibody fragment is an scFv (sFv) fragment. In some embodiments, the antibody fragment is an scFv-Fc fragment. In some embodiments, the antibody fragment is a fragment of a single domain antibody.

Sequences of MARCO Antibodies

Table B provides the names and SEQ ID NOs of exemplary anti-MARCO antibodies provided herein.

TABLE B

| Name | Revised Name (if applicable) | Description | SEQ ID NOs |
|---|---|---|---|
| PI-HX-3031 | | parental rat hybridoma | 1-10 |
| PI-3010-AB | PI-3010 | hIgG1/chimeric PI-HX- 3031 | 11-20 |
| PI-3011-AB | PI-3010.11 | humanized PI-HX- 3031/3031-1 hIgG1 | 21-30 |
| PI-3012-AB | PI-3010.12 | humanized PI-HX- 3031/3031-2 hIgG1 | 31-40 |
| PI-3013-AB | PI-3010.13 | humanized PI-HX- 3031/3031-3 hIgG1 | 41-50 |
| PI-3014-AB | PI-3010.14 | humanized PI-HX- 3031/3031-4 hIgG1 | 51-60 |
| PI-3015-AB | PI-3010.15 | humanized PI-HX- 3031/3031-5 hIgG1 | 61-70 |
| PI-3020-AB | PI-3010.20 | chimeric PI-HX- 3031 - hIgG4 | 71-80 |
| PI-3022-AB | PI-3010.22 | humanized PI-HX- 3031/3031-2 hIgG1 | 81-90 |
| PI-3023-AB | PI-3010.23 | humanized PI-HX- 3031/3031-2 hIgG1 | 91-100 |
| PI-3024-AB | PI-3010.24 | humanized PI-HX- 3031/3031-2 hIgG1 | 101-110 |
| PI-3025-AB | PI-3010.25 | humanized PI-HX- 3031/3031-2 hIgG1 | 434-443 |
| PI-3026-AB | PI-3010.26 | humanized PI-HX- 3031/3031-2 hIgG1 | 121-130 |
| PI-3027-AB | PI-3010.27 | humanized PI-HX- 3031/3031-2 hIgG1 | 131-140 |
| PI-3046-AB | PI-3010.46 | humanized PI-HX- 3031/3031-2 hIgG4 | 474-483 |
| PI-3048-AB | PI-3010.48 | humanized PI-HX- 3031/3031-2 hIgG4 | 444-453 |
| PI-HX-3061 | | parental rat hybridoma | 141-150 |
| PI-3016-AB | | humanized PI-HX- 3061/3061-1 hIgG1 | 151-160 |
| PI-3017-AB | | humanized PI-HX- 3061/3061-2 hIgG1 | 161-170 |
| PI-3018-AB | | humanized PI-HX- 3061/3061-3 hIgG1 | 171-180 |
| PI-3019-AB | | PI-HX-3061 mIgG2a chimera | 181-190 |
| PI-3028-AB | | PI-HX-3061 hIgG1 chimera | 191-200 |
| PI-3029-AB | | PI-HX-3061 hIgG4 chimera | 201-210 |
| PI-3032-AB | | humanized PI-HX- 3061/3061-2 hIgG1 | 211-220 |
| PI-3033-AB | | humanized PI-HX- 3061/3061-2 hIgG1 | 221-230 |
| PI-HX-3011 | | parental rat hybridoma | 231-240 |
| PI-3030-AB | PI-3030 | HX3011-h1 Chimera hIgG1 | 241-250 |
| PI-3036-AB | PI-3030.36 | humanized PI-HX- 3011/3011-1 hIgG1 | 311-320 |
| PI-3037-AB | PI-3030.37 | humanized PI-HX- 3011/3011-2 hIgG1 | 321-330 |
| PI-3038-AB | PI-3030.38 | humanized PI-HX- 3011/3011-3 hIgG1 | 331-340 |
| PI-3039-AB | PI-3030.39 | humanized PI-HX- 3011/3011-4 hIgG1 | 341-350 |
| PI-3040-AB | PI-3030.40 | humanized PI-HX- 3011/3011-5 hIgG1 | 351-360 |
| PI-3041-AB | PI-3030.41 | humanized PI-HX- 3011/3011-5 hIgG1 | 454-463 |
| PI-3047-AB | PI-3030.47 | humanized PI-HX- 3011/3011-5 hIgG4 | 464-473 |
| PI-HX-3043 | | parental rat hybridoma | 251-260 |
| PI-3031-AB | | HX3043-h1 Chimera hIgG1 | 261-270 |
| PI-HX-3092 | | parental rat hybridoma | 361-370 |
| PI-3035 | | HX3092 (A mutation) - mIgG2a | 371-380 |

CDRs

In some embodiments, an isolated antibody or antigen binding fragment thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GFSLTSYHVS (SEQ ID NO: 2), CDR-H2 comprises the sequence AIWTGGSIA (SEQ ID NO: 3), CDR-H3 comprises the sequence DLSDYYSSYTSFDY (SEQ ID NO: 4), CDR-L1 comprises the sequence ASEGISNDLA (SEQ ID NO: 431) or XASEGISNDLA (SEQ ID NO: 383), wherein X is arginine (R) or leucine (L), CDR-L2 comprises the sequence AASRLQD (SEQ ID NO: 8), and CDR-L3 comprises the sequence QQSYKYPLT (SEQ ID NO: 9).

In some embodiments, CDR-L1 comprises the sequence LASEGISNDLA (SEQ ID NO: 7). In some embodiments, CDR-L1 comprises the sequence RASEGISNDLA (SEQ ID NO: 27). In some embodiments, CDR-L1 comprises the sequence ASEGISNDLA (SEQ ID NO: 431).

In some embodiments, an antibody provided herein comprises a CDR-H3 of SEQ ID NO: 4, a CDR-H2 of SEQ ID NO: 3, a CDR-H1 of SEQ ID NO: 2, a CDR-L3 of SEQ ID NO: 9, a CDR-L2 of SEQ ID NO: 8, and a CDR-L1 of SEQ ID NO: 7. In some embodiments, an antibody provided herein comprises a CDR-H3 of SEQ ID NO: 4, a CDR-H2 of SEQ ID NO: 3, a CDR-H1 of SEQ ID NO: 2, a CDR-L3 of SEQ ID NO: 9, a CDR-L2 of SEQ ID NO: 8, and a CDR-L1 of SEQ ID NO: 27. In some embodiments, an antibody provided herein comprises a CDR-H3 of SEQ ID NO: 4, a CDR-H2 of SEQ ID NO: 3, a CDR-H1 of SEQ ID NO: 2, a CDR-L3 of SEQ ID NO: 9, a CDR-L2 of SEQ ID NO: 8, and a CDR-L1 of SEQ ID NO: 431. In some embodiments, the CDR-H3 has at least about 50%, 75%, 80%, 85%, 90%, or 95% identity with a CDR-H3 of SEQ ID NO: 4, the CDR-H2 has at least about 50%, 75%, 80%, 85%, 90%, or 95% identity with a CDR-H2 of SEQ ID NO: 3, the CDR-H1 has at least about 50%, 75%, 80%, 85%, 90%, or 95% identity with a CDR-H1 of SEQ ID NO: 2, the CDR-L3 has at least about 50%, 75%, 80%, 85%, 90%, or 95% identity with a CDR-L3 of SEQ ID NO: 9, the CDR-L2 has at least about 50%, 75%, 80%, 85%, 90%, or 95% identity with a CDR-L2 of SEQ ID NO: 8, and the CDR-L1 has at least about 50%, 75%, 80%, 85%, 90%, or 95% identity with a CDR-L1 of SEQ ID NO: 431, 383, 7, or 27. In some embodiments, the CDR-H3 is a CDR-H3 of SEQ ID NO: 4, with up to 1, 2, 3, 4, 5, 6, 7, or 8 amino acid substitutions; the CDR-H2 is a CDR-H2 of SEQ ID NO: 3, with up to 1, 2, 3, 4, 5, 6, 7, or 8 amino acid substitutions; the CDR-H1 is a CDR-H1 of SEQ ID NO: 2, with up to 1, 2, 3, 4, or 5 amino acid substitutions; the CDR-L3 is a CDR-L3 of SEQ ID NO: 9, with up to 1, 2, 3, 4, or 5 amino acid substitutions; the CDR-L2 is a CDR-L2 of SEQ ID NO: 8, with up to 1, 2, 3, or 4 amino acid substitutions; and the CDR-L1 is a CDR-L1 of SEQ ID NO: 431, 383, 7, or 27 with up to 1, 2, 3, 4, 5, or 6 amino acid substitutions.

In some embodiments, an isolated antibody or antigen binding fragment thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GYTFTDYAVN (SEQ ID NO: 232), CDR-H2 comprises the sequence WINTQTGKPT (SEQ ID NO: 233), CDR-H3 comprises the sequence DSYYYSSSLDY (SEQ ID NO: 234), CDR-L1 comprises the sequence ASAGISNDLA (SEQ ID NO: 432) or XAS-AGISNDLA (SEQ ID NO: 381), wherein X is leucine (L) or arginine (R), CDR-L2 comprises the sequence AASRLQD (SEQ ID NO: 238), and CDR-L3 comprises the sequence QQSYKYPWT (SEQ ID NO: 239). In some embodiments, CDR-L1 comprises the sequence LASAGISNDLA (SEQ ID NO: 237). In some embodiments, CDR-L1 comprises the sequence RASAGISNDLA (SEQ ID NO: 317). In some embodiments, CDR-L1 comprises the sequence ASAGISNDLA (SEQ ID NO: 432).

In some embodiments, an antibody provided herein comprises a CDR-H3 of SEQ ID NO: 234, a CDR-H2 of SEQ ID NO: 233, a CDR-H1 of SEQ ID NO: 232, a CDR-L3 of SEQ ID NO: 239, a CDR-L2 of SEQ ID NO: 238, and a CDR-L1 of SEQ ID NO: 237. In some embodiments, an antibody provided herein comprises a CDR-H3 of SEQ ID NO: 234, a CDR-H2 of SEQ ID NO: 233, a CDR-H1 of SEQ ID NO: 232, a CDR-L3 of SEQ ID NO: 319, a CDR-L2 of SEQ ID NO: 318, and a CDR-L1 of SEQ ID NO: 317. In some embodiments, an antibody provided herein comprises a CDR-H3 of SEQ ID NO: 234, a CDR-H2 of SEQ ID NO: 233, a CDR-H1 of SEQ ID NO: 232, a CDR-L3 of SEQ ID NO: 239, a CDR-L2 of SEQ ID NO: 238, and a CDR-L1 of SEQ ID NO: 432. In some embodiments, the CDR-H3 has at least about 50%, 75%, 80%, 85%, 90%, or 95% identity with a CDR-H3 of SEQ ID NO: 234, the CDR-H2 has at least about 50%, 75%, 80%, 85%, 90%, or 95% identity with a CDR-H2 of SEQ ID NO: 233, the CDR-H1 has at least about 50%, 75%, 80%, 85%, 90%, or 95% identity with a CDR-H1 of SEQ ID NO: 232, the CDR-L3 has at least about 50%, 75%, 80%, 85%, 90%, or 95% identity with a CDR-L3 of SEQ ID NO: 239, the CDR-L2 has at least about 50%, 75%, 80%, 85%, 90%, or 95% identity with a CDR-L2 of SEQ ID NO: 238, and the CDR-L1 has at least about 50%, 75%, 80%, 85%, 90%, or 95% identity with a CDR-L1 of SEQ ID NO: 432, 237, 317, or 381. In some embodiments, the CDR-H3 is a CDR-H3 of SEQ ID NO: 234, with up to 1, 2, 3, 4, 5, 6, 7, or 8 amino acid substitutions; the CDR-H2 is a CDR-H2 of SEQ ID NO: 233, with up to 1, 2, 3, 4, 5, 6, 7, or 8 amino acid substitutions; the CDR-H1 is a CDR-H1 of SEQ ID NO: 232, with up to 1, 2, 3, 4, or 5 amino acid substitutions; the CDR-L3 is a CDR-L3 of SEQ ID NO: 239, with up to 1, 2, 3, 4, or 5 amino acid substitutions; the CDR-L2 is a CDR-L2 of SEQ ID NO: 238, with up to 1, 2, 3, or 4 amino acid substitutions; and the CDR-L1 is a CDR-L1 of SEQ ID NO: 432, 237, 317, or 381 with up to 1, 2, 3, 4, 5, or 6 amino acid substitutions.

In some embodiments, an isolated antibody or antigen binding fragment thereof that binds to human MARCO (SEQ ID NO: 363), comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GYTFTDYYLH (SEQ ID NO: 252), CDR-H2 comprises the sequence YINPNNAYTS (SEQ ID NO: 253), CDR-H3 comprises the sequence DTTDYYNLHFAY (SEQ ID NO: 254), CDR-L1 comprises the sequence LTSEGISNDLA (SEQ ID NO: 257), CDR-L2 comprises the sequence DASRLED (SEQ ID NO: 258), and CDR-L3 comprises the sequence QQSYKYPLT (SEQ ID NO: 259).

In some embodiments, an antibody provided herein comprises a CDR-H3 of SEQ ID NO: 254, a CDR-H2 of SEQ ID NO: 253, a CDR-H1 of SEQ ID NO: 252, a CDR-L3 of SEQ ID NO: 259, a CDR-L2 of SEQ ID NO: 258, and a CDR-L1 of SEQ ID NO: 257. In some embodiments, the CDR-H3 has at least about 50%, 75%, 80%, 85%, 90%, or 95% identity with a CDR-H3 of SEQ ID NO: 254, the CDR-H2 has at least about 50%, 75%, 80%, 85%, 90%, or 95% identity with a CDR-H2 of SEQ ID NO: 253, the CDR-H1 has at least about 50%, 75%, 80%, 85%, 90%, or 95% identity with a CDR-H1 of SEQ ID NO: 252, the CDR-L3 has at least about 50%, 75%, 80%, 85%, 90%, or 95% identity with a CDR-L3 of SEQ ID NO: 259, the CDR-L2 has at least about 50%, 75%, 80%, 85%, 90%, or 95% identity with a CDR-L2 of SEQ ID NO: 258, and the CDR-L1 has at least about 50%, 75%, 80%, 85%, 90%, or 95% identity with a CDR-L1 of SEQ ID NO: 257. In some embodiments, the CDR-H3 is a CDR-H3 of SEQ ID NO: 254, with up to 1, 2, 3, 4, 5, 6, 7, or 8 amino acid substitutions; the CDR-H2 is a CDR-H2 of SEQ ID NO: 253, with up to 1, 2, 3, 4, 5, 6, 7, or 8 amino acid substitutions; the CDR-H1 is a CDR-H1 of SEQ ID NO: 252, with up to 1, 2, 3, 4, or 5 amino acid substitutions; the CDR-L3 is a CDR-L3 of SEQ ID NO: 259, with up to 1, 2, 3, 4, or 5 amino acid substitutions; the CDR-L2 is a CDR-L2 of SEQ ID NO: 258, with up to 1, 2, 3, or 4 amino acid substitutions; and the CDR-L1 is a CDR-L1 of SEQ ID NO: 257, with up to 1, 2, 3, 4, 5, or 6 amino acid substitutions.

In some embodiments, an isolated antibody or antigen binding fragment thereof that binds to human MARCO (SEQ ID NO: 363), comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence KFTFSNYGMN (SEQ ID NO: 142), CDR-H2 comprises the sequence LIYYNSNNKY (SEQ ID NO: 143), CDR-H3 comprises the sequence SLTGGSDYFDS (SEQ ID NO: 144), CDR-L1 comprises the sequence ASKSIGTFLA (SEQ ID NO: 433) or XASKSIGTFLA (SEQ ID NO: 382), wherein X is lysine (K) or arginine (R), CDR-L2 comprises the sequence SGSTLQS (SEQ ID NO: 148), and CDR-L3 comprises the sequence QQHDEYPFT (SEQ ID NO: 149).

In some embodiments, CDR-L1 comprises the sequence KASKSIGTFLA (SEQ ID NO: 147). In some embodiments, CDR-L1 comprises the sequence RASKSIGTFLA (SEQ ID NO: 157). In some embodiments, CDR-L1 comprises the sequence ASKSIGTFLA (SEQ ID NO: 433).

In some embodiments, an antibody provided herein comprises a CDR-H3 of SEQ ID NO: 144, a CDR-H2 of SEQ ID NO: 143, a CDR-H1 of SEQ ID NO: 142, a CDR-L3 of SEQ ID NO: 149, a CDR-L2 of SEQ ID NO: 148, and a CDR-L1 of SEQ ID NO: 147. In some embodiments, an antibody provided herein comprises a CDR-H3 of SEQ ID NO: 144, a CDR-H2 of SEQ ID NO: 143, a CDR-H1 of SEQ ID NO: 142, a CDR-L3 of SEQ ID NO: 149, a CDR-L2 of SEQ ID NO: 148, and a CDR-L1 of SEQ ID NO: 157. In some embodiments, an antibody provided herein comprises a CDR-H3 of SEQ ID NO: 144, a CDR-H2 of SEQ ID NO: 143, a CDR-H1 of SEQ ID NO: 142, a CDR-L3 of SEQ ID NO: 149, a CDR-L2 of SEQ ID NO: 148, and a CDR-L1 of SEQ ID NO: 433. In some embodiments, the CDR-H3 has at least about 50%, 75%, 80%, 85%, 90%, or 95% identity with a CDR-H3 of SEQ ID NO: 144, the CDR-H2 has at least about 50%, 75%, 80%, 85%, 90%, or 95% identity with a CDR-H2 of SEQ ID NO: 143, the CDR-H1 has at least about 50%, 75%, 80%, 85%, 90%, or 95% identity with a CDR-H1 of SEQ ID NO: 142, the CDR-L3 has at least about 50%, 75%, 80%, 85%, 90%, or 95% identity with a CDR-L3 of SEQ ID NO: 149, the CDR-L2 has at least about 50%, 75%, 80%, 85%, 90%, or 95% identity with a CDR-L2 of SEQ ID NO: 148, and the CDR-L1 has at least about 50%, 75%, 80%, 85%, 90%, or 95% identity with a CDR-L1 of SEQ ID NO: 433, 382, 147, or 157. In some embodiments, the CDR-H3 is a CDR-H3 of SEQ ID NO: 144, with up to 1, 2, 3, 4, 5, 6, 7, or 8 amino acid substitutions; the CDR-H2 is a CDR-H2 of SEQ ID NO: 143, with up to 1, 2, 3, 4, 5, 6, 7, or 8 amino acid substitutions; the CDR-H1 is a CDR-H1 of SEQ ID NO: 142, with up to 1, 2, 3, 4, or 5 amino acid substitutions; the CDR-L3 is a CDR-L3 of SEQ ID NO: 149, with up to 1, 2, 3, 4, or 5 amino acid substitutions; the CDR-L2 is a CDR-L2 of SEQ ID NO: 148, with up to 1, 2, 3, or 4 amino acid substitutions; and the CDR-L1 is a CDR-L1 of SEQ ID NO: 433, 382, 147, or 157 with up to 1, 2, 3, 4, 5, or 6 amino acid substitutions.

In some embodiments, an isolated antibody or antigen binding fragment thereof that binds to human MARCO (SEQ ID NO: 384), comprising a a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GFSLTSYTLS (SEQ ID NO: 362), CDR-H2 comprises the sequence AIWGGDNTD (SEQ ID NO: 363), CDR-H3 comprises the sequence ELGGSFDY (SEQ ID NO: 364), CDR-L1 comprises the sequence KTSQNINKKLD (SEQ ID NO: 367), CDR-L2 comprises the sequence YTNNLQT (SEQ ID NO: 368), and CDR-L3 comprises the sequence YQYDSGFT (SEQ ID NO: 369).

In some embodiments, the CDR-H3 has at least about 50%, 75%, 80%, 85%, 90%, or 95% identity with a CDR-H3 of SEQ ID NO: 364, the CDR-H2 has at least about 50%, 75%, 80%, 85%, 90%, or 95% identity with a CDR-H2 of SEQ ID NO: 363, the CDR-H1 has at least about 50%, 75%, 80%, 85%, 90%, or 95% identity with a CDR-H1 of SEQ ID NO: 362, the CDR-L3 has at least about 50%, 75%, 80%, 85%, 90%, or 95% identity with a CDR-L3 of SEQ ID NO: 369, the CDR-L2 has at least about 50%, 75%, 80%, 85%, 90%, or 95% identity with a CDR-L2 of SEQ ID NO: 368, and the CDR-L1 has at least about 50%, 75%, 80%, 85%, 90%, or 95% identity with a CDR-L1 of SEQ ID NO: 367. In some embodiments, the CDR-H3 is a CDR-H3 of SEQ ID NO: 364, with up to 1, 2, 3, 4, 5, 6, 7, or 8 amino acid substitutions; the CDR-H2 is a CDR-H2 of SEQ ID NO: 363, with up to 1, 2, 3, 4, 5, 6, 7, or 8 amino acid substitutions; the CDR-H1 is a CDR-H1 of SEQ ID NO: 362, with up to 1, 2, 3, 4, or 5 amino acid substitutions; the CDR-L3 is a CDR-L3 of SEQ ID NO: 369, with up to 1, 2, 3, 4, or 5 amino acid substitutions; the CDR-L2 is a CDR-L2 of SEQ ID NO: 368, with up to 1, 2, 3, or 4 amino acid substitutions; and the CDR-L1 is a CDR-L1 of SEQ ID NO: 367 with up to 1, 2, 3, 4, 5, or 6 amino acid substitutions.

In some aspects, the amino acid substitutions are conservative amino acid substitutions. In some embodiments, the antibodies described herein are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477. In some aspects, the CDR-H3 has at least about 50%, 75%, 80%, 85%, 90%, or 95% identity with a CDR-H3 of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477. In some embodiments, the CDR-H3 is a CDR-H3 selected of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476. In some aspects, the CDR-H2 has at least about 50%, 75%, 80%, 85%, 90%, or 95% identity with a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476. In some embodiments, the CDR-H2 is a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 435, 445, 455, 465, or 475. In some aspects, the CDR-H1 has at least about 50%, 75%, 80%, 85%, 90%, or 95% identity with a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 435, 445, 455, 465, or 475. In some embodiments, the CDR-H1 is a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372 435, 445, 455, 465, or 475, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H3 of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477, a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476, and a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372 435, 445, 455, 465, or 475. In some embodiments, the CDR-H3 has at least about 50%, 75%, 80%, 85%, 90%, or 95% identity with a CDR-H3 of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477, the CDR-H2 has at least about 50%, 75%, 80%, 85%, 90%, or 95% identity with a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476, and the CDR-H1 has at least about 50%, 75%, 80%, 85%, 90%, or 95% identity with a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372 435, 445, 455, 465, or 475. In some embodiments, the CDR-H3 is a CDR-H3 of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477, with up to 1, 2, 3, 4, 5, 6, 7, or 8 amino acid substitutions; the CDR-H2 is a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476, with up to 1, 2, 3, 4, 5, 6, 7, or 8 amino acid substitutions; and the CDR-H1 is a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372 435, 445, 455, 465, or 475, with up to 1, 2, 3, 4, or 5 amino acid substitutions. In some aspects, the amino acid substitutions are conservative amino acid substitutions.

In some embodiments, an antibody provided herein comprises a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482. In some aspects, the CDR-L3 has at least about 50%, 75%, 80%, 85%, 90%, or 95% identity with a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482. In some embodiments, the CDR-L3 is a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481. In some aspects, the CDR-L2 has at least about 50%, 75%, 80%, 85%, 90%, or 95% identity with a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481. In some embodiments, the CDR-L2 is a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, 383, 440, 450, 460, 470, or 480. In some aspects, the CDR-L1 has at least about 50%, 75%, 80%, 85%, 90%, or 95% identity with a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, or 383, 440, 450, 460, 470, or 480. In some embodiments, the CDR-L1 is a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, 383, 440, 450, 460, 470, or 480, with up to 1, 2, 3, 4, 5, 6, 7, or 8 amino acid substitutions.

In some aspects, the amino acid substitutions are conservative amino acid substitutions. In some embodiments, an antibody provided herein comprises a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, and a CDR-L2 of SEQ ID N08, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481. In some embodiments, an antibody provided herein comprises a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481, and a CDR-L1 of SEQ ID NO: 77, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, or 383, 440, 450, 460, 470, or 480. In some embodiments, the CDR-L3 has at least about 50%, 75%, 80%, 85%, 90%, or 95% identity with a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, the CDR-L2 has at least about 50%, 75%, 80%, 85%, 90%, or 95% identity with a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481, and the CDR-L1 has at least about 50%, 75%, 80%, 85%, 90%, or 95% identity with a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, 383, 440, 450, 460, 470, or 480. In some embodiments, the CDR-L3 is a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, with up to 1, 2, 3, 4, or 5 amino acid substitutions; the CDR-L2 is a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481, with up to 1, 2, 3, or 4 amino acid substitutions; and the CDR-L1 is a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, 383, 440, 450, 460, 470, or 480, with up to 1, 2, 3, 4, 5, or 6 amino acid substitutions. In some aspects, the amino acid substitutions are conservative amino acid substitutions.

In some embodiments, an antibody provided herein comprises one to three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some embodiments, an antibody provided herein comprises two to three CDRs of a $V_H$ domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some embodiments, an antibody provided herein comprises three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDR-H1 is a CDR-H1 of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, with up to 1, 2, 3, 4, or 5 amino acid substitutions. In some embodiments, the CDR-H2 is a CDR-H2 of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, with up to 1, 2, 3, 4, 5, 6, 7, or 8 amino acid substitutions. In some embodiments, the CDR-H3 is a CDR-H3 of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some embodiments, an antibody provided herein comprises two to three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some embodiments, an antibody provided herein comprises three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDR-L1 is a CDR-L1 of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474, with up to 1, 2, 3, 4, or 5 amino acid substitutions. In some embodiments, the CDR-L2 is a CDR-L2 of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, or 376 with up to 1, 2, 3, 4, 5, 6, 7, or 8 amino acid substitutions. In some embodiments, the CDR-L3 is a CDR-L3 of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474 with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, and one to three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some embodiments, an antibody provided herein comprises two to three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, and two to three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some embodiments, an antibody provided herein comprises three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, and three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

$V_H$ Domains

In some embodiments, an antibody or antigen binding fragment thereof provided herein comprises a $V_H$ sequence selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some embodiments, an antibody provided herein comprises a $V_H$ sequence of SEQ ID NO: 1. In some embodiments, an antibody provided herein comprises a $V_H$ sequence of SEQ ID NO: 21. In some embodiments, an antibody provided herein comprises a $V_H$ sequence of SEQ ID NO: 121. In some embodiments, an antibody provided herein comprises a $V_H$ sequence of SEQ ID NO: 181. In some embodiments, an antibody provided herein comprises a $V_H$ sequence of SEQ ID NO: 191. In some embodiments, an antibody provided herein comprises a $V_H$ sequence of SEQ ID NO: 221. In some embodiments, an antibody provided herein comprises a $V_H$ sequence of SEQ ID NO: 241. In some embodiments, an antibody provided herein comprises a $V_H$ sequence of SEQ ID NO: 261. In some embodiments, an antibody provided herein comprises a $V_H$ sequence of SEQ ID NO: 351. In some embodiments, an antibody provided herein comprises a $V_H$ sequence of SEQ ID NO: 371. In some embodiments, an antibody provided herein comprises a $V_H$ sequence of SEQ ID NO: 434. In some embodiments, an antibody provided herein comprises a $V_H$ sequence of SEQ ID NO: 444. In some embodiments, an antibody provided herein comprises a $V_H$ sequence of SEQ ID NO: 454. In some embodiments, an antibody provided herein comprises a $V_H$ sequence of SEQ ID NO: 464. In some embodiments, an antibody provided herein comprises a $V_H$ sequence of SEQ ID NO: 474.

In some embodiments, the $V_H$ sequence has at least 70%, 80%, or 90% identity with SEQ ID NO: 1, wherein any variation from SEQ ID NO: 1 does not occur within CDR-H1, CDR-H2, or CDR-H3. In some embodiments, the $V_H$ sequence has at least 70%, 80%, or 90% identity with SEQ ID NO: 21, wherein any variation from SEQ ID NO: 21 does not occur within CDR-H1, CDR-H2, or CDR-H3. In some embodiments, the $V_H$ sequence has at least 70%, 80%, or 90% identity with SEQ ID NO: 121, wherein any variation from SEQ ID NO: 121 does not occur within CDR-H1, CDR-H2, or CDR-H3. In some embodiments, the $V_H$ sequence has at least 70%, 80%, or 90% identity with SEQ ID NO: 181, wherein any variation from SEQ ID NO: 181 does not occur within CDR-H1, CDR-H2, or CDR-H3. In some embodiments, the $V_H$ sequence has at least 70%, 80%, or 90% identity with SEQ ID NO: 191, wherein any variation from SEQ ID NO: 191 does not occur within CDR-H1, CDR-H2, or CDR-H3. In some embodiments, the $V_H$ sequence has at least 70%, 80%, or 90% identity with SEQ ID NO: 221, wherein any variation from SEQ ID NO: 221 does not occur within CDR-H1, CDR-H2, or CDR-H3. In some embodiments, the $V_H$ sequence has at least 70%, 80%, or 90% identity with SEQ ID NO: 241, wherein any variation from SEQ ID NO: 241 does not occur within CDR-H1, CDR-H2, or CDR-H3. In some embodiments, the $V_H$ sequence has at least 70%, 80%, or 90% identity with SEQ ID NO: 261, wherein any variation from SEQ ID NO: 261 does not occur within CDR-H1, CDR-H2, or CDR-H3. In some embodiments, the $V_H$ sequence has at least 70%, 80%, or 90% identity with SEQ ID NO: 351, wherein any variation from SEQ ID NO: 351 does not occur within CDR-H1, CDR-H2, or CDR-H3. In some embodiments, the $V_H$ sequence has at least 70%, 80%, or 90% identity with SEQ ID NO: 371, wherein any variation from SEQ ID NO: 371 does not occur within CDR-H1, CDR-H2, or CDR-H3. In some embodiments, the $V_H$ sequence has at least 70%, 80%, or 90% identity with SEQ ID NO: 434, wherein any variation from SEQ ID NO: 434 does not occur within CDR-H1, CDR-H2, or CDR-H3. In some embodiments, the $V_H$ sequence has at least 70%, 80%, or 90% identity with SEQ ID NO: 444, wherein any variation from SEQ ID NO: 444 does not occur within CDR-H1, CDR-H2, or CDR-H3. In some embodiments, the $V_H$ sequence has at least 70%, 80%, or 90% identity with SEQ ID NO: 454, wherein any variation from SEQ ID NO: 454 does not occur within CDR-H1, CDR-H2, or CDR-H3. In some embodiments, the $V_H$ sequence has at least 70%, 80%, or 90% identity with SEQ ID NO: 464, wherein any variation from SEQ ID NO: 464 does not occur within CDR-H1, CDR-H2, or CDR-H3. In some embodiments, the $V_H$ sequence has at least 70%, 80%, or 90% identity with SEQ ID NO: 474, wherein any variation from SEQ ID NO: 474 does not occur within CDR-H1, CDR-H2, or CDR-H3.

In some embodiments, an antibody provided herein comprises a $V_H$ sequence having at least about 50%, 60%, 70%, 80%, 90%, 95%, or 99% identity to SEQ ID NO: 1. In some embodiments, an antibody provided herein comprises a $V_H$ sequence having at least about 50%, 60%, 70%, 80%, 90%, 95%, or 99% identity to SEQ ID NO: 21. In some embodiments, an antibody provided herein comprises a $V_H$ sequence having at least about 50%, 60%, 70%, 80%, 90%, 95%, or 99% identity to SEQ ID NO: 121. In some embodiments, an antibody provided herein comprises a $V_H$ sequence having at least about 50%, 60%, 70%, 80%, 90%, 95%, or 99% identity to SEQ ID NO: 181. In some embodiments, an antibody provided herein comprises a $V_H$ sequence having at least about 50%, 60%, 70%, 80%, 90%, 95%, or 99% identity to SEQ ID NO: 191. In some embodiments, an antibody provided herein comprises a $V_H$ sequence having at least about 50%, 60%, 70%, 80%, 90%, 95%, or 99% identity to SEQ ID NO: 221. In some embodiments, an antibody provided herein comprises a $V_H$ sequence having at least about 50%, 60%, 70%, 80%, 90%, 95%, or 99% identity to SEQ ID NO: 241. In some embodiments, an antibody provided herein comprises a $V_H$ sequence having at least about 50%, 60%, 70%, 80%, 90%, 95%, or 99% identity to SEQ ID NO: 261. In some embodiments, an antibody provided herein comprises a $V_H$ sequence having at least about 50%, 60%, 70%, 80%, 90%, 95%, or 99% identity to SEQ ID NO: 351. In some embodiments, an antibody provided herein comprises a $V_H$ sequence having at least about 50%, 60%, 70%, 80%, 90%, 95%, or 99% identity to SEQ ID NO: 371. In some embodiments, an antibody provided herein comprises a $V_H$ sequence having at least about 50%, 60%, 70%, 80%, 90%, 95%, or 99% identity to SEQ ID NO: 434. In some embodiments, an antibody provided herein comprises a $V_H$ sequence having at least about 50%, 60%, 70%, 80%, 90%, 95%, or 99% identity to SEQ ID NO: 444. In some embodiments, an antibody provided herein comprises a $V_H$ sequence having at least about 50%, 60%, 70%, 80%, 90%, 95%, or 99% identity to SEQ ID NO: 454. In some embodiments, an antibody provided herein comprises a $V_H$ sequence having at least about 50%, 60%, 70%, 80%, 90%, 95%, or 99% identity to SEQ ID NO: 464. In some embodiments, an antibody provided herein comprises a $V_H$ sequence having at least about 50%, 60%, 70%, 80%, 90%, 95%, or 99% identity to SEQ ID NO: 474.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some embodiments, an antibody provided herein comprises a $V_H$ sequence provided in SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody or antigen binding fragment as described herein is encoded by the polynucleotide sequence as shown in any one of SEQ ID NOs: 385, 386, 387, 388, 389, 390, 391, 392, 393, 394, 395, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, or 426.

$V_L$ Domains

In some embodiments, an antibody or antigen binding fragment thereof provided herein comprises a $V_L$ sequence selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. In some embodiments, an antibody provided herein comprises a $V_L$ sequence of SEQ ID NO: 6. In some embodiments, an antibody provided herein comprises a $V_L$ sequence of SEQ ID NO: 26. In some embodiments, an antibody provided herein comprises a $V_L$ sequence of SEQ ID NO: 126. In some embodiments, an antibody provided herein comprises a $V_L$ sequence of SEQ ID NO: 186. In some embodiments, an antibody provided herein comprises a sequence of SEQ ID NO: 196. In some embodiments, an antibody provided herein comprises a $V_L$ sequence of SEQ ID NO: 226. In some embodiments, an antibody provided herein comprises a $V_L$ sequence of SEQ ID NO: 246. In some embodiments, an antibody provided herein comprises a $V_L$ sequence of SEQ ID NO: 266. In some embodiments, an antibody provided herein comprises a $V_L$ sequence of SEQ ID NO: 356. In some embodiments, an antibody provided herein comprises a $V_L$ sequence of SEQ ID NO: 376.

In some embodiments, the $V_L$ sequence has at least 70%, 80%, or 90% identity with SEQ ID NO: 6, wherein any variation from SEQ ID NO: 6 does not occur within CDR-L1, CDR-L2, or CDR-L3. In some embodiments, the $V_L$ sequence has at least 70%, 80%, or 90% identity with SEQ ID NO: 26, wherein any variation from SEQ ID NO: 26 does not occur within CDR-L1, CDR-L2, or CDR-L3. In some embodiments, the $V_L$ sequence has at least 70%, 80%, or 90% identity with SEQ ID NO: 126, wherein any variation from SEQ ID NO: 126 does not occur within CDR-L1, CDR-L2, or CDR-L3. In some embodiments, the sequence has at least 70%, 80%, or 90% identity with SEQ ID NO: 186, wherein any variation from SEQ ID NO: 186 does not occur within CDR-L1, CDR-L2, or CDR-L3. In some embodiments, the $V_L$ sequence has at least 70%, 80%, or 90% identity with SEQ ID NO: 196, wherein any variation from SEQ ID NO: 196 does not occur within CDR-L1, CDR-L2, or CDR-L3. In some embodiments, the $V_L$ sequence has at least 70%, 80%, or 90% identity with SEQ ID NO: 226, wherein any variation from SEQ ID NO: 226 does not occur within CDR-L1, CDR-L2, or CDR-L3. In some embodiments, the $V_L$ sequence has at least 70%, 80%, or 90% identity with SEQ ID NO: 246, wherein any variation from SEQ ID NO: 246 does not occur within CDR-L1, CDR-L2, or CDR-L3. In some embodiments, the sequence has at least 70%, 80%, or 90% identity with SEQ ID NO: 266, wherein any variation from SEQ ID NO: 266 does not occur within CDR-L1, CDR-L2, or CDR-L3. In some embodiments, the $V_L$ sequence has at least 70%, 80%, or 90% identity with SEQ ID NO: 356, wherein any variation from SEQ ID NO: 356 does not occur within CDR-L1, CDR-L2, or CDR-L3. In some embodiments, the $V_L$ sequence has at least 70%, 80%, or 90% identity with SEQ ID NO: 376, wherein any variation from SEQ ID NO: 376 does not occur within CDR-L1, CDR-L2, or CDR-L3. In some embodiments, the $V_L$ sequence has at least 70%, 80%, or 90% identity with SEQ ID NO: 439, wherein any variation from SEQ ID NO: 439 does not occur within CDR-L1, CDR-L2, or CDR-L3. In some embodiments, the sequence has at least 70%, 80%, or 90% identity with SEQ ID NO: 449, wherein any variation from SEQ ID NO: 449 does not occur within CDR-L1, CDR-L2, or CDR-L3. In some embodiments, the $V_L$ sequence has at least 70%, 80%, or 90% identity with SEQ ID NO: 459, wherein any variation from SEQ ID NO: 459 does not occur within CDR-L1, CDR-L2, or CDR-L3. In some embodiments, the $V_L$ sequence has at least 70%, 80%, or 90% identity with SEQ ID NO: 469, wherein any variation from SEQ ID NO: 469 does not occur within CDR-L1, CDR-L2, or CDR-L3. In some embodiments, the $V_L$ sequence has at least 70%, 80%, or 90% identity with SEQ ID NO: 479, wherein any variation from SEQ ID NO: 479 does not occur within CDR-L1, CDR-L2, or CDR-L3.

In some embodiments, an antibody provided herein comprises a $V_L$ sequence having at least about 50%, 60%, 70%, 80%, 90%, 95%, or 99% identity to SEQ ID NO: 6. In some embodiments, an antibody provided herein comprises a $V_L$ sequence having at least about 50%, 60%, 70%, 80%, 90%, 95%, or 99% identity to SEQ ID NO: 26. In some embodiments, an antibody provided herein comprises a $V_L$ sequence having at least about 50%, 60%, 70%, 80%, 90%, 95%, or 99% identity to SEQ ID NO: 126. In some embodiments, an antibody provided herein comprises a $V_L$ sequence having at least about 50%, 60%, 70%, 80%, 90%, 95%, or 99% identity to SEQ ID NO: 186. In some embodiments, an antibody provided herein comprises a $V_L$ sequence having at least about 50%, 60%, 70%, 80%, 90%, 95%, or 99% identity to SEQ ID NO: 196. In some embodiments, an antibody provided herein comprises a $V_L$ sequence having at least about 50%, 60%, 70%, 80%, 90%, 95%, or 99% identity to SEQ ID NO: 226. In some embodiments, an antibody provided herein comprises a $V_L$ sequence having at least about 50%, 60%, 70%, 80%, 90%, 95%, or 99% identity to SEQ ID NO: 246. In some embodiments, an antibody provided herein comprises a $V_L$ sequence having at least about 50%, 60%, 70%, 80%, 90%, 95%, or 99% identity to SEQ ID NO: 266. In some embodiments, an antibody provided herein comprises a $V_L$ sequence having at least about 50%, 60%, 70%, 80%, 90%, 95%, or 99% identity to SEQ ID NO: 356. In some embodiments, an antibody provided herein comprises a $V_L$ sequence having at least about 50%, 60%, 70%, 80%, 90%, 95%, or 99% identity to $V_L$ sequence of SEQ ID NO: 376. In some embodiments, an antibody provided herein comprises a $V_L$ sequence having at least about 50%, 60%, 70%, 80%, 90%, 95%, or 99% identity to $V_L$ sequence of SEQ ID NO: 439. In some embodiments, an antibody provided herein comprises a $V_L$ sequence having at least about 50%, 60%, 70%, 80%, 90%, 95%, or 99% identity to $V_L$ sequence of SEQ ID NO: 449. In some embodiments, an antibody provided herein comprises a $V_L$ sequence having at least about 50%, 60%, 70%, 80%, 90%, 95%, or 99% identity to $V_L$ sequence of SEQ ID NO: 459. In some embodiments, an antibody provided herein comprises a $V_L$ sequence having at least about 50%, 60%, 70%, 80%, 90%, 95%, or 99% identity to $V_L$ sequence of SEQ ID NO: 469. In some embodiments, an antibody provided herein comprises a $V_L$ sequence having at least about 50%, 60%, 70%, 80%, 90%, 95%, or 99% identity to $V_L$ sequence of SEQ ID NO: 479.

In some embodiments, an antibody provided herein comprises a $V_L$ sequence having at least about 50%, 60%, 70%, 80%, 90%, 95%, or 99% identity to an illustrative sequence provided in SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. In some embodiments, an antibody provided herein comprises a $V_L$ sequence provided in SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

$V_H$-$V_L$ Combinations

In some embodiments, an antibody or antigen binding fragment thereof provided herein comprises a $V_H$ sequence selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474; and a $V_L$ sequence selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479.

In some embodiments, an antibody provided herein comprises a $V_H$ sequence of SEQ ID NO: 1 and a $V_L$ sequence of SEQ ID NO: 6. In some embodiments, an antibody provided herein comprises a $V_H$ sequence of SEQ ID NO: 21 and a $V_L$ sequence of SEQ ID NO: 26. In some embodiments, an antibody provided herein comprises a $V_H$ sequence of SEQ ID NO: 121 and $V_L$ sequence of SEQ ID NO: 126. In some embodiments, an antibody provided herein comprises a $V_H$ sequence of SEQ ID NO: 181 and a $V_L$ sequence of SEQ ID NO: 186. In some embodiments, an antibody provided herein comprises a $V_H$ sequence of SEQ ID NO: 191 and a $V_L$ sequence of SEQ ID NO: 196. In some embodiments, an antibody provided herein comprises a $V_H$ sequence of SEQ ID NO: 221 and a $V_L$ sequence of SEQ ID NO: 226. In some embodiments, an antibody provided herein comprises a $V_H$ sequence of SEQ ID NO: 241 and a $V_L$ sequence of SEQ ID NO: 246. In some embodiments, an antibody provided herein comprises a $V_H$ sequence of SEQ ID NO: 261 and a $V_L$ sequence of SEQ ID NO: 266 In some embodiments, an antibody provided herein comprises a $V_H$ sequence of SEQ ID NO: 351 and a $V_L$ sequence of SEQ ID NO: 356. In some embodiments, an antibody provided herein comprises a $V_H$ sequence of SEQ ID NO: 371 and a $V_L$ sequence of SEQ ID NO: 376. In some embodiments, an antibody provided herein comprises a $V_H$ sequence of SEQ ID NO: 434 and a $V_L$ sequence of SEQ ID NO: 439. In some embodiments, an antibody provided herein comprises a $V_H$ sequence of SEQ ID NO: 444 and a $V_L$ sequence of SEQ ID NO: 449. In some embodiments, an antibody provided herein comprises a $V_H$ sequence of SEQ ID NO: 454 and a $V_L$ sequence of SEQ ID NO: 459. In some embodiments, an antibody provided herein comprises a $V_H$ sequence of SEQ ID NO: 464 and a $V_L$ sequence of SEQ ID NO: 469. In some embodiments, an antibody provided herein comprises a $V_H$ sequence of SEQ ID NO: 474 and a $V_L$ sequence of SEQ ID NO: 479.

In some embodiments, the $V_H$ sequence has at least 70%, 80%, or 90% identity with SEQ ID NO: 1 and wherein the variable region of the light chain has at least 70%, 80%, or 90% identity with SEQ ID NO: 6, wherein any variation from SEQ ID NO: 1 does not occur within CDR-H1, CDR-H2, or CDR-H3 and wherein any variation from SEQ ID NO: 6 does not occur within CDR-L1, CDR-L2, or CDR-L3. In some embodiments, the $V_H$ sequence has at least 70%, 80%, or 90% identity with SEQ ID NO: 21 and wherein the variable region of the light chain has at least 70%, 80%, or 90% identity with SEQ ID NO: 26, wherein any variation from SEQ ID NO: 21 does not occur within CDR-H1, CDR-H2, or CDR-H3 and wherein any variation from SEQ ID NO: 26 does not occur within CDR-L1, CDR-L2, or CDR-L3. In some embodiments, the $V_H$ sequence has at least 70%, 80%, or 90% identity with SEQ ID NO: 121 and wherein the variable region of the light chain has at least 70%, 80%, or 90% identity with SEQ ID NO: 126, wherein any variation from SEQ ID NO: 121 does not occur within CDR-H1, CDR-H2, or CDR-H3 and wherein any variation from SEQ ID NO: 126 does not occur within CDR-L1, CDR-L2, or CDR-L3. In some embodiments, the $V_H$ sequence has at least 70%, 80%, or 90% identity with SEQ ID NO: 181 and wherein the variable region of the light chain has at least 70%, 80%, or 90% identity with SEQ ID NO: 186, wherein any variation from SEQ ID NO: 181 does not occur within CDR-H1, CDR-H2, or CDR-H3 and wherein any variation from SEQ ID NO: 186 does not occur within CDR-L1, CDR-L2, or CDR-L3. In some embodiments, the $V_H$ sequence has at least 70%, 80%, or 90% identity with SEQ ID NO: 191 and wherein the variable region of the light chain has at least 70%, 80%, or 90% identity with SEQ ID NO: 196, wherein any variation from SEQ ID NO: 191 does not occur within CDR-H1, CDR-H2, or CDR-H3 and wherein any variation from SEQ ID NO: 196 does not occur within CDR-L1, CDR-L2, or CDR-L3. In some embodiments, the $V_H$ sequence has at least 70%, 80%, or 90% identity with SEQ ID NO: 221 and wherein the variable region of the light chain has at least 70%, 80%, or 90% identity with SEQ ID NO: 226, wherein any variation from SEQ ID NO: 221 does not occur within CDR-H1, CDR-H2, or CDR-H3 and wherein any variation from SEQ ID NO: 226 does not occur within CDR-L1, CDR-L2, or CDR-L3. In some embodiments, the $V_H$ sequence has at least 70%, 80%, or 90% identity with SEQ ID NO: 241 and wherein the variable region of the light chain has at least 70%, 80%, or 90% identity with SEQ ID NO: 246, wherein any variation from SEQ ID NO: 241 does not occur within CDR-H1, CDR-H2, or CDR-H3 and wherein any variation from SEQ ID NO: 246 does not occur within CDR-L1, CDR-L2, or CDR-L3. In some embodiments, the $V_H$ sequence has at least 70%, 80%, or 90% identity with SEQ ID NO: 261 and wherein the variable region of the light chain has at least 70%, 80%, or 90% identity with SEQ ID NO: 266, wherein any variation from SEQ ID NO: 261 does not occur within CDR-H1, CDR-H2, or CDR-H3 and wherein any variation from SEQ ID NO: 266 does not occur within CDR-L1, CDR-L2, or CDR-L3. In some embodiments, the $V_H$ sequence has at least 70%, 80%, or 90% identity with SEQ ID NO: 351 and wherein the variable region of the light chain has at least 70%, 80%, or 90% identity with SEQ ID NO: 356, wherein any variation from SEQ ID NO: 351 does not occur within CDR-H1, CDR-H2, or CDR-H3 and wherein any variation from SEQ ID NO: 356 does not occur within CDR-L1, CDR-L2, or CDR-L3. In some embodiments, the $V_H$ sequence has at least 70%, 80%, or 90% identity with SEQ ID NO: 371 and wherein the variable region of the light chain has at least 70%, 80%, or 90% identity with SEQ ID NO: 376, wherein any variation from SEQ ID NO: 371 does not occur within CDR-H1, CDR-H2, or CDR-H3 and wherein any variation from SEQ ID NO: 376 does not occur within CDR-L1, CDR-L2, or CDR-L3. In some embodiments, the $V_H$ sequence has at least 70%, 80%, or 90% identity with SEQ ID NO: 434 and wherein the variable region of the light chain has at least 70%, 80%, or 90% identity with SEQ ID NO: 439, wherein any variation from SEQ ID NO: 434 does not occur within CDR-H1, CDR-H2, or CDR-H3 and wherein any variation from SEQ ID NO: 439 does not occur within CDR-L1, CDR-L2, or CDR-L3. In some embodiments, the $V_H$ sequence has at least 70%, 80%, or 90% identity with SEQ ID NO: 444 and wherein the variable region of the light chain has at least 70%, 80%, or 90% identity with SEQ ID NO: 449, wherein any variation from SEQ ID NO: 444 does not occur within CDR-H1, CDR-H2, or CDR-H3 and wherein any variation from SEQ ID NO: 449 does not occur within CDR-L1, CDR-L2, or CDR-L3. In some embodiments, the $V_H$ sequence has at least 70%, 80%, or 90% identity with SEQ ID NO: 454 and wherein the variable region of the light chain has at least 70%, 80%, or 90% identity with SEQ ID NO: 459, wherein any variation from SEQ ID NO: 454 does not occur within CDR-H1, CDR-H2, or CDR-H3 and wherein any variation from SEQ ID NO: 459 does not occur within CDR-L1, CDR-L2, or CDR-L3. In some embodiments, the $V_H$ sequence has at least 70%, 80%, or 90% identity with SEQ ID NO: 464 and wherein the variable region of the light chain has at least 70%, 80%, or 90% identity with SEQ ID NO: 469, wherein any variation from SEQ ID NO: 464 does not occur within CDR-H1, CDR-H2, or CDR-H3 and wherein any variation from SEQ ID NO: 469 does not occur within CDR-L1, CDR-L2, or CDR-L3. In some embodiments, the $V_H$ sequence has at least 70%, 80%, or 90% identity with SEQ ID NO: 474 and wherein the variable region of the light chain has at least 70%, 80%, or 90% identity with SEQ ID NO: 479, wherein any variation from SEQ ID NO: 474 does not occur within CDR-H1, CDR-H2, or CDR-H3 and wherein any variation from SEQ ID NO: 479 does not occur within CDR-L1, CDR-L2, or CDR-L3.

In certain aspects, any of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474 can be combined with any of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. For example, SEQ ID NO: 11 can be combined with any of SEQ ID NO: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. As another example, SEQ ID NO: 16 can be combined with any of SEQ ID NO: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, or 371; and a $V_L$ sequence having at least about 50%, 60%, 70%, 80%, 90%, 95%, or 99% identity to an illustrative $V_L$ sequence provided in SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. In some embodiments, an antibody provided herein comprises a $V_H$ sequence provided in SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474 with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a VL sequence provided in SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, the percent homology of the variable heavy or variable light chain is to be calculated outside the CDRs. For instance, the percent homology can be calculated in the framework regions In some embodiments, an antibody or antigen binding fragment thereof comprises a heavy chain provided in SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 438, 448, 458, 468 or 478.

In some embodiments, an antibody or antigen binding fragment thereof comprises a light chain provided in SEQ ID NOs: 10, 20, 30, 40, 50, 60, 70, 80, 90, 100, 110, 120, 130, 140, 150, 160, 170, 180, 190, 210, 220, 230, 240, 250, 260, 270, 280, 290, 310, 320, 330, 340, 350, 360, 370, 380, 443, 453, 463, 473, or 483.

In certain aspects, any of SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 438, 448, 458, 468 or 478 can be combined with any of SEQ ID NOs: 10, 20, 30, 40, 50, 60, 70, 80, 90, 100, 110, 120, 130, 140, 150, 160, 170, 180, 190, 210, 220, 230, 240, 250, 260, 270, 280, 290, 310, 320, 330, 340, 350, 360, 370, 380, 443, 453, 463, 473, or 483.

In some embodiments, an antibody provided herein comprises a heavy chain sequence having at least about 50%, 60%, 70%, 80%, 90%, 95%, or 99% identity to an illustrative $V_H$ sequence provided in SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 438, 448, 458, 468 or 478; and a light chain sequence having at least about 50%, 60%, 70%, 80%, 90%, 95%, or 99% identity to an illustrative $V_L$ sequence provided in SEQ ID NOs 10, 20, 30, 40, 50, 60, 70, 80, 90, 100, 110, 120, 130, 140, 150, 160, 170, 180, 190, 210, 220, 230, 240, 250, 260, 270, 280, 290, 310, 320, 330, 340, 350, 360, 370, 380, 443, 453, 463, 473, or 483. In some embodiments, an antibody provided herein comprises a heavy chain sequence provided in SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 438, 448, 458, 468 or 478 with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a light chain sequence provided in SEQ ID NOs: 10, 20, 30, 40, 50, 60, 70, 80, 90, 100, 110, 120, 130, 140, 150, 160, 170, 180, 190, 210, 220, 230, 240, 250, 260, 270, 280, 290, 310, 320, 330, 340, 350, 360, 370, 380, 443, 453, 463, 473, or 483, with up to 1, 2, 3, 4, 5, 6, 7, 8, 9, 10, 11, 12, 13, 14, 15, 16, 17, 18, 19, 20, 21, 22, 23, 24, or 25 amino acid substitutions.

In some embodiments, an antibody or antigen binding fragment polynucleotide sequence comprises a signal sequence as shown in SEQ ID NOs: 427 or 430. In some embodiments, an antibody or antigen binding fragment polypeptide sequence comprises a signal sequence as shown in SEQ ID NOs: 428 or 429.

Fc Region

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, Md., 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

In some embodiments, an antibody is an IgG1 antibody.
In some embodiments, an antibody is an IgG3 antibody.
In some embodiments, an antibody is an IgG2 antibody.
In some embodiments, an antibody is an IgG4 antibody.

Modifications in the CH2 domain can affect the binding of FcRs to the Fc. A number of amino acid modifications in the Fc region are known in the art for selectively altering the affinity of the Fc for different Fc-gamma (Fcγ) receptors. In one embodiment, the Fc comprises one or more modifications to promote selective binding of Fc-gamma receptors.

In some embodiments an antibody described herein includes modifications to improve its ability to mediate effector function. Such modifications are known in the art and include afucosylation, or engineering of the affinity of the Fc towards an activating receptor, mainly FCGR3a for ADCC, and towards C1q for CDC.

In certain embodiments, an antibody provided herein comprises an Fc region with one or more amino acid substitutions which improve ADCC.

In some embodiments, an antibody provided herein comprises one or more alterations that improves or diminishes C1q binding and/or CDC. See U.S. Pat. No. 6,194,551; WO 99/51642; and Idusogie et al., J. Immunol., 2000, 164:4178-4184; each of which is incorporated by reference in its entirety.

Thus, in one embodiment, an antibody described herein can include a dimeric Fc that comprises one or more amino acid modifications that confer improved effector function. In another embodiment, the antibody can be afucosylated to improve effector function.

Fc modifications reducing FcγR and/or complement binding and/or effector function are known in the art. Recent publications describe strategies that have been used to engineer antibodies with reduced or silenced effector activity (see Strohl, W R (2009), Curr Opin Biotech 20:685-691, and Strohl, W R and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, US Patent Publication No. 2011/0212087 (Strohl), International Patent Publication No. WO 2006/105338 (Xencor), US Patent Publication No. 2012/0225058 (Xencor), US Patent Publication No. 2012/0251531 (Genentech), and Strop et al ((2012) J. Mol. Biol. 420: 204-219) describe specific modifications to reduce FcγR or complement binding to the Fc.

Methods of producing antibodies with little or no fucose on the Fc glycosylation site (Asn 297 EU numbering) without altering the amino acid sequence are well known in the art. The GlymaxX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 December; 20 (12):1607-18.) Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety). Another approach to obtaining antibodies with lowered levels of fucosylation can be found in U.S. Pat. No. 8,409,572, which teaches selecting cell lines for antibody production for their ability to yield lower levels of fucosylation on antibodies.

Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety).

Antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

In some aspects, an antibody provided herein comprises an IgG1 domain with reduced fucose content at position Asn 297 compared to a naturally occurring IgG1 domain. Such Fc domains are known to have improved ADCC. See Shields et al., J. Biol. Chem., 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In some embodiments, an antibody provided herein comprises a bisected oligosaccharide, such as a biantennary oligosaccharide attached to the Fc region of the antibody that is bisected by GlcNAc. Such antibody variants may have reduced fucosylation and/or improved ADCC function. Examples of such antibody variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., J. Mol. Biol., 2004, 336:1239-1249; and Yamane-Ohnuki et al., Biotech. Bioeng., 2004, 87: 614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which his incorporated by reference in its entirety.

Examples of cell lines capable of producing defucosylated antibodies include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety).

In some embodiments, an antibody has antibody-dependent cellular phagocytosis (ADCP) activity. ADCP can occur when antibodies bind to antigens on the surface of pathogenic or tumorigenic target-cells. Phagocytic cells bearing Fc receptors on their cell surface, including monocytes and macrophages, recognize and bind the Fc region of antibodies bound to target-cells. Upon binding of the Fc receptor to the antibody-bound target cell, phagocytosis of the target cell can be initiated. ADCP can be considered a form of ADCC.

In some embodiments, the antibodies are capable of forming an immune complex. For example, an immune complex can be a tumor cell covered by antibodies.

In some aspects, an anti-MARCO antibody does not substantially bind myeloid cells present outside of cancer tissue. In some aspects, an anti-MARCO antibody does not substantially bind stimulatory myeloid cells present in cancer tissue.

In some embodiments the antibodies are monoclonal antibodies.

In some embodiments the antibodies are polyclonal antibodies.

In some embodiments the antibodies are produced by hybridomas. In other embodiments, the antibodies are produced by recombinant cells engineered to express the desired variable and constant domains.

In some embodiments the antibodies may be single chain antibodies or other antibody derivatives retaining the antigen specificity and the lower hinge region or a variant thereof.

In some embodiments the antibodies may be polyfunctional antibodies, recombinant antibodies, human antibodies, humanized antibodies, fragments or variants thereof. In particular embodiments, the antibody fragment or a derivative thereof is selected from a Fab fragment, a Fab'2 fragment, a CDR and ScFv.

In some embodiments, antibodies are specific for surface antigens, such as MARCO protein. In some embodiments, therapeutic antibodies are specific for tumor antigens (e.g., molecules specifically expressed by tumor cells). In particular embodiments, the therapeutic antibodies may have human or non-human primate IgG1 or IgG3 Fc portions.

Binding

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. Crosslinking of an antigen target is a type of binding. In some embodiments, an anti-MARCO antibody crosslinks MARCO to MARCO on a MARCO+ cell.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D=k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" (M$^{-1}$), as used herein, refers to the association equilibrium constant of a particular antibody-antigen interaction. $K_A=k_a/k_d$.

When used herein in the context of two or more antibodies, the term "competes with" or "cross-competes with" indicates that the two or more antibodies compete for binding to an antigen (e.g., MARCO). In one exemplary assay, MARCO is coated on a surface and contacted with a first MARCO antibody, after which a second MARCO antibody is added. In another exemplary assay, a first MARCO antibody is coated on a surface and contacted with MARCO, and then a second MARCO antibody is added. If the presence of the first MARCO antibody reduces binding of the second MARCO antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the antibodies for MARCO and the valency of the antibodies. The assays described in this definition are illustrative, and a skilled artisan can utilize any suitable assay to determine if antibodies compete with each other. Suitable assays are described, for example, in Cox et al., "Immunoassay Methods," in *Assay Guidance Manual* [*Internet*], Updated Dec. 24, 2014 (ncbi.nlm.nih.gov/books/NBK92434/; accessed Sep. 29, 2015); Silman et al., Cytometry, 2001, 44:30-37; and Finco et al., *J. Pharm. Biomed. Anal.*, 2011, 54:351-358; each of which is incorporated by reference in its entirety.

In some embodiments, an antibody provided herein binds human MARCO. In some embodiments, an antibody provided herein binds mouse MARCO. In some embodiments, an antibody provided herein binds rhesus macaque MARCO. In some embodiments, an antibody provided herein binds cynomolgus MARCO. In some embodiments, an antibody provided herein binds human, rhesus macaque, and/or cynomolgus MARCO.

In some embodiments, an antibody provided herein binds human MARCO with a $K_D$ of less than or equal to about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.95, 2, 3, 4, 5, 6, 7, 8, 9, or 10×10$^{-9}$ M, as measured by Biacore assay. In some embodiments, the $K_D$ of the antibody provided herein is between about 0.001-0.01, 0.01-0.1, 0.01-0.05, 0.05-0.1, 0.1-0.5, 0.5-1, 0.25-0.75, 0.25-0.5, 0.5-0.75, 0.75-1, 0.75-2, 1.1-1.2, 1.2-1.3, 1.3-1.4, 1.4-1.5, 1.5-1.6, 1.6-1.7, 1.7-1.8, 1.8-1.9, 1.9-2, 1-2, 1-5, 2-7, 3-8, 3-5, 4-6, 5-7, 6-8, 7-9, 7-10, or 5-10×10$^{-9}$ M, as measured by Biacore assay.

In some embodiments, the antibody provided herein binds human MARCO with a $K_D$ of less than or equal to about 2, 1.98, 1.95, 1.9, 1.85, 1.8, 1.75, 1.7, 1.65, 1.6, 1.55, 1.50, 1.45, or 1.4×10$^{-9}$ M, or less, as measured by Biacore assay. In some embodiments, the antibody provided herein binds human MARCO with a $K_D$ between 1.9-1.8, 1.8-1.7, 1.7-1.6, 1.6-1.5, or 1.9-1.5×10$^{-9}$M as measured by Biacore assay. In some embodiments, the antibody provided herein binds human MARCO with a $K_d$ of less than or equal to about 10, 9.56, 9.5, 9.0, 8.88, 8.84, 8.5, 8, 7.5, 7.32, 7, 6.5, 6, 5.5, 5, 4.5, 4, 3.5, 3, 2.5, 2, 1.5, or $1 \times 10^{-4}$ (1/s), or less, as measured by Biacore assay. In some embodiments, the antibody provided herein binds human MARCO with a $K_d$ between 7-10, 7-8, 8-9, 9-10, 7-7.5, 7.5-8, 8.-8.5, 8.5-9, 9-9,5, or $9.5-10 \times 10^{-4}$ (1/s) as measured by Biacore assay. In some embodiments, the antibody provided herein binds human MARCO with a $K_d$ of greater than or equal to about 4, 4.1, 4.2, 4.3, 4.4, 4.5, 4.6, 4.7, 4.8, 4.9, 45, 5.1, 5.2, 5.3, 5.4, 5.5, 5.6, 5.7, 5.8, 5.9, 6, 7, 8, 9, or $10 \times 10^5$ (1/Ms), or more, as measured by Biacore assay. In some embodiments, the antibody provided herein binds human MARCO with a $K_d$ between 4-7, 4-4.5, 4.5-5, 5-5.5, 5.5-6, 6-6.5, or 6.5-7, 7-8, 8-9, or $9-10 \times 10^5$ (1/Ms) as measured by Biacore assay.

In some embodiments, the antibody provided herein binds human MARCO with an EC50 of less than or equal to 2, 1.9, 1.8, 1.7, 1.6, 1.5, 1.4, 1.3, 1.2, 1.1, 0.9, 0.8, 0.7, 0.6, 0.5, 0.4, 0.3, 0.2, or 0.1 nM as measured by measured by flow cytometry. In some embodiments, the antibody binds human MARCO with an EC50 between 0.6-1.4 nM as measured by measured by flow cytometry. In some embodiments, the antibody binds human MARCO with an EC50 of about 0.5, 0.6, 0.9, 1.1, 1.2, 1.3, 1.4, or 1.5 nM as measured by measured by flow cytometry.

In some embodiments, the antibody provided herein binds mouse MARCO with an EC50 of less than or equal to 2, 1.9, 1.8, 1.7, 1.6, 1.5, 1.4, 1.3, 1.2, 1.1, 0.9, 0.8, 0.7, 0.6, 0.5, 0.4, 0.3, 0.2, or 0.1 nM as measured by measured by flow cytometry. In some embodiments, the antibody binds mouse MARCO with an EC50 between 0.6-1.4 nM as measured by measured by flow cytometry. In some embodiments, the antibody binds mouse MARCO with an EC50 of about 0.5, 0.6, 0.9, 1.1, 1.2, 1.3, 1.4, or 1.5 nM as measured by measured by flow cytometry.

In some embodiments, the antibody provided herein does not bind human MARCO with an EC50 great than or equal to 20 nM or more as measured by measured by flow cytometry. In some embodiments, the antibody provided herein does not bind mouse MARCO with an EC50 great than or equal to 3 nM or more as measured by measured by flow cytometry.

To screen for antibodies which bind to an epitope on a target antigen bound by an antibody of interest (e.g., MARCO), a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art.

Competition between antibodies can be determined by an assay in which an antibody under test inhibits or blocks specific binding of a reference antibody to a common antigen (see, e.g., Junghans et al., Cancer Res. 50:1495, 1990; Fendly et al. Cancer Research 50: 1550-1558; U.S. Pat. No. 6,949,245). A test antibody competes with a reference antibody if an excess of a test antibody (e.g., at least 2×, 5×, 10×, 20×, or 100×) inhibits or blocks binding of the reference antibody by, e.g., at least 50%, 60%, 70%, 75%, 80%, 85%, 90%, 95%, or 99% as measured in a competitive binding assay. Antibodies identified by competition assay (competing antibody) include antibodies binding to the same epitope as the reference antibody and antibodies binding to an adjacent epitope sufficiently proximal to the epitope bound by the reference antibody for steric hindrance to occur. For example, a second, competing antibody can be identified that competes for binding to MARCO with a first antibody described herein. In certain instances, the second antibody can block or inhibit binding of the first antibody by, e.g., at least 50%, 60%, 70%, 75%, 80%, 85%, 90%, 95%, or 99% as measured in a competitive binding assay. In certain instances, the second antibody can displace the first antibody by greater than 50%, 60%, 70%, 75%, 80%, 85%, 90%, 95%, or 99%.

In some embodiments, the antibody binds to the Scavenger Receptor Cysteine-Rich (SRCR) domain of MARCO.

In some embodiments, the antibody binds to an epitope on SRCR comprising at least one of residues Q452, Y472, or K473 of wild type human MARCO (SEQ ID NO: 363). In some embodiments, the antibody binds to an epitope on SRCR comprising at least one of residues H505, D507, 5509, or E511 of wild type human MARCO (SEQ ID NO: 363). In some embodiments, the antibody binds to an epitope on SRCR comprising at least one of residues E450, Q452, Q487, or T499 of wild type human MARCO (SEQ ID NO: 363). In some embodiments, the antibody binds to an epitope on SRCR comprising at least one of residues E450, Q452, Q487, T499, H505, D507, 5509, or E511 of wild type human MARCO (SEQ ID NO: 363).

In some embodiments, the antibody or antigen binding fragment thereof binds to at least one of the following residues: Q452, Y472, K473, E450, Q487, T499, H505, D507, S509, or E511 of MARCO listed in SEQ ID NO: 363. In some embodiments, the antibody or antigen binding fragment thereof binds to at least two, three, four, five, six, seven, eight, nine, or ten of the following residues: Q452, Y472, K473, E450, Q487, T499, H505, D507, 5509, or E511 of SEQ ID NO: 363. In some embodiments, the antibody or antigen binding fragment thereof binds to at least two of the following residues: Q452, Y472, K473, E450, Q487, T499, H505, D507, 5509, or E511 of SEQ ID NO: 363. In some embodiments, the antibody or antigen binding fragment thereof binds to at least three of the following residues: Q452, Y472, K473, E450, Q487, T499, H505, D507, 5509, or E511 of SEQ ID NO: 363. In some embodiments, the antibody or antigen binding fragment thereof binds to at least four of the following residues: Q452, Y472, K473, E450, Q487, T499, H505, D507, 5509, or E511 of SEQ ID NO: 363.

In some embodiments, the antibody or antigen binding fragment thereof binds to at least Q452. In some embodiments, the antibody or antigen binding fragment thereof binds to at least Y472. In some embodiments, the antibody or antigen binding fragment thereof binds to at least K473. In some embodiments, the antibody or antigen binding fragment thereof binds to at least E450. In some embodiments, the antibody or antigen binding fragment thereof binds to at least Q487. In some embodiments, the antibody or antigen binding fragment thereof binds to at least T499. In some embodiments, the antibody or antigen binding fragment thereof binds to at least H505. In some embodiments, the antibody or antigen binding fragment thereof binds to at least D507. In some embodiments, the antibody or antigen binding fragment thereof binds to at least 5509. In some embodiments, the antibody or antigen binding fragment thereof binds to at least E511.

Function

In some embodiments, the antibody has antibody-dependent cellular cytotoxicity (ADCC) activity. ADCC can occur when antibodies bind to antigens on the surface of pathogenic or tumorigenic target-cells. Effector cells bearing Fc gamma receptors (FcγR or FCGR) on their cell surface, including cytotoxic T-cells, natural killer (NK) cells, macrophages, neutrophils, eosinophils, dendritic cells, or monocytes, recognize and bind the Fc region of antibodies bound to the target-cells. Such binding can trigger the activation of intracellular signaling pathways leading to cell death. In particular embodiments, the antibody's immunoglobulin Fc region subtypes (isotypes) include human IgG1 and IgG3. As used herein, ADCC refers to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci.* (*USA*) 95:652-656 (1998).

In some embodiments, the antibody has complement-dependent cytotoxicity (CDC) activity. Antibody-induced CDC is mediated through the proteins of the classical complement cascade and is triggered by binding of the complement protein C1q to the antibody. Antibody Fc region binding to C1q can induce activation of the complement cascade. In particular embodiments, the antibody's immunoglobulin Fc region subtypes (isotypes) include human IgG1 and IgG3. As used herein, CDC refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996), may be performed.

In some embodiments, an antibody is an agonistic antibody. An agonistic antibody can induce (e.g., increase) one or more activities or functions of MARCO-expressing cells after the antibody binds a MARCO protein expressed on the cell. The agonistic antibody may bind to and activate MARCO-expressing cells, causing changes in proliferation of the cell or modifying antigen presentation capabilities. The agonistic antibody may bind to and activate MARCO-expressing cells, triggering intracellular signaling pathways that lead to modified cell growth or apoptosis.

In some embodiments, an antibody is an antagonistic antibody. An antagonistic antibody can block (e.g. decrease) one or more activities or functions of MARCO-expressing cells after the antibody binds a MARCO protein expressed on the cell. For example, the antagonist antibody may bind to and block ligand binding to one or more MARCO proteins, preventing differentiation and proliferation of the cell or modifying antigen presentation capabilities. The antagonist antibody may bind to and prevent activation of a MARCO protein by its ligand, modifying intracellular signaling pathways that contribute to cell growth and survival.

In some embodiments an antibody is a depleting antibody. A depleting antibody is one that would kill a MARCO-expressing cell upon contact through the antibody's interaction with other immune cells of molecules. For example, antibodies, when bound to cells bearing MARCO proteins, could engage complement proteins and induce complement-dependent cell lysis. Antibodies, when bound to cells bearing MARCO proteins, could also trigger neighboring cells bearing Fc receptors to kill them by antibody-dependent cellular cytotoxicity (ADCC).

In some embodiments, an antibody is a neutralizing antibody, and the antibody neutralizes one or more biological activities of MARCO-expressing cells. In some embodiments, MARCO protein is expressed on the surface of MARCO-expressing cells and the antibody recognizes the extracellular domain of MARCO protein.

In some embodiments an antibody is selective for MARCO-expressing cells (preferentially binds to MARCO). In certain embodiments, an antibody that selectively binds to MARCO-expressing cells has a dissociation constant (Kd) of range of 0.0001 nM to 1 μM. In certain embodiments, an antibody specifically binds to an epitope on a MARCO protein that is conserved among the protein from different species. In another embodiment, selective binding includes, but does not require, exclusive binding.

In one embodiment an anti-MARCO antibody bound to its target is responsible for causing the in vivo depletion of MARCO-expressing cells to which it is bound. In some embodiments, effector proteins induced by clustered antibodies can trigger a variety of responses, including release of inflammatory cytokines, regulation of antigen production, endocytosis, or cell killing. In one embodiment the antibody is capable of recruiting and activating complement or mediating antibody-dependent cellular cytotoxicity (ADCC) in vivo, or mediating phagocytosis by binding Fc receptors in vivo. The antibody may also deplete MARCO-expressing cells by inducing apoptosis or necrosis of the MARCO-expressing cell upon binding.

In some embodiments the disabling of MARCO-expressing cells is in vitro and is achieved: a) by killing of the MARCO-expressing cells; b) magnetic bead depletion of the MARCO-expressing cells; or c) Fluorescence-activated cell sorting (FACS) sorting of the MARCO-expressing cells.

In some embodiments, an antibody is bound to, or conjugated to an effector molecule. In particular embodiments, an antibody is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

In certain embodiments an antibody is conjugated to a drug, e.g., a toxin, a chemotherapeutic agent, an immune modulator, or a radioisotope. Several methods of preparing ADCs (antibody drug conjugates) are known in the art and are described in U.S. Pat. No. 8,624,003 (pot method), U.S. Pat. No. 8,163,888 (one-step), and U.S. Pat. No. 5,208,020 (two-step method), for example. An antibody or antigen-binding fragment thereof can be conjugated to at least one agent including a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody, and a second antibody fragment that is antigen binding.

In some embodiments, an antibody modulates an immune response. In some embodiments, an antibody increases an immune response. In some embodiments, an antibody enhances or initiates an immune response.

Method of Treating Cancer

In another aspect, the invention provides methods of treating an immune-related condition (e.g., cancer) in an individual comprising administering to the individual an effective amount of a composition comprising an anti-MARCO antibody. In another aspect, the invention provides methods of enhancing an immune response in an individual comprising administering to the individual an effective amount of a composition comprising an anti-MARCO antibody.

In some embodiments, the methods provided herein are useful for the treatment of an immune-related condition in an individual. In one embodiment, the individual is a human.

In some embodiments, the methods provided herein (such as methods of enhancing an immune response) are useful for the treatment of cancer and as such an individual receiving the anti-MARCO antibody has cancer. In some embodiments, the cancer is a solid cancer. In some embodiments, the cancer is a liquid cancer. In some embodiments, the cancer is immunoevasive. In some embodiments, the cancer is immunoresponsive. In some embodiments, the cancer expresses IL-10. In some embodiments, the cancer is a hypoxic cancer. In particular embodiments, the cancer is selected from the group consisting of lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancers. In some embodiments, the cancer is colon cancer, breast cancer, basal-like breast cancer, ovarian cancer, or gastric cancer.

In some embodiments, the treatment results in a decrease in the cancer volume or size. In some embodiments, the treatment is effective at reducing a cancer volume as compared to the cancer volume prior to administration of the antibody. In some embodiments, the treatment results in a decrease in the cancer growth rate. In some embodiments, the treatment is effective at reducing a cancer growth rate as compared to the cancer growth rate prior to administration of the antibody. In some embodiments, the treatment is effective at eliminating the cancer.

In some embodiments, MARCO is expressed at a higher level in the cancer as compared to a non-cancer cell. In some embodiments, IL-10 is expressed at a higher level in the cancer as compared to a non-cancer cell. Levels of MARCO and/or IL-10 can be assessed by any technique known in the field, including, but not limited to, protein assays or nucleic assays such as FACS, Western blot, ELISA, immunoprecipitation, immunohistochemistry, monoplex immunohistochemistry, multiplex immunohistochemistry, flow cytometry, immunofluorescence, radioimmunoassay, dot blotting, immunodetection methods, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, Luminex, MSD, and FISH, and combinations thereof.

Combination Therapies

For the treatment of cancer, the anti-MARCO antibody may be combined with one or more antibodies that inhibit immune checkpoint proteins. Of particular interest are immune checkpoint proteins displayed on the surface of a tumor cell. The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279), are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD-1 are PD-1 ligand 1 (PD-L1; also known as B7-H1 and CD274) and PD-L2 (also known as B7-DC and CD273). PD-L1 is expressed on cancer cells and through binding to its receptor PD-1 on T cells it inhibits T cell activation/function. Inhibitors that block the interaction of PD-1 with its cognate ligands on the cancer cells, PD-L1 and PD-L2, can result in both increased T cell activation and function, and prevent cancer cells from evading the immune system.

In some embodiments, the immunotherapy is an agent that interferes with PD-1 and PD-L1 or PD-L2 binding. In some embodiments, the immunotherapy is an anti-PD1 antibody. In some embodiments, the immunotherapy is an anti-PD-L1 antibody. In some embodiments, the immunotherapy is an anti-PD-L2 antibody.

Various PD-1, PD-L1, and PD-L2 antibodies are known in the art. In some embodiments, the additional therapeutic agent is at least one of: Atezolizumab (PD-L1), Avelumab (PD-L1), Durvalumab (PD-L1), Nivolumab (PD-1), Pembrolizumab (PD-1), Cemiplimab (PD-1), Ipilimumab (CTLA-4), Tremelimumab (CTLA-4), or any combination thereof.

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where an antibody provided herein and the additional therapeutic agent are included in different pharmaceutical compositions, administration of the antibody can occur prior to, simultaneously, and/or following, administration of the additional therapeutic agent.

Method of Immune Modulation

Immunosuppressive M2-like MARCO expressing cells, such as MARCO+ tumor associated macrophages (TAMs), and MARCO+ mMDSCs, are upregulated in IL-10 enriched and hypoxic tumor micro environments (TME). These cells suppress immune cytotoxic activity. Immunosuppression also leads to increased angiogenesis and metastasis.

Anti-MARCO antibodies can activate intra-tumor immunity at least by mediating repolarization of MARCO+ myeloid M2-like TAMs to M1-like TAMs, and repolarization of mMDSCs to pro-inflammatory monocytes. This repolarization can lead to production of cytokines, chemokines, and activation receptors, which in turn leads to activation of T cells, B cells, and NK cells. The repolarization of myeloid M2-like TAMs and mMDSCs can activate T cells, B cells, and NK cells. Once activated, these NK cells, CD8+ T cells, M1-like TAMs and inflammatory monocytes can induce tumor destruction. In addition, the anti-tumor immunity can be modulated by decreasing the M2-like TAMs and immunosuppressive mMDSCs. Anti-tumor immunity may also be mediated by increased antigen presentation and activation of cells in the spleen and lymph nodes. Binding of the anti-MARCO antibody to medullary cord macrophages (MCMs) can induce changes in adhesion and motility in the lymph node, and binding of the anti-MARCO antibody to marginal zone macrophages (MZMs)

in the spleen can lead to changes in adhesion and motility, leading to potential B cell activation.

In some embodiments, repolarization of MARCO+ cells is observed by rapid modulation of phospho-signaling cascades involved in molecular association, enzymatic activity, transcription, translation, and pro-inflammatory signaling (Src, SYK, NF-kB, PI3K/AKT, TLR, STAT6, IL2RA, CAMK, PKC, Raf1, TPL2, MAPKs, cell cycle, survival, cell adhesion and migration, cytoskeletal rearrangement); changes in phagocytosis, adhesion, motility, and chemotaxis; activation of NF-kB reporter activity as single agent and in combination with TLRs agonists; induction of secretion of pro-inflammatory cytokines and chemokines, including but not limited to, IL-1α, IL-10, IL-2, IL-4, IL-6, IL7R, IL-12, IL12-p70, IL-15, IL-18, IL-27, IP-10, IFN-γ, TNFα, MIP1-α, MIP1-13, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, eotaxin; and increasing inflammasome activation and phagocytosis.

Methods of administration of a MARCO antibody as described herein can result in modulation of an immune response. Modulation can be an increase or decrease in an immune response. In some embodiments, modulation is an increase in an immune response.

In one aspect, administration of a MARCO antibody as described herein can result in induction of pro-inflammatory molecules, such as cytokines, chemokines, or expression of myeloid activation receptors by myeloid cells. Generally, induced pro-inflammatory molecules are present at levels greater than that achieved with isotype control. In some embodiments, the myeloid cells are MARCO-expressing (MARCO+) cells. In some embodiments, the MARCO+ myeloid cell is a monocyte or a macrophage. In some embodiments, the MARCO+ macrophage is a tumor associated macrophage (TAM) or a monocyte-derived macrophage (MDM). Such pro-inflammatory molecules in turn result in activation of anti-tumor immunity, including, but not limited to, T cell activation, T cell proliferation, T cell differentiation, M1-like macrophage activation, B cell regulation, and NK cell activation. Thus, the administration of an anti-MARCO antibody can induce multiple anti-tumor immune mechanisms that lead to tumor destruction.

In another aspect, provided herein are methods of increasing an immune response in an individual comprising administering to the individual an effective amount of a composition comprising an anti-MARCO antibody or antigen-binding fragment thereof. In some embodiments, the method of increasing an immune response in a subject comprises administering to the subject an antibody that binds to the SRCR domain of human MARCO (SEQ ID NO: 363). In some embodiments, the method of increasing an immune response in a subject comprises administering to the subject an antibody that competes for binding to human MARCO (SEQ ID NO: 363) with a reference antibody. In some embodiments, the method of increasing an immune response in a subject comprises comprising administering to the subject an antibody that competes for binding to human MARCO (SEQ ID NO: 363), wherein the antibody binds at least one of residues Q452, Y472, and K473 of human MARCO (SEQ ID NO: 363). In some embodiments, the method of increasing an immune response in a subject comprises comprising administering to the subject an antibody that competes for binding to human MARCO (SEQ ID NO: 363), wherein the antibody binds at least one of residues E450, Q452, Q487, and T499 of human MARCO (SEQ ID NO: 363). In some embodiments, the method of increasing an immune response in a subject comprises comprising administering to the subject an antibody that competes for binding to human MARCO (SEQ ID NO: 363), wherein the antibody binds at least one of residues H505, D507, 5509, or E511 of human MARCO (SEQ ID NO: 363).

In some embodiments, the antibody is present in a pharmaceutical composition further comprising a pharmaceutically acceptable excipient.

In any and all aspects of increasing an immune response as described herein, any increase or decrease or alteration of an aspect of characteristic(s) or function(s) is as compared to a cell not contacted with an anti-MARCO antibody.

Increasing an immune response can be both enhancing an immune response or inducing an immune response. For instance, increasing an immune response encompasses both the start or initiation of an immune response, or ramping up or amplifying an on-going or existing immune response. In some embodiments, the treatment induces an immune response. In some embodiments, the induced immune response is an adaptive immune response. In some embodiments, the induced immune response is an innate immune response. In some embodiments, the treatment enhances an immune response. In some embodiments, the enhanced immune response is an adaptive immune response. In some embodiments, the enhanced immune response is an innate immune response. In some embodiments, the treatment increases an immune response. In some embodiments, the increased immune response is an adaptive immune response. In some embodiments, the increased immune response is an innate immune response. In some embodiments, the immune response is started or initiated by administration of an anti-MARCO antibody. In some embodiments, the immune response is enhanced by administration of an anti-MARCO antibody.

In another aspect, the present application provides methods of contacting a cell with an anti-MARCO antibody, which results in the modulation of the immune function of the cell. The modulation can be increasing an immune response or reprogramming of MARCO-expressing cells. In some embodiments, the modulation is an increase in immune function. In some embodiments, the modulation of function leads to the activation of MARCO-expressing myeloid cells. In some embodiments, the modulation of function leads to the reprogramming of MARCO-expressing myeloid cells.

In some embodiments, the cells are myeloid cells. In some embodiments, the cells are MARCO-expressing cells (MARCO+ cells). In some embodiments, the MARCO+ cells are one or more of monocytes, macrophages, tumor associated macrophage (TAM), and monocyte-derived macrophages (MDM). In some embodiments, the MARCO+ cell is a monocyte. In some embodiments, the MARCO+ cell is a macrophage. In some embodiments, the MARCO+ cell is a tumor associated macrophage (TAM). In some embodiments, the MARCO+ cell is a monocyte-derived macrophage (MDM). In some embodiments, contacting a MARCO-expressing cell with a MARCO antibody induces activation of the cell.

In some embodiments, the modulation of function of the MARCO+ cells leads to an increase in the cells' abilities to stimulate both native and activated CD8+ T-cells, for example, by increasing the ability of MARCO-expressing cells to cross-present tumor antigen on MHCI molecules to naive CD8+ T-cells or by increasing cytokine or chemokine secretion by the MARCO-expressing cells. In some embodiments, the modulation of function of the MARCO+ cells leads to an increase in the cells' abilities to stimulate both native and activated CD4+ T-cells, for example, by increasing the ability of MARCO-expressing cells to cross-present tumor antigen on MHCII molecules to naive CD4+ T-cells. In some embodiments, the modulation of function enhances or increases the cells' ability to produce cytokines, chemokines, or costimulatory or activating receptors. In some embodiments, the modulation increases the T-cell stimulatory function of the MARCO+ cell, including, for example, the cells' abilities to trigger T-cell receptor (TCR) signaling, T-cell proliferation, or T-cell cytokine production.

In some embodiments, the increased immune response is secretion of cytokines and chemokines. In some embodiments, the MARCO antibody has agonist activity. In some embodiments, the MARCO antibody induces increased expression of at least one cytokine or chemokine in a cell as compared to an isotype control antibody. In some embodiments, the MARCO antibody induces increased expression of at least one pro-inflammatory cytokine or chemokine in a cell as compared to an isotype control antibody. In some embodiments, the at least one cytokine or chemokine is selected from the group consisting of: IL-1α, IL-1α, IL-2, IL-4, IL-6, IL7R, IL-12, IL12-p70, IL-15, IL-18, IL-27, IP-10, IFN-γ, TNFα, MIP1-α, MIP1-13, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin. In some embodiments, the cytokine or chemokine is IL-2. In some embodiments, the cytokine or chemokine is IL-12. In some embodiments, the cytokine or chemokine secretion is increased between about 1-100-fold 1, 5, 10, 20, 30, 40, 50, 60, 70, 80, 90, 100, 1-10, 10-20, 20-30, 30-40, 40-50, 50-60, 60-70, 70-80, 80-90, or 90-100 fold as compared to an untreated cell or a cell treated with an isotype control antibody. In some embodiments, the chemokine is IL-2 and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody. In some embodiments, the cytokine is IL-12 and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody.

In some embodiments, the MARCO antibody induces decreased expression of at least one gene in a cell as compared to an isotype control antibody. In some embodiments, the at least one gene is ALK, MPB, TMEM37, NHSL2, or SLC46A2. In some embodiments, the gene is decreased between about 1-100-fold 1, 5, 10, 20, 30, 40, 50, 60, 70, 80, 90, 100, 1-10, 10-20, 20-30, 30-40, 40-50, 50-60, 60-70, 70-80, 80-90, or 90-100 fold as compared to an untreated cell or a cell treated with an isotype control antibody.

In some embodiments, the MARCO antibody induces inflammasome activation as compared to an isotype control antibody. Inflammasome activation can be determined by measuring IL-1β and/or IL-18 secretion.

In some embodiments, the MARCO antibody induces repolarization of myeloid M2-like TAMs to M1-like TAMS, and/or repolarization of mMDSCs to pro-inflammatory monocytes as compared to an isotype control antibody.

In some embodiments, the MARCO antibody increases CD8+ T cells, CD4+ T cells, NK cells, dendritic cells, MHCII$^{high}$ monocytes, MHCII$^{mid}$ monocytes, marginal zone macrophages, follicular B cells, and/or red pulp macrophages as compared to an isotype control antibody.

In some embodiments, upon cell contact the antibody decreases TAMs, neutrophils, marginal zone B cells, CD19+ B cells, and/or MHCII− monocytes, as compared to an isotype control antibody.

In some embodiments, the MARCO antibody modulates motility and/or phagocytosis changes by altering cytoskeletal, actin and muscles, and cell-adhesion related pathways in the tumor. In some embodiments, the MARCO antibody results in a pro-inflammatory activation within the TME, comprising M2 to M1 macrophage reprogramming, an increase in the phagocytosis and/or inflammasome, activation of NK cells, and/or activation of T cells.

In some embodiments, the MARCO antibody modulates cell signaling, cell adhesion, cytoskeletal, and motility changes in the lymph nodes. In some embodiments, the MARCO antibody binds to medullary cord macrophages in the lymph nodes and modulates cell adhesion and motility.

In some embodiments, the MARCO antibody modulates cell adhesion, cytoskeletal, migration, motility, cell signaling, and B cell activation in the spleen. In some embodiments, the MARCO antibody binds to marginal zone macrophages in the spleen and modulates cell adhesion, motility, and B cell activation.

In some embodiments, the modulation increases cell adhesion, cytoskeletal, and cell migration as compared to an isotype control antibody. In some embodiments, the modulation induces B cell maturation in the spleen as compared to an isotype control antibody. In some embodiments, the modulation induces cell signaling pathways comprising cell cycle, T cell receptor, phagocytosis, autophagy, and wnt pathways as compared to an isotype control antibody.

In some embodiments, the enhanced immune response is anti-tumor immune cell recruitment and activation.

In some embodiments, the antibody induces a memory immune response as compared to an isotype control antibody. In general, a memory immune response is a protective immune response upon a subsequent exposure to pathogens or antigens that the immune system encountered previously. Exemplary memory immune responses include the immune response after infection or vaccination with an antigen. In general, memory immune responses are mediated by lymphocytes such as T cells or B cells. In some embodiments, the memory immune response is a protective immune response to cancer, including cancer cell growth, proliferation, or metastasis. In some embodiments, the memory immune response inhibits, prevents, or reduces cancer cell growth, proliferation, or metastasis.

In some embodiments, the MARCO antibody induces or increases at least one of the following pathways or a gene associated with: B cell maturation in the spleen, the actin mediated cell contraction pathway, the kinase activation and activity pathway, the Toll-like receptor signaling pathway, the TLR 4 and 9 pathways, GTPase binding and activity, and/or the RAS-Rho signal transduction pathways, as compared to isotype antibody. In some embodiments, the MARCO antibody induces or increases at least one of the following pathways or a gene associated with: the humoral immune response, NK mediated immunity, NK activation, IL-2 and IL-12 production, cell killing, regulation of effector process, T cell proliferation, activation, differentiation, chemotaxis and migration, cell-cell adhesion, phagocytosis, and/or myeloid differentiation, as compared to isotype antibody.

In some embodiments, the MARCO antibody induces or increases at least one of the following pathways or a gene associated with: Natural Killer cell mediated cytotoxicity, T cell receptor signaling pathway, JAK/STAT signaling pathway, cytokine-cytokine receptor interaction, Intestinal immune network for IgA production, leukocyte trans-endothelial migration, chemokine signaling pathway, hematopoietic cell lineage, type II diabetes mellitus, and Fc-epsilon RI signaling pathway, as compared to isotype antibody. In some embodiments, the MARCO antibody decreases or suppresses at least one of the following pathways or a gene associated with: homologous recombination, Alzheimer's disease, RNA polymerase, arginine and proline metabolism, citrate cycle (TCA cycle), porphyrin and chlorophyll metabolism, valine, leucine, and isoleucine degradation, biosynthesis of unsaturated fatty acids, N-glycan biosynthesis, and aminoacyl tRNA biosynthesis, as compared to isotype antibody.

In some embodiments, the MARCO antibody induces or increases at least one of the following pathways or a gene associated with: cytokine-cytokine receptor interaction, Natural Killer cell mediated cytotoxicity, primary immunodeficiency, chemokine signaling pathway, hematopoietic cell lineage, JAK/STAT signaling pathway, T cell receptor signaling pathway, Intestinal immune network for IgA production, neuroactive ligand receptor interaction, and Fc-epsilon RI signaling pathway, as compared to isotype antibody. In some embodiments, the MARCO antibody decreases or suppresses at least one of the following pathways or a gene associated with: glycolysis gluconeogenesis, propanoate metabolism, proteasome, citrate cycle TCA cycle, cardiac muscle contraction, Alzheimer's disease, Huntington's disease, oxidative phosphorylation, ribosome, and Parkinson's disease, as compared to isotype antibody.

In some embodiments, the MARCO antibody induces or increases at least one of the following pathways or a gene associated with: phosphatidylinositol signaling system, focal adhesion, inositol phosphate metabolism, axon guidance, adherens junction, pathways in cancer, regulation of actin cytoskeleton, progesterone mediated oocyte maturation, ERBB signaling pathway, and Wnt signaling pathway, as compared to isotype antibody. In some embodiments, the MARCO antibody decreases or suppresses at least one of the following pathways or a gene associated with: aminoacyl tRNA biosynthesis, lysosome, histidine metabolism, drug metabolism cytochrome p450, proteasome, Alzheimer's disease, Huntington's disease, Parkinson disease, oxidative phosphorylation, and ribosome, as compared to isotype antibody.

In some embodiments, the MARCO antibody induces or increases at least one of the following pathways or a gene associated with: focal adhesion, phosphatidylinositol signaling system, neurotrophin signaling pathway, insulin signaling pathway, inositol phosphate metabolism, MAPK signaling pathway, pathways in cancer, regulation of actin cytoskeleton, ERBB signaling pathway, and adherens junction, as compared to isotype antibody. In some embodiments, the MARCO antibody decreases or suppresses at least one of the following pathways or a gene associated with: metabolism of xenobiotics by cytochrome p450, hematopoietic cell lineage, lysosome, Alzheimer's disease, proteasome, cytokine-cytokine receptor interaction, Huntington's disease, Parkinson's disease, oxidative phosphorylation, and ribosome, as compared to isotype antibody.

In some embodiments, the MARCO antibody induces or increases at least one of the following pathways or a gene associated with: ECM receptor interaction, focal adhesion, tight junction, adheres junction, proteasome, complement and coagulation cascades, cell adhesion molecules and CAMs, pathways in cancers, arrhythmogenic right ventricular cardiomyopathy ARVC, Wnt signaling pathway, regulation of actin skeleton, axon guidance, Huntington's disease, pathogenic *Escherichia coli* infection, Alzheimer's disease, leukocyte transendothelial migration, cytokine-cytokine receptor interaction, basal cell carcinoma, melanogenesis, and hedgehog signaling pathway, as compared to isotype antibody. In some embodiments, the MARCO antibody decreases or suppresses at least one of the following pathways or a gene associated with: cell cycle, aminoacyl tRNA biosynthesis, mismatch repair, glycosylphosphatidylinositol GPI anchor biosynthesis, glycerophospholipid metabolism, and homologous recombination, as compared to isotype antibody.

In some embodiments, the MARCO antibody induces or increases at least one of the following pathways or a gene associated with: cell cycle, proteasome, T cell receptor signaling pathway, DNA replication, ubiquitin mediated proteolysis, regulation of actin cytoskeleton, adherens junction, pathogenic *Escherichia coli* infection, basal transcription factors, pentose phosphate pathway, Fc gamma R mediated phagocytosis, neurotrophin signaling pathway, regulation of autophagy, glycolysis gluconeogenesis, oocyte meiosis, chronic myeloid leukemia, citrate cycle TCA cycle, Wnt signaling pathway, P53 signaling pathway, and natural killer cell mediated cytotoxicity, as compared to isotype antibody. In some embodiments, the MARCO antibody decreases or suppresses at least one of the following pathways or a gene associated with: ABC transporters, glycosylphosphatidylinositol GPI anchor biosynthesis, RNA polymerase, ribosome, arachidonic acid metabolism, glycerophospholipid metabolism, as compared to isotype antibody.

In some embodiments, the MARCO antibody induces IL-2-STAT5 signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response, an complement, inflammatory response pathway, or allograft rejection pathways as compared to an isotype control antibody.

In some embodiments, the MARCO antibody decreases oxidative phosphorylation, mTOR signaling, unfolded protein response, cholesterol homeostasis, fatty acid metabolism, myc targets, glycolysis pathways, a cell cycle pathway, cell survival, cell adhesion, E2F targets pathway, hypoxia, PI3K-AKT signaling pathway, Src signaling pathway, PKC signaling pathway, epithelial to mesenchymal transition signaling pathway, oxidative phosphorylation, or MAPK signaling pathways as compared to an isotype control antibody.

In some embodiments, the MARCO antibody induces increased expression of at least one pro-inflammatory or activation gene in a cell in the tumor as compared to an isotype control antibody. In some embodiments, the MARCO antibody induces or increases expression of at least one of the following genes: Klrk1, Nrc1, Prf1, Cd40, Cd8α, Nod2, Tlr4, Tnf, Nlrp3, Cd274, Clec9α, Cd200r3, 11-27, Cxcl9, Cxcl10, or Cxcl12.

In some embodiments, the MARCO antibody increases CD8+ T cells, CD4+ T cells, NK cells, dendritic cells, MHCII+ macrophages, MHCIIhigh monocytes, and/or MHCIImid monocytes in the spleen and/or tumor.

In some embodiments, the MARCO antibody increases macrophages, marginal zone macrophages, follicular B cells, and/or red pulp macrophages in the spleen and/or tumor.

In some embodiments, the MARCO antibody decreases TAMs, tumor associated neutrophils, plasma B cells, marginal zone B cells, CD19+ B cells, MHCII− monocytes, and/or MHCII− macrophages in the spleen and/or tumor.

In some embodiments, the expression level of the chemokine, cytokine, gene, or pathway is detected by a nucleic acid or protein assay. Exemplary nucleic acid or protein assays include, but are not limited to, FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof.

In some embodiments, the MARCO antibody induces changes in cell adhesion, cytoskeletal, chemotaxis and cell migration upon binding to a MARCO+ cell.

In some embodiments, the antibody crosslinks MARCO to MARCO on the cell surface of a MARCO+ cell. In some embodiments, the contacting is in vitro. In some embodiments, the contacting is in vivo. In some particular embodiments, the contacting is in vivo in a human. In some embodiments, the contacting is effected by administering an anti-MARCO antibody. In some embodiments, the individual receiving the antibody (such as a human) has cancer.

Methods of Disabling, Killing, or Depleting MARCO-Expressing Cells

In one aspect, the present application provides methods of contacting cells with an anti-MARCO antibody, such as a human or humanized antibody, which results in the disabling of the MARCO-expressing cells. Disabling MARCO-expressing cells also encompasses killing and/or depleting MARCO-expressing cells.

In another aspect, the present application provides methods of contacting MARCO-expressing cells with an anti-MARCO antibody, which results in the disabling of the MARCO-expressing cells.

In some embodiments, the MARCO-expressing are myeloid cells. In some embodiments, the MARCO-expressing are one or more of monocytes or macrophages. In some embodiments, the MARCO-expressing cells are one or more of TAM cells and monocyte-derived macrophages (MDM). In some embodiments, the MARCO-expressing cells are monocytic Myeloid Derived Suppressor Cells (mMDSC).

In some embodiments, the present application provides methods of disabling MARCO-expressing cells, comprising contacting the MARCO-expressing cells with a MARCO antibody, thereby killing the MARCO-expressing cells. Disabling refers to rendering a cell partially or completely non-functional. In some embodiments, the disabling of the cells leads to inducing growth arrest in the cells. In some embodiments, the disabling of the cells leads to apoptosis in the cells. In some embodiments, the disabling of the cells leads to lysis of the cells, as for example by complement dependent cytotoxicity (CDC) or antibody-dependent cell cytotoxicity (ADCC). In some embodiments, the disabling of the MARCO-expressing cells leads to necrosis in the cells. In some embodiments, the disabling of the MARCO-expressing cells leads to inducing growth arrest in the cells.

In some embodiments, the disabling of the MARCO-expressing cells leads to inactivating the cells. In some embodiments, the disabling of the MARCO-expressing cells leads to neutralizing the activity of a MARCO protein in the cells. In some embodiments, the disabling of the MARCO-expressing cells leads to reduction in proliferation of the cells. In some embodiments, the disabling of MARCO-expressing cells leads to differentiation of the cells. In some embodiments, the disabling of the MARCO-expressing leads to a decrease in the cells' ability to act as inhibitory antigen presenting cells or leads to an increase in the cells' ability to act as activating antigen-presenting cells. In some embodiments, the disabling of the MARCO-expressing cells leads to the mislocalization of the cells within tumor tissue or tumor microenvironment (TME). In some embodiments, the disabling of the MARCO-expressing cells leads to an altered spatial organization of the cells within tumor tissue or tumor microenvironment. In some embodiments, the disabling of the MARCO-expressing cells leads to an altered temporal expression of the cells within tumor tissue or TME. In some embodiments, the method further comprises removing the MARCO-expressing cells.

In any and all aspects of disabling MARCO-expressing cells as described herein, any increase or decrease or alteration of an aspect of characteristic(s) or function(s) is as compared to a cell not contacted with an anti-MARCO antibody.

In another aspect, the present application provides methods of contacting MARCO-expressing cells with an anti-MARCO antibody, which results in the modulation of function of the MARCO-expressing cells. The modulation can be any one or more of the following. In some embodiments the MARCO-expressing cells are one or more of monocytes, macrophages, TAMs, and MDMs. In some embodiments, the modulation of function of the cells leads to an increase in the cells' abilities to stimulate both native and activated CD8+ T-cells, for example, by increasing the ability of MARCO-expressing cells to cross-present tumor antigen on MHCI molecules to naive CD8+ T-cells. In some embodiments, the modulation of function of the MARCO-expressing cells leads to an increase in the cells' abilities to stimulate both native and activated CD4+ T-cells, for example, by increasing the ability of MARCO-expressing cells to cross-present tumor antigen on MHCII molecules to naive CD4+ T-cells. In some embodiments, the modulation increases the T-cell stimulatory function of the myeloid cells, including, for example, the cells' abilities to trigger T-cell receptor (TCR) signaling, T-cell proliferation, or T-cell cytokine production. In some embodiments, the modulation of function enhances or increases the cells' ability to produce cytokines, chemokines, or costimulatory or activating receptors.

In any and all aspects of decreasing the function of MARCO-expressing cells as described herein, any increase or decrease or alteration of an aspect of characteristic(s) or function(s) is as compared to a cell not contacted with an anti-MARCO antibody.

In some embodiments, the present application provides methods of killing (also referred to as inducing cell death) MARCO-expressing cells, comprising contacting the MARCO-expressing cells with an anti-MARCO antibody, thereby killing the MARCO-expressing cells. In some embodiments the killing is increased relative to MARCO-expressing cells that have not been contacted with an anti-MARCO antibody. In some embodiments, the contacting induces apoptosis in the MARCO-expressing cells. In some embodiments, the MARCO-expressing cells are in a population of immune cells comprising MARCO-expressing cells and non-MARCO expressing cells. In some embodiments, the method further comprises removing the MARCO-expressing cells. In some embodiments, 10%-100% of the cells are killed. In some embodiments, at least 10%, 20%, 30%, 40%, 50%, 60%, 70%, 80%, 90% or 100% of the cells are killed.

In some embodiments, the MARCO-expressing cells are reduced in number. In some embodiments, the MARCO-expressing cells are killed, for example by necrosis, or apoptosis. In some embodiments, the MARCO-expressing cells are induced to undergo growth arrest. In some embodiments, the MARCO-expressing cells no longer proliferate. In some embodiments the spatial localization of the MARCO-expressing cells is altered, and the ratio is increased in a particular region of the TME. In some embodiments the temporal expression of the MARCO-expressing cells is altered, and the ratio is increased during a particular time during the development of the tumor.

Additional Methods

Determining Expression of MARCO

Also provided herein are methods of treating a cancer or modulating an immune response in an individual comprising: determining or having determined the expression of MARCO in the subject; and administering or having administered to the subject an isolated antibody or antigen binding fragment that binds to MARCO.

In some embodiments, the method further comprises determining or having determined the expression level of MARCO in a biological sample from the individual. In some embodiments the biological sample includes, but is not limited to a body fluid, a tissue sample, an organ sample, urine, feces, blood, saliva, CSF and any combination thereof. In some embodiments the biological sample is derived from a tumor tissue. In some embodiments, the expression level of MARCO comprises the mRNA expression level of MARCO. In some embodiments, the expression level of MARCO comprises the protein expression level of MARCO. In some embodiments the expression level of MARCO is detected in the sample using a method selected from the group consisting of FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof.

In some aspects, provided herein are methods of determining an expression level of MARCO protein in a sample from a subject comprising contacting the sample with an anti-MARCO antibody and performing an immunohistochemistry assay. In some embodiments, the antibody comprises RDM5, RDM9, PI-3010.15, PI-3010.25, or PI-3030.41.

In embodiments described herein for detection and/or quantification, the anti-MARCO antibody binds to the MARCO protein, but does not necessarily have to effect a biological response, such as ADCC, although it may have an effect on a biological response. In some embodiments, the antibody binds to soluble MARCO.

In another aspect, the present invention provides methods for identifying an individual who may respond to immunotherapy (e.g. with an anti-MARCO antibody) for the treatment of an immune-related condition (e.g. cancer) comprising: detecting the expression level of MARCO in a biological sample from the individual; and determining based on the expression level of MARCO, whether the individual may respond immunotherapy, wherein an elevated level of MARCO in the individual relative to that in a healthy individual indicates that the individual may respond to immunotherapy. In some embodiments, the MARCO expression in the individual has already been determined. In some embodiments, these methods may also be used for diagnosing an immune-related condition (e.g. cancer) in the individual and are based the expression level of MARCO, wherein an elevated level of MARCO in the individual relative to that in a healthy individual indicates that the individual suffers from cancer. In some embodiments, the expression level of MARCO comprises the mRNA expression level of MARCO. In other embodiments, the expression level of MARCO comprises the protein expression level of MARCO. In some embodiments the expression level of MARCO is detected in the sample using a nucleic acid or protein assay. Exemplary a nucleic acid or protein assays include, but are not limited to, FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof. In these embodiments, the anti-MARCO antibody binds to the MARCO protein, but does not necessarily have to effect a biological response, such as ADCC. In some embodiments the biological sample is derived from a tumor tissue. In some embodiments the biological sample includes, but is not limited to a body fluid, a tissue sample, an organ sample, urine, feces, blood, saliva, CSF and any combination thereof.

In some embodiments, the assay is an immunohistochemistry assay and the antibody comprises RDM5, RDM9, PI-3010.15, PI-3010.25, or PI-3030.41.

Method of Administration

In some embodiments, the anti-MARCO antibody is administered intravenously, intramuscularly, subcutaneously, topically, orally, transdermally, intraperitoneally, intraorbitally, by implantation, by inhalation, intrathecally, intraventricularly, or intranasally. An effective amount of the anti-MARCO antibody may be administered for the treatment of cancer. The appropriate dosage of the anti-MARCO antibody may be determined based on the type of cancer to be treated, the type of the anti-MARCO antibody, the severity and course of the cancer, the clinical condition of the individual, the individual's clinical history and response to the treatment, and the discretion of the attending physician.

Method of Preparation

Antibodies described herein can be produced using recombinant methods and compositions, e.g., as described in U.S. Pat. No. 4,816,567.

In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody) or an amino acid sequence comprising the VHH of a single domain antibody. In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making an antibody is provided, wherein the method comprises culturing a host cell comprising nucleic acid encoding the antibody, as provided above, under conditions suitable for expression of the antibody, and optionally recovering the antibody from the host cell (or host cell culture medium).

For recombinant production of the antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

The term "substantially purified" refers to a construct described herein, or variant thereof that may be substantially or essentially free of components that normally accompany or interact with the protein as found in its naturally occurring environment, i.e. a native cell, or host cell in the case of recombinantly produced heteromultimer that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the heteromultimer or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the heteromultimer or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" heteromultimer produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antibody-encoding vectors include prokaryotic or eukaryotic cells described herein.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome. Host cells can include CHO, derivatives of CHO, NS0, Sp2O, CV-1, VERO-76, HeLa, HepG2, Per.C6, or BHK.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, *flagellates*, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

For example, antibody may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the antibodies described herein are produced in stable mammalian cells, by a method comprising: transfecting at least one stable mammalian cell with: nucleic acid encoding the antibody, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antibody in the expressed product.

In some embodiments is the method of producing an antibody in stable mammalian cells as described herein wherein the expression product of the at least one stable mammalian cell comprises a larger percentage of the desired glycosylated antibody as compared to the monomeric heavy or light chain polypeptides, or other antibodies.

In some embodiments is the method of producing a glycosylated antibody in stable mammalian cells described herein, said method comprising identifying and purifying the desired glycosylated antibody. In some embodiments, the said identification is by one or both of liquid chromatography and mass spectrometry.

If required, the antibodies can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, Ni+2 affinity chromatography if a His-tag is employed or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference. The degree of purification necessary will vary depending on the use of the antibodies. In some instances no purification is necessary.

In certain embodiments the antibodies are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antibodies described herein can be chemically synthesized using techniques known in the art (e.g., see Creighton, 1983, Proteins: Structures and Molecular Principles, W. H. Freeman & Co., N. Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alanine, fluoro-amino acids, designer amino acids such as methyl amino acids, C-methyl amino acids, N-methyl amino acids, and amino acid analogs in general. Furthermore, the amino acid can be D (dextrorotary) or L (levorotary).

Pharmaceutical Compositions

Methods for treatment of immune-related diseases (e.g., cancer) are also encompassed by the present invention. Said methods of the invention include administering a therapeutically effective amount of an anti-MARCO antibody or antigen-binding fragment. The MARCO antibody or antigen-binding fragment can be formulated in pharmaceutical compositions. These compositions can comprise, in addition to one or more of the anti-MARCO antibodies or antigen-binding fragments, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a polypeptide, antibody, or antigen-binding fragment or other pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Kits and Articles of Manufacture

The present application provides kits comprising any one or more of the antibody compositions described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

Additional Embodiments

In one aspect, provided herein are isolated antibodies or antigen binding fragments thereof that binds to human Macrophage Receptor with Collagenous Structure (MARCO) (SEQ ID NO: 384) and competes for binding with a reference antibody, wherein the reference antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:
CDR-H1 comprises the sequence GFSLTSYHVS (SEQ ID NO: 2),
CDR-H2 comprises the sequence AIWTGGSIA (SEQ ID NO: 3),
CDR-H3 comprises the sequence DLSDYYSSYTSFDY (SEQ ID NO: 4),
CDR-L1 comprises the sequence ASEGISNDLA (SEQ ID NO: 431) or XASEGISNDLA (SEQ ID NO: 383), wherein X is arginine (R) or leucine (L),
CDR-L2 comprises the sequence AASRLQD (SEQ ID NO: 8), and
CDR-L3 comprises the sequence QQSYKYPLT (SEQ ID NO: 9).

In some embodiments, CDR-L1 comprises the sequence ASEGISNDLA (SEQ ID NO: 431).

In some embodiments, CDR-L1 comprises the sequence RASEGISNDLA (SEQ ID NO: 27).

In some embodiments, the VH sequence comprises the VH sequence set forth in SEQ ID NO: 61; and the VL sequence comprises the VL sequence set forth in SEQ ID NO: 66.

In some embodiments, the VH sequence comprises the VH sequence set forth in SEQ ID NO: 111; and the and the VL sequence comprises the VL sequence set forth in SEQ ID NO: 116.

In some embodiments, the VH sequence comprises the VH sequence set forth in SEQ ID NO: 1, 11, 21, 31, 41, 51, 61, 71, 81, 91, 101, 111, 121, 131, 434, 444, or 474.

In some embodiments, the VL sequence comprises the VL sequence set forth in SEQ ID NO: 6, 16, 26, 36, 46, 57, 66, 76, 86, 96, 106, 116, 126, 136, 439, 449, or 479.

In some embodiments, the VH sequence comprises the VH sequence set forth in SEQ ID NO: 1, 11, 21, 31, 41, 51, 61, 71, 81, 91, 101, 111, 121, 131, 434, 444, or 474; and the VL sequence comprises the VL sequence set forth in SEQ ID NO: 6, 16, 26, 36, 46, 57, 66, 76, 86, 96, 106, 116, 126, 136, 439, 449, or 479.

In some embodiments, the antibody comprises a heavy chain sequence as set forth in SEQ ID NO: 65; and a light chain sequence as set forth in SEQ ID NO: 70.

In some embodiments, the antibody comprises a heavy chain sequence as set forth in SEQ ID NO: 115; and a light chain sequence as set forth in SEQ ID NO: 120.

In some embodiments, the antibody comprises a heavy chain sequence selected from the sequences set forth in SEQ ID NO: 5, 15, 125, 35, 45, 55, 65, 75, 85, 95, 105, 115, 125, 145, 438, 448, and 478 and a light chain sequence selected from the sequences set forth in SEQ ID NO: 10, 20, 30, 40, 50, 6, 70, 80, 90, 100, 110, 120, 130, 140, 443, 453, and 483.

In some embodiments, the VH sequence consists of the VH sequence set forth in SEQ ID NO: 61; and the VL sequence consists of the VL sequence set forth in SEQ ID NO: 66.

In some embodiments, the VH sequence consists of the VH sequence set forth in SEQ ID NO: 111; and the and the VL sequence consists of the VL sequence set forth in SEQ ID NO: 116.

In some embodiments, the VH sequence consists of the VH sequence selected from the sequences set forth in SEQ ID NO: 1, 11, 21, 31, 41, 51, 61, 71, 81, 91, 101, 111, 121, 131, 434, 444, or 474; and the VL sequence consists of the VL sequence selected from the sequences set forth in SEQ ID NOs: 6, 16, 26, 36, 46, 57, 66, 76, 86, 96, 106, 116, 126, 136, 439, 449, or 479.

In some embodiments, the antibody comprises a heavy chain and a light chain, wherein the sequence of the heavy chain consists of the heavy chain sequence set forth in SEQ ID NO: 65 and the sequence of the light chain consists of the light chain sequence set forth in SEQ ID NO: 70.

In some embodiments, the antibody comprises a heavy chain and a light chain, wherein the sequence of the heavy chain consists of the heavy chain sequence set forth in SEQ ID NO: 115 and the sequence of the light chain consists of the light chain sequence set forth in SEQ ID NO: 120.

In some embodiments, the antibody comprises a human Fc region.

In some embodiments, the human Fc region is a wild-type human IgG1 Fc.

In some embodiments, the antibody comprises a wild type human IgG1 Fc, and wherein the VH sequence comprises the VH sequence set forth in SEQ ID NO: 61, and the VL sequence comprises the VL sequence set forth in SEQ ID NO: 66.

In some embodiments, the antibody comprises a wild type human IgG1 Fc, and wherein the VH sequence comprises the VH sequence set forth in SEQ ID NO: 111, and the VL sequence comprises the VL sequence set forth in SEQ ID NO: 116.

In some embodiments, the antibody binds to human MARCO with a KD of less than or equal to about 0.5, 1, 2, 3, 4, 5, 6, or 7×10-9 M, as measured by surface plasmon resonance (SPR) assay.

In some embodiments, the antibody is humanized.

In one aspect, provided herein are methods of producing an antibody comprising expressing the antibody as disclosed herein from a host cell and isolating the expressed antibody.

In one aspect, provided herein are pharmaceutical compositions comprising the antibody as disclosed herein and a pharmaceutically acceptable excipient.

In one aspect, provided herein are kits comprising the antibody as disclosed herein and instructions for use.

In one aspect, provided herein are isolated antibodies or antigen binding fragments thereof that binds to human MARCO (SEQ ID NO: 384) and competes for binding with a reference antibody, wherein the reference antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:
CDR-H1 comprises the sequence GYTFTDYAVN (SEQ ID NO: 232),
CDR-H2 comprises the sequence WINTQTGKPT (SEQ ID NO: 233),
CDR-H3 comprises the sequence DSYYYSSSLDY (SEQ ID NO: 234),
CDR-L1 comprises the sequence ASAGISNDLA (SEQ ID NO: 432) or XASAGISNDLA (SEQ ID NO: 381), wherein X is arginine (R) or leucine (L),
CDR-L2 comprises the sequence AASRLQD (SEQ ID NO: 238), and
CDR-L3 comprises the sequence QQSYKYPWT (SEQ ID NO: 239).

In one aspect, provided herein are methods of treating cancer in a subject, comprising administering to the subject an antibody that competes for binding to human MARCO (SEQ ID NO: 384) with a reference antibody, wherein the reference antibody comprises a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
CDR-H1 comprises the sequence GFSLTSYHVS (SEQ ID NO: 2),
CDR-H2 comprises the sequence AIWTGGSIA (SEQ ID NO: 3),
CDR-H3 comprises the sequence DLSDYYSSYTSFDY (SEQ ID NO: 4),
CDR-L1 comprises the sequence ASEGISNDLA (SEQ ID NO: 431) or XASEGISNDLA (SEQ ID NO: 383), wherein X is arginine (R) or leucine (L),
CDR-L2 comprises the sequence AASRLQD (SEQ ID NO: 8), and
CDR-L3 comprises the sequence QQSYKYPLT (SEQ ID NO: 9).

In some embodiments, the subject has previously received, is concurrently receiving, or will subsequently receive an immunotherapy, wherein the immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; chemotherapy; a radiotherapy; a small molecule inhibitor; a small molecule agonist; an immunomodulator; and an epigenetic modulator.

In some embodiments, the immunotherapy is an anti-PD1 antibody, an anti-PDL1 antibody, or an anti-CTLA4 antibody.

In one aspect, provided herein are methods of increasing an immune response in a subject, comprising administering to the subject an antibody that competes for binding to human MARCO (SEQ ID NO: 384) with a reference antibody, wherein the reference antibody comprises a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
CDR-H1 comprises the sequence GFSLTSYHVS (SEQ ID NO: 2),
CDR-H2 comprises the sequence AIWTGGSIA (SEQ ID NO: 3),
CDR-H3 comprises the sequence DLSDYYSSYTSFDY (SEQ ID NO: 4),
CDR-L1 comprises the sequence ASEGISNDLA (SEQ ID NO: 431) or XASEGISNDLA (SEQ ID NO: 383), wherein X is arginine (R) or leucine (L),
CDR-L2 comprises the sequence AASRLQD (SEQ ID NO: 8), and
CDR-L3 comprises the sequence QQSYKYPLT (SEQ ID NO: 9).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* 3rd Ed. (Plenum Press) Vols A and B (1992).

Example 1: MARCO is Expressed in Multiple Tumor Types

MARCO bulk RNA expression in multiple cancer types
MARCO mRNA expression in tumor and normal tissues across all indications in The Cancer Genome Atlas (TCGA)

was generated by the BROAD Institute gene expression viewer on firebrowse.org.

Figure 1:
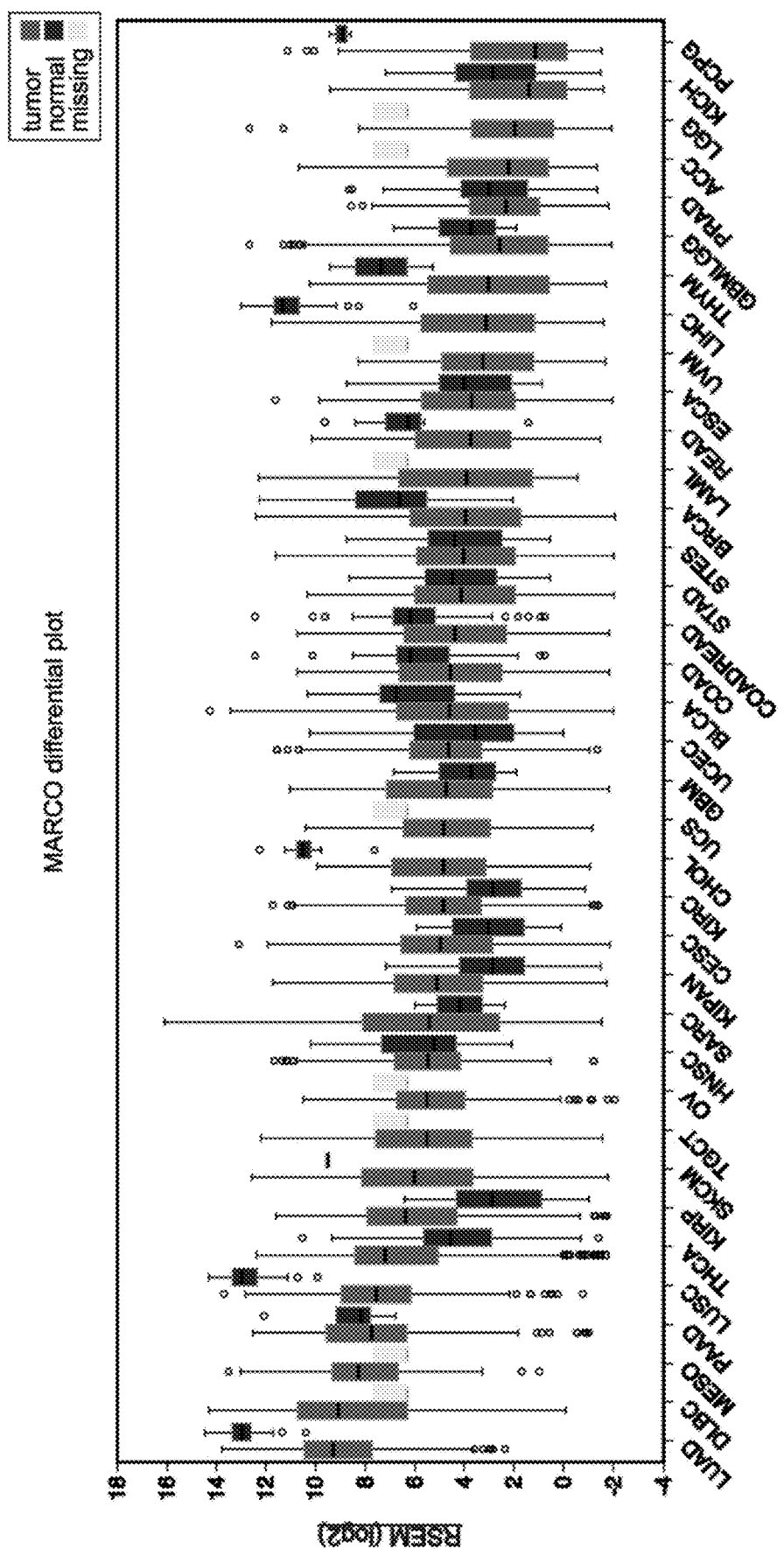
FIG. 1 shows the ordered MARCO mRNA expression in tumor (left bar) vs normal (right bar) tissue.

Ordered MARCO mRNA expression in tumor (left bar) vs normal (right bar) tissue is shown in FIG. 1. The x-axis lists the following tumor types: ACC, adrenocortical carcinoma; BLCA, bladder urothelial carcinoma; BRCA, breast invasive carcinoma; CESC, cervical squamous cell carcinoma and endocervical adenocarcinoma; CHOL, cholangiocarcinoma; COAD, colon adenocarcinoma; COADREAD, colon adenocarcinoma and rectum adenocarcinoma; DLBC, diffuse large b-cell lymphoma; ESCA, esophageal carcinoma; GBM, glioblastoma multiforme; GBMLGG, glioblastoma multiforme and lower grade glioma; HNSC, head and neck squamous cell carcinoma; KICH, kidney chromophobe; KIRC, kidney renal clear cell carcinoma; KIRP, kidney renal papillary cell carcinoma; KIPAN, pan-kidney cohort (KICH+KIRC+KIRP); LAML, acute myeloid leukemia; LGG, brain lower grade glioma; LIHC, liver hepatocellular carcinoma; LUAD, lung adenocarcinoma; LUSC, lung squamous cell carcinoma; MESO, mesothelioma; OV, ovarian serous cystadenocarcinoma; PAAD, pancreatic adenocarcinoma; PCPG, pheochromocytoma and paraganglioma; PRAD, prostate adenocarcinoma; READ, rectum adenocarcinoma; SARC, sarcoma; SKCM, skin cutaneous melanoma; STAD, stomach adenocarcinoma; STES, stomach and esophageal cancer; TGCT, testicular germ cell tumors; THYM, thymoma; THCA, thyroid carcinoma; UCS, uterine carcinosarcoma; UCEC, uterine corpus endometrial carcinoma; UVM, uveal melanoma. The y-axis represents log 2-transformed values of transcript abundance from RNA-seq data, quantified using RNAseq by Expectation-Maximization (RSEM).

MARCO expression in primary tumors by scRNA-seq

Single Cell RNA Sequencing (scRNA-Seq)

1 mL of frozen, dissociated tumor cells from various tumors were purchased from Discovery Life Sciences. The frozen pellet was thawed in a 37C water bath and gradually diluted with 25 mL of warm RPMI containing 10% FBS and 10 mM HEPES, and centrifuged for 5 min at 550 rcf. The cell pellet was stained with anti-CD45-PE (clone HI30, Biolegend). DAPI−, CD45+ cells were sorted on a BD FACSAria Fusion. After sorting, cells were washed with 3 mL of 0.04% BSA/PBS three times and resuspended at $5 \times 10^5$ cells/mL. The cells were loaded into a Chromium Chip B for a targeted cell encapsulation of 10,000 cells, and placed into the Chromium Controller (10× Genomics, Single Cell 3' v3 Reagent Kit). Post GEM-RT cleanup, cDNA amplification and library construction were performed according to the Single Cell 3' v3 user manual from 10× Genomics. The libraries were sequenced on a NovaSeq by MedGenome Inc.

Single Cell Data Processing

Sequencing data was processed using 10× Genomics Cell Ranger v3.0.2 pipeline. MedGenome Inc. provided fastq files for each sample by converting raw, Illumina bcl files into fastq files using the Cell Ranger subroutine mkfastq. Afterwards, Cell Ranger count was run, which utilizes STAR (Dobin et al., 2013) to align reads against the GRCh38 human reference genome. After filtering reads with redundant unique molecular identifiers (UMI), count generated gene-cellular barcode files (filtered_feature_bc_matrix folder consisting of barcodes.tsv, features.tsv, and matrix.mtx). Both mkfastq and count were run with default parameters.

Cellular Identification, Clustering, and Visualization

For each sample, the filtered_feature_bc_matrix files were passed to the R (v. 3.6.0) software package Seurat (Satija et al., 2015) (https://satijalab.org/seurat) (v2.3.4) for all downstream analyses. The features.tsv file was renamed to genes.tsv to be compatible with the Read10× function. Data was filtered for cells that expressed a minimum of 200 genes, all genes were expressed in at least 3 cells, and had no more than 8500 UMI. Cells that contained >20% of reads associated with mitochondrial genes and >45% of reads associated with ribosomal genes were removed. Count data was then log transformed and scaled using each remaining cell's UMI count and proportion of mitochondrial and ribosomal genes as nuisance factors (implemented in Seurat's ScaleData function) to correct for any remaining unwanted effects in downstream clustering and differential expression analyses. For each sample, principal component (PC) analysis was performed on a set of highly variable genes defined by Seurat's FindVariableGenes function. Genes associated with the resulting top PCs (chosen by visual inspection of scree plots) were then used for graph-based cluster identification and subsequent dimensionality reduction using t-distributed stochastic neighbor embedding (tSNE). Cluster-based marker identification and differential expression were performed using Seurat's FindAllMarkers for all between-cluster comparisons. Graphs were plotted using built-in visualization functions in Seurat (TSNEPlot, FeaturePlot).

MARCO is predominantly expressed in human tumor monocytes and macrophages as determined by the scRNA-seq analysis (data not shown). Tumor cells from lung cancer, kidney (RCC) cancer, ovarian cancer, colorectal cancer, and head and neck cancer all showed expression of MARCO on monocytes and macrophages.

MARCO RNA expression is induced by IL-10

Differentiated human macrophages were polarized by adding the following cytokines to the media for 24 hours at 37 C: 50 ng/ml lipopolysaccharide (LPS) (InvivoGen), 25 ng/ml recombinant human IFN-γ (PeproTech), LPS+ IFN-γ, IL-4, IL-10, TGF-β, TGF-β+, or IL-10. The media was then removed and macrophages lysed in 300 μl of RLT buffer+ BME, followed by RNA extraction using the Qiagen kit. The mRNA quantity and quality were assessed by Nanodrop and the Agilent Bioanalyzer before sending the samples to Medgenome for library preparation and RNAseq. MARCO mRNA expression in each of the polarization conditions was then extracted from the RNAseq analysis and plotted in log 2 CPM units.

Figure 2:
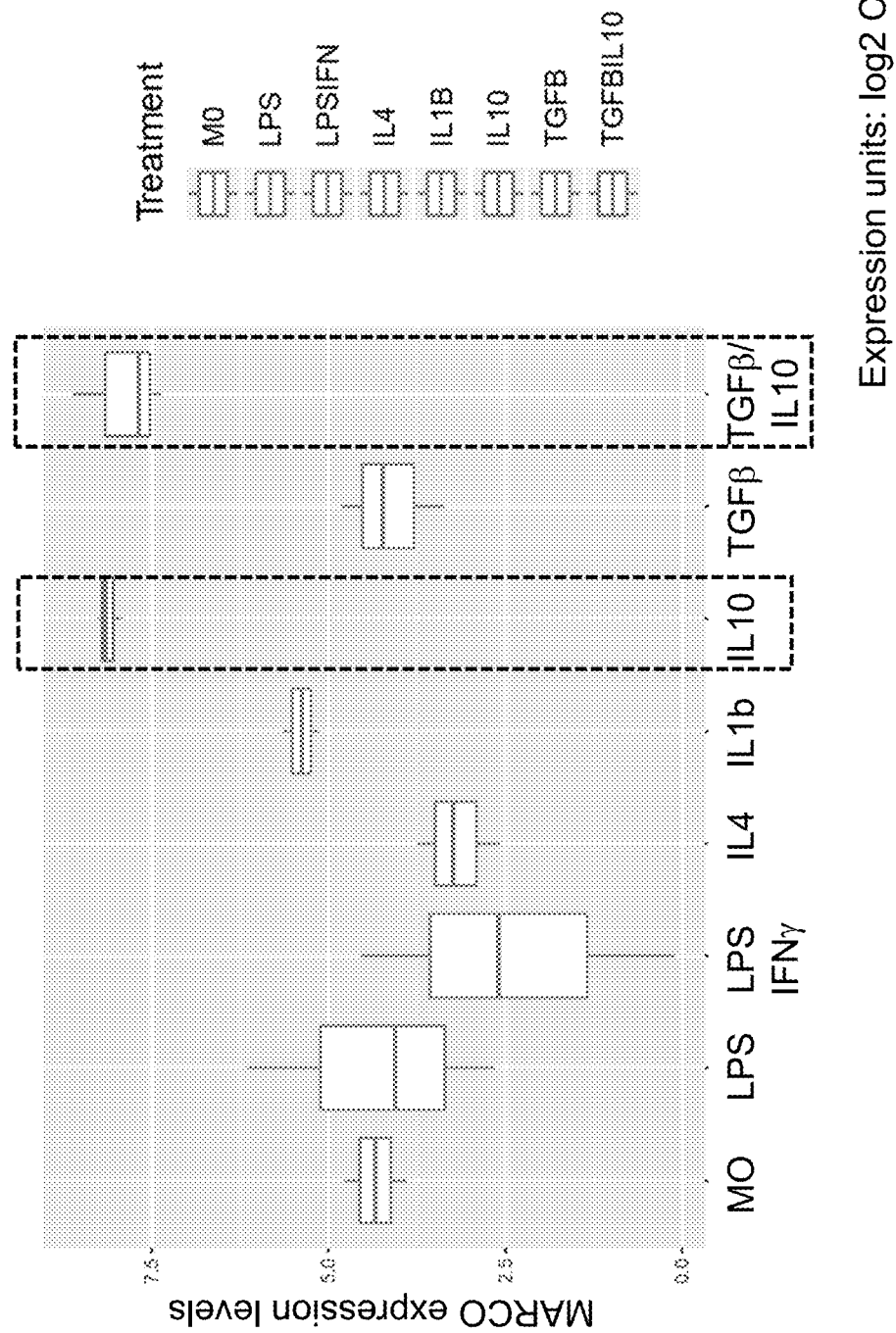
FIG. 2 shows that MARCO RNA expression was induced by IL-10 in Human Monocyte-derived Macrophages (MDMs).

As shown in FIG. 2, MARCO RNA expression was induced by IL-10 in Human Monocyte-derived Macrophages (MDMs)

IL10 and MARCO expression correlate across indications

All single indication, Level 2, RNAseq data from TCGA were downloaded from the Broad Institute using firehose_get. RSEM values for MARCO, IL-10, PTPRC (CD45), and TREM2 expression from tumor samples were converted to log 2 counts per million. Per-indication, median values for MARCO and IL10 expression were plotted in R. Dot size was scaled by the degree of IL10-MARCO Spearman rank correlation. The matrix of per-indication, median expression values for the genes listed above was transformed into a matrix of Spearman correlations and plotted as a heatmap using the pheatmap package in R.

Figures 3A, 3B:
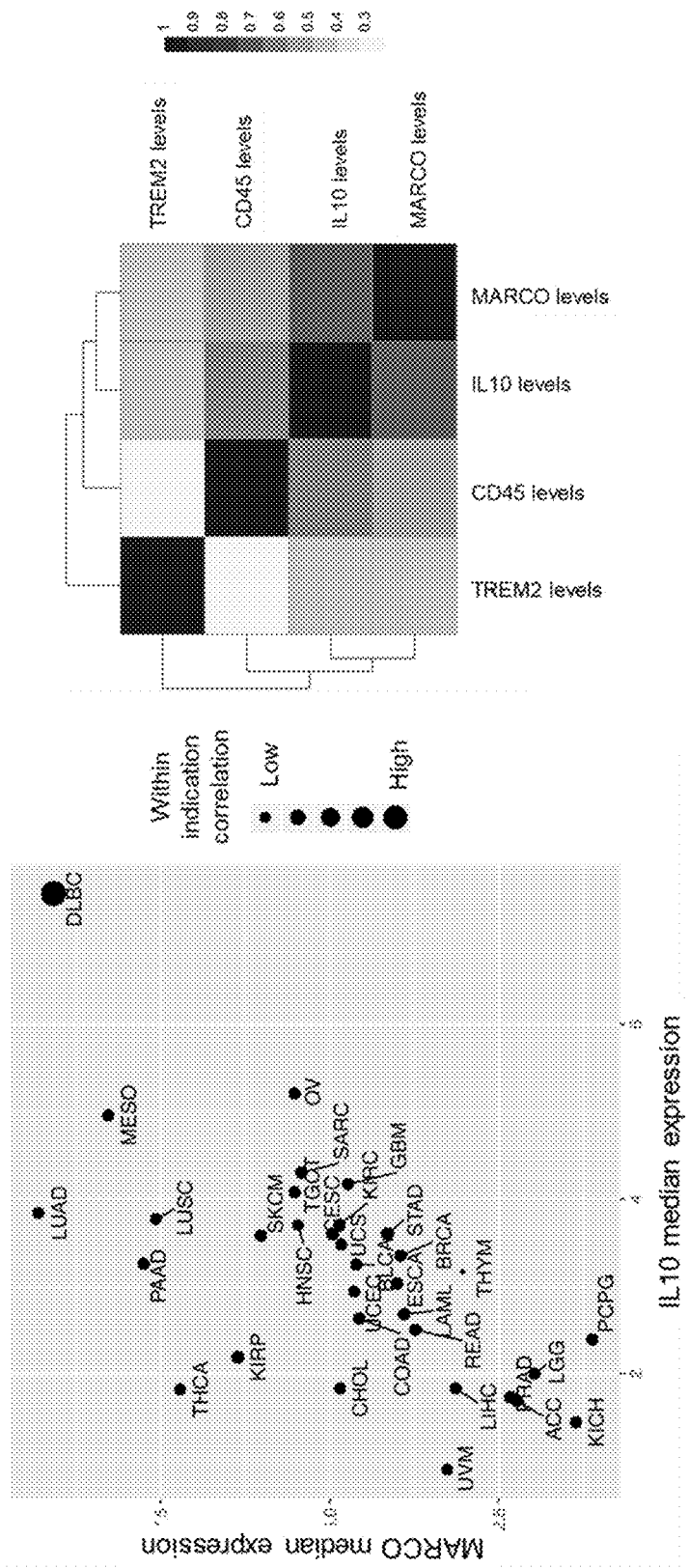
FIG. 3A shows the correlation of MARCO and IL-10 expression in various tumor types.
FIG. 3B shows a heat map of the correlation between TREM2 expression, CD45 expression, IL-10 expression, and MARCO expression.

FIG. 3A shows the correlation of MARCO and IL-10 expression in various tumor types, and FIG. 3B shows a heat map of the correlation between TREM2 expression, CD45 expression, IL-10 expression, and MARCO expression. As shown in FIGS. 3A and 3B, IL10 and MARCO expression are well correlated across cancer indications.

MARCO expression and correlation with patient survival in different indications

In Colorectal Cancer (CRC)

Figure 4A:
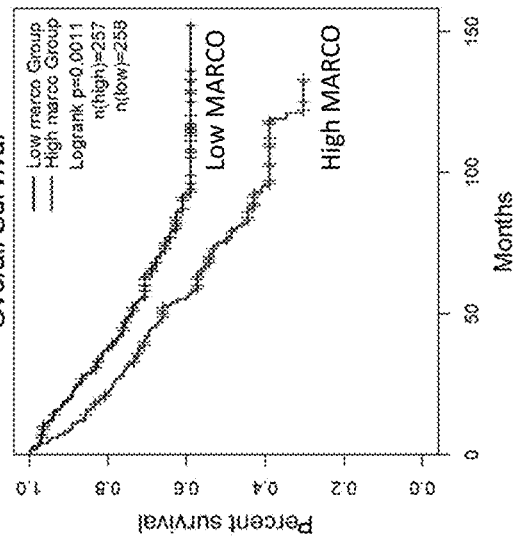
FIG. 4A shows that MARCO expression is inversely correlated with patient survival probability in CRC.

Prenormalized MARCO expression profiles and associated clinical data across 55 colorectal tumors were downloaded from NCBI's GEO website (accession GSE17537). Expression profiles were divided into two cohorts based on median level of MARCO. Kaplan-Meier survival curves were plotted for each cohort and the associated logrank test was carried using the survival and survminer packages in R. As shown in FIG. 4A, MARCO expression inversely correlated with patient survival probability in CRC; higher MARCO expression correlated with lower patient survival probability and lower MARCO expression correlated with higher patient survival probability.

In Renal Cell Carcinoma (RCC)

Survival associations of two cohorts of kidney cancer (renal cell carcinoma) from TCGA based on median split of MARCO mRNA expression generated by the Gene Expression Profiling Interactive Analysis (GEPIA2) viewer at http://gepia2.cancer-pku.cn/#index.

Figure 4B:
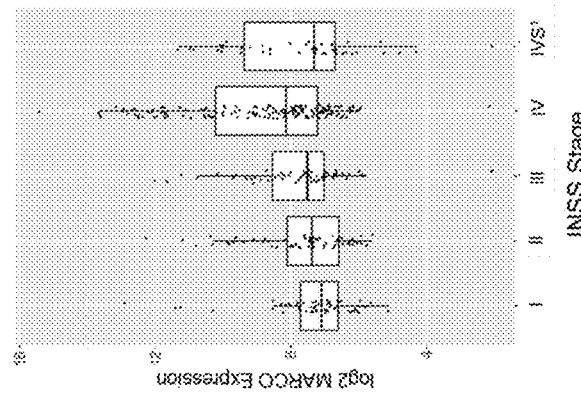
FIG. 4B shows that MARCO expression is inversely correlated with patient survival probability in RCC.

As shown in FIG. 4B, MARCO expression is inversely correlated with patient survival probability in RCC; higher MARCO expression correlated with lower patient survival probability and lower MARCO expression correlated with higher patient survival probability in RCC.

In Neuroblastoma

Pre-normalized MARCO expression profiles and associated clinical data across 498 neuroblastoma tumors were downloaded from NCBI's GEO website (accession GSE62564). Expression profiles were divided into two cohorts based on median level of MARCO. Kaplan-Meier survival curves were plotted for each cohort and the associated logrank test was carried using the survival and survminer packages in R.

Figure 4C:
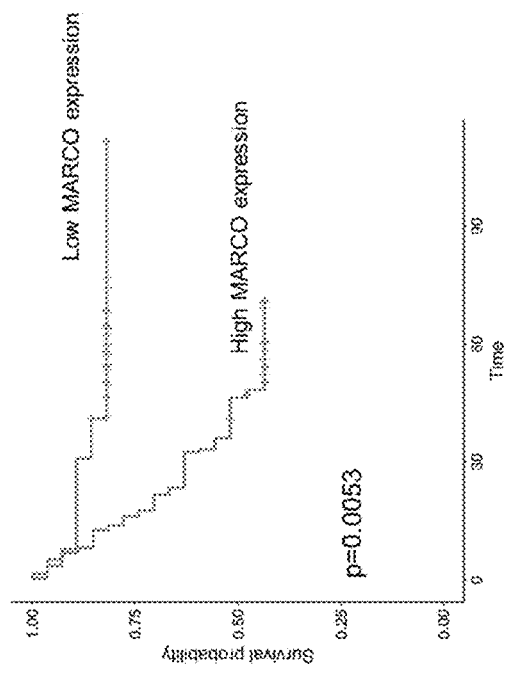
FIG. 4C shows that MARCO expression is inversely correlated with patient survival probability in neuroblastoma.

As shown in FIG. 4C, MARCO expression is inversely correlated with patient survival probability in neuroblastoma; higher MARCO expression correlated with lower patient survival probability and lower MARCO expression correlated with higher patient survival probability in neuroblastoma.

Figure 4D:
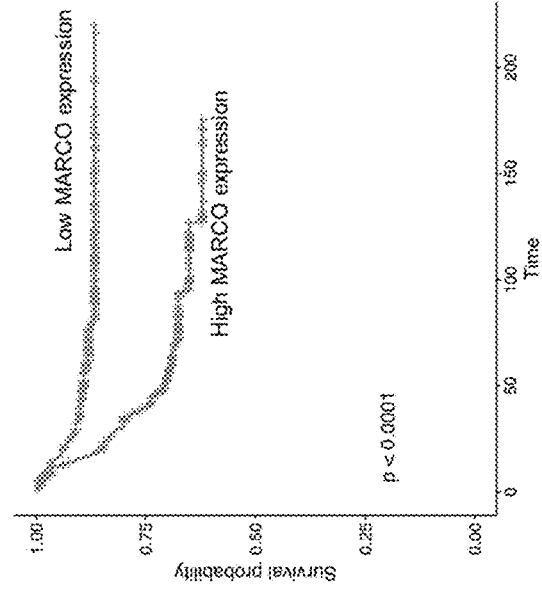
FIG. 4D shows that MARCO expression increased as function of disease severity in neuroblastoma, according to INSS stage.

Prenormalized MARCO expression profiles and associated clinical data across 394 neuroblastoma tumors were downloaded from NCBI's GEO website (accession GSE120572). MARCO expression profiles were plotted for all samples with an identified INSS Stage. Statistics for paired comparisons were generated using the Wilcoxon Rank Sum Test in R. As shown in FIG. 4D, MARCO expression increased as function of disease severity in neuroblastoma, according to INSS stage.

In Basal-Like Breast cancer

MARCO expression from TCGA across PAM50 subtyping of human breast cancer generated by the Gene Expression Profiling Interactive Analysis (GEPIA2) viewer at gepia2.cancer-pku.cn/#index. METABRIC expression profiling and associated clinical data was downloaded from cBioPortal at cbioportal.org. Normalized MARCO expression profiles were plotted in R across cohorts based on PAM50 subtyping. Statistics for paired comparisons were generated using the Wilcoxon Rank Sum Test in R.

Figure 5:
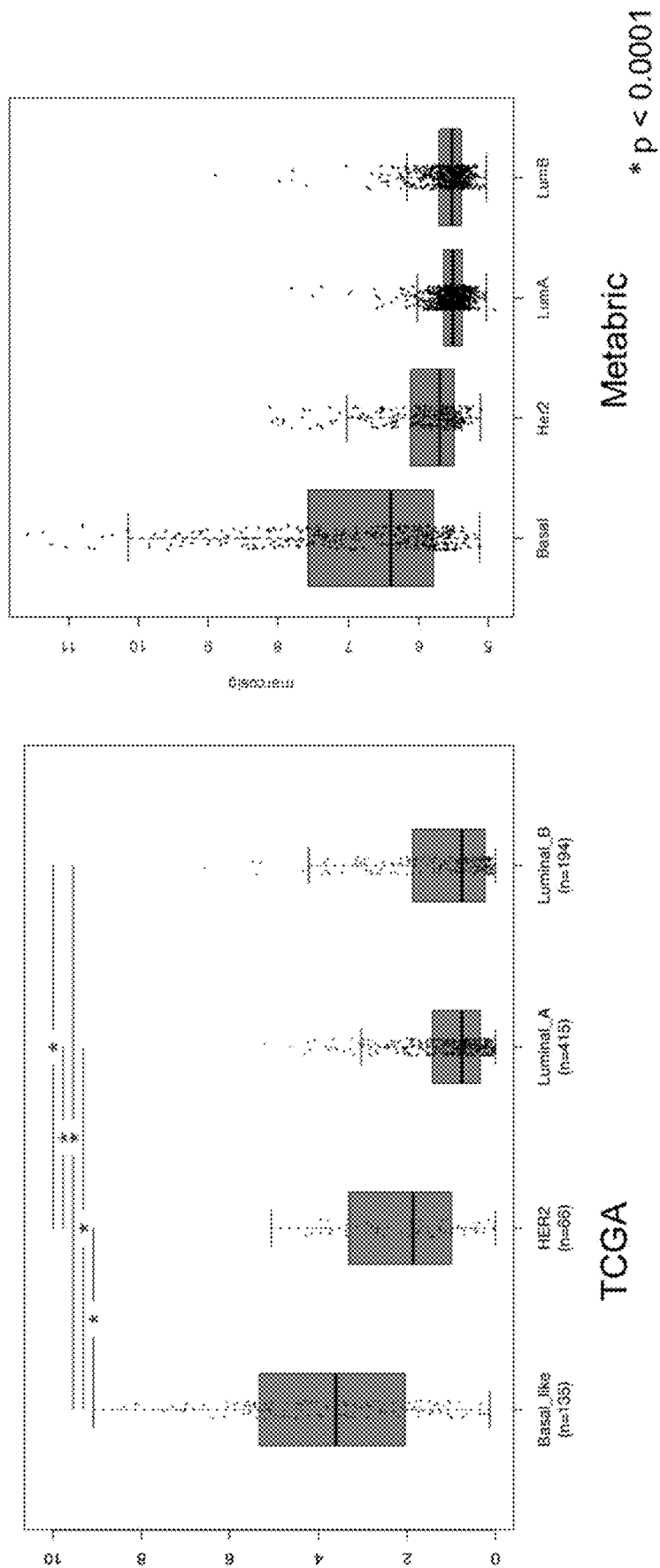
FIG. 5 shows that MARCO is upregulated in basal-like breast cancer relative to other breast cancer subtypes.

As shown in FIG. 5, MARCO is upregulated in basal-like breast cancer relative to other breast cancer subtypes. The left panel shows the MARCO expression from TCGA, the right panel shows the MARCO expression from METABRIC.

MARCO is highly expressed on a population of intratumoral intermediate monocytes. Gene signatures of immune desert and exclusion were upregulated in the MARCO+ cluster. Aggregated TAMs and monocytes derived from single cell sequencing of human immune cells from bladder, breast, colorectal, endometrial, gastric, head and neck, kidney, lung, and ovarian tumors yielded a single cluster with substantially elevated MARCO expression in transitioning monocytes (cluster 2). Gene Set Enrichment Analysis (GSEA) of Hallmark pathways (MARCO-rich cluster 2 vs. all other macrophages and monocytes) showed that MARCO expression was associated with immunosuppressive, matrix-associated gene sets (e.g., angiogenesis, EMT) and downregulated for inflammatory, interferon-based pathways. Significant (FDR <0.05) pathways identified that were upregulated in MARCO+ cells were glycolysis, oxidative phosphorylation, epithelial mesenchymal transition, hypoxia, xenobiotic metabolism, angiogenesis, cholesterol homeostasis, adipogenesis, fatty acid metabolism, reactive oxygen species pathway, and mTORC1 signaling. Significant (FDR <0.05) pathways identified that were downregulated in MARCO+ cells were allograft rejection, TGF-b signaling, KRAS signaling DN, TNFα signaling vi NF-kB, IFNγ response, and IFNα response.

Example 2: Production and Characterization of Anti-Human MARCO Antibodies

First Generation of Hybridomas

An antibody campaign was performed at Antibody Solutions (Sunnyvale, Calif.) with two Rapid campaigns on 3 Balb/c mice each and one standard campaign on 4 Balb/c mice using a human MARCO His-tagged extracellular domain (His-ECD 147-520, using residues 147-419 of the Collagen-like domain (CLD) and residues 424-520 of the Scavenger Receptor Cysteine-Rich (SRCR) domain, Pi-114) as the immunogen. The rapid immunization program consisted of 10 injections, 2× a week, utilizing the footpad as the route. The standard immunization program consisted of 5 injections over the course of 12 weeks, utilizing the subQ as the route. Rapid 1 campaign included TLR+ anti-CTLA4 for adjuvants while Rapid 2 campaign included TLR+ anti-GITR. The mouse serum was tested at different timepoints for antigen titer by ELISA. Spleen and lymph nodes from the mouse from Rapid 1 campaign with the highest titer were fused and the hybridoma library was created to provide an immortal population of antibody producing cells representing the stimulated B-cell population responding to the antigen. Single cell cloning by FACS sorting was performed to generate single clones hybridomas for monoclonal antibody cultures. 2,880 clones were then screened by dual flow cytometry for binding to mouse and human 293T overexpressing MARCO cell lines and using a GFP expressing cell line (GFP-293T) as the negative control for no binding. 33 clones were identified from the primary screen with cross-reactivity to both human and mouse MARCO and with no to low background binding and were additionally screened by ELISA on the MARCO human antigen Pi-114. Hybridoma supernatants from the 33 clones were checked for cell binding by flow cytometry.

Generation of Stably Overexpressing Cell Lines

Mouse and human MARCO DNA sequences were cloned in the pLenti-GIII-CMV-GFP-2A-Puro lentiviral vector at Abmgood (Vancouver, Canada) and amplified using standard bacterial transformation protocols using *E. coli* DH5-alpha strains to produce high yields of plasmid for lentiviral packaging. Viral particles from the empty GFP control vector, Human MARCO, and mouse MARCO cloned lentiviral vectors were produced and packaged in 293T cells and concentrated for high titers. 293T cells were used as the target cells for infection using the virus provided by Abmgood following their protocols and guidelines. Puromycin was used to select for infected pools and single clones expressing homogeneous high levels of Mouse MARCO (293T_MuMARCO), human MARCO (293T_HuMARCO), and GFP (293T_GFP) were expanded.

pD2109-CMV-puromycin lentiviral backbone was subsequently generated to clone additional MARCO plasmids without and with IRES-GFP: Human MARCO full length with GFP (plasmid 3012) and without GFP (plasmid 3010), Mouse MARCO full length with GFP (plasmid 3013) and without GFP (plasmid 3011), Cynomolgus MARCO (cyno MARCO) full length with GFP (plasmid 3021) and without GFP (plasmid 3014), Human MARCO CLD only (1-419, plasmid 3022), and the chimera Mouse MARCO CLD— human MARCO SRCR with IRES-GFP (plasmid 3020). 293FT cells from Sigma were transfected with the above constructs using Fugene to produce lentiviral particles and subsequently transduce 293T cells. Puromycin was used to select the positive clones, which were expanded to generate the following stable pools of cells for in vitro use: 3010 (Hu_MARCO), 3012 (Hu_MARCO_GFP), 3011 (Mu_MARCO), 3013 (Mu_MARCO_GFP), 3014 (Cy_MARCO), 3021 (Cy_MARCO_GFP), 3020 (Mu-CLD_HuSRCR_GFP), and 3022 (Hu_MARCO_CLD).

Characterization of Binding of the Anti-MARCO Hybridomas and Anti-MARCO Antibodies to Cell Surface Expressed MARCO HEK293T cells expressing human MARCO (293T HuMARCO), mouse MARCO (293T_MuMARCO), cyno MARCO (CyMARCO), and GFP-expressing control cell line (293T_GFP) were maintained in DMEM (Gibco) with 10% FBS at 37° C. Cells were counted and then harvested by centrifugation at 400×g for 5 minutes (min). Supernatants were removed and cell pellets were resuspended in $Ca^{2+}$+ and $Mg^{2+}$+ Dulbecco's phosphate-buffered saline (D-PBS) at $1\times10^6$ cells/ml. 100,000 cells/well were plated onto U-bottom 96-well plates for staining and all centrifugation steps were performed at 1500 rpm at 4° C. for 5 min and samples were kept protected from light throughout the protocol. Cells were pelleted and resuspended in 100 µl of Zombie NIR viability dye (BioLegend) prepared by diluting Zombie NIR dimethyl sulfoxide (DMSO) stock 1000-fold in D-PBS. Cells were stained by incubation for 10 min at room temperature (RT) in the dark, followed by quenching the staining reaction with the addition of 100 µl of Staining Medium (D-PBS containing 2% FBS and 2 mM ethylenediaminetetraacetic acid (EDTA). Cells were pelleted and resuspended in 100 µl of the different antibodies and hybridomas supernatants needed for screening and corresponding isotype controls in freshly prepared staining medium, such as PI-M014 and mIgG2b isotype. All mAbs were tested at the final top concentration of 100 nM (15 µg/ml) followed by an 8-point three-fold serial dilution, including 0 mg/ml control. Staining was carried out for 1 hour (hr) on ice, followed by 2 washes in Staining Medium. Cells were then pelleted and resuspended in 100 µl of allophycocyanin (APC)-conjugated goat anti-mouse IgG (Fc-specific) secondary antibody, prepared by 500-fold dilution of the antibody stocks in Staining Medium, and incubated for 30 min on ice. Plates were then washed two times with Staining Medium, followed by resuspension in 150 µl of the same buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8). Half-maximal effective concentrations ($EC_{50}$) were calculated based on geometric mean fluorescence intensities (gMFI). In case when the plates were not able to be analyzed on the cytometer, cells were pelleted after the washes and fixed in 100 µl of 2% paraformaldehyde (PFA), prepared by diluting the 16% (w/v) stock (Thermo Fisher) in DPBS, for 15 min at RT. Cells were then pelleted and the fixative was removed, followed by resuspension in 150 µl of Staining Medium and stored at 4° C. until acquisition on the flow cytometer.

FIG. 6A shows the binding of the 33 antibodies to GFP-239T control cells (left bar), or cells expressing human MARCO (middle bar) or mouse MARCO (right bar). FIG. 6B shows flow cytometry histograms of one MARCO antibody, PI-M014, binding to cells expressing huMARCO, muMARCO, and CynoMARCO, as compared to control cells (GFP control). FIG. 6C shows a titration of PI-M014 and isotype control antibody binding to cells expressing huMARCO. PI-M014 bound to huMARCO with an EC50 of 1.37 nM.

Characterization of binding of the anti-MARCO hybridomas and anti-MARCO antibodies to recombinant MARCO by ELISA Hybridomas from Antibody Solutions or the anti-MARCO antibodies were screened by enzyme-linked immunosorbent assay (ELISA) on recombinant human MARCO protein (Pi-114 His tag). Briefly, 96-well plates (Biolegend) were coated with 1 ug/well of recombinant MARCO protein, overnight in D-PBS. Plates were washed 3× with PBS/0.1% TWEEN-20/2 mM EDTA (ELISA wash buffer) and blocked with 1% BSA for 2 hrs at RT. Antibodies were incubated for 1 h at RT at the final top concentration of 5 µg/ml followed by an 8-point three-fold serial dilution in PBS, including 0 mg/ml control. Plates were washed as above and incubated with goat anti-mouse IgG F(ab')2 Fragment-HRP conjugated secondary antibody (Jackson Immuno) at 1:5000 dilution for 1 hr at room temperature. Plates were washed 4 times in the above ELISA wash buffer and developed with TMB substrate for 10 min (Thermo) and stopped with TMB Stop Solution (1M $H_3PO_4$ Phosphoric Acid), and the A450 determined using a plate reader (SpectraMax i3x).

MARCO Antibody Kinetics Characterization by SPR

Surface plasmon resonance (SPR) was performed on the BIAcore™ T200 (GE Healthcare) instrument and all data were collected at 25° C. using multi cycle kinetics. An anti-mouse Fc mAb (GE Healthcare) was immobilized on a CM4 biosensor chip (GE Healthcare) using amine coupling chemistry with 4500 RUs as target for immobilization of the mAb. Serial dilution of were made in mobile buffer containing 10 mM HEPES pH 7.4, 150 mM NaCl, 3 mM EDTA and 0.05% (v/v) surfactant P20. Anti-mouse Fc mAb was used to capture select monoclonal antibodies against human MARCO antigen (ligand). The anti-MARCO antibodies tested were PI-M014, PI-M015, PI-M017, and PI-M018. The interacting analyte used was N-terminally polyhistidine tagged human MARCO ECD (147-520) termed PI-RG-3000 The following range of antibody concentrations was injected into flow cells: 0.625 nM, 1.25 nM, 2.5 nM, 5 nM and 10 nM. A flow rate of 304/min, with an association and dissociation time of 90 and 600 seconds, respectively. After each cycle (comprising of the antigen capture, antibody association and dissociation phases), the cell surface was regenerated by injecting 10 mM glycine HCl buffer pH 1.7 for 100 seconds at 504/min flowrate. Kinetic evaluation was performed using BIAevaluation 3.1 software to determine single cycle and multi cycle kinetics.

PI-M014 monomer had a $K_D$ of 3.91 nM in a single SPR cycle, and a $K_D$ of 1.32 nM in a multi cycle assay. PI-M015 monomer had a $K_D$ of 0.39 nM in a multi cycle assay. PI-M017 monomer had a $K_D$ of 0.96 nM in a multi cycle assay. PI-M018 monomer had a $K_D$ of 1.65 nM in a multi cycle assay.

MARCO Cell Surface Expression on Human Monocyte Derived Macrophages

Frozen human peripheral blood CD14$^+$ monocytes isolated from peripheral blood mononuclear cells using negative immunomagnetic selection (StemCell Technologies) were thawed and cultured in RPMI 1640 medium supplemented with 10% (v/v) heat-inactivated FBS (HyClone), 1 mM sodium pyruvate, non-essential amino-acids, 2 mM L-glutamine, 55 uM 2-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 12-15×10$^6$ cells in 15 cm dish. At day 3 of differentiation, media was replenished with the addition of fresh M-CSF. After 7 days of differentiation, macrophages were gently harvested non-enzymatically using a sterile cell scraper (Nunc) into FACS buffer (D-PBS containing 2 mM EDTA and 0.5% (w/v) bovine serum albumin (BSA) (Sigma)) followed by centrifugation at 400×g for 5 min at ~20° C.

Cells were counted and seeded onto 96-well plates at 250,000 cells per well. 100 ul of Zombie NIR viability dye (BioLegend), prepared by diluting the stock 1000-fold in D-PBS, was added to each well and incubated for 10 min at RT in the dark. The reaction was quenched by addition of 150 ul of FACS buffer, followed by centrifugation at 400×g for 5 min at 4° C. Cells were then incubated in 100 ul of blocking solution, containing 2.5% mouse and 2.5% rat serum and human TruStain FcX (BioLegend) diluted 50-fold in Fc receptor blocker (Innovex Biosciences), for 20 min in the dark. Cells were then washed and resuspended in 100 μl of the different antibodies needed for screening and corresponding isotype controls in freshly prepared in FACS buffer (PI-M014, PI-M015, PI-M017, PI-M018, mouse IgG2a and mouse IgG2b all APC-conjugated with the Thermo Fisher conjugation kit). mAbs were tested in single point concentrations (3.33 μg/ml for PI-M014 or 5 μg/ml for the other mAbs) and primary incubation was carried out for 20-30 min on ice, followed by 2 washes in FACS buffer. Cells were resuspended in 150 ul of the same buffer for acquisition on the flow cytometer (Attune NxT, Life Technologies). Flow cytometry data were analyzed using FlowJo software and data were processed and further analyzed in Microsoft Excel and GraphPad Prism software.

PI-M014 bound to human monocyte-derived macrophages, as shown in FIG. 6D.

Mouse Antibody-Dependent Cellular Phagocytosis (ADCP) Assay

Bone marrow derived macrophages were generated as demonstrated previously, using 25 ng/ml of murine CSF-1 (Peprotech) for differentiation. On day 6 of culture, 25 ng/ml of murine IFN-γ (peprotech) was added to the BMDM culture for 18 hours. The following day, cells were stimulated with 200 ng/ml LPS (invivogen) for 2 hours before use in ADCP assay. IFN-γ/LPS-induced BMDM served as effector cells and the GFP+ HEK293T cells transduced with human MARCO (293T Hu_MARCO) or control (293T_GFP) were targets. After harvest, effector BMDM were stained with Cell-Trace Violet dye (invitrogen) for 20 minutes at 37° C. 50,000 target cells were plated in 96-well U-bottom plates and co-incubated with anti-MARCO mAbs or corresponding isotype (PI-M014 to PI-M018). Antibodies were serially diluted and prepared in media for 30 minutes at 37° C. Effector cells were then added to Antibody-Target plates at a 3:1 ratio (150,000 effectors to 50,000 targets) and incubated for 2 hours at 37° C. Following incubation, cells were viability stained using Zombie NIR (BioLegend) then fixed using 2% Paraformaldehyde (Invitrogen) for 20 minutes at room temperature prior to being run on an Attune NXT flow cytometer (ThermoFisher). ADCP activity was assessed based on double-positivity of Cell Trace Violet and GFP levels, gated downstream of live cells.

Incubation of target cells with PI-M015 and PI-M017 both induced ADCP activity by effector cells. The results are summarized in Table 1, below.

HuMARCO Antibody Epitope Binning

The ForteBio Blitz label free system was used to analyze the epitopes for the anti-MARCO antibodies.

For the tandem format, N-terminal his-tagged MARCO protein was loaded onto the ForteBio anti-his probe followed by baseline and then association with the first antibody. Following binding of the first antibody, a second antibody was added and the association of the second set of antibodies was measured. Any additional binding observed for the second antibody, measured as an increased signal indicates that the second antibody bound to a different epitope than the first antibody.

Figure 7:
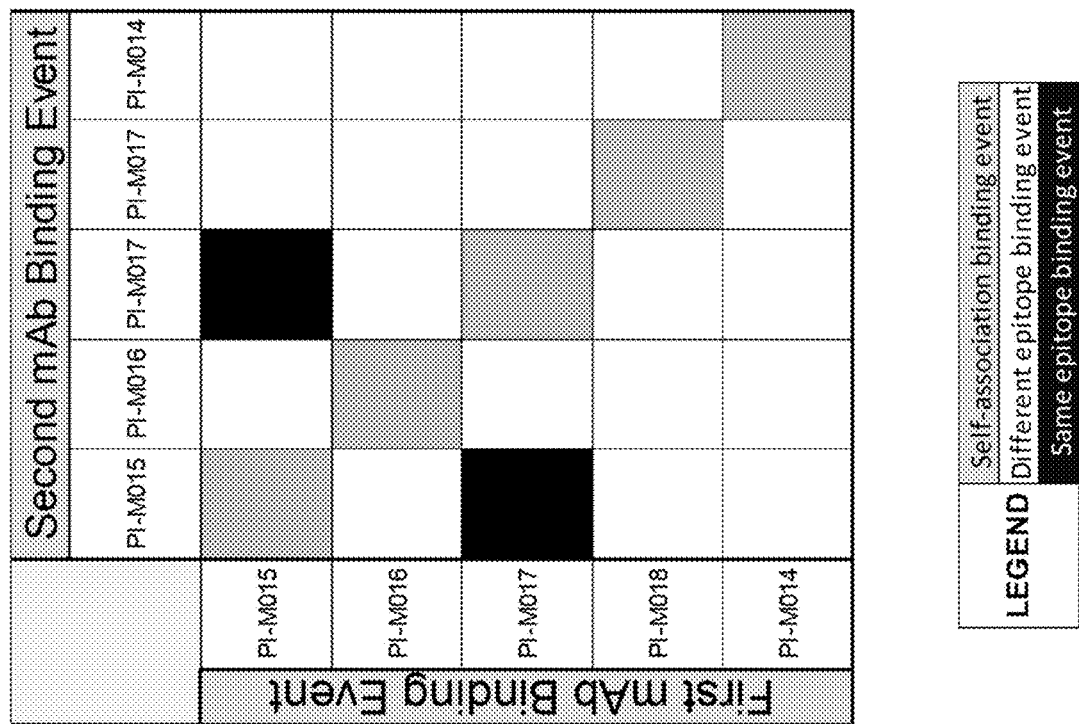
FIG. 7 shows a summary of the binding competition assay and that PI-M015 and PI-M017 competed with each other for binding to the MARCO antigen, indicating they bound to the same MARCO epitope.

PI-M015 and PI-M017 competed with each other for binding to the MARCO antigen, indicating they bind to the same MARCO epitope (FIG. 7). All other antibodies bound to different epitopes and did not compete with any other antibody for binding to MARCO. However, the antibodies only bound to the CLD domain of human MARCO and did not bind to the SRCR domain of human MARCO.

MARCO Expression on Primary Human DTCs Tumors and Peripheral Blood Leukocytes (PBLs)

MARCO expression was assessed in the microenvironment of human tumors from three indications by flow cytometry, ovarian cancer and gastric cancer, using the newly developed human MARCO antibodies. Tumor tissues were previously dissociated as "dissociate tumor cells" (DTCs) and snap frozen (Folio Conversant). DTCs were thawed following the manufacturer's guidelines and were counted to assess total viable cells. PBLs were isolated from buffy coats (two donors from Stanford Blood Center). The single cell suspensions from DTCs and PBLs were diluted in PBS (Gibco), washed once, and stained with Zombie NIR (Biolegend) to determine cell viability. Fc receptors were also blocked with a combination of human serum (Jackson Immunoresearch), human FcX (Biolegend), and a peptide-based FcR block solution (Innovex Biosciences). After incubation with FcR blocking reagents, surface receptors on the DTCs were stained with a flow cytometry cocktail encompassing markers for major intratumoral immune subsets as well as isotypes control (5 μg/ml mIgG2a or mIgG2b or Rat IgG2a) and anti-human MARCO antibodies directly conjugated (5 μg/ml PI-M017 or PI-M018 or PI-HX-3031). Cells were also fixed and permeabilized (True-Nuclear Transcription Buffer Set, Biolegend) in order to determine intracellular CD68 expression. PBLs were stained with a flow cytometry cocktail encompassing markers for major blood immune subsets as well as the isotype control (10 μg/ml hIgG1-conjugated with PE Zenon labeling) and anti-human MARCO antibodies (10 μg/ml PI-3010, PI-3030, and PI-3031-conjugated with PE Zenon labeling). Data from DTCs and PBLs was acquired using an Attune NxT analyzer (ThermoFisher) and analyzed using FlowJo (BD Biosciences).

Figures 8A, 8B:
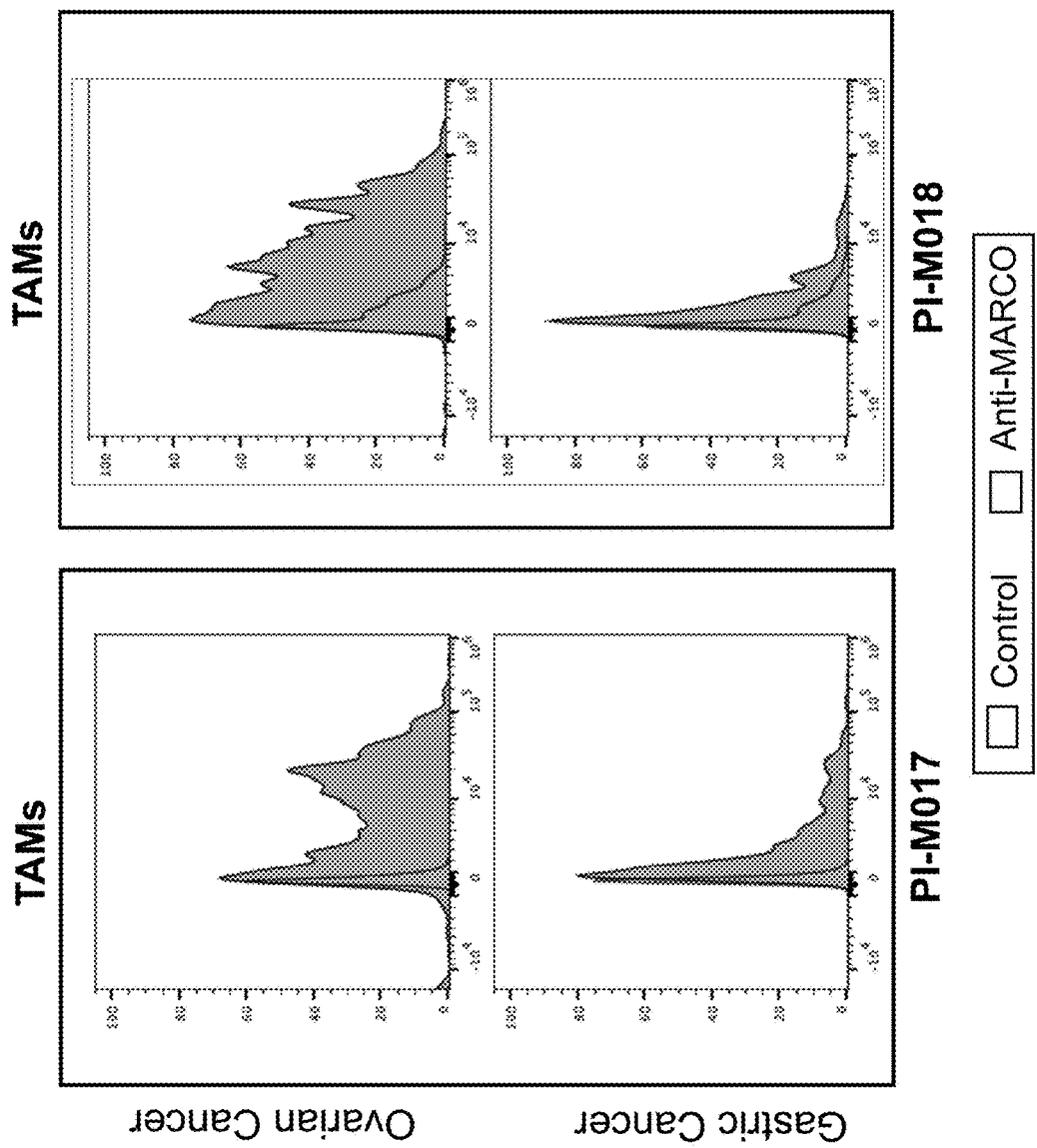
FIG. 8A shows that MARCO is expressed in human MDMs.
FIG. 8B shows that MARCO is expressed in tumor associated macrophages (TAMs) from primary human tumor samples (gastric cancer and ovarian cancer).

FIGS. 8A and 8B show that MARCO is expressed in human MDMs (FIG. 8A) and tumor associated macrophages (TAMs) from primary human tumor samples (gastric cancer and ovarian cancer, FIG. 8B). In FIGS. 8A and 8B, the right peak(s) indicates MARCO antibody PI-M018 or PI-M017 binding and staining, while the left peak indicates isotype mIgG2a binding.

A summary of the binding and functional characterization of selected antibodies from the first antibody campaign is shown in Table 1.

TABLE 1

| Anti-huMARCO mAb | Isotype | Epitope bin and map | $K_D$ (nM) | Endogenous cell binding | Human $EC_{50}$ 293T (HuMARCO) (nM) | Cyno $EC_{50}$ 293T (CyMARCO) (nM) | Mouse $EC_{50}$ 293T (MuMARCO) (nM) | ADCP/ADCC in BMDM assay in vitro |
|---|---|---|---|---|---|---|---|---|
| PI-M014 | mIgG2b | 4 (CLD) | 1.32 | + | 7.861 | 11.07 | 41.57 | No |
| PI-M015 (RDM1) | mIgG2a | 1 (CLD) | 0.39 | + | 1.606 | 1.206 | NB | Yes |
| PI-M017 (RDM7) | mIgG2a | 1 (CLD) | 0.96 | + | 1.59 | 1.522 | NB | Yes |
| PI-M018 (RDM9) | mIgG2b | 3 (CLD) | 1.65 | + | 1.851 | 45.4 | NB | No |

*NB: No binding

Example 3: Production and Characterization of Anti-Mouse MARCO Antibodies

Materials and Methods

Immunization for Generating Anti-Mouse MARCO Antibodies

Rat anti-mouse MARCO hybridomas were generate by immunizing Sprague Dawley rats with recombinant N-terminal-his-tagged mouse MARCO protein produced at Pionyr, using Sigma Adjuvant System (SAS) alone or alternating with mouse MARCO expressing HEK293 cells, also in SAS. The sequence of the recombinant N-terminal-his-tagged mouse MARCO protein used is shown below. Recombinant mouse MARCO protein was analyzed by SDS-PAGE and using size exclusion chromatography to confirm that the protein molecular weight was correct.

Rats were immunized twice weekly in the hock at Antibody Solutions (Santa Clara, Calif.) and serum titers tested at day 21 by ELISA. Rats with sufficient serum antibody titers to mouse MARCO were chosen for electrofusion to generate hybridomas. Two final boosts were given on days −3 and −2 prior to harvest in phosphate buffered saline (PBS).

The mouse MARCO mAb RDM-9514 was purchased from R&D biosystems (CUST017 MABP, Clone 57914) as a custom purified hybridoma clone, raised in rat against NS0-derived recombinant mouse MARCO Gln70-Ser518.

Hybridoma Generation

Lymph node cells were harvested from immunized rats and single cell suspensions generated. Lymphocytes were fused with the myeloma cell line, SP2/0-Ag 14 (ATCC) using electrofusion with the BTX EC2000+ electrofusion apparatus (Harvard Bioscience). Fused cells were plated into 96-well flat-bottom plates (Corning) and recovered overnight in Clona-Cell Medium E containing HT (Stem Cell Technologies). The following day, aminopterin (Sigma) was added to the cultures to a 1× final concentration. Fusions were fed on day 6 and day 8, and screened on day 11.

Hybridoma Screening

Hybridomas were screened by enzyme-linked immunosorbent assay (ELISA) on either recombinant mouse MARCO protein or recombinant human MARCO protein depending on the immunization. Briefly, 96-well Maxisorp plates (Nunc) were coated with 0.1 ug/well of recombinant MARCO protein, overnight in DPBS containing Ca2+ and Mg2+ (Gibco Cat #14040117)-. Plates were washed 3× with PBS/0.05% TWEEN-20 and blocked with PBS/Ca2+ containing 2% fetal bovine serum. Hybridoma supernatants were added 1:1 to the wells with PBS/Ca2+/2% FBS buffer and incubated at room temperature for 1 hour. Plates were washed as above and incubated with goat anti-rat IgG-HRP conjugated secondary antibody (Jackson Immuno) or mouse anti-rat IgG (1, 2a, 2b) HRP conjugated antibodies (Southern Biotech) for 1 hr at room temperature. Plates were washed and developed with TMB substrate (Thermo) and stopped with TMB Stop Solution (Suromodics), and the A450 determined using a platereader (Tecan). Hybridomas producing anti-MARCO antibodies were transferred to a 24-well plate and the supernatant from positive clones re-tested for MARCO reactivity and further tested in additional binding assays. Hybridomas were screened on recombinant human MARCO, recombinant mouse MARCO, and control recombinant his-tagged protein to eliminate any non-specific or his-tag specific clones and also tested on mouse MSR1 (R&D Systems) or human MSR1 (R&D Systems) to check for cross-reactivity to related scavenger receptor proteins. Hybridomas were also tested for binding to two chimeric proteins, N-terminal recombinant human MARCO SRCR/mouse CLD protein and N-terminal recombinant mouse MARCO SRCR/human CLD protein to determine the domain on the MARCO protein for which antibodies were specific. The sequences for the recombinant proteins used in these studies is below:

N-terminal his-tagged mouse MARCO protein:
(SEQ ID NO: 484)
HHHHHHHHGERGSPGPKGAPGAPGIPGLPGPAAEKGEKGAAGRDGTPGVQ

GPQGPPGSKGEAGLQGLTGAPGKQGATGAPGPRGEKGSKGDIGLTGPKGE

HGTKGDKGDLGLPGNKGDMGMKGDTGPMGSPGAQGGKGDAGKPGLPGLAG

SPGVKGDQGKPGVQGVPGPQGAPGLSGAKGEPGRTGLPGPAGPPGIAGNP

GIAGVKGSKGDTGIQGQKGTKGESGVPGLVGRKGDTGSPGLAGPKGEPGR

VGQKGDPGMKGSSGQQGQKGEKGQKGESFQRVRIMGGTNRGRAEVYYNNE

WGTICDDDWDNNDATVFCRMLGYSRGRALSSYGGGSGNIWLDNVNCRGTE

NSLWDCSKNSWGNHNCVHNEDAGVECS

-continued

N-terminal his tagged chimeric MARCO protein
(human SRCR/mouse CLD domains):
(SEQ ID NO: 485)
HHHHHHHHKGERGSPGPKGAPGAPGIPGLPGPAAEKGEKGAAGRDGTPGV

QGPQGPPGSKGEAGLQGLTGAPGKQGATGAPGPRGEKGSKGDIGLTGPKG

EHGTKGDKGDLGLPGNKGDMGMKGDTGPMGSPGAQGGKGDAGKPGLPGLA

GSPGVKGDQGKPGVQGVPGPQGAPGLSGAKGEPGRTGLPGPAGPPGIAGN

PGIAGVKGSKGDTGIQGQKGTKGESGVPGLVGRKGDTGSPGLAGPKGEPG

RVGQKGDPGMKGSSGQQGQKGEKGQKGENSVSVRIVGSSNRGRAEVYYSG

TWGTICDDEWQNSDAIVFCRMLGYSKGRALYKVGAGTGQIWLDNVQCRGT

ESTLWSCTKNSWGHHDCSHEEDAGVECSV

N-terminal his tagged chimeric MARCO protein
(mouse SRCR/human CLD domains):
(SEQ ID NO: 486)
HHHHHHKGEQGAPGLQGHKGAMGMPGAPGPPGPPAEKGAKGAMGRDGATG

PSGPQGPPGVKGEAGLQGPQGAPGKQGATGTPGPQGEKGSKGDGGLIGPK

GETGTKGEKGDLGLPGSKGDRGMKGDAGVMGPPGAQGSKGDFGRPGPPGL

AGFPGAKGDQGQPGLQGVPGPPGAVGHPGAKGEPGSAGSPGRAGLPGSPG

SPGATGLKGSKGDTGLQGQQGRKGESGVPGPAGVKGEQGSPGLAGPKGAP

GQAGQKGDQGVKGSSGEQGVKGEKGERGESFQRVRIMGGTNRGRAEVYYN

NEWGTICDDDWDNNDATVFCRMLGYSRGRALSSYGGGSGNIWLDNVNCRG

TENSLWDCSKNSWGNHNCVHNEDAGVECS

Cell Binding

Clones positive for binding to MARCO by ELISA were tested for binding to cell surface MARCO by staining human MARCO-293 cells, mouse MARCO-293 cells, or control 293 cells and testing by flow cytometry using the Intellicyt iQue flow cytometer. Hybridomas that were positive for binding to MARCO by ELISA and to cell surface MARCO by flow cytometry were chosen for subcloning and purification.

Hybridoma Subcloning and Purification

Subcloning of parental hybridomas was performed by single cell sorting on the FACSAria. Single cells were sorted into flat-bottom 96-well tissue culture plates into Clona-Cell Medium E. Single cells were cultured for 7-9 days and then assayed for anti-MARCO specific clones by ELISA, as described above.

Monoclonal hybridomas were then culture for purification by growth in serum-free expansion medium (AOF, Stem Cell Technologies) and purified using either protein A or protein G.

Hybridoma Antibody Variable Region Sequences Generation

Total RNA was extracted from (104 to 106) monoclonal hybridoma cells using the RNeasy purification kit (Qiagen Cat #74134), then reverse transcription (RT) was performed to synthesize cDNA using Maxima H Minus First Strand cDNA Synthesis Kit (Thermofisher Cat #K1651) and reverse gene specific primers (GSP1). cDNA was purified to remove GSP and enzymes in the RT reaction using the QIAquick PCR Purification Kit (Qiagen Cat #28104). Terminal Deoxynucleotidyl Transferase was used to add a string of oligo-dA to the 3' end of the cDNA (Thermo Scientific Cat #10533065), the product was purified again (QIAquick PCR Purification Kit Cat #28104) before amplification. PCR was then carried out using a second gene specific primer (GSP2) and the Oligo-dT forward primer that binds the Oligo-dA tail previously added to the 3' ends of the cDNAs. PCR products were sequenced. In cases where sequences of insufficient quality were generated from PCR products, the PCR products were TOPO cloned and transformed into E. coli, and single colonies processed for sequencing.

The primers used are listed below:

GSP1-mk:
(SEQ ID NO: 487)
TTGTCGTTCACTGCCATCAATC

GSP2-mk:
(SEQ ID NO: 488)
ACATTGATGTCTTTGGGGTAGAAG

GSP1-mHC:
(SEQ ID NO: 489)
AGCTGGGAAGGTGTGCACAC

GSP2-mHC:
(SEQ ID NO: 490)
GGGATCCAGAGTTCCAGGTC

GSP1-rk:
(SEQ ID NO: 491)
GT GAG GAT GAT GTC TTA TGA ACA

GSP2-rk:
(SEQ ID NO: 492)
GCCATCAATCTTCCACTTGACAC

GSP1-rHC:
(SEQ ID NO: 493)
GAG ATG STT TTC TCG ATG GG

GSP2-rHC:
(SEQ ID NO: 494)
GS GGG AAG ATG AAG ACA GAT G

Calcium Dependency ELISA Assay

The purpose of this assay was to determine the calcium dependency for binding to MARCO by the anti-MARCO antibodies. This assay can apply to both hybridoma supernatant and purified antibodies.

0.05 µg/ml of the human or mouse MARCO recombinant proteins were coated on 4 Nunc-Immuno™ MicroWell plates using the following conditions: in DPBS with Ca2+ (Gibco Cat #14040117), in DPBS without Ca2+ (Gibco Cat #14190136) with 2 mM EDTA (Invitrogen Cat #15575020)-Plate B, in DPBS without Ca2+ with 10 mM EDTA, and in DPBS without Ca2+ with 50 mM EDTA.

After the plates were incubated at room temperature for 1 hour or 4° C. overnight, the plates were wash 3 times with ELISA wash buffer (PBS/0.05% TWEEN-20), then hybridoma supernatant (1:5 dilution) or purified antibody (1 ug) was diluted in DPBS/Ca2+/2% FBS, DPBS without Ca2+/2 mM EDTA/2% FBS, DPBS without Ca2+/10 mM EDTA/2% FBS, and DPBS without Ca2+/50 mM EDTA/2% FBS. Plates again were incubated at room temperature for 1 hour.

Plates were washed as above and incubated with goat anti-mouse IgG-HRP (Jackson) or a mixture of mouse anti-rat IgG-HRP (1+2a+2b) 1:1:1 (SouthernBiotech Cat #3060-05, 3065-05, 3070-05) diluted 1:5000 for 1 hr at room temperature in the 4 different buffers as above. Plates were then washed and developed with TMB substrate (Thermofisher) and stopped with TMB Stop Solution (Surmodics), and read at A450 using a Tecan plate reader.

Kinetics and Epitope Binning Using the ProbeLife Gator Instrument

The Probe-Life Gator™ label free system was used to analyze binding kinetics and epitopes for the anti-MARCO antibodies.

The kinetics assay used either anti-mouse Fc or anti-human Fc probes to capture the anti-MARCO antibodies onto the probe, and then a five-step kinetic protocol was used to measure the affinity of the antibodies to the antigen, including the following steps: baseline, loading, baseline, association, and dissociation. The kinetics buffer (K buffer) provided by ProbeLife was used to establish the baseline for 60 seconds, and then the anti-mFc or anti-hFc probes were loaded with 200 nM of the antibodies for 120s until the capture reached saturation, measurement of the baseline in K buffer was performed for another 60s, followed by the association step using 200 nM antigen (human MARCO, mouse MARCO or cyno MARCO), and the dissociation step performed in K buffer for 5-10 minutes. The assay was done at 37° C. to maximize antibody:antigen dissociation.

For epitope binning of the antibodies, both tandem and sandwich formats were used.

For tandem format, 200 nM of the N-terminal his-tagged MARCO protein was loaded onto ProbeLife anti-his probe for 120s or until binding reached saturation, followed by baseline for 60s and then association with the first set of saturating antibodies loaded at 200 nM. Following binding of the first antibody, a second antibody was added at 100-200 nM) and the association of the second set of antibodies was measured. Any additional binding observed for the second antibody, measured as an increased signal indicates that the second antibody bound to a different epitope than the first antibody.

For sandwich assay format, the first antibody at 200 nM was loaded onto anti-mFc or anti-hFc probes for 120s, followed by a baseline step, and then association with MARCO antigen (200 nM) for 120s. Association of the second antibody at 200 nM was then measured for 120s to determine if there was additional binding. In this format, where the first antibody was at low concentration, additional isotype control antibody was added after the first association in order to saturate free binding sites on the probe. All probes and buffers were directly ordered from ProbeLife.

MARCO Staining on BMDMs with the Anti-Mouse MARCO Hybridomas

Femurs and tibias from three female C57BL/6 mice (Jackson Laboratories) were cleaned and crushed in Staining Medium (0.5% (w/v) BSA (Sigma) and 2 mM EDTA in D-PBS) using a mortar and pestle. Samples were then passed through a 40 um filter, washed with D-PBS and pelleted at 400×g for 5 min at RT. Cell pellets were resuspended in 5 ml of BD Pharm Lyse buffer (BD Biosciences) and red blood cell lysis was carried out at RT for 5 min, followed by quenching with 10 volumes of Staining Medium. Cells were pelleted at 400×g for 5 min at RT and resuspended in Macrophage Medium composed of Iscove's modified Dulbecco Medium supplemented with 10% (v/v) fetal bovine serum (FBS) (HyClone) and antibiotic-antimycotic solution (Gibco), at the density of 15×106 cells/ml in 15 cm plates. These bone marrow mononuclear cells were stimulated with 25 ng/ml of mouse macrophage colony-stimulating factor (M-CSF) (PeproTech) for 7 days to generate M0-macrophages and differentiated into M1-like by supplementing the medium with LPS at 100 ng/ml on day 6 and into M2-like macrophages by adding 20 ng/ml of IL-10. After 18 hours of incubation at 37C with polarizing cytokines, M0, M1, and M2-like macrophages were rinsed with DPBS and incubated in 6 ml of 2 mM EDTA for 10 minutes to promote cell detachment. Cells were gently scraped into an additional 6 ml of the Staining Medium described above, counted and seeded onto 96-well plates at 250,000 cells per well. 100 ul of Zombie NIR viability dye (BioLegend), prepared by diluting the stock 1000-fold in D-PBS, was added to each well and incubated for 10 min at RT in the dark. The reaction was quenched by addition of 150 ul of Staining Medium, followed by centrifugation at 400×g for 5 min at 4° C. Cells were then incubated in 100 ul of blocking solution, containing 2.5% mouse and 2.5% rat serum and mouse TruStain FcX PLUS (BioLegend) diluted 50-fold in Fc receptor blocker (Innovex Biosciences), for 20 min in the dark. Cells were then washed and resuspended in 100 μl of the different antibodies and hybridomas needed for screening and corresponding isotype controls in freshly prepared FACS buffer containing 2% FBS in DPBS with Ca2+(RDM-9514, HX-3012, HX-3014, HX-3016, HX-3017, Rat IgG2a and Rat IgG1 all PE-conjugated with the PE Lightning kit). RDM-9514 was tested at the final top concentration of 10 μg/ml followed by an 8-point three-fold serial dilution in PBS the highest dose of 10 μg/ml. The internal hybridomas were tested at the single point concentrations of 5 μg/ml. Staining was carried out for 20-30 min on ice, followed by 2 washes in FACS buffer. Cells were resuspended in 150 ul of the same buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8). Data was plotted as Delta gmfi between the antibody and corresponding isotype. In case when the plates were not able to be analyzed on the cytometer, cells were pelleted after the washes and fixed in 100 μl of 2% paraformaldehyde (PFA), prepared by diluting the 16% (w/v) stock (Thermo Fisher) in DPBS, for 15 min at RT. Cells were then pelleted and the fixative was removed, followed by resuspension in 150 μl of Staining Medium and stored at 4° C. until acquisition on the flow cytometer.

MARCO Staining on Tumors with Anti-Mouse MARCO PE Conjugated mAbs

Py8119 and CT26 tumors were harvested from mice when they reached a volume of 400 mm3. Fat and fibrous material were removed from the tumors by dissection. The tumors were then weighed and processed for single-cell suspension by a combination of mechanical and enzymatic dissociation. After mincing the tissues, tumors were enzymatically digested using an optimized enzyme cocktail (Miltenyi Biotec, Tumor Dissociation Kit, mouse 130-096-830) with gentleMACS C tubes (Miltenyi Biotec, 130-093-235) in a gentleMACS Octo Dissociator (Miltenyi Biotec, 130-095-937). After dissociation, the sample was applied to a filter to remove any remaining larger particles. Single cell suspension of tumor tissues was surface stained using a panel of antibodies for flow cytometry. The antibody panel for evaluating myeloid subsets included antibodies specific for CD45, XCR1, F4/80, CD64, CD11c, Ly6C, CD11b, Ly6G, CD24, MHC class II as well as lineage markers in the dump channel (CD45R, CD90.2, CD3e, NKp46, CD19, Siglec F). The antibody panel for evaluating lymphoid subsets included antibodies specific for CD45, CD4, CD25, B220, NKp46, CD44, CD90.2, CD8a, CD11b, and CD49b. The anti-MARCO antibodies used to stain the mouse tumors were RDM-9514, PI-HX-3012, PI-HX-3021, PI-HX-3016, PI-HX-3017, rat IgG1 and rat IgG2a isotypes at 5 μg/ml. All data were collected on an Attune flow cytometer (Thermo Fisher) and analyzed using FlowJo software.

LDL Competition Assay on Mouse and Human Recombinant MARCO

A high-binding, 96-well MSD plate was coated with 4 μg/ml mouse MARCO or 4 μg/ml human MARCO (R&D biosystems). After the plate was blocked with PBST and 5% BSA for an hour, titrated anti-mouse or anti-human MARCO antibodies were added to the plate and incubated for 30 minutes. Biotinylated hLDL (860 pM or 2 μg/ml) were added to the antibody, and the antibody/LDL mixture was incubated for an hour to allow the mixture to reach binding equilibrium. The plates were washed and bound biotinylated LDL was detected with Sulfo-tagged streptavidin that generates an electrocheminlumenscent signal when read buffer is added and electricity is applied to the electrodes in the MSD plate. IC50's were calculated using a 4-parameter curve fit in GraphPad Prism software.

Results

Figure 11A:
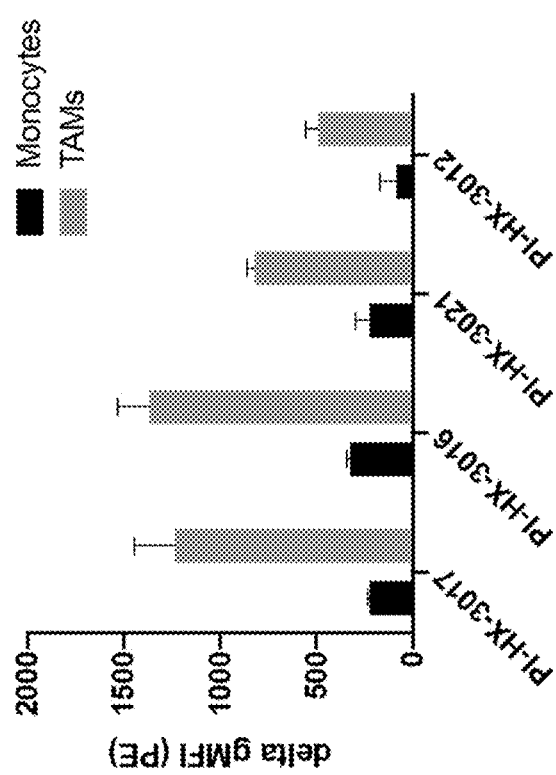
FIG. 11A shows that anti-mouse MARCO antibodies PI-HX-3017 (left bar, renamed PI-3009), PI-HX-3016 (middle left bar, renamed PI-3008), PI-HX-3021 (middle right bar, renamed PI-3007) and PI-HX-3012 (right bar) each bound to mouse BMDMs.
Figure 11B:
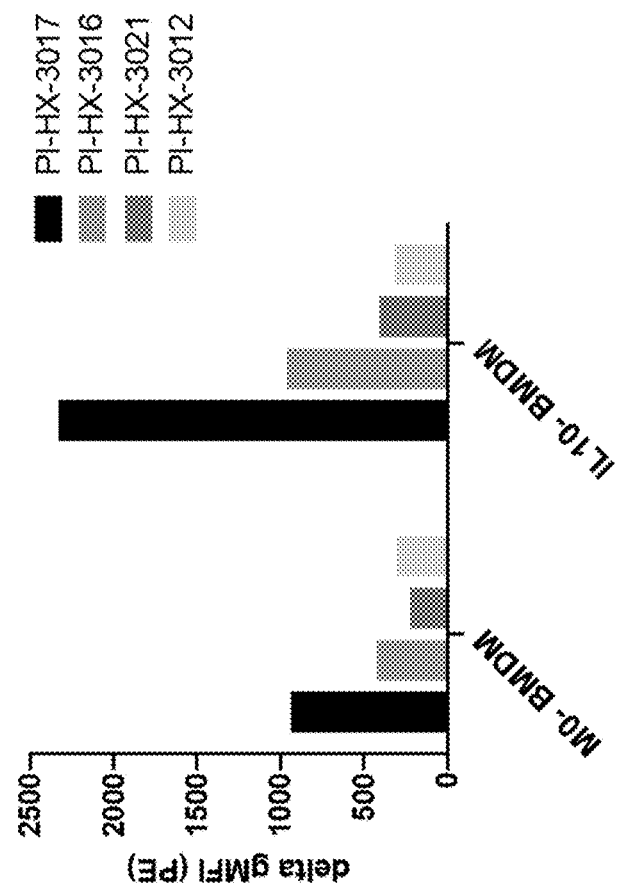
FIG. 11B shows that the same antibodies also bound to MARCO on TAMs (right bar) and monocytes (left bar) isolated from tumors in the CT26 syngeneic tumor model (n=2).

Multiple antibodies that bound to the SRCR domain of mouse MARCO were generated and characterized. 909 candidate antibodies were identified in the primary ELISA screen using purified mouse MARCO, human MARCO, mouse CLD-human SRCR, human-CLD-mouse-SRCR, and mouse MSR1. Secondary screening of binding to 293T cells expressing mouse MARCO or GFP control resulted in 275 candidates. Screening of binding to endogenous mouse BMDMs resulted in 40 candidates. A final screen for just SRCR binders resulted in 20 candidates. The candidates were screened for additional biophysical characteristics. The biophysical characterization of the top anti-mouse MARCO antibodies generated is shown in Table 2. These antibodies showed no binding to 293T HuMARCO cells or 293T CyMARCO cells. The sequences of selected mouse MARCO antibodies are shown in the sequence listing table. The CDRs were defined using the AbM definition.

generated mouse MARCO antibodies. PI-HX-3017 (left bar, renamed PI-3009), PI-HX-3016 (middle left bar, renamed PI-3008), PI-HX-3021 (middle right bar, renamed PI-3007) and PI-HX-3012 (right bar) each bound to mouse BMDMs (FIG. 11A). The same antibodies also bound to MARCO on TAMs (right bar) and monocytes (left bar) isolated from tumors in the CT26 syngeneic tumor model (FIG. 11B, n=2).

Example 4: In Vivo Efficacy of Anti-Mouse MARCO Antibodies in Mono and Combination Therapy Materials and Methods In Vivo Combination Therapy with PD-1 Antibody in CT26 Syngeneic Model Antibodies for in vivo use were all tested for endotoxin and used at or below 0.2 EU/mg protein. Anti-PD-1 [clone RMP1-14] in a mouse IgG1 D265A format was obtained. Mouse IgG1 [clone MOPC-21] and mouse IgG2a [clone C1.18.4] isotype controls were obtained. PI-3006, PI-3007, PI-3008, and PI-3009 were produced in HEK293 cells and evaluated for monodispersity and purity by SEC and CE-SDS as well as endotoxin tested. Antibodies were also tested for binding to mouse MARCO overexpressing 293T cells and for lack of binding to the parental 293T cells by flow cytometry.

Female BALB/c mice at about eight weeks of age were obtained from Taconic Biosciences (Rensselaer, N.Y.). Mouse tumor cell line CT26.WT (CRL-2638) was obtained from American Type Culture Collection (ATCC), and cultured according to their guidelines. Low passage cells were resuspended at $1 \times 10^7$ cells/ml in serum-free 1× DPBS (Gibco). The tumor cell suspension was subcutaneously injected on the shaved lower right ventral flank of BALB/c

| Anti-muMARCO mAb | Isotype | SRCR Bin (CDR3 sequence) | Epitope Bin | Biacore $K_{on}$ (1/Ms) | Biacore $K_{off}$ (1/s) | Mouse $EC_{50}$ 293T (MuMAR (nM) | $EC_{50}$ LDL competition assay (nM) | MSR1 binding | Binding to BMDM |
|---|---|---|---|---|---|---|---|---|---|
| RDM-9514 | Rat IgG1 | 11 | 2 | 1.36E+05 | 6.95E−07 | 0.83-0.86 | 0.38 | − | + |
| PI-HX-3001 (PI-3006) | Rat IgG2a | 1 | 2 | 1.88E+05 | 7.89E−07 | 0.48-1.09 | 0.4 | − | NA |
| PI-HX-3003 | Rat IgG2a | 8 | 2 | 2.16E+05 | 5.40E−07 | 1.00 | 0.23 | +/− | + |
| PI-HX-3004 | Rat IgG2a | 10 | 2 | 3.45E+05 | 3.58E−08 | 0.92 | 0.17 | +/− | NA |
| PI-HX-3012 | Rat IgG2a | 1 | 2 | 1.54E+05 | 2.48E−07 | 0.80 | 0.17 | − | + |
| PI-HX-3013 | Rat IgG2a | 2 | 2 | 2.40E+05 | 4.50E−07 | 0.34 | 0.36 | +/− | + |
| PI-HX-3021 (PI-3007) | Rat IgG2a | 3 | 2 | 1.91E+05 | 2.11E−05 | 0.47-0.75 | 0.25 | − | + |
| PI-HX-3016 (PI-3008) | Rat IgG1 | 1 | 2 | 1.84E+05 | 1.27E−06 | 0.36-0.59 | 0.34 | − | + |
| PI-HX-3017 (PI-3009) | Rat IgG1 | 6 | 2 | 1.55E+05 | 2.35E−07 | 0.66-1.30 | 0.14 | − | + |

Figure 9:
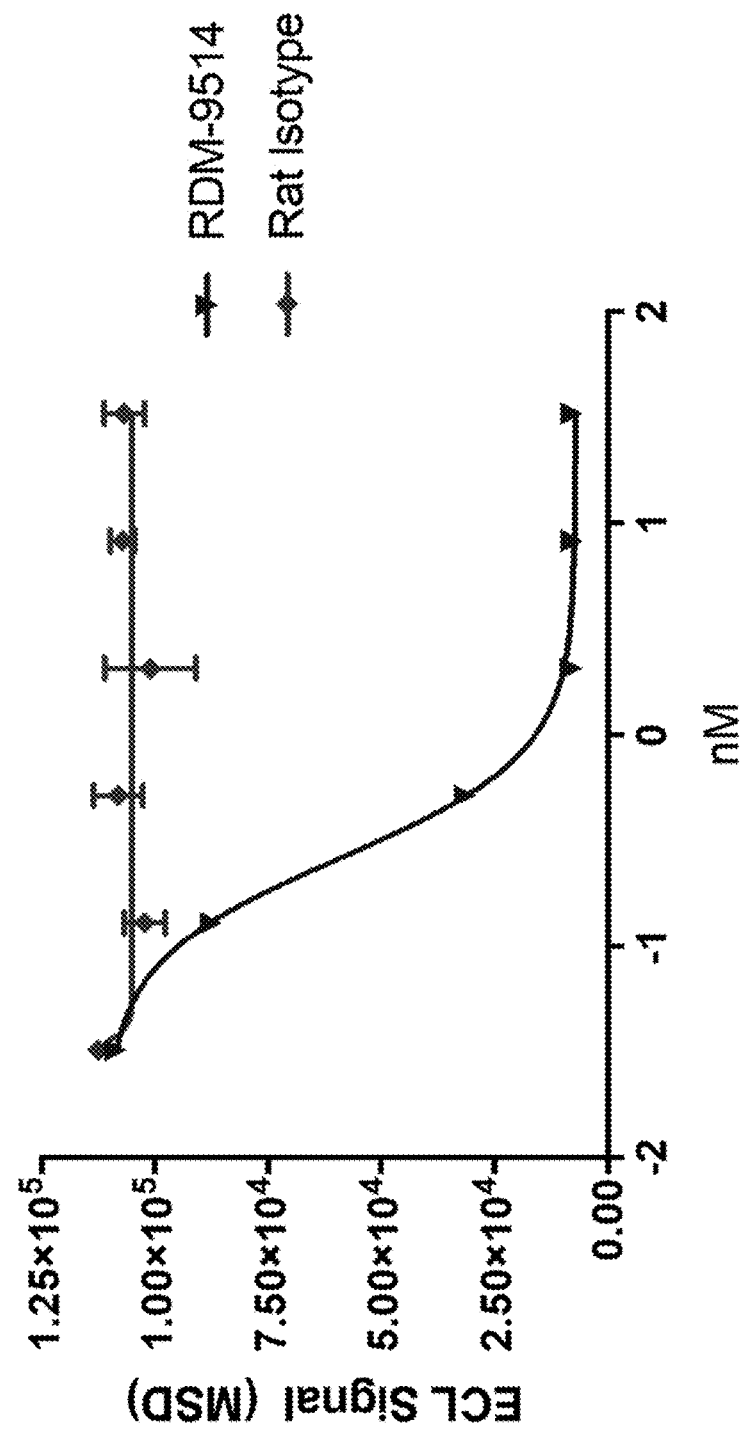
FIG. 9 shows that RDM-9514 also blocked LDL binding to MARCO in a dose dependent manner.
Figure 10A:
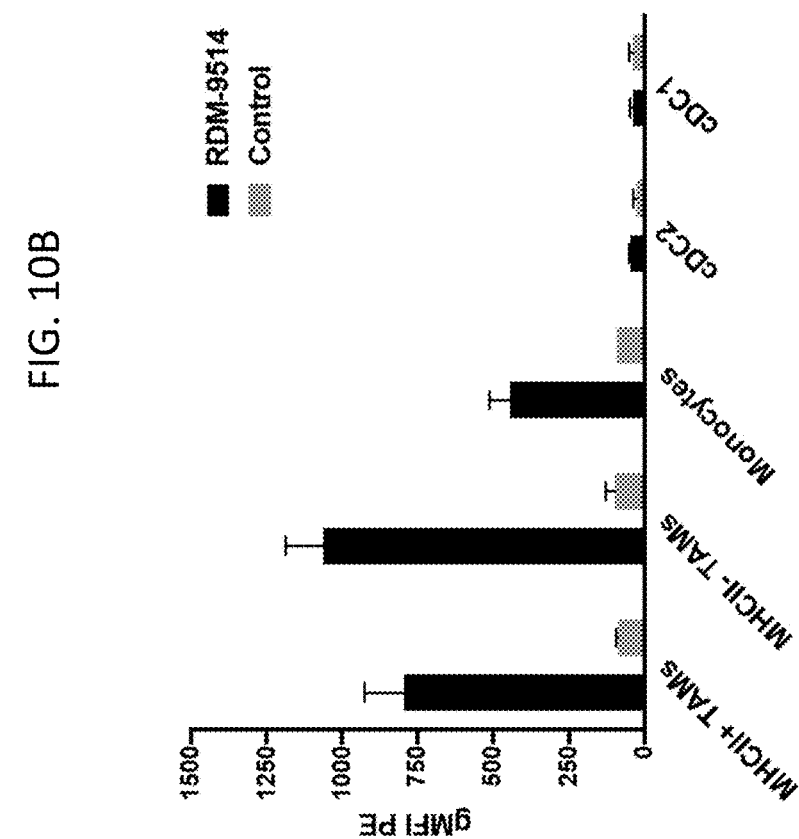
FIG. 10A shows that RDM-9514 bound to surface expressed MARCO on MHCII$^{high}$ TAMs and MHCII$^{low}$ TAMs isolated from CT26 tumors and Py8119 tumors.
Figure 10B:
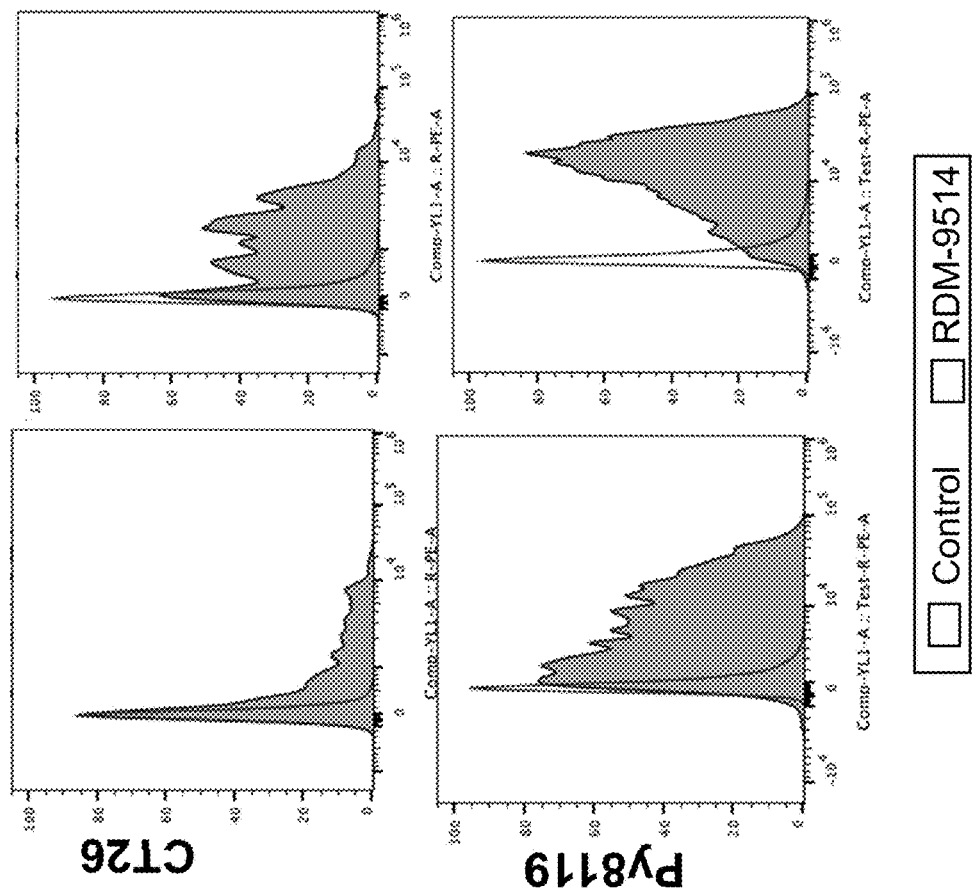
FIG. 10B shows that MARCO is expressed on TAMs and monocytes in the CT26 syngeneic tumor model.

RDM-9514 bound to the SRCR domain of MARCO. RDM-9514 also blocked LDL binding to MARCO in a dose dependent manner (FIG. 9) and bound to surface expressed MARCO on MHCII$^{high}$ TAMs and MHCII$^{low}$ TAMs isolated from CT26 tumors and Py8119 tumors (FIG. 10A). Staining with mouse antibody RDM-9514 also showed that MARCO is expressed on TAMs and monocytes in the CT26 syngeneic tumor model (FIG. 10B).

MARCO expression on mouse BDMDs after macrophage and IL-10 polarization was also assessed with the newly mice under isoflurane anesthesia. Tumor volume growth was monitored twice a week via perpendicular tumor diameter measurements and calculated using the formula (mm$^3$)=0.5× (length)×(width). Six treatment groups were randomly assigned with 10 animals each when tumors reached an average of 97 mm$^3$. For drug treatments, mice were dosed intraperitoneally once every 5 days for 4 doses total (Q5Dx 4) with anti-mouse isotype control IgG2a (Clone C1.18.4) at 15 mg/kg, anti-mouse isotype control IgG1 (Clone MOPC-21) at 5 mg/kg, anti-mouse PD-1 (clone RMP1-14 recombinantly produced as mouse IgG1 D265A format and called PI-0004-AB) at 5 mg/kg alone or in combination with the anti-mouse MARCO antibodies (PI-3006, PI-3007, PI-3008, and PI-3009) at 10 mg/kg. All studies were conducted in accordance with the Explora Biolabs institutional animal care and use committee under the protocol EB17-010. Mice were housed under conditions outlined in the NIH Guide for Care and Use of Laboratory Animals in compliance with the USDA Laboratory Animal Welfare Act. The animals were allowed ad libitum access to Lab Diet rodent chow and water. Mice were monitored a minimum of twice per week by the investigator or veterinary staff for clinical abnormalities which may require euthanasia. Mice showing a net body weight loss >20% compared to baseline weight measurement were euthanized.

Anti-Tumor Immune Memory Assay

BALB/c mice that were tumor-free from the CT26 tumor model study with the anti-MARCO antibodies plus anti-PD-1 antibody treatment as described above were re-challenged with $1 \times 10^6$ CT26 tumor cells on the left ventral flank. EMT6 cells were injected subcutaneously on the opposite right ventral flank as a control cell line to track for tumor growth during the study period. No additional treatment was provided to the mice during the study period. Tumor volume was measured for 35 days after the re-challenge implant.

Pharmacodynamics (PD) and In Vivo Anti-MARCO Antibody Single Agent Efficacy in CT26 Model Female BALB/c mice at about eight weeks of age were obtained from Taconic Biosciences (Rensselaer, N.Y.). Mouse tumor cell line CT26.WT (CRL-2638) was obtained from American Type Culture Collection (ATCC), and cultured according to their guidelines. Low passage cells were resuspended at $1 \times 107$ cells/ml in serum-free 1× DPBS (Gibco). The tumor cell suspension was subcutaneously injected on the shaved lower right ventral flank of BALB/c mice under isoflurane anesthesia. Tumor volume growth was monitored twice a week via perpendicular tumor diameter measurements and calculated using the formula $(mm^3)=0.5 \times (length) \times (width)$. Two treatment groups were randomly assigned with 10 animals each when tumors reached an average of 109 $mm^3$. For drug treatments, mice were dosed iv once every 7 days (Q7D) with anti-mouse isotype control IgG2a (Clone C1.18.4) and anti-mouse MARCO antibody (PI-3008) at 10 mg/kg. All studies were conducted in accordance with the Explora Biolabs institutional animal care and use committee under the protocol EB17-010. Mice were housed under conditions outlined in the NIH Guide for Care and Use of Laboratory Animals in compliance with the USDA Laboratory Animal Welfare Act. The animals were allowed ad libitum access to Lab Diet rodent chow and water. Mice were monitored a minimum of twice per week by the investigator or veterinary staff for clinical abnormalities which may require euthanasia. Mice showing a net body weight loss >20% compared to baseline weight measurement were euthanized. A schematic of the study time line is shown in FIG. 15A.

Pharmacokinetics (PK) Assay

The mouse MARCO PK assay was used for quantification of drug antibody levels in mouse serum. A high-binding 96-well MSD plate was coated with 2 µg/ml mMARCO (PI-RG-3016). After blocking for an hour with blocking buffer (PBST, 5% BSA (PBS, 0.01% Tween-20, BSA), a standard curve and diluted serum samples were added to the plate and incubated for 2 hours on a plate shaker. Both the samples and the standard curve were normalized to a final concentration of 5% mouse serum. The plate was washed in DPBS++ (Gibco), 0.05% Tween-20, 1% BSA, and the bound MARCO antibody was detected using a sulfo-tagged anti-mouse IgG2a (Jackson Immuno). The sulfo tagged antibody generates an electrochemiluminescent signal when read buffer was added and electricity was applied to the electrodes in the MSD plate. Antibody levels in the serum samples are quantitated by interpolating from the standard curve using a 4-parameter curve fit in the MSD software.

RNAseq and Pathway Analysis of the Tumors, LNs, and Spleens from the CT26 PD Study The first timepoint for PD takedown was 4 h following iv dosing of the antibodies. Blood (serum), spleen, tumor, and tumor draining lymph nodes from each mouse was harvested and tissues snap frozen in liquid nitrogen. The second timepoint was 4 h after the second iv dosing of the antibodies, which occurred 6 days after the first iv dose. Blood (serum), spleen, tumor, and tumor draining lymph nodes from each mouse was harvested and tissues snap frozen in liquid nitrogen. Snap frozen samples were shipped to Medgenome Inc. for tissue homogenization using the Biospec Beadbeater in buffer RLT+BME and RNA extraction using the Qiagen All Prep kit and Biospec Beadbe. The mRNA quantity and quality were assessed by Nanodrop and the Agilent Bioanalyzer before moving to library preparation and RNAseq analysis to determine changes in gene expression induced by MARCO at the early and late PD timepoints. Differentially expressed genes (upregulated and downregulated) with FDR (<0.05) and cpm>2 cutoffs were generated and GSEA pathway analysis was performed and plotted using Cytoscape, KEGG, and Hallmarks analyses. The IgV genes observed in the differentially expressed gene list from the spleens treated with PI-3008 at 4 h were plotted using a heatmap.

Afucosylated Antibody Assay

Afucosylated PI-3008 with an mIgG2a mouse Fc was generated and tested in vivo. Fucosylated PI-3008 antibody and an mIgG2a isotype antibody were used as controls.

CT26 tumor cells ($1 \times 10^6$ cells per mouse) were implanted on Day 0. Afucosylated PI-3008 antibody IV (10 mg/kg; Q7dx3) dosing was initiated when tumors reached an average of ~100 mm3 in volume.

Effector Dead Antibody Assay

An N297A mutation was engineered in the mouse IgG2a Fc of PI-3008 to generate an effector dead mAb, PI-3021. PI-3008 and effector dead PI-3021 were tested alone and in combination with anti-PD-1 antibody in the CT26 mouse model. Balb/c female mice were inoculated subcutaneously with syngeneic CT26 tumor cells ($1 \times 10^6$ cells per mouse) on Day 0, and dosed with PI-3008 (WT Fc; 10 mg/kg), PI-3021 (Effector dead; 10 mg/kg), anti-PD-1 (5 mg/kg), and appropriate isotype controls (10 mg/kg) as single agent or in combination. with anti-PD1 (N=10/group) was initiated when tumor volumes reached an average of ~100 mm3. Animals were dosed intraperitoneally every 5 days, for total of four doses. Tumor volumes were monitored over time and presented as averages per group, individual tumor volumes at the end of study, or as % TGI.

Results

Figure 12:
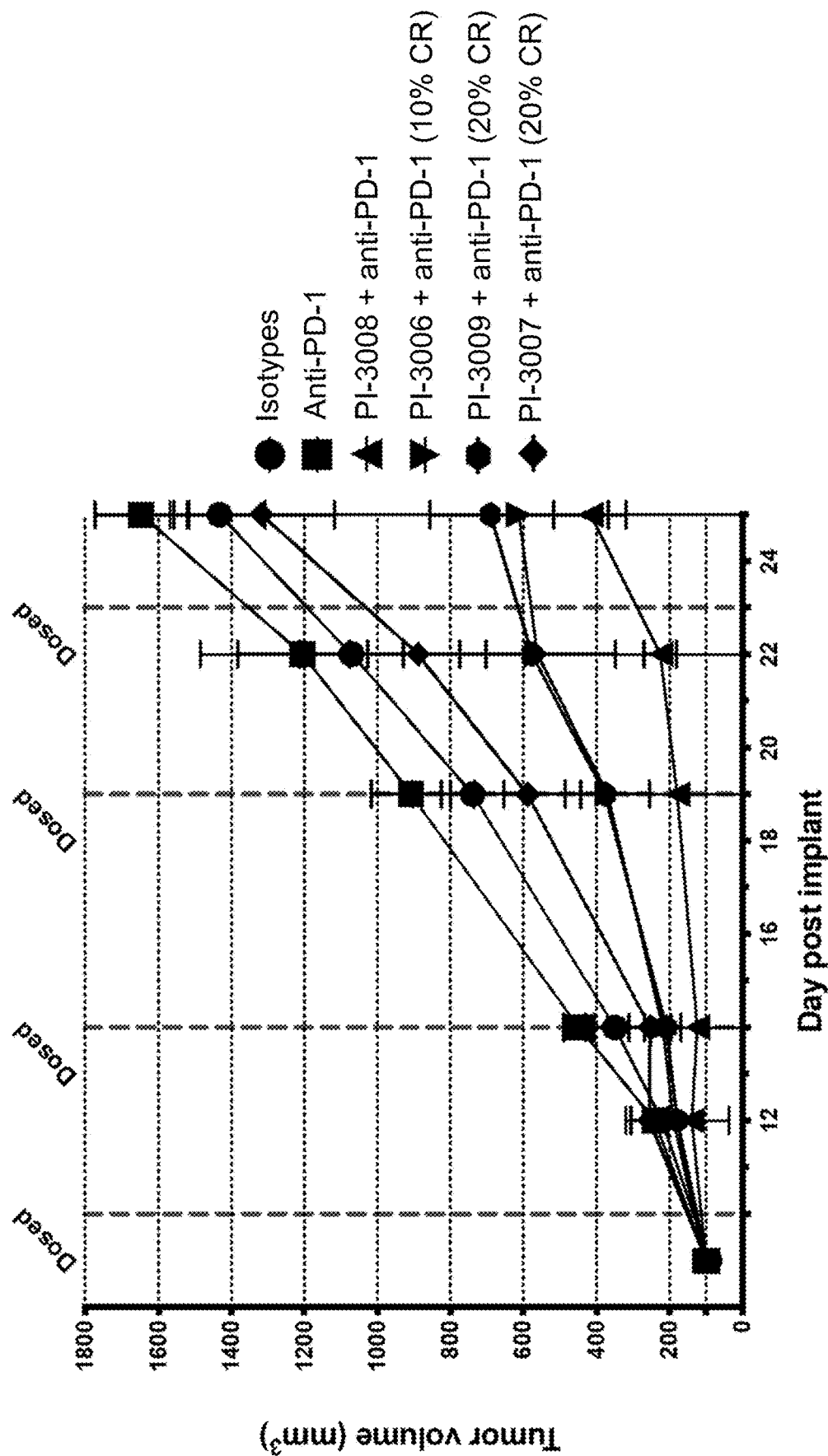
FIG. 12 shows the tumor volume in mice groups treated with isotype antibody; PD-1 antibody only; or PI-3008 plus PD-1 antibodies, PI-3007 plus PD-1 antibodies, PI-3009 plus PD-1 antibodies, and PI-3007 plus PD-1 antibodies.

The mouse anti-MARCO antibodies demonstrated significant anti-tumor efficacy in the CT26 model in combination with an anti-PD-1 antibody. FIG. 12 shows the tumor volume in mice groups treated with isotype antibody; PD-1 antibody only; or PI-3008 plus PD-1 antibodies, PI-3007 plus PD-1 antibodies, PI-3009 plus PD-1 antibodies, and PI-3007 plus PD-1 antibodies. PI-3006 and PD-1 antibodies resulted in 10% cancer remission (CR), while PI-3007 and PI-3009 in combination with PD-1 antibodies resulted in 20% CR. PI-3008 had the best response and TGI overall.

FIG. 13A-D show the responses in the individual mice after treatment with isotype control, anti-PD-1, PI-3008+PD-1 antibodies, or PI-3009+PD-1 antibodies. PI-3008 (FIG. 13C) and PI-3009 (FIG. 13D) demonstrated the best ant-tumor efficacy in combination with the anti-PD-1 antibody.

Afucosylated Antibody Assay

Figure 13B:
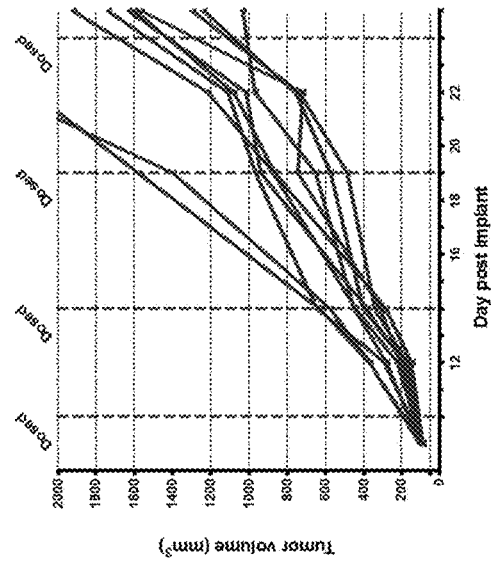
FIG. 13B shows the tumor volumes in individual mice treated with anti-PD-1 antibody.
Figure 13D:
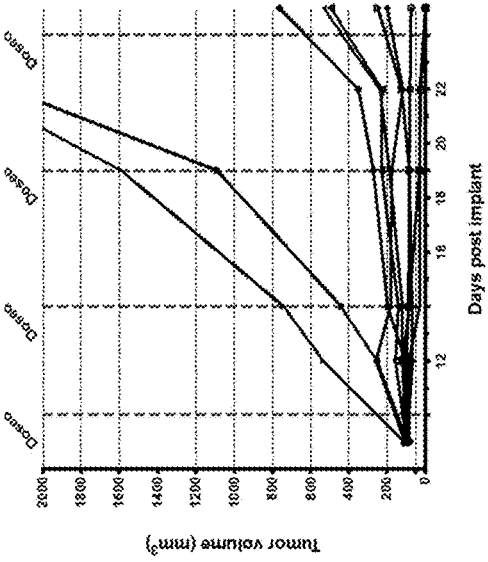
FIG. 13D shows the tumor volumes in individual mice treated with PI-3009 and anti-PD-1 antibody.
Figure 13A:
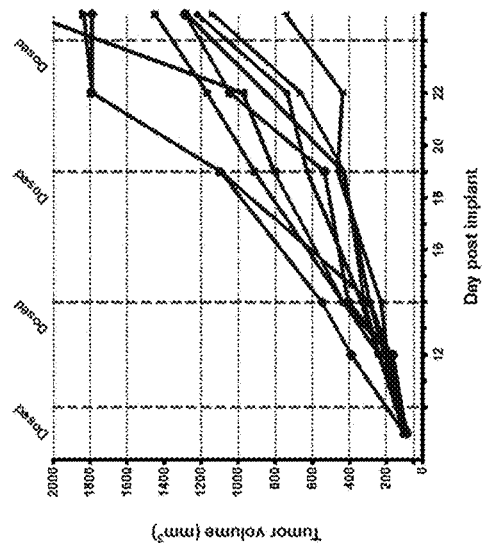
FIG. 13A shows the tumor volumes in individual mice treated with isotype control antibody.
Figure 13C:
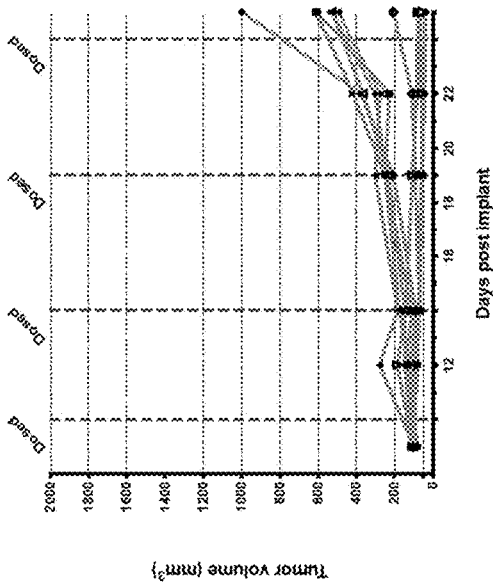
FIG. 13C shows the tumor volumes in individual mice treated with PI-3008 and anti-PD-1 antibody.
Figure 13H:
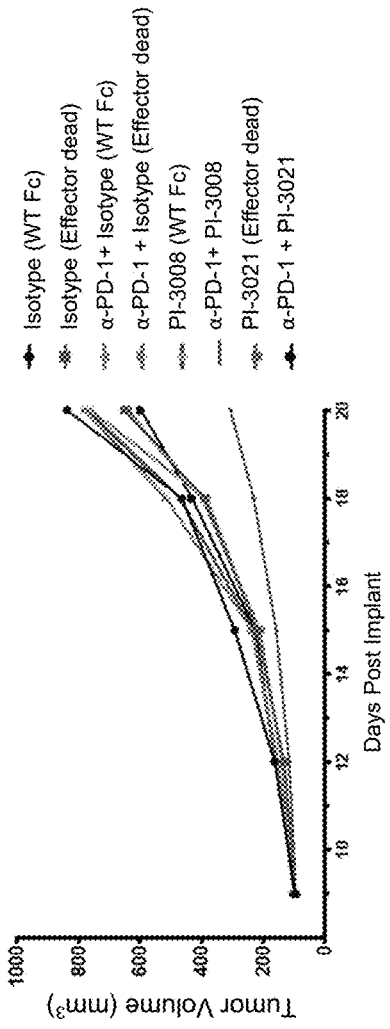
FIG. 13H shows the tumor volumes in mice treated with the indicated antibody.
Figure 13I:
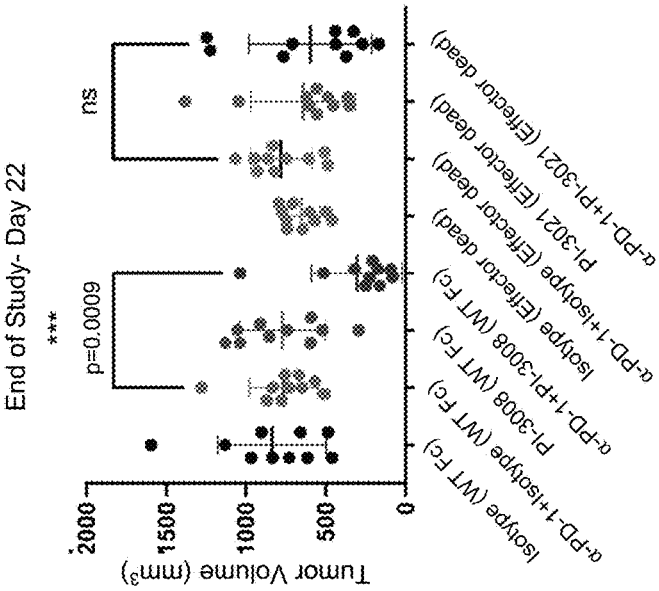
FIG. 13I shows the shows the tumor volumes in mice treated with the indicated antibody
Figure 13K:
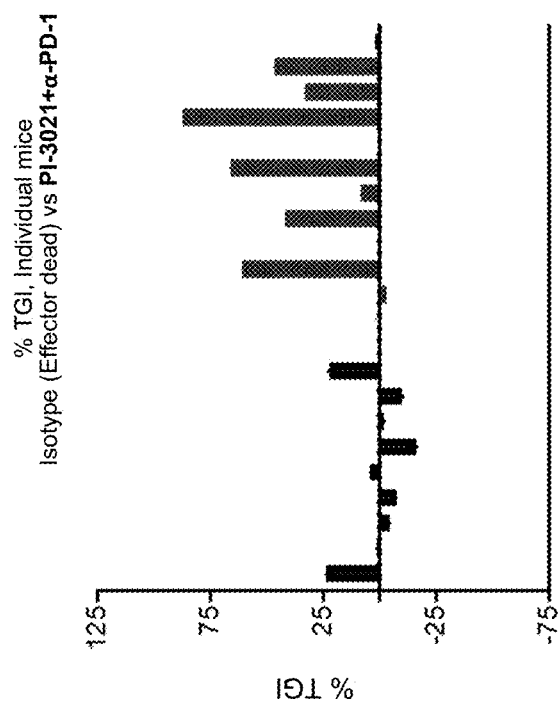
FIG. 13E shows the tumor volumes in individual mice treated with isotype control antibody.
FIG. 13F shows the tumor volumes in individual mice treated with fucosylated PI-3008.
FIG. 13G shows the tumor volumes in individual mice treated with afucosylated PI-3008.
FIG. 13J shows the percentage of tumor growth inhibition (% TGI) in mice treated with isotype control antibody (wt Fc) as compared to wt Fc PI-3008 and PD-1 antibody. FIG.
Figure 13J:
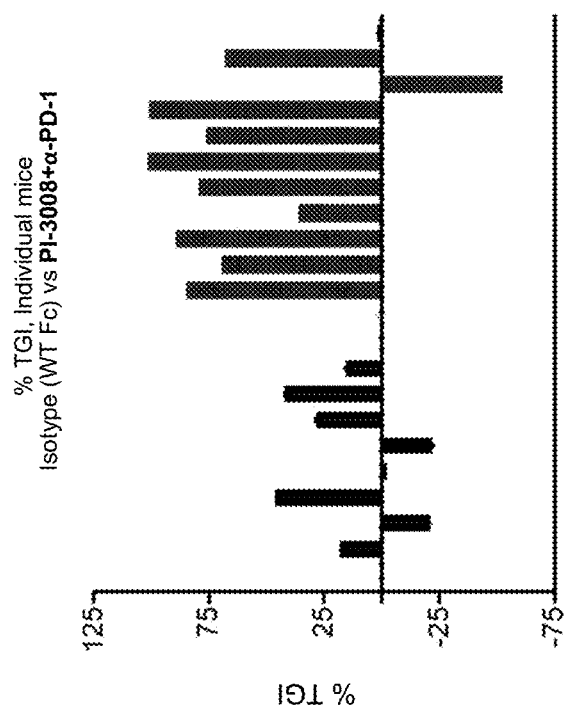

PI-3008 demonstrated better single agent (monotherapy) anti-tumor activity than the Fc enhanced variant (PI-3008-Afuc). Afucosylated PI-3008 did not show appreciable monotherapy when compared to fucosylated PI-3008 (FIGS. 13E, 13F, and 13G). Without wishing to be bound by theory, this data suggests that enhanced Fc mediated engagement is not required for monotherapy Effector Dead Antibody Assay The effector dead PI-3008 (PI-3021) also did not result in increased anti-tumor efficacy. Anti-tumor efficacy of PI-3008 in combination with anti-PD-1 was robust and more pronounced than that of PI-3021/anti-PD-1 combination (FIG. 13H). In the CT26 model, PI-3021 in combination with anti-PD1 did not lead to same level anti-tumor activity as observed with PI-3008 (FIG. 13H). At the end of study, day 22, PI-3008 had significant reduction in tumor volume compared to anti-PD-1 alone while PI-3021 did not reach statistical significance (FIG. 13I). In addition, percentage of tumor growth inhibition (% TGI) was higher in PI-3008 compared to PI-3021 in individual mice treated with combination therapy (FIGS. 13J and 13K). Finally, mouse BMDMs treated in vitro with PI-3021 did not show activation of the pro-inflammatory pathways as seen with PI-3008 after 4 hr of treatment (data not shown). Without wishing to be bound by theory, this data suggests that PI-3008 with a fucosylated Fc is the optimal Fc format for the desired anti-tumor activity in vivo in in the anti-PD-1 resistant CT26 mouse model. However, PI-3021 demonstrated equal anti-tumor activity as PI-3008 in the E0771 anti-PD1 sensitive model (Example 11 and FIG. 38), suggesting that anti-MARCO antibody activity could also be due to target activity on MARCO in addition to Fc-mediated signaling.

Anti-MARCO and PD-1 combination treatment also resulted in long-term, anti-tumor immune memory after CT26 tumor challenge (FIG. 14). The mice that were tumor free after the first treatment of anti-MARCO antibodies were re-implanted with CT26 tumor cells, or EMT6 tumor cells. As shown in FIG. 14, no growth of the re-implanted CT26 tumor cells was observed in the mice that had been previously treated with anti-MARCO and anti-PD-1 antibodies.

The pharmacodynamics (PD) and anti-tumor efficacy of one anti-MARCO antibody, PI-3008, was also assessed in the CT26 colorectal tumor model as single agent monotherapy (FIG. 15A-15C). The PI-3008 anti-MARCO antibody demonstrated significant monotherapy in the CT26 model. FIG. 15A shows a timeline of the PD study. FIG. 15B shows that treatment with PI-3008 reduced mouse tumor size 6 days after the first dose, as compared to isotype control antibody. FIG. 15C shows quantification of the PI-3008 antibody in the mice after the first and second dose.

Molecular profiling analysis of CT26 tumors was also performed on samples taken 4 hours after the first and second dose of PI-3008 and isotype antibodies. The anti-MARCO antibody activated multiple immune pathways. After dose 1, genes in the actin mediated cell contraction pathway were upregulated, with a pathway FDR<0.1. 4 hours after the second dose, genes in kinase activation and activity pathway, Toll-like receptor signaling pathway, TLR 4 and 9 pathways, GTPase binding and activity, and RAS-Rho signal transduction pathways were upregulated. After both the first and second dose, the following pathways were upregulated: humoral immune response, NK mediated immunity, NK activation, IL-2 and IL-12 production, cell killing, regulation of effector process, T cell proliferation, activation, differentiation, chemotaxis and migration, cell-cell adhesion, phagocytosis, and myeloid differentiation.

The KEGG pathways induced by anti-MARCO antibody in the CT26 tumors in vivo were determined. After dose 1, the top 10 most differentially upregulated pathways were: Natural Killer cell mediated cytotoxicity, T cell receptor signaling pathway, JAK/STAT signaling pathway, cytokine-cytokine receptor interaction, Intestinal immune network for IgA production, leukocyte trans-endothelial migration, chemokine signaling pathway, hematopoietic cell lineage, type II diabetes mellitus, and Fc-epsilon RI signaling pathway. After dose 1, the top 10 most differentially downregulated pathways were: homologous recombination, Alzheimer's disease, RNA polymerase, arginine and proline metabolism, citrate cycle (TCA cycle), porphyrin and chlorophyll metabolism, valine, leucine, and isoleucine degradation, biosynthesis of unsaturated fatty acids, N-glycan biosynthesis, and aminoacyl tRNA biosynthesis.

After dose 2, the top 10 most differentially upregulated pathways in the CT26 tumors were: cytokine-cytokine receptor interaction, Natural Killer cell mediated cytotoxicity, primary immunodeficiency, chemokine signaling pathway, hematopoietic cell lineage, JAK/STAT signaling pathway, T cell receptor signaling pathway, Intestinal immune network for IgA production, neuroactive ligand receptor interaction, and Fc-epsilon RI signaling pathway. After dose 2, the top 10 most differentially downregulated pathways were: glycolysis gluconeogenesis, propanoate metabolism, proteasome, citrate cycle TCA cycle, cardiac muscle contraction, Alzheimer's disease, Huntington's disease, oxidative phosphorylation, ribosome, and Parkinson's disease.

The KEGG pathways induced by anti-MARCO antibody in the tumor draining lymph nodes in vivo were also determined. After dose 1, the top 10 most differentially upregulated pathways were: phosphatidylinositol signaling system, focal adhesion, inositol phosphate metabolism, axon guidance, adherens junction, pathways in cancer, regulation of actin cytoskeleton, progesterone mediated oocyte maturation, ERBB signaling pathway, and Wnt signaling pathway. After dose 1, the top 10 most differentially downregulated pathways were: aminoacyl tRNA biosynthesis, lysosome, histidine metabolism, drug metabolism cytochrome p450, proteasome, Alzheimer's disease, Huntington's disease, Parkinson disease, oxidative phosphorylation, and ribosome.

After dose 2, the top 10 most differentially upregulated pathways in the tumor draining lymph nodes were: focal adhesion, phosphatidylinositol signaling system, neurotrophin signaling pathway, insulin signaling pathway, inositol phosphate metabolism, MAPK signaling pathway, pathways in cancer, regulation of actin cytoskeleton, ERBB signaling pathway, and adherens junction. After dose 2, the top 10 most differentially downregulated pathways were: metabolism of xenobiotics by cytochrome p450, hematopoietic cell lineage, lysosome, Alzheimer's disease, proteasome, cytokine-cytokine receptor interaction, Huntington's disease, Parkinson's disease, oxidative phosphorylation, and ribosome.

The KEGG pathways induced by anti-MARCO antibody in the spleen in vivo were also determined. After dose 1, upregulated pathways included: ECM receptor interaction, focal adhesion, tight junction, adheres junction, proteasome, complement and coagulation cascades, cell adhesion molecules and CAMs, pathways in cancers, arrhythmogenic right ventricular cardiomyopathy ARVC, Wnt signaling pathway, regulation of actin skeleton, axon guidance, Huntington's disease, pathogenic *Escherichia coli* infection, Alzheimer's disease, leukocyte transendothelial migration, cytokine-cytokine receptor interaction, basal cell carcinoma, melanogenesis, and hedgehog signaling pathway. Downregulated pathways included: cell cycle, aminoacyl tRNA biosynthesis, mismatch repair, glycosylphosphatidylinositol GPI anchor biosynthesis, glycerophospholipid metabolism, and homologous recombination.

After dose 2, upregulated pathways in the spleen included: cell cycle, proteasome, T cell receptor signaling pathway, DNA replication, ubiquitin mediated proteolysis, regulation of actin cytoskeleton, adherens junction, pathogenic *Escherichia coli* infection, basal transcription factors, pentose phosphate pathway, Fc gamma R mediated phagocytosis, neurotrophin signaling pathway, regulation of autophagy, glycolysis gluconeogenesis, oocyte meiosis, chronic myeloid leukemia, citrate cycle TCA cycle, Wnt signaling pathway, P53 signaling pathway, and natural killer cell mediated cytotoxicity. Downregulated pathways included: ABC transporters, glycosylphosphatidylinositol GPI anchor biosynthesis, RNA polymerase, ribosome, arachidonic acid metabolism, glycerophospholipid metabolism.

A more in depth analysis of the differentially expressed genes in the PI-3008-treated CT26 tumors after dose 1 and dose 2 was also performed. Genes associated with NK cells, such as Klrk1, Nrc1, and Prf1; genes associated with pro-inflammatory and immune activation, such as Cd40, Cd8a, Nod2, Tlr4, Tnf, Nlrp3, Cd274, Clec9a, and Cd200r3; and pro-inflammatory cytokines, such as 11-27, Cxcl9, Cxcl10, and Cxcl12 were upregulated. FIG. 16A shows the expression levels of Klrk1, Nrc1, Tlr4, 11-27, Cd8a, Cxcl9, Cxcl10, and Tnf in the CT26 tumor microenvironment after treatment with PI-3008 or an isotype control antibody. In each case, treatment with PI-3008 increased expression of the gene. FIG. 16B shows a comparison of the genes upregulated in BMDMs and CT26 tumors after treatment with PI-3008.

In addition, anti-Marco antibody 3008 upregulated IG-V genes in CT26 spleens after the first dose. 154 annotated IG-V genes with CPM>1 are known. All of the 154 annotated IG-V genes were upregulated with PI-3008 treatment, while 138/154 were differentially expressed with an FDR<0.05. Thus, polyclonal expansion of plasma cells or activated B-cells in the Marginal Zone in the spleen may be occurring upon anti-MARCO antibody treatment to activate self-antigens or tumor antigens, such as NK activation.

Example 5: Production and Characterization of Additional Anti-Human MARCO Antibodies Materials and Methods A further antibody campaign to develop antibodies that bind to the SRCR domain of human MARCO was performed.

Immunization for Generating Anti-Human MARCO Antibodies

Rat anti-human MARCO hybridomas were generated by immunizing Sprague Dawley rats with recombinant N-terminal-his tagged human MARCO protein in Sigma Adjuvant System (SAS) alone or alternating with human MARCO expressing HEK 293 cells. The recombinant N-terminal his-tagged human MARCO protein comprised residues 147-520 of human MARCO. The recombinant human MARCO protein was quality control for proper folding and trimer formation. In contrast, the human MARCO protein (Pi 114) previously used for the unsuccessful anti-human MARCO campaign described in Example 2 consisted of a modified MARCO ECD domain comprising residues 147-419 of the CLD domain and residues 424-520 of the SRCR domain.

Rats were immunized twice weekly in the hock and serum titers tested at day 21 at Antibody Solutions (Santa Clara, Calif.). Rats with sufficient serum antibody titers to human MARCO were chosen for electrofusion to generate hybridomas. Two final boosts were given on days −3 and −2 prior to harvest Immunizations in phosphate buffered saline (PBS).

Hybridoma Generation and Screening

Hybridoma generation and screening assays for human MARCO antibodies were performed as described in Example 3.

Cell Binding

Cell binding assays for human MARCO antibodies were performed as described in Example 3.

Hybridoma Subcloning and Purification

Hybridoma subcloning and purification for human MARCO antibodies were performed as described in Example 3.

Hybridoma Antibody Variable Region Sequences Generation

Hybridoma antibody variable region sequences for human MARCO antibodies were generated as described in Example 3.

Chimeric and Humanized Antibody Generation

Chimeric antibodies were made by replacing the rat IgG1 or IgG2a Fc domain with human IgG1 or IgG4 domains.

Humanized antibodies were also synthesized from the rat parental hybridomas.

The VH and VL sequences of the rat hybridomas were compared to libraries of known human germline sequences on the NCBI website (ncbi.nlm.nih.gov/igblast/; Ye, J. et al. Nucleic Acids Research 41:W34-W40 (2013)). The databases used were IMGT human VH genes (F+ORF, 273 germline sequences) and IMGT human VLkappa genes (F+ORF, 74 germline sequences) as used by the NCBI IgBLAST program. The acceptor human germline was chosen from those closest in sequence to the parental antibody.

Human germline IGHV1-46 (allele 1) was chosen as the acceptor sequence and the human heavy chain IGHJ4(allele 1) joining region (J gene) was chosen from human joining region sequences compiled at IMGT® the international ImMunoGeneTics information System® imgt.org (founder and director: Marie-Paule Lefranc, Montpellier, France).

Human germline IGKV1-39(allele 1) was chosen as the acceptor sequence and human light chain IGKJ2(allele 1) joining region (J gene) was chosen from human joining region sequences compiled at IMGT® the international ImMunoGeneTics information System® imgt.org (founder and director: Marie-Paule Lefranc, Montpellier, France). Sequence alignments of the HX-3061 rat parental and humanized VH and VL sequences are shown in FIGS. 17A and 17B, respectively. Sequence alignments of the HX-3031 rat parental and humanized VL sequences are shown in FIG. 18.

Additional back mutations were made in the humanized antibody VH derived from the HX-3061 hybridoma and the VL derived from the HX-3031 hybridoma. The back mutations made in the HX-3061 VH were: V37I, V48I, and S49A, based on the human framework VH sequence. The back mutations made in the HX-3031 VL were: A13T, A43P, S56D, F71Y, L78M, F83E, and Y87F, based on the human framework VL sequence.

CDRs were defined according to the AbM definition (bioinforg.uk/abs/ for a table comparing CDR definitions).

Calcium Dependency ELISA Assay

The calcium dependency ELISA assay was performed as described in Example 3.

Kinetics and Epitope Binning Using the ProbeLife Gator Instrument

Kinetics and epitope binning analysis of the newly generated anti-human MARCO antibodies was performed as described in Example 3.

LDL Competition Assay on Mouse and Human Recombinant MARCO

LDL competition assay on mouse and human recombinant MARCO was performed as described in Example 3.

MARCO Bacteria Competition Assay 293T cells expressing human or mouse MARCO were harvested along with the parental 293T cells. Zombie NIR viability dye (BioLegend) was prepared by diluting the stock 1000-fold in D-PBS and added to the cells. The cells were incubated with the dye for 10 min at RT in the dark. The reaction was quenched by adding 1 m of 4× Staining buffer (2% FBS in DBPS containing $Ca^{2+}$), followed by centrifugation at 400×g for 5 min at 4° C. Cells were then plated in V-shaped 96 well plates at a density of 100,000 cells. A488-fluorescently labeled bacteria (*E. coli* from Invitrogen) was added at 10 μg/ml with the anti-human or anti-mouse antibodies of interest for a 30 min incubation at 37 C. Plates were then washed twice followed by resuspension in 100 ul of staining buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8).

Results

Primary screening of anti-human MARCO antibodies via ELISA screening for binding to human MARCO resulted in 304 candidates. A secondary screening 304 candidate antibodies were identified in the primary ELISA screen using purified human MARCO. Secondary screening of binding to 293T cells expressing human, cyno, and mouse MARCO or GFP control cells resulted in 138 candidates. An additional secondary screen for SRCR verus CLD binding was also performed via ELISA. 90 SRCR binding antibodies and 47 CLD binding antibodies were identified. Candidate antibodies were then screened for binding on endogenous cells, binding kinetics, LDL competition, and binding to human MSR1. 42 candidate antibodies were identified, 37 SRCR binding antibodies and 5 CLD binding antibodies. Of these, 11 candidate anti-human MARCO antibodies were identified with good binding characteristics. The sequences of selected human MARCO antibodies are shown in the sequence listing table. The CDRs are defined using the AbM definition.

The characterization of the rat hybridoma anti-human MARCO antibodies generated are shown in Table 3.

TABLE 3

| Anti-huMARCO mAb | Isotype | Bin | $Ca^{2+}/Mg^{2+}$ req for binding | $K_{on}$ (1/Ms) | $K_{off}$ (1/s) | Human $EC_{50}$ 293T(HuMARCO) (nM) | Cyno $EC_{50}$ 293T(CyMARCO) (nM) | $EC_{50}$ LDL competition assay (nM) | MSR1 binding |
|---|---|---|---|---|---|---|---|---|---|
| PI-HX-3011 | Rat IgG2a | 3 | + | 4.01E+05 | 9.14E−04 | 0.096 | 0.094 | NA | − |
| PI-HX-3023 | Rat IgG2a | 2 | +/− | 2.27E+05 | 4.75E−04 | 0.451 | 0.071 | 1.5 | − |
| PI-HX-3026 | Rat IgG2a | 2 | + | 2.42E+05 | 6.01E−04 | 0.23 | 0.162 | 1.3 | − |
| PI-HX-3028 | Rat IgG2a | 2 | +/− | 2.42E+05 | 4.79E−04 | 0.332 | 0.144 | 1.5 | − |
| PI-HX-3031 | Rat IgG2a | 3 | + | 4.43E+05 | 7.98E−04 | 0.141 | 0.046 | NA | − |
| PI-HX-3033 | Rat IgG2a | 2 | + | 2.70E+05 | 8.07E−04 | 0.272 | 0.067 | NA | − |
| PI-HX-3040 | Rat IgG2a | 3 | + | 2.41E+05 | 6.72E−04 | 0.229 | 0.107 | 2.9 | − |
| PI-HX-3041 | Rat IgG2a | 3 | + | 3.08E+05 | 7.96E−04 | 0.215 | 0.110 | NA | − |
| PI-HX-3043 | Rat IgG2a | 3 | + | 2.33E+05 | 8.49E−04 | 0.438 | 0.067 | 3.4 | − |
| PI-HX-3047 | Rat IgG2a | 1 | − | 4.84E+05 | 6.55E−04 | 0.326 | 0.100 | NA | − |
| PI-HX-3061 | Rat IgG2a | 4 | − | | | 0.49 | 0.45 | 8.2 | − |

Five of the eleven candidate anti-MARCO antibodies were selected for further development based on CDR sequence analysis: PI-HX-3011, PI-HX-3031, PI-HX-3043, PI-HX-3061, and PI-HX-3092. Human chimeric antibodies were made by exchanging the rat IgG2a Fc region with human IgG1 (for PI-HX-3011 and PI-HX-3043) or both IgG1 and IgG4 (for PI-3031 ad PI-HX-3061). Additional chimeric antibodies were also made by exchanging the rat IgG2a Fc region with mouse IgG2a (for PI-HX-3036, and PI-HX-3092). Further humanization of the VH and VL frameworks was performed on antibodies derived from the PI-HX-3011, PI-HX-3031, and PI-HX-3061 rat parental antibodies.

Table 4 provides a summary of the selected rat parental antibodies, the chimeric antibodies, and the humanized antibodies generated.

TABLE 4

| Name | Revised Name (if applicable) | Description | SEQ ID NOs |
|---|---|---|---|
| PI-HX-3031 | | parental rat hybridoma | 1-10 |
| PI-3010-AB | PI-3010 | hIgG1/chimeric PI-HX- 3031 | 11-20 |
| PI-3011-AB | PI-3010.11 | humanized PI-HX- 3031/3031-1 hIgG1 | 21-30 |
| PI-3012-AB | PI-3010.12 | humanized PI-HX- 3031/3031-2 hIgG1 | 31-40 |
| PI-3013-AB | PI-3010.13 | humanized PI-HX- 3031/3031-3 hIgG1 | 41-50 |
| PI-3014-AB | PI-3010.14 | humanized PI-HX- 3031/3031-4 hIgG1 | 51-60 |
| PI-3015-AB | PI-3010.15 | humanized PI-HX- 3031/3031-5 hIgG1 | 61-70 |
| PI-3020-AB | PI-3010.20 | chimeric PI-HX- 3031 - hIgG4 | 71-80 |
| PI-3022-AB | PI-3010.22 | humanized PI-HX- 3031/3031-2 hIgG1 | 81-90 |
| PI-3023-AB | PI-3010.23 | humanized PI-HX- 3031/3031-2 hIgG1 | 91-100 |
| PI-3024-AB | PI-3010.24 | humanized PI-HX- 3031/3031-2 hIgG1 | 101-110 |
| PI-3025-AB | PI-3010.25 | humanized PI-HX- 3031/3031-2 hIgG1 | 434-443 |
| PI-3026-AB | PI-3010.26 | humanized PI-HX- 3031/3031-2 hIgG1 | 121-130 |
| PI-3027-AB | PI-3010.27 | humanized PI-HX- 3031/3031-2 hIgG1 | 131-140 |

TABLE 4-continued

| Name | Revised Name (if applicable) | Description | SEQ ID NOs |
|---|---|---|---|
| PI-3046-AB | PI-3010.46 | humanized PI-HX- 3031/3031-2 hIgG4 | 474-483 |
| PI-3048-AB | PI-3010.48 | humanized PI-HX- 3031/3031-2 hIgG4 | 444-453 |
| PI-HX-3061 | | parental rat hybridoma | 141-150 |
| PI-3016-AB | | humanized PI-HX- 3061/3061-1 hIgG1 | 151-160 |
| PI-3017-AB | | humanized PI-HX- 3061/3061-2 hIgG1 | 161-170 |
| PI-3018-AB | | humanized PI-HX- 3061/3061-3 hIgG1 | 171-180 |
| PI-3019-AB | | PI-HX-3061 mIgG2a chimera | 181-190 |
| PI-3028-AB | | PI-HX-3061 hIgG1 chimera | 191-200 |
| PI-3029-AB | | PI-HX-3061 hIgG4 chimera | 201-210 |
| PI-3032-AB | | humanized PI-HX- 3061/3061-2 hIgG1 | 211-220 |
| PI-3033-AB | | humanized PI-HX- 3061/3061-2 hIgG1 | 221-230 |
| PI-HX-3011 | | parental rat hybridoma | 231-240 |
| PI-3030-AB | PI-3030 | HX3011-h1 Chimera hIgG1 | 241-250 |
| PI-3036-AB | PI-3030.36 | humanized PI-HX- 3011/3011-1 hIgG1 | 311-320 |
| PI-3037-AB | PI-3030.37 | humanized PI-HX- 3011/3011-2 hIgG1 | 321-330 |
| PI-3038-AB | PI-3030.38 | humanized PI-HX- 3011/3011-3 hIgG1 | 331-340 |
| PI-3039-AB | PI-3030.39 | humanized PI-HX- 3011/3011-4 hIgG1 | 341-350 |
| PI-3040-AB | PI-3030.40 | humanized PI-HX- 3011/3011-5 hIgG1 | 351-360 |
| PI-3041-AB | PI-3030.41 | humanized PI-HX- 3011/3011-5 hIgG1 | 454-463 |
| PI-3047-AB | PI-3030.47 | humanized PI-HX- 3011/3011-5 hIgG4 | 464-473 |
| PI-HX-3043 | | parental rat hybridoma | 251-260 |
| PI-3031-AB | | HX3043-h1 Chimera hIgG1 | 261-270 |
| PI-HX-3092 | | parental rat hybridoma | 361-370 |
| PI-3035 | | HX3092 (A mutation) - mIgG2a | 371-380 |

The newly generated rat hybridoma anti-human MARCO antibodies were characterized as previously described. The characterization of the rat parental antibodies HX-3031 and HX-3061 is shown in Table 5. Neither antibody bound to MSR1. Binding kinetics were determined via Multi Cycle Kinetics analysis using the huMARCO antigen as previously described.

TABLE 5

| Anti-hu MARCO) mAb | Bin | Ca2+/ Mg2+ req for binding | $EC_{50}$ (raIgG2a) ELISA (hu/SRCR/cyn) | $K_D$ (M) Hu | $K_D$ (M) Cyno | Human $EC_{50}$ 293T (Hu MARCO) (nM) | Cyno $EC_{50}$ 293T (Cy MARCO) (nM) | Mouse $EC_{50}$ 293T (Mu MARCO) (nM) | $EC_{50}$ Bac competition assay (nM) | $EC_{50}$ LDL competition assay (nM) |
|---|---|---|---|---|---|---|---|---|---|---|
| PI-HX-3031 | 3 | + | 0.13/0.15/0.14 | 9.13E−11 | 1.09E−10 | 0.56 | 0.51 | nb | 0.18 | 6.2 |
| PI-HX-3061 | 4 | − | 0.24/0.24/0.23 | 2.56E−10 | 1.19E−10 | 0.49 | 0.45 | 1.52 | 0.52 | 8.2 |

One anti-huMARCO antibody (PI-HX-3061) was determined to be cross reactive with human and mouse MARCO.

Three antibodies, two anti-mouse MARCO antibodies, PI-3008 and PI-3009, and the cross reactive anti-human MARCO antibody PI-HX-3061, were further characterized in a bacterial binding assay. As shown in FIG. 19, incubation of muMARCO 293T cells with increasing concentrations of each of PI-3008, PI-3009, or PI-HX-3061 decreased bacterial binding in a dose dependent manner, while incubation with isotype controls rat IgG1 or mouse IgG2a did not affect bacteria binding to the cells.

A comparison of the physical properties of PI-3008, PI-3009, and PI-HX-3061 is provided in Table 6.

TABLE 6

| Anti-muMARCO mAb | Mouse bin | Ca2+/Mg2+ req for binding | Biacore $K_D$ (nM) | Mouse $EC_{50}$ 293T(muMARCO) (nM) | $EC_{50}$ Bac competition assay (nM) | MSR1 binding | Binding to BMDM | Binding to TAMs in vivo |
|---|---|---|---|---|---|---|---|---|
| PI-3008 | 2 | Yes | <0.02 | 1.097 | 1.81 | – | + | + |
| PI-3009 | 4 | Yes | <0.02 | TBD | 3.84 | – | + | + |
| PI-HX-3061 (Cross-reactive) | 5 | No | <0.02 | 2.526 | 0.85 | – | + | TBD |

ELISA screening of selected rat hybridoma parental antibodies with 4 EDTA concentrations on recombinant human MARCO showed differential dependency on divalent cations for binding to MARCO with the various anti-MARCO antibodies and different epitopes. The results are shown in Table 7.

TABLE 7

| | Clone ID | EDTA [Conc] | | | |
|---|---|---|---|---|---|
| | | 0 | 2 mM | 10 mM | 50 mM |
| SRCR | PI-HX-3010 | 0.9525 | 0.8158 | 0.101 | 0.1055 |
| | PI-HX-3011 | 1.1743 | 0.0636 | 0.0811 | 0.082 |
| | PI-HX-3047 | 0.9688 | 1.2065 | 0.9205 | 0.9986 |
| | PI-HX-3031 | 1.3709 | 0.0678 | 0.0589 | 0.0754 |
| | PI-HX-3043 | 1.1971 | 0.0595 | 0.06 | 0.1002 |
| CLD | PI-HX-3049 | 1.1909 | 1.1447 | 1.0708 | 1.1915 |
| | PI-HX-3048 | 1.1987 | 1.2159 | 1.0695 | 1.2002 |

Select human chimera and further humanized antibodies were also characterized for species binding specificity, divalent cation binding requirement, SRCR and CLD domain binding kinetics, and cell binding.

As shown in FIG. 52, binding of some anti-MARCO antibodies to MARCO was calcium dependent. Addition of 2 mM EDTA abrogated binding of PI-3010.15, PI-3010.25, and PI-3030.41 to MARCO while the binding of a calcium independent mAb, PI-3032 was not affected. The surrogate anti-mouse MARCO mAb, PI-3008-AB also bound to mouse MARCO in a calcium dependent manner. Addition of 2 mM EDTA abrogated binding, while a calcium independent anti-mouse MARCO mAb, PI-3000 was not affected.

A summary of the characterization results for PI-3010 (hIgG1), PI-3030 (hIgG1), and PI-3031 (hIgG1) are shown in Table 8.

TABLE 8

| Anti-huMARCO mAb | Specificity | Ca²⁺ dependent binding | $K_D$ (nM) Human | $K_D$ (nM) Cyno | $K_{off}$ (1/s) ProbeLife | $EC_{50}$ (nM) OVX Human | $EC_{50}$ (nM) OVX HuSRCR-mouse CLD | $EC_{50}$ (nM) OVX Cyno | Binding to PBLs |
|---|---|---|---|---|---|---|---|---|---|
| PI-3010-AB (hIgG1) | hu/cy | Yes | 0.43–0.64 | 0.26 | 2.34E–03 | 0.68 | 0.25 | 0.34 | No |
| PI-3030-AB (hIgG1) | hu/cy | Yes | 0.44 | n.d. | 3.51E–03 | 0.55 | 0.17 | 0.38 | No |
| PI-3031-AB (hIgG1) | hu/cy | Yes | 0.60 | n.d. | 2.81E–03 | 1.6 | 1.071 | 1.092 | No |

Results for the PI-3031 (hIgG1) chimera and two further humanized antibodies based on the PI-3031 chimera are shown in Table 9.

TABLE 9

| mAb | SRCR Epitope | $Ca^{2+}$ dep | $EC_{50}$ (raIgG2a) ELISA (hu/SRCR/cyn) | $K_D$ (M; sc) Human | $K_D$ (M; sc) Cyno | $EC_{50}$ (nM) OVX Human | $EC_{50}$ (nM) OVX Cyno | $EC_{50}$ Bac (nM) Cell-based | MSRI Binding |
|---|---|---|---|---|---|---|---|---|---|
| PI-3031-chi (PI-3010) | Bin 3 | Yes | 0.04/0.12/0.07 | 4.30E−10 | 2.59E−10 | 0.68 | 1.48 | 0.44 | − |
| PI-3031-h2 (PI-3012) | Bin 3 | Yes | 0.08/0.27/0.07 | 1.13E−09 | 7.35E−10 | 0.57 | 1.40 | 0.12 | − |
| PI-3031-h5 (PI-3015) | Bin 3 | Yes | 0.08/0.25/0.09 | 9.11E−10 | 6.11E−10 | 0.86 | 1.73 | 0.50 | − |

The chimera antibodies PI-3010, PI-3030, and PI-3031 were also assessed for PBL binding. As shown in FIG. 20A, the chimera antibodies bound to 293T cells overexpressing MARCO but not to the immune cells present in PBLs. The binding to eosinophils was non-specific across all tested antibodies including the hIgG1 isotype control. PI-3010 is shown on the left, PI-3030 is shown on the left middle, PI-3031 is shown on the right middle, and isotype control hIgG1 is shown on the right. Binding of PI-HX-3031 in immune cells from Endometrial cancer (primary human tumor) was also assessed. As shown in FIG. 20B, the antibody bound to TAMs and monocytes from the tumor sample. Antibody binding is the right peak, isotype control binding is the left peak.

Example 6: Epitope Mapping by Surface Residues Swapping

Materials and Methods

Mouse MARCO SRCR crystal structure (PDB Entry 2OY3) was used to design the constructs. Mouse and human MARCO SRCR sequences were aligned and different residues on the protein surface were swapped with each other in clusters. N-term his tag and CLD domain were added to the SRCR sequences to produce recombinant proteins. The sequences for the recombinant proteins used in these studies are listed below. Bold and underlined residues are the swapped epitope residues:

hMARCO(His-CLD-SRCR) (RG3033)
(SEQ ID NO: 495)
HHHHHHKGEQGAPGLQGHKGAMGMPGAPGPPGPPAEKGAKGAMGRDGATG

PSGPQGPPGVKGEAGLQGPQGAPGKQGATGTPGPQGEKGSKGDGGLIGPK

GETGTKGEKGDLGLPGSKGDRGMKGDAGVMGPPGAQGSKGDFGRPGPPGL

AGFPGAKGDQGQPGLQGVPGPPGAVGHPGAKGEPGSAGSPGRAGLPGSPG

SPGATGLKGSKGDTGLQGQQGRKGESGVPGPAGVKGEQGSPGLAGPKGAP

GQAGQKGDQGVKGSSGEQGVKGEKGERGENSVSVRIVGSSNRGRAEVYYS

GTWGTICDDEWQNSDAIVFCRMLGYSKGRALYKVGAGTGQIWLDNVQCRG

TESTLWSCTKNSWGHHDCSHEEDAGVECSV* hVar1 (RG3034)
(SEQ ID NO: 496)
HHHHHHKGEQGAPGLQGHKGAMGMPGAPGPPGPPAEKGAKGAMGRDGATG

PSGPQGPPGVKGEAGLQGPQGAPGKQGATGTPGPQGEKGSKGDGGLIGPK

GETGTKGEKGDLGLPGSKGDRGMKGDAGVMGPPGAQGSKGDFGRPGPPGL

AGFPGAKGDQGQPGLQGVPGPPGAVGHPGAKGEPGSAGSPGRAGLPGSPG

SPGATGLKGSKGDTGLQGQQGRKGESGVPGPAGVKGEQGSPGLAGPKGAP

GQAGQKGDQGVKGSSGEQGVKGEKGERGENSVSVRIVGSSNRGRAEVYYN

NEWGTICDDEWQNSDAIVFCRMLGYSKGRALYKVGAGTGQIWLDNVQCRG

TESTLWSCTKNSWGHHDCSHEEDAGVECSV* hVar2 (RG3035)
(SEQ ID NO: 497)
HHHHHHKGEQGAPGLQGHKGAMGMPGAPGPPGPPAEKGAKGAMGRDGATG

PSGPQGPPGVKGEAGLQGPQGAPGKQGATGTPGPQGEKGSKGDGGLIGPK

GETGTKGEKGDLGLPGSKGDRGMKGDAGVMGPPGAQGSKGDFGRPGPPGL

AGFPGAKGDQGQPGLQGVPGPPGAVGHPGAKGEPGSAGSPGRAGLPGSPG

SPGATGLKGSKGDTGLQGQQGRKGESGVPGPAGVKGEQGSPGLAGPKGAP

GQAGQKGDQGVKGSSGEQGVKGEKGERGENSVSVRIVGSSNRGRAEVYYS

GTWGTICDDDWDNNDAIVFCRMLGYSRGRALYKVGAGTGQIWLDNVQCRG

TESTLWSCTKNSWGHHDCSHEEDAGVECSV* hVar3 (RG3036)
(SEQ ID NO: 498)
HHHHHHKGEQGAPGLQGHKGAMGMPGAPGPPGPPAEKGAKGAMGRDGATG

PSGPQGPPGVKGEAGLQGPQGAPGKQGATGTPGPQGEKGSKGDGGLIGPK

GETGTKGEKGDLGLPGSKGDRGMKGDAGVMGPPGAQGSKGDFGRPGPPGL

AGFPGAKGDQGQPGLQGVPGPPGAVGHPGAKGEPGSAGSPGRAGLPGSPG

SPGATGLKGSKGDTGLQGQQGRKGESGVPGPAGVKGEQGSPGLAGPKGAP

GQAGQKGDQGVKGSSGEQGVKGEKGERGENSVSVRIVGSSNRGRAEVYYS

GTWGTICDDEWDNSDAIVFCRMLGYSKGRALSSVGAGTGQIWLDNVQCRG

TESTLWSCTKNSWGHHDCSHEEDAGVECSV* hVar4 (RG3037)
(SEQ ID NO: 499)
HHHHHHKGEQGAPGLQGHKGAMGMPGAPGPPGPPAEKGAKGAMGRDGATG

PSGPQGPPGVKGEAGLQGPQGAPGKQGATGTPGPQGEKGSKGDGGLIGPK

GETGTKGEKGDLGLPGSKGDRGMKGDAGVMGPPGAQGSKGDFGRPGPPGL

AGFPGAKGDQGQPGLQGVPGPPGAVGHPGAKGEPGSAGSPGRAGLPGSPG

SPGATGLKGSKGDTGLQGQQGRKGESGVPGPAGVKGEQGSPGLAGPKGAP hVar5 (RG3038)

(SEQ ID NO: 500)
HHHHHHKGEQGAPGLQGHKGAMGMPGAPGPPGPPAEKGAKGAMGRDATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYS
GTWGTICDDEWQNSDAIVFCRMLGYSKGRALYKVGAGTGQIWLDNVQCRG
TESTLWSCTKNSWGNHNCVHNEDAGVECSV* hVar6 (RG3039)

(SEQ ID NO: 501)
HHHHHHKGEQGAPGLQGHKGAMGMPGAPGPPGPPAEKGAKGAMGRDATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYS
GTWGTICDDDWDNSDAIVFCRMLGYSKGRALYKVGAGTGQIWLDNVNCRG
TESTLWSCSKNSWGHHDCSHEEDAGVECSV* hVar7 (RG3040)

(SEQ ID NO: 502)
HHHHHHKGEQGAPGLQGHKGAMGMPGAPGPPGPPAEKGAKGAMGRDATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGESFQRVRIVGGTNRGRAEVYYS
GTWGTICDDEWQNSDAIVFCRMLGYSKGRALYKVGAGTGQIWLDNVQCRG
TESTLWSCTKNSWGHHDCSHEEDAGVECSV* mMARCO (RG3016)

(SEQ ID NO: 484)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTSPGLAGPKGEPGR
VGQKGDPGMKGSSGQQGQKGEKGQKGESFQRVRIMGGTNRGRAEVYYNNE
WGTICDDDWDNNDATVFCRMLGYSRGRALSSYGGGSGNIWLDNVNCRGTE
NSLWDCSKNSWGNHNCVHNEDAGVECS mVar1 (RG3026)

(SEQ ID NO: 504)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTSPGLAGPKGEPGR
VGQKGDPGMKGSSGQQGQKGEKGQKGESFQRVRIMGGTNRGRAEVYYSGT
WGTICDDDWDNNDATVFCRMLGYSRGRALSSYGGGSGNIWLDNVNCRGTE
NSLWDCSKNSWGNHNCVHNEDAGVECS* mVar2 (RG3027)

(SEQ ID NO: 505)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTSPGLAGPKGEPGR
VGQKGDPGMKGSSGQQGQKGEKGQKGESFQRVRIMGGTNRGRAEVYYNNE
WGTICDDEWQNSDATVFCRMLGYSKGRALSSYGGGSGNIWLDNVNCRGTE
NSLWDCSKNSWGNHNCVHNEDAGVECS* mVar3 (RG3028)

(SEQ ID NO: 506)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTSPGLAGPKGEPGR
VGQKGDPGMKGSSGQQGQKGEKGQKGESFQRVRIMGGTNRGRAEVYYNNE
WGTICDDDWQNNDATVFCRMLGYSRGRALYKYGGGSGNIWLDNVNCRGTE
NSLWDCSKNSWGNHNCVHNEDAGVECS* mVar4 (RG3029)

(SEQ ID NO: 507)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTSPGLAGPKGEPGR
VGQKGDPGMKGSSGQQGQKGEKGQKGESFQRVRIMGGTNRGRAEVYYNNE
WGTICDDDWDNNDATVFCRMLGYSRGRALSSYGGGSGNIWLDNVNCRGTE
STLWSCTKNSWGNHNCVHNEDAGVECS* mVar5 (RG3030)

(SEQ ID NO: 508)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG

-continued
SPGVKGDQGKPGVQGVPGPQGAPGLSGAKGEPGRTGLPGPAGPPGIAGNP

GIAGVKGSKGDTGIQGQKGTKGESGVPGLVGRKGDTGSPGLAGPKGEPGR

VGQKGDPGMKGSSGQQGQKGEKGQKGESFQRVRIMGGTNRGRAEVYYNNE

WGTICDDDWDNNDATVFCRMLGYSRGRALSSYGGGSGNIWLDNVNCRGTE

NSLWDCSKNSWGHHDCSHEEDAGVECS* mVar6 (RG3031)
(SEQ ID NO: 509)
HHHHHHHHGERGSPGPKGAPGAPGIPGLPGPAAEKGEKGAAGRDGTPGVQ

GPQGPPGSKGEAGLQGLTGAPGKQGATGAPGPRGEKGSKGDIGLTGPKGE

HGTKGDKGDLGLPGNKGDMGMKGDTGPMGSPGAQGGKGDAGKPGLPGLAG

SPGVKGDQGKPGVQGVPGPQGAPGLSGAKGEPGRTGLPGPAGPPGIAGNP

GIAGVKGSKGDTGIQGQKGTKGESGVPGLVGRKGDTGSPGLAGPKGEPGR

VGQKGDPGMKGSSGQQGQKGEKGQKGESFQRVRIMGGTNRGRAEVYYNNE

WGTICDDEWQNNDATVFCRMLGYSRGRALSSYGGGSGNIWLDNVQCRGTE

NSLWDCTKNSWGNHNCVHNEDAGVECS* mVar7 (RG3032)
(SEQ ID NO: 510)
HHHHHHHHGERGSPGPKGAPGAPGIPGLPGPAAEKGEKGAAGRDGTPGVQ

GPQGPPGSKGEAGLQGLTGAPGKQGATGAPGPRGEKGSKGDIGLTGPKGE

HGTKGDKGDLGLPGNKGDMGMKGDTGPMGSPGAQGGKGDAGKPGLPGLAG

SPGVKGDQGKPGVQGVPGPQGAPGLSGAKGEPGRTGLPGPAGPPGIAGNP

GIAGVKGSKGDTGIQGQKGTKGESGVPGLVGRKGDTGSPGLAGPKGEPGR

VGQKGDPGMKGSSGQQGQKGEKGQKGENSVSVRIMGSSNRGRAEVYYNNE

WGTICDDDWDNNDATVFCRMLGYSRGRALSSYGGGSGNIWLDNVNCRGTE

NSLWDCSKNSWGNHNCVHNEDAGVECS*

Sequence comparisons of the wild type human and mouse SRCR domain, and the mouse and human variant sequences made are shown in FIG. 21.

Binding Kinetics Using the ProbeLife Gator Instrument

The Probe-Life Gator™ label free system was used to analyze binding of the top anti-human and anti-mouse antibodies to the mouse/human SRCR antigen variants.

The kinetics assay used either anti-mouse Fc or anti-human Fc probes to capture the anti-MARCO antibodies onto the probe, and then a five-step kinetic protocol was used to measure the affinity of the antibodies to the different variant antigens described above, including the following steps: baseline, loading, baseline, association, and dissociation. The kinetics buffer (K buffer) provided by ProbeLife was used to establish the baseline for 60 seconds, and then the anti-mFc or anti-hFc probes were loaded with 200 nM of the antibodies for 120s until the capture reached saturation, measurement of the baseline in K buffer was performed for another 60s, followed by the association step using 200 nM antigen (human SRCR MARCO variants and mouse SRCR MARCO variants), and the dissociation step performed in K buffer for 5-10 minutes. The assay was done at 37° C. to maximize antibody:antigen dissociation.

Antibodies used for loading were PI-3010, PI-3008, PI-3019, PI-3030, PI-3031, and PI-3035. PI-3008, PI-3010, and PI-3030 are $Ca2^+$ dependent binders, while PI-3019, and PI-3035 are $Ca2^+$ independent binders. PI-3019 and PI-3035 also have cross reactivity with both human and mouse MARCO.

Results

PI-3008 binding to mMARCO was most affected by the mutations in mVar2, mVar 3, mVar 4, mVar, 5, and mVar6 (data not shown). However, binding of PI-3008 to mMARCO SRCR was the most affected by the mutations in mVar6, and thus the altered residues in mVar6 are likely part of the mMARCO epitope (D450, D452, N487, 5499 of mouse MARCO). The mutations in mVar 1 and mVar 7 had minimal adverse effect on PI-3008 binding to mMARCO. A sequence comparison of wild type (wt) mMARCO SRCR domain and the mVar6 sequence is shown in FIG. 22.

The cross reactive antibodies with Ca2+ independent binding, PI-3019 and PI-3035, were tested with both the mouse and human MARCO variants. PI-3019 was most adversely affected by the mutations in hVar3 (Q452D, Y472S, and K473S of human MARCO), while PI-3035 was adversely affected by hVar5 and hVar6 (data not shown). Similar binding reductions were seen with mVar3 for PI-3019 and mVar 3 and mVar 5 for PI-3035. A sequence comparison of wild type (wt) hMARCO SRCR domain and the hVar3, hVar5, and hVar6 sequences are shown in FIG. 22. The bolded and underlined amino acids were mutated as compared to wild type human or mouse MARCO.

The human-only and Ca2+ dependent antibodies PI-3010, PI-3030, and PI-3031 all showed significantly reduced binding with hVar3 (data not shown). Thus, hVar3 affected binding of PI-3010, PI-3030, PI-3031 and PI-3019, while hVar5 and hVar6 affected binding of PI-3035.

A summary of the antibody binding and cation dependence is shown in Table 10.

TABLE 10

| Antibody | Variant Reduced Binding | Species binding | Ca+ Dependent? |
|---|---|---|---|
| PI-3010 (HX-3031) | hVar3 | Human/Cyno | + |
| PI-3030 (HX-3011) | hVar3 | Human/Cyno | + |
| PI-3033 (HX-3043) | hVar3 | Human/Cyno | + |
| PI-3019 (HX-3061) | hVar3 | Human/Cyno/Mouse | − (independent) |
| PI-3035 (HX-3092) | hVar5, hVar6 | Human/Cyno/Mouse | − (independent) |
| PI-3008 | mVar6 | Mouse | + |

Binding of various human antibodies to hVar3 as measured by ELISA are shown in FIG. 23. hIgG1 and mIgG2a were used as antibody controls. PI-3008 and PI-300 were used as negative controls. Antibodies with single reactivity to human MARCO (PI-3010, PI-3020, PI-3030, PI-3031) did not bind to hVar3, while antibodies derived from the cross reactive HX-3061 hybridoma (PI-3028, PI-3029, PI-319) or HX-3092 (PI-3035) bound to hVar3.

To confirm the importance of the residues identified in hVar3 (Q452, Y472, and K473) as the binding epitope for the single reactive hMARCO antibodies, PI-3010 was bound to both hVar3, which has mutant Q452D, Y472S, and K473S residues, and mVar3, which has the same residues as the wild type human MARCO, Q452, Y472, and K473. The binding of PI-3010 was lost on the hVar3, but restored on mVar3 (data not shown). This confirmed that at least one, some, or all of residues Q452, Y472, and K473 are likely part of the MARCO epitope for the antibodies generated against human MARCO derived from HX-3011, HX-3043, HX-3031, and HX-3061 (e.g., those including, but not limited to, PI-3010, PI-3020, PI-3030, PI-3031, PI-3019, and PI-3033). These residues are also near the D447 D448 E511 acidic cluster on MARCO.

The residues that were mutated in hVar5 that affected binding of PI-3035 were H505, D507, 5509, and E511. The residues that were mutated in hVar6 that affected binding of PI-3035 were E450, Q452, Q487, and T499. Thus, at least one, some, or all of residues E450, Q452, Q487, T499, H505, D507, 5509, and E511 likely represent another binding epitope for antibodies derived from HX-3092 (e.g., those including, but not limited to, PI-3035).

The mouse and human antibodies have overlapping epitopes in the SRCR domain, with one overlapping residue, Q452 for the human SRCR and D452 for mouse SRCR, shown in FIG. 24. The overlapping residue is circled on both the mouse SRCR domain on the left and the human SRCR domain on the right.

Example 7: Non-Human Primate Pharamacokinetics Study

To assess drug exposure and safety of the humanized drug candidates, two pharmacokinetic (PK) assays, total and free (ligand binding), were developed to quantify PI-3025-AB2 (IgG1 format) and PI-3048-AB (IgG4 format) antibody concentrations in an exploratory single dose non-human primate (NHP) PK and tolerability study. The single dose study consisted of four animals (1 male and 1 female per group) dosed at 10 mg/kg with PI-3025-AB2 (IgG1) and PI-3048-AB (IgG4). Table 11 shows the study design.

TABLE 11

| Group | Test Material | Dose Level (mg/kg) | Dose Vol. (ml/kg) | Dose . Conc (mg/ml) | No. animals Males | No. animals Females |
|---|---|---|---|---|---|---|
| 1 | Control Article | 0 | 2 | 0 | 1 | 1 |
| 2 | PI-3025-AB2 | 10 | 2 | 5 | 1 | 1 |
| 3 | PI-3048-AB | 10 | 2 | 5 | 1 | 1 |

Ligand Binding Assay

A standard MSD Plate (Meso Scale Discovery, Catalog #L15XA-3) was coated with recombinant human MARCO protein at 1 μg/mL. The plate was incubated at room temperature for 60 min and then washed. The plate was then blocked with 5% bovine serum albumin (BSA) for 60 min at room temperature.

PI-3025-AB2 and PI-3048-AB protein standards and quality control samples, and animal samples were diluted in buffer (PBS/0.5% BSA/0.05% Tween+Ca2+/Mg2+) and added to the coated plate in salt buffer. The plate was incubated for 60 min at room temperature and washed. 0.5 μg/mL of the detection antibody, anti-human IgG CH2 (Thermo Fisher, Catalog #MA5-16929) was added and the plate incubated for 60 min at room temperature. The plate was washed and 1× Read Buffer (Meso Scale Discovery, Catalog #R92TC-1) was added to the MSD plate. The plate was read on an MSD Sector Imager.

Total PK Assay Format

A streptavidin MSD plate (Meso Scale Discovery, Catalog #L15SA-1) was coated with biotinylated anti-human kappa antibody (Invitrogen, Catalog #SA1-19155) at 1 μg/mL. The plate was incubated at room temperature for 60 min and then washed. PI-3025-AB2 and PI-3048-AB protein standards and quality control samples, and animal samples were diluted in buffer (PBS/0.5% BSA/0.05% Tween+Ca2+/Mg2+) and added to the coated plate in salt buffer. The plate was incubated for 60 min at room temperature and washed. 0.5 μg/mL of the detection antibody, anti-human IgG CH2 (Thermo Fisher, Catalog #MA5-16929) was added and the plate incubated for 60 min at room temperature. The plate was washed and 1× Read Buffer (Meso Scale Discovery, Catalog #R92TC-1) was added to the MSD plate. The plate was read on an MSD Sector Imager.

Results

The single dose study demonstrated that PI-3025 and PI-3048 antibodies have an acceptable PK and were well tolerated. Both total and free assay formats measured similar drug concentrations for each antibody.

The PK calibration curve for PI-3025-AB2 is shown in FIG. 25A and Table 12.

TABLE 12

| | LBA Assay Format | | | Total Assay Format | | |
|---|---|---|---|---|---|---|
| Nominal Conc. ng/ml | Detected Mean Conc. (ng/ml) | Calc. Mean Conc. CV | % Recovery Mean | Detected Mean Conc. (ng/ml) | Calc. Mean Conc CV | % Recovery Mean |
| 240 | 233 | 5 | 94 | 280 | 10 | 116 |
| 100 | 109 | 5 | 106 | 120 | 3 | 120 |
| 50 | 46 | 5 | 96 | 56 | 0 | 111 |
| 10 | 9 | 5 | 89 | 10 | 5 | 100 |
| 5 | 4 | 3 | 77 | 5 | 6 | 91 |

The PK calibration curve for PI-3048-AB is shown in FIG. 25B and Table 13.

TABLE 13

| | LBA Assay Format | | | Total Assay Format | | |
|---|---|---|---|---|---|---|
| Nominal Conc. ng/ml | Detected Mean Conc. (ng/ml) | Calc. Mean Conc. CV | % Recovery Mean | Detected Mean Conc. (ng/ml) | Calc. Mean Conc CV | % Recovery Mean |
| 240 | 217 | 4.1 | 88 | 295 | 0 | 123 |
| 100 | 98 | 0.8 | 97 | 88 | 21 | 88 |
| 50 | 47 | 2.2 | 94 | 58 | 9 | 116 |
| 10 | 10 | 1.8 | 99 | 10 | 16 | 104 |
| 5 | 4 | 2.4 | 85 | 6 | 3 | 129 |

The PK assays were successfully developed to measure drug concentrations in the exploratory NHP study. The PK assay range was 1.85 ng/mL to 300 ng/mL (in assay) with a minimum required dilution (MRD) of 20. The LLOQ was 1.85 ng/mL and the ULOQ was 240 ng/mL. The quality controls (QCs) ranged from 5 ng/mL to 240 ng/mL.

The in vivo ligand binding PK assay results are shown in FIG. 26A. PI-3025-AB2 showed no detectable drug levels post Day 21 (504 hr) in the ligand binding assay (FIG. 26A). PI-3048-AB was detected up to Day 28 (672 hr) in the ligand binding assay (FIG. 26A). The in vivo total PK assay results are shown in FIG. 26B. PI-3025-AB2 was detected up to Day 21 (504 hr) and Day 28 (672 hr) (FIG. 26B). PI-3048-AB was detected up to Day 28 (672 hr) (FIG. 26B). Animals dosed with PI-3048-AB showed slightly better exposure than dosed with PI-3025-AB2.

The PK results for PI-3025-AB2 and PI-3048-AB were comparable using both the total and free assay. PI-3025-AB2 and PI-3048-AB antibodies had an acceptable tolerability and good exposure following the single dose study.

Example 8: Additional Characterization of Anti-Human MARCO Antibodies

Materials and Methods

Anti-MARCO antibody cell binding, SPR binding kinetics ($K_D$) and macrophage binding were performed as previously described in Examples 2 and 5.

Ligand Binding Block Assay 293T cells expressing human MARCO were harvested along with the parental 293T cells. Zombie NIR viability dye (BioLegend), prepared by diluting the stock 1000-fold in D-PBS, was added to the cells and incubated for 10 min at RT in the dark. The reaction was quenched by adding 1 m of 4× Staining buffer (2% FBS in DBPS containing Ca2+), followed by centrifugation at 400×g for 5 min at 4° C. Cells were then plated in V-shaped 96 well plates at a density of 100,000 cells. A488-fluorescently labeled bacteria (*E. coli* from Invitrogen) was added at 10 µg/ml with the anti-human MARCO antibodies of interest for a 30 min incubation at 37 C. Plates were then washed twice followed by resuspension in 100 ul of staining buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8).

T-Cell Binding Assay

A standard flow binding assay using Jurkat T-cells obtained from ATCC was performed. 100,000 cells/well of Jurkat T cells were plated onto U-bottom 96-well plates for staining and all centrifugation steps were performed at 1500 rpm at 4° C. for 5 min and samples were kept protected from light throughout the protocol. Cells were pelleted and resuspended in 100 µl of Zombie NIR viability dye (BioLegend) prepared by diluting Zombie NIR dimethyl sulfoxide (DMSO) stock 1000-fold in D-PBS. Cells were stained by incubation for 10 min at room temperature (RT) in the dark, followed by quenching the staining reaction with the addition of regular Medium containing 10% FBS. Cells were pelleted and resuspended in 100 µl of the different anti-human MARCO antibodies and the corresponding hIgG1 and hIgG4 isotype controls in freshly prepared staining medium (2% FBS in DBPS containing Ca2+). All mAbs were tested at the final top concentration of 100 nM (15 µg/ml) followed by an 8-point three-fold serial dilution, including 0 mg/ml control. Staining was carried out for 1 hour (hr) on ice, followed by 2 washes in Staining Medium. Cells were then pelleted and resuspended in 100 ul of allophycocyanin (APC)-conjugated goat anti-mouse IgG (Fc-specific) secondary antibody, prepared by 500-fold dilution of the antibody stocks in Staining Medium, and incubated for 30 min on ice. Plates were then washed two times with Staining Medium, followed by resuspension in 150 ul of the same buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8). Half-maximal effective concentrations (EC50) were calculated based on geometric mean fluorescence intensities (gMFI).

mAb Thermal Stability Assessment Using Dynamic Light Scattering (DLS)

Dynamic light scattering takes advantage of the Brownian motion of particles in solution or suspension to measure their size. The rate of fluctuation corresponds directly to the diffusion rate of the scattering particles. Larger particles diffuse more slowly, leading to slow optical fluctuations, while smaller particles diffuse more rapidly, leading to fast optical fluctuations. The diffusion coefficient of the particles can be determined from the autocorrelation analysis on the raw optical signals and fitting the resulting autocorrelation function. The particle size is then determined from the diffusion coefficient using the Stokes-Einstein equation.

DLS measurements were made using the Dynapro plate reader III (Wyatt Technology). Antibodies to be evaluated were diluted in 1× PBS (Gibco catalog #14190-144), filtered through a 0.02 um filter to remove particulate matter and large aggregates, to a final concentration of 1-2 mg/mL. Twenty-five microliters of the antibody solution was added to wells of a 384 well plate (Aurora catalog #ABA210100A), followed by 5 uL of silicone oil (Alfa Aesar catalog #A12728). The plate was covered and centrifuged at 1000×g for 1 min to ensure removal of air bubbles. The plate was then loaded on the DLS instrument, and data collected using the following setup along with default instrument settings.

The initial temperature was set at 25° C., followed by a steady increase in temperature by 1° C./min up to 85° C. with enabled auto attenuation of laser intensity. Continuous measurements were made for each well to determine the diffusion coefficient and hydrodynamic radii. The temperature onset for aggregation (Tagg) value was obtained by using the integrated Dynamics7.1 software, which analyzed changes in radii corresponding to change in temperature and identified the temperature corresponding to increase in hydrodynamic radius as the Tagg.

mAb Thermal Stability Assessment Using Differential Scanning Fluorimetry (DSF)

DSF was carried out with the QuantStudio5 real-time PCR instrument (Life Technologies) using the protein thermal shift Protein Thermal Shift™ Dye Kit (Life Technologies Catalog #4461146) following manufacturer protocols. MicroAmp 384-well plates (Thermo Fisher catalog #AB1384/W) were used with 20 µL sample per well. Monoclonal antibodies were diluted to a 1 mg/mL concentration in the respective formulation buffer, and samples were prepared as follows: five microliters of Protein Thermal Shift™ Buffer, 12.5 µL of the antibody (1 mg/mL) or buffer (negative control), and 2.5 µL of Diluted Protein Thermal Shift™ Dye (8×) were added together for a total volume of 20.0 µL for each reaction. SYPRO Orange was diluted 125-fold from the 1000× concentrated stock solution to the working dye solution in the provided thermal shift buffer prior to addition to the reaction mixture. To prevent bleaching, the working solution of SYPRO Orange was added to the reaction mixture just prior to the experiment. Each sample was measured in quadruplicate. Thermal denaturation was carried out by increasing the temperature from 25° C. to 95° C. at a rate of 0.017° C. per second. Fluorescence intensity (excitation at 490 nm and emission with the use of a ROX filter at 600 to 630 nm) was collected at 0.07° C. intervals and analyzed with Protein Thermal Shift Software (Life Technologies), using the first derivative approach to calculate Tm. In this method, Tm is the temperature corresponding to the maximum value of the first derivative of the DSF melting curve.

Immune Pathway Activation in Human Dissociated Tumor Cells (DTCs)

Dissociated Tumor Cells (DTCs) from four NSCLC patients were purchased from DLS and thawed per manufacturer's recommendation. Cells were counted and plated at around 2M cells per 24 well in 3 wells in Ex vivo media with anti-mot but no serum. 5 µg/ml of R&D, RDM5 and RDM9, PI-3030, and hIgG1 (ultra-LEAF) were added to each well containing 1 ml of media. Four hours later at 37 C, cells were collected in 15 ml canonical tubes and centrifuged at 400×g for 5 min at 4° C. Each pellet was resuspended in 600 ul of RLT buffer with B-mercapthoethanol (at 1:100 dilution).

Total RNA was isolated from the above DTCs samples using the Qiagen RNeasy Mini kit and control treated human and submitted for high-throughput RNA sequencing. Libraries were prepared using Illumina's TruSeq Stranded mRNA kit and sequenced on an Illumina Novaseq 6000. Subsequent data was aligned to the human genome (GRCh38.p12) and per-gene expression values were tabulated using the STAR aligner. The resulting expression matrices were used as input for differential expression analysis using DESeq2. Resulting fold changes from PI-3010 vs control comparisons for all protein coding genes were submitted to Gene Set Enrichment Analysis (GSEA) software, using the preRanked test, available from the Broad Institute at https://www.gsea-msigdb.org/gsea/index.jsp. MSigDB's Hallmark pathways were assessed and resulting Normalized Enrichment Scores were plotted using ggplot2 in R. FDR values were determined via permutation test implanted within GSEA using standard parameters.

Proinflammatory Signature in Human Suppressive Macrophages (M2c)

Four Frozen human peripheral blood CD14+ monocytes isolated from peripheral blood mononuclear cells using negative immunomagnetic selection (StemCell Technologies) were thawed and cultured in RPMI 1640 medium supplemented with 10% (v/v) heat-inactivated FBS (HyClone), 1 mM sodium pyruvate, non-essential amino-acids, 2 mM L-glutamine, 55 uM β-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 500,000 cells per well in 24 well plates. At day 3 of differentiation, media was replenished with the addition of fresh M-CSF. Differentiated human macrophages were polarized by adding the following cytokines to the media for 24 hours at 37 C: M0 (no cytokine addition) and 25 ng/ml of recombinant human IL-10 (M2 condition) for 24 hours at 37 C. On day 7, the media was aspirated and cells washed gently. Fresh complete RPMI 1640 medium macrophage medium with 5 μg/ml of PI-3010.15, PI-3030.41, and hIgG1 (Ultra-LEAF from Biolegend) were added to each well from the above 2 conditions. 4 hours later, media was aspirated and cells lysed in RLT buffer with β-mercapthoethanol (at 1:100 dilution).

Total RNA was isolated from the IL-10 polarized hMDMs using Qiagen RNeasy Mini kit and submitted for high-throughput RNA sequencing. Libraries were prepared using Illumina's TruSeq Stranded mRNA kit and sequenced on an Illumina Novaseq 6000. Subsequent data was aligned to the human genome (GRCh38.p12) and per-gene expression values were tabulated for all MDM using the STAR aligner. The resulting expression matrices were used as input for differential expression analysis using DESeq2. Resulting fold changes from PI-3010.15 vs control comparisons for all protein coding genes were submitted to Gene Set Enrichment Analysis (GSEA) software, using the preRanked test, available from the Broad Institute at www.gsea-msigdb.org/gsea/index.jsp. MSigDB's Hallmark pathways were assessed and resulting Normalized Enrichment Scores were plotted using ggplot2 in R. FDR values were determined via permutation test implanted within GSEA using standard parameters.

Hallmark Pathways: PI-3008 Treated BMDMs vs PI-3008 Treated CT26 Tumors

Individual femurs and tibias from four females BALB/c mice were cleaned and crushed in Macrophage Medium composed of Iscove's modified Dulbecco Medium supplemented with 10% (v/v) fetal bovine serum (FBS) (HyClone) and antibiotic-antimycotic solution (Gibco), using a mortar and pestle. Samples were then passed through a 40 um filter, washed with media and pelleted at 400×g for 5 min at RT. Cell pellets were resuspended in 5 ml of BD Pharm Lyse buffer (BD Biosciences) and red blood cell lysis was carried out at RT for 5 min, followed by quenching with 10 volumes of Macrophage Medium. Cells were pelleted at 400×g for 5 min at RT and resuspended in Macrophage Medium at the density of 500,000 cells per well in 24 well plates. These bone marrow mononuclear cells were stimulated with 25 ng/ml of mouse macrophage colony-stimulating factor (M-CSF) (PeproTech) for 6 days to generate M0-macrophages and polarized into M1-like and M2-like macrophages by supplementing the medium with LPS (ing/nil) and mouse IL-10 at 20 ng/ml respectively for 24 hours at 37C.

On day 7, the media was aspirated and cells washed gently with macrophage medium. Fresh media with 5 ug/ml of PI-3008 or its mIgG2a isotype control was added to each well from the three conditions: M0, M1, and M2. 4 hours later, media was aspirated and cells lysed in RLT buffer with B-mercapthoethanol (at 1:100 dilution).

Total RNA was isolated from these BMDMs using the Qiagen RNeasy Mini kit and CT26 tumors (previously described for FIGS. 12C-12H) and submitted for high-throughput RNA sequencing. Libraries were prepared using Illumina's TruSeq Stranded mRNA kit and sequenced on an Illumina Novaseq 6000. Subsequent data was aligned to the murine genome (GRCm38.p6) and per-gene expression values were tabulated for all BMDM samples and CT26 samples, respectively, using the STAR aligner. The resulting expression matrices were used as input for differential expression analysis using DESeq2. Resulting fold changes from PI3008 vs control comparisons (from both BMDM and CT26 subsets) for all protein coding genes were submitted to Gene Set Enrichment Analysis (GSEA) software, using the preRanked test, available from the Broad Institute at gsea-msigdb.org/gsea/index.jsp. MSigDB's Hallmark pathways were assessed for both the BMDM and CT26 comparisons and resulting Normalized Enrichment Scores were plotted using ggplot2 in R.

Cytokine qPCR Assay

Two frozen human peripheral blood CD14+ monocytes isolated from peripheral blood mononuclear cells using negative immunomagnetic selection (StemCell Technologies) were thawed and cultured in RPMI 1640 medium supplemented with 10% (v/v) heat-inactivated FBS (HyClone), 1 mM sodium pyruvate, non-essential amino-acids, 2 mM L-glutamine, 55 uM β-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 500,000 cells per well in 24 well plates. At day 3 of differentiation, media was replenished with the addition of fresh M-CSF. Differentiated human macrophages were polarized on day 6 by adding 25 ng/ml of recombinant human IL-10 (M2 condition) for 24 hours at 37 C. On day 7, the media was aspirated and cells washed gently. Fresh complete RPMI 1640 macrophage medium with 5 μg/ml of PI-3010.15 (PI-3015), PI-3010.25 (PI-3025), PI-3030.41 (PI-3041), or hIgG1 isotype control (Ultra-LEAF from Biolegend) and 5 μg/ml of PI-3010.46 (PI-3046), PI-3030.47 (PI-3047), PI-3010.48 (PI-3048), or hIgG4 isotype control (Ultra-LEAF from Biolegend) were added to the corresponding wells. 4 hours later, media was collected into 96 well plates for Luminex cytokine secretion and cells lysed in RLT buffer with β-mercapthoethanol (at 1:100 dilution). Total RNA was isolated from the IL-10 polarized hMDMs using Qiagen RNeasy Mini kit and 250 ng of RNA was made into single strand DNA using the High-capacity cDNA Reverse Transcription kit (Applied Biosystems). qPCR was performed using the 5 ul of SYBR green mix and primers specific to IL-6, IL-1b, IL10, TNFα, CXCL10, IL18, CCL20, CCL24, ILIA. The endogenous housekeeping primers tested were GAPDH and RPL37A. The plates were ran on the QuantStudio 5 qPCR machine from Thermo Fisher.

This cytokine expression qPCR assay was repeated in multiple hMDMs donors and different runs with titrating down the concentration of the hIgG1 lead antibodies to be 1 ug/ml compared to hIgG1 isotype (PI-0003). In addition, this assay was used to confirm the activation of the pro-inflammatory gene signature The expression of IL-6, TNFα, IL-1b, IL10, IL18, CCL20, CCL24, CXCL8, ILIA was assessed for pro-inflammatory activation was tested in all assays.

In addition this assay was used to confirm the activation of the pro-inflammatory gene signature downstream of PI-3010.15-AB in THP-1 monocytic cells overexpressing human full length MARCO.

The qPCR analysis was done by calculating the fold changes of the treated samples over the corresponding isotype control using the 2^-(ddCT). Each gene CT value was normalized to the CT value of the endogenous control used (such as GAPDH or RPL37A).

Human Cytokine and Chemokines Secretion by MSD 200 ul of Supernatant collected from hMDMs cells treated with the human anti-MARCO PI-3010.15, PI-3010.25, and PI-3030.41 and isotype were evaluated for cytokine levels using the V-PLEX human proinflammatory panel 1 human kit measuring 10 cytokines (MSD, Cat. No. K15049D) and the V-PLEX human chemokine panel 1 human kit measuring 10 chemokines (MSD, Cat. No. K15049D) from Meso Scale Discovery (MSD, Cat. No. K15047D) or a customized human PrecartaPlex 26-plex kit from Thermo Fisher (Cat. No. PPX-26-MX-3222A). The MSD multiplex assay plates were precoated with capture antibodies. Samples for analysis or kit standards were added at a volume of 50 µl per well after pre-diluting the original sample with assay diluent. The plates were washed after a two-hour incubation at room temperature with agitations.

For the V-PLEX assay, sulfo-tagged detection antibodies were added and incubated for another two hours at room temperature with agitations. Following the incubation, plates were washed once again. 2× Read Substrate was added and plates were read on MSD reader. All data were analyzed by MSD Discovery Workbench® Software 4.0.

For the customized human 26-plex kit, biotinylated labeled detection antibodies were added and incubated for one hour at room temperature with agitations. Plates were washed. PE (Phycoerythrin)-labeled Streptavidin were added and incubated for 30 min at room temperature with agitations. After the plates were washed, Luminex reading buffer was added and plates were read on Luminex 200 analyzer. All data were analyzed by xPONENT Software.

Results

DNA sequences for the heavy and light chain of antibodies PI-3010.15, PI-3010.25, and PI-3030.41 were codon optimized and incorporated into proprietary vectors at Atum (Newark, Calif.). The heavy and light chain encoding vectors were transfected in CHO cells at 2 L scale, followed by purification using MabSelect Sure Protein A resin. Both candidates showed high titers and <5% aggregates post Protein A purification. Data are summarized in Table 14.

TABLE 14

| Antibody | Germline | Isotype | Expression CHO - transient (mg/L) | Theoretical pI | % Monomer (post Protein A) |
|---|---|---|---|---|---|
| PI-3010.15-H1 | IGHV1-46 IGKV1-39 | hIgG1 | 585 | 8.45 | >95 |
| PI-3010.25-H1 | IGHV1-46 IGKV1-39 | hIgG1 | 818 | 8.11 | >95 |
| PI-3030.41-H1 | IGHV1-59 IGKV1-39 | hIgG1 | 868 | 8.44 | >95 |

Binding of PI-3010.15, PI-3010.25, and PI-3030.41 was assessed by Biacore on recombinant human and cynomolgus MARCO protein and demonstrated high affinity binding to both human and cynoMARCO, with the affinity of binding to cynoMARCO within 2-3 fold of the human MARCO affinity.

Flow cytometry was used to assess the binding of the antibodies to human and cynomolgus MARCO expressing cell lines, including MARCO transfectants in HEK 293T cells and human monocyte derived macrophages (MDM) expressing endogenous MARCO.

The antibodies bound to human and cynoMARCO with comparable EC50s and bound to endogenous MARCO on human MDMs with high affinity. No off-target binding was observed to parental HEK 293T cells that did not express MARCO or to Jurkat T cells by flow cytometry (Table 15 and FIG. 53).

TABLE 15

| Humanized mAb | EC50 OVX Cell binding (nM) (hu/cyn) | $K_D$(nM) Human | $K_D$(nM) Cyno | $K_{off}$(1/s) Human | Binding on human macrophages | Block ligand(s) binding | Binding to T-cells |
|---|---|---|---|---|---|---|---|
| PI-3010.15 PI-3015 (hIgG1) | 0.798/1.16 | 0.51 | 1.65 | 2.94E−04 | + | + | − |
| PI-3010.46 PI-3046 (hIgG4) | 0.821/1.07 | 0.78 | 1.10 | 3.71E−04 | + |  | − |
| PI-3010.25 PI-3025 (hIgG1) | 0.790/1.01 | 1.09 | 1.79 | 4.30E−04 | + | + | − |

TABLE 15-continued

| Humanized mAb | EC50 OVX Cell binding (nM) (hu/cyn) | $K_D$(nM) Human | $K_D$(nM) Cyno | $K_{off}$(1/s) Human | Binding on human macrophages | Block ligand(s) binding | Binding to T-cells |
|---|---|---|---|---|---|---|---|
| PI-3010.48 PI-3048 (hIgG4) | 0.721/2.39 | 1.05 | 1.81 | 3.86E−04 | + | | − |
| PI-3030.41 PI-3041 (hIgG1) | 0.704/1.028 | 0.82 | 1.12 | 3.34E−04 | + | + | − |
| PI-3030.47 PI-3047 (hIgG4) | 0.796/1.39 | 0.72 | 0.79 | 3.37E−04 | + | | − |

Thermal stability assessment to determine the temperature for melting (Tm1) and aggregation (Tagg) using differential scanning fluorimetry (DSF) and dynamic light scattering (DLS) respectively showed that all 3 antibodies have acceptable and similar properties. In addition, all 3 antibodies were soluble and stable up to 30 mg/ml as determined by size exclusion chromatography (SEC) and DLS in citrate and histidine buffers ranging between pH 5.0-6.5. A summary of the data is shown in Table 16 below.

FIG. 28 provides the qPCR mRNA data (TNFα, IL-1 β, IL-18, and CXCL8) and MSD cytokine data (TNFα, IL-1α, IL-6, MIP1-α) for PI-3010.15, PI-3010.25, and PI-3030.41 as well as the hIgG1 control. qPCR mRNA analysis of pro-inflammatory genes was plotted as fold induction over the hIgG1 control isotype of one representative donor (top row). Data is presented as mean values of technical duplicates ±standard deviation (SD). Cytokine secretion was also measured by MSD and data plotted for the levels (pg/ml) of

TABLE 16

| | Analysis Method | PI-3010.25 (PI-3025) (hIg1) | PI-3010.48 (PI-3048) (hIg4) | PI-3010.15 (PI-3015) (hIg1) | PI-3010.46 (PI-3046) (hIg4) | PI-3030.41 (PI-3041) (hIg1) | PI-3030.47 (PI-3047) (hIg4) |
|---|---|---|---|---|---|---|---|
| Binding affinity to human MARCO (KD) | Biacore (SPR, nM) | 1.09 | 1.05 | 0.51 | 0.78 | 0.82 | 0.72 |
| Thermal Stability (PBS) | Tm1 (DSF, ° C.) | 68 | 65 | 68 | 64 | 68 | 64 |
| Thermal Stability (PBS) | Tagg (DLS, ° C.) | 83 | 73 | 78 | 72 | 78 | 71 |
| Solubility (30 mg/mL) | SEC, DLS | Soluble and stable up to 30 mg/mL in citrate and acetate buffers, pH 5.0-6.0 | | | | | |

Cytokine expression induced by human anti-MARCO antibodies in hMDMs was also assessed. As shown in Table 17, all of PI-3010.15, PI-3010.46, PI-3010.25, PI-3010.48, PI-3030.41, and PI-3030.47 induced expression of the indicated cytokine genes in Donor 1. Cytokine and other relevant gene expression (MIP-1α, IL-27, LIF, IL-1β, IL-2, IL-4, IP-10, IL-6, IL-10, CD40, IL-12p70, G-CSF, IFNγ, GM-CSF, TNFα, MIP-1β, MCP-1, MIG, gro-alpha, IL-1α, IL-15, MCP-3, M-CSF, and VEGF-A) in hMDMs from two different donors (Donor 1 and Donor 2) is also shown in FIG. 27.

TABLE 17

Gene fold induction over corresponding isotype

| Donor 1 | IL-6 | TNFα | CXCL10 | IL18 | CCL20 | IL1A |
|---|---|---|---|---|---|---|
| PI-3010.15 IgG1 | 1.3 | 2.2 | 1.5 | 1.8 | 1.4 | 2.4 |
| PI-3010.46 IgG4 | 1.8 | 1.9 | 1 | 1.8 | 1.7 | 3.6 |
| PI-3010.25 IgG1 | 1.2 | 2.5 | 1.5 | 3.9 | 1.5 | 4.1 |
| PI-3010.48 IgG4 | 1 | 2.1 | 0.9 | 1.5 | 1.3 | 3.6 |
| PI-3030.41 IgG1 | 1.3 | 3.2 | 1.9 | 4.3 | 1.6 | 7.8 |
| PI-3030.47 IgG4 | 2 | 3.2 | 1.8 | 1.3 | 1.8 | 6.6 | representative pro-inflammatory cytokines and chemokines levels (bottom row). Data is presented as mean values of technical duplicates of the same representative donor ±standard deviation (SD).

PI-3010.15 hIgG1 control treated human disassociated tumor cells and PI3008/control treated CT26 tumors were processed as described above (FIG. 16B). GSEA derived Normalized Enrichment Scores from both experiments were plotted using ggplot2 in R. As shown in FIG. 29, human and mouse MARCO mAbs drive similar pathway regulation.

PI-3010.15 activated anti-tumor immune pathways in human dissociated tumor cells (DTCs) (FIG. 30). The top immune activation genes and pathways increased by anti-MARCO antibody in hDTCs including IL-2-STAT5 signaling, TNFα signaling via NF-kB, IL-6-JAK-STAT3 signaling, the inflammatory response, IFNγ response, and IFNα response (FIG. 30). These pathways were also upregulated by PI-3008 in mouse tumor cells and BMDMs as shown in Example 4. The pathways decreased by anti-MARCO antibody in hDTCs included hypoxia, apical junctions, Myc targets, PI3K-AKT-mTOR, E2F targets and oxidative phosphorylation. These pathways were also downregulated by PI-3008 in mouse tumor cells and BMDMs as shown in Example 4. Pathways were defined using the Hallmark pathway set.

PI-3010.15 also induced a pro-inflammatory signature in human suppressive macrophages (M2c) (FIG. 31). Upregulated cytokines and genes were CXCL3, CXCL8, TNFα, CCL3, IL7R, CCL4, CCL5, CCL24, CCL20, IL-1α, IL-6, IDO, CD274, SF2, LAMP3, CCR7, CXCL11, and CXCL9. Down regulated cytokines and genes were ALK, MPB, TMEM37, NHSL2, SLC46A2. Upregulated pathways were TNFα signaling via NF-kB, inflammatory response, INFg response, Myc targets, hypoxia, IL6/JAK/STAT3 signaling, IFNα response, unfolded protein response, IL2/STATS signaling, UV response, allograft rejection, epithelial mesenchymal rejection, apoptosis, mTORC1 signaling, estrogen response early, KRAS signaling up, cholesterol homeostasis, notch signaling, apical junction, wnt beta catenin signaling, oxidative phosphorylation, complement, PI3k Akt mTOR signaling, reactive oxygen species pathway, hedgehog signaling, angiogenesis, glycolysis, KRAS signaling DN, DNA repair, p53 pathway, myogenesis, coagulation, apical surface, androgen response, TGFβ signaling, fatty acid metabolism, and xenobiotic metabolism.

Pathways down regulated were bile acid metabolism, estrogen response late, adipogenesis, peroxisome, heme metabolism, UV response DN, mitotic spindle, protein secretion, spermatogenesis, G2M checkpoint, and E2F targets. The key pro-inflammatory genes and pathways induced by PI-3010.15 in M2c hMDMs included IL-2-STATS signaling, TNFα signaling via NF-kB, IL-6-JAK-STAT3 signaling, the inflammatory response, IFNγ response, and IFNα response. Pathways were defined using the Hallmark pathway set. Similar pathways were induced in BMDMs treated with PI-3008.

A comparison of the fold change induced in cytokine expression by PI-3010.15 and PI3030.41 is shown in FIG. 32. PI-3010.15 induced higher levels of IL-1α, CSF3, CSF2, IL-1α, IL-6, TNFα, CCL4, CXCL1, CCL3, and CXCL10 as compared to PI-3030.41.

Tables 18 and 19 provide a comparison summary of a selection of anti-MARCO antibodies and characteristics. (−) indicates no difference between antibodies, (+) indicates an advantage.

TABLE 19

| In vitro assays | PI-3010.15 | PI-3010.25 | PI-3030.41 |
|---|---|---|---|
| Binding to overexpressed cells and absence of binding on negative cells | − | − | − |
| Compete for the binding of ligands to the SRCR domain | − | − | − |
| Cell surface expression in hMDMs and THP1 cells polarized with IL-10 | + | | |
| RNAseq in DTCs | + | + | |
| RNAseq in hMDMs | + | Not tested | |
| qPCR for gene expression in hMDMs | − | − | − |
| Cytokine secretion assay by MSD and/or Luminex | − | − | − |
| Increase Inflammasome in hMDMs | + | | |
| NF-κB reporter assay in THP1-Blue ™ NF-κB Cells | + | + | |
| Mild Increase in Phagocytosis | + | + | |

In order to determine if any potential liabilities exist in the sequences of three selected antibodies, Sentinel APART algorithm (Lonza) was used for in-silico sequence analysis of the candidates. Points of concern that were flagged by in-silico analysis were: increased hydrophobicity, aggregation propensity, aspartate isomerization, and oxidation liability.

Previous in silico assessment showed similar liabilities that were flagged but proved to be minor liabilities when tested under various stress conditions and forced degradation assays. Table 20 below shows a summary of the experimental data in comparison with the theoretical data.

TABLE 18

| Criteria/Test | P1-3010.15 | P-3010.25 | P-3030.41 |
|---|---|---|---|
| $K_D$ human (avid) | − | − | − |
| $K_D$ cyno (avid) | − | − | − |
| ELISA binding | − | − | − |
| Calculated (In silico) sequence liability | Oxidation (low) Deamidation (low) + | Deamidation (low) Isomerization (high) | Deamidation (low) Isomerization (high) |
| Observed liabilities (forced degradation) | Oxidation (low) + | Isomerization (low) | Deamidation (lhigh) Isomerization (high) |
| Aggregation (SEC, DLS, HIC from transient expression) | + | + | |
| Aggregation (SEC from Lonza stable pooled transfected materials) | + | + | |
| Thermal Stress (DLS, DSF) | − | − | − |
| Stability over time (DLS, SEC, SPR) | + | | |
| Deamidation and Isomerization Risk | + | | |
| Functional in vitro assays | + | | |

TABLE 20

| Antibody | Aggregation | | Deamidation | | Isomerization/Fragmentation | | Oxidation | |
|---|---|---|---|---|---|---|---|---|
| | Calculated (in silico) | Observed (HIC) | Calculated (in silico) | Observed (HIC) | Calculated (in silico) | Observed (HIC) | Calculated (in silico) | Observed (HIC) |
| PI-3010.15 | High | Low | 0 (1) | 0 (0) | 0 (0) | 0 (0) | 0 (2) | 0 (2) |
| PI-3010.25 | High | Low | 0 (1) | 0 (0) | 1 (0) | 0 (1) | 0 (1) | 0 (0) |
| PI-3030.41 | High | Low | 0 (2) | 1 (1) | 2 (0) | 1 (1) | 0 (3) | 0 (0) |

Total hydrophobicity of lead candidates was evaluated using hydrophobic interaction chromatography (HIC). Longer retention time indicates more hydrophobicity. An anti-TREM1 antibody was used as a positive control in this assay. The PI-3010.15, PI-3010.25 and PI-3030.41 antibodies all showed hydrophobicity in the range expected for antibodies (Table 21). High levels of main peak % indicate fewer modifications and lower retention time corresponds to lower hydrophobicity.

TABLE 21

| Sample Number | Main Peak (%) | Retention Time (min) |
|---|---|---|
| P1-3010.15 | 88.7 | 15.7 |
| P1-3010.25 | 95.8 | 15.6 |
| P1-3030.41 | 70.7 | 11.5 |

A forced degradation study to understand liabilities of selected antibodies was conducted. PI-3010.15-H1, PI-3010.25-H1 and PI-3030.41-H1 samples were incubated under stress conditions (oxidation, low pH, and high pH) and analyzed by peptide mapping (LC-MS/MS) to identify protein modifications in the mAbs. The focus was on the analysis of isomerization and oxidation liabilities. In addition, other parameters were used to assess the stability of each antibody at the various stress conditions (Table 22).

TABLE 22

| Sample | Source | Isoytpe | Conc (mg/mL) | Condition | Time | Readout |
|---|---|---|---|---|---|---|
| PI-3010.25 | CHO-ATUM | hIgG1 | 8.4 | 4° C. (PBS control) | 2 weeks | Nanodrop (A280) |
| PI-3010.41 | CHO-ATUM | hIgG1 | 9.5 | 40° C. (PBS) | | SEC (aggregation) |
| PI-3010.15 | CHO-ATUM | hIgG1 | 10.5 | 40° C. (pH 5.5) | | DLS (Tagg, size) |
| | | | | 40° C. (pH 8.5) | | DSF (domain stability) |
| | | | | 40° C. (PBS) + AAPH (6 hrs) | | LC-MS (peptide mapping to detect modifications) |
| | | | | 25° C. (pH 3.5) | | Charge variant analysis |
| | | | | | | Biacore (binding) |

Isomerization

PI-3010.15 was incubated at the following conditions: 40° C. in PBS for 2 weeks, control in PBS at −80° C., 40° C. (PBS)+1 mM AAPH for 6 h, and 40° C. in pH 5.5 sodium acetate for 2 weeks. Post treatment the samples were analyzed by LC-MS/MS which identified the % modification on isolated peptides derived from the antibody after trypsin digest.

LC/MS peptide mapping was done on PI-3010.15 after incubation at low pH for extended periods to identify potential hotspots. PI-3010.15 did not show any Isoaspartate (IsoAsp), deamidation or succinimide formation. PI-3010.25 showed IsoAsp formation in residue D56 of light chain (>2%, only under pH 5.5, 40° C.) and D72 of heavy chain (3.7% at pH 3.5) while PI-3030.41 showed IsoAsp in D56 of light chain (>2.7%, under pH 5.5, 40° C.) and succinimide at residue N52 of heavy chain (6-9% under all conditions, including control).

Oxidation:

PI-3010.15 was incubated at the following conditions: control in PBS at −80° C., 40° C. (PBS)+1 mM AAPH for 6 h, 0.5 and 1.5% $H_2O_2$ in PBS for 24 h, which was compared to a previous experiment at 40° C. (PBS)+1 mM AAPH for 6 h. Post treatment the samples were analyzed by LC-MS/MS which identified the % modification on isolated peptides derived from the antibody after trypsin digest.

PI-3010.15 showed oxidation of Met-48 and Trp-52 with AAPH and $H_2O_2$ treatment. Trp-52 was flagged as a potential liability in the in-silico assessment. Met-48 residue is expected to be buried in the structure, and not solvent accessible. It was not possible to unambiguously assign oxidation liability to either residue as they are found as part of the same peptide during LC-MS/MS analysis.

Binding of the stressed samples to recombinant human MARCO was assessed by Biacore. The binding of the stressed samples had similar KDs and Rmax levels compared to the control conditions suggesting that binding potency was not significantly affected (Table 23), including various oxidized stress samples from PI-3010.15 (Table 24).

TABLE 23

Binding to MARCO

| Antibody | Control | | 40° C. 2 week | | Deamidation (40° C. 2 week) | | Isomerization/ Fragmentation | | Oxidation (1 mM AAPH, 6 hrs) | |
|---|---|---|---|---|---|---|---|---|---|---|
| | $K_D$ (nM) | Rmax | $K_D$ (nM) | Rmax | $K_D$ (nM) | Rmax | $K_D$ (nM) | Rmax | $K_D$ (nM) | Rmax |
| PI-3010.15 | 1.2 | 131.7 | 1.2 | 103.8 | 1.24 | 111.3 | 1.24 | 108.6 | 1.29 | 104.5 |
| PI-3010.25 | 0.54 | 63.2 | 0.58 | 62.2 | 0.66 | 62.4 | 0.66 | 62.4 | | |
| PI-3030.41 | 0.24 | 62 | 0.36 | 54.3 | 0.39 | 54.8 | 0.34 | 48.9 | | |

TABLE 24

Oxidation

| Antibody | Control | | 0.5% H2O2 (24 hr, RT) | | 1.5% H2O2 (24 hr, RT) | | 1 mM AAPH, 6 hrs 40° C.) | |
|---|---|---|---|---|---|---|---|---|
| | $K_D$ (nM) | Rmax | $K_D$ (nM) | Rmax | $K_D$ (nM) | Rmax | $K_D$ (nM) | Rmax |
| PI-3010.15 | 0.97 | 111.7 | 1.05 | 97.1 | 1.07 | 109.5 | 1.10 | 97.6 |

The 3 antibodies (PI-3010.15, PI-3010.25, and PI-3030.41) were successfully concentrated up to 30 mg/mL in the following buffers in pH range 5.0-6.0 without any other excipients. PBS was used a control. The antibodies were incubated at 4° C. overnight prior to the following analyses: % aggregation by SEC-HPLC; Size (radius) and polydispersity using DLS; Thermal stability [Tagg (DLS), Tm (DSF)]; Colloidal stability (kd) by SLS.

PI-3010.25 was concentrated in the following buffers (Table 25).

TABLE 25

| Buffer | pH | mAb Concentration (mg/mL) for PI-3010.25 |
|---|---|---|
| 10 mM Histidine HCl | 6.0 | 27.1 |
| 10 mM Histidine HCl | 5.5 | 36.4 |
| 10 mM Sodium Citrate | 6.0 | 33.2 |
| 10 mM Sodium Citrate | 5.5 | 35.8 |
| 10 mM Sodium Citrate | 5.0 | 29.7 |
| 10 mM Sodium Acetate | 5.5 | 33.4 |
| 10 mM Sodium Acetate | 5.0 | 36.1 |
| PBS (control) | 7.4 | 30.4 |

PI-3010.25 could be concentrated to 30 mg/mL without increase in HMW aggregates.

Example 9: Anti-MARCO Antibody Induces Inflammasome Activation

Materials and Methods
Inflammasome Assay in mBMDMs

Femurs and tibias from three females C57BL/6 mice and three females BALB/c were cleaned and crushed in Staining Medium (0.5% (w/v) BSA (Sigma) and 2 mM EDTA in D-PBS) using a mortar and pestle. Samples were then passed through a 40 um filter, washed with D-PBS and pelleted at 400×g for 5 min at RT. Cell pellets were resuspended in 5 ml of BD Pharm Lyse buffer (BD Biosciences) and red blood cell lysis was carried out at RT for 5 min, followed by quenching with 10 volumes of Staining Medium. Cells were pelleted at 400×g for 5 min at RT and resuspended in Macrophage Medium composed of Iscove's modified Dulbecco Medium supplemented with 10% (v/v) fetal bovine serum (FBS) (HyClone) and antibiotic-antimycotic solution (Gibco), at the density of 15×10^6 cells/ml in 15 cm plates. These bone marrow mononuclear cells were stimulated with 25 ng/ml of mouse macrophage colony-stimulating factor (M-CSF) (PeproTech) for 7 days to generate M0-macrophages and differentiated into M2-like by supplementing the medium with mouse IL-1b at 20 ng/ml on day 6 for 24 hours at 37C. On day 7, macrophages were rinsed with DPBS and incubated in 6 ml of 2 mM EDTA for 10 minutes to promote cell detachment. Cells were gently scraped into an additional 6 ml of the Staining Medium described above, counted and seeded onto 96-well plates at 100,000 cells per well.

After 30 minutes to 1 h at 37C to allow the cells to attach, BMDMs were treated with 5 μg/ml of the anti-mouse MARCO antibody PI-3008 and its corresponding isotype control mIgG2a. After 3 hours of incubation with the antibodies, LPS (tested 0.5 and 50 ng/ml) was added to prime the inflammasome pathway for an additional 2.5 hours. ATP (5 mM) was then added for 30 minutes to activate the inflammasome and induce cytokine secretion of IL-1(3 that was measured by MSD. Sidak's multiple comparisons test was used to calculate statistical significance of secreted IL-1(3 fold change over untreated isotype (no LPS and no ATP). Sidak's multiple comparisons test, **P<0.01.

Inflammasome Assay in hMDMs

Frozen human peripheral blood CD14+ monocytes isolated from peripheral blood mononuclear cells using negative immunomagnetic selection (StemCell Technologies) were thawed and cultured in RPMI 1640 medium supplemented with 10% (v/v) heat-inactivated FBS (HyClone), 1 mM sodium pyruvate, non-essential amino-acids, 2 mM L-glutamine, 55 uM 2-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 12-15×10^6 cells in 15 cm dish. At day 3 of differentiation, media was replenished with the addition of fresh M-CSF. Differentiated human macrophages were polarized by adding the following cytokines to the media for 24 hours at 37 C: 100 ng/ml of IFNγ (M1 condition) and 25 ng/ml of recombinant human IL-10 (M2 condition) for 24 hours at 37 C. On day 7, polarized macrophages were gently harvested non-enzymatically using a sterile cell scraper (Nunc) into FACS buffer (D-PBS containing 2 mM EDTA and 0.5% (w/v) bovine serum albumin (BSA) (Sigma)) followed by centrifugation at 400×g for 5 min at ~20° C.

Cells were counted and seeded onto 96-well plates at 100,000 cells per well. After 30 minutes to 1 h at 37° C. to allow the cells to attach, hMDMs were treated with 5 μg/ml of the anti-human MARCO antibodies PI-3010.15, PI-3010.25 (PI-3025), PI-3030.41 (PI-3041), and PI-3010.48 (PI-3048) and their corresponding isotypes controls hIgG1 and hIgG4 (Ultra-leaf from Biolegend). After 3 hours of incubation with the antibodies, LPS (tested 0.1 and 1 μg/ml) was added to prime the inflammasome pathway for an additional 2.5 hours. ATP (5 mM) was then added for 30 minutes to activate the inflammasome and induce cytokine secretion of IL-1β that was measured by MSD. Tukey's multiple comparison test was used to calculate statistical significance of secreted IL-1β fold change over untreated (no LPS and no ATP) hIgG1. Tukey's multiple comparisons test (*P<0.05; *P<0.0006, **P<0.0001).

*E. coli* Phagocytosis Assay

Human monocyte-derived macrophages (MDM) were generated by culturing CD14+ human monocytes in RPMI 1640 medium (Gibco) supplemented with 10% Fetal Bovine Serum (Gibco), 1% B-mercaptoethanol (ThermoFisher), 1× non-essential amino acids (Gibco), 1× Sodium Pyruvate (Gibco), 1× GlutaMax (Gibco), 1× anti-anti (Gibco), 50 ng/ml of M-CSF (Peprotech) in 15 cm plate. Medium was refreshed after 3 days. On day 6 of culture, 100 ng/ml of human IFN-g (Peprotech)+50 ng/ml of LPS (Invivogen) or 25 ng/ml of IL-10 (Peprotech) were added to the culture. The following day, cells were harvested, and 200,000 cells were plated per well of 96-well flat bottom plate and incubated with a dose titration of PI-3101.15, PI-3010.25 or PI-3030.41 and isotype control antibody for 2 hours at 37° C. and 5% CO2 to allow cells to adhere.

To measure phagocytosis, the Vybrant Phagocytosis Assay Kit (Molecular Probes) was used. After the 2-hour antibody incubation, media was removed, and cells were incubated with *E. coli* fluorescent BioParticles solution for 2 hours at 37° C. and 5% CO2. The particles solution was removed and replaced by the trypan blue solution. After 1 min incubation at room temperature, the solution was removed, and fluorescence was measured using 480 nm for excitation and 520 nm emission wavelengths on the Tecan microplate plate reader.

Results

PI-3008 induced statistically significant IL-1β secretion by the inflammasome in both non-polarized macrophages (FIGS. 33A and 33C) and IL-10 polarized macrophages (FIGS. 33B and 33D). This effect was observed in two separate murine lineages, C57BL/6 mice (FIGS. 33A and 33B) and Balb/c mice (FIGS. 33C and 33D). Thus, PI-3008 enhances and increases inflammasome activation in mouse BMDMs.

A similar results was observed in human MDMs (FIGS. 34A, 34B, and 35). Both PI-3010.25 (IgG1 format) and PI-3010.48 (IgG4 format) induced statistically significant IL-1β secretion in IL-10 polarized macrophages after incubation with 0.1 μg/ml LPS+ATP and 1 μg/ml LSP+ATP (FIG. 34A). In IFN-γ polarized hMDMs, PI-3025 induced IL-1β secretion after incubation with 0.1 μg/ml LPS+ATP, while PI-3010.48 induced IL-1β secretion after treatment with 1 μg/ml LPS+ATP (FIG. 34B). Bars for PI-3010.25 are shown second from the left in each grouping, bars for PI-3010.48 are shown on the right in each grouping.

In a separate assay, all of PI-3010.15, PI-3010.25, and PI-3030.41 induced IL-1β production when treated with LPS and ATP compared to the untreated condition (FIG. 35), indicating that anti-human MARCO antibodies induce inflammasome activation.

The percent induction of phagocytosis by PI-3010.15, PI-3101.25, and PI-3030.41 in the IL-10 hMDM donor cells is provided in Table 26.

TABLE 26

| Antibody | Isotype | Phagocytosis |
| --- | --- | --- |
| PI-3010.25 | IgG1 | 90% |
| PI-3010.15 | IgG1 | 88% |
| PI-3030.41 | IgG1 | 50% |

PI-3010.25 and PI-3010.15 showed more consistent phagocytosis induction across multiple donors when hDMMs were polarized with IL-10.

Example 10: In Vivo Monotherapy Efficacy of Anti-Mouse MARCO Antibodies in EMT6 Model Methods EMT6 breast cancer tumor cells (1×10^6 cells per mouse) were implanted on Day 0, and dosing (10 mg/kg; Q5dx4; ip) was initiated when tumors reached an average volume of ~90 mm3. Animals were dosed intraperitoneally every 5 days, for total of four doses. Tumor volumes were monitored over time and presented as averages per group, individual tumor volumes at the end of study, or as % TGI.

Results

PI-3008 demonstrated anti-tumor activity as a single agent in the EMT6 model (FIG. 36). In some groups, up to a 20% complete response (CR) was achieved (responders).

Example 11: In Vivo Monotherapy Efficacy of Anti-Mouse MARCO Antibodies in E0771 Model Methods E0771 Syngeneic Mouse Model The mouse studies were performed under the guidance of and approved by the Institutional Animal Care and Use Committee of Explora BioLabs, South San Francisco, Calif.

Eight to ten-week old female C57/BL6 mice (Taconic) were implanted with subconfluent E0771 cells (ATCC) grown in log-phase. One million tumor cells resuspended in serum-free media with Matrigel were implanted orthotopically in the mammary fat pad of the mice under isoflurane anesthesia. When the majority of tumors were between 110-120 cubic millimeters (mm3), mice were randomized into the treatment groups (PI-3008-AB and PI-0002 mIgG2a isotype) before initiation of treatment.

PD Study

Mice randomized in 2 groups were dosed intraperitoneally with 10 mg/kg of PI-3008-AB or PI-0002-AB (isotype) based on group average body weight for each group. Tumor volume was calculated using the formula [length×(width)2]/2 after measuring two orthogonal diameters using digital calipers. At three different timepoints (2 days after 1 dose, 5 days after 1 dose, 24 hours after second dose Q5dx2), 15 mice per group were sacrificed and tumor, spleen and blood were collected. 9 animals were used for flow cytometry processing of tumors and spleen, and 6 mice were used for IHC evaluation of tumors and spleen. Tumor volumes were monitored over time and presented as averages per group, individual tumor volumes at the end of study, or as % TGI.

Effector Dead Antibody Efficacy

The effector dead anti-MARCO antibody, PI-3021 (PI-3008 with an N297A mutation) was also assessed in the E0771 model. Mice were dosed as described in Example 4. Briefly, 10 mice per group, IP dosing initiated when tumors were ~100 mm$^3$. Dosing was 10 mg/kg; Q5dx4. mIgG2a isotypes of both PI-3008 and the effector dead PI-3021 were used. An anti-PD-1 antibody was also used.

PK/PD Efficacy in E0771 Syngeneic Mouse Model

To determine PK-PD-efficacy relationships, the E0771 orthotopic breast cancer model was used since PI-3008 elicited monotherapy in this model. The study design included a PD arm where tumors and spleens were collected 24 hr after the second dose, and a "PK" arm to determine PI-3008 serum levels. A schematic of the study timeline is shown in FIG. 39A.

C57BL/6 female mice were injected into mammary fat pad with syngeneic E0771 tumor cells (5×105 cells per mouse) on Day 0, and dosing with PI-3008 or isotype controls (10 mg/kg, N=10/group) was initiated when tumor volumes reached an average of ~100 mm3. Animals were dosed intraperitoneally every 5 days, for total of four doses. A subset of animals was sampled 24 hr after the second dose for the assessment of PD changes in tumors and spleens. Additional PD takedown were done at 2 days and 5 days after first dose. Tissues sampled were tumors, spleens, and blood via Luminex and flow cytometry.

The rest of the animals were monitored for anti-tumor efficacy and were sampled at end of study for drug exposure analysis. The endpoint PD assays included flow cytometry profiling on the tumors and spleens to determine changes in myeloid and lymphoid composition, measurement of cytokines/chemokines in tumor and spleen, and assessment of CD8 T cells, NK cells, MARCO cells, and CD19 B cells frequencies and tissue distribution by IHC (monoplex and multiplex).

Flow Cytometry Assay

Mouse tumor tissue was harvested and placed in ice cold RPMI-1640 (Invitrogen) media. Tumors were enzymatically dissociated using the Mouse Tumor Dissociation Kit (Miltenyi) according to the manufacturer's recommendation. Following dissociation, single cell suspensions were pelleted and tumor supernatant was collected, spun at high speed to remove insoluble material, enzymatically inactivated using Halt™ Protease Inhibitor Cocktail (Thermo Scientific) and promptly frozen at −80 degC until downstream analysis was performed. Cell pellets were resuspended in stain media (DPBS/1% BSA/2 mM EDTA) and passed through a 100 uM filter to remove undissociated material. Single cell suspensions were counted on a ViCell XR (Beckman Coulter) and plated in 96-well V bottom plates for flow cytometric staining.

Cells were incubated with Zombie NIR (BioLegend), followed by FcgR block using a combination cocktail of TruStain FcX PLUS (Biolegend), Mouse Serum, Rat Serum, Hamster Serum (Jackson Immuno Research), all prepared in Fc Receptor Blocker (Innovex). Cell surface proteins were stained for 30 minutes on ice, followed by either a secondary stain step or fixation with 1% PFA overnight at 4° C. For staining intracellular proteins, cells were fixed and permeabilized with the FoxP3/Transcription Factor Staining Buffer Set (Thermo Fisher Scientific). Intracellular antibodies were prepared in permeabilization buffer with 2% rat serum and cells were incubated for at least 30 minutes at room temperature. Cells were run on an Attune NXT (ThermoFisher). Flow cytometric analysis was performed using FlowJo (Beckton Dickinson).

The flow antibodies used for each panel are described in Table 27 below and were prepared by adding the appropriate antibodies to the FACS buffer containing Ca2+/Mg2+PBS and 2% FBS.

TABLE 27

| Immune Population | Cell Surface Markers |
| --- | --- |
| Neutrophils | Ly6G+ |
| Monocytes | Ly6G−/Ly6C+ and sub-gating on MHCII−, MHCII$^{int}$, MHCII$^{high}$ |
| TAMs | CD11b+/F4/80+ and sub-gating on MHCII−, MHCII$^{int}$, MECII$^{high}$ |
| DCs | F4/80−/CD11c+/MHC−II+ |
| CD4+ T cell | CD90.2+/CD8−/CD4 |
| CD8+ T cell | CD90.2+/CD4−/CD8+ |
| NK cell | CD90.2+/CD4−/CD8−/NK1.1+ |
| Memory B cells | CD90.2− /CD45R+/CD19+ |
| Plasma B cells | CD 90.2− /CD45R+/CD19$^{Low}$/Blimp1+ |
| Marginal Zone B cells | CD90.2− /CD45R+/CD21+/CD35$^{mid}$/CD23+ |
| Follicular B cells | CD90.2− /CD45R+/CD21+/CD35$^{high}$ |
| Spleen macrophages | CD11b+/F4/80+ and sub-gating on MHCII− and MHCII+ |
| Red pulp macrophages | CD11b+/F4/80+/CD206+ |
| Marginal zone macrophages | CD11b$^{int}$/F480+ And/or CD11 CD11b$^{int}$/F480+/TIM4+ |
| Non marginal zone macrophages | All CD11b/F480+ populations for the exception of CD11b$^{int}$/F480+ marginal zone |

Receptor Occupancy (RO) Assay

For the tumor/spleen myeloid and blood flow cytometry antibody panels, the PI-3008 antibody conjugated with PE at BioLegend or the mIgG2a-PE from BioLegend were added to the staining cocktail at 10 μg/ml to assess receptor occupancy (RO) in the various myeloid cells in the tumors, spleen, and blood.

In Vivo Serum Concentrations

Serum levels of anti-mouse MARCO mAbs were determined using a standard ligand-binding ELISA (LBA) format with coated recombinant extracellular domain (ECD) mouse MARCO His-tagged fusion construct protein. PI-3008 mAb levels in the serum of CT26 tumor-bearing mice were assessed for multiple studies and various timepoints. For the PD study, PI-3008 was measured 4 h after the first IV dose and 4 h after the second IV dose, 7 days apart.

In vivo antibody serum levels in the CT26 combination studies with anti-MARCO antibody and anti-PD-1 antibody were also assessed for comparison. PI-3008 and PD-1 were dosed IP at 10 mg/kg or 5 mg/kg at Q5d X4 in the CT26 efficacy study (Example 4). The serum samples for PI-3008 and PD-1 concentration determinations were collected before the third dose (pre dose) and 24 hr after the final dose (post dose).

Mouse Cytokine and Chemokine Secretion by Luminex

Mouse plasma, spleen supernatants, or tumor supernatants were evaluated for cytokine levels using ProcartaPlex Multiplex Immunoassay from ThermoFisher Scientific (Cat #PPX-25-MX47WJ7). The kit uses color coded beads for measurement of multiple cytokines via Luminex xMAP technology. The beads are internally dyed with different proportions of red and infrared fluorophores that correspond to distinct spectral regions. For the experiment, 50 μl of magnetic capture beads are first added to the plate. Samples for analysis or kit standards were added at 25 μl per well volume and an equal amount of universal assay buffer was added to adjust the matrix. Following a two-hour incubation at room temperature, the beads are captured on a magnetic plate and were then washed followed by the addition of 25 μl/well of detection antibody. Following a one-hour incubation at room temperature, the beads were washed again and streptavidin phycoerythrin (SAPE) was added at 50 μl/well. After a final one-hour incubation, the beads were washed and 120 μl/well of read buffer was added. The plate was run on the Luminex 200 Instrument. Data was analyzed using Luminex Xponent software v4.3 and analytes levels in pg were normalized to the tumor or spleen weight. Cytokine/chemokine data was presented as fold changes of PI-3008 treated supernatants over the average of the isotype treated supernatants for each analyte.

Detection of IgG/IgM in Mouse Tissue and Serum

25 μL/well of Diluent 100 (MSD, Catalog R50AA-4) was added to the pre-coated plate with capture antibodies (MSD, Catalog #K15183B-1 and K15203D-1). The plate was incubated at room temperature for 30 min with vigorous shaking. Standards (Mouse Isotyping Panel 1, MSD Catalog #K15183B-1) and samples were diluted in Diluent 100 (MSD, Catalog #R50AA-4) and added to the coated plate. The plate was incubated for 120 min with vigorous shaking at room temperature and washed. 25 4 of 1× detection antibody solution was added to each well, and the plate was incubated for 120 min with vigorous shaking at room temperature. The plate was washed and 2× Read Buffer (MSD, Catalog #R92TC-3) was added to the MSD plate. The plate was read on an MSD Sector Imager. The IgG/IgM assay range for the Mouse Isotyping Panel was 24 pg/mL to 100,000 pg/mL. The LLOQ was 97.7 pg/mL and the ULOQ was 100,000 pg/mL. The IgG levels in mouse tissue samples ranged from 0.8 μg/mL to 1 μg/mL. The IgM levels in Mouse Tissue samples ranged from 0.2 μg/mL to 1 μg/mL. The IgG levels in mouse serum samples ranged from 41 μg/mL to 56 μg/mL. The IgM levels in mouse serum samples ranged from 15 μg/mL to 24 μg/mL.

Histology of Mouse Tissues and Antibody Staining in a Monoplex DAB IHC Assay

Animals were euthanized as per the institutionally approved standard operating procedure (SOP) for CO2 asphyxiation followed by cervical dislocation. Animals were sprayed with 70% ethanol to ensure sterility and reduce airborne allergens. Tumors and spleens were then collected in 10% Neutral Buffered Formalin (VWR, 16004). Formalin was removed 24 hrs later and tumors and spleen were transferred to 70% ethanol.

All tumors and spleens were shipped to Cureline (Brisbane, Calif.). Cureline performed histology based on their institutional SOP and fully automated workflow. Larger tumors were cut in half and smaller tumor were left intact and were then processed, embedded in paraffin, and cut into 5 μm thin sections. Spleens were cut cross sectionally and were then processed, embedded in paraffin, and cut into 3 μm thin sections.

CD8a (Cell Signaling, 989415) immunohistochemistry (IHC) was performed using a Bond Rx autostainer (Leica Biosystems) with Heat-Induced Epitope Retrieval (HIER) at pH 9.0 for 20 minutes. The CD8a primary antibody (98941S, Cell Signaling Technologies, diluted for use at 3.2 μg/ml) and Bond Polymer Refine Detection (Leica Biosystems) were used according to manufacturer's protocol. Both spleen and tumor tissues were stained. Marco (Abcam, ab239369) IHC was performed using a Bond Rx autostainer (Leica Biosystems) with HIER at pH 6.0 for 20 minutes. The Marco primary antibody (ab239369, Abcam, diluted for use at 1.5 μg/ml) and Bond Polymer Refine Detection (Leica Biosystems) were used according to manufacturer's protocol. Both spleen and tumor tissues were stained.

NCR1 IHC was performed using a Bond Rx autostainer (Leica Biosystems) with HIER at pH 9.0 for 20 minutes. The NCR1 primary antibody (ab233558, Abcam, diluted for use at 1.25 μg/ml) and Bond Polymer Refine Detection (Leica Biosystems) were used according to manufacturer's protocol. Both spleen and tumor tissues were stained.

CD19 (Abcam, ab245235) IHC was performed using a Bond Rx autostainer (Leica Biosystems) with HIER at pH 9.0 for 20 minutes. The CD19 primary antibody (ab245235, Abcam, diluted for use at 0.91 μg/ml) and Bond Polymer Refine Detection (Leica Biosystems) were used according to manufacturer's protocol. Both spleen and tumor tissues were stained.

CD206 (MRC1; Invitrogen, PA5-114370) IHC was performed using a Bond Rx autostainer (Leica Biosystems) with HIER at pH 9.0 for 20 minutes. The CD206 primary antibody (PA5-114370, ThermoFisher Scientific, diluted for use at 0.5 μg/ml for spleen and 1 μg/ml for tumor) and Bond Polymer Refine Detection (Leica Biosystems) were used according to manufacturer's protocol. Both spleen and tumor tissues were stained.

After staining, sections were rinsed in dH2O and mounted with Xylene and Cytoseal XYL (ThermoFisher Scientific) mounting medium. Whole slide scanning (40×) was performed on an Aperio AT2 (Leica Biosystems) and all scans were deposited electronically on the Pionyr Pathcore webpage.

CD8a, MARCO, NCR1, CD19 and CD206 Quantification

The tissue sections were analyzed using the image analysis software HALO v3.3.2541.202 (Indica Labs). The images were imported into the HALO database, and brush annotation tool was used to identify the area for analysis (labelled layer 1). The entire spleen and tumor tissue areas were included, excluding any artifact staining, folds, necrotic regions, glass, or skin regions using the scissor annotation tool. IHC analysis was performed on each annotation layer for all markers separately (CD8a, MARCO, NCR1, CD19 and CD206) using the Indica Labs—Area Quantification v2.1.11 algorithm. The algorithm was set to detect the blue pixels from the hematoxylin stain, and brown pixels from the DAB IHC stain. The data was exported as an excel file and the % positive DAB staining over total annotated area was collected for each individual marker and was used to plot the data in prism.

Multiplex Immunofluorescent (IF) Staining and Image Analysis

FFPE sections from mouse spleens and tumors were stained using 5-plex IF panels. Spleens from 6 PI-3008 treated, and 6 isotype treated mice, and tumors from 4 PI-3008 treated, and 4 isotype treated mice were stained and analyzed. All IHC antibodies included in the multiplex mouse spleen panel and the mouse tumor (E0771) panel were first optimized by DAB IHC on FFPE mouse spleen and tumor sections (E0771 tumors). Optimal antibody concentrations and staining conditions were then considered when developing the multiplex panels. Antibodies used were: CD8a from Cell Signaling, 98941S; MARCO from Abcam, ab239369; CD19 from Abcam, ab245235, CD206 (MRC1) from Invitrogen; PA5-114370; NCRI from Abcam ab233558; and nuclei from Akoya, SKU FP1490.

Sections were subjected to 4 sequential rounds of staining with each primary antibody followed by a secondary HRP-conjugated polymer, and signal amplification using TSA-Opal fluorophores. A heat-induced epitope retrieval step was performed after each round of staining to remove the primary-secondary-HRP complexes. The slides were then counterstained with Spectral DAPI and mounted using anti-fade mounting medium.

Stained slides were imaged using the Vectra 3 imaging system (Akoya Biosciences). After a low magnification scan, regions of interest (ROI) were stamped by using the Phenochart viewer (Akoya Bioscience) and these stamps were subsequently scanned at a higher resolution (20×). Four stamps per spleen section were selected by choosing regions where representative white pulp, red pulp and marginal zone areas were included. In the tumor sections, stamps were selected to cover the majority of the tumor area, purposely selecting edge regions and center regions to facilitate comparative analysis of these tumor areas. The acquired ROI image files were opened in InForm (Akoya Biosciences) and there spectrally unmixed followed by removal of auto fluorescent staining. Image analysis was performed in InForm by first manually segmenting the spleen tissue into red pulp, white pulp, and marginal zone. Glass regions were excluded from analysis. Tumor tissues were manually segmented to just include tumor and exclude skin, glass, and necrotic regions. Nuclei were identified and segmented using the DAPI counterstain, followed by training of the cell phenotyping algorithm for the identification of the cell types of interest. The data generated by InForm was then loaded into R studio and using the phenoptrReports package (Akoya Biosciences) from which data including cell counts, cell percentages, cell densities, and nearest neighbor analysis for the different tissue compartments was generated Results PI-3008-AB also demonstrated anti-tumor activity as single agent in the orthotopic E0771 model as compared to isotype control antibodies (FIG. 37). At the end of the study on day 33, mice dosed with PI-3008 showed a statistically significant reduction in tumor volume as compared to isotype controls (p=0.0037) (FIG. 38A). The percentage of tumor growth inhibition (TGI) is shown in FIG. 38B for isotype antibody and PI-3008.

In addition, both PI-3008 and effector dead PI-elicited similar single agent activity in the orthotopic E0771 Model (FIG. 38C). Individual panels show the tumor volume in individual mice after treatment with the indicated antibody or isotypes control. The upper right panel shows the tumor valiums in each mouse at Day 28. The lower right panel shows the antibody concentration in serum for PI-3008 and PI-3021.

PK-PD-Efficacy Assay

The in vivo PK-PD study in E0771 showed that PI-3008 elicited single agent activity compared to the isotype antibody after 4 doses of treatment. Significant differences in tumor size was observed starting at the second dose (FIG. 39B). Individual tumor volumes in the isotype control mice are provided in FIG. 39C. Individual tumor volumes in the PI-3008 mice on are provided in FIG. 39D. The final tumor volumes at Day 28 are provided in FIG. 39E. In addition, the serum levels of PI-3008 maintained robust exposure until the end of the study (FIG. 39F).

The serum concentrations of anti-PD-1 when combined with PI-3008 were also in the expected exposure range as seen in previous studies when dosed as single agent (FIGS. 40A and 40B). FIG. 40A provides the PI-3008 concentrations in mono and combination experiments with PD-1 antibody, while FIG. 40B provides the PD-1 concentrations in combination experiments.

PI-3008 also activated intra-tumoral immunity in the E0771 model, as seen by an increase in CD8+ T cells and NK cells in the TME after administration of the antibody. FIG. 41A provides IHC images of CD8 T cells and NCR1 (NK cells) stained with DAB after administration of isotype control or PI-3008. FIG. 41B provides quantification of the cytotoxic CD8+ T cells and NK cells in the tumor area by HALO image analysis of the IHC staining. PI-3008 promoted changes in the TME indicative of improved anti-tumor response. The anti-MARCO antibody increased $MHCII^{High}$ Ly6C+ monocytes, DC infiltration, and NK1.1 NK cells in the TME by flow cytometry (FIG. 41C). Without wishing to be bound by theory, increases in these cells may increase intra-tumoral immune activation and improve antigen presentation in the TME.

Increases in CD8+ T cells and NK cells in the TME were also observed by multiplex IF. FIG. 41D provides quantification of CD206+, cells, MARCO+ cells, NCR1+ cells, and CD8a+ cells at the tumor edge, the cell density of the indicated cell at the tumor edge, the median distance to the nearest neighbor from CD206 and the indicated cell types, and the median distance to the nearest neighbor from MARCO and the indicated cell types in mice after treatment with isotype antibody or PI-3008. Data for isotype antibody is provided on the left of each data pair with circle icons, while data for PI-3008 is provided on the right of each data pair with diamond icons. This multiplex analysis showed that NK cells and CD8T cells are increased in the tumors after anti-MARCO treatment. The spatial mapping showed a closer distance of CD8+ T cells and NK cells with MARCO+ cells in the TME in the PI-3008 treated tumors compared to isotype.

Proinflammatory cytokines and chemokines induced by PI-3008 in the E0771 model tumor supernatants were also assessed (FIG. 42A). PI-3008 treatment induced cytokines and chemokines in the tumor supernatants in the E0771 model. The same cytokines were induced in the E0771 model as identified via RNAseq in the CT26 study. Cytokines associated with T-cell activation and NK cells activation were also observed at Day 1 post-dose 2 in the tumor supernatants (FIG. 42B).

MARCO is highly expressed in the spleen, primarily on marginal zone macrophages, monocytes and dendritic cells (FIG. 43). The samples from mice treated with isotype antibody are provided on the left of each sample pair, the samples from mice treated with PI-3008 antibody are provided on the right of each sample pair. The data in FIG. 43 is plotted based on the delta gMFI between the PI-3008-PE and the mIgG2a-PE isotype antibody used in the flow cytometry analysis. In this assay, the MARCO flow antibody competes with the previously administered therapeutic PI-3008 for binding on the MARCO+ cells in the samples.

Thus, receptor occupancy and competition were expected and observed in the samples from the PI-3008 treated mice, provided on the right side of the sample pairs, as evidenced by the low delta gMFI levels indicating low anti-MARCO binding in the flow assay (FIG. 43). No receptor occupancy and competition for MARCO staining in the flow cytometry assay was observed in the isotype treated mice samples, provided on the left side of the sample pairs, as evidence by high delta gMFI levels indicating high anti-MARCO binding in the flow assay (FIG. 43). Higher RO and lower gMFI in PI-3008 treated samples as compared to isotype treated samples for each myeloid target population confirmed the expression of MARCO on each specific population. The isotype treated group thus shows MARCO expression (using the PI-3008 flow antibody) to detect MARCO levels on the myeloid target population when no therapeutic antibody is present. MARCO expression was observed on dendritic cells, CD11bint F480+ macrophages, TM4+ marginal macrophages, Ly6C+ MHCII$^{High}$ monocytes, and Ly6C+ MHCII$^{mid}$ monocytes. MARCO expression was highest on the marginal zone macrophages, identified by CD11bintF480+ and TIM4+ marginal zone macrophages. MARCO was also expressed on the MHCII+ monocytes. Receptor occupancy was achieved in the PI-3008 antibody treated group (24 hours following 2$^{nd}$ dose) in those myeloid populations.

In sum, FIG. 43 shows that the delta gMFI in the isotype group showed expression of MARCO receptor in the spleen and the delta gMFI on the PI-3008 treated groups confirmed that PI-3008 was bound on the MARCO positive myeloid cells and thus could not be detected with the PI-3008 flow antibody. The samples from mice treated with isotype antibody are provided on the left of each sample pair, the samples from mice treated with PI-3008 antibody are provided on the right of each sample pair.

PI-3008 did not affect the myeloid populations in the spleen but potentially affected B-cells 24 hours after the second dose. As shown in FIGS. 44A, 44B, and 44C, PI-3008 treatment did not alter the MARCO+ myeloid or lymphoid cell populations in the spleen. However, PI-3008 treatment did result in a decrease of CD19+ B-cells and plasma B-cells in the spleen (FIG. 44D). The samples from mice treated with isotype antibody are provided on the left of each sample pair, the samples from mice treated with PI-3008 antibody are provided on the right of each sample pair.

PI-3008 treatment decreased IgM production and increased IgG production in the spleen and serum at Dose 2 (FIG. 45).

MARCO expression on the marginal zone macrophages decreased with PI-3008 treatment in spleen when measured by IHC (FIG. 46). MARCO+ cells in the spleen were assessed at the second dose and at the end of the study. PI-3008 mice showed a decreased number of MARCO+ marginal zone macrophages as compared to isotype antibody treated mice. Monoplex IHC was also used to determine changes in the spleen after PI-3008 treatment (FIG. 47A-D). An increase in CD8+ T cells and NK cells was observed in the total area after PI-3008 treatment (FIGS. 47A and 47B). The CD19+ cell population was variable and challenging to measure by IHC (FIG. 47C). A significant increase in CD206 (red pulp macrophages) was observed after PI-3008 treatment (FIG. 47D). The samples from mice treated with isotype antibody are provided on the left of each sample pair, the samples from mice treated with PI-3008 antibody are provided on the right of each sample pair.

The percentage positive cells per tissue compartment after treatment with isotype antibody and PI-3008 was determined via image analysis of multiplex IF (FIG. 48A-D). A decrease in MARCO in the red pulp after PI-3008 therapy and in total areas was observed (FIG. 48A). A small decrease in CD19 across all tissue compartments was observed in the total area after PI-3008 treatment (FIG. 48B). An increase in CD8a across all tissue compartments was observed after PI-3008 treatment (FIG. 48C). A small increase in CD206 in the red pulp was observed after PI-3008 treatment (FIG. 48D). The samples from mice treated with isotype antibody are provided on the left of each sample pair, the samples from mice treated with PI-3008 antibody are provided on the right of each sample pair.

Day 2 and Day 5 PD Sample Analysis

Digested supernatants and plasma from tumors, spleen and blood sampled at 2 days and 5 days post antibody treatment were analyzed via Luminex. Anti-MARCO treatment induced cytokines and chemokines in the tumor supernatants in the E0771 model at early timepoints (FIG. 58 and FIG. 59). Samples from Day 2 are shown on the right, samples from Day 5 are shown on the left. Changes in cytokines and chemokines were observed at both timepoints, G-CSF, IL27, IL10, and TNFα increased at day 2, IL12p70, IL10, IL6, and IL4 increased at day 5. Chemokines involved in migration and chemotaxis were increased in the spleen at day 2 after the first antibody dose.

Anti-MARCO treatment also modulated IgG1 production in the mouse tumor (Table 28).

TABLE 28

| | IgA | IgG1 | IgG2a | IgG2b | IgM | Total IgG |
|---|---|---|---|---|---|---|
| Day 2 | | | | | | |
| Isotype (μg/ml) | 1.22 | 14.67 | 2.39 | 9.58 | 4.83 | 26.65 |
| PI-3008 (μg/ml) | 1.12 | 19.42 | 2.48 | 8.48 | 4.57 | 30.38 |
| Day 5 | | | | | | |
| Isotype (μg/ml) | 1.10 | 20.61 | 1.69 | 13.56 | 6.54 | 35.86 |
| PI-3008 (μg/ml) | 1.20 | 15.52 | 2.25 | 12.34 | 6.59 | 30.12 |

Anti-MARCO treatment decreased IgM production at day 2 and IgG1 decreased slightly at day 5 in the spleen (Table 29).

TABLE 29

| | IgA | IgG1 | IgG2a | IgG2b | IgM | Total IgG |
|---|---|---|---|---|---|---|
| Day 2 | | | | | | |
| Isotype (μg/ml) | 4.36 | 15.50 | 5.08 | 12.73 | 43.58 | 33.31 |
| PI-3008 (μg/ml) | 3.65 | 14.02 | 3.18 | 10.69 | 28.13 | 27.88 |
| Day 5 | | | | | | |
| Isotype (μg/ml) | 1.90 | 14.58 | 1.46 | 7.74 | 18.37 | 23.77 |
| PI-3008 (μg/ml) | 2.43 | 10.99 | 2.01 | 9.63 | 17.22 | 22.62 |

Anti-MARCO treatment decreased IgG1 and IgG2b in the plasma after PI-3008 treatment (Table 30).

TABLE 30

| | IgA | IgG1 | IgG2a | IgG2b | IgM | Total IgG |
|---|---|---|---|---|---|---|
| Day 5 | | | | | | |
| Isotype (μg/ml) | 21 | 16 | 13 | 45 | 6 | 74 |
| PI-3008 (μg/ml) | 18 | 6 | 13 | 37 | 6 | 56 |

First, tumor myeloid cells were assessed at Days 2 and 5 after one does of MARCO antibody treatment. Anti-MARCO affected the total number of TAMs (decreased, FIG. 60) and monocytes (increased, FIG. 61) in tumors at D2 and D5. Anti-MARCO also reprogramed TAMs from immunosuppressive MHCII− to pro-inflammatory MHCII+ at day 2 (FIG. 60) and monocytes from immunosuppressive MHCII− to proinflammatory MHCII+ at D2 (FIG. 61).

Anti-MARCO increased CD11c+ MHCII+ DCs at D2 and D5, and slightly decreased Ly6G+ neutrophils at D2 and D5 (FIG. 62). In summary, in the tumor myeloid cells, anti-MARCO antibody increased pro-inflammatory monocytes and DCs, and decreased tumor associated neutrophils (TANs) and TAMs. In addition, 2 days after first dose, anti-MARCO reprogrammed MHCII− TAMs to MHCII+ TAMs, and MHCII− monocytes to MHCII+ monocytes.

Next, tumor lymphoid cells were assessed at Days 2 and 5 after one dose of MARCO antibody treatment. Anti-MARCO increased CD8+ T cells and CD4+ T at day 2 and 5 in the tumors (FIG. 63). Anti-MARCO also increased NK1.1 NK cells at day 5 in the tumors (FIG. 63).

Next, spleen lymphoid cells were assessed at Days 2 and 5 after 1 dose of MARCO antibody treatment. Anti-MARCO decreased CD19+ B cells at both days and did not change Plasma B Cells (FIG. 64 and data not shown). Anti-MARCO increased follicular B cells and decreased marginal zone B cells at day 5 in the spleen (FIG. 64). Anti-MARCO affected B-cell populations in the spleen by decreasing CD19+ B-cells, decreasing marginal zone B-cells, and increasing follicular B cells at day 5 (FIG. 64). Anti-MARCO increased splenic CD8+ and CD4+ T cells at both days (FIG. 65 and data not shown). Anti-MARCO did not change NK1.1 NK cells at day 2, but increased them at day 5 (FIG. 65 and data not shown). Anti-MARCO also increased splenic DCs, and did not alter neutrophil levels in the spleen (FIG. 65).

Spleen myeloid cells were also assessed at Day 5 after one dose of MARCO antibody treatment. Anti-MARCO decreased MHCII− monocytes and increased MHCII+ monocytes (high and intermediate) at day 5 by subtyping Ly6C+ monocytes into various MHCII level cells (FIG. 66). Anti-MARCO increased the number of total macrophages in the spleen at D2 and D5, including red pulp macrophages (FIG. 67 and data not shown). Anti-MARCO also increased the number of Marginal Zone Macrophages (MZMs) at D5, MHCII+ DCs, and increased the non-marginal zone macrophages at D5 (FIGS. 67 and 68).

Blood was also profiled by flow cytometry at Day 5. A slight decrease in Ly6C$^{high}$ monocytes and DCs at day 5 and an increase in T-cells was observed. No change in B-cells was observed. (FIG. 69).

MARCO expression and Receptor Occupancy in mouse spleens, E0771 tumors, and blood (FIG. 70) at Day 5 was also assessed. As shown in FIG. 70, MARCO was expressed at high levels in the spleen, in particular on the marginal zone (MZ) macrophages gated by CD11b$^{int}$ F480+ and TIM4+ Macs. MARCO was not expressed on the non-Marginal zone macrophages (non-MZ), as evidenced by the MARCO flow cytometry staining of the mIgG2a isotype samples, in which the flow cytometry MARCO antibody did not compete with prior MARCO antibody for binding to cells. MARCO was expressed on MHCII+ monocytes (MHCII$^{high}$ and MHCII$^{inter}$) and on DCs. MARCO was also expressed on CD206+ red pulp macrophages outside the marginal zone and on MHCII+ Macs. Receptor Occupancy of the therapeutic MARCO antibody was achieved in the positive MARCO expressing cells of FIG. 70 listed above, as evidenced by the lack of MARCO flow cytometry staining of the MARCO samples, in which the flow cytometry MARCO antibody was out competed for binding to cells by the prior therapeutic MARCO antibody.

In the E0771 tumors, MARCO was expressed at low levels inside the tumors. Receptor Occupancy could not be accurately measured at day 2 but was achieved in MHCII$^{high}$ and intermediate monocytes; MHCII+ DCs; and both MHCII+ TAMs and MHCII-TAMs at day 5 (FIG. 70). No MARCO expression was observed on blood immune cells (FIG. 70).

In sum, PI-3008 induced motility and/or phagocytosis changes in the tumor, as evidenced by altered gene expression in cytoskeletal, actin and muscle, migration, and cell-adhesion and migration related pathways. PI-3008 also induced immune activation as evidenced by NK cell activation, T cell activation, and myeloid cell differentiation. In the lymph nodes, PI-3008 altered gene expression in pathways associated with cell signaling, cell-adhesion, cytoskeletal, and motility genes. In the spleen, PI-3008 altered gene expression in pathways associated with cell signaling, cell-adhesion, cytoskeletal, chemotaxis, and motility genes as well as B cell activation. Without wishing to be bound by theory, taken together, this data indicates that anti-MARCO antibodies activate intra-tumor immunity at least by mediating repolarization of MARCO+ myeloid M2-like TAMs to M1-like TAMs, and repolarization of mMDSCs to pro-inflammatory monocytes. This repolarization leads to production of cytokines, chemokines, and activation receptors, which in turn leads to activation of T and NK cells. The repolarization of myeloid M2-like TAMs and mMDSCs and activation of T and NK cells then leads to tumor destruction mediated by NK cells, CD8 cells, and M1-like macrophages. Further, without wishing to be bound by theory, potential binding of the anti-MARCO antibody to medullary cord macrophages (MCMs) may induce changes in adhesion and motility in the lymph node, and potential binding of the anti-MARCO antibody to marginal zone macrophages (MZMs) in the spleen may lead to changes in adhesion and motility, leading to potential B cell activation.

Example 12: Pharmacodynamic Assay in CT26 In Vivo Model

Methods

A PD study was conducted in CT26 tumor bearing mice. Eight to ten-week old female BALB/c mice (Taconic) were implanted with subconfluent CT26.WT cells (ATCC, banked at Pionyr) grown in log-phase. One million tumor cells resuspended in serum-free media were implanted subcutaneously on the right ventral flank of the mice under isoflurane anesthesia. For the pilot CT26 PD study, mice with tumor volumes of 150-200 mm3, were dosed once intravenously with 10 mg/kg of PI-3008-AB or PI-0002-AB (isotype) and tumors and spleens were collected 4 days after treatment inn 10% formalin for IHC staining with anti-mouse MARCO, anti-CD8, and anti-granzyme B. HALO image analysis software (Indica Labs) was used to quantify the percentage of CD8+ T cells and Granzyme B+ cells over the whole tumor area. Spleens were stained with a non-PI-3008 competing anti-mouse MARCO IHC compatible antibody.

Results

The anti-MARCO antibody PI-3008 induced an increase in CD8+ T-cells and the cytotoxic marker granzyme B in tumors as compared to isotype control treated tumors (FIG.

49). Data is presented as mean percentage values from 3 mice within each treatment group of ±standard error of the mean (SEM).

In the spleen, changes in MARCO levels on the marginal zone macrophages were observed with noticeable gaps in the marginal zone area (FIG. 50). Control spleens showed several layers of MARCO+ stained cells in the marginal zone. Layers continue around most of the periarteriolar lymphoid sheath (PALS) and B cell follicle caps. Spleens from PI-3008 treated mice showed much less MARCO+ staining that include fewer cells and layers. There were also gaps in the coverage of the PALS and B cell caps. Thus, there was a decrease in MARCO-positive cells in the splenic marginal zone of animals treated with PI-3008. Without wishing to be bound by theory, these data suggest that anti-MARCO induces proinflammatory actuation within the TME and leads to changes in adhesion and motility as seen in the spleen.

Example 13: Immunohistochemistry MARCO Assay

To identify a suitable anti-human MARCO IHC antibody to profile MARCO expression in human FFPE tissues, 15 commercial and internal antibodies were screened. The primary screening comprised staining FFPE embedded MARCO over-expressing (CL3010), endogenous (L1236), and negative control (HEK-293T cells and Jurkat cells that do not express MARCO) cell pellets. Antibodies that passed the primary screen were included in the secondary screen, in which lung cancer and colon cancer FFPE sections, identified as having high RNA expression by in situ hybridization (ISH), were stained using different IHC staining conditions (different antibody concentrations, incubation times, and antigen retrieval). Two potential human MARCO specific off the shelf IHC antibodies from R&D, RDM5 (clone #858428.11, catalog CUST017MABP) and RDM9 (clone #858423.11, catalog CUST017MABP), were identified. RDM5 was slightly superior to RDM9 and thus was selected for further optimization of IHC assay conditions on additional control tissues. RDM5 demonstrated specific, strong, and sensitive labeling of MARCO-positive cells when used at 2.5 µg/mL with a high pH antigen retrieval (ER2), on an automated Leica platform (FIG. 51A). The staining was validated on normal and tumor tissue microarrays (TMAs) and MARCO specificity was confirmed by a certified-board pathologist. In addition, MARCO expression in normal tissues was restricted to the tissue resident macrophages in the lung, liver, and spleen, confirming the previous RNA data.

Next, further profiling of MARCO expression was explored on 20 tissue microarrays (TMA) from 17 different tumor indications and contained duplicate cores per subject with different diagnoses (Pathology, Grade, and TNM stage). The TMA at Reveal Biosciences was made by acquiring tissues that were fixed in 10% neutral buffer formalin for 24 hours and processed using identical SOPs. Sections were picked onto Superfrost Plus or Startfrost Adhesive slides and all TMAs were cut fresh in 4 um serial sections upon ordering and stored at 4degC prior to IHC staining.

After whole slide scanning of each TMA at 40× using the Aperio AT2 Scanner, quantification of the MARCO+ cells in the tumor intervening stroma were assessed by a board-certified pathologist using the following scoring system: 0=<1% positive cells, 0.5=1-10% positive cells, 1=10-25% positive cells, 1.5=25-50% positive cells, 2=approximately 50% positive cells, 2.5=50-75% positive cells, 3=approximately 75% positive cells, and 3.5=>75% positive cells over stroma. Lost or folded cores with more than half of the area distorted were removed from the analysis and not scored. The staining for each patient was considered positive if MARCO+ cells were expressed at 1% or above 1% over stroma. Each dot represents one case, and the median for each indication is depicted as a line The percentage of positive cases, with a cutoff at 1% MARCO+ cells in the stroma, was highest in colon cancer (92%), followed by lung cancer (87%), endometrial cancer (78%), mesothelioma (64%), ovarian cancer (61%), lymphoma (60%), thyroid cancer (60%), TNBC (53%), breast cancer (51%), head and neck cancer (45%), stomach cancer (44%), pancreatic cancer (43%), liver cancer (39%), and kidney cancer (33%) (FIG. 51B). The median MARCO IHC scores were highest with a score of 1 in colon, lung, thyroid, and mesothelioma, followed by a median score of 0.75 in lymphoma and endometrial cancer for all tumor grades (data not shown). When focusing only on the advanced grade III tumors, the median MARCO IHC scores increased from 0.5 to 1 in breast cancer and from 0 to 0.5 in kidney cancer, indicating that increased MARCO expression is correlated to higher tumor grade in these tumor indications (FIG. 51C). Moreover, the MARCO IHC score in normal tissues was highest in normal liver, lung, spleen, colon, ovary and nerve tissue, corroborating previously described MARCO RNA expression data. Thus, based on MARCO IHC scoring using the RDM5 antibody, colon cancer, lung cancer, mesothelioma, lymphoma, thyroid cancer, endometrial cancer, and ovarian cancer have the highest IHC scores and number of MARCO positive cases.

Example 14: Cell Line Development for MARCO Antibody Production

Two independent transfections were performed per double gene vector, with three static 96-shallow well plates per transfection. A transfer to suspension culture in 96-deep well plates occurs, then four transfection pools are generated from top cultures. All cultures maintained viabilities of ≥97% throughout 6 days of culture.

Evaluation of the transfection pool product quality was performed following partial purification (i.e., MabSelect™ SuRe™ affinity chromatography and sample neutralization to pH 7). Lonza performed product quality evaluation by gel permeation high performance liquid chromatography (GP-HPLC), sodium dodecyl sulfate (SDS) electrophoresis (reduced and non-reduced) and imaged capillary isoelectric focusing (iCIEF). Aggregation data for PI-3030.41 was significantly elevated compared to the other candidates. The results of the transfection pool analysis are shown in Tables 31 through 36 below.

TABLE 31

Transfection Pool Concentration Data

| Transfection Pool | Partially Purified Concentration (mg/mL) | Partially Purified Volume (µL) | Total Quantity (mg) |
| --- | --- | --- | --- |
| 3010.15 (1) | 0.818 | 650 | 0.53 |
| 3010.15 (2) | 0.959 | 645 | 0.62 |
| 3010.15 (3) | 1.372 | 650 | 0.89 |
| 3010.15 (4) | 1.150 | 750 | 0.86 |
| 3010.25 (1) | 1.248 | 740 | 0.92 |
| 3010.25 (2) | 0.936 | 655 | 0.61 |
| 3010.25 (3) | 1.243 | 590 | 0.73 |
| 3010.25 (4) | 1.271 | 605 | 0.77 |
| 3030.41 (1) | 0.972 | 650 | 0.63 |

TABLE 31-continued

Transfection Pool Concentration Data

| Transfection Pool | Partially Purified Concentration (mg/mL) | Partially Purified Volume (μL) | Total Quantity (mg) |
|---|---|---|---|
| 3030.41 (2) | 1.073 | 655 | 0.70 |
| 3030.41 (3) | 1.025 | 655 | 0.67 |
| 3030.41 (4) | 0.871 | 650 | 0.57 |

TABLE 32

Transfection Pool Aggregation by GP-HPLC Data

| Transfection Pool | Fragments (Iv) | Monomer (%) | | Aggregates (%) | |
|---|---|---|---|---|---|
| 3010.15 (1) | <0.10 | 89.98 | 90.0 - 92.1 | 10.02 | 7.9 - 10.0 |
| 3010.15 (2) | <0.10 | 91.52 | | 8.48 | |
| 3010.15 (3) | <0.10 | 92.06 | | 7.94 | |
| 3010.15 (4) | <0.10 | 91.63 | | 8.37 | |
| 3010.25 (1) | <0.10 | 95.15 | 90.2 - 95.2 | 4.85 | 4.9 - 9.8 |
| 3010.25 (2) | <0.10 | 90.20 | | 9.80 | |
| 3010.25 (3) | <0.10 | 94.47 | | 5.53 | |
| 3010.25 (4) | <0.10 | 92.49 | | 7.51 | |
| 3030.41 (1) | <0.10 | 80.83 | 80.3 - 82.5 | 19.17 | 17.5 - 19.7 |
| 3030.41 (2) | <0.10 | 81.69 | | 18.31 | |
| 3030.41 (3) | <0.10 | 82.46 | | 17.54 | |
| 3030.41 (4) | <0.10 | 80.33 | | 19.67 | |

TABLE 33

Transfection Pool SDS Electrophoresis (Reduced) Data

| Transfection Pool | LC Size (kDa) | | LC Purity (%) | | HC Size (kDa) | | HC Purity (%) | | LC + HC Purity (%) | |
|---|---|---|---|---|---|---|---|---|---|---|
| 3010.15 (1) | 27.36 | 27.3- | 42.11 | 41.8- | 62.47 | 62.2- | 57.66 | 56.4- | 99.77 | 99.8 |
| 3010.15 (2) | 27.27 | 27.6 | 43.33 | 43.3 | 62.24 | 62.8 | 56.42 | 58.0 | 99.75 | |
| 3010.15 (3) | 27.61 | | 41.77 | | 62.82 | | 58.02 | | 99.80 | |
| 3010.15 (4)* | 27.52 | | 36.73 | | 62.61 | | 57.55 | | 94.27 | |
| 3010.25 (1)* | 27.02 | 26.5- | 26.93 | 39.8- | 63.01 | 61.5- | 32.45 | 58.1- | 59.38 | 99.6- |
| 3010.25 (2) | 26.70 | 27.0 | 41.47 | 41.5 | 62.09 | 63.0 | 58.13 | 59.9 | 99.60 | 99.7 |
| 3010.25 (3) | 26.48 | | 40.72 | | 61.48 | | 58.95 | | 99.67 | |
| 3010.25 (4) | 26.59 | | 39.77 | | 61.55 | | 59.89 | | 99.65 | |
| 3030.41 (1) | 26.51 | 26.5- | 43.32 | 42.5- | 61.65 | 61.7- | 56.47 | 56.0- | 99.79 | 98.7- |
| 3030.41 (2) | 26.48 | 26.8 | 43.53 | 43.5 | 61.78 | 62.2 | 56.27 | 57.3 | 99.80 | 99.8 |
| 3030.41 (3) | 26.72 | | 42.71 | | 62.24 | | 56.01 | | 98.72 | |
| 3030.41 (4) | 26.75 | | 42.49 | | 62.21 | | 57.30 | | 99.79 | |

*Difference in value may be due to not fully reduced samples (supported by reduced electropherogram and sample non-reduced data). Small amount of higher molecular weight species for 3010.15 (4) and significant amount of higher molecular weight species for 3010.25 (1). These values were excluded in the purity ranges for per candidate.

TABLE 34

Transfection Pool SDS Electrophoresis (Non-Reduced) Data

| Transfection Pool | IgG Size (kDa) | | IgG Purity (%) | |
|---|---|---|---|---|
| 3010.15 (1) | 170.16 | 167.8 - 170.2 | 96.04 | 95.8 - 97.0 |
| 3010.15 (2) | 169.62 | | 95.83 | |
| 3010.15 (3) | 167.81 | | 96.67 | |
| 3010.15 (4) | 168.09 | | 96.99 | |
| 3010.25 (1) | 168.83 | 167.7 - 169.2 | 96.72 | 95.7 - 96.7 |
| 3010.25 (2) | 168.47 | | 96.53 | |
| 3010.25 (3) | 169.19 | | 96.43 | |
| 3010.25 (4) | 167.72 | | 95.70 | |
| 3030.41 (1) | 165.78 | 165.0 - 167.5 | 96.04 | 95.2 - 96.0 |
| 3030.41 (2) | 164.99 | | 95.59 | |
| 3030.41 (3) | 167.45 | | 95.90 | |
| 3030.41 (4) | 166.61 | | 95.24 | |

TABLE 35

Transfection Pool iCIEF Isoform Data

| Transfection Pool | Acidic Variant Peaks | | | | Main Peak | | Basic Variant Peaks | | | |
|---|---|---|---|---|---|---|---|---|---|---|
| | Isoform 5 | | Isoform 4 | | Isoform 3 | | Isoform 2 | | Isoform 1 | |
| 3010.15 (1) | 5.7 | <LOQ- | 18.4 | 17-20 | 67.7 | 67-71 | 6.8 | 6-7 | <LOQ | <LOQ |
| 3010.15 (2) | 5.3 | 6 | 17.3 | | 69.2 | | 6.9 | | <LOQ | |
| 3010.15 (3) | 5.1 | | 20.1 | | 67.4 | | 6.4 | | <LOQ | |
| 3010.15 (4) | <LOQ | | 19.2 | | 70.6 | | 5.8 | | <LOQ | |
| 3010.25 (1) | <LOQ | <LOQ | 15.9 | 15-16 | 72.8 | 72-73 | 6.6 | 7 | <LOQ | <LOQ |
| 3010.25 (2) | <LOQ | | 15.9 | | 72.3 | | 6.8 | | <LOQ | |
| 3010.25 (3) | <LOQ | | 15.4 | | 72.9 | | 6.7 | | <LOQ | |
| 3010.25 (4) | <LOQ | | 16.2 | | 71.9 | | 6.7 | | <LOQ | |
| 3030.41 (1) | 5.4 | 5-7 | 19.4 | 19-21 | 69.5 | 68-70 | <LOQ | <LOQ-5 | <LOQ | <LOQ |
| 3030.41 (2) | 7.0 | | 20.0 | | 67.8 | | <LOQ | | <LOQ | |
| 3030.41 (3) | 5.8 | | 20.5 | | 68.9 | | <LOQ | | <LOQ | |
| 3030.41 (4) | 6.5 | | 20.2 | | 67.6 | | 5.0 | | <LOQ | |

* LOQ is 4.9%.
3010.15: calculated pI: 9.1; Isoform 5: pI 8.87 to 8.89; Isoform 4: pI 8.96; Isoform 3: pI 9.04 to 9.05; Isoform 2: pI 9.15 to 9.16; Isoform 1: pI 9.24 to 9.25.
3010.25: calculated pI: 8.8; Isoform 5: pI 8.30 to 8.31; Isoform 4: pI 8.46 to 8.47; Isoform 3: pI 8.61 to 8.62; Isoform 2: pI 8.75; Isoform 1: pI 8.90.
3030.41: calculated pI: 9.1; Isoform 5: pI 8.80 to 8.82; Isoform 4: pI 8.89; Isoform 3: pI 8.99 to 9.00; Isoform 2: pI 9.10 to 9.11; Isoform 1: pI 9.20.

TABLE 36

Transfection Pool iCIEF Summarized Data

| Transfection Pool | Acidic Variant Peaks | | Main Peak | | Basic Variant Peaks | |
|---|---|---|---|---|---|---|
| 3010.15 (1) | 24.1 | 23-25 | 67.7 | 67-71 | 8.2 | 7-8 |
| 3010.15 (2) | 22.6 | | 69.2 | | 8.2 | |
| 3010.15 (3) | 25.2 | | 67.4 | | 7.5 | |
| 3010.15 (4) | 22.6 | | 70.6 | | 6.8 | |
| 3010.25 (1) | 19.8 | 20-21 | 72.8 | 72-73 | 7.4 | 7-8 |
| 3010.25 (2) | 20.0 | | 72.3 | | 7.7 | |
| 3010.25 (3) | 19.6 | | 72.9 | | 7.4 | |
| 3010.25 (4) | 20.6 | | 71.9 | | 7.5 | |
| 3030.41 (1) | 24.8 | 25-27 | 69.5 | 68-70 | 5.7 | 5-6 |
| 3030.41 (2) | 27.0 | | 67.8 | | 5.2 | |
| 3030.41 (3) | 26.3 | | 68.9 | | 4.8 | |
| 3030.41 (4) | 26.7 | | 67.6 | | 5.7 | |

Transfection pools for the 3 antibodies were tested for binding by ELISA and flow cytometry on MARCO transfectant cells. The binding of the pool material was compared to reference antibodies produced by transient transfection in CHO-S cells. Antibodies produced by the stable transfection method demonstrated comparable binding to the reference antibodies made via transient transfection (FIG. 53).

Example 15: Soluble MARCO Assay

Materials and Methods

A streptavidin MSD Plate (MSD, Catalog #L15SA-1) was coated with biotinylated anti-MARCO antibody (PI-3041-AB, Pionyr) at 2 μg/mL. The plate was incubated at room temperature for 60 min and then washed.

Protein standards (RG-3000A, Atum) and serum samples (BioVT) were diluted in buffer (PBS/0.5% BSA/0.05% Tween+Ca2+/Mg2+) and added to the coated plate in D43 diluent (MSD, Catalog #R50AG-2) with 2 mM Ca2+. The plate was incubated for 90 min at room temperature and washed. 1 μg/mL of the detection antibody, anti-MARCO (PI-3071-AB, Pionyr) was added, and the plate incubated for 60 min at room temperature. The plate was washed and 1× Read Buffer [MSD, Catalog #R92TC-1] was added to the MSD plate. The plate was read on an MSD Sector Imager.

Results

The sMARCO assay range was 0.1 ng/mL to 100 ng/mL. The LLOQ was 0.1 ng/mL and the ULOQ was 100 ng/mL. The sMARCO calibration curve for RG-3000A is shown in FIG. 55A and Table 37.

TABLE 37

| Nominal Conc. ng/ml | Detected Mean Conc. (ng/ml) | % Recovery Mean |
|---|---|---|
| 100 | 102.2 | 102.2 |
| 25.0 | 23.5 | 94.0 |
| 6.25 | 7.09 | 113.4 |
| 1.56 | 1.76 | 113.0 |
| 0.39 | 0.32 | 83.1 |
| 0.10 | 0.10 | 100.0 |

The sMARCO levels in normal human serum samples ranged from 9 ng/mL to 13 ng/mL. The sMARCO levels in cancer serum samples ranged from 6 ng/mL to 22 ng/mL. The sMARCO levels are shown in FIG. 55B.

An immunoassay to detect sMARCO from serum samples (human, cynomolgus monkey and mouse) was successfully developed. The sMARCO assay was qualified for its specificity, sensitivity, dilution linearity and selectivity and accurately determined sMARCO levels in patient serum samples obtained from commercial sources. sMARCO levels were observed to be higher in patients diagnosed with breast, colorectal, mesothelioma, cervical, small lymphocytic lymphoma, and non-Hodgkin lymphoma (FIG. 55B).

Example 16: In Vivo B-Cell Deficient Mouse Study

Methods

Balb/c mice with J B-cell mutation were obtained from Taconic. The mouse experiment was set up as described in Example 4. Briefly, IP dosing was initiated when CT26 tumors reached a median of ~100 $mm^3$ Mice were dosed with 10 mg/kg PI-3008 or 5 mg/kg PD-1 antibody at Q5dx4. WT mice were used as a control.

Results

The absence of B-cells dampened the combination efficacy of PI-3008 with anti-PD1 in CT26 tumors (FIG. 56).

PI-3008 antibody in combination with PD-1 antibody resulted in greater tumor reduction in WT mice (top row) as compared to the combination treatment in the B-cell knock out mice (middle row). The bottom graph provides tumor volumes in individual mice in each condition.

Example 17: PI-3010.15 Induces NF-kB Signaling Pathway

Materials and Methods

THP1-Blue™ NF-κB cells were obtained from Invivogen and cultured in RPMI 1640 medium (Gibco) supplemented with 10% Fetal Bovine Serum (Gibco), 25 mM HEPES (Gibco), 1× GlutaMax (Gibco), 100 ug/ml Normacin (Gibco), 10 ug/mL Blasticidin (ThermoFisher). Approximately 50,000 cells were transduced with lentivirus containing the full-length MARCO construct (CL #3010) at MOI 10 in 500 ul media containing 8 ug/mL polybrene per well of 24-well plate. After overnight incubation at 37° C. with 5% CO2, cells were washed in PBS and plated in 6-well plate in complete growth media. After 2-3 days, media was replaced with growth media containing 0.3 ug/ml puromycin (Invitrogen) for stable cell selection, and pooled cells were cultured and expanded For the reporter assay, 300,000 cells were plated per well of 96-well U-bottom plate and co-incubated with a dose titration of PI-3010.15 or isotype antibody control and 10e6/ml of HKLM (Invivogen) or 10 ng/ml of FALSTup (Invivogen) agonist and incubated for 4 hours or overnight at 37° C. with 5% $CO_2$. After incubation, 20 ul of supernatant was transferred to a new 96-well plate and incubated with 180 ul/well of QuantiBlue Solution (Invivogen) for 30-60 minutes at 37° C. with 5% $CO_2$. Alkaline Phosphatase activity was calculated by measuring the optical density (OD) at 650 nm using the Tecan microplate reader.

The THP-1 MARCO overexpressing cells were also used to validate the biomarker signature of pro-inflammatory genes activated after PI-3010.15 treatment. $1\times10^{\wedge}6$ cells in 1 ml of media were plated per well in a 24 well plate. PI-3010.15 and PI-0003 (corresponding hIgG1 isotype) were added to the cells at 1 μg/ml, 5 μg/ml, and 10 μg/ml for 4 hours and 24 hours. Cells were lysed with RLT buffer and RNA extracted for qPCR testing using the human primers to measure TNFα, IL-6, IL-1α, IL-10, CCL24, CXCL8, IL-1α, IL-18, and CCL20 expression.

Results

PI-3010.15 induced the NF-kB signaling pathway after 4 hrs with the addition of HKLM, FSL-1, and FLA-ST UP after 24 hrs. PI-3010.15 also induced the NF-KB pathway in non-treated cells after 24 hrs (FIG. 57).

The THP-1 OVX cells were also used as a surrogate for primary hMDMs cells to test pro-inflammatory cytokine activation by MARCO antibody PI-3010.15. Cells were incubated with PI-3010.15 or isotype antibody at 1 μg/ml, 5 μg/ml, or 10 μg/ml (TNFα only) for 4 hrs or 24 hrs. Cells were collected and assessed for TNFα, IL-6, IL-1β, CXCL8, CCL20, CCL24, and IL-18 gene expression via qRT-PCR. PI-3010.15 induced TNFα gene expression after 4 h and 24 h at all antibody concentrations tested (FIG. 71). PI-3010.15 also induced expression of pro-inflammatory cytokines IL-6, IL1β, and CXCL8 at 4 hrs and 24 hrs (FIG. 71). The 5 μg/ml dosage of PI-3010.15 also induced pro-inflammatory cytokines such as CCL20, CCL24, and IL18 at 24 hrs (FIG. 71).

Example 18: Phospho Array Assay in hMDMs

Methods

A phospho array assay was performed using the Full Moon Biosystems Phospho Explorer Antibody Array on primary human monocyte derived macrophages (hMDMs) polarized with IL10 (2 donors).

Two frozen human peripheral blood CD14+ monocytes isolated from peripheral blood mononuclear cells using negative immunomagnetic selection (StemCell Technologies) were thawed and cultured in RPMI 1640 medium supplemented with 10% (v/v) heat-inactivated FBS (HyClone), 1 mM sodium pyruvate, non-essential amino-acids, 2 mM L-glutamine, 55 uM 2-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 500,000 cells per well in 24 well plates. At day 3 of differentiation, media was replenished with the addition of fresh M-CSF. Differentiated human macrophages were polarized on day 6 by adding 25 ng/ml of recombinant human IL-10 (M2 condition) for 24 hours at 37° C. On day 7, the media was aspirated and cells washed gently. 500 μl of incubation medium (1×RPMI with 0.5% BSA) was added to the wells with 5 μg/ml of PI-3010.15 or hIgG1 isotype control (PI-0003). Treatment was terminated after 5 minutes and 15 minutes by washing with ice cold PBS and lysing cells with 300 μl of mPer and 1:100 HALT proteases and phosphatase inhibitors. Approximately 300 μg of protein lysate was sent to Full Moon Biosystems to perform the Phospho Explorer Antibody Array. Full Moon Biosystems used their standard protocol to label, couple, and detect the Average Signal Intensity of Replicate Spots, for each pair of site-specific antibody and phospho site-specific antibody, and determine the Signal Ratio of the paired antibodies. Fold changes between control and control samples were calculated using the following formula: Treatment Sample/Control Sample (hIgG1 treated or untreated).

Phospho hits were considered significant when the fold change was less than 0.6 or greater than 1.8 for both PI-3010.15/isotype and PI-3010.15/untreated ratio analysis. In addition, few hits were included if the isotype by itself had a substantial effect over the untreated due to Fc mediated signaling changes in the hMDMs (less than 0.75 fold decrease or greater than 1.5 fold increase compared to untreated). For those hits, a ratio of PI-3010.15/untreated was considered significant when below 0.75 fold decrease and above 1.5 fold increase if the ratio of PI-3010.15/isotype fell in the significant range (<0.6 and above 1.8 fold).

Results

Table 38 shows significant phosphorylation in PI-3010.15 vs. Isotype treated cells and PI-3010.15 vs. untreated (UT) cells at 5 minutes.

TABLE 38

| Gene | 3015 vs. Isotype (5 minutes) | 3015 vs. UT (5 minutes) |
|---|---|---|
| UP (>1.8 FC) | | |
| Cyclin B1 (Phospho-Ser147) | 5.084445769 | 2.561147785 |
| IRS-1 (Phospho-Ser794) | 4.447939568 | 2.871815775 |
| PDGFR alpha (Phospho-Tyr849) | 3.247023728 | 2.0112109 |
| Elk1 (Phospho-Ser389) | 2.650795969 | 1.93843226 |
| HSP27 (Phospho-Ser78) | 2.618765237 | 2.781365032 |
| CDK1/CDC2 (Phospho-Tyr15) | 2.495918288 | 2.915628441 |
| CDK5 (Phospho-Tyr15) | 2.495088042 | 3.772464066 |
| IL-2RA/CD25 (Phospho-Ser268) | 2.385317047 | 2.26149298 |
| Raf1 (Phospho-Ser259) | 2.345569464 | 2.986531327 |
| GluR1 (Phospho-Ser863) | 2.218294441 | 2.416141632 |

TABLE 38-continued

| Gene | 3015 vs. Isotype (5 minutes) | 3015 vs. UT (5 minutes) |
|---|---|---|
| LYN (Phospho-Tyr507)- Src pathway | 2.16499766 | 1.97114872 |
| Ezrin (Phospho-Thr566) | 2.148744088 | 2.992168753 |
| Lamin A/C (Phospho-Ser392) | 2.141294348 | 2.948772441 |
| BAD (Phospho-Ser91/128) | 2.011033931 | 2.461349555 |
| Tau (Phospho-Ser396) | 1.955441551 | 1.918036853 |
| MAP3K8/COT (Phospho-Thr290) | 1.943373784 | 1.967650786 |
| HDAC5 (Phospho-Ser259) | 1.922487843 | 2.088809947 |
| PAK3 (Phospho-Ser154) | 1.910328132 | 2.017578127 |
| mTOR (Phospho-Thr2446) | 1.8 | 2.42 |
| DOWN (<0.6 FC) | | |
| 14-3-3 beta/zeta (Phospho-Ser186/184) | 0.528463565 | 0.574004751 |
| Synapsin (Phospho-Ser9) | 0.468698508 | 0.444984245 |
| PKC delta (Phospho-Ser645) | 0.452312753 | 0.359573251 |
| 14-3-3 zeta (Phospho-Ser58) | 0.446714092 | 0.3453927 |
| Abl1 (Phospho-Thr754/735) | 0.399803417 | 0.334055031 |
| AKT1 (Phospho-Ser246) | 0.38984194 | 0.479793736 |
| Smad1 (Phospho-Ser187) | 0.380264132 | 0.442638779 |

Table 39 provides additional hits for the 5 minute samples that fell outside the first filtering bucket.

TABLE 39

| Gene | 3015 vs. Isotype | 3015 vs. Untreated | Iso vs. Untreated |
|---|---|---|---|
| ATF2 (Phospho-Ser62/44) | 2.13 | 1.59 | 0.75 |
| Claudin 3 (Phospho-Tyr219) | 0.22 | 0.68 | 3.04 |
| Connexin 43 (Phospho-Ser367) | 0.29 | 0.67 | 2.32 |
| LCK (Phospho-Tyr192) | 0.30 | 0.63 | 2.06 |
| Src (Phospho-Tyr529) | 0.32 | 0.78 | 2.45 |
| IKK-beta (Phospho-Tyr188) | 0.42 | 0.77 | 1.84 |
| PLD1 (Phospho-Ser561) | 0.42 | 0.78 | 1.86 |

Table 40 provides additional hits for the 5 minute samples where the isotype decreased the signal (below <0.6 fold over untreated) and PI-3010.15 rescued the effect with a biological significance. The fold increase over PI-3010.15/untreated could be >0.9.

TABLE 40

| Gene | 3015 vs. Isotype | 3015 vs. Untreated | Iso vs. Untreated |
|---|---|---|---|
| CaMK1-alpha (Phospho-Thr177) | 4.58 | 1.13 | 0.25 |
| p27Kip1 (Phospho-Thr187) | 3.35 | 0.95 | 0.28 |
| Cortactin (Phospho-Tyr421) | 3.00 | 1.29 | 0.43 |
| Keratin 18 (Phospho-Ser52) | 2.36 | 0.96 | 0.41 |
| FAK (Phospho-Tyr397) | 2.19 | 0.88 | 0.40 |
| IkB-beta (Phospho-Thr19) | 2.13 | 1.10 | 0.52 |
| PLC beta3 (Phospho-Ser1105) | 2.11 | 1.10 | 0.52 |

Table 41 shows the significant phosphorylation in PI-3010.15 vs. Isotype treated cells and PI-3010.15 vs. untreated (UT) cells at 15 minutes.

TABLE 41

| Gene | Gene | Gene |
|---|---|---|
| UP (>1.8 FC) | | |
| SYK (Phospho-Tyr525) | 3.763491432 | 2.629401334 |
| Dok-1 (Phospho-Tyr398) | 3.086467586 | 2.609649844 |
| IKK-alpha/beta (Phospho-Ser180/181) | 2.959202923 | 1.934873037 |
| HSP90B (Phospho-Ser226) | 2.870020923 | 3.546965968 |
| GluR1 (Phospho-Ser863) | 2.609270653 | 2.21995696 |
| Synaptotagmin (Phospho-Ser309) | 2.600941915 | 2.136658796 |
| SHP-2 (Phospho-Tyr580) | 2.597416517 | 2.242046774 |
| Filamin A (Phospho-Ser2152) | 2.335627516 | 1.996061335 |
| CaMK4 (Phospho-Thr196/200) | 2.279954736 | 1.893568987 |
| Synuclein alpha (Phospho-Tyr133) | 2.131004882 | 1.874499543 |
| HDAC5 (Phospho-Ser498) | 2.110924432 | 2.744099757 |
| P70S6K (Phospho-Ser424) | 2.076974184 | 1.870856295 |
| 4E-BP1 (Phospho-Ser65) | 2.06037659 | 2.827767866 |
| Calmodulin (Phospho-Thr79/Ser81) | 2.046380319 | 2.662693319 |
| MKK4/SEK1 (Phospho-Thr261) | 2.035499973 | 3.040392853 |
| IL-2RA/CD25 (Phospho-Ser268) | 1.973584034 | 2.080305927 |
| Synaptotagmin (Phospho-Thr202) | 1.930362488 | 1.991073071 |
| Rb (Phospho-Ser780) | 1.874035219 | 1.974833058 |
| Tyrosine Hydroxylase (Phospho-Ser40) | 1.852127179 | 1.934979677 |
| DOWN (>0.6 FC) | | |
| PLCG2 (Phospho-Tyr1217) | 0.591517857 | 0.563418522 |
| Kv1.3/KCNA3 (Phospho-Tyr135) | 0.57141834 | 0.586825891 |
| DARPP-32 (Phospho-Thr34) | 0.55741993 | 0.41127774 |
| Claudin 7 (Phospho-Tyr210) | 0.556173961 | 0.597139861 |
| Re1 (Phospho-Ser503) | 0.554992754 | 0.509612791 |
| Ezrin (Phospho-Tyr478) | 0.535586574 | 0.508394478 |
| LKB1 (Phospho-Ser428) | 0.531130409 | 0.520111023 |
| AurA (Phospho-Ser342) | 0.527800917 | 0.49832997 |
| p130Cas (Phospho-Tyr165) | 0.519493014 | 0.521059511 |
| Cortactin (Phospho-Tyr421) | 0.474466269 | 0.464638242 |
| Dok-1 (Phospho-Tyr362) | 0.456406193 | 0.482008648 |
| Keratin 18 (Phospho-Ser33) | 0.417597114 | 0.288197731 |
| CaMK2-beta/gamma/delta (Phospho-Thr287) | 0.410587574 | 0.537483464 |
| ETK (Phospho-Tyr40) | 0.409259434 | 0.437316317 |
| NFkB-p65 (Phospho-Thr435) | 0.400460795 | 0.344387917 |
| p27Kip1 (Phospho-Ser10) | 0.383076583 | 0.540101088 |
| NFkB-p100/p52 (Phospho-Ser869) | 0.37145326 | 0.532229421 |
| VEGFR2 (Phospho-Tyr1175) | 0.368651283 | 0.39699714 |
| PKC delta (Phospho-Ser645) | 0.3449432 | 0.538228023 |
| Estrogen Receptor-alpha (Phospho-Ser118) | 0.322713977 | 0.305382748 |
| HSL (Phospho-Ser554) | 0.31391716 | 0.411180773 |
| CD3Z (Phospho-Tyr142) | 0.309319341 | 0.377863121 |
| PAK3 (Phospho-Ser154) | 0.288315803 | 0.472978229 |
| Raf1 (Phospho-Ser296) | 0.241201384 | 0.310819568 |
| CDK1/CDC2 (Phospho-Thr14) | 0.232456135 | 0.311120574 |

Table 42 provides additional hits that fell outside the first filtering bucket for the 15 minute samples.

TABLE 42

| Gene | 3015 vs. Isotype | 3015 vs. Untreated | Iso vs. Untreated |
|---|---|---|---|
| PKC epsilon (Phospho-Ser729) | 0.34 | 0.75 | 2.19 |
| EGFR (Phospho-Tyr1110) | 0.41 | 0.71 | 1.71 |
| ASK1 (Phospho-Ser966) | 0.42 | 0.67 | 1.58 |
| c-Jun (Phospho-Ser63) | 0.43 | 0.76 | 1.78 |
| TOP2A/DNA topoisomerase II (Phospho-Ser1106) | 0.45 | 0.77 | 1.72 |
| STAT6 (Phospho-Thr645) | 0.48 | 0.74 | 1.53 |

Based on the phospho array screen, the pathways downregulated after 5 minutes were: Cell adhesion: Claudin 3, Connexin 43, Syapsin; 14-3-3 beta and zeta: adaptor that modulates multiple inflammatory pathways; PI3K master regulator pathway: AKT1; PKC delta (upstream of Src); TGFb signaling: Smad1; c-Abl signaling (modulates STAT signaling); and Src pathway: LCK, Src (cytoskeletal rearrangement, phagocytosis and survival).

The pathways upregulated after 5 minutes were: Cell cycle: Cyclin B1, CDK1/CDCl$_2$, CDK5, PAK3; IRS-1: insulin receptor activated by Insulin and IL-4, upstream of AKT; PDGFR: platelet derived factor receptor activates Ras/ERK to regulate angiogenesis, proliferation, migration genes; ELK1: transcription factor downstream of ERK/

PDGFR and Rac/JNK during inflammasome; Raf1: activated by LPS or mCSF and upstream of ERK1/2 activation for proliferation and activation; LYN: activated by LDL on CD36 and BCR, and phosphorylates AKT and SYK among others (metabolic reprogramming); IL-2RA/CD25: activates JAK/STAT, PI3K and Ras signaling; Lamin A/C, Ezrin, PAK3 (group 1 PAK downstream effectors of Ras-related Rho GTPase Cdc42 and Rac, and AKT), cytoskeletal rearrangement; MAPK38 (TPL2): (MAP3 K) activated downstream of TNFαR, IL1R, TLR, CD40, IL17R. TPL2 regulates the MEK1/2 and ERK1/2 pathways to regulate a cascade of inflammatory responses; BAD: Survival, downstream of AKT; and Chromatin modification: HDAC5.

The pathways upregulated after 15 minutes were: Regulation: Calmodulin, GLUR1, HSP90; Induction of Enzymatic activity: SYK, GLUR1, SHP-2, MKK4, CAMK4; Molecular Association: DOK1, GLUR1, SHP-2, HSP90; Cell motility and cytoskeletal Reorganization: Filamin A, IKKa/b, SHP-2; Activation of transcription: IKKa/b, CAMK4, MKK4; IL2 Receptor activation; mTOR and Translation modification: P70S6K, 4E-BP1; and Calcium signaling, endocytosis, exocytosis, Synapses, microtubules: Synaptogamin, CAMK4, Synuclein alpha.

The pathways downregulated after 15 minutes were: Regulation (survival): Raf1, VEGFR2, PKC delta, EGFR, STAT6; Molecular Association: DOK1, GLUR1, SHP-2, HSP90; Cell motility and cytoskeletal reorganization: Claudin 7, Cortactin, PKC delta, p130Cas, Ezrin, PAK3; NfkB pathway regulation: NFkb p100, Rel, Nfkb-p65; Cell Cycle progression: CDK1, p27Kip1, AurA, PKC, CAMK2; Calcium signaling: PKC, CaMK2; TCR signaling: CD3z is downstream of LCK signaling and upstream of ZAP70.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

```
                          Sequence listing

SEQ
ID
NO  Name          Sequence

1  HX-3031       QVQLKESGPGLVQPSQTLSLTCTVSGFSLTSYHVSWVRQPPGKGLEWMGAIWTGGSIAYNSLLKSRL
    Heavy Chain   SISRDTSKSQVFLKMNSLQTEDTATYYCARDLSDYYSSYTSFDYWGQGVMVTVST
    Variable

2  HX-3031       GFSLTSYHVS
    CDR-H1

3  HX-3031       AIWTGGSIA
    CDR-H2

4  HX-3031       DLSDYYSSYTSFDY
    CDR-H3

5  HX-3031       QVQLKESGPGLVQPSQTLSLTCTVSGFSLTSYHVSWVRQPPGKGLEWMGAIWTGGSIAYNSLLKSRL
    Heavy chain   SISRDTSKSQVFLKMNSLQTEDTATYYCARDLSDYYSSYTSFDYWGQGVMVTVSTAETTAPSVYPLA
                  PGTALKSNSMVTLGCLVKGYFPEPVTVTWNSGALSSGVHTFPAVLQSGLYTLTSSVTVPSSTWSSQA
                  VTCNVAHPASSTKVDKKIVPRECNPCGCTGSEVSSVFIFPPPKTKDVLTITLTPKVTCVVVDISQNDP
                  EVRFSWFIDDVEVHTAQTHAPEKQSNSTLRSVSELPIVHRDWLNGKTFKCKVNSGAFPAPIEKSISK
                  PEGTPRGPQVYTMAPPKEEMTQSQVSITCMVKGFYPPDIYTEWKMNGQPQENYKNTPPTMDTDGSYF
                  LYSKLNVKKETWQQGNTFTCSVLHEGLHNHHTEKSLSHSP*

6  HX-3031       DIQMTQSPASLSTSLGETVSIECLASEGISNDLAWYQQKSGKSPQLLIYAASRLQDGVPSRFSGSGS
    Light Chain   GTRYSLKISGMQPEDEADYFCQQSYKYPLTFGSGTKLEIK
    Variable

7  HX-3031       LASEGISNDLA
    CDR-L1

8  HX-3031       AASRLQD
    CDR-L2

9  HX-3031       QQSYKYPLT
    CDR-L3

10  HX-3031       DIQMTQSPASLSTSLGETVSIECLASEGISNDLAWYQQKSGKSPQLLIYAASRLQDGVPSRFSGSGS
    Light chain   GTRYSLKISGMQPEDEADYFCQQSYKYPLTFGSGTKLEIKRADAAPTVSIFPPSTEQLATGGASVVC
                  LMNNFYPRDISVKWKIDGTERRDGVLDSVTDQDSKDSTYSMSSTLSLTKADYESHNLYTCEVVHKTS
                  SSPVVKSFNRNEC*

11  PI-3010-AB    QVQLKESGPGLVQPSQTLSLTCTVSGFSLTSYHVSWVRQPPGKGLEWMGAIWTGGSIAYNSLLKSRL
    Heavy Chain   SISRDTSKSQVFLKMNSLQTEDTATYYCARDLSDYYSSYTSFDYWGQGVMVTVST
    Variable

12  PI-3010-AB    GFSLTSYHVS
    CDR-H1

13  PI-3010-AB    AIWTGGSIA
    CDR-H2
```

| SEQ ID NO | Name | Sequence |
|---|---|---|
| 14 | PI-3010-AB CDR-H3 | DLSDYYSSYTSFDY |
| 15 | PI-3010-AB Heavy chain | QVQLKESGPGLVQPSQTLSLTCTVSGFSLTSYHVSWVRQPPGKGLEWMGAIWTGGSIAYNSLLKSRL SISRDTSKSQVFLKMNSLQTEDTATYYCARDLSDYYSSYTSFDYWGQGVMVTVSTASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 16 | PI-3010-AB Light Chain Variable | DIQMTQSPASLSTSLGETVSIECLASEGISNDLAWYQQKSGKSPQLLIYAASRLQDGVPSRFSGSGS GTRYSLKISGMQPEDEADYFCQQSYKYPLTFGSGTKLEIK |
| 17 | PI-3010-AB CDR-L1 | LASEGISNDLA |
| 18 | PI-3010-AB CDR-L2 | AASRLQD |
| 19 | PI-3010-AB CDR-L3 | QQSYKYPLT |
| 20 | PI-3010-AB Light chain | DIQMTQSPASLSTSLGETVSIECLASEGISNDLAWYQQKSGKSPQLLIYAASRLQDGVPSRFSGSGS GTRYSLKISGMQPEDEADYFCQQSYKYPLTFGSGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 21 | PI-3011-AB Heavy Chain Variable | QVQLQESGPGLVKPSETLSLTCTVSGFSLTSYHVSWIRQPPGKGLEWIGAIWTGGSIAYNPSLKSRV TISVDTSKNQFSLKLSSVTAADTAVYYCARDLSDYYSSYTSFDYWGQGTLVTVSS |
| 22 | PI-3011-AB CDR-H1 | GFSLTSYHVS |
| 23 | PI-3011-AB CDR-H2 | AIWTGGSIA |
| 24 | PI-3011-AB CDR-H3 | DLSDYYSSYTSFDY |
| 25 | PI-3011-AB Heavy chain | QVQLQESGPGLVKPSETLSLTCTVSGFSLTSYHVSWIRQPPGKGLEWIGAIWTGGSIAYNPSLKSRV TISVDTSKNQFSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 26 | PI-3011-AB Light Chain Variable | DIQMTQSPSSLSASVGDRVTITCRASEGISNDLAWYQQKPGKAPKLLIYAASRLQSGVPSRFSGSGS GTDFTLTISSLQPEDFATYYCQQSYKYPLTFGQGTKLEIK |
| 27 | PI-3011-AB CDR-L1 | RASEGISNDLA |
| 28 | PI-3011-AB CDR-L2 | AASRLQD |
| 29 | PI-3011-AB CDR-L3 | QQSYKYPLT |
| 30 | PI-3011-AB Light chain | DIQMTQSPSSLSASVGDRVTITCRASEGISNDLAWYQQKPGKAPKLLIYAASRLQSGVPSRFSGSGS GTDFTLTISSLQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 31 | PI-3012-AB Heavy Chain Variable | QVQLQESGPGLVKPSETLSLTCTVSGFSLTSYHVSWRQPPGKGLEWIGAIWTGGSIAYNPSLKSRV TISRDTSKNQVSLKLSSVTAADTAVYYCARDLSDYYSSYTSFDYWGQGTLVTVSS |

Sequence listing

| SEQ ID NO | Name | Sequence |
|---|---|---|
| 32 | PI-3012-AB CDR-H1 | GFSLTSYHVS |
| 33 | PI-3012-AB CDR-H2 | AIWTGGSIA |
| 34 | PI-3012-AB CDR-H3 | DLSDYYSSYTSFDY |
| 35 | PI-3012-AB Heavy chain | QVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSSASTKGPSVFPLA<br>PSSKSTSGGTAALGCLVKDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK* |
| 36 | PI-3012-AB Light Chain Variable | DIQMTQSPSSLSASVGDRVTITCRASEGISNDLAWYQQKPGKAPKLLIYAASRLQSGVPSRFSGSGS<br>GTDYTLTISSLQPEDFATYYCQQSYKYPLTFGQGTKLEIK |
| 37 | PI-3012-AB CDR-L1 | RASEGISNDLA |
| 38 | PI-3012-AB CDR-L2 | AASRLQD |
| 39 | PI-3012-AB CDR-L3 | QQSYKYPLT |
| 40 | PI-3012-AB Light chain | DIQMTQSPSSLSASVGDRVTITCRASEGISNDLAWYQQKPGKAPKLLIYAASRLQSGVPSRFSGSGS<br>GTDYTLTISSLQPEDFATYYCQQSYKYPLTFGQGTKLEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC* |
| 41 | PI-3013-AB Heavy Chain Variable | QVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSS |
| 42 | PI-3013-AB CDR-H1 | GFSLTSYHVS |
| 43 | PI-3013-AB CDR-H2 | AIWTGGSIA |
| 44 | PI-3013-AB CDR-H3 | DLSDYYSSYTSFDY |
| 45 | PI-3013-AB Heavy chain | QVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSSASTKGPSVFPLA<br>PSSKSTSGGTAALGCLVKDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK* |
| 46 | PI-3013-AB Light Chain Variable | DIQMTQSPSSLSASVGDRVTITCRASEGISNDLAWYQQKPGKAPKLLIYAASRLQSGVPSRFSGSGS<br>GTDYTLTISSMQPEDFATYYCQQSYKYPLTFGQGTKLEIK |
| 47 | PI-3013-AB CDR-L1 | RASEGISNDLA |
| 48 | PI-3013-AB CDR-L2 | AASRLQD |
| 49 | PI-3013-AB CDR-L3 | QQSYKYPLT |
| 50 | PI-3013-AB Light chain | DIQMTQSPSSLSASVGDRVTITCRASEGISNDLAWYQQKPGKAPKLLIYAASRLQSGVPSRFSGSGS<br>GTDYTLTISSMQPEDFATYYCQQSYKYPLTFGQGTKLEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC* |

| SEQ ID NO | Name | Sequence |
|---|---|---|
| 51 | PI-3014-AB Heavy Chain Variable | QVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSS |
| 52 | PI-3014-AB CDR-H1 | GFSLTSYHVS |
| 53 | PI-3014-AB CDR-H2 | AIWTGGSIA |
| 54 | PI-3014-AB CDR-H3 | DLSDYYSSYTSFDY |
| 55 | PI-3014-AB Heavy chain | QVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 56 | PI-3014-AB Light Chain Variable | DIQMTQSPSSLSASVGDRVTITCRASEGISNDLAWYQQKPGKAPKLLIYAASRLQSGVPSRFSGSGS GTDYTLTISSLQPEDFATYYCQQSYKYPLTFGQGTKLEIK |
| 57 | PI-3014-AB CDR-L1 | RASEGISNDLA |
| 58 | PI-3014-AB CDR-L2 | AASRLQD |
| 59 | PI-3014-AB CDR-L3 | QQSYKYPLT |
| 60 | PI-3014-AB Light chain | DIQMTQSPSSLSASVGDRVTITCRASEGISNDLAWYQQKPGKAPKLLIYAASRLQSGVPSRFSGSGS GTDYTLTISSLQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 61 | PI-3015-AB Heavy Chain Variable | QVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSS |
| 62 | PI-3015-AB CDR-H1 | GFSLTSYHVS |
| 63 | PI-3015-AB CDR-H2 | AIWTGGSIA |
| 64 | PI-3015-AB CDR-H3 | DLSDYYSSYTSFDY |
| 65 | PI-3015-AB Heavy chain | QVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 66 | PI-3015-AB Light Chain Variable | DIQMTQSPSSLSASVGDRVTITCRASEGISNDLAWYQQKPGKAPKLLIYAASRLQSGVPSRFSGSGS GTDYTLTISSMQPEDFATYYCQQSYKYPLTFGQGTKLEIK |
| 67 | PI-3015-AB CDR-L1 | RASEGISNDLA |
| 68 | PI-3015-AB CDR-L2 | AASRLQD |

| SEQ ID NO | Name | Sequence |
|---|---|---|
| 69 | PI-3015-AB CDR-L3 | QQSYKYPLT |
| 70 | PI-3015-AB Light chain | DIQMTQSPSSLSASVGDRVTITCRASEGISNDLAWYQQKPGKAPKLLIYAASRLQSGVPSRFSGSGSGTDYTLTISSMQPEDFATYYCQQSYKYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| 71 | PI-3020-AB Heavy Chain Variable | QVQLKESGPGLVQPSQTLSLTCTVSGFSLTSYHVSWVRQPPGKGLEWMGAIWTGGSIAYNSLLKSRLSISRDTSKSQVFLKMNSLQTEDTATYYCARDLSDYYSSYTSFDYWGQGVMVTVST |
| 72 | PI-3020-AB CDR-H1 | GFSLTSYHVS |
| 73 | PI-3020-AB CDR-H2 | AIWTGGSIA |
| 74 | PI-3020-AB CDR-H3 | DLSDYYSSYTSFDY |
| 75 | PI-3020-AB Heavy chain | QVQLKESGPGLVQPSQTLSLTCTVSGFSLTSYHVSWVRQPPGKGLEWMGAIWTGGSIAYNSLLKSRLSISRDTSKSQVFLKMNSLQTEDTATYYCARDLSDYYSSYTSFDYWGQGVMVTVSTASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK* |
| 76 | PI-3020-AB Light Chain Variable | DIQMTQSPASLSTSLGETVSIECLASEGISNDLAWYQQKSGKSPQLLIYAASRLQDGVPSRFSGSGSGTRYSLKISGMQPEDEADYFCQQSYKYPLTFGSGTKLEIK |
| 77 | PI-3020-AB CDR-L1 | LASEGISNDLA |
| 78 | PI-3020-AB CDR-L2 | AASRLQD |
| 79 | PI-3020-AB CDR-L3 | QQSYKYPLT |
| 80 | PI-3020-AB Light chain | DIQMTQSPASLSTSLGETVSIECLASEGISNDLAWYQQKSGKSPQLLIYAASRLQDGVPSRFSGSGSGTRYSLKISGMQPEDEADYFCQQSYKYPLTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| 81 | PI-3022-AB Heavy Chain Variable | QVQLQESGPGLVKPSETLSLTCTVSGFSLTSYHVSWVRQPPGKGLEWIGAIWTGGSIAYNPSLKSRVTISRDTSKNQVSLKLSSVTAADTAVYYCARDLSDYYSSYTSFDYWGQGTLVTVSS |
| 82 | PI-3022-AB CDR-H1 | GFSLTSYHVS |
| 83 | PI-3022-AB CDR-H2 | AIWTGGSIA |
| 84 | PI-3022-AB CDR-H3 | DLSDYYSSYTSFDY |
| 85 | PI-3022-AB Heavy chain | QVQLQESGPGLVKPSETLSLTCTVSGFSLTSYHVSWVRQPPGKGLEWIGAIWTGGSIAYNPSLKSRVTISRDTSKNQVSLKLSSVTAADTAVYYCARDLSDYYSSYTSFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK* |
| 86 | PI-3022-AB Light Chain Variable | DIQMTQSPSSLSASVGDRVTITCRASEGISNDLAWYQQKPGKAPKLLIYAASRLQDGVPSRFSGSGSGTDYTLTISSLQPEDFATYYCQQSYKYPLTFGQGTKLEIK |

| SEQ ID NO | Name | Sequence |
|---|---|---|
| 87 | PI-3022-AB CDR-L1 | RASEGISNDLA |
| 88 | PI-3022-AB CDR-L2 | AASRLQD |
| 89 | PI-3022-AB CDR-L3 | QQSYKYPLT |
| 90 | PI-3022-AB Light chain | DIQMTQSPSSLSASVGDRVTITCRASEGISNDLAWYQQKPGKAPKLLIYAASRLQDGVPSRFSGSGS<br>GTDYTLTISSLQPEDFATYYCQQSYKYPLTFGQGTKLEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC* |
| 91 | PI-3023-AB Heavy Chain Variable | QVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSS |
| 92 | PI-3023-AB CDR-H1 | GFSLTSYHVS |
| 93 | PI-3023-AB CDR-H2 | AIWTGGSIA |
| 94 | PI-3023-AB CDR-H3 | DLSDYYSSYTSFDY |
| 95 | PI-3023-AB Heavy chain | QVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSSASTKGPSVFPLA<br>PSSKSTSGGTAALGCLVKDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK* |
| 96 | PI-3023-AB Light Chain Variable | DIQMTQSPSSLSTSVGDRVTITCRASEGISNDLAWYQQKPGKSPKLLIYAASRLQSGVPSRFSGSGS<br>GTDYTLTISSLQPEDFATYFCQQSYKYPLTFGQGTKLEIK |
| 97 | PI-3023-AB CDR-L1 | RASEGISNDLA |
| 98 | PI-3023-AB CDR-L2 | AASRLQD |
| 99 | PI-3023-AB CDR-L3 | QQSYKYPLT |
| 100 | PI-3023-AB Light chain | DIQMTQSPSSLSTSVGDRVTITCRASEGISNDLAWYQQKPGKSPKLLIYAASRLQSGVPSRFSGSGS<br>GTDYTLTISSLQPEDFATYFCQQSYKYPLTFGQGTKLEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC* |
| 101 | PI-3024-AB Heavy Chain Variable | QVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSS |
| 102 | PI-3024-AB CDR-H1 | GFSLTSYHVS |
| 103 | PI-3024-AB CDR-H2 | AIWTGGSIA |
| 104 | PI-3024-AB CDR-H3 | DLSDYYSSYTSFDY |
| 105 | PI-3024-AB Heavy chain | QVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSSASTKGPSVFPLA<br>PSSKSTSGGTAALGCLVKDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK* |

| SEQ ID NO | Name | Sequence |
|---|---|---|
| 106 | PI-3024-AB Light Chain Variable | DIQMTQSPSSLSTSVGDRVTITCRASEGISNDLAWYQQKPGKSPKLLIYAASRLQDGVPSRFSGSGSGTDYTLTISSLQPEDEATYFCQQSYKYPLTFGQGTKLEIK |
| 107 | PI-3024-AB CDR-L1 | RASEGISNDLA |
| 108 | PI-3024-AB CDR-L2 | AASRLQD |
| 109 | PI-3024-AB CDR-L3 | QQSYKYPLT |
| 110 | PI-3024-AB Light chain | DIQMTQSPSSLSTSVGDRVTITCRASEGISNDLAWYQQKPGKSPKLLIYAASRLQDGVPSRFSGSGSGTDYTLTISSLQPEDEATYFCQQSYKYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| 111 | PI-3025-AB Heavy Chain Variable | EVQLQESGPGLVKPSETLSLTCTVSGFSLTSYHVSWVRQPPGKGLEWIGAIWTGGSIAYNPSLKSRVTISRDTSKNQVSLKLSSVTAADTAVYYCARDLSDYYSSYTSFDYWGQGTLVTVSS |
| 112 | PI-3025-AB CDR-H1 | GFSLTSYHVS |
| 113 | PI-3025-AB CDR-H2 | AIWTGGSIA |
| 114 | PI-3025-AB CDR-H3 | DLSDYYSSYTSFDY |
| 115 | PI-3025-AB Heavy chain | EVQLQESGPGLVKPSETLSLTCTVSGFSLTSYHVSWVRQPPGKGLEWIGAIWTGGSIAYNPSLKSRVTISRDTSKNQVSLKLSSVTAADTAVYYCARDLSDYYSSYTSFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK* |
| 116 | PI-3025-AB Light Chain Variable | DIQMTQSPSSLSTSVGDRVTITCRASEGISNDLAWYQQKPGKSPKLLIYAASRLQDGVPSRFSGSGSGTDYTLTISSLQPEDEATYFCQQSYKYPLTFGQGTKLEIK |
| 117 | PI-3025-AB CDR-L1 | RASEGISNDLA |
| 118 | PI-3025-AB CDR-L2 | AASRLQD |
| 119 | PI-3025-AB CDR-L3 | QQSYKYPLT |
| 120 | PI-3025-AB Light chain | DIQMTQSPSSLSTSVGDRVTITCRASEGISNDLAWYQQKPGKSPKLLIYAASRLQDGVPSRFSGSGSGTDYTLTISSLQPEDEATYFCQQSYKYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| 121 | PI-3026-AB Heavy Chain Variable | VQLQESGPGLVKPSETLSLTCTVSGFSLTSYHVSWVRQPPGKGLEWIGAIWTGGSIAYNPSLKSRVTISRDTSKNQVSLKLSSVTAADTAVYYCARDLSDYYSSYTSFDYWGQGTLVTVSS |
| 122 | PI-3026-AB CDR-H1 | GFSLTSYHVS |
| 123 | PI-3026-AB CDR-H2 | AIWTGGSIA |
| 124 | PI-3026-AB CDR-H3 | DLSDYYSSYTSFDY |

| SEQ ID NO | Name | Sequence |
|---|---|---|
| 125 | PI-3026-AB Heavy chain | EVQLQESGPGLVKPSETLSLTCTVSGFSLTSYHVSWVRQPPGKGLEWIGAIWTGGSIAYNPSLKSRVTISRDTSKNQVSLKLSSVTAADTAVYYCARDLSDYYSSYTSFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK* |
| 126 | PI-3026-AB Light Chain Variable | DIQMTQSPSSLSTSVGDRVTITCRASEGISNDLAWYQQKPGKSPKLLIYAASRLQSGVPSRFSGSGSGTDYTLTISSLQPEDFATYFCQQSYKYPLTFGQGTKLEIK |
| 127 | PI-3026-AB CDR-L1 | RASEGISNDLA |
| 128 | PI-3026-AB CDR-L2 | AASRLQD |
| 129 | PI-3026-AB CDR-L3 | QQSYKYPLT |
| 130 | PI-3026-AB Light chain | DIQMTQSPSSLSTSVGDRVTITCRASEGISNDLAWYQQKPGKSPKLLIYAASRLQSGVPSRFSGSGSGTDYTLTISSLQPEDFATYFCQQSYKYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| 131 | PI-3027-AB Heavy Chain Variable | EVQLQESGPGLVKPSETLSLTCTVSGFSLTSYHVSWVRQPPGKGLEWIGAIWTGGSIAYNPSLKSRVTISRDTSKNQVSLKLSSVTAADTAVYYCARDLSDYYSSYTSFDYWGQGTLVTVSS |
| 132 | PI-3027-AB CDR-H1 | GFSLTSYHVS |
| 133 | PI-3027-AB CDR-H2 | AIWTGGSIA |
| 134 | PI-3027-AB CDR-H3 | DLSDYYSSYTSFDY |
| 135 | PI-3027-AB Heavy chain | EVQLQESGPGLVKPSETLSLTCTVSGFSLTSYHVSWVRQPPGKGLEWIGAIWTGGSIAYNPSLKSRVTISRDTSKNQVSLKLSSVTAADTAVYYCARDLSDYYSSYTSFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK* |
| 136 | PI-3027-AB Light Chain Variable | DIQMTQSPSSLSTSVGDRVTITCRASEGISNDLAWYQQKPGKSPKLLIYAASRLQDGVPSRFSGSGSGTDYTLTISSLQPEDEATYFCQQSYKYPLTFGQGTKLEIK |
| 137 | PI-3027-AB CDR-L1 | RASEGISNDLA |
| 138 | PI-3027-AB CDR-L2 | AASRLQD |
| 139 | PI-3027-AB CDR-L3 | QQSYKYPLT |
| 140 | PI-3027-AB Light chain | DIQMTQSPSSLSTSVGDRVTITCRASEGISNDLAWYQQKPGKSPKLLIYAASRLQDGVPSRFSGSGSGTDYTLTISSLQPEDEATYFCQQSYKYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| 141 | HX-3061 Heavy Chain Variable | EVQLVESGGGLVQPGSSLKLSCVASKFTFSNYGMNWIRQAPKKGLEWIALIYYNSNNKYYADSVKGRFTISRDNSKNTLYLEMNSLRSEDTAMYYCAKSLTGGSDYFDSWGQGVMVTVSS |
| 142 | HX-3061 CDR-H1 | KFTFSNYGMN |

| SEQ ID NO | Name | Sequence |
|---|---|---|
| 143 | HX-3061 CDR-H2 | LIYYNSNNKY |
| 144 | HX-3061 CDR-H3 | SLTGGSDYFDS |
| 145 | HX-3061 Heavy chain | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSSAETTAPSVYPLAPG TALKSNSMVTLGCLVKGYFPEPVTVTWNSGALSSGVHTFPAVLQSGLYTLTSSVTVPSSTWPSQTVT CNVAHPASSTKVDKKIVPRNCGGDCKPCICTGSEVSSVFIFPPKPKDVLTITLTPKVTCVVVDISQD DPEVHFSWFVDDVEVHTAQTRPPEEQFNSTFRSVSELPILHQDWLNGRTFRCKVTSAAFPSPIEKTI SKPEGRTQVPHVYTMSPTKEEMTQNEVSITCMVKGFYPPDIYVEWQMNGQPQENYKNTPPTMDTDGS YFLYSKLNVKKEKWQQGNTFTCSVLHEGLHNHHTEKSLSHSP* |
| 146 | HX-3061 Light Chain Variable | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIK |
| 147 | HX-3061 CDR-L1 | KASKSIGTFLA |
| 148 | HX-3061 CDR-L2 | SGSTLQS |
| 149 | HX-3061 CDR-L3 | QQHDEYPFT |
| 150 | HX-3061 Light chain | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIKRADAAPTVSIFPPSTEQLATGGASVVC LMNNFYPRDISVKWKIDGTERRDGVLDSVTDQDSKDSTYSMSSTLSLTKADYESHNLYTCEVVHKTS SSPVVKSFNRNEC* |
| 151 | PI-3016-AB Heavy Chain Variable | EVQLVESGGGLVQPGGSLRLSCAASKFTFSNYGMNWVRQAPGKGLEWVSLIYYNSNNKYYADSVKGR FTISRDNSKNTLYLQMNSLRAEDTAVYYCAKSLTGGSDYFDSWGQGTLVTVSS |
| 152 | PI-3016-AB CDR-H1 | KFTFSNYGMN |
| 153 | PI-3016-AB CDR-H2 | LIYYNSNNKY |
| 154 | PI-3016-AB CDR-H3 | SLTGGSDYFDS |
| 155 | PI-3016-AB Heavy chain | EVQLVESGGGLVQPGGSLRLSCAASKFTFSNYGMNWVRQAPGKGLEWVSLIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 156 | PI-3016-AB Light Chain Variable | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIK |
| 157 | PI-3016-AB CDR-L1 | RASKSIGTFLA |
| 158 | PI-3016-AB CDR-L2 | SGSTLQS |
| 159 | PI-3016-AB CDR-L3 | QQHDEYPFT |
| 160 | PI-3016-AB Light chain | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |

-continued

| SEQ ID NO | Name | Sequence |
|---|---|---|
| 161 | PI-3017-AB Heavy Chain Variable | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSS |
| 162 | PI-3017-AB CDR-H1 | KFTFSNYGMN |
| 163 | PI-3017-AB CDR-H2 | LIYYNSNNKY |
| 164 | PI-3017-AB CDR-H3 | SLTGGSDYFDS |
| 165 | PI-3017-AB Heavy chain | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 166 | PI-3017-AB Light Chain Variable | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIK |
| 167 | PI-3017-AB CDR-L1 | RASKSIGTFLA |
| 168 | PI-3017-AB CDR-L2 | SGSTLQS |
| 169 | PI-3017-AB CDR-L3 | QQHDEYPFT |
| 170 | PI-3017-AB Light chain | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 171 | PI-3018-AB Heavy Chain Variable | EVQLVESGGGLVQPGGSLRLSCAASGFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSS |
| 172 | PI-3018-AB CDR-H1 | KFTFSNYGMN |
| 173 | PI-3018-AB CDR-H2 | LIYYNSNNKY |
| 174 | PI-3018-AB CDR-H3 | SLTGGSDYFDS |
| 175 | PI-3018-AB Heavy chain | EVQLVESGGGLVQPGGSLRLSCAASGFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 176 | PI-3018-AB Light Chain Variable | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIK |
| 177 | PI-3018-AB CDR-L1 | RASKSIGTFLA |
| 178 | PI-3018-AB CDR-L2 | SGSTLQS |
| 179 | PI-3018-AB CDR-L3 | QQHDEYPFT |

| SEQ ID NO | Name | Sequence |
|---|---|---|
| 180 | PI-3018-AB Light chain | DIQMTQSPSSLSASVGDRVTITCRASKSIGTFLAWYQQKPGKAPKLLIYSGSTLQSGVPSRFSGSGS<br>GTDFTLTISSLQPEDFATYYCQQHDEYPFTFGQGTKLEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC* |
| 181 | PI-3019-AB Heavy Chain Variable | EVQLVESGGGLVQPGSSLKLSCVASKFTFSNYGMNWIRQAPKKGLEWIALIYYNSNNKYYADSVKGR<br>FTISRDNSKNTLYLEMNSLRSEDTAMYYCAKSLTGGSDYFDSWGQGVMVTVSS |
| 182 | PI-3019-AB CDR-H1 | KFTFSNYGMN |
| 183 | PI-3019-AB CDR-H2 | LIYYNSNNKY |
| 184 | PI-3019-AB CDR-H3 | SLTGGSDYFDS |
| 185 | PI-3019-AB Heavy chain | EVQLVESGGGLVQPGSSLKLSCVASKFTFSNYGMNWIRQAPKKGLEWIALIYYNSNNKYYADSVKGR<br>FTISRDNSKNTLYLEMNSLRSEDTAMYYCAKSLTGGSDYFDSWGQGVMVTVSSAKTTAPSVYPLAPV<br>CGDTTGSSVTLGCLVKGYFPEPVTLTWNSGSLSSGVHTFPAVLQSDLYTLSSSVTVTSSTWPSQSIT<br>CNVAHPASSTKVDKKIEPRGPTIKPCPPCKCPAPNLLGGPSVFIFPPKIKDVLMISLSPIVTCVVVD<br>VSEDDPDVQISWFVNNVEVHTAQTQTHREDYNSTLRVVSALPIQHQDWMSGKEFKCKVNNKDLPAPI<br>ERTISKPKGSVRAPQVYVLPPPEEEMTKKQVTLTCMVTDFMPEDIYVEWTNNGKTELNYKNTEPVLD<br>SDGSYFMYSKLRVEKKNWVERNSYSCSVVHEGLHNHHTTKSFSRTPGK* |
| 186 | PI-3019-AB Light Chain Variable | DVQMTQSPSYLAASPGESVSISCKASKSIGTFLAWYQEKPEKTNKLLIYSGSTLQSGTPSRFSGSGS<br>GTDFTLTIRNLEPEDFAVYYCQQHDEYPFTFGSGTKLEIK |
| 187 | PI-3019-AB CDR-L1 | KASKSIGTFLA |
| 188 | PI-3019-AB CDR-L2 | SGSTLQS |
| 189 | PI-3019-AB CDR-L3 | QQHDEYPFT |
| 190 | PI-3019-AB Light chain | DVQMTQSPSYLAASPGESVSISCKASKSIGTFLAWYQEKPEKTNKLLIYSGSTLQSGTPSRFSGSGS<br>GTDFTLTIRNLEPEDFAVYYCQQHDEYPFTFGSGTKLEIKRADAAPTVSIFPPSSEQLTSGGASVVC<br>FLNNFYPKDINVKWKIDGSERQNGVLNSWTDQDSKDSTYSMSSTLTLTKDEYERHNSYTCEATHKTS<br>TSPIVKSFNRNEC* |
| 191 | PI-3028-AB Heavy Chain Variable | EVQLVESGGGLVQPGSSLKLSCVASKFTFSNYGMNWIRQAPKKGLEWIALIYYNSNNKYYADSVKGR<br>FTISRDNSKNTLYLEMNSLRSEDTAMYYCAKSLTGGSDYFDSWGQGVMVTVSS |
| 192 | PI-3028-AB CDR-H1 | KFTFSNYGMN |
| 193 | PI-3028-AB CDR-H2 | LIYYNSNNKY |
| 194 | PI-3028-AB CDR-H3 | SLTGGSDYFDS |
| 195 | PI-3028-AB Heavy chain | EVQLVESGGGLVQPGSSLKLSCVASKFTFSNYGMNWIRQAPKKGLEWIALIYYNSNNKYYADSVKGR<br>FTISRDNSKNTLYLEMNSLRSEDTAMYYCAKSLTGGSDYFDSWGQGVMVTVSSAKTTAPSVYPLAPV<br>CGDTTGSSVTLGCLVKGYFPEPVTLTWNSGSLSSGVHTFPAVLQSDLYTLSSSVTVTSSTWPSQSIT<br>CNVAHPASSTKVDKKIEPRGPTIKPCPPCKCPAPNLLGGPSVFIFPPKIKDVLMISLSPIVTCVVVD<br>VSEDDPDVQISWFVNNVEVHTAQTQTHREDYNSTLRVVSALPIQHQDWMSGKEFKCKVNNKDLPAPI<br>ERTISKPKGSVRAPQVYVLPPPEEEMTKKQVTLTCMVTDFMPEDIYVEWTNNGKTELNYKNTEPVLD<br>SDGSYFMYSKLRVEKKNWVERNSYSCSVVHEGLHNHHTTKSFSRTPGK* |
| 196 | PI-3028-AB Light Chain Variable | DVQMTQSPSYLAASPGESVSISCKASKSIGTFLAWYQEKPEKTNKLLIYSGSTLQSGTPSRFSGSGS<br>GTDFTLTIRNLEPEDFAVYYCQQHDEYPFTFGSGTKLEIK |
| 197 | PI-3028-AB CDR-L1 | KASKSIGTFLA |

| SEQ ID NO | Name | Sequence |
|---|---|---|
| 198 | PI-3028-AB CDR-L2 | SGSTLQS |
| 199 | PI-3028-AB CDR-L3 | QQHDEYPFT |
| 200 | PI-3028-AB Light chain | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIKRADAAPTVSIFPPSSEQLTSGGASVVC FLNNFYPKDINVKWKIDGSERQNGVLNSWTDQDSKDSTYSMSSTLTLTKDEYERHNSYTCEATHKTS TSPIVKSFNRNEC* |
| 201 | PI-3029-AB Heavy Chain Variable | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSS |
| 202 | PI-3029-AB CDR-H1 | KFTFSNYGMN |
| 203 | PI-3029-AB CDR-H2 | LIYYNSNNKY |
| 204 | PI-3029-AB CDR-H3 | SLTGGSDYFDS |
| 205 | PI-3029-AB Heavy chain | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSSAKTTAPSVYPLAPV CGDTTGSSVTLGCLVKGYFPEPVTLTWNSGSLSSGVHTFPAVLQSDLYTLSSSVTVTSSTWPSQSIT CNVAHPASSTKVDKKIEPRGPTIKPCPPCKCPAPNLLGGPSVFIFPPKIKDVLMISLSPIVTCVVVD VSEDDPDVQISWFVNNVEVHTAQTQTHREDYNSTLRVVSALPIQHQDWMSGKEFKCKVNNKDLPAPI ERTISKPKGSVRAPQVYVLPPPEEEMTKKQVTLTCMVTDFMPEDIYVEWTNNGKTELNYKNTEPVLD SDGSYFMYSKLRVEKKNWVERNSYSCSVVHEGLHNHHTTKSFSRTPGK* |
| 206 | PI-3029-AB Light Chain Variable | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIK |
| 207 | PI-3029-AB CDR-L1 | KASKSIGTFLA |
| 208 | PI-3029-AB CDR-L2 | SGSTLQS |
| 209 | PI-3029-AB CDR-L3 | QQHDEYPFT |
| 210 | PI-3029-AB Light chain | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIKRADAAPTVSIFPPSSEQLTSGGASVVC FLNNFYPKDINVKWKIDGSERQNGVLNSWTDQDSKDSTYSMSSTLTLTKDEYERHNSYTCEATHKTS TSPIVKSFNRNEC* |
| 211 | PI-3032-AB Heavy Chain Variable | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSS |
| 212 | PI-3032-AB CDR-H1 | KFTFSNYGMN |
| 213 | PI-3032-AB CDR-H2 | LIYYNSNNKY |
| 214 | PI-3032-AB CDR-H3 | SLTGGSDYFDS |
| 215 | PI-3032-AB Heavy chain | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |

| SEQ ID NO | Name | Sequence |
|---|---|---|
| 216 | PI-3032-AB Light Chain Variable | DIQMTQSPSSLSASVGDRVTITCRASKSIGTFLAWYQQKPGKAPKLLIYSGSTLESGVPSRFSGSGS GTDFTLTISSLQPEDFATYYCQQHDEYPFTFGQGTKLEIK |
| 217 | PI-3032-AB CDR-L1 | KASKSIGTFLA |
| 218 | PI-3032-AB CDR-L2 | SGSTLQS |
| 219 | PI-3032-AB CDR-L3 | QQHDEYPFT |
| 220 | PI-3032-AB Light chain | DIQMTQSPSSLSASVGDRVTITCRASKSIGTFLAWYQQKPGKAPKLLIYSGSTLESGVPSRFSGSGS GTDFTLTISSLQPEDFATYYCQQHDEYPFTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 221 | PI-3033-AB Heavy Chain Variable | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSS |
| 222 | PI-3033-AB CDR-H1 | KFTFSNYGMN |
| 223 | PI-3033-AB CDR-H2 | LIYYNSNNKY |
| 224 | PI-3033-AB CDR-H3 | SLTGGSDYFDS |
| 225 | PI-3033-AB Heavy chain | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 226 | PI-3033-AB Light Chain Variable | DIQMTQSPSSLSASVGDRVTITCRASKSIGTFLAWYQQKPGKAPKLLIYDASSLESGVPSRFSGSGS GTDFTLTISSLQPEDFATYYCQQHDEYPFTFGQGTKLEIK |
| 227 | PI-3033-AB CDR-L1 | KASKSIGTFLA |
| 228 | PI-3033-AB CDR-L2 | SGSTLQS |
| 229 | PI-3033-AB CDR-L3 | QQHDEYPFT |
| 230 | PI-3033-AB Light chain | DIQMTQSPSSLSASVGDRVTITCRASKSIGTFLAWYQQKPGKAPKLLIYDASSLESGVPSRFSGSGS GTDFTLTISSLQPEDFATYYCQQHDEYPFTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 231 | HX-3011 Heavy Chain Variable | QIQLVQSGPELKKPGESVKISCKASGYTFTDYAVNWVKQAPGNGLKWMGWINTQTGKPTYADDFKQR FVFSLETSASTSFLQINNLNIEDTATYFCTRDSYYYSSSLDYWGQGVMVTVSS |
| 232 | HX-3011 CDR-H1 | GYTFTDYAVN |
| 233 | HX-3011 CDR-H2 | WINTQTGKPT |
| 234 | HX-3011 CDR-H3 | DSYYYSSSLDY |

| SEQ ID NO | Name | Sequence |
|---|---|---|
| 235 | HX-3011 Heavy chain | QIQLVQSGPELKKPGESVKISCKASGYTFTDYAVNWVKQAPGNGLKWMGWINTQTGKPTYADDFKQR FVFSLETSASTSFLQINNLNIEDTATYFCTRDSYYYSSSLDYWGQGVMVTVSSAETTAPSVYPLAPG TALKSNSMVTLGCLVKGYFPEPVTVTWNSGALSSGVHTFPAVLQSGLYTLTSSVTVPSSTWSSQAVT CNVAHPASSTKVDKKIVPRECNPCGCTGSEVSSVFIFPPKTKDVLTITLTPKVTCVVVDISQNDPEV RFSWFIDDVEVHTAQTHAPEKQSNSTLRSVSELPIVHRDWLNGKTFKCKVNSGAFPAPIEKSISKPE GTPRGPQVYTMAPPKEEMTQSQVSITCMVKGFYPPDIYTEWKMNGQPQENYKNTPPTMDTDGSYFLY SKLNVKKETWQQGNTFTCSVLHEGLHNHHTEKSLSHSP* |
| 236 | HX-3011 Light Chain Variable | DIQMTQSPASLSASLGETVSIECLASAGISNDLAWYQQKSGKSPQLLIYAASRLQDGVPSRFSGSGS GTRFSLKISDMQPEDEADYFCQQSYKYPWTFGGGTKLELK |
| 237 | HX-3011 CDR-L1 | LASAGISNDLA |
| 238 | HX-3011 CDR-L2 | AASRLQD |
| 239 | HX-3011 CDR-L3 | QQSYKYPWT |
| 240 | HX-3011 Light chain | DIQMTQSPASLSASLGETVSIECLASAGISNDLAWYQQKSGKSPQLLIYAASRLQDGVPSRFSGSGS GTRFSLKISDMQPEDEADYFCQQSYKYPWTFGGGTKLELKRADAAPTVSIFPPSTEQLATGGASVVC LMNNFYPRDISVKWKIDGTERRDGVLDSVTDQDSKDSTYSMSSTLSLTKADYESHNLYTCEVVHKTS SSPVVKSFNRNEC* |
| 241 | PI-3030-AB Heavy Chain Variable | QIQLVQSGPELKKPGESVKISCKASGYTFTDYAVNWVKQAPGNGLKWMGWINTQTGKPTYADDFKQR FVFSLETSASTSFLQINNLNIEDTATYFCTRDSYYYSSSLDYWGQGVMVTVSS |
| 242 | PI-3030-AB CDR-H1 | GYTFTDYAVN |
| 243 | PI-3030-AB CDR-H2 | WINTQTGKPT |
| 244 | PI-3030-AB CDR-H3 | DSYYYSSSLDY |
| 245 | PI-3030-AB Heavy chain | QIQLVQSGPELKKPGESVKISCKASGYTFTDYAVNWVKQAPGNGLKWMGWINTQTGKPTYADDFKQR FVFSLETSASTSFLQINNLNIEDTATYFCTRDSYYYSSSLDYWGQGVMVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 246 | PI-3030-AB Light Chain Variable | DIQMTQSPASLSASLGETVSIECLASAGISNDLAWYQQKSGKSPQLLIYAASRLQDGVPSRFSGSGS GTRFSLKISDMQPEDEADYFCQQSYKYPWTFGGGTKLELK |
| 247 | PI-3030-AB CDR-L1 | LASAGISNDLA |
| 248 | PI-3030-AB CDR-L2 | AASRLQD |
| 249 | PI-3030-AB CDR-L3 | QQSYKYPWT |
| 250 | PI-3030-AB Light chain | DIQMTQSPASLSASLGETVSIECLASAGISNDLAWYQQKSGKSPQLLIYAASRLQDGVPSRFSGSGS GTRFSLKISDMQPEDEADYFCQQSYKYPWTFGGGTKLELKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 251 | HX-3043 Heavy Chain Variable | QVNLLQSRAALVKPGASVKLSCKASGYTFTDYYLHWVKQSHAKSLEWIGYINPNNAYTSYNEKFKSK ATLTVDKSTNTAYMELSRLTSADSATYYCARDTTDYYNLHFAYWGQGTLVTVSS |
| 252 | HX-3043 CDR-H1 | GYTFTDYYLH |

| Sequence listing | | |
|---|---|---|
| SEQ ID NO | Name | Sequence |
| 253 | HX-3043 CDR-H2 | YINPNNAYTS |
| 254 | HX-3043 CDR-H3 | DTTDYYNLHFAY |
| 255 | HX-3043 Heavy chain | QVNLLQSRAALVKPGASVKLSCKASGYTFTDYYLHWVKQSHAKSLEWIGYINPNNAYTSYNEKFKSK ATLTVDKSTNTAYMELSRLTSADSATYYCARDTTDYYNLHFAYWGQGTLVTVSSAETTAPSVYPLAP GTALKSNSMVTLGCLVKGYFPEPVTVTWNSGALSSGVHTFPAVLQSGLYTLTSSVTVPSSTWSSQAV TCNVAHPASSTKVDKKIVPRECNPCGCTGSEVSSVFIFPPKTKDVLTITLTPKVTCVVVDISQNDPE VRFSWFIDDVEVHTAQTHAPEKQSNSTLRSVSELPIVHRDWLNGKTFKCKVNSGAFPAPIEKSISKP EGTPRGPQVYTMAPPKEEMTQSQVSITCMVKGFYPPDIYTEWKMNGQPQENYKNTPPTMDTDGSYFL YSKLNVKKETWQQGNTFTCSVLHEGLHNHHTEKSLSHSP* |
| 256 | HX-3043 Light Chain Variable | DIQMTQSPASLSASLGETVSIECLTSEGISNDLAWYQQKSGKSPQLLIYDASRLEDGVPSRFSGSGS GTRYSLKISGMQTEDEADYFCQQSYKYPLTFGSGTKLEIK |
| 257 | HX-3043 CDR-L1 | LTSEGISNDLA |
| 258 | HX-3043 CDR-L2 | DASRLED |
| 259 | HX-3043 CDR-L3 | QQSYKYPLT |
| 260 | HX-3043 Light chain | DIQMTQSPASLSASLGETVSIECLTSEGISNDLAWYQQKSGKSPQLLIYDASRLEDGVPSRFSGSGS GTRYSLKISGMQTEDEADYFCQQSYKYPLTFGSGTKLEIKRADAAPTVSIFPPSTEQLATGGASVVC LMNNFYPRDISVKWKIDGTERRDGVLDSVTDQDSKDSTYSMSSTLSLTKADYESHNLYTCEVVHKTS SSPVVKSFNRNEC* |
| 261 | PI-3031-AB Heavy Chain Variable | QVNLLQSRAALVKPGASVKLSCKASGYTFTDYYLHWVKQSHAKSLEWIGYINPNNAYTSYNEKFKSK ATLTVDKSTNTAYMELSRLTSADSATYYCARDTTDYYNLHFAYWGQGTLVTVSS |
| 262 | PI-3031-AB CDR-H1 | GYTFTDYYLH |
| 263 | PI-3031-AB CDR-H2 | YINPNNAYTS |
| 264 | PI-3031-AB CDR-H3 | DTTDYYNLHFAY |
| 265 | PI-3031-AB Heavy chain | QVNLLQSRAALVKPGASVKLSCKASGYTFTDYYLHWVKQSHAKSLEWIGYINPNNAYTSYNEKFKSK ATLTVDKSTNTAYMELSRLTSADSATYYCARDTTDYYNLHFAYWGQGTLVTVSSASTKGPSVFPLAP SSKSTSGGTAALGCLVKDYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK* |
| 266 | PI-3031-AB Light Chain Variable | DIQMTQSPASLSASLGETVSIECLTSEGISNDLAWYQQKSGKSPQLLIYDASRLEDGVPSRFSGSGS GTRYSLKISGMQTEDEADYFCQQSYKYPLTFGSGTKLEIK |
| 267 | PI-3031-AB CDR-L1 | LTSEGISNDLA |
| 268 | PI-3031-AB CDR-L2 | DASRLED |
| 269 | PI-3031-AB CDR-L3 | QQSYKYPLT |
| 270 | PI-3031-AB Light chain | DIQMTQSPASLSASLGETVSIECLTSEGISNDLAWYQQKSGKSPQLLIYDASRLEDGVPSRFSGSGS GTRYSLKISGMQTEDEADYFCQQSYKYPLTFGSGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |

| Sequence listing | | |
|---|---|---|
| SEQ ID NO | Name | Sequence |
| 271 | PI-3006-AB Heavy Chain Variable | EVQLVESGGGLVKPGASLKLSCVASGFTFSDYWMNWVRQTPGKTMEWIGDIKDDGSYTNYTPSLKNR FTISRDNAKSTLYLQMNNVRSEDTGTYYCTSGGVFDYWGQGVMVTVSS |
| 272 | PI-3006-AB CDR-H1 | GFTFSDYW |
| 273 | PI-3006-AB CDR-H2 | IKDDGSYT |
| 274 | PI-3006-AB CDR-H3 | TSGGVFDY |
| 275 | PI-3006-AB Heavy chain | EVQLVESGGGLVKPGASLKLSCVASGFTFSDYWMNWVRQTPGKTMEWIGDIKDDGSYTNYTPSLKNR FTISRDNAKSTLYLQMNNVRSEDTGTYYCTSGGVFDYWGQGVMVTVSSAKTTAPSVYPLAPVCGDTT GSSVTLGCLVKGYFPEPVTLTWNSGSLSSGVHTFPAVLQSDLYTLSSSVTVTSSTWPSQSITCNVAH PASSTKVDKKIEPRGPTIKPCPPCKCPAPNLLGGPSVFIFPPKIKDVLMISLSPIVTCVVVDVSEDD PDVQISWFVNNVEVHTAQTQTHREDYNSTLRVVSALPIQHQDWMSGKEFKCKVNNKDLPAPIERTIS KPKGSVRAPQVYVLPPPEEEMTKKQVTLTCMVTDFMPEDIYVEWTNNGKTELNYKNTEPVLDSDGSY FMYSKLRVEKKNWVERNSYSCSVVHEGLHNHHTTKSFSRTPGK* |
| 276 | PI-3006-AB Light Chain Variable | EIVLTQSPTTMAASPGEMVTITCRASSSVNYMHWFQQKSGTSPKPWIYDTSKLASGVPDRFSGSGSG TSYSLTISSMEAEDAASYYCLQRSTFPPTFGAGTKLELK |
| 277 | PI-3006-AB CDR-L1 | SSVNY |
| 278 | PI-3006-AB CDR-L2 | DTS |
| 279 | PI-3006-AB CDR-L3 | LQRSTFPPT |
| 280 | PI-3006-AB Light chain | EIVLTQSPTTMAASPGEMVTITCRASSSVNYMHWFQQKSGTSPKPWIYDTSKLASGVPDRFSGSGSG TSYSLTISSMEAEDAASYYCLQRSTFPPTFGAGTKLELKRADAAPTVSIFPPSSEQLTSGGASVVCF LNNFYPKDINVKWKIDGSERQNGVLNSWTDQDSKDSTYSMSSTLTLTKDEYERHNSYTCEATHKTST SPIVKSFNRNEC* |
| 281 | PI-3007-AB Heavy Chain Variable | QVRLVQSGTALVRPGASVRMSCTASGYSFTDYWVSWVKQSHGQSLEWIGEIYPNSGTTNFNEKFEGK ATLTVDKSTSTAYMELSRLTSEDSAIYYCTGEGTFDYWGQGVMVTVSS |
| 282 | PI-3007-AB CDR-H1 | GYSFTDYW |
| 283 | PI-3007-AB CDR-H2 | IYPNSGTT |
| 284 | PI-3007-AB CDR-H3 | TGEGTFDY |
| 285 | PI-3007-AB Heavy chain | QVRLVQSGTALVRPGASVRMSCTASGYSFTDYWVSWVKQSHGQSLEWIGEIYPNSGTTNFNEKFEGK ATLTVDKSTSTAYMELSRLTSEDSAIYYCTGEGTFDYWGQGVMVTVSSAKTTAPSVYPLAPVCGDTT GSSVTLGCLVKGYFPEPVTLTWNSGSLSSGVHTFPAVLQSDLYTLSSSVTVTSSTWPSQSITCNVAH PASSTKVDKKIEPRGPTIKPCPPCKCPAPNLLGGPSVFIFPPKIKDVLMISLSPIVTCVVVDVSEDD PDVQISWFVNNVEVHTAQTQTHREDYNSTLRVVSALPIQHQDWMSGKEFKCKVNNKDLPAPIERTIS KPKGSVRAPQVYVLPPPEEEMTKKQVTLTCMVTDFMPEDIYVEWTNNGKTELNYKNTEPVLDSDGSY FMYSKLRVEKKNWVERNSYSCSVVHEGLHNHHTTKSFSRTPGK* |
| 286 | PI-3007-AB Light Chain Variable | EIVLTQSPTTMAASPGEKVTITCRPSSSLSNMHWFQQKSGTSPKPWIYDTSKLASGVPDRFSGSGSG TSYSLTISSMEAEDAATYYCLQRSSYPPTFGAGTKLELK |
| 287 | PI-3007-AB CDR-L1 | SSLSN |
| 288 | PI-3007-AB CDR-L2 | DTS |
| 289 | PI-3007-AB CDR-L3 | LQRSSYPPT |

| SEQ ID NO | Name | Sequence |
|---|---|---|
| 290 | PI-3007-AB Light chain | EIVLTQSPTTMAASPGEKVTITCRPSSSLSNMHWFQQKSGTSPKPWIYDTSKLASGVPDRFSGSGSGTSYSLTISSMEAEDAATYYCLQRSSYPPTFGAGTKLELKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC* |
| 291 | PI-3008-AB Heavy Chain Variable | EVQLVESGGGLVKPGASLKLSCVASGFTFSDDWMNWVRQTPGKAMEWIGDIKYDGSYTNYVPSLKNRLTISRDNAKNTLYLQMTNVRSEDTATYYCTSGGVFDYWGQGVMVTVSS |
| 292 | PI-3008-AB CDR-H1 | GFTFSDDW |
| 293 | PI-3008-AB CDR-H2 | IKYDGSYT |
| 294 | PI-3008-AB CDR-H3 | TSGGVFDY |
| 295 | PI-3008-AB Heavy chain | EVQLVESGGGLVKPGASLKLSCVASGFTFSDDWMNWVRQTPGKAMEWIGDIKYDGSYTNYVPSLKNRLTISRDNAKNTLYLQMTNVRSEDTATYYCTSGGVFDYWGQGVMVTVSSAKTTAPSVYPLAPVCGDTTGSSVTLGCLVKGYPPEPVTLTWNSGSLSSGVHTFPAVLQSDLYTLSSSVTVTSSTWPSQSITCNVAHPASSTKVDKKIEPRGPTIKPCPPCKCPAPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK* |
| 296 | PI-3008-AB Light Chain Variable | EIVLSQSPTTMAASPGEKVTITCRASSSVSYMHWFQQKSGTSPKPWIYDTSKLASGVPDRFSGSGSGTSYSLTISSMEAEDAATYYCLQRSGYPPTFGAGTKLEVK |
| 297 | PI-3008-AB CDR-L1 | SSVSY |
| 298 | PI-3008-AB CDR-L2 | DTS |
| 299 | PI-3008-AB CDR-L3 | LQRSGYPPT |
| 300 | PI-3008-AB Light chain | EIVLSQSPTTMAASPGEKVTITCRASSSVSYMHWFQQKSGTSPKPWIYDTSKLASGVPDRFSGSGSGTSYSLTISSMEAEDAATYYCLQRSGYPPTFGAGTKLEVKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC* |
| 301 | PI-3009-AB Heavy Chain Variable | EVQLVESGGGLVQPGRSLKFSCSASGFTFSAYSMAWVRQAPKTGLEWVATIIYDGSSTYYRDSVKGRFTISRDNAKNTLYLQMDSLRSEDTATYYCARLGYSGHYFDYWGQGVMVTVSS |
| 302 | PI-3009-AB CDR-H1 | GFTFSAYS |
| 303 | PI-3009-AB CDR-H2 | IIYDGSST |
| 304 | PI-3009-AB CDR-H3 | ARLGYSGHYFDY |
| 305 | PI-3009-AB Heavy chain | EVQLVESGGGLVQPGRSLKFSCSASGFTFSAYSMAWVRQAPKTGLEWVATIIYDGSSTYYRDSVKGRFTISRDNAKNTLYLQMDSLRSEDTATYYCARLGYSGHYFDYWGQGVMVTVSSAKTTAPSVYPLAPVCGDTTGSSVTLGCLVKGYPPEPVTLTWNSGSLSSGVHTFPAVLQSDLYTLSSSVTVTSSTWPSQSITCNVAHPASSTKVDKKIEPRGPTIKPCPPCKCPAPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK* |
| 306 | PI-3009-AB Light Chain Variable | DTVLTQSPALAVSLGQRVTISCQASESVSSSLHSYLHWYQQKPGQQPKLLIYRASNLESGVPARFSGSGSGTDFTLNIDPVEADDIATYFCQQSWNDPRTFGGGTKLELK |
| 307 | PI-3009-AB CDR-L1 | ESVSSSLHSY |

| SEQ ID NO | Name | Sequence |
|---|---|---|
| 308 | PI-3009-AB CDR-L2 | RAS |
| 309 | PI-3009-AB CDR-L3 | QQSWNDPRT |
| 310 | PI-3009-AB Light chain | DTVLTQSPALAVSLGQRVTISCQASESVSSSLHSYLHWYQQKPGQQPKLLIYRASNLESGVPARFSGSGSGTDFTLNIDPVEADDIATYFCQQSWNDPRTFGGGTKLELKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC* |
| 311 | PI-3036-AB Heavy Chain Variable | VQLVQSGAEVKKPGASVKVSCKASGYTFTDYAVNWVRQAPGQGLEWMGWINTQTGKPTYAQKFQGRVTMTRDTSTSTVYMELSSLRSEDTAVYYCARDSYYYSSSLDYWGQGTLVTVSS |
| 312 | PI-3036-AB CDR-H1 | GYTFTDYAVN |
| 313 | PI-3036-AB CDR-H2 | WINTQTGKPT |
| 314 | PI-3036-AB CDR-H3 | DSYYYSSSLDY |
| 315 | PI-3036-AB Heavy chain | QVQLVQSGAEVKKPGASVKVSCKASGYTFTDYAVNWVRQAPGQGLEWMGWINTQTGKPTYAQKFQGRVTMTRDTSTSTVYMELSSLRSEDTAVYYCARDSYYYSSSLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK* |
| 316 | PI-3036-AB Light Chain Variable | DIQMTQSPSSLSASVGDRVTITCRASAGISNDLAWYQQKPGKAPKLLIYAASRLQDGVPSRFSGSGSGTDFTLTISSLQPEDFATYYCQQSYKYPWTFGQGTKLEIK |
| 317 | PI-3036-AB CDR-L1 | RASAGISNDLA |
| 318 | PI-3036-AB CDR-L2 | AASRLQD |
| 319 | PI-3036-AB CDR-L3 | QQSYKYPWT |
| 320 | PI-3036-AB Light chain | DIQMTQSPSSLSASVGDRVTITCRASAGISNDLAWYQQKPGKAPKLLIYAASRLQDGVPSRFSGSGSGTDFTLTISSLQPEDFATYYCQQSYKYPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| 321 | PI-3037-AB Heavy Chain Variable | QVQLVQSGAEVKKPGASVKVSCKASGYTFTDYAVNWVRQAPGQGLEWMGWINTQTGKPTYAQKFQGRVTMTLDTSTSTAYMELSSLRSEDTAVYYCTRDSYYYSSSLDYWGQGTLVTVSS |
| 322 | PI-3037-AB CDR-H1 | GYTFTDYAVN |
| 323 | PI-3037-AB CDR-H2 | WINTQTGKPT |
| 324 | PI-3037-AB CDR-H3 | DSYYYSSSLDY |
| 325 | PI-3037-AB Heavy chain | QVQLVQSGAEVKKPGASVKVSCKASGYTFTDYAVNWVRQAPGQGLEWMGWINTQTGKPTYAQKFQGRVTMTLDTSTSTAYMELSSLRSEDTAVYYCTRDSYYYSSSLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK* |

-continued

| SEQ ID NO | Name | Sequence |
|---|---|---|
| 326 | PI-3037-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 327 | PI-3037-AB CDR-L1 | RASAGISNDLA |
| 328 | PI-3037-AB CDR-L2 | AASRLQD |
| 329 | PI-3037-AB CDR-L3 | QQSYKYPWT |
| 330 | PI-3037-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 331 | PI-3038-AB Heavy Chain Variable | QVQLVQSGAEVKKPGASVKISCKASGYTFTDYAVNWVRQAPGQGLEWMGWINTQTGKPTYAQKFQGR FTFTLDTSTSTAYLEISSLRSEDTAVYYCTRDSYYYSSSLDYWGQGTLVTVSS |
| 332 | PI-3038-AB CDR-H1 | GYTFTDYAVN |
| 333 | PI-3038-AB CDR-H2 | WINTQTGKPT |
| 334 | PI-3038-AB CDR-H3 | DSYYYSSSLDY |
| 335 | PI-3038-AB Heavy chain | QVQLVQSGAEVKKPGASVKISCKASGYTFTDYAVNWVRQAPGQGLEWMGWINTQTGKPTYAQKFQGR FTFTLDTSTSTAYLEISSLRSEDTAVYYCTRDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 336 | PI-3038-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 337 | PI-3038-AB CDR-L1 | RASAGISNDLA |
| 338 | PI-3038-AB CDR-L2 | AASRLQD |
| 339 | PI-3038-AB CDR-L3 | QQSYKYPWT |
| 340 | PI-3038-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 341 | PI-3039-AB Heavy Chain Variable | QVQLVQSGAEVKKPGASVKVSCKASGYTFTDYAVNWVRQAPGQGLEWMGWINTQTGKPTYAQKFQGR VTMTLDTSTSTSYMELSSLRSEDTAVYYCTRDSYYYSSSLDYWGQGTLVTVSS |
| 342 | PI-3039-AB CDR-H1 | GYTFTDYAVN |
| 343 | PI-3039-AB CDR-H2 | WINTQTGKPT |
| 344 | PI-3039-AB CDR-H3 | DSYYYSSSLDY |

| SEQ ID NO | Name | Sequence |
|---|---|---|
| 345 | PI-3039-AB Heavy chain | QVQLVQSGAEVKKPGASVKVSCKASGYTFTDYAVNWVRQAPGQGLEWMGWINTQTGKPTYAQKFQGR VTMTLDTSTSTSYMELSSLRSEDTAVYYCTRDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 346 | PI-3039-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 347 | PI-3039-AB CDR-L1 | RASAGISNDLA |
| 348 | PI-3039-AB CDR-L2 | AASRLQD |
| 349 | PI-3039-AB CDR-L3 | QQSYKYPWT |
| 350 | PI-3039-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 351 | PI-3040-AB Heavy Chain Variable | QVQLVQSGAEVKKPGASVKISCKASGYTFTDYAVNWVRQAPGQGLEWMGWINTQTGKPTYAQKFQGR FTFTLDTSTSTSYLEISSLRSEDTAVYYCTRDSYYYSSSLDYWGQGTLVTVSS |
| 352 | PI-3040-AB CDR-H1 | GYTFTDYAVN |
| 353 | PI-3040-AB CDR-H2 | WINTQTGKPT |
| 354 | PI-3040-AB CDR-H3 | DSYYYSSSLDY |
| 355 | PI-3040-AB Heavy chain | QVQLVQSGAEVKKPGASVKISCKASGYTFTDYAVNWVRQAPGQGLEWMGWINTQTGKPTYAQKFQGR FTFTLDTSTSTSYLEISSLRSEDTAVYYCTRDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 356 | PI-3040-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 357 | PI-3040-AB CDR-L1 | RASAGISNDLA |
| 358 | PI-3040-AB CDR-L2 | AASRLQD |
| 359 | PI-3040-AB CDR-L3 | QQSYKYPWT |
| 360 | PI-3040-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 361 | PI-HX-3092 Heavy Chain Variable | QVQLKESGPGLVQPSQTLSLTCTVSGFSLTSYTLSWVRQPPGKGLEWIGAIWGGDNTDYNSALKSRL SITWDTSKSQVLLKMNSLQTEDTAIYFCTRELGGSFDYWGQGVMVTVSS |
| 362 | PI-HX-3092 CDR-H1 | GFSLTSYTLS |

| | | |
|---|---|---|
| SEQ ID NO | Name | Sequence |
| 363 | PI-HX-3092 CDR-H2 | AIWGGDNTD |
| 364 | PI-HX-3092 CDR-H3 | ELGGSFDY |
| 365 | PI-HX-3092 Heavy chain | QVQLKESGPGLVQPSQTLSLTCTVSGFSLTSYTLSWVRQPPGKGLEWIGAIWGGDNTDYNSALKSRL SITWDTSKSQVLLKMNSLQTEDTAIYFCTRELGGSFDYWGQGVMVTVSSAETTAPSVYPLAPGTALK SNSMVTLGCLVKGYFPEPVTVTWNSGALSSGVHTFPAVLQSGLYTLTSSVTVPSSTWSSQAVTCNVA HPASSTKVDKKIVPRECNPCGCTGSEVSSVFIFPPKTKDVLTITLTPKVTCVVVDISQNDPEVRFSW FIDDVEVHTAQTHAPEKQSNSTLRSVSELPIVHRDWLNGKTFKCKVNSGAFPAPIEKSISKPEGTPR GPQVYTMAPPKEEMTQSQVSITCMVKGFYPPDIYTEWKMNGQPQENYKNTPPTMDTDGSYFLYSKLN VKKETWQQGNTFTCSVLHEGLHNHHTEKSLSHSP* |
| 366 | PI-HX-3092 Light Chain Variable | DIQMTQSPPVLSASVGDRVTLSCKTSQNINKKLDWYQQKHGEAPKLLIYYTNNLQTGIPSRFSGSGS GTDFTLTISTLQPEDVATYYCYQYDSGFTFGAGTKLELK |
| 367 | PI-HX-3092 CDR-L1 | KTSQNINKKLD |
| 368 | PI-HX-3092 CDR-L2 | YTNNLQT |
| 369 | PI-HX-3092 CDR-L3 | YQYDSGFT |
| 370 | PI-HX-3092 Light chain | DIQMTQSPPVLSASVGDRVTLSCKTSQNINKKLDWYQQKHGEAPKLLIYYTNNLQTGIPSRFSGSGS GTDFTLTISTLQPEDVATYYCYQYDSGFTFGAGTKLELKRADAAPTVSIFPPSTEQLATGGASVVCL MNNFYPRDISVKWKIDGTERRDGVLDSVTDQDSKDSTYSMSSTLSLTKADYESHNLYTCEVVHKTSS SPVVKSFNRNEC |
| 371 | PI-3035-AB Heavy Chain Variable | QVQLKESGPGLVQPSQTLSLTCTVSGFSLTSYTLSWVRQPPGKGLEWIGAIWGGDNTDYNSALKSRL SISRDTSKSQVLLKMNSLQTEDTAIYFCTRELGGSFDYWGQGVMVTVSS |
| 372 | PI-3035-AB CDR-H1 | GFSLTSYTLS |
| 373 | PI-3035-AB CDR-H2 | AIWGGDNTD |
| 374 | PI-3035-AB CDR-H3 | ELGGSFDY |
| 375 | PI-3035-AB Heavy chain | QVQLKESGPGLVQPSQTLSLTCTVSGFSLTSYTLSWVRQPPGKGLEWIGAIWGGDNTDYNSALKSRL SISRDTSKSQVLLKMNSLQTEDTAIYFCTRELGGSFDYWGQGVMVTVSSAKTTAPSVYPLAPVCGDT TGSSVTLGCLVKGYFPEPVTLTWNSGSLSSGVHTFPAVLQSDLYTLSSSVTVTSSTWPSQSITCNVA HPASSTKVDKKIEPRGPTIKPCPPCKCPAPNLLGGPSVFIFPPKIKDVLMISLSPIVTCVVVDVSED DPDVQISWFVNNVEVHTAQTQTHREDYNSTLRVVSALPIQHQDWMSGKEFKCKVNNKDLPAPIERTI SKPKGSVRAPQVYVLPPPEEEMTKKQVTLTCMVTDFMPEDIYVEWTNNGKTELNYKNTEPVLDSDGS YFMYSKLRVEKKNWVERNSYSCSVVHEGLHNHHTTKSFSRTPGK* |
| 376 | PI-3035-AB Light Chain Variable | DIQMTQSPPVLSASVGDRVTLSCKTSQNINKKLDWYQQKHGEAPKLLIYYTNNLQTGIPSRFSGSGS GTDFTLTISTLQPEDVATYYCYQYDSGFTFGAGTKLELK |
| 377 | PI-3035-AB CDR-L1 | KTSQNINKKLD |
| 378 | PI-3035-AB CDR-L2 | YTNNLQT |
| 379 | PI-3035-AB CDR-L3 | YQYDSGFT |
| 380 | PI-3035-AB Light chain | DIQMTQSPPVLSASVGDRVTLSCKTSQNINKKLDWYQQKHGEAPKLLIYYTNNLQTGIPSRFSGSGS GTDFTLTISTLQPEDVATYYCYQYDSGFTFGAGTKLELKRADAAPTVSIFPPSSEQLTSGGASVVCF LNNFYPKDINVKWKIDGSERQNGVLNSWTDQDSKDSTYSMSSTLTLTKDEYERHNSYTCEATHKTST SPIVKSFNRNEC |

| SEQ ID NO | Name | Sequence |
|---|---|---|
| 381 | HX-3011 CDR-L1 Consensus sequence | XASAGISNDLA |
| 382 | HX-3061 CDR-L1 Consensus sequence | XASKSIGTFLA |
| 383 | HX-3031 CDR-L1 Consensus sequence | XASEGISNDLA |
| 384 | Human MARCO protein UNIPROT Q9UEW3 | MRNKKILKEDELLSETQQAAFHQIAMEPPFEINVPKPKRRNGVNFSLAVVVIYLILLTAGAGLLVVQV LNLQARLRVLEMYFLNDTLAAEDSPSFSLLQSAHPGEHLAQGASRLQVLQAQLTWVRVSHEHLLQRV DNFTQNPGMFRIKGEQGAPGLQGHKGAMGMPGAPGPPGPPAEKGAKGAMGRDGATGPSGPQGPPGVK GEAGLQGPQGAPGKQGATGTPGPQGEKGSKGDGGLIGPKGETGTKGEKGDLGLPGSKGDRGMKGDAG VMGPPGAQGSKGDFGRPGPPGLAGFPGAKGDQGQPGLQGVPGPPGAVGHPGAKGEPGSAGSPGRAGL PGSPGSPGATGLKGSKGDTGLQGQQGRKGESGVPGPAGVKGEQGSPGLAGPKGAPGQAGQKGDQGVK GSSGEQGVKGEKGERGENSVSVRIVGSSNRGRAEVYYSGTWGTICDDEWQNSDAIVFCRMLGYSKGR ALYKVGAGTGQIWLDNVQCRGTESTLWSCTKNSWGHHDCSHEEDAGVECSV |
| 385 | PI-3010-AB HC cDNA | ATGGATTGGACTTGGCGCTTCTTGTTTGTGGTGGCGGCGGCTACTGGAGTGCAGTCACAAGTGCAAC TTAAGGAATCCGGACCGGGACTCGTGCAGCCGTCACAAACTCTTTCGCTTACCTGTACCGTGTCCGG ATTTTCCCTGACTTCCTACCATGTGTCCTGGGTCAGACAGCCGTCCTGGAAAGGGACTGGAATGGATG GGTGCCATTTGGACTGGGGGATCCATTGCGTATAACTCGCTGCTGAAGTCGCGCTTGTCCATTTCGA GAGATACCTCCAAGTCCCAAGTGTTTCTGAAGATGAACTCCCTGCAAACTGAAGATACTGCCACTTA CTACTGTGCCCGCGATCTGTCCGACTATTACTCGAGTTACACCTCGTTCGATTACTGGGGACAGGGT GTAATGGTCACTGTGTCGACTGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCTCCAACAAAGCCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 386 | PI-3010-AB LC cDNA | ATGGATATGCGGGTGCCGGCCCAGCTTCTGGGGCCTGTTGCTGCTCTGGCTCTCCGGAGCGCGCTGTG ACATCCAAATGACTCAGTCCCCCGCCTCGCTTTCAACCTCCTGGGAGAAACCGTGTCCATCGAATG CCTGGCTTCCAAGGGATTTCCAACGATCTGGCCTGGTACCAGCAGAAGTCCGGAAAGTCACCTCAG CTCCTGATCTACGCGGCCAGCCGGCTGCAGGACGGCGTGCCTTCCCGCTTTTCCGGTTCGGGATCAG GGACTCGGTACTCGCTGAAGATTTCCGGGATGCAGCCTGAGGACGAAGCGGACTACTTCTGCCAACA ATCCTACAAGTACCCGCTGACCTTCGGCTCCGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 387 | PI-3011-AB HC cDNA | ATGGATTGGACTTGGCGCTTCTTGTTTGTGGTGGCGGCGGCTACTGGAGTGCAGTCACAAGTGCAAC TTCAAGGAATCCGGACCGGGACTCGTGAAGCCGTCACAAACTCTTTCGCTTACCTGTACCGTGTCCGG ATTTTCCCTGACTTCCTACCATGTGTCCTGGATCAGACAGCCGTCCTGGAAAGGGACTGGAATGGATC GGTGCCATTTGGACTGGGGGATCCATTGCGTATAACCCGTCCCTGAAGTCGCGCGTGACTATTTCGG TGGATACCTCCAAGAACCAATTCAGCCTGAAGTTGTCCTCCGTGACTGCCGCCGATACTGCCGTATA CTACTGTGCCCGCGATCTGTCCGACTATTACTCGAGTTACACCTCGTTCGATTACTGGGGACAGGGT ACTCTCGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA |

| SEQ ID NO | Name | Sequence |
|---|---|---|
| | | GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 388 | PI-3011-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAGCCTCCGTGGGAGACAGAGTGACCATCACTTG<br>CCGGGCTTCCGAAGGGATTTCCAACGATCTGGCCTGGTACCAGCAGAAGCCCGGAAAGGCCCCTAAG<br>CTCCTGATCTACGCGGCCAGCCGGCTGCAGTCCGGCGTGCCTTCCCGCTTTTCCGGTTCGGGATCAG<br>GGACTGACTTCACCCTGACCATTTCCAGCCTGCAGCCTGAGGACTTCGCGACCTACTACTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 389 | PI-3012-AB HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCGTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCGTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 390 | PI-3012-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAGCCTCCGTGGGAGACAGAGTGACCATCACTTG<br>CCGGGCTTCCGAAGGGATTTCCAACGATCTGGCCTGGTACCAGCAGAAGCCCGGAAAGGCCCCTAAG<br>CTCCTGATCTACGCGGCCAGCCGGCTGCAGTCCGGCGTGCCTTCCCGCTTTTCCGGTTCGGGATCAG<br>GGACTGACTACACCCTGACCATTTCCAGCCTGCAGCCTGAGGACTTCGCGACCTACTACTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 391 | PI-3013-AB HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCGTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA |

| SEQ ID NO | Name | Sequence |
|---|---|---|
| | | AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 392 | PI-3013-AB<br>LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAGCCTCCGTGGGAGACAGAGTGACCATCACTTG<br>CCGGGCTTCCGAAGGGATTTCCAACGATCTGGCCTGGTACCAGCAGAAGCCCGGAAAGGCCCCTAAG<br>CTCCTGATCTACGCGGCCAGCCGGCTGCAGTCCGGCGTGCCTTCCCGCTTTTCCGGTTCGGGATCAG<br>GGACTGACTACACCCTGACCATTTCCAGCATGCAGCCTGAGGACTTCGCGACCTACTACTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 393 | PI-3014-AB<br>HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATG<br>GGTGCCATTTGGACTGGGGGATCCATTGCGTATAACCCGTCCCTGAAGTCGCGCTTGACTATTTCGA<br>GAGATACCTCCAAGAACCAAGTGTCGCTGAAGATGTCCTCCCTGACTGCCGCCGATACTGCCGTATA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 394 | PI-3014-AB<br>LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAGCCTCCGTGGGAGACAGAGTGACCATCACTTG<br>CCGGGCTTCCGAAGGGATTTCCAACGATCTGGCCTGGTACCAGCAGAAGCCCGGAAAGGCCCCTAAG<br>CTCCTGATCTACGCGGCCAGCCGGCTGCAGTCCGGCGTGCCTTCCCGCTTTTCCGGTTCGGGATCAG<br>GGACTGACTACACCCTGACCATTTCCAGCTGCAGCCTGAGGACTTCGCGACCTACTACTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 395 | PI-3015-AB<br>HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATG<br>GGTGCCATTTGGACTGGGGGATCCATTGCGTATAACCCGTCCCTGAAGTCGCGCTTGACTATTTCGA<br>GAGATACCTCCAAGAACCAAGTGTCGCTGAAGATGTCCTCCCTGACTGCCGCCGATACTGCCGTATA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG |

| SEQ ID NO | Name | Sequence |
|---|---|---|
| | | ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 396 | PI-3015-AB LC cDNA | ATGGATATGCGGGTGCCGGCCCAGCTTCTGGGCCTGTTGCTGCTCTGGCTCTCCGGAGCGCGCTGTG ACATCCAAATGACTCAGTCCCCCTCATCGCTTTCAGCCTCCGTGGGAGACAGAGTGACCATCACTTG CCGGGCTTCCGAAGGGATTTCCAACGATCTGGCCTGGTACCAGCAGAAGCCCGGAAAGGCCCCTAAG CTCCTGATCTACGCGGCCAGCCGGCTGCAGTCCGGCGTGCCTTCCCGCTTTTCCGGTTCGGGATCAG GGACTGACTACACCCTGACCATTTCCAGCATGCAGCCTGAGGACTTCGCGACCTACTACTGCCAACA ATCCTACAAGTACCCGCTGACCTTCGGCCAAGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 397 | PI-3022-AB HC cDNA | ATGGATTGGACTTGGCGCTTCTTGTTTGTGGTGGCGGCGGCTACTGGAGTGCAGTCACAAGTGCAAC TTCAAGAATCCGGACCGGGACTCGTGAAGCCGTCAGAAACTCTTTCGCTTACCTGTACCGTGTCCGG ATTTTCCCTGACTTCCTACCATGTGTCCTGGGTCAGACAGCCTCCTGGAAAGGGACTGGAATGGATC GGTGCCATTTGGACTGGGGGATCCATTGCGTATAACCCGTCCCTGAAGTCGCGCGTAACTATTTCGA GAGATACCTCCAAGAACCAAGTGTCCCTGAAGCTGTCGTCCGTGACTGCCGCCGATACTGCCGTGTA CTACTGTGCCCGCGATCTGTCCGACTATTACTGAGTTACACCTCGTTCGATTACTGGGGACAGGGT ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCAACAAACCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 398 | PI-3022-AB LC cDNA | ATGGATATGCGGGTGCCGGCCCAGCTTCTGGGCCTGTTGCTGCTCTGGCTCTCCGGAGCGCGCTGTG ACATCCAAATGACTCAGTCCCCCTCATCGCTTTCAGCCTCCGTGGGAGACAGAGTGACCATCACTTG CCGGGCTTCCGAAGGGATTTCCAACGATCTGGCCTGGTACCAGCAGAAGCCCGGAAAGGCCCCTAAG CTCCTGATCTACGCGGCCAGCCGGCTGCAGGACGGCGTGCCTTCCCGCTTTTCCGGTTCGGGATCAG GGACTGACTACACCCTGACCATTTCCAGCCTGCAGCCTGAGGACTTCGCGACCTACTACTGCCAACA ATCCTACAAGTACCCGCTGACCTTCGGCCAAGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 399 | PI-3023-AB HC cDNA | ATGGATTGGACTTGGCGCTTCTTGTTTGTGGTGGCGGCGGCTACTGGAGTGCAGTCACAAGTGCAAC TTCAAGAATCCGGACCGGGACTCGTGAAGCCGTCAGAAACTCTTTCGCTTACCTGTACCGTGTCCGG ATTTTCCCTGACTTCCTACCATGTGTCCTGGGTCAGACAGCCTCCTGGAAAGGGACTGGAATGGATC GGTGCCATTTGGACTGGGGGATCCATTGCGTATAACCCGTCCCTGAAGTCGCGCGTAACTATTTCGA GAGATACCTCCAAGAACCAAGTGTCCCTGAAGCTGTCGTCCGTGACTGCCGCCGATACTGCCGTGTA CTACTGTGCCCGCGATCTGTCCGACTATTACTGAGTTACACCTCGTTCGATTACTGGGGACAGGGT ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCAACAAACCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |

| SEQ ID NO | Name | Sequence |
|---|---|---|
| 400 | PI-3023-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCTCATCGCTTTCAACCTCCGTGGGAGACAGAGTGACCATCACTTG<br>CCGGGCTTCCGAAGGGATTTCCAACGATCTGGCCTGGTACCAGCAGAAGCCCGGAAAGTCGCCTAAG<br>CTCCTGATCTACGCGGCCAGCCGGCTGCAGTCCGGCGTGCCTTCCCGCTTTTCCGGTTCGGGATCAG<br>GGACTGACTACACCCTGACCATTTCCAGCCTGCAGCCTGAGGACTTCGCGACCTACTTCTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 401 | PI-3024-AB HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCGTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 402 | PI-3024-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCTCATCGCTTTCAACCTCCGTGGGAGACAGAGTGACCATCACTTG<br>CCGGGCTTCCGAAGGGATTTCCAACGATCTGGCCTGGTACCAGCAGAAGCCCGGAAAGTCCCCTAAG<br>CTCCTGATCTACGCGGCCAGCCGGCTGCAGGACGGCGTGCCTTCCCGCTTTTCCGGTTCGGGATCAG<br>GGACTGACTACACCCTGACCATTTCCAGCCTGCAGCCTGAGGACGAAGCGACCTACTTCTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 403 | PI-3025-AB HC cDNA | ATGGATTGGACTTGGCGCTTCTTGTTTGTGGTGGCGGCGGCTACTGGAGTGCAGTCAGAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCGTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |

| SEQ ID NO | Name | Sequence |
|---|---|---|
| 404 | PI-3025-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAGCCTCCGTGGGAGACAGAGTGACCATCACTTG<br>CCGGGCTTCCGAAGGGATTTCCAACGATCTGGCCTGGTACCAGCAGAAGCCCGGAAAGGCCCCTAAG<br>CTCCTGATCTACGCGGCCAGCCGGCTGCAGGACGGCGTGCCTTCCCGCTTTTCCGGTTCGGGATCAG<br>GGACTGACTACACCCTGACCATTTCCAGCCTGCAGCCTGAGGACTTCGCGACCTACTACTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 405 | PI-3026-AB HC cDNA | ATGGATTGGACTTGGCGCTTCTTGTTTGTGGTGGCGGCGGCTACTGGAGTGCAGTCAGAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCGTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 406 | PI-3026-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAACCTCCGTGGGAGACAGAGTGACCATCACTTG<br>CCGGGCTTCCGAAGGGATTTCCAACGATCTGGCCTGGTACCAGCAGAAGCCCGGAAAGGTCGCTAAG<br>CTCCTGATCTACGCGGCCAGCCGGCTGCAGTCCGGCGTGCCTTCCCGCTTTTCCGGTTCGGGATCAG<br>GGACTGACTACACCCTGACCATTTCCAGCCTGCAGCCTGAGGACTTCGCGACCTACTTCTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 407 | PI-3027-AB HC cDNA | ATGGATTGGACTTGGCGCTTCTTGTTTGTGGTGGCGGCGGCTACTGGAGTGCAGTCAGAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCGTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |

| Sequence listing | | |
|---|---|---|
| SEQ ID NO | Name | Sequence |
| 408 | PI-3027-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCTCATCGCTTTCAACCTCCGTGGGAGACAGAGTGACCATCACTTG<br>CCGGGCTTCCGAAGGGATTTCCAACGATCTGGCCTGGTACCAGCAGAAGCCCGGAAAGTCCCCTAAG<br>CTCCTGATCTACGCGGCCAGCCGGCTGCAGGACGGCGTGCCTTCCCGCTTTTCCGGTTCGGGATCAG<br>GGACTGACTACACCCTGACCATTTCCAGCCTGCAGCCTGAGGACGAAGCGACCTACTTCTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 409 | PI-3030-AB HC cDNA | ATGGATTGGACTTGGCGCTTCTTGTTTGTGGTGGCGGCGGCTACTGGAGTGCAGTCACAAATCCAGC<br>TCGTGCAGTCCGGGCCAGAGCTGAAAAAGCCCGGAGAATCCGTCAAGATTAGCTGCAAGGCCTCCG<br>GCTACACCTTCACCGACTACGCAGTGAACTGGGTCAAGCAGGCCCCGGGAAATGGTCTGAAGTGGATG<br>GGCTGGATTAACACGCAGACCGGGAAGCCTACCTACGCCGACGACTTCAAGCAACGGTTCGTGTTCT<br>CGCTTGAAACTAGCGCCTCGACCTCGTTCCTGCAAATCAACAACCTGAACATCGAGGACACCGCCAC<br>CTACTTCTGCACAAGAGACTCCTACTATTACTCATCCTCCCTCGATTACTGGGGACAGGGCGTGATC<br>GTCACTGTGTCCAGCGCCAGCACCAAGGGCCCATCGGTCTTCCCCCTGGCACCCTCCTCCAAGAGCA<br>CCTCTGGGGGCACAGCGGCCCTGGGCTGCCTGGTCAAGGACTACTTCCCCGAACCGGTGACGGTGTC<br>GTGGAACTCAGGCGCCCTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAATCTTGTGACAAAACTCA<br>CACATGCCCACCGTGCCCAGCACCTGAACTCCTGGGGGGACCGTCAGTCTTCCTCTTCCCCCCAAAA<br>CCCAAGGACACCCTCATGATCTCCCGGACCCCTGAGGTCACATGCGTGGTGGTGGACGTGAGCCACG<br>AAGACCCTGAGGTCAAGTTCAACTGGTACGTGGACGGCGTGGAGGTGCATAATGCCAAGACAAAGCC<br>GCGGGAGGAGCAGTACAACAGCACGTACCGGGTGGTCAGCGTCCTCACCGTCCTGCACCAGGACTGG<br>CTGAATGGCAAGGAGTACAAGTGCAAGGTCAGCAACAAAGCCCTCCCAGCCCCCATCGAGAAACCA<br>TCTCCAAAGCCAAAGGGCAGCCCCGAGAACCACAGGTGTACACCCTGCCCCCATCCCGGGATGAGCT<br>GACCAAGAACCAGGTCAGCCTGACCTGCCTGGTCAAAGGCTTCTATCCCAGCGACATCGCCGTGGAG<br>TGGGAGAGCAATGGGCAGCCGGAGAACAACTACAAGACCACGCCTCCCGTGCTGGACTCCGACGGCT<br>CCTTCTTCCTCTACAGCAAGCTCACCGTGGACAAGAGCAGGTGGCAGCAGGGGAACGTCTTCTCATG<br>CTCCGTGATGCATGAGGCTCTGCACAACCACTACACGCAGAAGTCCCTCTCCCTGTCTCCGGGTAAA<br>TAG |
| 410 | PI-3030-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCTGCATCCCTGAGCGCGAGCCTGGGGGAGACAGTGTCATTGAATG<br>CCTGCCTCCGCCGGAATTTCTAACGACCTGGCCTGGTACCAGCAGAAGTCCGGAAAGTCGCCCCAG<br>CTGCTGATCTACGCCGCTTCGAGGCTTCAGGATGGTGTCCCGTCACGGTTTAGCGGATCAGGATCCG<br>GCACCAGATTCTCCCTGAAAATCAGCGACATGCAGCCAGAGGACGAAGCCGACTACTTCTGCCAACA<br>ATCGTACAAGTATCCCTGGACCTTCGGCGGGGGCACCAAGCTCGAACTGAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 411 | PI-3036-AB HC cDNA | ATGGACTGGACCTGGAGATTTTTATTCGTCGTCGCTGCCGCCACCGGAGTGCAATCACAAGTACAAC<br>TGGTGCAGAGCGGGCCGAAGTCAAGAAGCCCGGCGCCTCCGTGAAAGTGTCGTGCAAAGCCTCGGG<br>TTACACATTCACTGACTACGCAGTGAACTGGGTCAGACAGGCACCGGGCCAGGGACTCGAGTGGATG<br>GGCTGGATAACACTCAGACTGGGAAGCCCACCTATGCTCAGAAGTTCCAGGGAAGGGTCACCATGA<br>CCCGCGACACCAGCACCTCCACCGTGTACATGGAATTGAGCAGCCTGCGGTCCGAAGATACAGCCGT<br>GTACTATTGTGCGAGGGACTCCTACTACTACTCCTCGCTCGACTACTGGGGCCAGGGTACCCTC<br>GTGACCGTTAGCTCGGCCTCTACTAAGGGTCCGTCCGTGTCCCGTTGGCCCCGAGCTCGAAGTCCA<br>CCTCCGGGGAACCGCTGCGCTTGGATGCCTGGTCAAGGACTACTTCCCCGAGCCCGTGACGGTGTC<br>CTGGAACTCCGGGGCCCTGACCTCGGGAGTGCACACTTTCCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCATGCAGCAAGACTCA<br>CACTTGCCCGCCGTGCCCCGCGCCTGAGCTTCTTGGCGGGCCCTCCGTGTTCCTGTTTCCGCCAAAG<br>CCCAAGGATACTCTGATGATTTCGCGGACTCCTGAAGTGACCTGTGTGGTCGTCGATGTGTCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTCTCAACAAGGCCCTGCCTCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |

| SEQ ID NO | Name | Sequence |
|---|---|---|
| 412 | PI-3036-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 413 | PI-3038-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAGTGTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGGTCACCATGA<br>CCCTGACACAGACCAGCACCTCCACCGCATACATGGAATTGAGCAGCCTGCGGTCCGAAGATACAGCCGT<br>GTACTATTGTACTAGGGACTCCTACTACTACTCATCCTCGCTCGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCCGTGACGGTGTC<br>CTGGAACTCCGGGGCCCTGACCTCGGGAGTGCACACTTTCCCTGCGGTGCTGCAGAGCTCAGGACTG<br>TACAGCCTCAGCTCCGTCGTGACCGTGCCTTCGTCCTGCAGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCAAAG<br>CCCAAGGATACTCTGATGATTTCGCGGACTCCTGAAGTGACCTGTGTGGTCGTCGATGTGTCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGCCCTGCCTGCCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |
| 414 | PI-3038-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 415 | PI-3039-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAATCTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGTTCACCTTTA<br>CCTTGGACACCAGCACCTCCACCGCGTACTTGGAAATTAGCAGCCTGCGGTCCGAAGATACAGCCGT<br>GTACTATTGTACTAGGGACTCCTACTACTACTCATCCTCGCTCGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCCGTGACGGTGTC<br>CTGGAACTCCGGGGCCCTGACCTCGGGAGTGCACACTTTCCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCAAAG<br>CCCAAGGATACTCTGATGATTTCGCGGACTCCTGAAGTGACCTGTGTGGTCGTCGATGTGTCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGCCCTGCCTGCCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |

| SEQ ID NO | Name | Sequence |
|---|---|---|
| 416 | PI-3039-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 417 | PI-3040-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAGTGTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGGTCACCATGA<br>CCTTGGACACCAGCACCTCCACCTCCTACATGGAATTGAGCAGCCTGCGGTCCGAAGATACAGCCGT<br>GTACTATTGTACTAGGGACTCCTACTACTACTCATCCTCGCTCGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCCGTGACGGTGTC<br>CTGGAACTCCGGGGCCCTGACCTCGGGAGTGCACACTTTCCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCAAAG<br>CCCAAGGATACTCTGATGATTTCGCGGACTCCTGAAGTGACCTGTGTGGTCGTCGATGTGTCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGCCCTGCCTGCCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |
| 418 | PI-3040-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 419 | PI-3041-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAATCTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGGTTTACCTTCA<br>CCCTCGACACCAGCACCTCCACCTCCTACTTGGAAATTAGCAGCCTGCGGTCCGAAGATACAGCCGT<br>GTACTATTGTACTAGGGACTCCTACTACTACTCATCCTCGCTCGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCCGTGACGGTGTC<br>CTGGAACTCCGGGGCCCTGACCTCGGGAGTGCACACTTTCCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCAAAG<br>CCCAAGGATACTCTGATGATTTCGCGGACTCCTGAAGTGACCTGTGTGGTCGTCGATGTGTCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGCCCTGCCTGCCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |

| Sequence listing | | |
|---|---|---|
| SEQ ID NO | Name | Sequence |
| 420 | PI-3041-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 421 | PI-3028-AB HC cDNA | ATGGATTGGACTTGGAGATTTTTGTTTGTGGTGGCGGCGGCCACTGGAGTGCAATCCGAAGTGCAAT<br>TGGTGGAATCGGGTGGTGGACTTGTGCAGCCTGGATCGTCACTTAAGCTGTCCTGTGTGGCCTCGAA<br>GTTTACCTTCTCCAACTATGGGATGAACTGGATTAGACAAGCCCCGAAGAAGGGACTGGAATGGATT<br>GCGCTGATCTATTACAACTCGAACAACAAGTACTACGCTGATTCCGTGAAGGGTCGCTTCACTATTT<br>CCCGCGACAACTCGAAGAACACTCTGTACCTTGAGATGAACTCCCTGCGCTCGGAAGATACTGCCAT<br>GTACTACTGTGCCAAGTCGCTGACTGGCGGATCCGATTACTTCGATTCCTGGGGACAAGGAGTGATG<br>GTCACTGTATCCAGTGCCAGCACCAAGGGCCCATCGGTCTTCCCCCTGGCACCCTCCTCCAAGAGCA<br>CCTCTGGGGGCACAGCGGCCCTGGGCTGCCTGGTCAAGGACTACTTCCCCGAACCGGTGACGGTGTC<br>GTGGAACTCAGGCGCCCTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAATCTTGTGACAAAACTCA<br>CACATGCCCACCGTGCCCAGCACCTGAACTCCTGGGGGGACCGTCAGTCTTCCTCTTCCCCCCAAAA<br>CCCAAGGACACCCTCATGATCTCCCGGACCCCTGAGGTCACATGCGTGGTGGTGGACGTGAGCCACG<br>AAGACCCTGAGGTCAAGTTCAACTGGTACGTGGACGGCGTGGAGGTGCATAATGCCAAGACAAAGCC<br>GCGGGAGGAGCAGTACAACAGCACGTACCGGGTGGTCAGCGTCCTCACCGTCCTGCACCAGGACTGG<br>CTGAATGGCAAGGAGTACAAGTGCAAGGTCAGCAACAAAGCCCTCCCAGCCCCCATCGAGAAAACCA<br>TCTCCAAAGCCAAAGGGCAGCCCCGAGAACCACAGGTGTACACCCTGCCCCCATCCCGGGATGAGCT<br>GACCAAGAACCAGGTCAGCCTGACCTGCCTGGTCAAAGGCTTCTATCCCAGCGACATCGCCGTGGAG<br>TGGGAGAGCAATGGGCAGCCGGAGAACAACTACAAGACCACGCCTCCCGTGCTGGACTCCGACGGCT<br>CCTTCTTCCTCTACAGCAAGCTCACCGTGGACAAGAGCAGGTGGCAGCAGGGGAACGTCTTCTCATG<br>CTCCGTGATGCATGAGGCTCTGCACAACCACTACACGCAGAAGTCCCTCTCCCTGTCTCCGGGTAAA<br>TAG |
| 422 | PI-3028-AB LC cDNA | ATGGACATGCGCGTGCCTGCGCAATTGCTGGGGCTGCTTCTCCTGTGGCTTTCGGGAGCCCGCTGCG<br>ACGTGCAGATGACCCAGTCCCCTTCCTACCTGGCTGCGTCACCGGGAGAATCAGTGTCCATCAGCTG<br>CAAGGCCTCCAAGTCCATTGGTACCTTCCTGGCCTGGTACCAAGAGAAGCCTGAAAAGACCAACAAG<br>CTCCTGATCTACTCGGGATCAACCCTGCAATCCGGCACTCCGTCGCGGTTCTCCGGATCCGGGTCCG<br>GCACCGACTTTACTCTGACCATTCGGAACCTGGAACCCGAAGATTTCGCCGTGTACTACTGTCAGCA<br>GCACGACGAATACCCGTTTACTTTCGGCTCCGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 423 | PI-3029-AB HC cDNA | ATGGATTGGACTTGGAGATTTTTGTTTGTGGTGGCGGCGGCCACTGGAGTGCAATCCGAAGTGCAAT<br>TGGTGGAATCGGGTGGTGGACTTGTGCAGCCTGGATCGTCACTTAAGCTGTCCTGTGTGGCCTCGAA<br>GTTTACCTTCTCCAACTATGGGATGAACTGGATTAGACAAGCCCCGAAGAAGGGACTGGAATGGATT<br>GCGCTGATCTATTACAACTCGAACAACAAGTACTACGCTGATTCCGTGAAGGGTCGCTTCACTATTT<br>CCCGCGACAACTCGAAGAACACTCTGTACCTTGAGATGAACTCCCTGCGCTCGGAAGATACTGCCAT<br>GTACTACTGTGCCAAGTCGCTGACTGGCGGATCCGATTACTTCGATTCCTGGGGACAAGGAGTGATG<br>GTCACTGTATCCAGTGCCAGCACAAAGGGCCCATCCGTCTTCCCCCTGGCGCCCTGCTCCAGGAGCA<br>CCTCCGAGAGCACAGCCGCCCTGGGCTGCCTGGTCAAGGACTACTTCCCCGAACCGGTGACGGTGTC<br>GTGGAACTCAGGCGCCCTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACGAAGACCTACACCTGCAACG<br>TAGATCACAAGCCCAGCAACACCAAGGTGGACAAGAGAGTTGAGTCCAAATATGGTCCCCCATGCCC<br>ATCCTGCCCAGCACCTGAGTTCCTGGGGGGACCATCAGTCTTCCTGTTCCCCCCAAAACCCAAGGAC<br>ACTCTCATGATCTCCCGGACCCCTGAGGTCACGTGCGTGGTGGTGGACGTGAGCCAGGAAGACCCCG<br>AGGTCCAGTTCAACTGGTACGTGGATGGCGTGGAGGTGCATAATGCCAAGACAAAGCCGCGGGAGGA<br>GCAGTTCAACAGCACGTACCGTGTGGTCAGCGTCCTCACCGTCCTGCACCAGGACTGGCTGAACGGC<br>AAGGAGTACAAGTGCAAGGTCAGCAACAAAGGCCTCCCGTCCTCCATCGAGAAAACCATCTCCAAAG<br>CCAAAGGGCAGCCCCGAGAGCCACAGGTGTACACCCTGCCCCCATCCCAGGAGGAGATGACCAAGAA<br>CCAGGTCAGCCTGACCTGCCTGGTCAAAGGCTTCTACCCCAGCGACATCGCCGTGGAGTGGGAGAGC<br>AATGGGCAGCCGGAGAACAACTACAAGACCACGCCTCCCGTGCTGGACTCCGACGGCTCCTTCTTCC<br>TCTACAGCAGGCTAACCGTGGACAAGAGCAGGTGGCAGGAGGGGAATGTCTTCTCATGCTCCGTGAT<br>GCATGAGGCTCTGCACAACCACTACACACAGAAGTCCCTCTCCCTGTCTCTGGGTAAATAG |

| SEQ ID NO | Name | Sequence |
|---|---|---|
| 424 | PI-3029-AB LC cDNA | ATGGACATGCGCGTGCCTGCGCAATTGCTGGGGCTGCTTCTCCTGTGGCTTTCGGGAGCCCGCTGCG<br>ACGTGCAGATGACCCAGTCCCCTTCCTACCTGGCTGCGTCACCGGGAGAATCAGTGTCCATCAGCTG<br>CAAGGCCTCCAAGTCCATTGGTACCTTCCTGGCCTGGTACCAAGAGAAGCCTGAAAAGACCAACAAG<br>CTCCTGATCTACTCGGGATCAACCCTGCAATCCGGCACTCCGTCGCGGTTCTCCGGATCCGGTCCG<br>GCACCGACTTTACTCTGACCATTCGGAACCTGGAACCCGAAGATTTCGCCGTGTACTACTGTCAGCA<br>GCACGACGAATACCCGTTTACTTTCGGCTCCGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 425 | PI-3031-AB HC cDNA | ATGGATTGGACTTGGCGCTTCTTGTTTGTGGTGGCGGCGGCTACTGGAGTGCAGTCACAAGTCAACC<br>TTCTGCAATCCCGGGCAGCACTCGTGAAGCCCGGTGCTTCAGTGAAGCTGAGCTGCAAGGCCTCCGG<br>GTACACCTTCACCGACTACTATCTGCATTGGGTCAAGCAGTCCCACGCCAAGAGCCTGGAGTGGATT<br>GGCTACATCAACCCGAACAACGCCTACACCTCGTACAATGAGAAGTTCAAGTCCAAAGCGACCCTGA<br>CCGTGGATAAGTCCACTAACACCGCCTACATGGAACTGTCCAGACTCACGTCCGCCGACTCGGCCAC<br>CTATTACTGTGCCCGGGACACCACAGACTACTACAACCTCCACTTCGCCTACTGGGGCCAGGGAACT<br>CTGGTCACCGTGTCGAGCGCCAGCACCAAGGGCCCATCGGTCTTCCCCCTGGCACCCTCCTCCAAGA<br>GCACCTCTGGGGGCACAGCGGCCCTGGGCTGCCTGGTCAAGGACTACTTCCCCGAACCGGTGACGGT<br>GTCGTGGAACTCAGGCGCCCTGACCAGCGGCGTGCACACCTTCCCGGCTGTCCTACAGTCCTCAGGA<br>CTCTACTCCCTCAGCAGCGTGGTGACCGTGCCCTCCAGCAGCTTGGGCACCCAGACCTACATCTGCA<br>ACGTGAATCACAAGCCCAGCAACACCAAGGTGGACAAGAAAGTTGAGCCCAAATCTTGTGACAAAAC<br>TCACACATGCCCACCGTGCCCAGCACCTGAACTCCTGGGGGGACCGTCAGTCTTCCTCTTCCCCCCA<br>AAACCCAAGGACACCCTCATGATCTCCCGGACCCCTGAGGTCACATGCGTGGTGGTGGACGTGAGCC<br>ACGAAGACCCTGAGGTCAAGTTCAACTGGTACGTGGACGGCGTGGAGGTGCATAATGCCAAGACAAA<br>GCCGCGGGAGGAGCAGTACAACAGCACGTACCGGGTGGTCAGCGTCCTCACCGTCCTGCACCAGGAC<br>TGGCTGAATGGCAAGGAGTACAAGTGCAAGGTCAGCAACAAAGCCCTCCCAGCCCCCATCGAGAAAA<br>CCATCTCCAAAGCCAAAGGGCAGCCCCGAGAACCACAGGTGTACACCCTGCCCCCATCCCGGGATGA<br>GCTGACCAAGAACCAGGTCAGCCTGACCTGCCTGGTCAAAGGCTTCTATCCCAGCGACATCGCCGTG<br>GAGTGGGAGAGCAATGGGCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAGCAGGGGAACGTCTTCTC<br>ATGCTCCGTGATGCATGAGGCTCTGCACAACCACTACACGCAGAAGTCCCTCTCCCTGTCTCCGGGT<br>AAATAG |
| 426 | PI-3031-AB LC cDNA | ATGGATATGCGGGTGCCGGCCCAGCTTCTGGGCCTGTTGCTGCTCTGGCTCTCCGGAGCGCGCTGTG<br>ACATTCAAATGACCCAGTCCCCTGCATCACTGAGCGCCTCACTGGGGGAAACTGTCAGCATTGAGTG<br>CCTGACCTCCGAGGGAATCTCGAACGACCTGGCCTGGTATCAGCAGAAGTCCGGAAAGTCGCCGCAG<br>CTGCTTATCTACGACGCCAGCAGACTCGAGGACGGCGTGCCCTCCCGCTTTTCCGGCTCTGGTTCCG<br>GCACTCGGTACAGCCTGAAGATCTCCGGAATGCAGACCGAAGATGAAGCTGACTACTTCTGCCAACA<br>ATCGTACAAATACCCACTGACCTTCGGTTCCGGGACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 427 | HC signal peptide sequence | ATGGATTGGACTTGGCGCTTCTTGTTTGTGGTGGCGGCGGCTACTGGAGTGCAGTCA |
| 428 | HC signal peptide sequence | MDWTWRFLFVVAAATGVQS |
| 429 | LC signal peptide sequence | MDMRVPAQLLGLLLLWLSGARC |
| 430 | LC signal peptide sequence | ATGGATATGCGGGTGCCGGCCCAGCTTCTGGGCCTGTTGCTGCTCTGGCTCTCCGGAGCGCGCTGT |
| 431 | CDR L1 | ASEGISNDLA |
| 432 | CDR L1 | ASAGISNDLA |
| 433 | CDR L1 | ASKSIGTFLA |
| 434 | PI-3025-AB2 Heavy Chain Variable | EVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSS |

-continued

| SEQ ID NO | Name | Sequence |
|---|---|---|
| 435 | PI-3025-AB2 CDR-H1 | GFSLTSYHVS |
| 436 | PI-3025-AB2 CDR-H2 | AIWTGGSIA |
| 437 | PI-3025-AB2 CDR-H3 | DLSDYYSSYTSFDY |
| 438 | PI-3025-AB2 Heavy chain | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 439 | PI-3025-AB2 Light Chain Variable | DIQMTQSPSSLSASVGDRVTITCRASEGISNDLAWYQQKPGKAPKLLIYAASRLQDGVPSRFSGSGS GTDYTLTISSLQPEDFATYYCQQSYKYPLTFGQGTKLEIK |
| 440 | PI-3025-AB2 CDR-L1 | RASEGISNDLA |
| 441 | PI-3025-AB2 CDR-L2 | AASRLQD |
| 442 | PI-3025-AB2 CDR-L3 | QQSYKYPLT |
| 443 | PI-3025-AB Light chain | DIQMTQSPSSLSASVGDRVTITCRASEGISNDLAWYQQKPGKAPKLLIYAASRLQDGVPSRFSGSGS GTDYTLTISSLQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC |
| 444 | PI-3048-AB Heavy Chain Variable | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSS |
| 445 | PI-3048-AB CDR-H1 | GFSLTSYHVS |
| 446 | PI-3048-AB CDR-H2 | AIWTGGSIA |
| 447 | PI-3048-AB CDR-H3 | DLSDYYSSYTSFDY |
| 448 | PI-3048-AB Heavy chain | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PCSRSTSESTAALGCLVKDYFPEPVTVSWNSGALTSGVHTFPAVLQSSGLYSLSSVVTVPSSSLGTK TYTCNVDHKPSNTKVDKRVESKYGPPCPPCPAPEFLGGPSVFLFPPKPKDTLMISRTPEVTCVVVDV SQEDPEVQFNWYVDGVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 449 | PI-3048-AB Light Chain Variable | DIQMTQSPSSLSASVGDRVTITCRASEGISNDLAWYQQKPGKAPKLLIYAASRLQDGVPSRFSGSGS GTDYTLTISSLQPEDFATYYCQQSYKYPLTFGQGTKLEIK |
| 450 | PI-3048-AB CDR-L1 | RASEGISNDLA |
| 451 | PI-3048-AB CDR-L2 | AASRLQD |
| 452 | PI-3048-AB CDR-L3 | QQSYKYPLT |

| SEQ ID NO | Name | Sequence |
|---|---|---|
| 453 | PI-3048-AB Light chain | DIQMTQSPSSLSASVGDRVTITCRASEGISNDLAWYQQKPGKAPKLLIYAASRLQDGVPSRFSGSGSGTDYTLTISSLQPEDFATYYCQQSYKYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 454 | PI-3041-AB Heavy Chain Variable | QVQLVQSGAEVKKPGASVKISCKASGYTFTDYAVNWVRQAPGQGLEWMGWINTQTGKPTYAQKFQGRFTFTLDTSTSTSYLEISSLRSEDTAVYYCTRDSYYYSSSLDYWGQGTLVTVSS |
| 455 | PI-3041-AB CDR-H1 | GYTFTDYAVN |
| 456 | PI-3041-AB CDR-H2 | WINTQTGKPT |
| 457 | PI-3041-AB CDR-H3 | DSYYYSSSLDY |
| 458 | PI-3041-AB Heavy chain | QVQLVQSGAEVKKPGASVKISCKASGYTFTDYAVNWVRQAPGQGLEWMGWINTQTGKPTYAQKFQGRFTFTLDTSTSTSYLEISSLRSEDTAVYYCTRDSYYYSSSLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 459 | PI-3041-AB Light Chain Variable | DIQMTQSPSSLSASVGDRVTITCRASAGISNDLAWYQQKPGKAPKLLIYAASRLQDGVPSRFSGSGSGTDFTLTISSMQPEDFATYYCQQSYKYPWTFGQGTKLEIK |
| 460 | PI-3041-AB CDR-L1 | RASAGISNDLA |
| 461 | PI-3041-AB CDR-L2 | AASRLQD |
| 462 | PI-3041-AB CDR-L3 | QQSYKYPWT |
| 463 | PI-3041-AB Light chain | DIQMTQSPSSLSASVGDRVTITCRASAGISNDLAWYQQKPGKAPKLLIYAASRLQDGVPSRFSGSGSGTDFTLTISSMQPEDFATYYCQQSYKYPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 464 | PI-3047-AB Heavy Chain Variable | EVQLVQSGAEVKKPGASVKISCKASGYTFTDYAVNWVRQAPGQGLEWMGWINTQTGKPTYAQKFQGRFTFTLDTSTSTSYLEISSLRSEDTAVYYCTRDSYYYSSSLDYWGQGTLVTVSS |
| 465 | PI-3047-AB CDR-H1 | GYTFTDYAVN |
| 466 | PI-3047-AB CDR-H2 | WINTQTGKPT |
| 467 | PI-3047-AB CDR-H3 | DSYYYSSSLDY |
| 468 | PI-3047-AB Heavy chain | EVQLVQSGAEVKKPGASVKISCKASGYTFTDYAVNWVRQAPGQGLEWMGWINTQTGKPTYAQKFQGRFTFTLDTSTSTSYLEISSLRSEDTAVYYCTRDSYYYSSSLDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 469 | PI-3047-AB Light Chain Variable | DIQMTQSPSSLSASVGDRVTITCRASAGISNDLAWYQQKPGKAPKLLIYAASRLQDGVPSRFSGSGSGTDFTLTISSMQPEDFATYYCQQSYKYPWTFGQGTKLEIK |
| 470 | PI-3047-AB CDR-L1 | RASAGISNDLA |

| SEQ ID NO | Name | Sequence |
|---|---|---|
| 471 | PI-3047-AB CDR-L2 | AASRLQD |
| 472 | PI-3047-AB CDR-L3 | QQSYKYPWT |
| 473 | PI-3047-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC |
| 474 | PI-3046-AB Heavy Chain Variable | EVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSS |
| 475 | PI-3046-AB CDR-H1 | GFSLTSYHVS |
| 476 | PI-3046-AB CDR-H2 | AIWTGGSIA |
| 477 | PI-3046-AB CDR-H3 | DLSDYYSSYTSFDY |
| 478 | PI-3046-AB Heavy chain | EVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSSASTKGPSVFPLA PCSRSTSESTAALGCLVKDYFPEPVTVSWNSGALTSGVHTFPAVLQSSGLYSLSSVVTVPSSSLGTK TYTCNVDHKPSNTKVDKRVESKYGPPCPPCPAPEFLGGPSVFLFPPKPKDTLMISRTPEVTCVVVDV SQEDPEVQFNWYVDGVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 479 | PI-3046-AB Light Chain Variable | DIQMTQSPSSLSASVGDRVTITCRASEGISNDLAWYQQKPGKAPKLLIYAASRLQSGVPSRFSGSGS GTDYTLTISSMQPEDFATYYCQQSYKYPLTFGQGTKLEIK |
| 480 | PI-3046-AB CDR-L1 | RASEGISNDLA |
| 481 | PI-3046-AB CDR-L2 | AASRLQD |
| 482 | PI-3046-AB CDR-L3 | QQSYKYPLT |
| 483 | PI-3046-AB Light chain | DIQMTQSPSSLSASVGDRVTITCRASEGISNDLAWYQQKPGKAPKLLIYAASRLQSGVPSRFSGSGS GTDYTLTISSMQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC |

The invention claimed is:

1. An isolated antibody or antigen binding fragment thereof that binds to human Macrophage Receptor with Collagenous Structure (MARCO) (SEQ ID NO: 384) comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:
   a. CDR-H1 comprises the sequence GFSLTSYHVS (SEQ ID NO: 2),
   b. CDR-H2 comprises the sequence AIWTGGSIA (SEQ ID NO: 3),
   c. CDR-H3 comprises the sequence DLSDYYS-SYTSFDY (SEQ ID NO: 4),
   d. CDR-L1 comprises the sequence ASEGISNDLA (SEQ ID NO: 431) or XASEGISNDLA (SEQ ID NO: 383), wherein X is arginine (R) or leucine (L),
   e. CDR-L2 comprises the sequence AASRLQD (SEQ ID NO: 8), and
   f. CDR-L3 comprises the sequence QQSYKYPLT (SEQ ID NO: 9).

2. The isolated antibody of claim 1, wherein: CDR-L1 comprises the sequence RASEGISNDLA (SEQ ID NO: 27).

3. The isolated antibody of claim 1, wherein the VH sequence comprises the VH sequence set forth in SEQ ID NO: 61; and the VL sequence comprises the VL sequence set forth in SEQ ID NO: 66.

4. The isolated antibody of claim 1, wherein the VH sequence comprises the VH sequence set forth in SEQ ID NO: 111; and the and the VL sequence comprises the VL sequence set forth in SEQ ID NO: 116.

5. The isolated antibody of claim 1, wherein the VH sequence comprises the VH sequence set forth in SEQ ID NO: 1, 11, 21, 31, 41, 51, 61, 71, 81, 91, 101, 111, 121, 131, 434, 444, or 474.

6. The isolated antibody of claim 1, wherein the VL sequence comprises the VL sequence set forth in SEQ ID NO: 6, 16, 26, 36, 46, 57, 66, 76, 86, 96, 106, 116, 126, 136, 439, 449, or 479.

7. The isolated antibody of claim 1, wherein the VH sequence comprises the VH sequence set forth in SEQ ID NO: 1, 11, 21, 31, 41, 51, 61, 71, 81, 91, 101, 111, 121, 131, 434, 444, or 474; and the VL sequence comprises the VL sequence set forth in SEQ ID NO: 6, 16, 26, 36, 46, 57, 66, 76, 86, 96, 106, 116, 126, 136, 439, 449, or 479.

8. The isolated antibody of claim 1, wherein the antibody comprises a heavy chain sequence as set forth in SEQ ID NO: 65; and a light chain sequence as set forth in SEQ ID NO: 70.

9. The isolated antibody of claim 1, wherein the antibody comprises a heavy chain sequence as set forth in SEQ ID NO: 115; and a light chain sequence as set forth in SEQ ID NO: 120.

10. The isolated antibody of claim 1, wherein the antibody comprises a heavy chain sequence selected from the sequences set forth in SEQ ID NO: 5, 15, 125, 35, 45, 55, 65, 75, 85, 95, 105, 115, 125, 145, 438, 448, and 478 and a light chain sequence selected from the sequences set forth in SEQ ID NO: 10, 20, 30, 40, 50, 6, 70, 80, 90, 100, 110, 120, 130, 140, 443, 453, and 483.

11. The isolated antibody of claim 1, wherein the VH sequence consists of the VH sequence set forth in SEQ ID NO: 61; and the VL sequence consists of the VL sequence set forth in SEQ ID NO: 66.

12. The isolated antibody of claim 1, wherein the VH sequence consists of the VH sequence set forth in SEQ ID NO: 111; and the and the VL sequence consists of the VL sequence set forth in SEQ ID NO: 116.

13. The isolated antibody claim 1, wherein the VH sequence consists of the VH sequence selected from the sequences set forth in SEQ ID NO: 1, 11, 21, 31, 41, 51, 61, 71, 81, 91, 101, 111, 121, 131, 434, 444, or 474; and the VL sequence consists of the VL sequence selected from the sequences set forth in SEQ ID NOs: 6, 16, 26, 36, 46, 57, 66, 76, 86, 96, 106, 116, 126, 136, 439, 449, or 479.

14. The isolated antibody of claim 1, wherein the antibody comprises a heavy chain and a light chain, wherein the sequence of the heavy chain consists of the heavy chain sequence set forth in SEQ ID NO: 65 and the sequence of the light chain consists of the light chain sequence set forth in SEQ ID NO: 70.

15. The isolated antibody of claim 1, wherein the antibody comprises a heavy chain and a light chain, wherein the sequence of the heavy chain consists of the heavy chain sequence set forth in SEQ ID NO: 115 and the sequence of the light chain consists of the light chain sequence set forth in SEQ ID NO: 120.

16. The isolated antibody of claim 1, wherein the antibody comprises a human Fc region.

17. The isolated antibody of claim 1, wherein the human Fc region is a wild-type human IgG1 Fc.

18. The isolated antibody of claim 1, wherein the antibody comprises a wild type human IgG1 Fc, and wherein the VH sequence comprises the VH sequence set forth in SEQ ID NO: 61, and the VL sequence comprises the VL sequence set forth in SEQ ID NO: 66.

19. The isolated antibody of claim 1, wherein the antibody comprises a wild type human IgG1 Fc, and wherein the VH sequence comprises the VH sequence set forth in SEQ ID NO: 111, and the VL sequence comprises the VL sequence set forth in SEQ ID NO: 116.

20. The isolated antibody of claim 1, wherein the antibody binds to human MARCO with a KD of less than or equal to 0.5, 1, 2, 3, 4, 5, 6, or $7 \times 10^{-9}$M, as measured by surface plasmon resonance (SPR) assay.

21. The isolated antibody of claim 1, wherein the antibody is humanized.

22. A pharmaceutical composition comprising the antibody of claim 1 and a pharmaceutically acceptable excipient.

23. A kit comprising the antibody of claim 1.

24. The isolated antibody of claim 1, wherein CDR-L1 comprises the sequence LASEGISNDLA (SEQ ID NO: 7).

25. The isolated antibody of claim 1, wherein the antibody comprises a wild type human IgG1 Fc, and wherein the VH sequence consists of the VH sequence set forth in SEQ ID NO: 61, and the VL sequence consists of the VL sequence set forth in SEQ ID NO: 66.

26. The isolated antibody of claim 1, wherein the VH chain sequence comprises the VH sequence shown in SEQ ID NO: 434; and the VL chain sequence comprises the VL sequence shown in SEQ ID NO: 439.

27. The isolated antibody of claim 1, wherein the VH chain sequence consists of the VH sequence shown in SEQ ID NO: 434; and the VL chain sequence consists of the VL sequence shown in SEQ ID NO: 439.

28. The isolated antibody of claim 1, wherein the antibody comprises a wild type human IgG1 Fc, and wherein the VH sequence comprises the VH sequence set forth in SEQ ID NO: 434, and the VL sequence comprises the VL sequence set forth in SEQ ID NO: 439.

29. The isolated antibody of claim 1, wherein the antibody comprises a wild type human IgG1 Fc, and wherein the VH sequence consists of the VH sequence set forth in SEQ ID NO: 434, and the VL sequence consists of the VL sequence set forth in SEQ ID NO: 439.

30. The isolated antibody of claim 1, wherein the antibody comprises a heavy chain and a light chain, wherein the sequence of the heavy chain comprises the heavy chain sequence set forth in SEQ ID NO: 438 and the sequence of the light chain comprises the light chain sequence set forth in SEQ ID NO: 443.

31. The isolated antibody of claim 1, wherein the antibody comprises a heavy chain and a light chain, wherein the sequence of the heavy chain consists of the heavy chain sequence set forth in SEQ ID NO: 438 and the sequence of the light chain consists of the light chain sequence set forth in SEQ ID NO: 443.

32. A pharmaceutical composition comprising the antibody of claim 2 and a pharmaceutically acceptable excipient.

33. A pharmaceutical composition comprising the antibody of claim 3 and a pharmaceutically acceptable excipient.

34. A pharmaceutical composition comprising the antibody of claim 8 and a pharmaceutically acceptable excipient.

35. A pharmaceutical composition comprising the antibody of claim 11 and a pharmaceutically acceptable excipient.

36. A pharmaceutical composition comprising the antibody of claim 14 and a pharmaceutically acceptable excipient.

37. A pharmaceutical composition comprising the antibody of claim 18 and a pharmaceutically acceptable excipient.

38. A pharmaceutical composition comprising the antibody of claim 25 and a pharmaceutically acceptable excipient.

39. A pharmaceutical composition comprising the antibody of claim 26 and a pharmaceutically acceptable excipient.

40. A pharmaceutical composition comprising the antibody of claim 27 and a pharmaceutically acceptable excipient.

41. A pharmaceutical composition comprising the antibody of claim 28 and a pharmaceutically acceptable excipient.

42. A pharmaceutical composition comprising the antibody of claim 29 and a pharmaceutically acceptable excipient.

43. A pharmaceutical composition comprising the antibody of claim 30 and a pharmaceutically acceptable excipient.

44. A pharmaceutical composition comprising the antibody of claim 31 and a pharmaceutically acceptable excipient.

45. The isolated antibody of claim 1, wherein the VH sequence comprises the VH sequence set forth in SEQ ID NO: 61.

46. The isolated antibody of claim 1, wherein the VH sequence comprises the VH sequence set forth in SEQ ID NO: 434.

47. The isolated antibody of claim 1, wherein the VL sequence comprises the VL sequence set forth in SEQ ID NO: 66.

48. The isolated antibody of claim 1, wherein the VL sequence comprises the VL sequence set forth in SEQ ID NO: 439.

49. The isolated antibody of claim 1, wherein the VH sequence consists of the VH sequence set forth in SEQ ID NO: 61.

50. The isolated antibody of claim 1, wherein the VH sequence consists of the VH sequence set forth in SEQ ID NO: 434.

51. The isolated antibody of claim 1, wherein the VL sequence consists of the VL sequence set forth in SEQ ID NO: 66.

52. The isolated antibody of claim 1, wherein the VL sequence consists of the VL sequence set forth in SEQ ID NO: 439.

53. The isolated antibody of claim 1, wherein the antibody comprises a wild type human IgG1 Fc, and wherein the VH sequence comprises the VH sequence set forth in SEQ ID NO: 61.

54. The isolated antibody of claim 1, wherein the antibody comprises a wild type human IgG1 Fc, and wherein the VH sequence comprises the VH sequence set forth in SEQ ID NO: 434.

55. The isolated antibody of claim 1, wherein the antibody comprises a heavy chain and a light chain, wherein the sequence of the heavy chain comprises the heavy chain sequence set forth in SEQ ID NO: 65.

56. The isolated antibody of claim 1, wherein the antibody comprises a heavy chain and a light chain, wherein the sequence of the light chain comprises the light chain sequence set forth in SEQ ID NO: 70.

57. The isolated antibody of claim 1, wherein the antibody comprises a heavy chain and a light chain, wherein the sequence of the heavy chain comprises the heavy chain sequence set forth in SEQ ID NO: 438.

58. The isolated antibody of claim 1, wherein the antibody comprises a heavy chain and a light chain, wherein the sequence of the light chain comprises the light chain sequence set forth in SEQ ID NO: 443.

* * * * *